(12) United States Patent
Posada et al.

(10) Patent No.: US 10,947,295 B2
(45) Date of Patent: Mar. 16, 2021

(54) HETERODIMERS OF SOLUBLE INTERFERON RECEPTORS AND USES THEREOF

(71) Applicant: Sanabio, LLC, St. Petersburg, FL (US)

(72) Inventors: James Arthur Posada, St. Petersburg, FL (US); Pamela Smolak, Seattle, WA (US)

(73) Assignee: Sanabio, LLC, St. Petersburg, FL (US)

( * ) Notice: Subject to any disclaimer, the term of this patent is extended or adjusted under 35 U.S.C. 154(b) by 0 days.

(21) Appl. No.: 16/109,672

(22) Filed: Aug. 22, 2018

(65) Prior Publication Data

US 2019/0194293 A1 Jun. 27, 2019

Related U.S. Application Data

(60) Provisional application No. 62/548,737, filed on Aug. 22, 2017.

(51) Int. Cl.
*C07K 14/715* (2006.01)
*A61K 38/00* (2006.01)

(52) U.S. Cl.
CPC .......... *C07K 14/7156* (2013.01); *A61K 38/00* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 4,973,556 A | 11/1990 | Bove et al. | |
| 5,643,749 A | 7/1997 | Revel et al. | |
| 5,731,168 A | 3/1998 | Carter et al. | |
| 5,731,169 A | 3/1998 | Mogensen et al. | |
| 5,780,027 A | 7/1998 | Maroun | |
| 5,807,706 A | 9/1998 | Carter et al. | |
| 5,821,333 A | 10/1998 | Carter et al. | |
| 5,827,516 A | 10/1998 | Urban et al. | |
| 5,994,514 A | 11/1999 | Jardieu et al. | |
| 6,331,396 B1 | 12/2001 | Silverman et al. | |
| 6,372,207 B1 | 4/2002 | Tepper et al. | |
| 6,475,983 B1 | 11/2002 | Eid et al. | |
| 6,635,416 B2 | 10/2003 | Palese et al. | |
| 6,787,634 B2 | 9/2004 | Benoit et al. | |
| 7,087,726 B2 | 8/2006 | Chuntharapai et al. | |
| 7,442,527 B2 | 10/2008 | Palese et al. | |
| 7,608,395 B2 | 10/2009 | Pascual et al. | |
| 7,642,228 B2 | 1/2010 | Carter et al. | |
| 7,695,936 B2 | 4/2010 | Carter et al. | |
| 7,732,167 B2 | 6/2010 | Smith et al. | |
| 7,749,735 B2 | 7/2010 | Schreiber | |
| 7,892,740 B2 | 2/2011 | Weichselbaum et al. | |
| 7,910,707 B2 | 3/2011 | Chuntharapai et al. | |
| 8,133,699 B2 | 3/2012 | Chatellard et al. | |
| 8,216,805 B2 | 7/2012 | Carter et al. | |
| 8,349,331 B2 | 1/2013 | Chuntharapai et al. | |
| 8,586,713 B2 | 11/2013 | Davis et al. | |
| 8,679,785 B2 | 3/2014 | Carter et al. | |
| 8,828,393 B2 | 9/2014 | Pickford et al. | |
| 8,871,912 B2 | 10/2014 | Davis et al. | |
| 9,150,663 B2 | 10/2015 | Labrijn et al. | |
| 9,181,345 B2 | 11/2015 | Zmuda et al. | |
| 9,249,226 B2 | 2/2016 | de Weers et al. | |
| 9,493,570 B2 | 11/2016 | Higgs et al. | |
| 9,499,634 B2 | 11/2016 | Dixit et al. | |
| 9,505,848 B2 | 11/2016 | Davis et al. | |
| 9,540,433 B2 | 1/2017 | Verploegen et al. | |
| 9,562,109 B2 | 2/2017 | Von Kreudenstein et al. | |
| 9,574,010 B2 | 2/2017 | Spreter Von Kreudenstein et al. | |
| 9,636,420 B2 | 5/2017 | Song et al. | |
| 9,822,173 B2 | 11/2017 | Kannan et al. | |
| 9,861,681 B2 | 1/2018 | Golden et al. | |
| 9,895,433 B2 | 2/2018 | Portnoy et al. | |
| 9,919,062 B2 | 3/2018 | Kirn | |
| 2002/0160974 A1 | 10/2002 | Banchereau et al. | |
| 2003/0175778 A1 | 9/2003 | Ni et al. | |
| 2004/0266993 A1 | 12/2004 | Evans | |
| 2005/0013813 A1 | 1/2005 | Maroun | |
| 2006/0074225 A1 | 4/2006 | Chamberlain et al. | |
| 2006/0240419 A1 | 10/2006 | Nakamura et al. | |
| 2009/0155286 A1 | 6/2009 | Gilliet et al. | |
| 2009/0196870 A1 | 8/2009 | Ledbetter et al. | |
| 2009/0252729 A1 | 10/2009 | Farrington et al. | |
| 2009/0263474 A1 | 10/2009 | Banchereau et al. | |
| 2010/0104564 A1 | 4/2010 | Hansen et al. | |

(Continued)

FOREIGN PATENT DOCUMENTS

EP 369877 B1 5/1995
EP 601052 B1 10/1996

(Continued)

OTHER PUBLICATIONS

Bennett, L. et al., "Interferon and Granulopoiesis Signatures in Systemic Lupus Erythematosus Blood," J. Exp. Med., vol. 197 (6): 711-723 (2003).

De Weerd, N. et al., "Type I Interferon Receptors: Biochemistry and Biological Functions," The Journal of Biological Chemistry, vol. 282(28): 20053-20057 (2007).

Deshpande, A. et al., "Kinetic analysis of cytokine-mediated receptor assembly using engineered FC heterodimers," Protein Science, vol. 22 (8):1100-1108 (2013).

Doedens, J. et al., "Blood-Borne RNA Correlates with Disease Activity and IFN-Stimulated Gene Expression in Systemic Lupus Erythematosus," The Journal of Immunology, vol. 197: 18 pages (2016).

(Continued)

*Primary Examiner* — Elly-Gerald Stoica
(74) *Attorney, Agent, or Firm* — Nelson Mullins Riley & Scarborough LLP; Amy E. Mandragouras, Esq.; Erika E. Wallace, Esq.

(57) ABSTRACT

The present disclosure provides soluble interferon receptors. The methods of the disclosure can be used to treat or prevent a condition associated with an abnormal immune response.

46 Claims, 7 Drawing Sheets

Specification includes a Sequence Listing.

(56) References Cited

U.S. PATENT DOCUMENTS

| | | |
|---|---|---|
| 2010/0254986 A1 | 10/2010 | Carter et al. |
| 2010/0273220 A1 | 10/2010 | Yanik et al. |
| 2011/0123440 A1 | 5/2011 | Hansen et al. |
| 2012/0010387 A1 | 1/2012 | Niwa et al. |
| 2012/0201746 A1 | 8/2012 | Liu et al. |
| 2012/0208278 A1 | 8/2012 | Yanik et al. |
| 2013/0177555 A1 | 7/2013 | Wilkinson et al. |
| 2013/0330345 A1 | 12/2013 | Igawa et al. |
| 2013/0336973 A1 | 12/2013 | Spreter Von Kreudenstein et al. |
| 2014/0154253 A1 | 6/2014 | Ng et al. |
| 2014/0154254 A1 | 6/2014 | Kannan et al. |
| 2014/0170148 A1 | 6/2014 | De Goeij et al. |
| 2014/0170149 A1 | 6/2014 | Neijssen et al. |
| 2014/0227300 A1 | 8/2014 | Chin et al. |
| 2014/0303356 A1 | 10/2014 | Gramer et al. |
| 2016/0046727 A1 | 2/2016 | Labrijn et al. |
| 2016/0051696 A1 | 2/2016 | Song et al. |
| 2016/0102135 A1 | 4/2016 | Escobar-Cabrera |
| 2016/0257763 A1 | 9/2016 | Von Kreudenstein et al. |
| 2017/0100488 A1 | 4/2017 | Park et al. |
| 2017/0158779 A1 | 6/2017 | Dixit et al. |
| 2017/0166650 A1 | 6/2017 | Niwa et al. |
| 2017/0173151 A1 | 6/2017 | Verploegen et al. |
| 2017/0233497 A1 | 8/2017 | Labrijn et al. |
| 2017/0313769 A1 | 11/2017 | Gulla et al. |
| 2017/0368169 A1 | 12/2017 | Loew et al. |
| 2017/0369590 A1 | 12/2017 | De Goeij et al. |
| 2017/0369594 A1 | 12/2017 | Neijssen et al. |
| 2018/0009908 A1 | 1/2018 | Aldaz et al. |
| 2018/0016347 A1 | 1/2018 | Spreter Von Kreudenstein et al. |
| 2018/0016354 A1 | 1/2018 | Wozniak-Knopp et al. |
| 2018/0057567 A1 | 3/2018 | Rao et al. |

FOREIGN PATENT DOCUMENTS

| | | | |
|---|---|---|---|
| EP | 495907 B1 | 7/1998 | |
| EP | 0679717 B1 | 8/1999 | |
| EP | 1037658 B1 | 6/2002 | |
| EP | 812357 B1 | 1/2007 | |
| EP | 1675956 B1 | 10/2010 | |
| EP | 2543727 B1 | 8/2016 | |
| EP | 3248618 A1 | 11/2017 | |
| WO | 93004699 A1 | 3/1993 | |
| WO | 2000024417 A1 | 5/2000 | |
| WO | 2006/138610 A2 | 12/2006 | |
| WO | 2007136789 A2 | 11/2007 | |
| WO | 2012068630 A1 | 5/2012 | |
| WO | 2012068636 A1 | 5/2012 | |
| WO | 2013059299 A1 | 4/2013 | |
| WO | 2014009707 A1 | 1/2014 | |
| WO | 20140150973 A1 | 9/2014 | |
| WO | WO2015107025 * | 7/2015 | ............ C07K 16/22 |
| WO | 2016087648 A1 | 6/2016 | |
| WO | 2016179707 A1 | 11/2016 | |
| WO | 2017185177 A1 | 11/2017 | |
| WO | 2018005954 A2 | 1/2018 | |

OTHER PUBLICATIONS

Gunasekaran, K. et al., "Enhancing antibody Fc heterodimer formation through electrostatic steering effects: applications to bispecific molecules and monovalent IgG.," J. Biol. Chem.,285(25):19637-19646 (2010).

Ha, J-H, et al. "Immunoglobulin Fc Heterodimer Platform Technology: From Design to Applications in Therapeutic Antibodies and Proteins," Frontier in Immunology, vol. 7: 16 pages (2016).

Haak-Frendscho, M. et al., "Inhibition of interferon-γ by an interferon-γ receptor immunoadhesin," Immunology, vol. 79:594-599 (1993).

International Nonproprietary Names for Pharmaceutical Substances (INN): Recommended INN: List 75, WHO Drug Information vol. 30 (1) 78 pages (2016 ).

International Search Report and Written Opinion, PCT/US2018/047614, dated Jan. 4, 2019, 15 pages.

Kennedy, W. et al., "Association of the interferon signature metric with serological disease manifestations but not global activity scores in multiple cohorts of patients with SLE," Lupus Science & Medicine, vol. 2:e000080: 12 pages (2015).

Khamashta, M. et al., "Sifalimumab, an anti-interferon-? monoclonal antibody, in moderate to severe systemic lupus erythematosus: a randomised, double-blind, placebo-controlled study," Ann Rheum Dis., pp. 1-8 (2016).

Langer, J.A., et al., "Bovine type I interferon receptor protein BoIFNAR-1 has high-affinity and broad specificity for human type I interferons," FEBS Letters, vol. 421: 131-135 (1998).

Lewis, S et al., "Generation of bispecific igG antibodies by structure-based design of an orthogonal Fab interface," Nature Biotechnology, vol. 32(2):45 pages (2014).

Li, H. et al., "Dynamic Modulation of Binding Affinity as a Mechanism for Regulating Interferon Signaling," J Mol Biol., vol. 429(16):2571-2589 (2017).

Piehler, J. et al., "Structural and dynamic determinants of type I interferon receptor assembly and their functional interpretation," Immunological Reviews, vol. 250: 317-334 (2012).

Ridgway, J. et al., "Knobs-into-holes' engineering of antibody CH3 domains for heavy chain heterodimerization," Protein Engineering, vol. 9(7):617-621 (1996).

Spiess, C. et al., "Alternative molecular formats and therapeutic applications forbispecific antibodies," Molecular Immunology, vol. 67(2 Pt A):95-106 (2015).

Van Der Neut Kolfschoten, M. et al., "Anti-Inflammatory Activity of Human IgG4 Antibodies by Dynamic Fab Arm Exchange," Science, vol. 317(5844):1554-1557 (2007).

Von Kreudenstein, T.S. et al., "Improving biophysical properties of a bispecific antibody scaffold to aid developability : Quality by molecular design," MABS, vol. 5(5):646-654 (2013).

Furie, R. et al., "Anifrolumab, an Anti-Interferon-α Receptor Monoclonal Antibody, in Moderate-to-Severe Systemic Lupus Erythematosus," Arthritis & Rheumatology, vol. 69(2): 376-386 (2017).

Atwell, S. et al., "Stable heterodimers from remodeling the domain interface of a homodimer using a phage display library," J. Mol. Biol., vol. 270: 26-35 (1997).

Davis, J. et al., "SEEDbodies: fusion proteins based on strand-exchange engineered domain (SEED) CH3 heterodimers in an Fc analogue platform for asymmetric binders or immunofusions and bispecific antibodies," Protein Eng Des Sel., vol. 23(4):195-202 (2010).

Dulaglutide, Drug Bank, Accession No. DB09045, Drug created Apr. 29, 2015, 6 pages.

Klein, C. et al., "Progress in overcoming the chain association issue in bispecific heterodimeric IgG antibodies," mAbs, vol. 4(6):653-663 (2012).

Labrijn, A. et al., "Efficient generation of stable bispecific IgG1 by controlled Fab-arm exchange," PNAS, vol. 110 (13):5145-5150 (2013).

Merchant, A. et al., "An efficient route to human bispecific IgG," Nat Biotechnol., vol. 16(7):677-681 (1998).

Moore, G., et al. "A novel bispecific antibody format enables simultaneous bivalent and monovalent co-engagement of distinct target antigens," MABS, vol. 3(6):546-557 (2011).

Sampei, Z. et al., "Identification and Multidimensional Optimization of an Asymmetric Bispecific IgG Antibody Mimicking the Function of Factor VIII Cofactor Activity," PLOS One, vol. 8(2): e57479: 13 pages (2013).

Strop, P. et al., "Generating bispecific human IgG1 and IgG2 antibodies from any antibody pair," J. Mol. Biol., vol. 420 (3):204-219 (2012).

International Preliminary Report on Patentability, PCT/US2018/047614, dated Feb. 25, 2020, 7 pages.

* cited by examiner

SEQUENCE LISTING

```
<160> NUMBER OF SEQ ID NOS: 155

<210> SEQ ID NO 1
<211> LENGTH: 680
<212> TYPE: PRT
<213> ORGANISM: Artificial Sequence
<220> FEATURE:
<223> OTHER INFORMATION: Synthetic: RSLV-601 Leader-IFNAR1 (aa28-436)-
      (Gly4Ser)4- IgG1 Fc (aa216-447)with mutations C220S, P238S,
      P331S,T350V, T366L, K392L, T394W

<400> SEQUENCE: 1
```

Met Asp Trp Thr Trp Arg Ile Leu Phe Leu Val Ala Ala Ala Thr Gly
1               5                   10                  15

Thr His Ala Lys Asn Leu Lys Ser Pro Gln Lys Val Glu Val Asp Ile
                20                  25                  30

Ile Asp Asp Asn Phe Ile Leu Arg Trp Asn Arg Ser Asp Glu Ser Val
            35                  40                  45

Gly Asn Val Thr Phe Ser Phe Asp Tyr Gln Lys Thr Gly Met Asp Asn
        50                  55                  60

Trp Ile Lys Leu Ser Gly Cys Gln Asn Ile Thr Ser Thr Lys Cys Asn
65                  70                  75                  80

Phe Ser Ser Leu Lys Leu Asn Val Tyr Glu Glu Ile Lys Leu Arg Ile
                85                  90                  95

Arg Ala Glu Lys Glu Asn Thr Ser Ser Trp Tyr Glu Val Asp Ser Phe
            100                 105                 110

Thr Pro Phe Arg Lys Ala Gln Ile Gly Pro Pro Glu Val His Leu Glu
        115                 120                 125

Ala Glu Asp Lys Ala Ile Val Ile His Ile Ser Pro Gly Thr Lys Asp
    130                 135                 140

Ser Val Met Trp Ala Leu Asp Gly Leu Ser Phe Thr Tyr Ser Leu Val
145                 150                 155                 160

Ile Trp Lys Asn Ser Ser Gly Val Glu Glu Arg Ile Glu Asn Ile Tyr
                165                 170                 175

Ser Arg His Lys Ile Tyr Lys Leu Ser Pro Glu Thr Thr Tyr Cys Leu
            180                 185                 190

Lys Val Lys Ala Ala Leu Leu Thr Ser Trp Lys Ile Gly Val Tyr Ser
        195                 200                 205

Pro Val His Cys Ile Lys Thr Thr Val Glu Asn Glu Leu Pro Pro Pro
    210                 215                 220

```
Glu Asn Ile Glu Val Ser Val Gln Asn Gln Asn Tyr Val Leu Lys Trp
225                 230                 235                 240

Asp Tyr Thr Tyr Ala Asn Met Thr Phe Gln Val Gln Trp Leu His Ala
            245                 250                 255

Phe Leu Lys Arg Asn Pro Gly Asn His Leu Tyr Lys Trp Lys Gln Ile
            260                 265                 270

Pro Asp Cys Glu Asn Val Lys Thr Thr Gln Cys Val Phe Pro Gln Asn
            275                 280                 285

Val Phe Gln Lys Gly Ile Tyr Leu Leu Arg Val Gln Ala Ser Asp Gly
            290                 295                 300

Asn Asn Thr Ser Phe Trp Ser Glu Glu Ile Lys Phe Asp Thr Glu Ile
305                 310                 315                 320

Gln Ala Phe Leu Leu Pro Pro Val Phe Asn Ile Arg Ser Leu Ser Asp
                325                 330                 335

Ser Phe His Ile Tyr Ile Gly Ala Pro Lys Gln Ser Gly Asn Thr Pro
                340                 345                 350

Val Ile Gln Asp Tyr Pro Leu Ile Tyr Glu Ile Ile Phe Trp Glu Asn
            355                 360                 365

Thr Ser Asn Ala Glu Arg Lys Ile Ile Glu Lys Lys Thr Asp Val Thr
370                 375                 380

Val Pro Asn Leu Lys Pro Leu Thr Val Tyr Cys Val Lys Ala Arg Ala
385                 390                 395                 400

His Thr Met Asp Glu Lys Leu Asn Lys Ser Ser Val Phe Ser Asp Ala
                405                 410                 415

Val Cys Glu Lys Thr Lys Pro Gly Asn Thr Ser Lys Gly Gly Gly Gly
            420                 425                 430

Ser Gly Gly Gly Gly Ser Gly Gly Gly Gly Ser Gly Gly Gly Gly Ser
            435                 440                 445

Glu Pro Lys Ser Ser Asp Lys Thr His Thr Cys Pro Pro Cys Pro Ala
450                 455                 460

Pro Glu Leu Leu Gly Gly Ser Ser Val Phe Leu Phe Pro Pro Lys Pro
465                 470                 475                 480

Lys Asp Thr Leu Met Ile Ser Arg Thr Pro Glu Val Thr Cys Val Val
            485                 490                 495

Val Asp Val Ser His Glu Asp Pro Glu Val Lys Phe Asn Trp Tyr Val
            500                 505                 510

Asp Gly Val Glu Val His Asn Ala Lys Thr Lys Pro Arg Glu Glu Gln
            515                 520                 525

Tyr Asn Ser Thr Tyr Arg Val Val Ser Val Leu Thr Val Leu His Gln
            530                 535                 540

Asp Trp Leu Asn Gly Lys Glu Tyr Lys Cys Lys Val Ser Asn Lys Ala
545                 550                 555                 560

Leu Pro Ala Ser Ile Glu Lys Thr Ile Ser Lys Ala Lys Gly Gln Pro
                565                 570                 575

Arg Glu Pro Gln Val Tyr Val Leu Pro Pro Ser Arg Asp Glu Leu Thr
            580                 585                 590

Lys Asn Gln Val Ser Leu Leu Cys Leu Val Lys Gly Phe Tyr Pro Ser
            595                 600                 605

Asp Ile Ala Val Glu Trp Glu Ser Asn Gly Gln Pro Glu Asn Asn Tyr
            610                 615                 620

Leu Thr Trp Pro Pro Val Leu Asp Ser Asp Gly Ser Phe Phe Leu Tyr
625                 630                 635                 640

Ser Lys Leu Thr Val Asp Lys Ser Arg Trp Gln Gln Gly Asn Val Phe
```

```
                         645                 650                 655
Ser Cys Ser Val Met His Glu Ala Leu His Asn His Tyr Thr Gln Lys
                660                 665                 670

Ser Leu Ser Leu Ser Pro Gly Lys
        675                 680

<210> SEQ ID NO 2
<211> LENGTH: 488
<212> TYPE: PRT
<213> ORGANISM: Artificial Sequence
<220> FEATURE:
<223> OTHER INFORMATION: Synthetic: RSLV-602 Leader-IFNAR2 (aa27-243)
      (Gly4Ser)4- IgG1 Fc (aa 216-447)with mutations C220S, P238S,
      P331S,T350V, T366L, K392L, T394W

<400> SEQUENCE: 2

Met Asp Trp Thr Trp Arg Ile Leu Phe Leu Val Ala Ala Ala Thr Gly
1               5                   10                  15

Thr His Ala Ile Ser Tyr Asp Ser Pro Asp Tyr Thr Asp Glu Ser Cys
            20                  25                  30

Thr Phe Lys Ile Ser Leu Arg Asn Phe Arg Ser Ile Leu Ser Trp Glu
        35                  40                  45

Leu Lys Asn His Ser Ile Val Pro Thr His Tyr Thr Leu Leu Tyr Thr
    50                  55                  60

Ile Met Ser Lys Pro Glu Asp Leu Lys Val Val Lys Asn Cys Ala Asn
65                  70                  75                  80

Thr Thr Arg Ser Phe Cys Asp Leu Thr Asp Glu Trp Arg Ser Thr His
                85                  90                  95

Glu Ala Tyr Val Thr Val Leu Glu Gly Phe Ser Gly Asn Thr Thr Leu
            100                 105                 110

Phe Ser Cys Ser His Asn Phe Trp Leu Ala Ile Asp Met Ser Phe Glu
        115                 120                 125

Pro Pro Glu Phe Glu Ile Val Gly Phe Thr Asn His Ile Asn Val Met
    130                 135                 140

Val Lys Phe Pro Ser Ile Val Glu Glu Glu Leu Gln Phe Asp Leu Ser
145                 150                 155                 160

Leu Val Ile Glu Glu Gln Ser Glu Gly Ile Val Lys Lys His Lys Pro
                165                 170                 175

Glu Ile Lys Gly Asn Met Ser Gly Asn Phe Thr Tyr Ile Ile Asp Lys
            180                 185                 190

Leu Ile Pro Asn Thr Asn Tyr Cys Val Ser Val Tyr Leu Glu His Ser
        195                 200                 205

Asp Glu Gln Ala Val Ile Lys Ser Pro Leu Lys Cys Thr Leu Leu Pro
    210                 215                 220

Pro Gly Gln Glu Ser Glu Ser Ala Glu Ser Ala Lys Gly Gly Gly Gly
225                 230                 235                 240

Ser Gly Gly Gly Ser Gly Gly Gly Ser Gly Gly Gly Ser
                245                 250                 255

Glu Pro Lys Ser Ser Asp Lys Thr His Thr Cys Pro Pro Cys Pro Ala
            260                 265                 270

Pro Glu Leu Leu Gly Gly Ser Ser Val Phe Leu Phe Pro Pro Lys Pro
        275                 280                 285

Lys Asp Thr Leu Met Ile Ser Arg Thr Pro Glu Val Thr Cys Val Val
    290                 295                 300

Val Asp Val Ser His Glu Asp Pro Glu Val Lys Phe Asn Trp Tyr Val
305                 310                 315                 320
```

```
Asp Gly Val Glu Val His Asn Ala Lys Thr Lys Pro Arg Glu Glu Gln
                325                 330                 335

Tyr Asn Ser Thr Tyr Arg Val Val Ser Val Leu Thr Val Leu His Gln
            340                 345                 350

Asp Trp Leu Asn Gly Lys Glu Tyr Lys Cys Lys Val Ser Asn Lys Ala
        355                 360                 365

Leu Pro Ala Ser Ile Glu Lys Thr Ile Ser Lys Ala Lys Gly Gln Pro
    370                 375                 380

Arg Glu Pro Gln Val Tyr Val Leu Pro Pro Ser Arg Asp Glu Leu Thr
385                 390                 395                 400

Lys Asn Gln Val Ser Leu Leu Cys Leu Val Lys Gly Phe Tyr Pro Ser
                405                 410                 415

Asp Ile Ala Val Glu Trp Glu Ser Asn Gly Gln Pro Glu Asn Asn Tyr
            420                 425                 430

Leu Thr Trp Pro Pro Val Leu Asp Ser Asp Gly Ser Phe Phe Leu Tyr
        435                 440                 445

Ser Lys Leu Thr Val Asp Lys Ser Arg Trp Gln Gln Gly Asn Val Phe
    450                 455                 460

Ser Cys Ser Val Met His Glu Ala Leu His Asn His Tyr Thr Gln Lys
465                 470                 475                 480

Ser Leu Ser Leu Ser Pro Gly Lys
                485

<210> SEQ ID NO 3
<211> LENGTH: 680
<212> TYPE: PRT
<213> ORGANISM: Artificial Sequence
<220> FEATURE:
<223> OTHER INFORMATION: Synthetic: RSLV-603 Leader-IFNAR1 (aa28-436)-
      (Gly4Ser)4- IgG1 Fc (aa 216-447)with mutations C220S, P238S,
      P331S, T350V, L351Y, F405A, Y407V

<400> SEQUENCE: 3

Met Asp Trp Thr Trp Arg Ile Leu Phe Leu Val Ala Ala Ala Thr Gly
1               5                   10                  15

Thr His Ala Lys Asn Leu Lys Ser Pro Gln Lys Val Glu Val Asp Ile
            20                  25                  30

Ile Asp Asp Asn Phe Ile Leu Arg Trp Asn Arg Ser Asp Glu Ser Val
        35                  40                  45

Gly Asn Val Thr Phe Ser Phe Asp Tyr Gln Lys Thr Gly Met Asp Asn
    50                  55                  60

Trp Ile Lys Leu Ser Gly Cys Gln Asn Ile Thr Ser Thr Lys Cys Asn
65                  70                  75                  80

Phe Ser Ser Leu Lys Leu Asn Val Tyr Glu Glu Ile Lys Leu Arg Ile
                85                  90                  95

Arg Ala Glu Lys Glu Asn Thr Ser Ser Trp Tyr Glu Val Asp Ser Phe
            100                 105                 110

Thr Pro Phe Arg Lys Ala Gln Ile Gly Pro Pro Glu Val His Leu Glu
        115                 120                 125

Ala Glu Asp Lys Ala Ile Val Ile His Ile Ser Pro Gly Thr Lys Asp
    130                 135                 140

Ser Val Met Trp Ala Leu Asp Gly Leu Ser Phe Thr Tyr Ser Leu Val
145                 150                 155                 160

Ile Trp Lys Asn Ser Ser Gly Val Glu Glu Arg Ile Glu Asn Ile Tyr
                165                 170                 175
```

```
Ser Arg His Lys Ile Tyr Lys Leu Ser Pro Glu Thr Thr Tyr Cys Leu
            180                 185                 190

Lys Val Lys Ala Ala Leu Leu Thr Ser Trp Lys Ile Gly Val Tyr Ser
195                 200                 205

Pro Val His Cys Ile Lys Thr Thr Val Glu Asn Glu Leu Pro Pro Pro
            210                 215                 220

Glu Asn Ile Glu Val Ser Val Gln Asn Gln Asn Tyr Val Leu Lys Trp
225                 230                 235                 240

Asp Tyr Thr Tyr Ala Asn Met Thr Phe Gln Val Gln Trp Leu His Ala
            245                 250                 255

Phe Leu Lys Arg Asn Pro Gly Asn His Leu Tyr Lys Trp Lys Gln Ile
            260                 265                 270

Pro Asp Cys Glu Asn Val Lys Thr Thr Gln Cys Val Phe Pro Gln Asn
            275                 280                 285

Val Phe Gln Lys Gly Ile Tyr Leu Leu Arg Val Gln Ala Ser Asp Gly
            290                 295                 300

Asn Asn Thr Ser Phe Trp Ser Glu Glu Ile Lys Phe Asp Thr Glu Ile
305                 310                 315                 320

Gln Ala Phe Leu Leu Pro Pro Val Phe Asn Ile Arg Ser Leu Ser Asp
            325                 330                 335

Ser Phe His Ile Tyr Ile Gly Ala Pro Lys Gln Ser Gly Asn Thr Pro
            340                 345                 350

Val Ile Gln Asp Tyr Pro Leu Ile Tyr Glu Ile Ile Phe Trp Glu Asn
            355                 360                 365

Thr Ser Asn Ala Glu Arg Lys Ile Ile Glu Lys Thr Asp Val Thr
370                 375                 380

Val Pro Asn Leu Lys Pro Leu Thr Val Tyr Cys Val Lys Ala Arg Ala
385                 390                 395                 400

His Thr Met Asp Glu Lys Leu Asn Lys Ser Ser Val Phe Ser Asp Ala
            405                 410                 415

Val Cys Glu Lys Thr Lys Pro Gly Asn Thr Ser Lys Gly Gly Gly Gly
            420                 425                 430

Ser Gly Gly Gly Gly Ser Gly Gly Gly Gly Ser Gly Gly Gly Gly Ser
            435                 440                 445

Glu Pro Lys Ser Ser Asp Lys Thr His Thr Cys Pro Pro Cys Pro Ala
450                 455                 460

Pro Glu Leu Leu Gly Gly Ser Ser Val Phe Leu Phe Pro Pro Lys Pro
465                 470                 475                 480

Lys Asp Thr Leu Met Ile Ser Arg Thr Pro Glu Val Thr Cys Val Val
            485                 490                 495

Val Asp Val Ser His Glu Asp Pro Glu Val Lys Phe Asn Trp Tyr Val
            500                 505                 510

Asp Gly Val Glu Val His Asn Ala Lys Thr Lys Pro Arg Glu Glu Gln
            515                 520                 525

Tyr Asn Ser Thr Tyr Arg Val Val Ser Val Leu Thr Val Leu His Gln
            530                 535                 540

Asp Trp Leu Asn Gly Lys Glu Tyr Lys Cys Lys Val Ser Asn Lys Ala
545                 550                 555                 560

Leu Pro Ala Ser Ile Glu Lys Thr Ile Ser Lys Ala Lys Gly Gln Pro
            565                 570                 575

Arg Glu Pro Gln Val Tyr Val Tyr Pro Pro Ser Arg Asp Glu Leu Thr
            580                 585                 590

Lys Asn Gln Val Ser Leu Thr Cys Leu Val Lys Gly Phe Tyr Pro Ser
```

```
                    595                 600                 605
Asp Ile Ala Val Glu Trp Glu Ser Asn Gly Gln Pro Glu Asn Asn Tyr
    610                 615                 620

Lys Thr Thr Pro Pro Val Leu Asp Ser Asp Gly Ser Phe Ala Leu Val
625                 630                 635                 640

Ser Lys Leu Thr Val Asp Lys Ser Arg Trp Gln Gln Gly Asn Val Phe
                645                 650                 655

Ser Cys Ser Val Met His Glu Ala Leu His Asn His Tyr Thr Gln Lys
                660                 665                 670

Ser Leu Ser Leu Ser Pro Gly Lys
        675                 680

<210> SEQ ID NO 4
<211> LENGTH: 488
<212> TYPE: PRT
<213> ORGANISM: Artificial Sequence
<220> FEATURE:
<223> OTHER INFORMATION: Synthetic: RSLV-604 Leader-IFNAR2 (aa27-243)-
      (Gly4Ser)4- IgG1 Fc (aa 216-447) with mutations C220S, P238S,
      P331S, and ZW1 Chain A mutations T350V, L351Y, F405A, Y407V

<400> SEQUENCE: 4

Met Asp Trp Thr Trp Arg Ile Leu Phe Leu Val Ala Ala Ala Thr Gly
1               5                   10                  15

Thr His Ala Ile Ser Tyr Asp Ser Pro Asp Tyr Thr Asp Glu Ser Cys
            20                  25                  30

Th

-continued

Pro Glu Leu Leu Gly Gly Ser Ser Val Phe Leu Phe Pro Pro Lys Pro
             275                 280                 285

Lys Asp Thr Leu Met Ile Ser Arg Thr Pro Glu Val Thr Cys Val Val
        290                 295                 300

Val Asp Val Ser His Glu Asp Pro Glu Val Lys Phe Asn Trp Tyr Val
305                 310                 315                 320

Asp Gly Val Glu Val His Asn Ala Lys Thr Lys Pro Arg Glu Glu Gln
                325                 330                 335

Tyr Asn Ser Thr Tyr Arg Val Val Ser Val Leu Thr Val Leu His Gln
            340                 345                 350

Asp Trp Leu Asn Gly Lys Glu Tyr Lys Cys Lys Val Ser Asn Lys Ala
        355                 360                 365

Leu Pro Ala Ser Ile Glu Lys Thr Ile Ser Lys Ala Lys Gly Gln Pro
    370                 375                 380

Arg Glu Pro Gln Val Tyr Val Tyr Pro Pro Ser Arg Asp Glu Leu Thr
385                 390                 395                 400

Lys Asn Gln Val Ser Leu Thr Cys Leu Val Lys Gly Phe Tyr Pro Ser
                405                 410                 415

Asp Ile Ala Val Glu Trp Glu Ser Asn Gly Gln Pro Glu Asn Asn Tyr
            420                 425                 430

Lys Thr Thr Pro Pro Val Leu Asp Ser Asp Gly Ser Phe Ala Leu Val
        435                 440                 445

Ser Lys Leu Thr Val Asp Lys Ser Arg Trp Gln Gln Gly Asn Val Phe
    450                 455                 460

Ser Cys Ser Val Met His Glu Ala Leu His Asn His Tyr Thr Gln Lys
465                 470                 475                 480

Ser Leu Ser Leu Ser Pro Gly Lys
                485

<210> SEQ ID NO 5
<211> LENGTH: 557
<212> TYPE: PRT
<213> ORGANISM: Homo sapiens
<220> FEATURE:
<221> NAME/KEY: misc_feature
<223> OTHER INFORMATION: IFNAR1

<400> SEQUENCE: 5

Met Met Val Val Leu Leu Gly Ala Thr Thr Leu Val Leu Val Ala Val
1               5                   10                  15

Ala Pro Trp Val Leu Ser Ala Ala Gly Gly Lys Asn Leu Lys Ser
            20                  25                  30

Pro Gln Lys Val Glu Val Asp Ile Ile Asp Asp Asn Phe Ile Leu Arg
        35                  40                  45

Trp Asn Arg Ser Asp Glu Ser Val Gly Asn Val Thr Phe Ser Phe Asp
    50                  55                  60

Tyr Gln Lys Thr Gly Met Asp Asn Trp Ile Lys Leu Ser Gly Cys Gln
65                  70                  75                  80

Asn Ile Thr Ser Thr Lys Cys Asn Phe Ser Ser Leu Lys Leu Asn Val
                85                  90                  95

Tyr Glu Glu Ile Lys Leu Arg Ile Arg Ala Glu Lys Glu Asn Thr Ser
            100                 105                 110

Ser Trp Tyr Glu Val Asp Ser Phe Thr Pro Phe Arg Lys Ala Gln Ile
        115                 120                 125

Gly Pro Pro Glu Val His Leu Glu Ala Glu Asp Lys Ala Ile Val Ile

```
            130                 135                 140
His Ile Ser Pro Gly Thr Lys Asp Ser Val Met Trp Ala Leu Asp Gly
145                 150                 155                 160

Leu Ser Phe Thr Tyr Ser Leu Val Ile Trp Lys Asn Ser Ser Gly Val
                165                 170                 175

Glu Glu Arg Ile Glu Asn Ile Tyr Ser Arg His Lys Ile Tyr Lys Leu
            180                 185                 190

Ser Pro Glu Thr Thr Tyr Cys Leu Lys Val Lys Ala Ala Leu Leu Thr
                195                 200                 205

Ser Trp Lys Ile Gly Val Tyr Ser Pro Val His Cys Ile Lys Thr Thr
210                 215                 220

Val Glu Asn Glu Leu Pro Pro Glu Asn Ile Glu Val Ser Val Gln
225                 230                 235                 240

Asn Gln Asn Tyr Val Leu Lys Trp Asp Tyr Thr Tyr Ala Asn Met Thr
                245                 250                 255

Phe Gln Val Gln Trp Leu His Ala Phe Leu Lys Arg Asn Pro Gly Asn
                260                 265                 270

His Leu Tyr Lys Trp Lys Gln Ile Pro Asp Cys Glu Asn Val Lys Thr
                275                 280                 285

Thr Gln Cys Val Phe Pro Gln Asn Val Phe Gln Lys Gly Ile Tyr Leu
            290                 295                 300

Leu Arg Val Gln Ala Ser Asp Gly Asn Asn Thr Ser Phe Trp Ser Glu
305                 310                 315                 320

Glu Ile Lys Phe Asp Thr Glu Ile Gln Ala Phe Leu Leu Pro Pro Val
                325                 330                 335

Phe Asn Ile Arg Ser Leu Ser Asp Ser Phe His Ile Tyr Ile Gly Ala
                340                 345                 350

Pro Lys Gln Ser Gly Asn Thr Pro Val Ile Gln Asp Tyr Pro Leu Ile
            355                 360                 365

Tyr Glu Ile Ile Phe Trp Glu Asn Thr Ser Asn Ala Glu Arg Lys Ile
            370                 375                 380

Ile Glu Lys Lys Thr Asp Val Thr Val Pro Asn Leu Lys Pro Leu Thr
385                 390                 395                 400

Val Tyr Cys Val Lys Ala Arg Ala His Thr Met Asp Glu Lys Leu Asn
                405                 410                 415

Lys Ser Ser Val Phe Ser Asp Ala Val Cys Glu Lys Thr Lys Pro Gly
                420                 425                 430

Asn Thr Ser Lys Ile Trp Leu Ile Val Gly Ile Cys Ile Ala Leu Phe
            435                 440                 445

Ala Leu Pro Phe Val Ile Tyr Ala Ala Lys Val Phe Leu Arg Cys Ile
450                 455                 460

Asn Tyr Val Phe Phe Pro Ser Leu Lys Pro Ser Ser Ile Asp Glu
465                 470                 475                 480

Tyr Phe Ser Glu Gln Pro Leu Lys Asn Leu Leu Ser Thr Ser Glu
                485                 490                 495

Glu Gln Ile Glu Lys Cys Phe Ile Ile Glu Asn Ile Ser Thr Ile Ala
                500                 505                 510

Thr Val Glu Glu Thr Asn Gln Thr Asp Glu Asp His Lys Lys Tyr Ser
                515                 520                 525

Ser Gln Thr Ser Gln Asp Ser Gly Asn Tyr Ser Asn Glu Asp Glu Ser
            530                 535                 540

Glu Ser Lys Thr Ser Glu Glu Leu Gln Gln Asp Phe Val
545                 550                 555
```

<210> SEQ ID NO 6
<211> LENGTH: 515
<212> TYPE: PRT
<213> ORGANISM: Homo sapiens
<220> FEATURE:
<221> NAME/KEY: misc_feature
<223> OTHER INFORMATION: IFNAR2

<400> SEQUENCE: 6

```
Met Leu Leu Ser Gln Asn Ala Phe Ile Phe Arg Ser Leu Asn Leu Val
1               5                   10                  15

Leu Met Val Tyr Ile Ser Leu Val Phe Gly Ile Ser Tyr Asp Ser Pro
            20                  25                  30

Asp Tyr Thr Asp Glu Ser Cys Thr Phe Lys Ile Ser Leu Arg Asn Phe
        35                  40                  45

Arg Ser Ile Leu Ser Trp Glu Leu Lys Asn His Ser Ile Val Pro Thr
    50                  55                  60

His Tyr Thr Leu Leu Tyr Thr Ile Met Ser Lys Pro Glu Asp Leu Lys
65                  70                  75                  80

Val Val Lys Asn Cys Ala Asn Thr Thr Arg Ser Phe Cys Asp Leu Thr
                85                  90                  95

Asp Glu Trp Arg Ser Thr His Glu Ala Tyr Val Thr Val Leu Glu Gly
            100                 105                 110

Phe Ser Gly Asn Thr Thr Leu Phe Ser Cys Ser His Asn Phe Trp Leu
        115                 120                 125

Ala Ile Asp Met Ser Phe Glu Pro Pro Glu Phe Glu Ile Val Gly Phe
    130                 135                 140

Thr Asn His Ile Asn Val Met Val Lys Phe Pro Ser Ile Val Glu Glu
145                 150                 155                 160

Glu Leu Gln Phe Asp Leu Ser Leu Val Ile Glu Glu Gln Ser Glu Gly
                165                 170                 175

Ile Val Lys Lys His Lys Pro Glu Ile Lys Gly Asn Met Ser Gly Asn
            180                 185                 190

Phe Thr Tyr Ile Ile Asp Lys Leu Ile Pro Asn Thr Asn Tyr Cys Val
        195                 200                 205

Ser Val Tyr Leu Glu His Ser Asp Glu Gln Ala Val Ile Lys Ser Pro
    210                 215                 220

Leu Lys Cys Thr Leu Leu Pro Pro Gly Gln Glu Ser Glu Ser Ala Glu
225                 230                 235                 240

Ser Ala Lys Ile Gly Gly Ile Ile Thr Val Phe Leu Ile Ala Leu Val
                245                 250                 255

Leu Thr Ser Thr Ile Val Thr Leu Lys Trp Ile Gly Tyr Ile Cys Leu
            260                 265                 270

Arg Asn Ser Leu Pro Lys Val Leu Asn Phe His Asn Phe Leu Ala Trp
        275                 280                 285

Pro Phe Pro Asn Leu Pro Pro Leu Glu Ala Met Asp Met Val Glu Val
    290                 295                 300

Ile Tyr Ile Asn Arg Lys Lys Lys Val Trp Asp Tyr Asn Tyr Asp Asp
305                 310                 315                 320

Glu Ser Asp Ser Asp Thr Glu Ala Ala Pro Arg Thr Ser Gly Gly Gly
                325                 330                 335

Tyr Thr Met His Gly Leu Thr Val Arg Pro Leu Gly Gln Ala Ser Ala
            340                 345                 350

Thr Ser Thr Glu Ser Gln Leu Ile Asp Pro Glu Ser Glu Glu Glu Pro
```

```
                    355                 360                 365
Asp Leu Pro Glu Val Asp Val Glu Leu Pro Thr Met Pro Lys Asp Ser
    370                 375                 380

Pro Gln Gln Leu Glu Leu Leu Ser Gly Pro Cys Glu Arg Arg Lys Ser
385                 390                 395                 400

Pro Leu Gln Asp Pro Phe Pro Glu Glu Asp Tyr Ser Ser Thr Glu Gly
                405                 410                 415

Ser Gly Gly Arg Ile Thr Phe Asn Val Asp Leu Asn Ser Val Phe Leu
            420                 425                 430

Arg Val Leu Asp Asp Glu Asp Ser Asp Asp Leu Glu Ala Pro Leu Met
        435                 440                 445

Leu Ser Ser His Leu Glu Glu Met Val Asp Pro Glu Asp Pro Asp Asn
    450                 455                 460

Val Gln Ser Asn His Leu Leu Ala Ser Gly Gly Thr Gln Pro Thr
465                 470                 475                 480

Phe Pro Ser Pro Ser Ser Glu Gly Leu Trp Ser Glu Asp Ala Pro Ser
                485                 490                 495

Asp Gln Ser Asp Thr Ser Glu Ser Asp Val Asp Leu Gly Asp Gly Tyr
            500                 505                 510

Ile Met Arg
        515

<210> SEQ ID NO 7
<211> LENGTH: 436
<212> TYPE: PRT
<213> ORGANISM: Artificial Sequence
<220> FEATURE:
<223> OTHER INFORMATION: Synthetic: IFNAR1 Extracellular domain (with
      signal sequence)

<400> SEQUENCE: 7

Met Met Val Val Leu Leu Gly Ala Thr Thr Leu Val Leu Val Ala Val
1               5                   10                  15

Ala Pro Trp Val Leu Ser Ala Ala Gly Gly Lys Asn Leu Lys Ser
            20                  25                  30

Pro Gln Lys Val Glu Val Asp Ile Ile Asp Asp Asn Phe Ile Leu Arg
        35                  40                  45

Trp Asn Arg Ser Asp Glu Ser Val Gly Asn Val Thr Phe Ser Phe Asp
    50                  55                  60

Tyr Gln Lys Thr Gly Met Asp Asn Trp Ile Lys Leu Ser Gly Cys Gln
65                  70                  75                  80

Asn Ile Thr Ser Thr Lys Cys Asn Phe Ser Ser Leu Lys Leu Asn Val
                85                  90                  95

Tyr Glu Glu Ile Lys Leu Arg Ile Arg Ala Glu Lys Glu Asn Thr Ser
            100                 105                 110

Ser Trp Tyr Glu Val Asp Ser Phe Thr Pro Phe Arg Lys Ala Gln Ile
        115                 120                 125

Gly Pro Pro Glu Val His Leu Glu Ala Glu Asp Lys Ala Ile Val Ile
    130                 135                 140

His Ile Ser Pro Gly Thr Lys Asp Ser Val Met Trp Ala Leu Asp Gly
145                 150                 155                 160

Leu Ser Phe Thr Tyr Ser Leu Leu Ile Trp Lys Asn Ser Ser Gly Val
                165                 170                 175

Glu Glu Arg Ile Glu Asn Ile Tyr Ser Arg His Lys Ile Tyr Lys Leu
            180                 185                 190
```

Ser Pro Glu Thr Thr Tyr Cys Leu Lys Val Lys Ala Ala Leu Leu Thr
           195                 200                 205

Ser Trp Lys Ile Gly Val Tyr Ser Pro Val His Cys Ile Lys Thr Thr
210                 215                 220

Val Glu Asn Glu Leu Pro Pro Glu Asn Ile Glu Val Ser Val Gln
225                 230                 235                 240

Asn Gln Asn Tyr Val Leu Lys Trp Asp Tyr Thr Tyr Ala Asn Met Thr
                245                 250                 255

Phe Gln Val Gln Trp Leu His Ala Phe Leu Lys Arg Asn Pro Gly Asn
            260                 265                 270

His Leu Tyr Lys Trp Lys Gln Ile Pro Asp Cys Glu Asn Val Lys Thr
        275                 280                 285

Thr Gln Cys Val Phe Pro Gln Asn Val Phe Gln Lys Gly Ile Tyr Leu
    290                 295                 300

Leu Arg Val Gln Ala Ser Asp Gly Asn Asn Thr Ser Phe Trp Ser Glu
305                 310                 315                 320

Glu Ile Lys Phe Asp Thr Glu Ile Gln Ala Phe Leu Leu Pro Pro Val
                325                 330                 335

Phe Asn Ile Arg Ser Leu Ser Asp Ser Phe His Ile Tyr Ile Gly Ala
            340                 345                 350

Pro Lys Gln Ser Gly Asn Thr Pro Val Ile Gln Asp Tyr Pro Leu Ile
        355                 360                 365

Tyr Glu Ile Ile Phe Trp Glu Asn Thr Ser Asn Ala Glu Arg Lys Ile
    370                 375                 380

Ile Glu Lys Lys Thr Asp Val Thr Val Pro Asn Leu Lys Pro Leu Thr
385                 390                 395                 400

Val Tyr Cys Val Lys Ala Arg Ala His Thr Met Asp Glu Lys Leu Asn
                405                 410                 415

Lys Ser Ser Val Phe Ser Asp Ala Val Cys Glu Lys Thr Lys Pro Gly
            420                 425                 430

Asn Thr Ser Lys
        435

<210> SEQ ID NO 8
<211> LENGTH: 243
<212> TYPE: PRT
<213> ORGANISM: Artificial Sequence
<220> FEATURE:
<223> OTHER INFORMATION: Synthetic: IFNAR2 Extracellular domain (with
      signal sequence)

<400> SEQUENCE: 8

Met Leu Leu Ser Gln Asn Ala Phe Ile Phe Arg Ser Leu Asn Leu Val
1               5                   10                  15

Leu Met Val Tyr Ile Ser Leu Val Phe Gly Ile Ser Tyr Asp Ser Pro
            20                  25                  30

Asp Tyr Thr Asp Glu Ser Cys Thr Phe Lys Ile Ser Leu Arg Asn Phe
        35                  40                  45

Arg Ser Ile Leu Ser Trp Glu Leu Lys Asn His Ser Ile Val Pro Thr
    50                  55                  60

His Tyr Thr Leu Leu Tyr Thr Ile Met Ser Lys Pro Glu Asp Leu Lys
65                  70                  75                  80

Val Val Lys Asn Cys Ala Asn Thr Thr Arg Ser Phe Cys Asp Leu Thr
                85                  90                  95

Asp Glu Trp Arg Ser Thr His Glu Ala Tyr Val Thr Val Leu Glu Gly
            100                 105                 110

```
Phe Ser Gly Asn Thr Thr Leu Phe Ser Cys Ser His Asn Phe Trp Leu
        115                 120                 125

Ala Ile Asp Met Ser Phe Glu Pro Pro Glu Phe Glu Ile Val Gly Phe
    130                 135                 140

Thr Asn His Ile Asn Val Met Val Lys Phe Pro Ser Ile Val Glu Glu
145                 150                 155                 160

Glu Leu Gln Phe Asp Leu Ser Leu Val Ile Glu Glu Gln Ser Glu Gly
                165                 170                 175

Ile Val Lys Lys His Lys Pro Glu Ile Lys Gly Asn Met Ser Gly Asn
            180                 185                 190

Phe Thr Tyr Ile Ile Asp Lys Leu Ile Pro Asn Thr Asn Tyr Cys Val
        195                 200                 205

Ser Val Tyr Leu Glu His Ser Asp Glu Gln Ala Val Ile Lys Ser Pro
    210                 215                 220

Leu Lys Cys Thr Leu Leu Pro Pro Gly Gln Glu Ser Glu Ser Ala Glu
225                 230                 235                 240

Ser Ala Lys
```

<210> SEQ ID NO 9
<211> LENGTH: 232
<212> TYPE: PRT
<213> ORGANISM: Artificial Sequence
<220> FEATURE:
<223> OTHER INFORMATION: Synthetic: IgG1 Fc (aa 216-447) with mutations
      C220S, P238S, P331S, T350V, L351Y, F405A, Y407V

<400> SEQUENCE: 9

```
Glu Pro Lys Ser Ser Asp Lys Thr His Thr Cys Pro Pro Cys Pro Ala
1               5                   10                  15

Pro Glu Leu Leu Gly Gly Ser Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Ser Ile Glu Lys Thr Ile Ser Lys Ala Lys Gly Gln Pro
        115                 120                 125

Arg Glu Pro Gln Val Tyr Val Tyr Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Ala Leu Val
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220
```

Ser Leu Ser Leu Ser Pro Gly Lys
225                 230

<210> SEQ ID NO 10
<211> LENGTH: 232
<212> TYPE: PRT
<213> ORGANISM: Artificial Sequence
<220> FEATURE:
<223> OTHER INFORMATION: Synthetic: IgG1 Fc (aa216-447)with mutations
      C220S, P238S, P331S, T350V, T366L, K392L, T394W

<400> SEQUENCE: 10

Glu Pro Lys Ser Ser Asp Lys Thr His Thr Cys Pro Pro Cys Pro Ala
1               5                   10                  15

Pro Glu Leu Leu Gly Gly Ser Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Ser Ile Glu Lys Thr Ile Ser Lys Ala Lys Gly Gln Pro
        115                 120                 125

Arg Glu Pro Gln Val Tyr Val Leu Pro Pro Ser Arg Asp Glu Leu Thr
    130                 135                 140

Lys Asn Gln Val Ser Leu Leu Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Leu Thr Trp Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 11
<211> LENGTH: 409
<212> TYPE: PRT
<213> ORGANISM: Artificial Sequence
<220> FEATURE:
<223> OTHER INFORMATION: Synthetic: IFNAR1 (aa28-436)

<400> SEQUENCE: 11

Lys Asn Leu Lys Ser Pro Gln Lys Val Glu Val Asp Ile Ile Asp Asp
1               5                   10                  15

Asn Phe Ile Leu Arg Trp Asn Arg Ser Asp Glu Ser Val Gly Asn Val
            20                  25                  30

Thr Phe Ser Phe Asp Tyr Gln Lys Thr Gly Met Asp Asn Trp Ile Lys
        35                  40                  45

```
Leu Ser Gly Cys Gln Asn Ile Thr Ser Thr Lys Cys Asn Phe Ser Ser
 50                  55                  60

Leu Lys Leu Asn Val Tyr Glu Glu Ile Lys Leu Arg Ile Arg Ala Glu
 65                  70                  75                  80

Lys Glu Asn Thr Ser Ser Trp Tyr Glu Val Asp Ser Phe Thr Pro Phe
                 85                  90                  95

Arg Lys Ala Gln Ile Gly Pro Pro Glu Val His Leu Glu Ala Glu Asp
            100                 105                 110

Lys Ala Ile Val Ile His Ile Ser Pro Gly Thr Lys Asp Ser Val Met
            115                 120                 125

Trp Ala Leu Asp Gly Leu Ser Phe Thr Tyr Ser Leu Val Ile Trp Lys
130                 135                 140

Asn Ser Ser Gly Val Glu Glu Arg Ile Glu Asn Ile Tyr Ser Arg His
145                 150                 155                 160

Lys Ile Tyr Lys Leu Ser Pro Glu Thr Thr Tyr Cys Leu Lys Val Lys
                165                 170                 175

Ala Ala Leu Leu Thr Ser Trp Lys Ile Gly Val Tyr Ser Pro Val His
            180                 185                 190

Cys Ile Lys Thr Thr Val Glu Asn Glu Leu Pro Pro Pro Glu Asn Ile
            195                 200                 205

Glu Val Ser Val Gln Asn Gln Asn Tyr Val Leu Lys Trp Asp Tyr Thr
210                 215                 220

Tyr Ala Asn Met Thr Phe Gln Val Gln Trp Leu His Ala Phe Leu Lys
225                 230                 235                 240

Arg Asn Pro Gly Asn His Leu Tyr Lys Trp Lys Gln Ile Pro Asp Cys
                245                 250                 255

Glu Asn Val Lys Thr Thr Gln Cys Val Phe Pro Gln Asn Val Phe Gln
            260                 265                 270

Lys Gly Ile Tyr Leu Leu Arg Val Gln Ala Ser Asp Gly Asn Asn Thr
            275                 280                 285

Ser Phe Trp Ser Glu Glu Ile Lys Phe Asp Thr Glu Ile Gln Ala Phe
290                 295                 300

Leu Leu Pro Pro Val Phe Asn Ile Arg Ser Leu Ser Asp Ser Phe His
305                 310                 315                 320

Ile Tyr Ile Gly Ala Pro Lys Gln Ser Gly Asn Thr Pro Val Ile Gln
                325                 330                 335

Asp Tyr Pro Leu Ile Tyr Glu Ile Ile Phe Trp Glu Asn Thr Ser Asn
            340                 345                 350

Ala Glu Arg Lys Ile Ile Glu Lys Lys Thr Asp Val Thr Val Pro Asn
            355                 360                 365

Leu Lys Pro Leu Thr Val Tyr Cys Val Lys Ala Arg Ala His Thr Met
370                 375                 380

Asp Glu Lys Leu Asn Lys Ser Ser Val Phe Ser Asp Ala Val Cys Glu
385                 390                 395                 400

Lys Thr Lys Pro Gly Asn Thr Ser Lys
                405

<210> SEQ ID NO 12
<211> LENGTH: 217
<212> TYPE: PRT
<213> ORGANISM: Artificial Sequence
<220> FEATURE:
<223> OTHER INFORMATION: Synthetic: IFNAR2 (aa27-243)

<400> SEQUENCE: 12
```

-continued

```
Ile Ser Tyr Asp Ser Pro Asp Tyr Thr Asp Glu Ser Cys Thr Phe Lys
1               5                   10                  15

Ile Ser Leu Arg Asn Phe Arg Ser Ile Leu Ser Trp Glu Leu Lys Asn
            20                  25                  30

His Ser Ile Val Pro Thr His Tyr Thr Leu Leu Tyr Thr Ile Met Ser
            35                  40                  45

Lys Pro Glu Asp Leu Lys Val Val Lys Asn Cys Ala Asn Thr Thr Arg
    50                  55                  60

Ser Phe Cys Asp Leu Thr Asp Glu Trp Arg Ser Thr His Glu Ala Tyr
65                  70                  75                  80

Val Thr Val Leu Glu Gly Phe Ser Gly Asn Thr Thr Leu Phe Ser Cys
                85                  90                  95

Ser His Asn Phe Trp Leu Ala Ile Asp Met Ser Phe Glu Pro Pro Glu
                100                 105                 110

Phe Glu Ile Val Gly Phe Thr Asn His Ile Asn Val Met Val Lys Phe
            115                 120                 125

Pro Ser Ile Val Glu Glu Glu Leu Gln Phe Asp Leu Ser Leu Val Ile
    130                 135                 140

Glu Glu Gln Ser Glu Gly Ile Val Lys Lys His Lys Pro Glu Ile Lys
145                 150                 155                 160

Gly Asn Met Ser Gly Asn Phe Thr Tyr Ile Ile Asp Lys Leu Ile Pro
                165                 170                 175

Asn Thr Asn Tyr Cys Val Ser Val Tyr Leu Glu His Ser Asp Glu Gln
                180                 185                 190

Ala Val Ile Lys Ser Pro Leu Lys Cys Thr Leu Leu Pro Pro Gly Gln
            195                 200                 205

Glu Ser Glu Ser Ala Glu Ser Ala Lys
    210                 215

<210> SEQ ID NO 13
<211> LENGTH: 19
<212> TYPE: PRT
<213> ORGANISM: Artificial Sequence
<220> FEATURE:
<223> OTHER INFORMATION: Synthetic: Leader Sequence

<400> SEQUENCE: 13

Met Asp Trp Thr Trp Arg Ile Leu Phe Leu Val Ala Ala Thr Gly
1               5                   10                  15

Thr His Ala

<210> SEQ ID NO 14
<211> LENGTH: 20
<212> TYPE: PRT
<213> ORGANISM: Artificial Sequence
<220> FEATURE:
<223> OTHER INFORMATION: Synthetic: VK3LP leader sequence

<400> SEQUENCE: 14

Met Glu Thr Pro Ala Gln Leu Leu Phe Leu Leu Leu Leu Trp Leu Pro
1               5                   10                  15

Asp Thr Thr Gly
            20

<210> SEQ ID NO 15
<211> LENGTH: 20
<212> TYPE: PRT
<213> ORGANISM: Artificial Sequence
<220> FEATURE:
```

```
<223> OTHER INFORMATION: Synthetic: linker

<400> SEQUENCE: 15

Gly Gly Gly Gly Ser Gly Gly Gly Gly Ser Gly Gly Gly Ser Gly
1               5                   10                  15

Gly Gly Gly Ser
            20

<210> SEQ ID NO 16
<211> LENGTH: 15
<212> TYPE: PRT
<213> ORGANISM: Artificial Sequence
<220> FEATURE:
<223> OTHER INFORMATION: Synthetic: linker

<400> SEQUENCE: 16

Gly Gly Gly Gly Ser Gly Gly Gly Gly Ser Gly Gly Gly Gly Ser
1               5                   10                  15

<210> SEQ ID NO 17
<211> LENGTH: 25
<212> TYPE: PRT
<213> ORGANISM: Artificial Sequence
<220> FEATURE:
<223> OTHER INFORMATION: Synthetic: linker

<400> SEQUENCE: 17

Gly Gly Gly Gly Ser Gly Gly Gly Gly Ser Gly Gly Gly Ser Gly
1               5                   10                  15

Gly Gly Gly Ser Gly Gly Gly Gly Ser
            20                  25

<210> SEQ ID NO 18
<211> LENGTH: 18
<212> TYPE: PRT
<213> ORGANISM: Artificial Sequence
<220> FEATURE:
<223> OTHER INFORMATION: Synthetic: NLG linker

<400> SEQUENCE: 18

Val Asp Gly Ala Ser Ser Pro Val Asn Val Ser Ser Pro Ser Val Gln
1               5                   10                  15

Asp Ile

<210> SEQ ID NO 19
<211> LENGTH: 50
<212> TYPE: PRT
<213> ORGANISM: Artificial Sequence
<220> FEATURE:
<223> OTHER INFORMATION: Synthetic: linker

<400> SEQUENCE: 19

Leu Glu Ala Glu Ala Ala Ala Lys Glu Ala Ala Ala Lys Glu Ala Ala
1               5                   10                  15

Ala Lys Glu Ala Ala Lys Ala Leu Glu Ala Glu Ala Ala Ala Lys
            20                  25                  30

Glu Ala Ala Ala Lys Glu Ala Ala Ala Lys Glu Ala Ala Ala Lys Ala
        35                  40                  45

Leu Glu
    50

<210> SEQ ID NO 20
<211> LENGTH: 232
```

```
<212> TYPE: PRT
<213> ORGANISM: Artificial Sequence
<220> FEATURE:
<223> OTHER INFORMATION: Synthetic: IgG1 Fc (SCC hinge)

<400> SEQUENCE: 20

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 21
<211> LENGTH: 232
<212> TYPE: PRT
<213> ORGANISM: Artificial Sequence
<220> FEATURE:
<223> OTHER INFORMATION: Synthetic: IgG1 Fc domain  (SSS hinge)

<400> SEQUENCE: 21

Glu Pro Lys Ser Ser Asp Lys Thr His Thr Ser Pro Pro Ser Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95
```

```
Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
        130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
            165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
        210                 215                 220

Ser Leu Ser Leu Ser Pro Gly Lys
225                 230

<210> SEQ ID NO 22
<211> LENGTH: 232
<212> TYPE: PRT
<213> ORGANISM: Artificial Sequence
<220> FEATURE:
<223> OTHER INFORMATION: Synthetic: IgG1 Fc domain with P238S
      (SCC hinge)

<400> SEQUENCE: 22

Glu Pro Lys Ser Ser Asp Lys Thr His Thr Cys Pro Pro Cys Pro Ala
1               5                   10                  15

Pro Glu Leu Leu Gly Gly Ser Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
            85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
        130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
            165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
```

Ser Leu Ser Leu Ser Pro Gly Lys
225                 230

<210> SEQ ID NO 23
<211> LENGTH: 232
<212> TYPE: PRT
<213> ORGANISM: Artificial Sequence
<220> FEATURE:
<223> OTHER INFORMATION: Synthetic: IgG1 Fc domain with P331S

<400> SEQUENCE: 23

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
        50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Ser Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Lys
225                 230

<210> SEQ ID NO 24
<211> LENGTH: 232
<212> TYPE: PRT
<213> ORGANISM: Artificial Sequence
<220> FEATURE:
<223> OTHER INFORMATION: Synthetic: IgG1 Fc domain with SSS, P238S, and
      P331S

<400> SEQUENCE: 24

Glu Pro Lys Ser Ser Asp Lys Thr His Thr Ser Pro Pro Ser Pro Ala
1               5                   10                  15

Pro Glu Leu Leu Gly Gly Ser Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

```
Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                 85                  90                  95

Asp Trp Leu Asn Gly Lys Glu Tyr Lys Cys Lys Val Ser Asn Lys Ala
                100                 105                 110

Leu Pro Ala Ser Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
210                 215                 220

Ser Leu Ser Leu Ser Pro Gly Lys
225                 230

<210> SEQ ID NO 25
<211> LENGTH: 232
<212> TYPE: PRT
<213> ORGANISM: Artificial Sequence
<220> FEATURE:
<223> OTHER INFORMATION: Synthetic: IgG1 Fc domain with SCC, P238S, and
      P331S

<400> SEQUENCE: 25

Glu Pro Lys Ser Ser Asp Lys Thr His Thr Cys Pro Pro Cys Pro Ala
  1               5                  10                  15

Pro Glu Leu Leu Gly Gly Ser Ser Val Phe Leu Phe Pro Pro Lys Pro
                 20                  25                  30

Lys Asp Thr Leu Met Ile Ser Arg Thr Pro Glu Val Thr Cys Val Val
             35                  40                  45

Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                 85                  90                  95

Asp Trp Leu Asn Gly Lys Glu Tyr Lys Cys Lys Val Ser Asn Lys Ala
                100                 105                 110

Leu Pro Ala Ser Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
```

```
                165                 170                 175
Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
            210                 215                 220

Ser Leu Ser Leu Ser Pro Gly Lys
225                 230

<210> SEQ ID NO 26
<211> LENGTH: 232
<212> TYPE: PRT
<213> ORGANISM: Homo sapiens
<220> FEATURE:
<221> NAME/KEY: misc_feature
<223> OTHER INFORMATION: Human IgG1 Fc domain (wild-type)

<400> SEQUENCE: 26

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
        50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
            210                 215                 220

Ser Leu Ser Leu Ser Pro Gly Lys
225                 230

<210> SEQ ID NO 27
<211> LENGTH: 4
<212> TYPE: PRT
<213> ORGANISM: Artificial Sequence
<220> FEATURE:
<223> OTHER INFORMATION: Synthetic: linker

<400> SEQUENCE: 27
```

```
Gly Gly Ser Gly
1

<210> SEQ ID NO 28
<211> LENGTH: 4
<212> TYPE: PRT
<213> ORGANISM: Artificial Sequence
<220> FEATURE:
<223> OTHER INFORMATION: Synthetic: linker

<400> SEQUENCE: 28

Gly Ser Ala Thr
1

<210> SEQ ID NO 29
<211> LENGTH: 7
<212> TYPE: PRT
<213> ORGANISM: Artificial Sequence
<220> FEATURE:
<223> OTHER INFORMATION: Synthetic: O-linked glycosylation consensus
      site
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: X = T/S

<400> SEQUENCE: 29

Cys Xaa Xaa Gly Gly Xaa Cys
1               5

<210> SEQ ID NO 30
<211> LENGTH: 5
<212> TYPE: PRT
<213> ORGANISM: Artificial Sequence
<220> FEATURE:
<223> OTHER INFORMATION: Synthetic: O-linked glycosylation consensus
      site
<220> FEATURE:
<221> NAME/KEY: misc_feature
<222> LOCATION: (4)..(4)
<223> OTHER INFORMATION: X = E/D

<400> SEQUENCE: 30

Asn Ser Thr Xaa Ala
1               5

<210> SEQ ID NO 31
<211> LENGTH: 5
<212> TYPE: PRT
<213> ORGANISM: Artificial Sequence
<220> FEATURE:
<223> OTHER INFORMATION: Synthetic: O-linked glycosylation consensus
      site

<400> SEQUENCE: 31

Asn Ile Thr Gln Ser
1               5

<210> SEQ ID NO 32
<211> LENGTH: 5
<212> TYPE: PRT
<213> ORGANISM: Artificial Sequence
<220> FEATURE:
<223> OTHER INFORMATION: Synthetic: O-linked glycosylation consensus
      site
```

```
<400> SEQUENCE: 32

Gln Ser Thr Gln Ser
1               5

<210> SEQ ID NO 33
<211> LENGTH: 5
<212> TYPE: PRT
<213> ORGANISM: Artificial Sequence
<220> FEATURE:
<223> OTHER INFORMATION: Synthetic: O-linked glycosylation consensus
      site
<220> FEATURE:
<221> NAME/KEY: misc_feature
<222> LOCATION: (1)..(1)
<223> OTHER INFORMATION: X = D/E
<220> FEATURE:
<221> NAME/KEY: misc_feature
<222> LOCATION: (4)..(4)
<223> OTHER INFORMATION: X = R/K

<400> SEQUENCE: 33

Xaa Phe Thr Xaa Val
1               5

<210> SEQ ID NO 34
<211> LENGTH: 4
<212> TYPE: PRT
<213> ORGANISM: Artificial Sequence
<220> FEATURE:
<223> OTHER INFORMATION: Synthetic: O-linked glycosylation consensus
      site
<220> FEATURE:
<221> NAME/KEY: misc_feature
<222> LOCATION: (2)..(2)
<223> OTHER INFORMATION: X = E/D

<400> SEQUENCE: 34

Cys Xaa Ser Asn
1

<210> SEQ ID NO 35
<211> LENGTH: 5
<212> TYPE: PRT
<213> ORGANISM: Artificial Sequence
<220> FEATURE:
<223> OTHER INFORMATION: Synthetic: O-linked glycosylation consensus
      site
<220> FEATURE:
<221> NAME/KEY: misc_feature
<222> LOCATION: (5)..(5)
<223> OTHER INFORMATION: X = K/R

<400> SEQUENCE: 35

Gly Gly Ser Cys Xaa
1               5

<210> SEQ ID NO 36
<211> LENGTH: 530
<212> TYPE: PRT
<213> ORGANISM: Artificial Sequence
<220> FEATURE:
<223> OTHER INFORMATION: Synthetic: IFNAR1 (without signal sequence)

<400> SEQUENCE: 36

Lys Asn Leu Lys Ser Pro Gln Lys Val Glu Val Asp Ile Ile Asp Asp
1               5                   10                  15

Asn Phe Ile Leu Arg Trp Asn Arg Ser Asp Glu Ser Val Gly Asn Val
                20                  25                  30
```

```
Thr Phe Ser Phe Asp Tyr Gln Lys Thr Gly Met Asp Asn Trp Ile Lys
        35                  40                  45

Leu Ser Gly Cys Gln Asn Ile Thr Ser Thr Lys Cys Asn Phe Ser Ser
 50                  55                  60

Leu Lys Leu Asn Val Tyr Glu Glu Ile Lys Leu Arg Ile Arg Ala Glu
 65                  70                  75                  80

Lys Glu Asn Thr Ser Ser Trp Tyr Glu Val Asp Ser Phe Thr Pro Phe
                 85                  90                  95

Arg Lys Ala Gln Ile Gly Pro Pro Glu Val His Leu Glu Ala Glu Asp
                100                 105                 110

Lys Ala Ile Val Ile His Ile Ser Pro Gly Thr Lys Asp Ser Val Met
            115                 120                 125

Trp Ala Leu Asp Gly Leu Ser Phe Thr Tyr Ser Leu Val Ile Trp Lys
130                 135                 140

Asn Ser Ser Gly Val Glu Glu Arg Ile Glu Asn Ile Tyr Ser Arg His
145                 150                 155                 160

Lys Ile Tyr Lys Leu Ser Pro Glu Thr Thr Tyr Cys Leu Lys Val Lys
                165                 170                 175

Ala Ala Leu Leu Thr Ser Trp Lys Ile Gly Val Tyr Ser Pro Val His
            180                 185                 190

Cys Ile Lys Thr Thr Val Glu Asn Glu Leu Pro Pro Pro Glu Asn Ile
        195                 200                 205

Glu Val Ser Val Gln Asn Gln Asn Tyr Val Leu Lys Trp Asp Tyr Thr
            210                 215                 220

Tyr Ala Asn Met Thr Phe Gln Val Gln Trp Leu His Ala Phe Leu Lys
225                 230                 235                 240

Arg Asn Pro Gly Asn His Leu Tyr Lys Trp Lys Gln Ile Pro Asp Cys
                245                 250                 255

Glu Asn Val Lys Thr Thr Gln Cys Val Phe Pro Gln Asn Val Phe Gln
            260                 265                 270

Lys Gly Ile Tyr Leu Leu Arg Val Gln Ala Ser Asp Gly Asn Asn Thr
        275                 280                 285

Ser Phe Trp Ser Glu Glu Ile Lys Phe Asp Thr Glu Ile Gln Ala Phe
    290                 295                 300

Leu Leu Pro Pro Val Phe Asn Ile Arg Ser Leu Ser Asp Ser Phe His
305                 310                 315                 320

Ile Tyr Ile Gly Ala Pro Lys Gln Ser Gly Asn Thr Pro Val Ile Gln
                325                 330                 335

Asp Tyr Pro Leu Ile Tyr Glu Ile Ile Phe Trp Glu Asn Thr Ser Asn
            340                 345                 350

Ala Glu Arg Lys Ile Ile Glu Lys Lys Thr Asp Val Thr Val Pro Asn
        355                 360                 365

Leu Lys Pro Leu Thr Val Tyr Cys Val Lys Ala Arg Ala His Thr Met
370                 375                 380

Asp Glu Lys Leu Asn Lys Ser Ser Val Phe Ser Asp Ala Val Cys Glu
385                 390                 395                 400

Lys Thr Lys Pro Gly Asn Thr Ser Lys Ile Trp Leu Ile Val Gly Ile
                405                 410                 415

Cys Ile Ala Leu Phe Ala Leu Pro Phe Val Ile Tyr Ala Ala Lys Val
            420                 425                 430

Phe Leu Arg Cys Ile Asn Tyr Val Phe Phe Pro Ser Leu Lys Pro Ser
        435                 440                 445
```

```
Ser Ser Ile Asp Glu Tyr Phe Ser Glu Gln Pro Leu Lys Asn Leu Leu
    450                 455                 460

Leu Ser Thr Ser Glu Glu Gln Ile Glu Lys Cys Phe Ile Ile Glu Asn
465                 470                 475                 480

Ile Ser Thr Ile Ala Thr Val Glu Glu Thr Asn Gln Thr Asp Glu Asp
                485                 490                 495

His Lys Lys Tyr Ser Ser Gln Thr Ser Gln Asp Ser Gly Asn Tyr Ser
            500                 505                 510

Asn Glu Asp Glu Ser Glu Ser Lys Thr Ser Glu Glu Leu Gln Gln Asp
            515                 520                 525

Phe Val
    530

<210> SEQ ID NO 37
<211> LENGTH: 489
<212> TYPE: PRT
<213> ORGANISM: Artificial Sequence
<220> FEATURE:
<223> OTHER INFORMATION: Synthetic: IFNAR2 (without signal sequence)

<400> SEQUENCE: 37

Ile Ser Tyr Asp Ser Pro Asp Tyr Thr Asp Glu Ser Cys Thr Phe Lys
1               5                   10                  15

Ile Ser Leu Arg Asn Phe Arg Ser Ile Leu Ser Trp Glu Leu Lys Asn
            20                  25                  30

His Ser Ile Val Pro Thr His Tyr Thr Leu Leu Tyr Thr Ile Met Ser
        35                  40                  45

Lys Pro Glu Asp Leu Lys Val Val Lys Asn Cys Ala Asn Thr Thr Arg
50                  55                  60

Ser Phe Cys Asp Leu Thr Asp Glu Trp Arg Ser Thr His Glu Ala Tyr
65                  70                  75                  80

Val Thr Val Leu Glu Gly Phe Ser Gly Asn Thr Thr Leu Phe Ser Cys
                85                  90                  95

Ser His Asn Phe Trp Leu Ala Ile Asp Met Ser Phe Glu Pro Pro Glu
            100                 105                 110

Phe Glu Ile Val Gly Phe Thr Asn His Ile Asn Val Met Val Lys Phe
        115                 120                 125

Pro Ser Ile Val Glu Glu Glu Leu Gln Phe Asp Leu Ser Leu Val Ile
130                 135                 140

Glu Glu Gln Ser Glu Gly Ile Val Lys Lys His Lys Pro Glu Ile Lys
145                 150                 155                 160

Gly Asn Met Ser Gly Asn Phe Thr Tyr Ile Ile Asp Lys Leu Ile Pro
                165                 170                 175

Asn Thr Asn Tyr Cys Val Ser Val Tyr Leu Glu His Ser Asp Glu Gln
            180                 185                 190

Ala Val Ile Lys Ser Pro Leu Lys Cys Thr Leu Leu Pro Pro Gly Gln
        195                 200                 205

Glu Ser Glu Ser Ala Glu Ser Ala Lys Ile Gly Gly Ile Ile Thr Val
210                 215                 220

Phe Leu Ile Ala Leu Val Leu Thr Ser Thr Ile Val Thr Leu Lys Trp
225                 230                 235                 240

Ile Gly Tyr Ile Cys Leu Arg Asn Ser Leu Pro Lys Val Leu Asn Phe
                245                 250                 255

His Asn Phe Leu Ala Trp Pro Phe Pro Asn Leu Pro Pro Leu Glu Ala
            260                 265                 270
```

```
Met Asp Met Val Glu Val Ile Tyr Ile Asn Arg Lys Lys Val Trp
            275                 280                 285

Asp Tyr Asn Tyr Asp Asp Glu Ser Asp Ser Thr Glu Ala Ala Pro
            290                 295                 300

Arg Thr Ser Gly Gly Gly Tyr Thr Met His Gly Leu Thr Val Arg Pro
305                 310                 315                 320

Leu Gly Gln Ala Ser Ala Thr Ser Thr Glu Ser Gln Leu Ile Asp Pro
                325                 330                 335

Glu Ser Glu Glu Glu Pro Asp Leu Pro Glu Val Asp Val Glu Leu Pro
            340                 345                 350

Thr Met Pro Lys Asp Ser Pro Gln Gln Leu Glu Leu Ser Gly Pro
            355                 360                 365

Cys Glu Arg Arg Lys Ser Pro Leu Gln Asp Pro Phe Pro Glu Glu Asp
            370                 375                 380

Tyr Ser Ser Thr Glu Gly Ser Gly Gly Arg Ile Thr Phe Asn Val Asp
385                 390                 395                 400

Leu Asn Ser Val Phe Leu Arg Val Leu Asp Asp Glu Asp Ser Asp Asp
                405                 410                 415

Leu Glu Ala Pro Leu Met Leu Ser Ser His Leu Glu Glu Met Val Asp
                420                 425                 430

Pro Glu Asp Pro Asp Asn Val Gln Ser Asn His Leu Leu Ala Ser Gly
            435                 440                 445

Glu Gly Thr Gln Pro Thr Phe Pro Ser Pro Ser Glu Gly Leu Trp
            450                 455                 460

Ser Glu Asp Ala Pro Ser Asp Gln Ser Asp Thr Ser Glu Ser Asp Val
465                 470                 475                 480

Asp Leu Gly Asp Gly Tyr Ile Met Arg
                485

<210> SEQ ID NO 38
<211> LENGTH: 10
<212> TYPE: PRT
<213> ORGANISM: Artificial Sequence
<220> FEATURE:
<223> OTHER INFORMATION: Synthetic: linker

<400> SEQUENCE: 38

Gly Gly Gly Gly Ser Gly Gly Gly Gly Ser
1               5                   10

<210> SEQ ID NO 39
<211> LENGTH: 5
<212> TYPE: PRT
<213> ORGANISM: Artificial Sequence
<220> FEATURE:
<223> OTHER INFORMATION: Synthetic: linker

<400> SEQUENCE: 39

Gly Gly Gly Gly Ser
1               5

<210> SEQ ID NO 40
<211> LENGTH: 661
<212> TYPE: PRT
<213> ORGANISM: Artificial Sequence
<220> FEATURE:
<223> OTHER INFORMATION: Synthetic: RSLV-601 Without a leader sequence

<400> SEQUENCE: 40

Lys Asn Leu Lys Ser Pro Gln Lys Val Glu Val Asp Ile Ile Asp Asp
```

```
1               5                   10                  15
Asn Phe Ile Leu Arg Trp Asn Arg Ser Asp Glu Ser Val Gly Asn Val
                20                  25                  30

Thr Phe Ser Phe Asp Tyr Gln Lys Thr Gly Met Asp Asn Trp Ile Lys
                35                  40                  45

Leu Ser Gly Cys Gln Asn Ile Thr Ser Thr Lys Cys Asn Phe Ser Ser
                50                  55                  60

Leu Lys Leu Asn Val Tyr Glu Glu Ile Lys Leu Arg Ile Arg Ala Glu
65                  70                  75                  80

Lys Glu Asn Thr Ser Ser Trp Tyr Glu Val Asp Ser Phe Thr Pro Phe
                85                  90                  95

Arg Lys Ala Gln Ile Gly Pro Pro Glu Val His Leu Glu Ala Glu Asp
                100                 105                 110

Lys Ala Ile Val Ile His Ile Ser Pro Gly Thr Lys Asp Ser Val Met
                115                 120                 125

Trp Ala Leu Asp Gly Leu Ser Phe Thr Tyr Ser Leu Val Ile Trp Lys
                130                 135                 140

Asn Ser Ser Gly Val Glu Glu Arg Ile Glu Asn Ile Tyr Ser Arg His
145                 150                 155                 160

Lys Ile Tyr Lys Leu Ser Pro Glu Thr Thr Tyr Cys Leu Lys Val Lys
                165                 170                 175

Ala Ala Leu Leu Thr Ser Trp Lys Ile Gly Val Tyr Ser Pro Val His
                180                 185                 190

Cys Ile Lys Thr Thr Val Glu Asn Glu Leu Pro Pro Pro Glu Asn Ile
                195                 200                 205

Glu Val Ser Val Gln Asn Gln Asn Tyr Val Leu Lys Trp Asp Tyr Thr
                210                 215                 220

Tyr Ala Asn Met Thr Phe Gln Val Gln Trp Leu His Ala Phe Leu Lys
225                 230                 235                 240

Arg Asn Pro Gly Asn His Leu Tyr Lys Trp Lys Gln Ile Pro Asp Cys
                245                 250                 255

Glu Asn Val Lys Thr Thr Gln Cys Val Phe Pro Gln Asn Val Phe Gln
                260                 265                 270

Lys Gly Ile Tyr Leu Leu Arg Val Gln Ala Ser Asp Gly Asn Asn Thr
                275                 280                 285

Ser Phe Trp Ser Glu Glu Ile Lys Phe Asp Thr Glu Ile Gln Ala Phe
                290                 295                 300

Leu Leu Pro Pro Val Phe Asn Ile Arg Ser Leu Ser Asp Ser Phe His
305                 310                 315                 320

Ile Tyr Ile Gly Ala Pro Lys Gln Ser Gly Asn Thr Pro Val Ile Gln
                325                 330                 335

Asp Tyr Pro Leu Ile Tyr Glu Ile Ile Phe Trp Glu Asn Thr Ser Asn
                340                 345                 350

Ala Glu Arg Lys Ile Ile Glu Lys Lys Thr Asp Val Thr Val Pro Asn
                355                 360                 365

Leu Lys Pro Leu Thr Val Tyr Cys Val Lys Ala Arg Ala His Thr Met
                370                 375                 380

Asp Glu Lys Leu Asn Lys Ser Ser Val Phe Ser Asp Ala Val Cys Glu
385                 390                 395                 400

Lys Thr Lys Pro Gly Asn Thr Ser Lys Gly Gly Gly Ser Gly Gly
                405                 410                 415

Gly Gly Ser Gly Gly Gly Gly Ser Gly Gly Gly Gly Ser Glu Pro Lys
                420                 425                 430
```

```
Ser Ser Asp Lys Thr His Thr Cys Pro Pro Cys Pro Ala Pro Glu Leu
435 440 445

Leu Gly Gly Ser Ser Val Phe Leu Phe Pro Pro Lys Pro Lys Asp Thr
450 455 460

Leu Met Ile Ser Arg Thr Pro Glu Val Thr Cys Val Val Val Asp Val
465 470 475 480

Ser His Glu Asp Pro Glu Val Lys Phe Asn Trp Tyr Val Asp Gly Val
485 490 495

Glu Val His Asn Ala Lys Thr Lys Pro Arg Glu Glu Gln Tyr Asn Ser
500 505 510

Thr Tyr Arg Val Val Ser Val Leu Thr Val Leu His Gln Asp Trp Leu
515 520 525

Asn Gly Lys Glu Tyr Lys Cys Lys Val Ser Asn Lys Ala Leu Pro Ala
530 535 540

Ser Ile Glu Lys Thr Ile Ser Lys Ala Lys Gly Gln Pro Arg Glu Pro
545 550 555 560

Gln Val Tyr Val Leu Pro Pro Ser Arg Asp Glu Leu Thr Lys Asn Gln
565 570 575

Val Ser Leu Leu Cys Leu Val Lys Gly Phe Tyr Pro Ser Asp Ile Ala
580 585 590

Val Glu Trp Glu Ser Asn Gly Gln Pro Glu Asn Asn Tyr Leu Thr Trp
595 600 605

Pro Pro Val Leu Asp Ser Asp Gly Ser Phe Phe Leu Tyr Ser Lys Leu
610 615 620

Thr Val Asp Lys Ser Arg Trp Gln Gln Gly Asn Val Phe Ser Cys Ser
625 630 635 640

Val Met His Glu Ala Leu His Asn His Tyr Thr Gln Lys Ser Leu Ser
645 650 655

Leu Ser Pro Gly Lys
660

<210> SEQ ID NO 41
<211> LENGTH: 469
<212> TYPE: PRT
<213> ORGANISM: Artificial Sequence
<220> FEATURE:
<223> OTHER INFORMATION: Synthetic: RSLV-602 Without a leader sequence

<400> SEQUENCE: 41

Ile Ser Tyr Asp Ser Pro Asp Tyr Thr Asp Glu Ser Cys Thr Phe Lys
1 5 10 15

Ile Ser Leu Arg Asn Phe Arg Ser Ile Leu Ser Trp Glu Leu Lys Asn
20 25 30

His Ser Ile Val Pro Thr His Tyr Thr Leu Leu Tyr Thr Ile Met Ser
35 40 45

Lys Pro Glu Asp Leu Lys Val Val Lys Asn Cys Ala Asn Thr Thr Arg
50 55 60

Ser Phe Cys Asp Leu Thr Asp Glu Trp Arg Ser Thr His Glu Ala Tyr
65 70 75 80

Val Thr Val Leu Glu Gly Phe Ser Gly Asn Thr Thr Leu Phe Ser Cys
85 90 95

Ser His Asn Phe Trp Leu Ala Ile Asp Met Ser Phe Glu Pro Pro Glu
100 105 110

Phe Glu Ile Val Gly Phe Thr Asn His Ile Asn Val Met Val Lys Phe
115 120 125

```
Pro Ser Ile Val Glu Glu Leu Gln Phe Asp Leu Ser Leu Val Ile
    130                 135                 140
Glu Glu Gln Ser Glu Gly Ile Val Lys Lys His Lys Pro Glu Ile Lys
145                 150                 155                 160
Gly Asn Met Ser Gly Asn Phe Thr Tyr Ile Ile Asp Lys Leu Ile Pro
                165                 170                 175
Asn Thr Asn Tyr Cys Val Ser Val Tyr Leu Glu His Ser Asp Glu Gln
            180                 185                 190
Ala Val Ile Lys Ser Pro Leu Lys Cys Thr Leu Leu Pro Pro Gly Gln
        195                 200                 205
Glu Ser Glu Ser Ala Glu Ser Ala Lys Gly Gly Gly Ser Gly Gly
    210                 215                 220
Gly Gly Ser Gly Gly Gly Gly Ser Gly Gly Gly Gly Ser Glu Pro Lys
225                 230                 235                 240
Ser Ser Asp Lys Thr His Thr Cys Pro Pro Cys Pro Ala Pro Glu Leu
                245                 250                 255
Leu Gly Gly Ser Ser Val Phe Leu Phe Pro Pro Lys Pro Lys Asp Thr
            260                 265                 270
Leu Met Ile Ser Arg Thr Pro Glu Val Thr Cys Val Val Val Asp Val
        275                 280                 285
Ser His Glu Asp Pro Glu Val Lys Phe Asn Trp Tyr Val Asp Gly Val
    290                 295                 300
Glu Val His Asn Ala Lys Thr Lys Pro Arg Glu Glu Gln Tyr Asn Ser
305                 310                 315                 320
Thr Tyr Arg Val Val Ser Val Leu Thr Val Leu His Gln Asp Trp Leu
                325                 330                 335
Asn Gly Lys Glu Tyr Lys Cys Lys Val Ser Asn Lys Ala Leu Pro Ala
            340                 345                 350
Ser Ile Glu Lys Thr Ile Ser Lys Ala Lys Gly Gln Pro Arg Glu Pro
        355                 360                 365
Gln Val Tyr Val Leu Pro Pro Ser Arg Asp Glu Leu Thr Lys Asn Gln
    370                 375                 380
Val Ser Leu Leu Cys Leu Val Lys Gly Phe Tyr Pro Ser Asp Ile Ala
385                 390                 395                 400
Val Glu Trp Glu Ser Asn Gly Gln Pro Glu Asn Asn Tyr Leu Thr Trp
                405                 410                 415
Pro Pro Val Leu Asp Ser Asp Gly Ser Phe Phe Leu Tyr Ser Lys Leu
            420                 425                 430
Thr Val Asp Lys Ser Arg Trp Gln Gln Gly Asn Val Phe Ser Cys Ser
        435                 440                 445
Val Met His Glu Ala Leu His Asn His Tyr Thr Gln Lys Ser Leu Ser
    450                 455                 460
Leu Ser Pro Gly Lys
465

<210> SEQ ID NO 42
<211> LENGTH: 661
<212> TYPE: PRT
<213> ORGANISM: Artificial Sequence
<220> FEATURE:
<223> OTHER INFORMATION: Synthetic: RSLV-603 Without a leader sequence

<400> SEQUENCE: 42

Lys Asn Leu Lys Ser Pro Gln Lys Val Glu Val Asp Ile Ile Asp Asp
1               5                   10                  15
```

```
Asn Phe Ile Leu Arg Trp Asn Arg Ser Asp Glu Ser Val Gly Asn Val
                20                  25                  30

Thr Phe Ser Phe Asp Tyr Gln Lys Thr Gly Met Asp Asn Trp Ile Lys
            35                  40                  45

Leu Ser Gly Cys Gln Asn Ile Thr Ser Thr Lys Cys Asn Phe Ser Ser
 50                  55                  60

Leu Lys Leu Asn Val Tyr Glu Glu Ile Lys Leu Arg Ile Arg Ala Glu
 65                  70                  75                  80

Lys Glu Asn Thr Ser Ser Trp Tyr Glu Val Asp Ser Phe Thr Pro Phe
                85                  90                  95

Arg Lys Ala Gln Ile Gly Pro Pro Glu Val His Leu Glu Ala Glu Asp
            100                 105                 110

Lys Ala Ile Val Ile His Ile Ser Pro Gly Thr Lys Asp Ser Val Met
        115                 120                 125

Trp Ala Leu Asp Gly Leu Ser Phe Thr Tyr Ser Leu Val Ile Trp Lys
        130                 135                 140

Asn Ser Ser Gly Val Glu Glu Arg Ile Glu Asn Ile Tyr Ser Arg His
145                 150                 155                 160

Lys Ile Tyr Lys Leu Ser Pro Glu Thr Thr Tyr Cys Leu Lys Val Lys
                165                 170                 175

Ala Ala Leu Leu Thr Ser Trp Lys Ile Gly Val Tyr Ser Pro Val His
            180                 185                 190

Cys Ile Lys Thr Thr Val Glu Asn Glu Leu Pro Pro Pro Glu Asn Ile
        195                 200                 205

Glu Val Ser Val Gln Asn Gln Asn Tyr Val Leu Lys Trp Asp Tyr Thr
        210                 215                 220

Tyr Ala Asn Met Thr Phe Gln Val Gln Trp Leu His Ala Phe Leu Lys
225                 230                 235                 240

Arg Asn Pro Gly Asn His Leu Tyr Lys Trp Lys Gln Ile Pro Asp Cys
                245                 250                 255

Glu Asn Val Lys Thr Thr Gln Cys Val Phe Pro Gln Asn Val Phe Gln
            260                 265                 270

Lys Gly Ile Tyr Leu Leu Arg Val Gln Ala Ser Asp Gly Asn Asn Thr
        275                 280                 285

Ser Phe Trp Ser Glu Glu Ile Lys Phe Asp Thr Glu Ile Gln Ala Phe
        290                 295                 300

Leu Leu Pro Pro Val Phe Asn Ile Arg Ser Leu Ser Asp Ser Phe His
305                 310                 315                 320

Ile Tyr Ile Gly Ala Pro Lys Gln Ser Gly Asn Thr Pro Val Ile Gln
                325                 330                 335

Asp Tyr Pro Leu Ile Tyr Glu Ile Phe Trp Glu Asn Thr Ser Asn
            340                 345                 350

Ala Glu Arg Lys Ile Ile Glu Lys Lys Thr Asp Val Thr Val Pro Asn
        355                 360                 365

Leu Lys Pro Leu Thr Val Tyr Cys Val Lys Ala Arg Ala His Thr Met
        370                 375                 380

Asp Glu Lys Leu Asn Lys Ser Ser Val Phe Ser Asp Ala Val Cys Glu
385                 390                 395                 400

Lys Thr Lys Pro Gly Asn Thr Ser Lys Gly Gly Gly Ser Gly Gly
                405                 410                 415

Gly Gly Ser Gly Gly Gly Gly Ser Gly Gly Gly Gly Ser Glu Pro Lys
            420                 425                 430
```

```
Ser Ser Asp Lys Thr His Thr Cys Pro Pro Cys Pro Ala Pro Glu Leu
            435                 440                 445

Leu Gly Gly Ser Ser Val Phe Leu Phe Pro Pro Lys Pro Lys Asp Thr
450                 455                 460

Leu Met Ile Ser Arg Thr Pro Glu Val Thr Cys Val Val Val Asp Val
465                 470                 475                 480

Ser His Glu Asp Pro Glu Val Lys Phe Asn Trp Tyr Val Asp Gly Val
                485                 490                 495

Glu Val His Asn Ala Lys Thr Lys Pro Arg Glu Glu Gln Tyr Asn Ser
            500                 505                 510

Thr Tyr Arg Val Val Ser Val Leu Thr Val Leu His Gln Asp Trp Leu
        515                 520                 525

Asn Gly Lys Glu Tyr Lys Cys Lys Val Ser Asn Lys Ala Leu Pro Ala
530                 535                 540

Ser Ile Glu Lys Thr Ile Ser Lys Ala Lys Gly Gln Pro Arg Glu Pro
545                 550                 555                 560

Gln Val Tyr Val Tyr Pro Pro Ser Arg Asp Glu Leu Thr Lys Asn Gln
                565                 570                 575

Val Ser Leu Thr Cys Leu Val Lys Gly Phe Tyr Pro Ser Asp Ile Ala
            580                 585                 590

Val Glu Trp Glu Ser Asn Gly Gln Pro Glu Asn Asn Tyr Lys Thr Thr
        595                 600                 605

Pro Pro Val Leu Asp Ser Asp Gly Ser Phe Ala Leu Val Ser Lys Leu
610                 615                 620

Thr Val Asp Lys Ser Arg Trp Gln Gln Gly Asn Val Phe Ser Cys Ser
625                 630                 635                 640

Val Met His Glu Ala Leu His Asn His Tyr Thr Gln Lys Ser Leu Ser
                645                 650                 655

Leu Ser Pro Gly Lys
                660

<210> SEQ ID NO 43
<211> LENGTH: 469
<212> TYPE: PRT
<213> ORGANISM: Artificial Sequence
<220> FEATURE:
<223> OTHER INFORMATION: Synthetic: RSLV-604 without a leader sequence

<400> SEQUENCE: 43

Ile Ser Tyr Asp Ser Pro Asp Tyr Thr Asp Glu Ser Cys Thr Phe Lys
1               5                   10                  15

Ile Ser Leu Arg Asn Phe Arg Ser Ile Leu Ser Trp Glu Leu Lys Asn
            20                  25                  30

His Ser Ile Val Pro Thr His Tyr Thr Leu Leu Tyr Thr Ile Met Ser
        35                  40                  45

Lys Pro Glu Asp Leu Lys Val Val Lys Asn Cys Ala Asn Thr Thr Arg
50                  55                  60

Ser Phe Cys Asp Leu Thr Asp Glu Trp Arg Ser Thr His Glu Ala Tyr
65                  70                  75                  80

Val Thr Val Leu Glu Gly Phe Ser Gly Asn Thr Thr Leu Phe Ser Cys
                85                  90                  95

Ser His Asn Phe Trp Leu Ala Ile Asp Met Ser Phe Glu Pro Pro Glu
            100                 105                 110

Phe Glu Ile Val Gly Phe Thr Asn His Ile Asn Val Met Val Lys Phe
        115                 120                 125
```

Pro Ser Ile Val Glu Glu Leu Gln Phe Asp Leu Ser Leu Val Ile
    130                 135                 140

Glu Glu Gln Ser Glu Gly Ile Val Lys Lys His Lys Pro Glu Ile Lys
145                 150                 155                 160

Gly Asn Met Ser Gly Asn Phe Thr Tyr Ile Ile Asp Lys Leu Ile Pro
                165                 170                 175

Asn Thr Asn Tyr Cys Val Ser Val Tyr Leu Glu His Ser Asp Glu Gln
            180                 185                 190

Ala Val Ile Lys Ser Pro Leu Lys Cys Thr Leu Leu Pro Pro Gly Gln
        195                 200                 205

Glu Ser Glu Ser Ala Glu Ser Ala Lys Gly Gly Gly Ser Gly Gly
210                 215                 220

Gly Gly Ser Gly Gly Gly Ser Gly Gly Gly Ser Glu Pro Lys
225                 230                 235                 240

Ser Ser Asp Lys Thr His Thr Cys Pro Pro Cys Pro Ala Pro Glu Leu
                245                 250                 255

Leu Gly Gly Ser Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Ser Ile Glu Lys Thr Ile Ser Lys Ala Lys Gly Gln Pro Arg Glu Pro
        355                 360                 365

Gln Val Tyr Val Tyr Pro Pro Ser Arg Asp Glu Leu Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Ala Leu Val Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly Lys
465

<210> SEQ ID NO 44
<211> LENGTH: 478
<212> TYPE: PRT
<213> ORGANISM: Artificial Sequence
<220> FEATURE:
<223> OTHER INFORMATION: Synthetic: Leader-IFNAR2 (aa27-243)
      (Gly4Ser)2- IgG1 Fc (aa 216-447)with mutations C220S, P238S,
      P331S,T350V, T366L, K392L, T394W

<400> SEQUENCE: 44

Met Asp Trp Thr Trp Arg Ile Leu Phe Leu Val Ala Ala Ala Thr Gly

-continued

```
1               5                   10                  15
Thr His Ala Ile Ser Tyr Asp Ser Pro Asp Tyr Thr Asp Glu Ser Cys
            20                  25                  30

Thr Phe Lys Ile Ser Leu Arg Asn Phe Arg Ser Ile Leu Ser Trp Glu
            35                  40                  45

Leu Lys Asn His Ser Ile Val Pro Thr His Tyr Thr Leu Leu Tyr Thr
            50                  55                  60

Ile Met Ser Lys Pro Glu Asp Leu Lys Val Val Lys Asn Cys Ala Asn
65                  70                  75                  80

Thr Thr Arg Ser Phe Cys Asp Leu Thr Asp Glu Trp Arg Ser Thr His
                85                  90                  95

Glu Ala Tyr Val Thr Val Leu Glu Gly Phe Ser Gly Asn Thr Thr Leu
                100                 105                 110

Phe Ser Cys Ser His Asn Phe Trp Leu Ala Ile Asp Met Ser Phe Glu
                115                 120                 125

Pro Pro Glu Phe Glu Ile Val Gly Phe Thr Asn His Ile Asn Val Met
            130                 135                 140

Val Lys Phe Pro Ser Ile Val Glu Glu Glu Leu Gln Phe Asp Leu Ser
145                 150                 155                 160

Leu Val Ile Glu Glu Gln Ser Glu Gly Ile Val Lys Lys His Lys Pro
                165                 170                 175

Glu Ile Lys Gly Asn Met Ser Gly Asn Phe Thr Tyr Ile Ile Asp Lys
                180                 185                 190

Leu Ile Pro Asn Thr Asn Tyr Cys Val Ser Val Tyr Leu Glu His Ser
            195                 200                 205

Asp Glu Gln Ala Val Ile Lys Ser Pro Leu Lys Cys Thr Leu Leu Pro
            210                 215                 220

Pro Gly Gln Glu Ser Glu Ser Ala Glu Ser Ala Lys Gly Gly Gly Gly
225                 230                 235                 240

Ser Gly Gly Gly Gly Ser Glu Pro Lys Ser Ser Asp Lys Thr His Thr
                245                 250                 255

Cys Pro Pro Cys Pro Ala Pro Glu Leu Leu Gly Gly Ser Ser Val Phe
            260                 265                 270

Leu Phe Pro Pro Lys Pro Lys Asp Thr Leu Met Ile Ser Arg Thr Pro
            275                 280                 285

Glu Val Thr Cys Val Val Val Asp Val Ser His Glu Asp Pro Glu Val
            290                 295                 300

Lys Phe Asn Trp Tyr Val Asp Gly Val Glu Val His Asn Ala Lys Thr
305                 310                 315                 320

Lys Pro Arg Glu Glu Gln Tyr Asn Ser Thr Tyr Arg Val Val Ser Val
                325                 330                 335

Leu Thr Val Leu His Gln Asp Trp Leu Asn Gly Lys Glu Tyr Lys Cys
                340                 345                 350

Lys Val Ser Asn Lys Ala Leu Pro Ala Ser Ile Glu Lys Thr Ile Ser
                355                 360                 365

Lys Ala Lys Gly Gln Pro Arg Glu Pro Gln Val Tyr Val Leu Pro Pro
            370                 375                 380

Ser Arg Asp Glu Leu Thr Lys Asn Gln Val Ser Leu Thr Cys Leu Val
385                 390                 395                 400

Lys Gly Phe Tyr Pro Ser Asp Ile Ala Val Glu Trp Glu Ser Asn Gly
                405                 410                 415

Gln Pro Glu Asn Asn Tyr Leu Thr Trp Pro Pro Val Leu Asp Ser Asp
                420                 425                 430
```

Gly Ser Phe Phe Leu Tyr Ser Lys Leu Thr Val Asp Lys Ser Arg Trp
            435                 440                 445

Gln Gln Gly Asn Val Phe Ser Cys Ser Val Met His Glu Ala Leu His
    450                 455                 460

Asn His Tyr Thr Gln Lys Ser Leu Ser Leu Ser Pro Gly Lys
465                 470                 475

<210> SEQ ID NO 45
<211> LENGTH: 459
<212> TYPE: PRT
<213> ORGANISM: Artificial Sequence
<220> FEATURE:
<223> OTHER INFORMATION: Synthetic: IFNAR2 (aa27-243) (Gly4Ser)2- IgG1
      Fc (aa 216-447)with mutations C220S, P238S, P331S,T350V, T366L,
      K392L, T394W, without a leader sequence

<400> SEQUENCE: 45

Ile Ser Tyr Asp Ser Pro Asp Tyr Thr Asp Glu Ser Cys Thr Phe Lys
1               5                   10                  15

Ile Ser Leu Arg Asn Phe Arg Ser Ile Leu Ser Trp Glu Leu Lys Asn
            20                  25                  30

His Ser Ile Val Pro Thr His Tyr Thr Leu Leu Tyr Thr Ile Met Ser
        35                  40                  45

Lys Pro Glu Asp Leu Lys Val Val Lys Asn Cys Ala Asn Thr Thr Arg
50                  55                  60

Ser Phe Cys Asp Leu Thr Asp Glu Trp Arg Ser Thr His Glu Ala Tyr
65                  70                  75                  80

Val Thr Val Leu Glu Gly Phe Ser Gly Asn Thr Thr Leu Phe Ser Cys
                85                  90                  95

Ser His Asn Phe Trp Leu Ala Ile Asp Met Ser Phe Glu Pro Pro Glu
            100                 105                 110

Phe Glu Ile Val Gly Phe Thr Asn His Ile Asn Val Met Val Lys Phe
        115                 120                 125

Pro Ser Ile Val Glu Glu Glu Leu Gln Phe Asp Leu Ser Leu Val Ile
130                 135                 140

Glu Glu Gln Ser Glu Gly Ile Val Lys Lys His Lys Pro Glu Ile Lys
145                 150                 155                 160

Gly Asn Met Ser Gly Asn Phe Thr Tyr Ile Ile Asp Lys Leu Ile Pro
                165                 170                 175

Asn Thr Asn Tyr Cys Val Ser Val Tyr Leu Glu His Ser Asp Glu Gln
            180                 185                 190

Ala Val Ile Lys Ser Pro Leu Lys Cys Thr Leu Leu Pro Pro Gly Gln
        195                 200                 205

Glu Ser Glu Ser Ala Glu Ser Ala Lys Gly Gly Gly Gly Ser Gly Gly
210                 215                 220

Gly Gly Ser Glu Pro Lys Ser Ser Asp Lys Thr His Thr Cys Pro Pro
225                 230                 235                 240

Cys Pro Ala Pro Glu Leu Leu Gly Gly Ser Ser Val Phe Leu Phe Pro
                245                 250                 255

Pro Lys Pro Lys Asp Thr Leu Met Ile Ser Arg Thr Pro Glu Val Thr
            260                 265                 270

Cys Val Val Val Asp Val Ser His Glu Asp Pro Glu Val Lys Phe Asn
        275                 280                 285

Trp Tyr Val Asp Gly Val Glu Val His Asn Ala Lys Thr Lys Pro Arg
290                 295                 300

-continued

```
Glu Glu Gln Tyr Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
            325                 330                 335

Asn Lys Ala Leu Pro Ala Ser Ile Glu Lys Thr Ile Ser Lys Ala Lys
            340                 345                 350

Gly Gln Pro Arg Glu Pro Gln Val Tyr Val Leu Pro Pro Ser Arg Asp
            355                 360                 365

Glu Leu Thr Lys Asn Gln Val Ser Leu Leu Cys Leu Val Lys Gly Phe
            370                 375                 380

Tyr Pro Ser Asp Ile Ala Val Glu Trp Glu Ser Asn Gly Gln Pro Glu
385                 390                 395                 400

Asn Asn Tyr Leu Thr Trp Pro Pro Val Leu Asp Ser Asp Gly Ser Phe
            405                 410                 415

Phe Leu Tyr Ser Lys Leu Thr Val Asp Lys Ser Arg Trp Gln Gln Gly
            420                 425                 430

Asn Val Phe Ser Cys Ser Val Met His Glu Ala Leu His Asn His Tyr
            435                 440                 445

Thr Gln Lys Ser Leu Ser Leu Ser Pro Gly Lys
    450                 455
```

<210> SEQ ID NO 46
<211> LENGTH: 468
<212> TYPE: PRT
<213> ORGANISM: Artificial Sequence
<220> FEATURE:
<223> OTHER INFORMATION: Synthetic: Leader-IFNAR2 (aa27-243) IgG1 Fc
      (aa 216-447)with mutations C220S, P238S, P331S,T350V, T366L,
      K392L, T394W

<400> SEQUENCE: 46

```
Met Asp Trp Thr Trp Arg Ile Leu Phe Leu Val Ala Ala Ala Thr Gly
1               5                   10                  15

Thr His Ala Ile Ser Tyr Asp Ser Pro Asp Tyr Thr Asp Glu Ser Cys
            20                  25                  30

Thr Phe Lys Ile Ser Leu Arg Asn Phe Arg Ser Ile Leu Ser Trp Glu
        35                  40                  45

Leu Lys Asn His Ser Ile Val Pro Thr His Tyr Thr Leu Leu Tyr Thr
    50                  55                  60

Ile Met Ser Lys Pro Glu Asp Leu Lys Val Val Lys Asn Cys Ala Asn
65                  70                  75                  80

Thr Thr Arg Ser Phe Cys Asp Leu Thr Asp Glu Trp Arg Ser Thr His
                85                  90                  95

Glu Ala Tyr Val Thr Val Leu Glu Gly Phe Ser Gly Asn Thr Thr Leu
            100                 105                 110

Phe Ser Cys Ser His Asn Phe Trp Leu Ala Ile Asp Met Ser Phe Glu
        115                 120                 125

Pro Pro Glu Phe Glu Ile Val Gly Phe Thr Asn His Ile Asn Val Met
    130                 135                 140

Val Lys Phe Pro Ser Ile Val Glu Glu Glu Leu Gln Phe Asp Leu Ser
145                 150                 155                 160

Leu Val Ile Glu Glu Gln Ser Glu Gly Ile Val Lys Lys His Lys Pro
                165                 170                 175

Glu Ile Lys Gly Asn Met Ser Gly Asn Phe Thr Tyr Ile Ile Asp Lys
            180                 185                 190

Leu Ile Pro Asn Thr Asn Tyr Cys Val Ser Val Tyr Leu Glu His Ser
```

```
                195                 200                 205
Asp Glu Gln Ala Val Ile Lys Ser Pro Leu Lys Cys Thr Leu Leu Pro
    210                 215                 220

Pro Gly Gln Glu Ser Glu Ser Ala Glu Ser Ala Lys Glu Pro Lys Ser
225                 230                 235                 240

Ser Asp Lys Thr His Thr Cys Pro Pro Cys Pro Ala Pro Glu Leu Leu
                245                 250                 255

Gly Gly Ser Ser Val Phe Leu Phe Pro Pro Lys Pro Lys Asp Thr Leu
                260                 265                 270

Met Ile Ser Arg Thr Pro Glu Val Thr Cys Val Val Val Asp Val Ser
            275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Ser
                340                 345                 350

Ile Glu Lys Thr Ile Ser Lys Ala Lys Gly Gln Pro Arg Glu Pro Gln
            355                 360                 365

Val Tyr Val Leu Pro Pro Ser Arg Asp Glu Leu Thr Lys Asn Gln Val
    370                 375                 380

Ser Leu Leu Cys Leu Val Lys Gly Phe Tyr Pro Ser Asp Ile Ala Val
385                 390                 395                 400

Glu Trp Glu Ser Asn Gly Gln Pro Glu Asn Asn Tyr Leu Thr Trp Pro
                405                 410                 415

Pro Val Leu Asp Ser Asp Gly Ser Phe Phe Leu Tyr Ser Lys Leu Thr
                420                 425                 430

Val Asp Lys Ser Arg Trp Gln Gln Gly Asn Val Phe Ser Cys Ser Val
            435                 440                 445

Met His Glu Ala Leu His Asn His Tyr Thr Gln Lys Ser Leu Ser Leu
    450                 455                 460

Ser Pro Gly Lys
465

<210> SEQ ID NO 47
<211> LENGTH: 449
<212> TYPE: PRT
<213> ORGANISM: Artificial Sequence
<220> FEATURE:
<223> OTHER INFORMATION: Synthetic: IFNAR2 (aa27-243)  IgG1 Fc
      (aa 216-447)with mutations C220S, P238S, P331S,T350V, T366L,
      K392L, T394W, without a leader sequence

<400> SEQUENCE: 47

Ile Ser Tyr Asp Ser Pro Asp Tyr Thr Asp Glu Ser Cys Thr Phe Lys
1               5                   10                  15

Ile Ser Leu Arg Asn Phe Arg Ser Ile Leu Ser Trp Glu Leu Lys Asn
            20                  25                  30

His Ser Ile Val Pro Thr His Tyr Thr Leu Leu Tyr Thr Ile Met Ser
        35                  40                  45

Lys Pro Glu Asp Leu Lys Val Val Lys Asn Cys Ala Asn Thr Thr Arg
    50                  55                  60

Ser Phe Cys Asp Leu Thr Asp Glu Trp Arg Ser Thr His Glu Ala Tyr
65                  70                  75                  80
```

Val Thr Val Leu Glu Gly Ser Gly Asn Thr Thr Leu Phe Ser Cys
            85                  90                  95

Ser His Asn Phe Trp Leu Ala Ile Asp Met Ser Phe Glu Pro Pro Glu
        100                 105                 110

Phe Glu Ile Val Gly Phe Thr Asn His Ile Asn Val Met Val Lys Phe
        115                 120                 125

Pro Ser Ile Val Glu Glu Leu Gln Phe Asp Leu Ser Leu Val Ile
130                 135                 140

Glu Glu Gln Ser Glu Gly Ile Val Lys Lys His Lys Pro Glu Ile Lys
145                 150                 155                 160

Gly Asn Met Ser Gly Asn Phe Thr Tyr Ile Ile Asp Lys Leu Ile Pro
                165                 170                 175

Asn Thr Asn Tyr Cys Val Ser Val Tyr Leu Glu His Ser Asp Glu Gln
                180                 185                 190

Ala Val Ile Lys Ser Pro Leu Lys Cys Thr Leu Leu Pro Pro Gly Gln
        195                 200                 205

Glu Ser Glu Ser Ala Glu Ser Ala Lys Glu Pro Lys Ser Ser Asp Lys
210                 215                 220

Thr His Thr Cys Pro Pro Cys Pro Ala Pro Glu Leu Leu Gly Gly Ser
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Ser Ile Glu Lys
                325                 330                 335

Thr Ile Ser Lys Ala Lys Gly Gln Pro Arg Glu Pro Gln Val Tyr Val
                340                 345                 350

Leu Pro Pro Ser Arg Asp Glu Leu Thr Lys Asn Gln Val Ser Leu Leu
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Leu Thr Trp Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys

<210> SEQ ID NO 48
<211> LENGTH: 670
<212> TYPE: PRT
<213> ORGANISM: Artificial Sequence
<220> FEATURE:
<223> OTHER INFORMATION: Synthetic: Leader- IFNAR1 (aa28-436)-

(Gly4Ser)2- IgG1 Fc (aa 216-447) with mutations C220S, P238S, P331S, T350V, L351Y, F405A, Y407V

<400> SEQUENCE: 48

```
Met Asp Trp Thr Trp Arg Ile Leu Phe Leu Val Ala Ala Thr Gly
1               5                   10                  15

Thr His Ala Lys Asn Leu Lys Ser Pro Gln Lys Val Glu Val Asp Ile
                20                  25                  30

Ile Asp Asp Asn Phe Ile Leu Arg Trp Asn Arg Ser Asp Glu Ser Val
                35                  40                  45

Gly Asn Val Thr Phe Ser Phe Asp Tyr Gln Lys Thr Gly Met Asp Asn
        50                  55                  60

Trp Ile Lys Leu Ser Gly Cys Gln Asn Ile Thr Ser Thr Lys Cys Asn
65                  70                  75                  80

Phe Ser Ser Leu Lys Leu Asn Val Tyr Glu Glu Ile Lys Leu Arg Ile
                85                  90                  95

Arg Ala Glu Lys Glu Asn Thr Ser Ser Trp Tyr Glu Val Asp Ser Phe
                100                 105                 110

Thr Pro Phe Arg Lys Ala Gln Ile Gly Pro Pro Glu Val His Leu Glu
        115                 120                 125

Ala Glu Asp Lys Ala Ile Val Ile His Ile Ser Pro Gly Thr Lys Asp
        130                 135                 140

Ser Val Met Trp Ala Leu Asp Gly Leu Ser Phe Thr Tyr Ser Leu Val
145                 150                 155                 160

Ile Trp Lys Asn Ser Ser Gly Val Glu Glu Arg Ile Glu Asn Ile Tyr
                165                 170                 175

Ser Arg His Lys Ile Tyr Lys Leu Ser Pro Glu Thr Thr Tyr Cys Leu
                180                 185                 190

Lys Val Lys Ala Ala Leu Leu Thr Ser Trp Lys Ile Gly Val Tyr Ser
        195                 200                 205

Pro Val His Cys Ile Lys Thr Thr Val Glu Asn Glu Leu Pro Pro Pro
210                 215                 220

Glu Asn Ile Glu Val Ser Val Gln Asn Gln Asn Tyr Val Leu Lys Trp
225                 230                 235                 240

Asp Tyr Thr Tyr Ala Asn Met Thr Phe Gln Val Gln Trp Leu His Ala
                245                 250                 255

Phe Leu Lys Arg Asn Pro Gly Asn His Leu Tyr Lys Trp Lys Gln Ile
                260                 265                 270

Pro Asp Cys Glu Asn Val Lys Thr Thr Gln Cys Val Phe Pro Gln Asn
        275                 280                 285

Val Phe Gln Lys Gly Ile Tyr Leu Leu Arg Val Gln Ala Ser Asp Gly
        290                 295                 300

Asn Asn Thr Ser Phe Trp Ser Glu Glu Ile Lys Phe Asp Thr Glu Ile
305                 310                 315                 320

Gln Ala Phe Leu Leu Pro Pro Val Phe Asn Ile Arg Ser Leu Ser Asp
                325                 330                 335

Ser Phe His Ile Tyr Ile Gly Ala Pro Lys Gln Ser Gly Asn Thr Pro
                340                 345                 350

Val Ile Gln Asp Tyr Pro Leu Ile Tyr Glu Ile Ile Phe Trp Glu Asn
        355                 360                 365

Thr Ser Asn Ala Glu Arg Lys Ile Ile Glu Lys Lys Thr Asp Val Thr
        370                 375                 380

Val Pro Asn Leu Lys Pro Leu Thr Val Tyr Cys Val Lys Ala Arg Ala
385                 390                 395                 400
```

His Thr Met Asp Glu Lys Leu Asn Lys Ser Ser Val Phe Ser Asp Ala
            405                 410                 415

Val Cys Glu Lys Thr Lys Pro Gly Asn Thr Ser Lys Gly Gly Gly Gly
        420                 425                 430

Ser Gly Gly Gly Gly Ser Glu Pro Lys Ser Ser Asp Lys Thr His Thr
            435                 440                 445

Cys Pro Pro Cys Pro Ala Pro Glu Leu Leu Gly Gly Ser Ser Val Phe
        450                 455                 460

Leu Phe Pro Pro Lys Pro Lys Asp Thr Leu Met Ile Ser Arg Thr Pro
465                 470                 475                 480

Glu Val Thr Cys Val Val Val Asp Val Ser His Glu Asp Pro Glu Val
            485                 490                 495

Lys Phe Asn Trp Tyr Val Asp Gly Val Glu Val His Asn Ala Lys Thr
        500                 505                 510

Lys Pro Arg Glu Glu Gln Tyr Asn Ser Thr Tyr Arg Val Val Ser Val
        515                 520                 525

Leu Thr Val Leu His Gln Asp Trp Leu Asn Gly Lys Glu Tyr Lys Cys
    530                 535                 540

Lys Val Ser Asn Lys Ala Leu Pro Ala Ser Ile Glu Lys Thr Ile Ser
545                 550                 555                 560

Lys Ala Lys Gly Gln Pro Arg Glu Pro Gln Val Tyr Val Tyr Pro Pro
                565                 570                 575

Ser Arg Asp Glu Leu Thr Lys Asn Gln Val Ser Leu Thr Cys Leu Val
            580                 585                 590

Lys Gly Phe Tyr Pro Ser Asp Ile Ala Val Glu Trp Glu Ser Asn Gly
            595                 600                 605

Gln Pro Glu Asn Asn Tyr Lys Thr Thr Pro Pro Val Leu Asp Ser Asp
        610                 615                 620

Gly Ser Phe Ala Leu Val Ser Lys Leu Thr Val Asp Lys Ser Arg Trp
625                 630                 635                 640

Gln Gln Gly Asn Val Phe Ser Cys Ser Val Met His Glu Ala Leu His
                645                 650                 655

Asn His Tyr Thr Gln Lys Ser Leu Ser Leu Ser Pro Gly Lys
                660                 665                 670

<210> SEQ ID NO 49
<211> LENGTH: 651
<212> TYPE: PRT
<213> ORGANISM: Artificial Sequence
<220> FEATURE:
<223> OTHER INFORMATION: Synthetic: IFNAR1 (aa28-436)- (Gly4Ser)2- IgG1
      Fc (aa 216-447)with mutations C220S, P238S, P331S, T350V, L351Y,
      F405A, Y407V, without a leader sequence

<400> SEQUENCE: 49

Lys Asn Leu Lys Ser Pro Gln Lys Val Glu Val Asp Ile Ile Asp Asp
1               5                   10                  15

Asn Phe Ile Leu Arg Trp Asn Arg Ser Asp Glu Ser Val Gly Asn Val
            20                  25                  30

Thr Phe Ser Phe Asp Tyr Gln Lys Thr Gly Met Asp Asn Trp Ile Lys
        35                  40                  45

Leu Ser Gly Cys Gln Asn Ile Thr Ser Thr Lys Cys Asn Phe Ser Ser
    50                  55                  60

Leu Lys Leu Asn Val Tyr Glu Glu Ile Lys Leu Arg Ile Arg Ala Glu
65                  70                  75                  80

```
Lys Glu Asn Thr Ser Ser Trp Tyr Glu Val Asp Ser Phe Thr Pro Phe
                85                  90                  95
Arg Lys Ala Gln Ile Gly Pro Pro Glu Val His Leu Glu Ala Glu Asp
            100                 105                 110
Lys Ala Ile Val Ile His Ile Ser Pro Gly Thr Lys Asp Ser Val Met
        115                 120                 125
Trp Ala Leu Asp Gly Leu Ser Phe Thr Tyr Ser Leu Val Ile Trp Lys
    130                 135                 140
Asn Ser Ser Gly Val Glu Glu Arg Ile Glu Asn Ile Tyr Ser Arg His
145                 150                 155                 160
Lys Ile Tyr Lys Leu Ser Pro Glu Thr Thr Tyr Cys Leu Lys Val Lys
                165                 170                 175
Ala Ala Leu Leu Thr Ser Trp Lys Ile Gly Val Tyr Ser Pro Val His
            180                 185                 190
Cys Ile Lys Thr Thr Val Glu Asn Glu Leu Pro Pro Pro Glu Asn Ile
        195                 200                 205
Glu Val Ser Val Gln Asn Gln Asn Tyr Val Leu Lys Trp Asp Tyr Thr
    210                 215                 220
Tyr Ala Asn Met Thr Phe Gln Val Gln Trp Leu His Ala Phe Leu Lys
225                 230                 235                 240
Arg Asn Pro Gly Asn His Leu Tyr Lys Trp Lys Gln Ile Pro Asp Cys
                245                 250                 255
Glu Asn Val Lys Thr Thr Gln Cys Val Phe Pro Gln Asn Val Phe Gln
            260                 265                 270
Lys Gly Ile Tyr Leu Leu Arg Val Gln Ala Ser Asp Gly Asn Asn Thr
        275                 280                 285
Ser Phe Trp Ser Glu Glu Ile Lys Phe Asp Thr Glu Ile Gln Ala Phe
    290                 295                 300
Leu Leu Pro Pro Val Phe Asn Ile Arg Ser Leu Ser Asp Ser Phe His
305                 310                 315                 320
Ile Tyr Ile Gly Ala Pro Lys Gln Ser Gly Asn Thr Pro Val Ile Gln
                325                 330                 335
Asp Tyr Pro Leu Ile Tyr Glu Ile Ile Phe Trp Glu Asn Thr Ser Asn
            340                 345                 350
Ala Glu Arg Lys Ile Ile Glu Lys Lys Thr Asp Val Thr Val Pro Asn
        355                 360                 365
Leu Lys Pro Leu Thr Val Tyr Cys Val Lys Ala Arg Ala His Thr Met
    370                 375                 380
Asp Glu Lys Leu Asn Lys Ser Ser Val Phe Ser Asp Ala Val Cys Glu
385                 390                 395                 400
Lys Thr Lys Pro Gly Asn Thr Ser Lys Gly Gly Gly Ser Gly Gly
                405                 410                 415
Gly Gly Ser Glu Pro Lys Ser Ser Asp Lys Thr His Thr Cys Pro Pro
            420                 425                 430
Cys Pro Ala Pro Glu Leu Leu Gly Gly Ser Ser Val Phe Leu Phe Pro
        435                 440                 445
Pro Lys Pro Lys Asp Thr Leu Met Ile Ser Arg Thr Pro Glu Val Thr
    450                 455                 460
Cys Val Val Val Asp Val Ser His Glu Asp Pro Glu Val Lys Phe Asn
465                 470                 475                 480
Trp Tyr Val Asp Gly Val Glu Val His Asn Ala Lys Thr Lys Pro Arg
                485                 490                 495
Glu Glu Gln Tyr Asn Ser Thr Tyr Arg Val Val Ser Val Leu Thr Val
```

```
                    500                 505                 510
Leu His Gln Asp Trp Leu Asn Gly Lys Glu Tyr Lys Cys Lys Val Ser
            515                 520                 525

Asn Lys Ala Leu Pro Ala Ser Ile Glu Lys Thr Ile Ser Lys Ala Lys
        530                 535                 540

Gly Gln Pro Arg Glu Pro Gln Val Tyr Val Tyr Pro Pro Ser Arg Asp
545                 550                 555                 560

Glu Leu Thr Lys Asn Gln Val Ser Leu Thr Cys Leu Val Lys Gly Phe
                565                 570                 575

Tyr Pro Ser Asp Ile Ala Val Glu Trp Glu Ser Asn Gly Gln Pro Glu
            580                 585                 590

Asn Asn Tyr Lys Thr Thr Pro Pro Val Leu Asp Ser Asp Gly Ser Phe
        595                 600                 605

Ala Leu Val Ser Lys Leu Thr Val Asp Lys Ser Arg Trp Gln Gln Gly
610                 615                 620

Asn Val Phe Ser Cys Ser Val Met His Glu Ala Leu His Asn His Tyr
625                 630                 635                 640

Thr Gln Lys Ser Leu Ser Leu Ser Pro Gly Lys
                645                 650

<210> SEQ ID NO 50
<211> LENGTH: 660
<212> TYPE: PRT
<213> ORGANISM: Artificial Sequence
<220> FEATURE:
<223> OTHER INFORMATION: Synthetic: Leader- IFNAR1 (aa28-436)- IgG1 Fc
      (aa 216-447)with mutations C220S, P238S, P331S, T350V, L351Y,
      F405A, Y407V

<400> SEQUENCE: 50

Met Asp Trp Thr Trp Arg Ile Leu Phe Leu Val Ala Ala Ala Thr Gly
1               5                   10                  15

Thr His Ala Lys Asn Leu Lys Ser Pro Gln Lys Val Glu Val Asp Ile
            20                  25                  30

Ile Asp Asp Asn Phe Ile Leu Arg Trp Asn Arg Ser Asp Glu Ser Val
        35                  40                  45

Gly Asn Val Thr Phe Ser Phe Asp Tyr Gln Lys Thr Gly Met Asp Asn
    50                  55                  60

Trp Ile Lys Leu Ser Gly Cys Gln Asn Ile Thr Ser Thr Lys Cys Asn
65                  70                  75                  80

Phe Ser Ser Leu Lys Leu Asn Val Tyr Glu Glu Ile Lys Leu Arg Ile
                85                  90                  95

Arg Ala Glu Lys Glu Asn Thr Ser Ser Trp Tyr Glu Val Asp Ser Phe
            100                 105                 110

Thr Pro Phe Arg Lys Ala Gln Ile Gly Pro Pro Glu Val His Leu Glu
        115                 120                 125

Ala Glu Asp Lys Ala Ile Val Ile His Ile Ser Pro Gly Thr Lys Asp
    130                 135                 140

Ser Val Met Trp Ala Leu Asp Gly Leu Ser Phe Thr Tyr Ser Leu Val
145                 150                 155                 160

Ile Trp Lys Asn Ser Ser Gly Val Glu Glu Arg Ile Glu Asn Ile Tyr
                165                 170                 175

Ser Arg His Lys Ile Tyr Lys Leu Ser Pro Glu Thr Thr Tyr Cys Leu
            180                 185                 190

Lys Val Lys Ala Ala Leu Leu Thr Ser Trp Lys Ile Gly Val Tyr Ser
        195                 200                 205
```

-continued

```
Pro Val His Cys Ile Lys Thr Thr Val Glu Asn Glu Leu Pro Pro
    210                 215                 220
Glu Asn Ile Glu Val Ser Val Gln Asn Gln Asn Tyr Val Leu Lys Trp
225                 230                 235                 240
Asp Tyr Thr Tyr Ala Asn Met Thr Phe Gln Val Gln Trp Leu His Ala
                245                 250                 255
Phe Leu Lys Arg Asn Pro Gly Asn His Leu Tyr Lys Trp Lys Gln Ile
            260                 265                 270
Pro Asp Cys Glu Asn Val Lys Thr Thr Gln Cys Val Phe Pro Gln Asn
        275                 280                 285
Val Phe Gln Lys Gly Ile Tyr Leu Leu Arg Val Gln Ala Ser Asp Gly
290                 295                 300
Asn Asn Thr Ser Phe Trp Ser Glu Glu Ile Lys Phe Asp Thr Glu Ile
305                 310                 315                 320
Gln Ala Phe Leu Leu Pro Pro Val Phe Asn Ile Arg Ser Leu Ser Asp
                325                 330                 335
Ser Phe His Ile Tyr Ile Gly Ala Pro Lys Gln Ser Gly Asn Thr Pro
            340                 345                 350
Val Ile Gln Asp Tyr Pro Leu Ile Tyr Glu Ile Ile Phe Trp Glu Asn
        355                 360                 365
Thr Ser Asn Ala Glu Arg Lys Ile Ile Glu Lys Lys Thr Asp Val Thr
370                 375                 380
Val Pro Asn Leu Lys Pro Leu Thr Val Tyr Cys Val Lys Ala Arg Ala
385                 390                 395                 400
His Thr Met Asp Glu Lys Leu Asn Lys Ser Ser Val Phe Ser Asp Ala
                405                 410                 415
Val Cys Glu Lys Thr Lys Pro Gly Asn Thr Ser Lys Glu Pro Lys Ser
            420                 425                 430
Ser Asp Lys Thr His Thr Cys Pro Pro Cys Pro Ala Pro Glu Leu Leu
        435                 440                 445
Gly Gly Ser Ser Val Phe Leu Phe Pro Pro Lys Pro Lys Asp Thr Leu
450                 455                 460
Met Ile Ser Arg Thr Pro Glu Val Thr Cys Val Val Val Asp Val Ser
465                 470                 475                 480
His Glu Asp Pro Glu Val Lys Phe Asn Trp Tyr Val Asp Gly Val Glu
                485                 490                 495
Val His Asn Ala Lys Thr Lys Pro Arg Glu Glu Gln Tyr Asn Ser Thr
            500                 505                 510
Tyr Arg Val Val Ser Val Leu Thr Val Leu His Gln Asp Trp Leu Asn
        515                 520                 525
Gly Lys Glu Tyr Lys Cys Lys Val Ser Asn Lys Ala Leu Pro Ala Ser
530                 535                 540
Ile Glu Lys Thr Ile Ser Lys Ala Lys Gly Gln Pro Arg Glu Pro Gln
545                 550                 555                 560
Val Tyr Val Tyr Pro Pro Ser Arg Asp Glu Leu Thr Lys Asn Gln Val
                565                 570                 575
Ser Leu Thr Cys Leu Val Lys Gly Phe Tyr Pro Ser Asp Ile Ala Val
            580                 585                 590
Glu Trp Glu Ser Asn Gly Gln Pro Glu Asn Asn Tyr Lys Thr Thr Pro
        595                 600                 605
Pro Val Leu Asp Ser Asp Gly Ser Phe Ala Leu Val Ser Lys Leu Thr
610                 615                 620
```

```
Val Asp Lys Ser Arg Trp Gln Gln Gly Asn Val Phe Ser Cys Ser Val
625                 630                 635                 640

Met His Glu Ala Leu His Asn His Tyr Thr Gln Lys Ser Leu Ser Leu
                645                 650                 655

Ser Pro Gly Lys
            660

<210> SEQ ID NO 51
<211> LENGTH: 641
<212> TYPE: PRT
<213> ORGANISM: Artificial Sequence
<220> FEATURE:
<223> OTHER INFORMATION: Synthetic: IFNAR1 (aa28-436)- IgG1 Fc
      (aa 216-447)with mutations C220S, P238S, P331S, T350V, L351Y,
      F405A, Y407V, without a leader sequence

<400> SEQUENCE: 51

Lys Asn Leu Lys Ser Pro Gln Lys Val Glu Val Asp Ile Ile Asp Asp
1               5                   10                  15

Asn Phe Ile Leu Arg Trp Asn Arg Ser Asp Glu Ser Val Gly Asn Val
            20                  25                  30

Thr Phe Ser Phe Asp Tyr Gln Lys Thr Gly Met Asp Asn Trp Ile Lys
        35                  40                  45

Leu Ser Gly Cys Gln Asn Ile Thr Ser Thr Lys Cys Asn Phe Ser Ser
50                  55                  60

Leu Lys Leu Asn Val Tyr Glu Glu Ile Lys Leu Arg Ile Arg Ala Glu
65                  70                  75                  80

Lys Glu Asn Thr Ser Ser Trp Tyr Glu Val Asp Ser Phe Thr Pro Phe
                85                  90                  95

Arg Lys Ala Gln Ile Gly Pro Pro Glu Val His Leu Glu Ala Glu Asp
            100                 105                 110

Lys Ala Ile Val Ile His Ile Ser Pro Gly Thr Lys Asp Ser Val Met
        115                 120                 125

Trp Ala Leu Asp Gly Leu Ser Phe Thr Tyr Ser Leu Val Ile Trp Lys
130                 135                 140

Asn Ser Ser Gly Val Glu Glu Arg Ile Glu Asn Ile Tyr Ser Arg His
145                 150                 155                 160

Lys Ile Tyr Lys Leu Ser Pro Glu Thr Thr Tyr Cys Leu Lys Val Lys
                165                 170                 175

Ala Ala Leu Leu Thr Ser Trp Lys Ile Gly Val Tyr Ser Pro Val His
            180                 185                 190

Cys Ile Lys Thr Thr Val Glu Asn Glu Leu Pro Pro Pro Glu Asn Ile
        195                 200                 205

Glu Val Ser Val Gln Asn Gln Asn Tyr Val Leu Lys Trp Asp Tyr Thr
210                 215                 220

Tyr Ala Asn Met Thr Phe Gln Val Gln Trp Leu His Ala Phe Leu Lys
225                 230                 235                 240

Arg Asn Pro Gly Asn His Leu Tyr Lys Trp Lys Gln Ile Pro Asp Cys
                245                 250                 255

Glu Asn Val Lys Thr Thr Gln Cys Val Phe Pro Gln Asn Val Phe Gln
            260                 265                 270

Lys Gly Ile Tyr Leu Leu Arg Val Gln Ala Ser Asp Gly Asn Asn Thr
        275                 280                 285

Ser Phe Trp Ser Glu Glu Ile Lys Phe Asp Thr Glu Ile Gln Ala Phe
290                 295                 300

Leu Leu Pro Pro Val Phe Asn Ile Arg Ser Leu Ser Asp Ser Phe His
```

```
            305                 310                 315                 320
Ile Tyr Ile Gly Ala Pro Lys Gln Ser Gly Asn Thr Pro Val Ile Gln
                325                 330                 335

Asp Tyr Pro Leu Ile Tyr Glu Ile Ile Phe Trp Glu Asn Thr Ser Asn
                340                 345                 350

Ala Glu Arg Lys Ile Ile Glu Lys Thr Asp Val Thr Val Pro Asn
                355                 360                 365

Leu Lys Pro Leu Thr Val Tyr Cys Val Lys Ala Arg Ala His Thr Met
370                 375                 380

Asp Glu Lys Leu Asn Lys Ser Val Phe Ser Asp Ala Val Cys Glu
385                 390                 395                 400

Lys Thr Lys Pro Gly Asn Thr Ser Lys Glu Pro Lys Ser Ser Asp Lys
                405                 410                 415

Thr His Thr Cys Pro Pro Cys Pro Ala Pro Glu Leu Leu Gly Gly Ser
                420                 425                 430

Ser Val Phe Leu Phe Pro Pro Lys Pro Lys Asp Thr Leu Met Ile Ser
                435                 440                 445

Arg Thr Pro Glu Val Thr Cys Val Val Val Asp Val Ser His Glu Asp
                450                 455                 460

Pro Glu Val Lys Phe Asn Trp Tyr Val Asp Gly Val Glu Val His Asn
465                 470                 475                 480

Ala Lys Thr Lys Pro Arg Glu Glu Gln Tyr Asn Ser Thr Tyr Arg Val
                485                 490                 495

Val Ser Val Leu Thr Val Leu His Gln Asp Trp Leu Asn Gly Lys Glu
                500                 505                 510

Tyr Lys Cys Lys Val Ser Asn Lys Ala Leu Pro Ala Ser Ile Glu Lys
                515                 520                 525

Thr Ile Ser Lys Ala Lys Gly Gln Pro Arg Glu Pro Gln Val Tyr Val
                530                 535                 540

Tyr Pro Pro Ser Arg Asp Glu Leu Thr Lys Asn Gln Val Ser Leu Thr
545                 550                 555                 560

Cys Leu Val Lys Gly Phe Tyr Pro Ser Asp Ile Ala Val Glu Trp Glu
                565                 570                 575

Ser Asn Gly Gln Pro Glu Asn Asn Tyr Lys Thr Thr Pro Pro Val Leu
                580                 585                 590

Asp Ser Asp Gly Ser Phe Ala Leu Val Ser Lys Leu Thr Val Asp Lys
                595                 600                 605

Ser Arg Trp Gln Gln Gly Asn Val Phe Ser Cys Ser Val Met His Glu
                610                 615                 620

Ala Leu His Asn His Tyr Thr Gln Lys Ser Leu Ser Leu Ser Pro Gly
625                 630                 635                 640

Lys

<210> SEQ ID NO 52
<211> LENGTH: 670
<212> TYPE: PRT
<213> ORGANISM: Artificial Sequence
<220> FEATURE:
<223> OTHER INFORMATION: Synthetic: RSLV-606 Leader- IFNAR1 (aa28-436)-
      (Gly4Ser)2- Fc (aa216-447)with mutations C220S, P238S, P331S,
      T350V, T366L, K392L, T394W

<400> SEQUENCE: 52

Met Asp Trp Thr Trp Arg Ile Leu Phe Leu Val Ala Ala Ala Thr Gly
1               5                   10                  15
```

```
Thr His Ala Lys Asn Leu Lys Ser Pro Gln Lys Val Glu Val Asp Ile
             20                  25                  30

Ile Asp Asp Asn Phe Ile Leu Arg Trp Asn Arg Ser Asp Glu Ser Val
         35                  40                  45

Gly Asn Val Thr Phe Ser Phe Asp Tyr Gln Lys Thr Gly Met Asp Asn
     50                  55                  60

Trp Ile Lys Leu Ser Gly Cys Gln Asn Ile Thr Ser Thr Lys Cys Asn
65                  70                  75                  80

Phe Ser Ser Leu Lys Leu Asn Val Tyr Glu Glu Ile Lys Leu Arg Ile
                 85                  90                  95

Arg Ala Glu Lys Glu Asn Thr Ser Ser Trp Tyr Glu Val Asp Ser Phe
            100                 105                 110

Thr Pro Phe Arg Lys Ala Gln Ile Gly Pro Pro Glu Val His Leu Glu
        115                 120                 125

Ala Glu Asp Lys Ala Ile Val Ile His Ile Ser Pro Gly Thr Lys Asp
    130                 135                 140

Ser Val Met Trp Ala Leu Asp Gly Leu Ser Phe Thr Tyr Ser Leu Val
145                 150                 155                 160

Ile Trp Lys Asn Ser Ser Gly Val Glu Glu Arg Ile Glu Asn Ile Tyr
                165                 170                 175

Ser Arg His Lys Ile Tyr Lys Leu Ser Pro Glu Thr Thr Tyr Cys Leu
            180                 185                 190

Lys Val Lys Ala Ala Leu Leu Thr Ser Trp Lys Ile Gly Val Tyr Ser
        195                 200                 205

Pro Val His Cys Ile Lys Thr Thr Val Glu Asn Glu Leu Pro Pro Pro
    210                 215                 220

Glu Asn Ile Glu Val Ser Val Gln Asn Gln Asn Tyr Val Leu Lys Trp
225                 230                 235                 240

Asp Tyr Thr Tyr Ala Asn Met Thr Phe Gln Val Gln Trp Leu His Ala
                245                 250                 255

Phe Leu Lys Arg Asn Pro Gly Asn His Leu Tyr Lys Trp Lys Gln Ile
            260                 265                 270

Pro Asp Cys Glu Asn Val Lys Thr Thr Gln Cys Val Phe Pro Gln Asn
        275                 280                 285

Val Phe Gln Lys Gly Ile Tyr Leu Leu Arg Val Gln Ala Ser Asp Gly
    290                 295                 300

Asn Asn Thr Ser Phe Trp Ser Glu Glu Ile Lys Phe Asp Thr Glu Ile
305                 310                 315                 320

Gln Ala Phe Leu Leu Pro Pro Val Phe Asn Ile Arg Ser Leu Ser Asp
                325                 330                 335

Ser Phe His Ile Tyr Ile Gly Ala Pro Lys Gln Ser Gly Asn Thr Pro
            340                 345                 350

Val Ile Gln Asp Tyr Pro Leu Ile Tyr Glu Ile Ile Phe Trp Glu Asn
        355                 360                 365

Thr Ser Asn Ala Glu Arg Lys Ile Ile Glu Lys Lys Thr Asp Val Thr
    370                 375                 380

Val Pro Asn Leu Lys Pro Leu Thr Val Tyr Cys Val Lys Ala Arg Ala
385                 390                 395                 400

His Thr Met Asp Glu Lys Leu Asn Lys Ser Ser Val Phe Ser Asp Ala
                405                 410                 415

Val Cys Glu Lys Thr Lys Pro Gly Asn Thr Ser Lys Gly Gly Gly Gly
            420                 425                 430

Ser Gly Gly Gly Gly Ser Glu Pro Lys Ser Ser Asp Lys Thr His Thr
```

```
            435                 440                 445
Cys Pro Pro Cys Pro Ala Pro Glu Leu Leu Gly Gly Ser Ser Val Phe
450                 455                 460

Leu Phe Pro Pro Lys Pro Lys Asp Thr Leu Met Ile Ser Arg Thr Pro
465                 470                 475                 480

Glu Val Thr Cys Val Val Asp Val Ser His Glu Asp Pro Glu Val
                485                 490                 495

Lys Phe Asn Trp Tyr Val Asp Gly Val Glu Val His Asn Ala Lys Thr
                500                 505                 510

Lys Pro Arg Glu Glu Gln Tyr Asn Ser Thr Tyr Arg Val Val Ser Val
                515                 520                 525

Leu Thr Val Leu His Gln Asp Trp Leu Asn Gly Lys Glu Tyr Lys Cys
530                 535                 540

Lys Val Ser Asn Lys Ala Leu Pro Ala Ser Ile Glu Lys Thr Ile Ser
545                 550                 555                 560

Lys Ala Lys Gly Gln Pro Arg Glu Pro Gln Val Tyr Val Leu Pro Pro
                565                 570                 575

Ser Arg Asp Glu Leu Thr Lys Asn Gln Val Ser Leu Leu Cys Leu Val
                580                 585                 590

Lys Gly Phe Tyr Pro Ser Asp Ile Ala Val Glu Trp Glu Ser Asn Gly
                595                 600                 605

Gln Pro Glu Asn Asn Tyr Leu Thr Trp Pro Pro Val Leu Asp Ser Asp
610                 615                 620

Gly Ser Phe Phe Leu Tyr Ser Lys Leu Thr Val Asp Lys Ser Arg Trp
625                 630                 635                 640

Gln Gln Gly Asn Val Phe Ser Cys Ser Val Met His Glu Ala Leu His
                645                 650                 655

Asn His Tyr Thr Gln Lys Ser Leu Ser Leu Ser Pro Gly Lys
                660                 665                 670

<210> SEQ ID NO 53
<211> LENGTH: 651
<212> TYPE: PRT
<213> ORGANISM: Artificial Sequence
<220> FEATURE:
<223> OTHER INFORMATION: Synthetic: RSLV-606 Without a leader sequence

<400> SEQUENCE: 53

Lys Asn Leu Lys Ser Pro Gln Lys Val Glu Val Asp Ile Ile Asp Asp
1               5                   10                  15

Asn Phe Ile Leu Arg Trp Asn Arg Ser Asp Glu Ser Val Gly Asn Val
                20                  25                  30

Thr Phe Ser Phe Asp Tyr Gln Lys Thr Gly Met Asp Asn Trp Ile Lys
                35                  40                  45

Leu Ser Gly Cys Gln Asn Ile Thr Ser Thr Lys Cys Asn Phe Ser Ser
50                  55                  60

Leu Lys Leu Asn Val Tyr Glu Glu Ile Lys Leu Arg Ile Arg Ala Glu
65                  70                  75                  80

Lys Glu Asn Thr Ser Ser Trp Tyr Glu Val Asp Ser Phe Thr Pro Phe
                85                  90                  95

Arg Lys Ala Gln Ile Gly Pro Pro Glu Val His Leu Glu Ala Glu Asp
                100                 105                 110

Lys Ala Ile Val Ile His Ile Ser Pro Gly Thr Lys Asp Ser Val Met
                115                 120                 125

Trp Ala Leu Asp Gly Leu Ser Phe Thr Tyr Ser Leu Val Ile Trp Lys
```

```
                130             135             140
Asn Ser Ser Gly Val Glu Glu Arg Ile Glu Asn Ile Tyr Ser Arg His
145                 150                 155                 160

Lys Ile Tyr Lys Leu Ser Pro Glu Thr Thr Tyr Cys Leu Lys Val Lys
                165                 170                 175

Ala Ala Leu Leu Thr Ser Trp Lys Ile Gly Val Tyr Ser Pro Val His
                180                 185                 190

Cys Ile Lys Thr Thr Val Glu Asn Glu Leu Pro Pro Pro Glu Asn Ile
                195                 200                 205

Glu Val Ser Val Gln Asn Gln Asn Tyr Val Leu Lys Trp Asp Tyr Thr
                210                 215                 220

Tyr Ala Asn Met Thr Phe Gln Val Gln Trp Leu His Ala Phe Leu Lys
225                 230                 235                 240

Arg Asn Pro Gly Asn His Leu Tyr Lys Trp Lys Gln Ile Pro Asp Cys
                245                 250                 255

Glu Asn Val Lys Thr Thr Gln Cys Val Phe Pro Gln Asn Val Phe Gln
                260                 265                 270

Lys Gly Ile Tyr Leu Leu Arg Val Gln Ala Ser Asp Gly Asn Asn Thr
                275                 280                 285

Ser Phe Trp Ser Glu Glu Ile Lys Phe Asp Thr Glu Ile Gln Ala Phe
                290                 295                 300

Leu Leu Pro Pro Val Phe Asn Ile Arg Ser Leu Ser Asp Ser Phe His
305                 310                 315                 320

Ile Tyr Ile Gly Ala Pro Lys Gln Ser Gly Asn Thr Pro Val Ile Gln
                325                 330                 335

Asp Tyr Pro Leu Ile Tyr Glu Ile Ile Phe Trp Glu Asn Thr Ser Asn
                340                 345                 350

Ala Glu Arg Lys Ile Ile Glu Lys Lys Thr Asp Val Thr Val Pro Asn
                355                 360                 365

Leu Lys Pro Leu Thr Val Tyr Cys Val Lys Ala Arg Ala His Thr Met
                370                 375                 380

Asp Glu Lys Leu Asn Lys Ser Val Phe Ser Asp Ala Val Cys Glu
385                 390                 395                 400

Lys Thr Lys Pro Gly Asn Thr Ser Lys Gly Gly Gly Ser Gly Gly
                405                 410                 415

Gly Gly Ser Glu Pro Lys Ser Ser Asp Lys Thr His Thr Cys Pro Pro
                420                 425                 430

Cys Pro Ala Pro Glu Leu Leu Gly Gly Ser Ser Val Phe Leu Phe Pro
                435                 440                 445

Pro Lys Pro Lys Asp Thr Leu Met Ile Ser Arg Thr Pro Glu Val Thr
                450                 455                 460

Cys Val Val Val Asp Val Ser His Glu Asp Pro Glu Val Lys Phe Asn
465                 470                 475                 480

Trp Tyr Val Asp Gly Val Glu Val His Asn Ala Lys Thr Lys Pro Arg
                485                 490                 495

Glu Glu Gln Tyr Asn Ser Thr Tyr Arg Val Val Ser Val Leu Thr Val
                500                 505                 510

Leu His Gln Asp Trp Leu Asn Gly Lys Glu Tyr Lys Cys Lys Val Ser
                515                 520                 525

Asn Lys Ala Leu Pro Ala Ser Ile Glu Lys Thr Ile Ser Lys Ala Lys
                530                 535                 540

Gly Gln Pro Arg Glu Pro Gln Val Tyr Val Leu Pro Pro Ser Arg Asp
545                 550                 555                 560
```

```
Glu Leu Thr Lys Asn Gln Val Ser Leu Leu Cys Leu Val Lys Gly Phe
                565                 570                 575

Tyr Pro Ser Asp Ile Ala Val Glu Trp Glu Ser Asn Gly Gln Pro Glu
            580                 585                 590

Asn Asn Tyr Leu Thr Trp Pro Pro Val Leu Asp Ser Asp Gly Ser Phe
                595                 600                 605

Phe Leu Tyr Ser Lys Leu Thr Val Asp Lys Ser Arg Trp Gln Gln Gly
    610                 615                 620

Asn Val Phe Ser Cys Ser Val Met His Glu Ala Leu His Asn His Tyr
625                 630                 635                 640

Thr Gln Lys Ser Leu Ser Leu Ser Pro Gly Lys
                645                 650

<210> SEQ ID NO 54
<211> LENGTH: 478
<212> TYPE: PRT
<213> ORGANISM: Artificial Sequence
<220> FEATURE:
<223> OTHER INFORMATION: Synthetic: RSLV-611 Leader- IFNAR2 (aa27-243)-
      (Gly4Ser)2- Fc (aa 216-447) with mutations C220S, P238S, P331S,
      T350V, L351Y, F405A, Y407V

<400> SEQUENCE: 54

Met Asp Trp Thr Trp Arg Ile Leu Phe Leu Val Ala Ala Ala Thr Gly
1               5                   10                  15

Thr His Ala Ile Ser Tyr Asp Ser Pro Asp Tyr Thr Asp Glu Ser Cys
            20                  25                  30

Thr Phe Lys Ile Ser Leu Arg Asn Phe Arg Ser Ile Leu Ser Trp Glu
        35                  40                  45

Leu Lys Asn His Ser Ile Val Pro Thr His Tyr Thr Leu Leu Tyr Thr
    50                  55                  60

Ile Met Ser Lys Pro Glu Asp Leu Lys Val Val Lys Asn Cys Ala Asn
65                  70                  75                  80

Thr Thr Arg Ser Phe Cys Asp Leu Thr Asp Glu Trp Arg Ser Thr His
                85                  90                  95

Glu Ala Tyr Val Thr Val Leu Glu Gly Phe Ser Gly Asn Thr Thr Leu
            100                 105                 110

Phe Ser Cys Ser His Asn Phe Trp Leu Ala Ile Asp Met Ser Phe Glu
        115                 120                 125

Pro Pro Glu Phe Glu Ile Val Gly Phe Thr Asn His Ile Asn Val Met
    130                 135                 140

Val Lys Phe Pro Ser Ile Val Glu Glu Glu Leu Gln Phe Asp Leu Ser
145                 150                 155                 160

Leu Val Ile Glu Glu Gln Ser Glu Gly Ile Val Lys Lys His Lys Pro
                165                 170                 175

Glu Ile Lys Gly Asn Met Ser Gly Asn Phe Thr Tyr Ile Ile Asp Lys
            180                 185                 190

Leu Ile Pro Asn Thr Asn Tyr Cys Val Ser Val Tyr Leu Glu His Ser
        195                 200                 205

Asp Glu Gln Ala Val Ile Lys Ser Pro Leu Lys Cys Thr Leu Leu Pro
    210                 215                 220

Pro Gly Gln Glu Ser Glu Ser Ala Glu Ser Ala Lys Gly Gly Gly Gly
225                 230                 235                 240

Ser Gly Gly Gly Gly Ser Glu Pro Lys Ser Ser Asp Lys Thr His Thr
                245                 250                 255
```

```
Cys Pro Pro Cys Pro Ala Pro Glu Leu Leu Gly Gly Ser Ser Val Phe
            260                 265                 270

Leu Phe Pro Pro Lys Pro Lys Asp Thr Leu Met Ile Ser Arg Thr Pro
        275                 280                 285

Glu Val Thr Cys Val Val Val Asp Val Ser His Glu Asp Pro Glu Val
    290                 295                 300

Lys Phe Asn Trp Tyr Val Asp Gly Val Glu Val His Asn Ala Lys Thr
305                 310                 315                 320

Lys Pro Arg Glu Glu Gln Tyr Asn Ser Thr Tyr Arg Val Val Ser Val
                325                 330                 335

Leu Thr Val Leu His Gln Asp Trp Leu Asn Gly Lys Glu Tyr Lys Cys
            340                 345                 350

Lys Val Ser Asn Lys Ala Leu Pro Ala Ser Ile Glu Lys Thr Ile Ser
        355                 360                 365

Lys Ala Lys Gly Gln Pro Arg Glu Pro Gln Val Tyr Val Tyr Pro Pro
    370                 375                 380

Ser Arg Asp Glu Leu Thr Lys Asn Gln Val Ser Leu Thr Cys Leu Val
385                 390                 395                 400

Lys Gly Phe Tyr Pro Ser Asp Ile Ala Val Glu Trp Glu Ser Asn Gly
                405                 410                 415

Gln Pro Glu Asn Asn Tyr Lys Thr Thr Pro Pro Val Leu Asp Ser Asp
            420                 425                 430

Gly Ser Phe Ala Leu Val Ser Lys Leu Thr Val Asp Lys Ser Arg Trp
        435                 440                 445

Gln Gln Gly Asn Val Phe Ser Cys Ser Val Met His Glu Ala Leu His
    450                 455                 460

Asn His Tyr Thr Gln Lys Ser Leu Ser Leu Ser Pro Gly Lys
465                 470                 475

<210> SEQ ID NO 55
<211> LENGTH: 459
<212> TYPE: PRT
<213> ORGANISM: Artificial Sequence
<220> FEATURE:
<223> OTHER INFORMATION: Synthetic: RSLV-611 Without a leader sequence
<400> SEQUENCE: 55

Ile Ser Tyr Asp Ser Pro Asp Tyr Thr Asp Glu Ser Cys Thr Phe Lys
1               5                   10                  15

Ile Ser Leu Arg Asn Phe Arg Ser Ile Leu Ser Trp Glu Leu Lys Asn
            20                  25                  30

His Ser Ile Val Pro Thr His Tyr Thr Leu Leu Tyr Thr Ile Met Ser
        35                  40                  45

Lys Pro Glu Asp Leu Lys Val Val Lys Asn Cys Ala Asn Thr Thr Arg
    50                  55                  60

Ser Phe Cys Asp Leu Thr Asp Glu Trp Arg Ser Thr His Glu Ala Tyr
65                  70                  75                  80

Val Thr Val Leu Glu Gly Phe Ser Gly Asn Thr Thr Leu Phe Ser Cys
                85                  90                  95

Ser His Asn Phe Trp Leu Ala Ile Asp Met Ser Phe Glu Pro Pro Glu
            100                 105                 110

Phe Glu Ile Val Gly Phe Thr Asn His Ile Asn Val Met Val Lys Phe
        115                 120                 125

Pro Ser Ile Val Glu Glu Glu Leu Gln Phe Asp Leu Ser Leu Val Ile
    130                 135                 140
```

-continued

Glu Glu Gln Ser Glu Gly Ile Val Lys Lys His Lys Pro Glu Ile Lys
145 150 155 160

Gly Asn Met Ser Gly Asn Phe Thr Tyr Ile Ile Asp Lys Leu Ile Pro
165 170 175

Asn Thr Asn Tyr Cys Val Ser Val Tyr Leu Glu His Ser Asp Glu Gln
180 185 190

Ala Val Ile Lys Ser Pro Leu Lys Cys Thr Leu Leu Pro Pro Gly Gln
195 200 205

Glu Ser Glu Ser Ala Glu Ser Ala Lys Gly Gly Gly Gly Ser Gly Gly
210 215 220

Gly Gly Ser Glu Pro Lys Ser Ser Asp Lys Thr His Thr Cys Pro Pro
225 230 235 240

Cys Pro Ala Pro Glu Leu Leu Gly Gly Ser Ser Val Phe Leu Phe Pro
245 250 255

Pro Lys Pro Lys Asp Thr Leu Met Ile Ser Arg Thr Pro Glu Val Thr
260 265 270

Cys Val Val Val Asp Val Ser His Glu Asp Pro Glu Val Lys Phe Asn
275 280 285

Trp Tyr Val Asp Gly Val Glu Val His Asn Ala Lys Thr Lys Pro Arg
290 295 300

Glu Glu Gln Tyr Asn Ser Thr Tyr Arg Val Val Ser Val Leu Thr Val
305 310 315 320

Leu His Gln Asp Trp Leu Asn Gly Lys Glu Tyr Lys Cys Lys Val Ser
325 330 335

Asn Lys Ala Leu Pro Ala Ser Ile Glu Lys Thr Ile Ser Lys Ala Lys
340 345 350

Gly Gln Pro Arg Glu Pro Gln Val Tyr Val Tyr Pro Pro Ser Arg Asp
355 360 365

Glu Leu Thr Lys Asn Gln Val Ser Leu Thr Cys Leu Val Lys Gly Phe
370 375 380

Tyr Pro Ser Asp Ile Ala Val Glu Trp Glu Ser Asn Gly Gln Pro Glu
385 390 395 400

Asn Asn Tyr Lys Thr Thr Pro Pro Val Leu Asp Ser Asp Gly Ser Phe
405 410 415

Ala Leu Val Ser Lys Leu Thr Val Asp Lys Ser Arg Trp Gln Gln Gly
420 425 430

Asn Val Phe Ser Cys Ser Val Met His Glu Ala Leu His Asn His Tyr
435 440 445

Thr Gln Lys Ser Leu Ser Leu Ser Pro Gly Lys
450 455

<210> SEQ ID NO 56
<211> LENGTH: 660
<212> TYPE: PRT
<213> ORGANISM: Artificial Sequence
<220> FEATURE:
<223> OTHER INFORMATION: Synthetic: RSLV-608 Leader- IFNAR1 (aa28-436)-
Fc (aa216-447)with mutations C220S, P238S, P331S, T350V, T366L,
K392L, T394W

<400> SEQUENCE: 56

Met Asp Trp Thr Trp Arg Ile Leu Phe Leu Val Ala Ala Ala Thr Gly
1 5 10 15

Thr His Ala Lys Asn Leu Lys Ser Pro Gln Lys Val Glu Val Asp Ile
20 25 30

Ile Asp Asp Asn Phe Ile Leu Arg Trp Asn Arg Ser Asp Glu Ser Val

-continued

```
                 35                  40                  45
Gly Asn Val Thr Phe Ser Phe Asp Tyr Gln Lys Thr Gly Met Asp Asn
 50                  55                  60
Trp Ile Lys Leu Ser Gly Cys Gln Asn Ile Thr Ser Thr Lys Cys Asn
 65                  70                  75                  80
Phe Ser Ser Leu Lys Leu Asn Val Tyr Glu Ile Lys Leu Arg Ile
                 85                  90                  95
Arg Ala Glu Lys Glu Asn Thr Ser Ser Trp Tyr Glu Val Asp Ser Phe
                100                 105                 110
Thr Pro Phe Arg Lys Ala Gln Ile Gly Pro Pro Glu Val His Leu Glu
                115                 120                 125
Ala Glu Asp Lys Ala Ile Val Ile His Ile Ser Pro Gly Thr Lys Asp
                130                 135                 140
Ser Val Met Trp Ala Leu Asp Gly Leu Ser Phe Thr Tyr Ser Leu Val
145                 150                 155                 160
Ile Trp Lys Asn Ser Ser Gly Val Glu Glu Arg Ile Glu Asn Ile Tyr
                165                 170                 175
Ser Arg His Lys Ile Tyr Lys Leu Ser Pro Glu Thr Thr Tyr Cys Leu
                180                 185                 190
Lys Val Lys Ala Ala Leu Leu Thr Ser Trp Lys Ile Gly Val Tyr Ser
                195                 200                 205
Pro Val His Cys Ile Lys Thr Thr Val Glu Asn Glu Leu Pro Pro Pro
                210                 215                 220
Glu Asn Ile Glu Val Ser Val Gln Asn Gln Asn Tyr Val Leu Lys Trp
225                 230                 235                 240
Asp Tyr Thr Tyr Ala Asn Met Thr Phe Gln Val Gln Trp Leu His Ala
                245                 250                 255
Phe Leu Lys Arg Asn Pro Gly Asn His Leu Tyr Lys Trp Lys Gln Ile
                260                 265                 270
Pro Asp Cys Glu Asn Val Lys Thr Thr Gln Cys Val Phe Pro Gln Asn
                275                 280                 285
Val Phe Gln Lys Gly Ile Tyr Leu Leu Arg Val Gln Ala Ser Asp Gly
                290                 295                 300
Asn Asn Thr Ser Phe Trp Ser Glu Glu Ile Lys Phe Asp Thr Glu Ile
305                 310                 315                 320
Gln Ala Phe Leu Leu Pro Pro Val Phe Asn Ile Arg Ser Leu Ser Asp
                325                 330                 335
Ser Phe His Ile Tyr Ile Gly Ala Pro Lys Gln Ser Gly Asn Thr Pro
                340                 345                 350
Val Ile Gln Asp Tyr Pro Leu Ile Tyr Glu Ile Phe Trp Glu Asn
                355                 360                 365
Thr Ser Asn Ala Glu Arg Lys Ile Ile Glu Lys Lys Thr Asp Val Thr
                370                 375                 380
Val Pro Asn Leu Lys Pro Leu Thr Val Tyr Cys Val Lys Ala Arg Ala
385                 390                 395                 400
His Thr Met Asp Glu Lys Leu Asn Lys Ser Ser Val Phe Ser Asp Ala
                405                 410                 415
Val Cys Glu Lys Thr Lys Pro Gly Asn Thr Ser Lys Glu Pro Lys Ser
                420                 425                 430
Ser Asp Lys Thr His Thr Cys Pro Pro Cys Pro Ala Pro Glu Leu Leu
                435                 440                 445
Gly Gly Ser Ser Val Phe Leu Phe Pro Pro Lys Pro Lys Asp Thr Leu
                450                 455                 460
```

```
Met Ile Ser Arg Thr Pro Glu Val Thr Cys Val Val Asp Val Ser
465                 470                 475                 480

His Glu Asp Pro Glu Val Lys Phe Asn Trp Tyr Val Asp Gly Val Glu
                485                 490                 495

Val His Asn Ala Lys Thr Lys Pro Arg Glu Glu Gln Tyr Asn Ser Thr
            500                 505                 510

Tyr Arg Val Val Ser Val Leu Thr Val Leu His Gln Asp Trp Leu Asn
        515                 520                 525

Gly Lys Glu Tyr Lys Cys Lys Val Ser Asn Lys Ala Leu Pro Ala Ser
    530                 535                 540

Ile Glu Lys Thr Ile Ser Lys Ala Lys Gly Gln Pro Arg Glu Pro Gln
545                 550                 555                 560

Val Tyr Val Leu Pro Pro Ser Arg Asp Glu Leu Thr Lys Asn Gln Val
                565                 570                 575

Ser Leu Leu Cys Leu Val Lys Gly Phe Tyr Pro Ser Asp Ile Ala Val
            580                 585                 590

Glu Trp Glu Ser Asn Gly Gln Pro Glu Asn Asn Tyr Leu Thr Trp Pro
        595                 600                 605

Pro Val Leu Asp Ser Asp Gly Ser Phe Phe Leu Tyr Ser Lys Leu Thr
    610                 615                 620

Val Asp Lys Ser Arg Trp Gln Gln Gly Asn Val Phe Ser Cys Ser Val
625                 630                 635                 640

Met His Glu Ala Leu His Asn His Tyr Thr Gln Lys Ser Leu Ser Leu
                645                 650                 655

Ser Pro Gly Lys
            660

<210> SEQ ID NO 57
<211> LENGTH: 641
<212> TYPE: PRT
<213> ORGANISM: Artificial Sequence
<220> FEATURE:
<223> OTHER INFORMATION: Synthetic: RSLV-608 Without a leader sequence

<400> SEQUENCE: 57

Lys Asn Leu Lys Ser Pro Gln Lys Val Glu Val Asp Ile Ile Asp Asp
1               5                   10                  15

Asn Phe Ile Leu Arg Trp Asn Arg Ser Asp Glu Ser Val Gly Asn Val
            20                  25                  30

Thr Phe Ser Phe Asp Tyr Gln Lys Thr Gly Met Asp Asn Trp Ile Lys
        35                  40                  45

Leu Ser Gly Cys Gln Asn Ile Thr Ser Thr Lys Cys Asn Phe Ser Ser
    50                  55                  60

Leu Lys Leu Asn Val Tyr Glu Glu Ile Lys Leu Arg Ile Arg Ala Glu
65                  70                  75                  80

Lys Glu Asn Thr Ser Ser Trp Tyr Glu Val Asp Ser Phe Thr Pro Phe
                85                  90                  95

Arg Lys Ala Gln Ile Gly Pro Pro Glu Val His Leu Glu Ala Glu Asp
            100                 105                 110

Lys Ala Ile Val Ile His Ile Ser Pro Gly Thr Lys Asp Ser Val Met
        115                 120                 125

Trp Ala Leu Asp Gly Leu Ser Phe Thr Tyr Ser Leu Val Ile Trp Lys
    130                 135                 140

Asn Ser Ser Gly Val Glu Glu Arg Ile Glu Asn Ile Tyr Ser Arg His
145                 150                 155                 160
```

```
Lys Ile Tyr Lys Leu Ser Pro Glu Thr Thr Tyr Cys Leu Lys Val Lys
                165                 170                 175

Ala Ala Leu Leu Thr Ser Trp Lys Ile Gly Val Tyr Ser Pro Val His
            180                 185                 190

Cys Ile Lys Thr Thr Val Glu Asn Glu Leu Pro Pro Pro Glu Asn Ile
        195                 200                 205

Glu Val Ser Val Gln Asn Gln Asn Tyr Val Leu Lys Trp Asp Tyr Thr
    210                 215                 220

Tyr Ala Asn Met Thr Phe Gln Val Gln Trp Leu His Ala Phe Leu Lys
225                 230                 235                 240

Arg Asn Pro Gly Asn His Leu Tyr Lys Trp Lys Gln Ile Pro Asp Cys
                245                 250                 255

Glu Asn Val Lys Thr Thr Gln Cys Val Phe Pro Gln Asn Val Phe Gln
            260                 265                 270

Lys Gly Ile Tyr Leu Leu Arg Val Gln Ala Ser Asp Gly Asn Asn Thr
        275                 280                 285

Ser Phe Trp Ser Glu Glu Ile Lys Phe Asp Thr Glu Ile Gln Ala Phe
    290                 295                 300

Leu Leu Pro Pro Val Phe Asn Ile Arg Ser Leu Ser Asp Ser Phe His
305                 310                 315                 320

Ile Tyr Ile Gly Ala Pro Lys Gln Ser Gly Asn Thr Pro Val Ile Gln
                325                 330                 335

Asp Tyr Pro Leu Ile Tyr Glu Ile Ile Phe Trp Glu Asn Thr Ser Asn
            340                 345                 350

Ala Glu Arg Lys Ile Ile Glu Lys Thr Asp Val Thr Val Pro Asn
        355                 360                 365

Leu Lys Pro Leu Thr Val Tyr Cys Val Lys Ala Arg Ala His Thr Met
    370                 375                 380

Asp Glu Lys Leu Asn Lys Ser Val Phe Ser Asp Ala Val Cys Glu
385                 390                 395                 400

Lys Thr Lys Pro Gly Asn Thr Ser Lys Glu Pro Lys Ser Ser Asp Lys
                405                 410                 415

Thr His Thr Cys Pro Pro Cys Pro Ala Pro Glu Leu Leu Gly Gly Ser
            420                 425                 430

Ser Val Phe Leu Phe Pro Pro Lys Pro Lys Asp Thr Leu Met Ile Ser
    435                 440                 445

Arg Thr Pro Glu Val Thr Cys Val Val Val Asp Val Ser His Glu Asp
450                 455                 460

Pro Glu Val Lys Phe Asn Trp Tyr Val Asp Gly Val Glu Val His Asn
465                 470                 475                 480

Ala Lys Thr Lys Pro Arg Glu Glu Gln Tyr Asn Ser Thr Tyr Arg Val
                485                 490                 495

Val Ser Val Leu Thr Val Leu His Gln Asp Trp Leu Asn Gly Lys Glu
            500                 505                 510

Tyr Lys Cys Lys Val Ser Asn Lys Ala Leu Pro Ala Ser Ile Glu Lys
    515                 520                 525

Thr Ile Ser Lys Ala Lys Gly Gln Pro Arg Glu Pro Gln Val Tyr Val
530                 535                 540

Leu Pro Pro Ser Arg Asp Glu Leu Thr Lys Asn Gln Val Ser Leu Leu
545                 550                 555                 560

Cys Leu Val Lys Gly Phe Tyr Pro Ser Asp Ile Ala Val Glu Trp Glu
                565                 570                 575
```

```
Ser Asn Gly Gln Pro Glu Asn Asn Tyr Leu Thr Trp Pro Pro Val Leu
            580                 585                 590

Asp Ser Asp Gly Ser Phe Phe Leu Tyr Ser Lys Leu Thr Val Asp Lys
        595                 600                 605

Ser Arg Trp Gln Gln Gly Asn Val Phe Ser Cys Ser Val Met His Glu
        610                 615                 620

Ala Leu His Asn His Tyr Thr Gln Lys Ser Leu Ser Leu Ser Pro Gly
625                 630                 635                 640

Lys

<210> SEQ ID NO 58
<211> LENGTH: 468
<212> TYPE: PRT
<213> ORGANISM: Artificial Sequence
<220> FEATURE:
<223> OTHER INFORMATION: Synthetic: RSLV-613 Leader- IFNAR2 (aa27-243)-
      Fc (aa 216-447) with mutations C220S, P238S, P331S, T350V, L351Y,
      F405A, Y407V

<400> SEQUENCE: 58

Met Asp Trp Thr Trp Arg Ile Leu Phe Leu Val Ala Ala Ala Thr Gly
1               5                   10                  15

Thr His Ala Ile Ser Tyr Asp Ser Pro Asp Tyr Thr Asp Glu Ser Cys
            20                  25                  30

Thr Phe Lys Ile Ser Leu Arg Asn Phe Arg Ser Ile Leu Ser Trp Glu
        35                  40                  45

Leu Lys Asn His Ser Ile Val Pro Thr His Tyr Thr Leu Leu Tyr Thr
    50                  55                  60

Ile Met Ser Lys Pro Glu Asp Leu Lys Val Val Lys Asn Cys Ala Asn
65                  70                  75                  80

Thr Thr Arg Ser Phe Cys Asp Leu Thr Asp Glu Trp Arg Ser Thr His
                85                  90                  95

Glu Ala Tyr Val Thr Val Leu Glu Gly Phe Ser Gly Asn Thr Thr Leu
            100                 105                 110

Phe Ser Cys Ser His Asn Phe Trp Leu Ala Ile Asp Met Ser Phe Glu
        115                 120                 125

Pro Pro Glu Phe Glu Ile Val Gly Phe Thr Asn His Ile Asn Val Met
    130                 135                 140

Val Lys Phe Pro Ser Ile Val Glu Glu Glu Leu Gln Phe Asp Leu Ser
145                 150                 155                 160

Leu Val Ile Glu Glu Gln Ser Glu Gly Ile Val Lys Lys His Lys Pro
                165                 170                 175

Glu Ile Lys Gly Asn Met Ser Gly Asn Phe Thr Tyr Ile Ile Asp Lys
            180                 185                 190

Leu Ile Pro Asn Thr Asn Tyr Cys Val Ser Val Tyr Leu Glu His Ser
        195                 200                 205

Asp Glu Gln Ala Val Ile Lys Ser Pro Leu Lys Cys Thr Leu Leu Pro
    210                 215                 220

Pro Gly Gln Glu Ser Glu Ser Ala Glu Ser Ala Lys Glu Pro Lys Ser
225                 230                 235                 240

Ser Asp Lys Thr His Thr Cys Pro Pro Cys Pro Ala Pro Glu Leu Leu
                245                 250                 255

Gly Gly Ser Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285
```

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Ser
            340                 345                 350

Ile Glu Lys Thr Ile Ser Lys Ala Lys Gly Gln Pro Arg Glu Pro Gln
        355                 360                 365

Val Tyr Val Tyr Pro Pro Ser Arg Asp Glu Leu Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Ala Leu Val Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465

<210> SEQ ID NO 59
<211> LENGTH: 449
<212> TYPE: PRT
<213> ORGANISM: Artificial Sequence
<220> FEATURE:
<223> OTHER INFORMATION: Synthetic: RSLV-613 Without a leader sequence

<400> SEQUENCE: 59

Ile Ser Tyr Asp Ser Pro Asp Tyr Thr Asp Glu Ser Cys Thr Phe Lys
1               5                   10                  15

Ile Ser Leu Arg Asn Phe Arg Ser Ile Leu Ser Trp Glu Leu Lys Asn
            20                  25                  30

His Ser Ile Val Pro Thr His Tyr Thr Leu Leu Tyr Thr Ile Met Ser
        35                  40                  45

Lys Pro Glu Asp Leu Lys Val Val Lys Asn Cys Ala Asn Thr Thr Arg
    50                  55                  60

Ser Phe Cys Asp Leu Thr Asp Glu Trp Arg Ser Thr His Glu Ala Tyr
65                  70                  75                  80

Val Thr Val Leu Glu Gly Phe Ser Gly Asn Thr Thr Leu Phe Ser Cys
                85                  90                  95

Ser His Asn Phe Trp Leu Ala Ile Asp Met Ser Phe Glu Pro Pro Glu
            100                 105                 110

Phe Glu Ile Val Gly Phe Thr Asn His Ile Asn Val Met Val Lys Phe
        115                 120                 125

Pro Ser Ile Val Glu Glu Glu Leu Gln Phe Asp Leu Ser Leu Val Ile
    130                 135                 140

Glu Glu Gln Ser Glu Gly Ile Val Lys Lys His Lys Pro Glu Ile Lys
145                 150                 155                 160

Gly Asn Met Ser Gly Asn Phe Thr Tyr Ile Ile Asp Lys Leu Ile Pro
                165                 170                 175

```
Asn Thr Asn Tyr Cys Val Ser Val Tyr Leu Glu His Ser Asp Glu Gln
            180                 185                 190

Ala Val Ile Lys Ser Pro Leu Lys Cys Thr Leu Leu Pro Pro Gly Gln
        195                 200                 205

Glu Ser Glu Ser Ala Glu Ser Ala Lys Glu Pro Lys Ser Ser Asp Lys
210                 215                 220

Thr His Thr Cys Pro Pro Cys Pro Ala Pro Glu Leu Leu Gly Gly Ser
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Ser Ile Glu Lys
                325                 330                 335

Thr Ile Ser Lys Ala Lys Gly Gln Pro Arg Glu Pro Gln Val Tyr Val
                340                 345                 350

Tyr Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Ala Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 60
<211> LENGTH: 680
<212> TYPE: PRT
<213> ORGANISM: Artificial Sequence
<220> FEATURE:
<223> OTHER INFORMATION: Synthetic: Leader- IFNAR1 (aa28-436)-
      (Gly4Ser)4- IgG1 Fc domain with T366Y mutation

<400> SEQUENCE: 60

Met Asp Trp Thr Trp Arg Ile Leu Phe Leu Val Ala Ala Ala Thr Gly
1               5                   10                  15

Thr His Ala Lys Asn Leu Lys Ser Pro Gln Lys Val Glu Val Asp Ile
            20                  25                  30

Ile Asp Asp Asn Phe Ile Leu Arg Trp Asn Arg Ser Asp Glu Ser Val
        35                  40                  45

Gly Asn Val Thr Phe Ser Phe Asp Tyr Gln Lys Thr Gly Met Asp Asn
    50                  55                  60

Trp Ile Lys Leu Ser Gly Cys Gln Asn Ile Thr Ser Thr Lys Cys Asn
65                  70                  75                  80
```

Phe Ser Ser Leu Lys Leu Asn Val Tyr Glu Ile Lys Leu Arg Ile
                85                  90                  95

Arg Ala Glu Lys Glu Asn Thr Ser Ser Trp Tyr Glu Val Asp Ser Phe
                100                 105                 110

Thr Pro Phe Arg Lys Ala Gln Ile Gly Pro Pro Glu Val His Leu Glu
                115                 120                 125

Ala Glu Asp Lys Ala Ile Val Ile His Ile Ser Pro Gly Thr Lys Asp
130                 135                 140

Ser Val Met Trp Ala Leu Asp Gly Leu Ser Phe Thr Tyr Ser Leu Val
145                 150                 155                 160

Ile Trp Lys Asn Ser Ser Gly Val Glu Glu Arg Ile Glu Asn Ile Tyr
                165                 170                 175

Ser Arg His Lys Ile Tyr Lys Leu Ser Pro Glu Thr Thr Tyr Cys Leu
                180                 185                 190

Lys Val Lys Ala Ala Leu Leu Thr Ser Trp Lys Ile Gly Val Tyr Ser
                195                 200                 205

Pro Val His Cys Ile Lys Thr Thr Val Glu Asn Glu Leu Pro Pro Pro
                210                 215                 220

Glu Asn Ile Glu Val Ser Val Gln Asn Gln Asn Tyr Val Leu Lys Trp
225                 230                 235                 240

Asp Tyr Thr Tyr Ala Asn Met Thr Phe Gln Val Gln Trp Leu His Ala
                245                 250                 255

Phe Leu Lys Arg Asn Pro Gly Asn His Leu Tyr Lys Trp Lys Gln Ile
                260                 265                 270

Pro Asp Cys Glu Asn Val Lys Thr Thr Gln Cys Val Phe Pro Gln Asn
                275                 280                 285

Val Phe Gln Lys Gly Ile Tyr Leu Leu Arg Val Gln Ala Ser Asp Gly
                290                 295                 300

Asn Asn Thr Ser Phe Trp Ser Glu Glu Ile Lys Phe Asp Thr Glu Ile
305                 310                 315                 320

Gln Ala Phe Leu Leu Pro Pro Val Phe Asn Ile Arg Ser Leu Ser Asp
                325                 330                 335

Ser Phe His Ile Tyr Ile Gly Ala Pro Lys Gln Ser Gly Asn Thr Pro
                340                 345                 350

Val Ile Gln Asp Tyr Pro Leu Ile Tyr Glu Ile Ile Phe Trp Glu Asn
                355                 360                 365

Thr Ser Asn Ala Glu Arg Lys Ile Ile Glu Lys Lys Thr Asp Val Thr
370                 375                 380

Val Pro Asn Leu Lys Pro Leu Thr Val Tyr Cys Val Lys Ala Arg Ala
385                 390                 395                 400

His Thr Met Asp Glu Lys Leu Asn Lys Ser Ser Val Phe Ser Asp Ala
                405                 410                 415

Val Cys Glu Lys Thr Lys Pro Gly Asn Thr Ser Lys Gly Gly Gly Gly
                420                 425                 430

Ser Gly Gly Gly Gly Ser Gly Gly Ser Gly Gly Gly Gly Ser
                435                 440                 445

Glu Pro Lys Ser Cys Asp Lys Thr His Thr Cys Pro Pro Cys Pro Ala
450                 455                 460

Pro Glu Leu Leu Gly Gly Pro Ser Val Phe Leu Phe Pro Pro Lys Pro
465                 470                 475                 480

Lys Asp Thr Leu Met Ile Ser Arg Thr Pro Glu Val Thr Cys Val Val
                485                 490                 495

```
Val Asp Val Ser His Glu Asp Pro Glu Val Lys Phe Asn Trp Tyr Val
            500                 505                 510

Asp Gly Val Glu Val His Asn Ala Lys Thr Lys Pro Arg Glu Glu Gln
        515                 520                 525

Tyr Asn Ser Thr Tyr Arg Val Val Ser Val Leu Thr Val Leu His Gln
    530                 535                 540

Asp Trp Leu Asn Gly Lys Glu Tyr Lys Cys Lys Val Ser Asn Lys Ala
545                 550                 555                 560

Leu Pro Ala Pro Ile Glu Lys Thr Ile Ser Lys Ala Lys Gly Gln Pro
                565                 570                 575

Arg Glu Pro Gln Val Tyr Thr Leu Pro Pro Ser Arg Asp Glu Leu Thr
            580                 585                 590

Lys Asn Gln Val Ser Leu Tyr Cys Leu Val Lys Gly Phe Tyr Pro Ser
        595                 600                 605

Asp Ile Ala Val Glu Trp Glu Ser Asn Gly Gln Pro Glu Asn Asn Tyr
    610                 615                 620

Lys Thr Thr Pro Pro Val Leu Asp Ser Asp Gly Ser Phe Phe Leu Tyr
625                 630                 635                 640

Ser Lys Leu Thr Val Asp Lys Ser Arg Trp Gln Gln Gly Asn Val Phe
                645                 650                 655

Ser Cys Ser Val Met His Glu Ala Leu His Asn His Tyr Thr Gln Lys
            660                 665                 670

Ser Leu Ser Leu Ser Pro Gly Lys
        675                 680

<210> SEQ ID NO 61
<211> LENGTH: 661
<212> TYPE: PRT
<213> ORGANISM: Artificial Sequence
<220> FEATURE:
<223> OTHER INFORMATION: Synthetic: IFNAR1 (aa28-436)- (Gly4Ser)4- IgG1
      Fc domain with T366Y mutation without a leader sequence

<400> SEQUENCE: 61

Lys Asn Leu Lys Ser Pro Gln Lys Val Glu Val Asp Ile Ile Asp Asp
1               5                   10                  15

Asn Phe Ile Leu Arg Trp Asn Arg Ser Asp Glu Ser Val Gly Asn Val
            20                  25                  30

Thr Phe Ser Phe Asp Tyr Gln Lys Thr Gly Met Asp Asn Trp Ile Lys
        35                  40                  45

Leu Ser Gly Cys Gln Asn Ile Thr Ser Thr Lys Cys Asn Phe Ser Ser
    50                  55                  60

Leu Lys Leu Asn Val Tyr Glu Glu Ile Lys Leu Arg Ile Arg Ala Glu
65                  70                  75                  80

Lys Glu Asn Thr Ser Ser Trp Tyr Glu Val Asp Ser Phe Thr Pro Phe
                85                  90                  95

Arg Lys Ala Gln Ile Gly Pro Pro Glu Val His Leu Glu Ala Glu Asp
            100                 105                 110

Lys Ala Ile Val Ile His Ile Ser Pro Gly Thr Lys Asp Ser Val Met
        115                 120                 125

Trp Ala Leu Asp Gly Leu Ser Phe Thr Tyr Ser Leu Val Ile Trp Lys
    130                 135                 140

Asn Ser Ser Gly Val Glu Glu Arg Ile Glu Asn Ile Tyr Ser Arg His
145                 150                 155                 160

Lys Ile Tyr Lys Leu Ser Pro Glu Thr Thr Tyr Cys Leu Lys Val Lys
                165                 170                 175
```

```
Ala Ala Leu Leu Thr Ser Trp Lys Ile Gly Val Tyr Ser Pro Val His
            180                 185                 190

Cys Ile Lys Thr Thr Val Glu Asn Glu Leu Pro Pro Glu Asn Ile
        195                 200                 205

Glu Val Ser Val Gln Asn Gln Asn Tyr Val Leu Lys Trp Asp Tyr Thr
210                 215                 220

Tyr Ala Asn Met Thr Phe Gln Val Gln Trp Leu His Ala Phe Leu Lys
225                 230                 235                 240

Arg Asn Pro Gly Asn His Leu Tyr Lys Trp Lys Gln Ile Pro Asp Cys
                245                 250                 255

Glu Asn Val Lys Thr Thr Gln Cys Val Phe Pro Gln Asn Val Phe Gln
            260                 265                 270

Lys Gly Ile Tyr Leu Leu Arg Val Gln Ala Ser Asp Gly Asn Asn Thr
        275                 280                 285

Ser Phe Trp Ser Glu Glu Ile Lys Phe Asp Thr Glu Ile Gln Ala Phe
    290                 295                 300

Leu Leu Pro Pro Val Phe Asn Ile Arg Ser Leu Ser Asp Ser Phe His
305                 310                 315                 320

Ile Tyr Ile Gly Ala Pro Lys Gln Ser Gly Asn Thr Pro Val Ile Gln
                325                 330                 335

Asp Tyr Pro Leu Ile Tyr Glu Ile Ile Phe Trp Glu Asn Thr Ser Asn
            340                 345                 350

Ala Glu Arg Lys Ile Ile Glu Lys Lys Thr Asp Val Thr Val Pro Asn
        355                 360                 365

Leu Lys Pro Leu Thr Val Tyr Cys Val Lys Ala Arg Ala His Thr Met
    370                 375                 380

Asp Glu Lys Leu Asn Lys Ser Ser Val Phe Ser Asp Ala Val Cys Glu
385                 390                 395                 400

Lys Thr Lys Pro Gly Asn Thr Ser Lys Gly Gly Gly Ser Gly Gly
                405                 410                 415

Gly Gly Ser Gly Gly Gly Ser Gly Gly Gly Ser Glu Pro Lys
            420                 425                 430

Ser Cys Asp Lys Thr His Thr Cys Pro Pro Cys Pro Ala Pro Glu Leu
        435                 440                 445

Leu Gly Gly Pro Ser Val Phe Leu Phe Pro Pro Lys Pro Lys Asp Thr
    450                 455                 460

Leu Met Ile Ser Arg Thr Pro Glu Val Thr Cys Val Val Val Asp Val
465                 470                 475                 480

Ser His Glu Asp Pro Glu Val Lys Phe Asn Trp Tyr Val Asp Gly Val
                485                 490                 495

Glu Val His Asn Ala Lys Thr Lys Pro Arg Glu Glu Gln Tyr Asn Ser
            500                 505                 510

Thr Tyr Arg Val Val Ser Val Leu Thr Val Leu His Gln Asp Trp Leu
        515                 520                 525

Asn Gly Lys Glu Tyr Lys Cys Lys Val Ser Asn Lys Ala Leu Pro Ala
    530                 535                 540

Pro Ile Glu Lys Thr Ile Ser Lys Ala Lys Gly Gln Pro Arg Glu Pro
545                 550                 555                 560

Gln Val Tyr Thr Leu Pro Pro Ser Arg Asp Glu Leu Thr Lys Asn Gln
                565                 570                 575

Val Ser Leu Tyr Cys Leu Val Lys Gly Phe Tyr Pro Ser Asp Ile Ala
            580                 585                 590
```

-continued

```
Val Glu Trp Glu Ser Asn Gly Gln Pro Glu Asn Asn Tyr Lys Thr Thr
            595                 600                 605

Pro Pro Val Leu Asp Ser Asp Gly Ser Phe Phe Leu Tyr Ser Lys Leu
        610                 615                 620

Thr Val Asp Lys Ser Arg Trp Gln Gln Gly Asn Val Phe Ser Cys Ser
625                 630                 635                 640

Val Met His Glu Ala Leu His Asn His Tyr Thr Gln Lys Ser Leu Ser
                645                 650                 655

Leu Ser Pro Gly Lys
            660

<210> SEQ ID NO 62
<211> LENGTH: 488
<212> TYPE: PRT
<213> ORGANISM: Artificial Sequence
<220> FEATURE:
<223> OTHER INFORMATION: Synthetic: Leader- IFNAR2 (aa27-243)
      (Gly4Ser)4- IgG1 Fc domain with T366Y mutation

<400> SEQUENCE: 62

Met Asp Trp Thr Trp Arg Ile Leu Phe Leu Val Ala Ala Ala Thr Gly
1               5                   10                  15

Thr His Ala Ile Ser Tyr Asp Ser Pro Asp Tyr Thr Asp Glu Ser Cys
                20                  25                  30

Thr Phe Lys Ile Ser Leu Arg Asn Phe Arg Ser Ile Leu Ser Trp Glu
            35                  40                  45

Leu Lys Asn His Ser Ile Val Pro Thr His Tyr Thr Leu Leu Tyr Thr
        50                  55                  60

Ile Met Ser Lys Pro Glu Asp Leu Lys Val Val Lys Asn Cys Ala Asn
65                  70                  75                  80

Thr Thr Arg Ser Phe Cys Asp Leu Thr Asp Glu Trp Arg Ser Thr His
                85                  90                  95

Glu Ala Tyr Val Thr Val Leu Glu Gly Phe Ser Gly Asn Thr Thr Leu
                100                 105                 110

Phe Ser Cys Ser His Asn Phe Trp Leu Ala Ile Asp Met Ser Phe Glu
            115                 120                 125

Pro Pro Glu Phe Glu Ile Val Gly Phe Thr Asn His Ile Asn Val Met
        130                 135                 140

Val Lys Phe Pro Ser Ile Val Glu Glu Leu Gln Phe Asp Leu Ser
145                 150                 155                 160

Leu Val Ile Glu Glu Gln Ser Glu Gly Ile Val Lys Lys His Lys Pro
                165                 170                 175

Glu Ile Lys Gly Asn Met Ser Gly Asn Phe Thr Tyr Ile Ile Asp Lys
            180                 185                 190

Leu Ile Pro Asn Thr Asn Tyr Cys Val Ser Val Tyr Leu Glu His Ser
        195                 200                 205

Asp Glu Gln Ala Val Ile Lys Ser Pro Leu Lys Cys Thr Leu Leu Pro
    210                 215                 220

Pro Gly Gln Glu Ser Glu Ser Ala Glu Ser Ala Lys Gly Gly Gly Gly
225                 230                 235                 240

Ser Gly Gly Gly Gly Ser Gly Gly Gly Ser Gly Gly Gly Gly Ser
                245                 250                 255

Glu Pro Lys Ser Cys Asp Lys Thr His Thr Cys Pro Pro Cys Pro Ala
            260                 265                 270

Pro Glu Leu Leu Gly Gly Pro Ser Val Phe Leu Phe Pro Pro Lys Pro
        275                 280                 285
```

```
Lys Asp Thr Leu Met Ile Ser Arg Thr Pro Glu Val Thr Cys Val Val
        290                 295                 300

Val Asp Val Ser His Glu Asp Pro Glu Val Lys Phe Asn Trp Tyr Val
305                 310                 315                 320

Asp Gly Val Glu Val His Asn Ala Lys Thr Lys Pro Arg Glu Glu Gln
                325                 330                 335

Tyr Asn Ser Thr Tyr Arg Val Val Ser Val Leu Thr Val Leu His Gln
                340                 345                 350

Asp Trp Leu Asn Gly Lys Glu Tyr Lys Cys Lys Val Ser Asn Lys Ala
            355                 360                 365

Leu Pro Ala Pro Ile Glu Lys Thr Ile Ser Lys Ala Lys Gly Gln Pro
370                 375                 380

Arg Glu Pro Gln Val Tyr Thr Leu Pro Pro Ser Arg Asp Glu Leu Thr
385                 390                 395                 400

Lys Asn Gln Val Ser Leu Tyr Cys Leu Val Lys Gly Phe Tyr Pro Ser
                405                 410                 415

Asp Ile Ala Val Glu Trp Glu Ser Asn Gly Gln Pro Glu Asn Asn Tyr
                420                 425                 430

Lys Thr Thr Pro Pro Val Leu Asp Ser Asp Gly Ser Phe Phe Leu Tyr
            435                 440                 445

Ser Lys Leu Thr Val Asp Lys Ser Arg Trp Gln Gln Gly Asn Val Phe
450                 455                 460

Ser Cys Ser Val Met His Glu Ala Leu His Asn His Tyr Thr Gln Lys
465                 470                 475                 480

Ser Leu Ser Leu Ser Pro Gly Lys
                485

<210> SEQ ID NO 63
<211> LENGTH: 469
<212> TYPE: PRT
<213> ORGANISM: Artificial Sequence
<220> FEATURE:
<223> OTHER INFORMATION: Synthetic: IFNAR2 (aa27-243) (Gly4Ser)4- IgG1
      Fc domain with T366Y mutation without a leader sequence

<400> SEQUENCE: 63

Ile Ser Tyr Asp Ser Pro Asp Tyr Thr Asp Glu Ser Cys Thr Phe Lys
1               5                   10                  15

Ile Ser Leu Arg Asn Phe Arg Ser Ile Leu Ser Trp Glu Leu Lys Asn
            20                  25                  30

His Ser Ile Val Pro Thr His Tyr Thr Leu Leu Tyr Thr Ile Met Ser
        35                  40                  45

Lys Pro Glu Asp Leu Lys Val Val Lys Asn Cys Ala Asn Thr Thr Arg
50                  55                  60

Ser Phe Cys Asp Leu Thr Asp Glu Trp Arg Ser Thr His Glu Ala Tyr
65                  70                  75                  80

Val Thr Val Leu Glu Gly Phe Ser Gly Asn Thr Thr Leu Phe Ser Cys
                85                  90                  95

Ser His Asn Phe Trp Leu Ala Ile Asp Met Ser Phe Glu Pro Pro Glu
            100                 105                 110

Phe Glu Ile Val Gly Phe Thr Asn His Ile Asn Val Met Val Lys Phe
        115                 120                 125

Pro Ser Ile Val Glu Glu Glu Leu Gln Phe Asp Leu Ser Leu Val Ile
    130                 135                 140

Glu Glu Gln Ser Glu Gly Ile Val Lys Lys His Lys Pro Glu Ile Lys
```

-continued

```
                145                 150                 155                 160
        Gly Asn Met Ser Gly Asn Phe Thr Tyr Ile Ile Asp Lys Leu Ile Pro
                        165                 170                 175
        Asn Thr Asn Tyr Cys Val Ser Val Tyr Leu Glu His Ser Asp Glu Gln
                    180                 185                 190
        Ala Val Ile Lys Ser Pro Leu Lys Cys Thr Leu Leu Pro Pro Gly Gln
                    195                 200                 205
        Glu Ser Glu Ser Ala Glu Ser Ala Lys Gly Gly Gly Ser Gly Gly
            210                 215                 220
        Gly Gly Ser Gly Gly Gly Ser Gly Gly Gly Ser Glu Pro Lys
        225                 230                 235                 240
        Ser Cys Asp Lys Thr His Thr Cys Pro Pro Cys Pro Ala Pro Glu Leu
                        245                 250                 255
        Leu Gly Gly Pro Ser Val Phe Leu Phe Pro Pro Lys Pro Lys Asp Thr
                    260                 265                 270
        Leu Met Ile Ser Arg Thr Pro Glu Val Thr Cys Val Val Val Asp Val
                    275                 280                 285
        Ser His Glu Asp Pro Glu Val Lys Phe Asn Trp Tyr Val Asp Gly Val
                290                 295                 300
        Glu Val His Asn Ala Lys Thr Lys Pro Arg Glu Glu Gln Tyr Asn Ser
        305                 310                 315                 320
        Thr Tyr Arg Val Val Ser Val Leu Thr Val Leu His Gln Asp Trp Leu
                        325                 330                 335
        Asn Gly Lys Glu Tyr Lys Cys Lys Val Ser Asn Lys Ala Leu Pro Ala
                    340                 345                 350
        Pro Ile Glu Lys Thr Ile Ser Lys Ala Lys Gly Gln Pro Arg Glu Pro
                    355                 360                 365
        Gln Val Tyr Thr Leu Pro Pro Ser Arg Asp Glu Leu Thr Lys Asn Gln
                370                 375                 380
        Val Ser Leu Tyr Cys Leu Val Lys Gly Phe Tyr Pro Ser Asp Ile Ala
        385                 390                 395                 400
        Val Glu Trp Glu Ser Asn Gly Gln Pro Glu Asn Asn Tyr Lys Thr Thr
                        405                 410                 415
        Pro Pro Val Leu Asp Ser Asp Gly Ser Phe Phe Leu Tyr Ser Lys Leu
                    420                 425                 430
        Thr Val Asp Lys Ser Arg Trp Gln Gln Gly Asn Val Phe Ser Cys Ser
                    435                 440                 445
        Val Met His Glu Ala Leu His Asn His Tyr Thr Gln Lys Ser Leu Ser
                450                 455                 460
        Leu Ser Pro Gly Lys
        465

<210> SEQ ID NO 64
<211> LENGTH: 680
<212> TYPE: PRT
<213> ORGANISM: Artificial Sequence
<220> FEATURE:
<223> OTHER INFORMATION: Synthetic: Leader- IFNAR1 (aa28-436)-
      (Gly4Ser)4- IgG1 Fc domain with Y407T mutation

<400> SEQUENCE: 64

Met Asp Trp Thr Trp Arg Ile Leu Phe Leu Val Ala Ala Ala Thr Gly
1               5                   10                  15
Thr His Ala Lys Asn Leu Lys Ser Pro Gln Lys Val Glu Val Asp Ile
                20                  25                  30
```

-continued

```
Ile Asp Asp Asn Phe Ile Leu Arg Trp Asn Arg Ser Asp Glu Ser Val
         35                  40                  45

Gly Asn Val Thr Phe Ser Phe Asp Tyr Gln Lys Thr Gly Met Asp Asn
 50                  55                  60

Trp Ile Lys Leu Ser Gly Cys Gln Asn Ile Thr Ser Thr Lys Cys Asn
 65                  70                  75                  80

Phe Ser Ser Leu Lys Leu Asn Val Tyr Glu Glu Ile Lys Leu Arg Ile
                 85                  90                  95

Arg Ala Glu Lys Glu Asn Thr Ser Ser Trp Tyr Glu Val Asp Ser Phe
             100                 105                 110

Thr Pro Phe Arg Lys Ala Gln Ile Gly Pro Pro Glu Val His Leu Glu
         115                 120                 125

Ala Glu Asp Lys Ala Ile Val Ile His Ile Ser Pro Gly Thr Lys Asp
         130                 135                 140

Ser Val Met Trp Ala Leu Asp Gly Leu Ser Phe Thr Tyr Ser Leu Val
145                 150                 155                 160

Ile Trp Lys Asn Ser Ser Gly Val Glu Glu Arg Ile Glu Asn Ile Tyr
                 165                 170                 175

Ser Arg His Lys Ile Tyr Lys Leu Ser Pro Glu Thr Thr Tyr Cys Leu
             180                 185                 190

Lys Val Lys Ala Ala Leu Leu Thr Ser Trp Lys Ile Gly Val Tyr Ser
         195                 200                 205

Pro Val His Cys Ile Lys Thr Thr Val Glu Asn Glu Leu Pro Pro Pro
         210                 215                 220

Glu Asn Ile Glu Val Ser Val Gln Asn Gln Asn Tyr Val Leu Lys Trp
225                 230                 235                 240

Asp Tyr Thr Tyr Ala Asn Met Thr Phe Gln Val Gln Trp Leu His Ala
                 245                 250                 255

Phe Leu Lys Arg Asn Pro Gly Asn His Leu Tyr Lys Trp Lys Gln Ile
             260                 265                 270

Pro Asp Cys Glu Asn Val Lys Thr Thr Gln Cys Val Phe Pro Gln Asn
         275                 280                 285

Val Phe Gln Lys Gly Ile Tyr Leu Leu Arg Val Gln Ala Ser Asp Gly
         290                 295                 300

Asn Asn Thr Ser Phe Trp Ser Glu Glu Ile Lys Phe Asp Thr Glu Ile
305                 310                 315                 320

Gln Ala Phe Leu Leu Pro Pro Val Phe Asn Ile Arg Ser Leu Ser Asp
                 325                 330                 335

Ser Phe His Ile Tyr Ile Gly Ala Pro Lys Gln Ser Gly Asn Thr Pro
             340                 345                 350

Val Ile Gln Asp Tyr Pro Leu Ile Tyr Glu Ile Phe Trp Glu Asn
         355                 360                 365

Thr Ser Asn Ala Glu Arg Lys Ile Ile Glu Lys Lys Thr Asp Val Thr
         370                 375                 380

Val Pro Asn Leu Lys Pro Leu Thr Val Tyr Cys Val Lys Ala Arg Ala
385                 390                 395                 400

His Thr Met Asp Glu Lys Leu Asn Lys Ser Ser Val Phe Ser Asp Ala
                 405                 410                 415

Val Cys Glu Lys Thr Lys Pro Gly Asn Thr Ser Lys Gly Gly Gly Gly
             420                 425                 430

Ser Gly Gly Gly Gly Ser Gly Gly Gly Gly Ser Gly Gly Gly Gly Ser
         435                 440                 445

Glu Pro Lys Ser Cys Asp Lys Thr His Thr Cys Pro Pro Cys Pro Ala
```

```
            450                 455                 460
Pro Glu Leu Leu Gly Gly Pro Ser Val Phe Leu Phe Pro Pro Lys Pro
465                 470                 475                 480

Lys Asp Thr Leu Met Ile Ser Arg Thr Pro Glu Val Thr Cys Val Val
                485                 490                 495

Val Asp Val Ser His Glu Asp Pro Glu Val Lys Phe Asn Trp Tyr Val
                500                 505                 510

Asp Gly Val Glu Val His Asn Ala Lys Thr Lys Pro Arg Glu Glu Gln
            515                 520                 525

Tyr Asn Ser Thr Tyr Arg Val Val Ser Val Leu Thr Val Leu His Gln
        530                 535                 540

Asp Trp Leu Asn Gly Lys Glu Tyr Lys Cys Lys Val Ser Asn Lys Ala
545                 550                 555                 560

Leu Pro Ala Pro Ile Glu Lys Thr Ile Ser Lys Ala Lys Gly Gln Pro
                565                 570                 575

Arg Glu Pro Gln Val Tyr Thr Leu Pro Pro Ser Arg Asp Glu Leu Thr
            580                 585                 590

Lys Asn Gln Val Ser Leu Thr Cys Leu Val Lys Gly Phe Tyr Pro Ser
        595                 600                 605

Asp Ile Ala Val Glu Trp Glu Ser Asn Gly Gln Pro Glu Asn Asn Tyr
    610                 615                 620

Lys Thr Thr Pro Pro Val Leu Asp Ser Asp Gly Ser Phe Phe Leu Thr
625                 630                 635                 640

Ser Lys Leu Thr Val Asp Lys Ser Arg Trp Gln Gln Gly Asn Val Phe
                645                 650                 655

Ser Cys Ser Val Met His Glu Ala Leu His Asn His Tyr Thr Gln Lys
            660                 665                 670

Ser Leu Ser Leu Ser Pro Gly Lys
        675                 680

<210> SEQ ID NO 65
<211> LENGTH: 661
<212> TYPE: PRT
<213> ORGANISM: Artificial Sequence
<220> FEATURE:
<223> OTHER INFORMATION: Synthetic: IFNAR1 (aa28-436)- (Gly4Ser)4- IgG1
      Fc domain with Y407T mutation without a leader sequence

<400> SEQUENCE: 65

Lys Asn Leu Lys Ser Pro Gln Lys Val Glu Val Asp Ile Ile Asp Asp
1               5                   10                  15

Asn Phe Ile Leu Arg Trp Asn Arg Ser Asp Glu Ser Val Gly Asn Val
            20                  25                  30

Thr Phe Ser Phe Asp Tyr Gln Lys Thr Gly Met Asp Asn Trp Ile Lys
        35                  40                  45

Leu Ser Gly Cys Gln Asn Ile Thr Ser Thr Lys Cys Asn Phe Ser Ser
    50                  55                  60

Leu Lys Leu Asn Val Tyr Glu Glu Ile Lys Leu Arg Ile Arg Ala Glu
65                  70                  75                  80

Lys Glu Asn Thr Ser Ser Trp Tyr Glu Val Asp Ser Phe Thr Pro Phe
                85                  90                  95

Arg Lys Ala Gln Ile Gly Pro Pro Glu Val His Leu Glu Ala Glu Asp
            100                 105                 110

Lys Ala Ile Val Ile His Ile Ser Pro Gly Thr Lys Asp Ser Val Met
        115                 120                 125
```

```
Trp Ala Leu Asp Gly Leu Ser Phe Thr Tyr Ser Leu Val Ile Trp Lys
    130                 135                 140

Asn Ser Ser Gly Val Glu Glu Arg Ile Glu Asn Ile Tyr Ser Arg His
145                 150                 155                 160

Lys Ile Tyr Lys Leu Ser Pro Glu Thr Thr Tyr Cys Leu Lys Val Lys
                165                 170                 175

Ala Ala Leu Leu Thr Ser Trp Lys Ile Gly Val Tyr Ser Pro Val His
            180                 185                 190

Cys Ile Lys Thr Thr Val Glu Asn Glu Leu Pro Pro Pro Glu Asn Ile
        195                 200                 205

Glu Val Ser Val Gln Asn Gln Asn Tyr Val Leu Lys Trp Asp Tyr Thr
    210                 215                 220

Tyr Ala Asn Met Thr Phe Gln Val Gln Trp Leu His Ala Phe Leu Lys
225                 230                 235                 240

Arg Asn Pro Gly Asn His Leu Tyr Lys Trp Lys Gln Ile Pro Asp Cys
                245                 250                 255

Glu Asn Val Lys Thr Thr Gln Cys Val Phe Pro Gln Asn Val Phe Gln
            260                 265                 270

Lys Gly Ile Tyr Leu Leu Arg Val Gln Ala Ser Asp Gly Asn Asn Thr
        275                 280                 285

Ser Phe Trp Ser Glu Glu Ile Lys Phe Asp Thr Glu Ile Gln Ala Phe
    290                 295                 300

Leu Leu Pro Pro Val Phe Asn Ile Arg Ser Leu Ser Asp Ser Phe His
305                 310                 315                 320

Ile Tyr Ile Gly Ala Pro Lys Gln Ser Gly Asn Thr Pro Val Ile Gln
                325                 330                 335

Asp Tyr Pro Leu Ile Tyr Glu Ile Ile Phe Trp Glu Asn Thr Ser Asn
            340                 345                 350

Ala Glu Arg Lys Ile Ile Glu Lys Lys Thr Asp Val Thr Val Pro Asn
        355                 360                 365

Leu Lys Pro Leu Thr Val Tyr Cys Val Lys Ala Arg Ala His Thr Met
    370                 375                 380

Asp Glu Lys Leu Asn Lys Ser Ser Val Phe Ser Asp Ala Val Cys Glu
385                 390                 395                 400

Lys Thr Lys Pro Gly Asn Thr Ser Lys Gly Gly Gly Ser Gly Gly
                405                 410                 415

Gly Gly Ser Gly Gly Gly Ser Gly Gly Gly Ser Glu Pro Lys
            420                 425                 430

Ser Cys Asp Lys Thr His Thr Cys Pro Pro Cys Pro Ala Pro Glu Leu
        435                 440                 445

Leu Gly Gly Pro Ser Val Phe Leu Phe Pro Pro Lys Pro Lys Asp Thr
    450                 455                 460

Leu Met Ile Ser Arg Thr Pro Glu Val Thr Cys Val Val Val Asp Val
465                 470                 475                 480

Ser His Glu Asp Pro Glu Val Lys Phe Asn Trp Tyr Val Asp Gly Val
                485                 490                 495

Glu Val His Asn Ala Lys Thr Lys Pro Arg Glu Glu Gln Tyr Asn Ser
            500                 505                 510

Thr Tyr Arg Val Val Ser Val Leu Thr Val Leu His Gln Asp Trp Leu
        515                 520                 525

Asn Gly Lys Glu Tyr Lys Cys Lys Val Ser Asn Lys Ala Leu Pro Ala
    530                 535                 540

Pro Ile Glu Lys Thr Ile Ser Lys Ala Lys Gly Gln Pro Arg Glu Pro
```

```
                545                 550                 555                 560
        Gln Val Tyr Thr Leu Pro Pro Ser Arg Asp Glu Leu Thr Lys Asn Gln
                        565                 570                 575

Val Ser Leu Thr Cys Leu Val Lys Gly Phe Tyr Pro Ser Asp Ile Ala
                        580                 585                 590

Val Glu Trp Glu Ser Asn Gly Gln Pro Glu Asn Asn Tyr Lys Thr Thr
                        595                 600                 605

Pro Pro Val Leu Asp Ser Asp Gly Ser Phe Phe Leu Thr Ser Lys Leu
                        610                 615                 620

Thr Val Asp Lys Ser Arg Trp Gln Gln Gly Asn Val Phe Ser Cys Ser
        625                 630                 635                 640

Val Met His Glu Ala Leu His Asn His Tyr Thr Gln Lys Ser Leu Ser
                        645                 650                 655

Leu Ser Pro Gly Lys
                        660

<210> SEQ ID NO 66
<211> LENGTH: 488
<212> TYPE: PRT
<213> ORGANISM: Artificial Sequence
<220> FEATURE:
<223> OTHER INFORMATION: Synthetic: Leader- IFNAR2 (aa27-243)-
      (Gly4Ser)4- IgG1 Fc domain with Y407T mutation

<400> SEQUENCE: 66

Met Asp Trp Thr Trp Arg Ile Leu Phe Leu Val Ala Ala Ala Thr Gly
1               5                   10                  15

Thr His Ala Ile Ser Tyr Asp Ser Pro Asp Tyr Thr Asp Glu Ser Cys
                20                  25                  30

Thr Phe Lys Ile Ser Leu Arg Asn Phe Arg Ser Ile Leu Ser Trp Glu
            35                  40                  45

Leu Lys Asn His Ser Ile Val Pro Thr His Tyr Thr Leu Leu Tyr Thr
        50                  55                  60

Ile Met Ser Lys Pro Glu Asp Leu Lys Val Val Lys Asn Cys Ala Asn
65                  70                  75                  80

Thr Thr Arg Ser Phe Cys Asp Leu Thr Asp Glu Trp Arg Ser Thr His
                85                  90                  95

Glu Ala Tyr Val Thr Val Leu Glu Gly Phe Ser Gly Asn Thr Thr Leu
                100                 105                 110

Phe Ser Cys Ser His Asn Phe Trp Leu Ala Ile Asp Met Ser Phe Glu
            115                 120                 125

Pro Pro Glu Phe Glu Ile Val Gly Phe Thr Asn His Ile Asn Val Met
        130                 135                 140

Val Lys Phe Pro Ser Ile Val Glu Glu Glu Leu Gln Phe Asp Leu Ser
145                 150                 155                 160

Leu Val Ile Glu Glu Gln Ser Glu Gly Ile Val Lys Lys His Lys Pro
                165                 170                 175

Glu Ile Lys Gly Asn Met Ser Gly Asn Phe Thr Tyr Ile Ile Asp Lys
            180                 185                 190

Leu Ile Pro Asn Thr Asn Tyr Cys Val Ser Val Tyr Leu Glu His Ser
        195                 200                 205

Asp Glu Gln Ala Val Ile Lys Ser Pro Leu Lys Cys Thr Leu Leu Pro
        210                 215                 220

Pro Gly Gln Glu Ser Glu Ser Ala Glu Ser Ala Lys Gly Gly Gly Gly
225                 230                 235                 240
```

```
Ser Gly Gly Gly Gly Ser Gly Gly Gly Gly Ser Gly Gly Gly Gly Ser
                245                 250                 255

Glu Pro Lys Ser Cys Asp Lys Thr His Thr Cys Pro Pro Cys Pro Ala
            260                 265                 270

Pro Glu Leu Leu Gly Gly Pro Ser Val Phe Leu Phe Pro Pro Lys Pro
        275                 280                 285

Lys Asp Thr Leu Met Ile Ser Arg Thr Pro Glu Val Thr Cys Val Val
    290                 295                 300

Val Asp Val Ser His Glu Asp Pro Glu Val Lys Phe Asn Trp Tyr Val
305                 310                 315                 320

Asp Gly Val Glu Val His Asn Ala Lys Thr Lys Pro Arg Glu Glu Gln
                325                 330                 335

Tyr Asn Ser Thr Tyr Arg Val Val Ser Val Leu Thr Val Leu His Gln
            340                 345                 350

Asp Trp Leu Asn Gly Lys Glu Tyr Lys Cys Lys Val Ser Asn Lys Ala
        355                 360                 365

Leu Pro Ala Pro Ile Glu Lys Thr Ile Ser Lys Ala Lys Gly Gln Pro
    370                 375                 380

Arg Glu Pro Gln Val Tyr Thr Leu Pro Pro Ser Arg Asp Glu Leu Thr
385                 390                 395                 400

Lys Asn Gln Val Ser Leu Thr Cys Leu Val Lys Gly Phe Tyr Pro Ser
                405                 410                 415

Asp Ile Ala Val Glu Trp Glu Ser Asn Gly Gln Pro Glu Asn Asn Tyr
            420                 425                 430

Lys Thr Thr Pro Pro Val Leu Asp Ser Asp Gly Ser Phe Phe Leu Thr
        435                 440                 445

Ser Lys Leu Thr Val Asp Lys Ser Arg Trp Gln Gln Gly Asn Val Phe
    450                 455                 460

Ser Cys Ser Val Met His Glu Ala Leu His Asn His Tyr Thr Gln Lys
465                 470                 475                 480

Ser Leu Ser Leu Ser Pro Gly Lys
                485
```

<210> SEQ ID NO 67
<211> LENGTH: 469
<212> TYPE: PRT
<213> ORGANISM: Artificial Sequence
<220> FEATURE:
<223> OTHER INFORMATION: Synthetic: IFNAR2 (aa27-243)- (Gly4Ser)4- IgG1 Fc domain with Y407T mutation without a leader sequence

<400> SEQUENCE: 67

```
Ile Ser Tyr Asp Ser Pro Asp Tyr Thr Asp Glu Ser Cys Thr Phe Lys
1               5                   10                  15

Ile Ser Leu Arg Asn Phe Arg Ser Ile Leu Ser Trp Glu Leu Lys Asn
            20                  25                  30

His Ser Ile Val Pro Thr His Tyr Thr Leu Leu Tyr Thr Ile Met Ser
        35                  40                  45

Lys Pro Glu Asp Leu Lys Val Val Lys Asn Cys Ala Asn Thr Thr Arg
    50                  55                  60

Ser Phe Cys Asp Leu Thr Asp Glu Trp Arg Ser Thr His Glu Ala Tyr
65                  70                  75                  80

Val Thr Val Leu Glu Gly Phe Ser Gly Asn Thr Thr Leu Phe Ser Cys
                85                  90                  95

Ser His Asn Phe Trp Leu Ala Ile Asp Met Ser Phe Glu Pro Pro Glu
            100                 105                 110
```

```
Phe Glu Ile Val Gly Phe Thr Asn His Ile Asn Val Met Val Lys Phe
            115                 120                 125
Pro Ser Ile Val Glu Glu Leu Gln Phe Asp Leu Ser Leu Val Ile
        130                 135                 140
Glu Glu Gln Ser Glu Gly Ile Val Lys Lys His Lys Pro Glu Ile Lys
145                 150                 155                 160
Gly Asn Met Ser Gly Asn Phe Thr Tyr Ile Ile Asp Lys Leu Ile Pro
                165                 170                 175
Asn Thr Asn Tyr Cys Val Ser Val Tyr Leu Glu His Ser Asp Glu Gln
                180                 185                 190
Ala Val Ile Lys Ser Pro Leu Lys Cys Thr Leu Leu Pro Pro Gly Gln
            195                 200                 205
Glu Ser Glu Ser Ala Glu Ser Ala Lys Gly Gly Gly Ser Gly Gly
        210                 215                 220
Gly Gly Ser Gly Gly Gly Ser Gly Gly Gly Ser Glu Pro Lys
225                 230                 235                 240
Ser Cys Asp Lys Thr His Thr Cys Pro Pro Cys Pro Ala Pro Glu Leu
                245                 250                 255
Leu Gly Gly Pro Ser Val Phe Leu Phe Pro Pro Lys Pro Lys Asp Thr
            260                 265                 270
Leu Met Ile Ser Arg Thr Pro Glu Val Thr Cys Val Val Val Asp Val
        275                 280                 285
Ser His Glu Asp Pro Glu Val Lys Phe Asn Trp Tyr Val Asp Gly Val
    290                 295                 300
Glu Val His Asn Ala Lys Thr Lys Pro Arg Glu Gln Tyr Asn Ser
305                 310                 315                 320
Thr Tyr Arg Val Val Ser Val Leu Thr Val Leu His Gln Asp Trp Leu
                325                 330                 335
Asn Gly Lys Glu Tyr Lys Cys Lys Val Ser Asn Lys Ala Leu Pro Ala
            340                 345                 350
Pro Ile Glu Lys Thr Ile Ser Lys Ala Lys Gly Gln Pro Arg Glu Pro
        355                 360                 365
Gln Val Tyr Thr Leu Pro Pro Ser Arg Asp Glu Leu Thr Lys Asn Gln
    370                 375                 380
Val Ser Leu Thr Cys Leu Val Lys Gly Phe Tyr Pro Ser Asp Ile Ala
385                 390                 395                 400
Val Glu Trp Glu Ser Asn Gly Gln Pro Glu Asn Asn Tyr Lys Thr Thr
                405                 410                 415
Pro Pro Val Leu Asp Ser Asp Gly Ser Phe Phe Leu Thr Ser Lys Leu
            420                 425                 430
Thr Val Asp Lys Ser Arg Trp Gln Gln Gly Asn Val Phe Ser Cys Ser
        435                 440                 445
Val Met His Glu Ala Leu His Asn His Tyr Thr Gln Lys Ser Leu Ser
    450                 455                 460
Leu Ser Pro Gly Lys
465

<210> SEQ ID NO 68
<211> LENGTH: 670
<212> TYPE: PRT
<213> ORGANISM: Artificial Sequence
<220> FEATURE:
<223> OTHER INFORMATION: Synthetic: Leader- IFNAR1 (aa28-436)-
      (Gly4Ser)2- IgG1 Fc domain with T366Y mutation
```

<400> SEQUENCE: 68

Met Asp Trp Thr Trp Arg Ile Leu Phe Leu Val Ala Ala Ala Thr Gly
1               5                   10                  15

Thr His Ala Lys Asn Leu Lys Ser Pro Gln Lys Val Glu Val Asp Ile
            20                  25                  30

Ile Asp Asp Asn Phe Ile Leu Arg Trp Asn Arg Ser Asp Glu Ser Val
        35                  40                  45

Gly Asn Val Thr Phe Ser Phe Asp Tyr Gln Lys Thr Gly Met Asp Asn
    50                  55                  60

Trp Ile Lys Leu Ser Gly Cys Gln Asn Ile Thr Ser Thr Lys Cys Asn
65                  70                  75                  80

Phe Ser Ser Leu Lys Leu Asn Val Tyr Glu Glu Ile Lys Leu Arg Ile
                85                  90                  95

Arg Ala Glu Lys Glu Asn Thr Ser Ser Trp Tyr Glu Val Asp Ser Phe
            100                 105                 110

Thr Pro Phe Arg Lys Ala Gln Ile Gly Pro Pro Glu Val His Leu Glu
        115                 120                 125

Ala Glu Asp Lys Ala Ile Val Ile His Ile Ser Pro Gly Thr Lys Asp
130                 135                 140

Ser Val Met Trp Ala Leu Asp Gly Leu Ser Phe Thr Tyr Ser Leu Val
145                 150                 155                 160

Ile Trp Lys Asn Ser Ser Gly Val Glu Glu Arg Ile Glu Asn Ile Tyr
                165                 170                 175

Ser Arg His Lys Ile Tyr Lys Leu Ser Pro Glu Thr Thr Tyr Cys Leu
            180                 185                 190

Lys Val Lys Ala Ala Leu Leu Thr Ser Trp Lys Ile Gly Val Tyr Ser
        195                 200                 205

Pro Val His Cys Ile Lys Thr Thr Val Glu Asn Glu Leu Pro Pro Pro
210                 215                 220

Glu Asn Ile Glu Val Ser Val Gln Asn Gln Asn Tyr Val Leu Lys Trp
225                 230                 235                 240

Asp Tyr Thr Tyr Ala Asn Met Thr Phe Gln Val Gln Trp Leu His Ala
                245                 250                 255

Phe Leu Lys Arg Asn Pro Gly Asn His Leu Tyr Lys Trp Lys Gln Ile
            260                 265                 270

Pro Asp Cys Glu Asn Val Lys Thr Thr Gln Cys Val Phe Pro Gln Asn
        275                 280                 285

Val Phe Gln Lys Gly Ile Tyr Leu Leu Arg Val Gln Ala Ser Asp Gly
290                 295                 300

Asn Asn Thr Ser Phe Trp Ser Glu Glu Ile Lys Phe Asp Thr Glu Ile
305                 310                 315                 320

Gln Ala Phe Leu Leu Pro Pro Val Phe Asn Ile Arg Ser Leu Ser Asp
                325                 330                 335

Ser Phe His Ile Tyr Ile Gly Ala Pro Lys Gln Ser Gly Asn Thr Pro
            340                 345                 350

Val Ile Gln Asp Tyr Pro Leu Ile Tyr Glu Ile Ile Phe Trp Glu Asn
        355                 360                 365

Thr Ser Asn Ala Glu Arg Lys Ile Ile Glu Lys Thr Asp Val Thr
370                 375                 380

Val Pro Asn Leu Lys Pro Leu Thr Val Tyr Cys Val Lys Ala Arg Ala
385                 390                 395                 400

His Thr Met Asp Glu Lys Leu Asn Lys Ser Ser Val Phe Ser Asp Ala
                405                 410                 415

Val Cys Glu Lys Thr Lys Pro Gly Asn Thr Ser Lys Gly Gly Gly
            420                 425                 430

Ser Gly Gly Gly Gly Ser Glu Pro Lys Ser Cys Asp Lys Thr His Thr
        435                 440                 445

Cys Pro Pro Cys Pro Ala Pro Glu Leu Leu Gly Gly Pro Ser Val Phe
    450                 455                 460

Leu Phe Pro Pro Lys Pro Lys Asp Thr Leu Met Ile Ser Arg Thr Pro
465                 470                 475                 480

Glu Val Thr Cys Val Val Val Asp Val Ser His Glu Asp Pro Glu Val
                485                 490                 495

Lys Phe Asn Trp Tyr Val Asp Gly Val Glu Val His Asn Ala Lys Thr
            500                 505                 510

Lys Pro Arg Glu Glu Gln Tyr Asn Ser Thr Tyr Arg Val Val Ser Val
        515                 520                 525

Leu Thr Val Leu His Gln Asp Trp Leu Asn Gly Lys Glu Tyr Lys Cys
    530                 535                 540

Lys Val Ser Asn Lys Ala Leu Pro Ala Pro Ile Glu Lys Thr Ile Ser
545                 550                 555                 560

Lys Ala Lys Gly Gln Pro Arg Glu Pro Gln Val Tyr Thr Leu Pro Pro
                565                 570                 575

Ser Arg Asp Glu Leu Thr Lys Asn Gln Val Ser Leu Tyr Cys Leu Val
            580                 585                 590

Lys Gly Phe Tyr Pro Ser Asp Ile Ala Val Glu Trp Glu Ser Asn Gly
        595                 600                 605

Gln Pro Glu Asn Asn Tyr Lys Thr Thr Pro Pro Val Leu Asp Ser Asp
    610                 615                 620

Gly Ser Phe Phe Leu Tyr Ser Lys Leu Thr Val Asp Lys Ser Arg Trp
625                 630                 635                 640

Gln Gln Gly Asn Val Phe Ser Cys Ser Val Met His Glu Ala Leu His
                645                 650                 655

Asn His Tyr Thr Gln Lys Ser Leu Ser Leu Ser Pro Gly Lys
            660                 665                 670

<210> SEQ ID NO 69
<211> LENGTH: 651
<212> TYPE: PRT
<213> ORGANISM: Artificial Sequence
<220> FEATURE:
<223> OTHER INFORMATION: Synthetic: IFNAR1 (aa28-436)- (Gly4Ser)2- IgG1
      Fc domain with T366Y mutation without a leader sequence

<400> SEQUENCE: 69

Lys Asn Leu Lys Ser Pro Gln Lys Val Glu Val Asp Ile Ile Asp Asp
1               5                   10                  15

Asn Phe Ile Leu Arg Trp Asn Arg Ser Asp Glu Ser Val Gly Asn Val
            20                  25                  30

Thr Phe Ser Phe Asp Tyr Gln Lys Thr Gly Met Asp Asn Trp Ile Lys
        35                  40                  45

Leu Ser Gly Cys Gln Asn Ile Thr Ser Thr Lys Cys Asn Phe Ser Ser
    50                  55                  60

Leu Lys Leu Asn Val Tyr Glu Glu Ile Lys Leu Arg Ile Arg Ala Glu
65                  70                  75                  80

Lys Glu Asn Thr Ser Ser Trp Tyr Glu Val Asp Ser Phe Thr Pro Phe
                85                  90                  95

Arg Lys Ala Gln Ile Gly Pro Pro Glu Val His Leu Glu Ala Glu Asp

-continued

```
                100                 105                 110
Lys Ala Ile Val Ile His Ile Ser Pro Gly Thr Lys Asp Ser Val Met
            115                 120                 125

Trp Ala Leu Asp Gly Leu Ser Phe Thr Tyr Ser Leu Val Ile Trp Lys
            130                 135                 140

Asn Ser Ser Gly Val Glu Glu Arg Ile Glu Asn Ile Tyr Ser Arg His
145                 150                 155                 160

Lys Ile Tyr Lys Leu Ser Pro Glu Thr Thr Tyr Cys Leu Lys Val Lys
                165                 170                 175

Ala Ala Leu Leu Thr Ser Trp Lys Ile Gly Val Tyr Ser Pro Val His
            180                 185                 190

Cys Ile Lys Thr Thr Val Glu Asn Glu Leu Pro Pro Glu Asn Ile
            195                 200                 205

Glu Val Ser Val Gln Asn Gln Asn Tyr Val Leu Lys Trp Asp Tyr Thr
            210                 215                 220

Tyr Ala Asn Met Thr Phe Gln Val Gln Trp Leu His Ala Phe Leu Lys
225                 230                 235                 240

Arg Asn Pro Gly Asn His Leu Tyr Lys Trp Lys Gln Ile Pro Asp Cys
                245                 250                 255

Glu Asn Val Lys Thr Thr Gln Cys Val Phe Pro Gln Asn Val Phe Gln
            260                 265                 270

Lys Gly Ile Tyr Leu Leu Arg Val Gln Ala Ser Asp Gly Asn Asn Thr
            275                 280                 285

Ser Phe Trp Ser Glu Glu Ile Lys Phe Asp Thr Glu Ile Gln Ala Phe
            290                 295                 300

Leu Leu Pro Pro Val Phe Asn Ile Arg Ser Leu Ser Asp Ser Phe His
305                 310                 315                 320

Ile Tyr Ile Gly Ala Pro Lys Gln Ser Gly Asn Thr Pro Val Ile Gln
                325                 330                 335

Asp Tyr Pro Leu Ile Tyr Glu Ile Ile Phe Trp Glu Asn Thr Ser Asn
                340                 345                 350

Ala Glu Arg Lys Ile Ile Glu Lys Lys Thr Asp Val Thr Val Pro Asn
            355                 360                 365

Leu Lys Pro Leu Thr Val Tyr Cys Val Lys Ala Arg Ala His Thr Met
            370                 375                 380

Asp Glu Lys Leu Asn Lys Ser Val Phe Ser Asp Ala Val Cys Glu
385                 390                 395                 400

Lys Thr Lys Pro Gly Asn Thr Ser Lys Gly Gly Gly Ser Gly Gly
                405                 410                 415

Gly Gly Ser Glu Pro Lys Ser Cys Asp Lys Thr His Thr Cys Pro Pro
            420                 425                 430

Cys Pro Ala Pro Glu Leu Leu Gly Gly Pro Ser Val Phe Leu Phe Pro
            435                 440                 445

Pro Lys Pro Lys Asp Thr Leu Met Ile Ser Arg Thr Pro Glu Val Thr
            450                 455                 460

Cys Val Val Val Asp Val Ser His Glu Asp Pro Glu Val Lys Phe Asn
465                 470                 475                 480

Trp Tyr Val Asp Gly Val Glu Val His Asn Ala Lys Thr Lys Pro Arg
                485                 490                 495

Glu Glu Gln Tyr Asn Ser Thr Tyr Arg Val Val Ser Val Leu Thr Val
                500                 505                 510

Leu His Gln Asp Trp Leu Asn Gly Lys Glu Tyr Lys Cys Lys Val Ser
            515                 520                 525
```

Asn Lys Ala Leu Pro Ala Pro Ile Glu Lys Thr Ile Ser Lys Ala Lys
            530                 535                 540

Gly Gln Pro Arg Glu Pro Gln Val Tyr Thr Leu Pro Pro Ser Arg Asp
545                 550                 555                 560

Glu Leu Thr Lys Asn Gln Val Ser Leu Tyr Cys Leu Val Lys Gly Phe
                565                 570                 575

Tyr Pro Ser Asp Ile Ala Val Glu Trp Glu Ser Asn Gly Gln Pro Glu
            580                 585                 590

Asn Asn Tyr Lys Thr Thr Pro Pro Val Leu Asp Ser Asp Gly Ser Phe
        595                 600                 605

Phe Leu Tyr Ser Lys Leu Thr Val Asp Lys Ser Arg Trp Gln Gln Gly
    610                 615                 620

Asn Val Phe Ser Cys Ser Val Met His Glu Ala Leu His Asn His Tyr
625                 630                 635                 640

Thr Gln Lys Ser Leu Ser Leu Ser Pro Gly Lys
                645                 650

<210> SEQ ID NO 70
<211> LENGTH: 478
<212> TYPE: PRT
<213> ORGANISM: Artificial Sequence
<220> FEATURE:
<223> OTHER INFORMATION: Synthetic: Leader- IFNAR2 (aa27-243)-
      (Gly4Ser)2- IgG1 Fc domain with T366Y mutation

<400> SEQUENCE: 70

Met Asp Trp Thr Trp Arg Ile Leu Phe Leu Val Ala Ala Thr Gly
1               5                   10                  15

Thr His Ala Ile Ser Tyr Asp Ser Pro Asp Tyr Thr Asp Glu Ser Cys
                20                  25                  30

Thr Phe Lys Ile Ser Leu Arg Asn Phe Arg Ser Ile Leu Ser Trp Glu
            35                  40                  45

Leu Lys Asn His Ser Ile Val Pro Thr His Tyr Thr Leu Leu Tyr Thr
        50                  55                  60

Ile Met Ser Lys Pro Glu Asp Leu Lys Val Val Lys Asn Cys Ala Asn
65                  70                  75                  80

Thr Thr Arg Ser Phe Cys Asp Leu Thr Asp Glu Trp Arg Ser Thr His
                85                  90                  95

Glu Ala Tyr Val Thr Val Leu Glu Gly Phe Ser Gly Asn Thr Thr Leu
                100                 105                 110

Phe Ser Cys Ser His Asn Phe Trp Leu Ala Ile Asp Met Ser Phe Glu
            115                 120                 125

Pro Pro Glu Phe Glu Ile Val Gly Phe Thr Asn His Ile Asn Val Met
130                 135                 140

Val Lys Phe Pro Ser Ile Val Glu Glu Glu Leu Gln Phe Asp Leu Ser
145                 150                 155                 160

Leu Val Ile Glu Glu Gln Ser Glu Gly Ile Val Lys Lys His Lys Pro
                165                 170                 175

Glu Ile Lys Gly Asn Met Ser Gly Asn Phe Thr Tyr Ile Ile Asp Lys
            180                 185                 190

Leu Ile Pro Asn Thr Asn Tyr Cys Val Ser Val Tyr Leu Glu His Ser
        195                 200                 205

Asp Glu Gln Ala Val Ile Lys Ser Pro Leu Lys Cys Thr Leu Leu Pro
    210                 215                 220

Pro Gly Gln Glu Ser Glu Ser Ala Glu Ser Ala Lys Gly Gly Gly Gly

```
225                 230                 235                 240
Ser Gly Gly Gly Ser Glu Pro Lys Ser Cys Asp Lys Thr His Thr
                245                 250                 255

Cys Pro Pro Cys Pro Ala Pro Glu Leu Leu Gly Gly Pro Ser Val Phe
                260                 265                 270

Leu Phe Pro Pro Lys Pro Lys Asp Thr Leu Met Ile Ser Arg Thr Pro
            275                 280                 285

Glu Val Thr Cys Val Val Val Asp Val Ser His Glu Asp Pro Glu Val
        290                 295                 300

Lys Phe Asn Trp Tyr Val Asp Gly Val Glu Val His Asn Ala Lys Thr
305                 310                 315                 320

Lys Pro Arg Glu Glu Gln Tyr Asn Ser Thr Tyr Arg Val Val Ser Val
                325                 330                 335

Leu Thr Val Leu His Gln Asp Trp Leu Asn Gly Lys Glu Tyr Lys Cys
            340                 345                 350

Lys Val Ser Asn Lys Ala Leu Pro Ala Pro Ile Glu Lys Thr Ile Ser
        355                 360                 365

Lys Ala Lys Gly Gln Pro Arg Glu Pro Gln Val Tyr Thr Leu Pro Pro
    370                 375                 380

Ser Arg Asp Glu Leu Thr Lys Asn Gln Val Ser Leu Tyr Cys Leu Val
385                 390                 395                 400

Lys Gly Phe Tyr Pro Ser Asp Ile Ala Val Glu Trp Glu Ser Asn Gly
                405                 410                 415

Gln Pro Glu Asn Asn Tyr Lys Thr Thr Pro Pro Val Leu Asp Ser Asp
            420                 425                 430

Gly Ser Phe Phe Leu Tyr Ser Lys Leu Thr Val Asp Lys Ser Arg Trp
        435                 440                 445

Gln Gln Gly Asn Val Phe Ser Cys Ser Val Met His Glu Ala Leu His
    450                 455                 460

Asn His Tyr Thr Gln Lys Ser Leu Ser Leu Ser Pro Gly Lys
465                 470                 475

<210> SEQ ID NO 71
<211> LENGTH: 459
<212> TYPE: PRT
<213> ORGANISM: Artificial Sequence
<220> FEATURE:
<223> OTHER INFORMATION: Synthetic: IFNAR2 (aa27-243)- (Gly4Ser)2- IgG1
      Fc domain with T366Y mutation without a leader sequence

<400> SEQUENCE: 71

Ile Ser Tyr Asp Ser Pro Asp Tyr Thr Asp Glu Ser Cys Thr Phe Lys
1               5                   10                  15

Ile Ser Leu Arg Asn Phe Arg Ser Ile Leu Ser Trp Glu Leu Lys Asn
            20                  25                  30

His Ser Ile Val Pro Thr His Tyr Thr Leu Leu Tyr Thr Ile Met Ser
        35                  40                  45

Lys Pro Glu Asp Leu Lys Val Val Lys Asn Cys Ala Asn Thr Thr Arg
    50                  55                  60

Ser Phe Cys Asp Leu Thr Asp Glu Trp Arg Ser Thr His Glu Ala Tyr
65                  70                  75                  80

Val Thr Val Leu Glu Gly Phe Ser Gly Asn Thr Thr Leu Phe Ser Cys
                85                  90                  95

Ser His Asn Phe Trp Leu Ala Ile Asp Met Ser Phe Glu Pro Pro Glu
            100                 105                 110
```

Phe Glu Ile Val Gly Phe Thr Asn His Ile Asn Val Met Val Lys Phe
            115                 120                 125

Pro Ser Ile Val Glu Glu Leu Gln Phe Asp Leu Ser Leu Val Ile
    130                 135                 140

Glu Glu Gln Ser Glu Gly Ile Val Lys Lys His Lys Pro Glu Ile Lys
145                 150                 155                 160

Gly Asn Met Ser Gly Asn Phe Thr Tyr Ile Ile Asp Lys Leu Ile Pro
                165                 170                 175

Asn Thr Asn Tyr Cys Val Ser Val Tyr Leu Glu His Ser Asp Glu Gln
                180                 185                 190

Ala Val Ile Lys Ser Pro Leu Lys Cys Thr Leu Leu Pro Pro Gly Gln
            195                 200                 205

Glu Ser Glu Ser Ala Glu Ser Ala Lys Gly Gly Gly Ser Gly Gly
    210                 215                 220

Gly Gly Ser Glu Pro Lys Ser Cys Asp Lys Thr His Thr Cys Pro Pro
225                 230                 235                 240

Cys Pro Ala Pro Glu Leu Leu Gly Gly Pro Ser Val Phe Leu Phe Pro
                245                 250                 255

Pro Lys Pro Lys Asp Thr Leu Met Ile Ser Arg Thr Pro Glu Val Thr
            260                 265                 270

Cys Val Val Val Asp Val Ser His Glu Asp Pro Glu Val Lys Phe Asn
    275                 280                 285

Trp Tyr Val Asp Gly Val Glu Val His Asn Ala Lys Thr Lys Pro Arg
290                 295                 300

Glu Glu Gln Tyr Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Ala Leu Pro Ala Pro Ile Glu Lys Thr Ile Ser Lys Ala Lys
            340                 345                 350

Gly Gln Pro Arg Glu Pro Gln Val Tyr Thr Leu Pro Pro Ser Arg Asp
    355                 360                 365

Glu Leu Thr Lys Asn Gln Val Ser Leu Tyr Cys Leu Val Lys Gly Phe
370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Tyr Ser Lys Leu Thr Val Asp Lys Ser Arg Trp Gln Gln Gly
            420                 425                 430

Asn Val Phe Ser Cys Ser Val Met His Glu Ala Leu His Asn His Tyr
    435                 440                 445

Thr Gln Lys Ser Leu Ser Leu Ser Pro Gly Lys
    450                 455

<210> SEQ ID NO 72
<211> LENGTH: 670
<212> TYPE: PRT
<213> ORGANISM: Artificial Sequence
<220> FEATURE:
<223> OTHER INFORMATION: Synthetic: Leader- IFNAR1 (aa28-436)-
      (Gly4Ser)2- IgG1 Fc domain with Y407T mutation

<400> SEQUENCE: 72

Met Asp Trp Thr Trp Arg Ile Leu Phe Leu Val Ala Ala Ala Thr Gly
1               5                   10                  15

```
Thr His Ala Lys Asn Leu Lys Ser Pro Gln Lys Val Glu Val Asp Ile
         20                  25                  30

Ile Asp Asp Asn Phe Ile Leu Arg Trp Asn Arg Ser Asp Glu Ser Val
             35                  40                  45

Gly Asn Val Thr Phe Ser Phe Asp Tyr Gln Lys Thr Gly Met Asp Asn
 50                  55                  60

Trp Ile Lys Leu Ser Gly Cys Gln Asn Ile Thr Ser Thr Lys Cys Asn
 65                  70                  75                  80

Phe Ser Ser Leu Lys Leu Asn Val Tyr Glu Glu Ile Lys Leu Arg Ile
                 85                  90                  95

Arg Ala Glu Lys Glu Asn Thr Ser Ser Trp Tyr Glu Val Asp Ser Phe
                100                 105                 110

Thr Pro Phe Arg Lys Ala Gln Ile Gly Pro Pro Glu Val His Leu Glu
            115                 120                 125

Ala Glu Asp Lys Ala Ile Val Ile His Ile Ser Pro Gly Thr Lys Asp
130                 135                 140

Ser Val Met Trp Ala Leu Asp Gly Leu Ser Phe Thr Tyr Ser Leu Val
145                 150                 155                 160

Ile Trp Lys Asn Ser Ser Gly Val Glu Glu Arg Ile Glu Asn Ile Tyr
                165                 170                 175

Ser Arg His Lys Ile Tyr Lys Leu Ser Pro Glu Thr Thr Tyr Cys Leu
            180                 185                 190

Lys Val Lys Ala Ala Leu Leu Thr Ser Trp Lys Ile Gly Val Tyr Ser
            195                 200                 205

Pro Val His Cys Ile Lys Thr Thr Val Glu Asn Glu Leu Pro Pro Pro
            210                 215                 220

Glu Asn Ile Glu Val Ser Val Gln Asn Gln Asn Tyr Val Leu Lys Trp
225                 230                 235                 240

Asp Tyr Thr Tyr Ala Asn Met Thr Phe Gln Val Gln Trp Leu His Ala
                245                 250                 255

Phe Leu Lys Arg Asn Pro Gly Asn His Leu Tyr Lys Trp Lys Gln Ile
            260                 265                 270

Pro Asp Cys Glu Asn Val Lys Thr Thr Gln Cys Val Phe Pro Gln Asn
            275                 280                 285

Val Phe Gln Lys Gly Ile Tyr Leu Leu Arg Val Gln Ala Ser Asp Gly
            290                 295                 300

Asn Asn Thr Ser Phe Trp Ser Glu Glu Ile Lys Phe Asp Thr Glu Ile
305                 310                 315                 320

Gln Ala Phe Leu Leu Pro Pro Val Phe Asn Ile Arg Ser Leu Ser Asp
                325                 330                 335

Ser Phe His Ile Tyr Ile Gly Ala Pro Lys Gln Ser Gly Asn Thr Pro
            340                 345                 350

Val Ile Gln Asp Tyr Pro Leu Ile Tyr Glu Ile Ile Phe Trp Glu Asn
            355                 360                 365

Thr Ser Asn Ala Glu Arg Lys Ile Ile Glu Lys Lys Thr Asp Val Thr
            370                 375                 380

Val Pro Asn Leu Lys Pro Leu Thr Val Tyr Cys Val Lys Ala Arg Ala
385                 390                 395                 400

His Thr Met Asp Glu Lys Leu Asn Lys Ser Ser Val Phe Ser Asp Ala
                405                 410                 415

Val Cys Glu Lys Thr Lys Pro Gly Asn Thr Ser Lys Gly Gly Gly Gly
            420                 425                 430
```

```
Ser Gly Gly Gly Gly Ser Glu Pro Lys Ser Cys Asp Lys Thr His Thr
            435                 440                 445

Cys Pro Pro Cys Pro Ala Pro Glu Leu Leu Gly Gly Pro Ser Val Phe
450                 455                 460

Leu Phe Pro Pro Lys Pro Lys Asp Thr Leu Met Ile Ser Arg Thr Pro
465                 470                 475                 480

Glu Val Thr Cys Val Val Val Asp Val Ser His Glu Asp Pro Glu Val
                485                 490                 495

Lys Phe Asn Trp Tyr Val Asp Gly Val Glu Val His Asn Ala Lys Thr
                500                 505                 510

Lys Pro Arg Glu Glu Gln Tyr Asn Ser Thr Tyr Arg Val Val Ser Val
                515                 520                 525

Leu Thr Val Leu His Gln Asp Trp Leu Asn Gly Lys Glu Tyr Lys Cys
530                 535                 540

Lys Val Ser Asn Lys Ala Leu Pro Ala Pro Ile Glu Lys Thr Ile Ser
545                 550                 555                 560

Lys Ala Lys Gly Gln Pro Arg Glu Pro Gln Val Tyr Thr Leu Pro Pro
                565                 570                 575

Ser Arg Asp Glu Leu Thr Lys Asn Gln Val Ser Leu Thr Cys Leu Val
                580                 585                 590

Lys Gly Phe Tyr Pro Ser Asp Ile Ala Val Glu Trp Glu Ser Asn Gly
                595                 600                 605

Gln Pro Glu Asn Asn Tyr Lys Thr Thr Pro Pro Val Leu Asp Ser Asp
                610                 615                 620

Gly Ser Phe Phe Leu Thr Ser Lys Leu Thr Val Asp Lys Ser Arg Trp
625                 630                 635                 640

Gln Gln Gly Asn Val Phe Ser Cys Ser Val Met His Glu Ala Leu His
                645                 650                 655

Asn His Tyr Thr Gln Lys Ser Leu Ser Leu Ser Pro Gly Lys
                660                 665                 670

<210> SEQ ID NO 73
<211> LENGTH: 651
<212> TYPE: PRT
<213> ORGANISM: Artificial Sequence
<220> FEATURE:
<223> OTHER INFORMATION: Synthetic: IFNAR1 (aa28-436)- (Gly4Ser)2- IgG1
      Fc domain with Y407T mutation without a leader sequence

<400> SEQUENCE: 73

Lys Asn Leu Lys Ser Pro Gln Lys Val Glu Val Asp Ile Ile Asp Asp
1               5                   10                  15

Asn Phe Ile Leu Arg Trp Asn Arg Ser Asp Glu Ser Val Gly Asn Val
                20                  25                  30

Thr Phe Ser Phe Asp Tyr Gln Lys Thr Gly Met Asp Asn Trp Ile Lys
            35                  40                  45

Leu Ser Gly Cys Gln Asn Ile Thr Ser Thr Lys Cys Asn Phe Ser Ser
        50                  55                  60

Leu Lys Leu Asn Val Tyr Glu Glu Ile Lys Leu Arg Ile Arg Ala Glu
65              70                  75                  80

Lys Glu Asn Thr Ser Ser Trp Tyr Glu Val Asp Ser Phe Thr Pro Phe
                85                  90                  95

Arg Lys Ala Gln Ile Gly Pro Pro Glu Val His Leu Glu Ala Glu Asp
                100                 105                 110

Lys Ala Ile Val Ile His Ile Ser Pro Gly Thr Lys Asp Ser Val Met
            115                 120                 125
```

```
Trp Ala Leu Asp Gly Leu Ser Phe Thr Tyr Ser Leu Val Ile Trp Lys
    130                 135                 140

Asn Ser Ser Gly Val Glu Glu Arg Ile Glu Asn Ile Tyr Ser Arg His
145                 150                 155                 160

Lys Ile Tyr Lys Leu Ser Pro Glu Thr Thr Tyr Cys Leu Lys Val Lys
                165                 170                 175

Ala Ala Leu Leu Thr Ser Trp Lys Ile Gly Val Tyr Ser Pro Val His
            180                 185                 190

Cys Ile Lys Thr Thr Val Glu Asn Glu Leu Pro Pro Glu Asn Ile
            195                 200                 205

Glu Val Ser Val Gln Asn Gln Asn Tyr Val Leu Lys Trp Asp Tyr Thr
    210                 215                 220

Tyr Ala Asn Met Thr Phe Gln Val Gln Trp Leu His Ala Phe Leu Lys
225                 230                 235                 240

Arg Asn Pro Gly Asn His Leu Tyr Lys Trp Lys Gln Ile Pro Asp Cys
                245                 250                 255

Glu Asn Val Lys Thr Thr Gln Cys Val Phe Pro Gln Asn Val Phe Gln
                260                 265                 270

Lys Gly Ile Tyr Leu Leu Arg Val Gln Ala Ser Asp Gly Asn Asn Thr
                275                 280                 285

Ser Phe Trp Ser Glu Glu Ile Lys Phe Asp Thr Glu Ile Gln Ala Phe
    290                 295                 300

Leu Leu Pro Pro Val Phe Asn Ile Arg Ser Leu Ser Asp Ser Phe His
305                 310                 315                 320

Ile Tyr Ile Gly Ala Pro Lys Gln Ser Gly Asn Thr Pro Val Ile Gln
                325                 330                 335

Asp Tyr Pro Leu Ile Tyr Glu Ile Ile Phe Trp Glu Asn Thr Ser Asn
                340                 345                 350

Ala Glu Arg Lys Ile Ile Glu Lys Lys Thr Asp Val Thr Val Pro Asn
    355                 360                 365

Leu Lys Pro Leu Thr Val Tyr Cys Val Lys Ala Arg Ala His Thr Met
370                 375                 380

Asp Glu Lys Leu Asn Lys Ser Val Phe Ser Asp Ala Val Cys Glu
385                 390                 395                 400

Lys Thr Lys Pro Gly Asn Thr Ser Lys Gly Gly Gly Ser Gly Gly
                405                 410                 415

Gly Gly Ser Glu Pro Lys Ser Cys Asp Lys Thr His Thr Cys Pro Pro
            420                 425                 430

Cys Pro Ala Pro Glu Leu Leu Gly Gly Pro Ser Val Phe Leu Phe Pro
            435                 440                 445

Pro Lys Pro Lys Asp Thr Leu Met Ile Ser Arg Thr Pro Glu Val Thr
    450                 455                 460

Cys Val Val Val Asp Val Ser His Glu Asp Pro Glu Val Lys Phe Asn
465                 470                 475                 480

Trp Tyr Val Asp Gly Val Glu Val His Asn Ala Lys Thr Lys Pro Arg
                485                 490                 495

Glu Glu Gln Tyr Asn Ser Thr Tyr Arg Val Val Ser Val Leu Thr Val
                500                 505                 510

Leu His Gln Asp Trp Leu Asn Gly Lys Glu Tyr Lys Cys Lys Val Ser
    515                 520                 525

Asn Lys Ala Leu Pro Ala Pro Ile Glu Lys Thr Ile Ser Lys Ala Lys
530                 535                 540
```

```
Gly Gln Pro Arg Glu Pro Gln Val Tyr Thr Leu Pro Pro Ser Arg Asp
545                 550                 555                 560

Glu Leu Thr Lys Asn Gln Val Ser Leu Thr Cys Leu Val Lys Gly Phe
                565                 570                 575

Tyr Pro Ser Asp Ile Ala Val Glu Trp Glu Ser Asn Gly Gln Pro Glu
            580                 585                 590

Asn Asn Tyr Lys Thr Thr Pro Pro Val Leu Asp Ser Asp Gly Ser Phe
            595                 600                 605

Phe Leu Thr Ser Lys Leu Thr Val Asp Lys Ser Arg Trp Gln Gln Gly
        610                 615                 620

Asn Val Phe Ser Cys Ser Val Met His Glu Ala Leu His Asn His Tyr
625                 630                 635                 640

Thr Gln Lys Ser Leu Ser Leu Ser Pro Gly Lys
                645                 650

<210> SEQ ID NO 74
<211> LENGTH: 478
<212> TYPE: PRT
<213> ORGANISM: Artificial Sequence
<220> FEATURE:
<223> OTHER INFORMATION: Synthetic: Leader- IFNAR2 (aa27-243)-
      (Gly4Ser)2- IgG1 Fc domain with Y407T mutation

<400> SEQUENCE: 74

Met Asp Trp Thr Trp Arg Ile Leu Phe Leu Val Ala Ala Thr Gly
1               5                   10                  15

Thr His Ala Ile Ser Tyr Asp Ser Pro Asp Tyr Thr Asp Glu Ser Cys
                20                  25                  30

Thr Phe Lys Ile Ser Leu Arg Asn Phe Arg Ser Ile Leu Ser Trp Glu
            35                  40                  45

Leu Lys Asn His Ser Ile Val Pro Thr His Tyr Thr Leu Leu Tyr Thr
        50                  55                  60

Ile Met Ser Lys Pro Glu Asp Leu Lys Val Val Lys Asn Cys Ala Asn
65                  70                  75                  80

Thr Thr Arg Ser Phe Cys Asp Leu Thr Asp Glu Trp Arg Ser Thr His
                85                  90                  95

Glu Ala Tyr Val Thr Val Leu Glu Gly Phe Ser Gly Asn Thr Thr Leu
                100                 105                 110

Phe Ser Cys Ser His Asn Phe Trp Leu Ala Ile Asp Met Ser Phe Glu
            115                 120                 125

Pro Pro Glu Phe Glu Ile Val Gly Phe Thr Asn His Ile Asn Val Met
130                 135                 140

Val Lys Phe Pro Ser Ile Val Glu Glu Glu Leu Gln Phe Asp Leu Ser
145                 150                 155                 160

Leu Val Ile Glu Glu Gln Ser Glu Gly Ile Val Lys Lys His Lys Pro
                165                 170                 175

Glu Ile Lys Gly Asn Met Ser Gly Asn Phe Thr Tyr Ile Ile Asp Lys
            180                 185                 190

Leu Ile Pro Asn Thr Asn Tyr Cys Val Ser Val Tyr Leu Glu His Ser
        195                 200                 205

Asp Glu Gln Ala Val Ile Lys Ser Pro Leu Lys Cys Thr Leu Leu Pro
210                 215                 220

Pro Gly Gln Glu Ser Glu Ser Ala Glu Ser Ala Lys Gly Gly Gly Gly
225                 230                 235                 240

Ser Gly Gly Gly Gly Ser Glu Pro Lys Ser Cys Asp Lys Thr His Thr
                245                 250                 255
```

Cys Pro Pro Cys Pro Ala Pro Glu Leu Leu Gly Gly Pro Ser Val Phe
            260                 265                 270

Leu Phe Pro Pro Lys Pro Lys Asp Thr Leu Met Ile Ser Arg Thr Pro
        275                 280                 285

Glu Val Thr Cys Val Val Val Asp Val Ser His Glu Asp Pro Glu Val
    290                 295                 300

Lys Phe Asn Trp Tyr Val Asp Gly Val Glu Val His Asn Ala Lys Thr
305                 310                 315                 320

Lys Pro Arg Glu Glu Gln Tyr Asn Ser Thr Tyr Arg Val Val Ser Val
            325                 330                 335

Leu Thr Val Leu His Gln Asp Trp Leu Asn Gly Lys Glu Tyr Lys Cys
        340                 345                 350

Lys Val Ser Asn Lys Ala Leu Pro Ala Pro Ile Glu Lys Thr Ile Ser
    355                 360                 365

Lys Ala Lys Gly Gln Pro Arg Glu Pro Gln Val Tyr Thr Leu Pro Pro
370                 375                 380

Ser Arg Asp Glu Leu Thr Lys Asn Gln Val Ser Leu Thr Cys Leu Val
385                 390                 395                 400

Lys Gly Phe Tyr Pro Ser Asp Ile Ala Val Glu Trp Glu Ser Asn Gly
            405                 410                 415

Gln Pro Glu Asn Asn Tyr Lys Thr Thr Pro Pro Val Leu Asp Ser Asp
        420                 425                 430

Gly Ser Phe Phe Leu Thr Ser Lys Leu Thr Val Asp Lys Ser Arg Trp
    435                 440                 445

Gln Gln Gly Asn Val Phe Ser Cys Ser Val Met His Glu Ala Leu His
    450                 455                 460

Asn His Tyr Thr Gln Lys Ser Leu Ser Leu Ser Pro Gly Lys
465                 470                 475

<210> SEQ ID NO 75
<211> LENGTH: 459
<212> TYPE: PRT
<213> ORGANISM: Artificial Sequence
<220> FEATURE:
<223> OTHER INFORMATION: Synthetic: IFNAR2 (aa27-243)- (Gly4Ser)2- IgG1
      Fc domain with Y407T mutation without a leader sequence

<400> SEQUENCE: 75

Ile Ser Tyr Asp Ser Pro Asp Tyr Thr Asp Glu Ser Cys Thr Phe Lys
1               5                   10                  15

Ile Ser Leu Arg Asn Phe Arg Ser Ile Leu Ser Trp Glu Leu Lys Asn
            20                  25                  30

His Ser Ile Val Pro Thr His Tyr Thr Leu Leu Tyr Thr Ile Met Ser
        35                  40                  45

Lys Pro Glu Asp Leu Lys Val Val Lys Asn Cys Ala Asn Thr Thr Arg
    50                  55                  60

Ser Phe Cys Asp Leu Thr Asp Glu Trp Arg Ser Thr His Glu Ala Tyr
65                  70                  75                  80

Val Thr Val Leu Glu Gly Phe Ser Gly Asn Thr Thr Leu Phe Ser Cys
                85                  90                  95

Ser His Asn Phe Trp Leu Ala Ile Asp Met Ser Phe Glu Pro Pro Glu
            100                 105                 110

Phe Glu Ile Val Gly Phe Thr Asn His Ile Asn Val Met Val Lys Phe
        115                 120                 125

Pro Ser Ile Val Glu Glu Glu Leu Gln Phe Asp Leu Ser Leu Val Ile

-continued

```
                130                 135                 140
Glu Glu Gln Ser Glu Gly Ile Val Lys Lys His Lys Pro Glu Ile Lys
145                 150                 155                 160

Gly Asn Met Ser Gly Asn Phe Thr Tyr Ile Ile Asp Lys Leu Ile Pro
                165                 170                 175

Asn Thr Asn Tyr Cys Val Ser Val Tyr Leu Glu His Ser Asp Glu Gln
            180                 185                 190

Ala Val Ile Lys Ser Pro Leu Lys Cys Thr Leu Leu Pro Pro Gly Gln
        195                 200                 205

Glu Ser Glu Ser Ala Glu Ser Ala Lys Gly Gly Gly Ser Gly Gly
    210                 215                 220

Gly Gly Ser Glu Pro Lys Ser Cys Asp Lys Thr His Thr Cys Pro Pro
225                 230                 235                 240

Cys Pro Ala Pro Glu Leu Leu Gly Gly Pro Ser Val Phe Leu Phe Pro
                245                 250                 255

Pro Lys Pro Lys Asp Thr Leu Met Ile Ser Arg Thr Pro Glu Val Thr
                260                 265                 270

Cys Val Val Val Asp Val Ser His Glu Asp Pro Glu Val Lys Phe Asn
            275                 280                 285

Trp Tyr Val Asp Gly Val Glu Val His Asn Ala Lys Thr Lys Pro Arg
        290                 295                 300

Glu Glu Gln Tyr Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Ala Leu Pro Ala Pro Ile Glu Lys Thr Ile Ser Lys Ala Lys
                340                 345                 350

Gly Gln Pro Arg Glu Pro Gln Val Tyr Thr Leu Pro Pro Ser Arg Asp
            355                 360                 365

Glu Leu Thr Lys Asn Gln Val Ser Leu Thr Cys Leu Val Lys Gly Phe
        370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Thr Ser Lys Leu Thr Val Asp Lys Ser Arg Trp Gln Gln Gly
                420                 425                 430

Asn Val Phe Ser Cys Ser Val Met His Glu Ala Leu His Asn His Tyr
            435                 440                 445

Thr Gln Lys Ser Leu Ser Leu Ser Pro Gly Lys
450                 455

<210> SEQ ID NO 76
<211> LENGTH: 660
<212> TYPE: PRT
<213> ORGANISM: Artificial Sequence
<220> FEATURE:
<223> OTHER INFORMATION: Synthetic: Leader- IFNAR1 (aa28-436)- IgG1 Fc
      domain with T366Y mutation

<400> SEQUENCE: 76

Met Asp Trp Thr Trp Arg Ile Leu Phe Leu Val Ala Ala Ala Thr Gly
1               5                   10                  15

Thr His Ala Lys Asn Leu Lys Ser Pro Gln Lys Val Glu Val Asp Ile
            20                  25                  30
```

Ile Asp Asp Asn Phe Ile Leu Arg Trp Asn Arg Ser Asp Glu Ser Val
           35                  40                  45

Gly Asn Val Thr Phe Ser Phe Asp Tyr Gln Lys Thr Gly Met Asp Asn
 50                  55                  60

Trp Ile Lys Leu Ser Gly Cys Gln Asn Ile Thr Ser Thr Lys Cys Asn
 65                  70                  75                  80

Phe Ser Ser Leu Lys Leu Asn Val Tyr Glu Glu Ile Lys Leu Arg Ile
                 85                  90                  95

Arg Ala Glu Lys Glu Asn Thr Ser Ser Trp Tyr Glu Val Asp Ser Phe
             100                 105                 110

Thr Pro Phe Arg Lys Ala Gln Ile Gly Pro Pro Glu Val His Leu Glu
             115                 120                 125

Ala Glu Asp Lys Ala Ile Val Ile His Ile Ser Pro Gly Thr Lys Asp
         130                 135                 140

Ser Val Met Trp Ala Leu Asp Gly Leu Ser Phe Thr Tyr Ser Leu Val
145                 150                 155                 160

Ile Trp Lys Asn Ser Ser Gly Val Glu Glu Arg Ile Glu Asn Ile Tyr
                 165                 170                 175

Ser Arg His Lys Ile Tyr Lys Leu Ser Pro Glu Thr Thr Tyr Cys Leu
             180                 185                 190

Lys Val Lys Ala Ala Leu Leu Thr Ser Trp Lys Ile Gly Val Tyr Ser
         195                 200                 205

Pro Val His Cys Ile Lys Thr Thr Val Glu Asn Glu Leu Pro Pro Pro
         210                 215                 220

Glu Asn Ile Glu Val Ser Val Gln Asn Gln Asn Tyr Val Leu Lys Trp
225                 230                 235                 240

Asp Tyr Thr Tyr Ala Asn Met Thr Phe Gln Val Gln Trp Leu His Ala
                 245                 250                 255

Phe Leu Lys Arg Asn Pro Gly Asn His Leu Tyr Lys Trp Lys Gln Ile
             260                 265                 270

Pro Asp Cys Glu Asn Val Lys Thr Thr Gln Cys Val Phe Pro Gln Asn
         275                 280                 285

Val Phe Gln Lys Gly Ile Tyr Leu Leu Arg Val Gln Ala Ser Asp Gly
         290                 295                 300

Asn Asn Thr Ser Phe Trp Ser Glu Glu Ile Lys Phe Asp Thr Glu Ile
305                 310                 315                 320

Gln Ala Phe Leu Leu Pro Pro Val Phe Asn Ile Arg Ser Leu Ser Asp
                 325                 330                 335

Ser Phe His Ile Tyr Ile Gly Ala Pro Lys Gln Ser Gly Asn Thr Pro
             340                 345                 350

Val Ile Gln Asp Tyr Pro Leu Ile Tyr Glu Ile Ile Phe Trp Glu Asn
         355                 360                 365

Thr Ser Asn Ala Glu Arg Lys Ile Ile Glu Lys Lys Thr Asp Val Thr
         370                 375                 380

Val Pro Asn Leu Lys Pro Leu Thr Val Tyr Cys Val Lys Ala Arg Ala
385                 390                 395                 400

His Thr Met Asp Glu Lys Leu Asn Lys Ser Ser Val Phe Ser Asp Ala
                 405                 410                 415

Val Cys Glu Lys Thr Lys Pro Gly Asn Thr Ser Lys Glu Pro Lys Ser
             420                 425                 430

Cys Asp Lys Thr His Thr Cys Pro Pro Cys Pro Ala Pro Glu Leu Leu
         435                 440                 445

Gly Gly Pro Ser Val Phe Leu Phe Pro Pro Lys Pro Lys Asp Thr Leu

```
                  450                 455                 460
Met Ile Ser Arg Thr Pro Glu Val Thr Cys Val Val Asp Val Ser
465                 470                 475                 480

His Glu Asp Pro Glu Val Lys Phe Asn Trp Tyr Val Asp Gly Val Glu
                    485                 490                 495

Val His Asn Ala Lys Thr Lys Pro Arg Glu Glu Gln Tyr Asn Ser Thr
                500                 505                 510

Tyr Arg Val Val Ser Val Leu Thr Val Leu His Gln Asp Trp Leu Asn
            515                 520                 525

Gly Lys Glu Tyr Lys Cys Lys Val Ser Asn Lys Ala Leu Pro Ala Pro
        530                 535                 540

Ile Glu Lys Thr Ile Ser Lys Ala Lys Gly Gln Pro Arg Glu Pro Gln
545                 550                 555                 560

Val Tyr Thr Leu Pro Pro Ser Arg Asp Glu Leu Thr Lys Asn Gln Val
                    565                 570                 575

Ser Leu Tyr Cys Leu Val Lys Gly Phe Tyr Pro Ser Asp Ile Ala Val
                580                 585                 590

Glu Trp Glu Ser Asn Gly Gln Pro Glu Asn Asn Tyr Lys Thr Thr Pro
            595                 600                 605

Pro Val Leu Asp Ser Asp Gly Ser Phe Phe Leu Tyr Ser Lys Leu Thr
        610                 615                 620

Val Asp Lys Ser Arg Trp Gln Gln Gly Asn Val Phe Ser Cys Ser Val
625                 630                 635                 640

Met His Glu Ala Leu His Asn His Tyr Thr Gln Lys Ser Leu Ser Leu
                    645                 650                 655

Ser Pro Gly Lys
            660

<210> SEQ ID NO 77
<211> LENGTH: 641
<212> TYPE: PRT
<213> ORGANISM: Artificial Sequence
<220> FEATURE:
<223> OTHER INFORMATION: Synthetic: IFNAR1 (aa28-436)- IgG1 Fc domain
      with T366Y mutation without a leader sequence

<400> SEQUENCE: 77

Lys Asn Leu Lys Ser Pro Gln Lys Val Glu Val Asp Ile Ile Asp Asp
1               5                   10                  15

Asn Phe Ile Leu Arg Trp Asn Arg Ser Asp Glu Ser Val Gly Asn Val
            20                  25                  30

Thr Phe Ser Phe Asp Tyr Gln Lys Thr Gly Met Asp Asn Trp Ile Lys
        35                  40                  45

Leu Ser Gly Cys Gln Asn Ile Thr Ser Thr Lys Cys Asn Phe Ser Ser
    50                  55                  60

Leu Lys Leu Asn Val Tyr Glu Glu Ile Lys Leu Arg Ile Arg Ala Glu
65                  70                  75                  80

Lys Glu Asn Thr Ser Ser Trp Tyr Glu Val Asp Ser Phe Thr Pro Phe
                85                  90                  95

Arg Lys Ala Gln Ile Gly Pro Pro Glu Val His Leu Glu Ala Glu Asp
            100                 105                 110

Lys Ala Ile Val Ile His Ile Ser Pro Gly Thr Lys Asp Ser Val Met
        115                 120                 125

Trp Ala Leu Asp Gly Leu Ser Phe Thr Tyr Ser Leu Val Ile Trp Lys
    130                 135                 140
```

-continued

```
Asn Ser Ser Gly Val Glu Glu Arg Ile Glu Asn Ile Tyr Ser Arg His
145                 150                 155                 160

Lys Ile Tyr Lys Leu Ser Pro Glu Thr Thr Tyr Cys Leu Lys Val Lys
                165                 170                 175

Ala Ala Leu Leu Thr Ser Trp Lys Ile Gly Val Tyr Ser Pro Val His
            180                 185                 190

Cys Ile Lys Thr Thr Val Glu Asn Glu Leu Pro Pro Glu Asn Ile
        195                 200                 205

Glu Val Ser Val Gln Asn Gln Asn Tyr Val Leu Lys Trp Asp Tyr Thr
    210                 215                 220

Tyr Ala Asn Met Thr Phe Gln Val Gln Trp Leu His Ala Phe Leu Lys
225                 230                 235                 240

Arg Asn Pro Gly Asn His Leu Tyr Lys Trp Lys Gln Ile Pro Asp Cys
                245                 250                 255

Glu Asn Val Lys Thr Thr Gln Cys Val Phe Pro Gln Asn Val Phe Gln
                260                 265                 270

Lys Gly Ile Tyr Leu Leu Arg Val Gln Ala Ser Asp Gly Asn Asn Thr
            275                 280                 285

Ser Phe Trp Ser Glu Glu Ile Lys Phe Asp Thr Glu Ile Gln Ala Phe
290                 295                 300

Leu Leu Pro Pro Val Phe Asn Ile Arg Ser Leu Ser Asp Ser Phe His
305                 310                 315                 320

Ile Tyr Ile Gly Ala Pro Lys Gln Ser Gly Asn Thr Pro Val Ile Gln
                325                 330                 335

Asp Tyr Pro Leu Ile Tyr Glu Ile Ile Phe Trp Glu Asn Thr Ser Asn
                340                 345                 350

Ala Glu Arg Lys Ile Ile Glu Lys Lys Thr Asp Val Thr Val Pro Asn
            355                 360                 365

Leu Lys Pro Leu Thr Val Tyr Cys Val Lys Ala Arg Ala His Thr Met
        370                 375                 380

Asp Glu Lys Leu Asn Lys Ser Ser Val Phe Ser Asp Ala Val Cys Glu
385                 390                 395                 400

Lys Thr Lys Pro Gly Asn Thr Ser Lys Glu Pro Lys Ser Cys Asp Lys
                405                 410                 415

Thr His Thr Cys Pro Pro Cys Pro Ala Pro Glu Leu Leu Gly Gly Pro
            420                 425                 430

Ser Val Phe Leu Phe Pro Pro Lys Pro Lys Asp Thr Leu Met Ile Ser
        435                 440                 445

Arg Thr Pro Glu Val Thr Cys Val Val Val Asp Val Ser His Glu Asp
450                 455                 460

Pro Glu Val Lys Phe Asn Trp Tyr Val Asp Gly Val Glu Val His Asn
465                 470                 475                 480

Ala Lys Thr Lys Pro Arg Glu Glu Gln Tyr Asn Ser Thr Tyr Arg Val
                485                 490                 495

Val Ser Val Leu Thr Val Leu His Gln Asp Trp Leu Asn Gly Lys Glu
            500                 505                 510

Tyr Lys Cys Lys Val Ser Asn Lys Ala Leu Pro Ala Pro Ile Glu Lys
        515                 520                 525

Thr Ile Ser Lys Ala Lys Gly Gln Pro Arg Glu Pro Gln Val Tyr Thr
    530                 535                 540

Leu Pro Pro Ser Arg Asp Glu Leu Thr Lys Asn Gln Val Ser Leu Tyr
545                 550                 555                 560

Cys Leu Val Lys Gly Phe Tyr Pro Ser Asp Ile Ala Val Glu Trp Glu
```

565                 570                 575

Ser Asn Gly Gln Pro Glu Asn Asn Tyr Lys Thr Thr Pro Val Leu
            580                 585                 590

Asp Ser Asp Gly Ser Phe Phe Leu Tyr Ser Lys Leu Thr Val Asp Lys
            595                 600                 605

Ser Arg Trp Gln Gln Gly Asn Val Phe Ser Cys Ser Val Met His Glu
            610                 615                 620

Ala Leu His Asn His Tyr Thr Gln Lys Ser Leu Ser Leu Ser Pro Gly
625                 630                 635                 640

Lys

<210> SEQ ID NO 78
<211> LENGTH: 468
<212> TYPE: PRT
<213> ORGANISM: Artificial Sequence
<220> FEATURE:
<223> OTHER INFORMATION: Synthetic: Leader- IFNAR2 (aa27-243)- IgG1 Fc
      domain with T366Y mutation

<400> SEQUENCE: 78

Met Asp Trp Thr Trp Arg Ile Leu Phe Leu Val Ala Ala Ala Thr Gly
1               5                   10                  15

Thr His Ala Ile Ser Tyr Asp Ser Pro Asp Tyr Thr Asp Glu Ser Cys
            20                  25                  30

Thr Phe Lys Ile Ser Leu Arg Asn Phe Arg Ser Ile Leu Ser Trp Glu
        35                  40                  45

Leu Lys Asn His Ser Ile Val Pro Thr His Tyr Thr Leu Leu Tyr Thr
50                  55                  60

Ile Met Ser Lys Pro Glu Asp Leu Lys Val Val Lys Asn Cys Ala Asn
65                  70                  75                  80

Thr Thr Arg Ser Phe Cys Asp Leu Thr Asp Glu Trp Arg Ser Thr His
                85                  90                  95

Glu Ala Tyr Val Thr Val Leu Glu Gly Phe Ser Gly Asn Thr Thr Leu
            100                 105                 110

Phe Ser Cys Ser His Asn Phe Trp Leu Ala Ile Asp Met Ser Phe Glu
        115                 120                 125

Pro Pro Glu Phe Glu Ile Val Gly Phe Thr Asn His Ile Asn Val Met
130                 135                 140

Val Lys Phe Pro Ser Ile Val Glu Glu Glu Leu Gln Phe Asp Leu Ser
145                 150                 155                 160

Leu Val Ile Glu Glu Gln Ser Glu Gly Ile Val Lys Lys His Lys Pro
                165                 170                 175

Glu Ile Lys Gly Asn Met Ser Gly Asn Phe Thr Tyr Ile Ile Asp Lys
            180                 185                 190

Leu Ile Pro Asn Thr Asn Tyr Cys Val Ser Val Tyr Leu Glu His Ser
        195                 200                 205

Asp Glu Gln Ala Val Ile Lys Ser Pro Leu Lys Cys Thr Leu Leu Pro
210                 215                 220

Pro Gly Gln Glu Ser Glu Ser Ala Glu Ser Ala Lys Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser

```
              275                 280                 285
His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Asp Glu Leu Thr Lys Asn Gln Val
    370                 375                 380

Ser Leu Tyr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465

<210> SEQ ID NO 79
<211> LENGTH: 449
<212> TYPE: PRT
<213> ORGANISM: Artificial Sequence
<220> FEATURE:
<223> OTHER INFORMATION: Synthetic: IFNAR2 (aa27-243)- IgG1 Fc domain
      with T366Y mutation without a leader sequence

<400> SEQUENCE: 79

Ile Ser Tyr Asp Ser Pro Asp Tyr Thr Asp Glu Ser Cys Thr Phe Lys
1               5                   10                  15

Ile Ser Leu Arg Asn Phe Arg Ser Ile Leu Ser Trp Glu Leu Lys Asn
            20                  25                  30

His Ser Ile Val Pro Thr His Tyr Thr Leu Leu Tyr Thr Ile Met Ser
        35                  40                  45

Lys Pro Glu Asp Leu Lys Val Val Lys Asn Cys Ala Asn Thr Thr Arg
    50                  55                  60

Ser Phe Cys Asp Leu Thr Asp Glu Trp Arg Ser Thr His Glu Ala Tyr
65                  70                  75                  80

Val Thr Val Leu Glu Gly Phe Ser Gly Asn Thr Thr Leu Phe Ser Cys
                85                  90                  95

Ser His Asn Phe Trp Leu Ala Ile Asp Met Ser Phe Glu Pro Pro Glu
            100                 105                 110

Phe Glu Ile Val Gly Phe Thr Asn His Ile Asn Val Met Val Lys Phe
        115                 120                 125

Pro Ser Ile Val Glu Glu Glu Leu Gln Phe Asp Leu Ser Leu Val Ile
    130                 135                 140

Glu Glu Gln Ser Glu Gly Ile Val Lys Lys His Lys Pro Glu Ile Lys
145                 150                 155                 160
```

Gly Asn Met Ser Gly Asn Phe Thr Tyr Ile Ile Asp Lys Leu Ile Pro
            165                 170                 175

Asn Thr Asn Tyr Cys Val Ser Val Tyr Leu Glu His Ser Asp Glu Gln
        180                 185                 190

Ala Val Ile Lys Ser Pro Leu Lys Cys Thr Leu Leu Pro Pro Gly Gln
    195                 200                 205

Glu Ser Glu Ser Ala Glu Ser Ala Lys Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
        260                 265                 270

Pro Glu Val Lys Phe Asn Trp Tyr Val Asp Gly Val Glu Val His Asn
    275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
        340                 345                 350

Leu Pro Pro Ser Arg Asp Glu Leu Thr Lys Asn Gln Val Ser Leu Tyr
    355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
    435                 440                 445

Lys

<210> SEQ ID NO 80
<211> LENGTH: 660
<212> TYPE: PRT
<213> ORGANISM: Artificial Sequence
<220> FEATURE:
<223> OTHER INFORMATION: Synthetic: Leader- IFNAR1 (aa28-436)- IgG1 Fc
      domain with Y407T mutation

<400> SEQUENCE: 80

Met Asp Trp Thr Trp Arg Ile Leu Phe Leu Val Ala Ala Ala Thr Gly
1               5                   10                  15

Thr His Ala Lys Asn Leu Lys Ser Pro Gln Lys Val Glu Val Asp Ile
            20                  25                  30

Ile Asp Asp Asn Phe Ile Leu Arg Trp Asn Arg Ser Asp Glu Ser Val
        35                  40                  45

Gly Asn Val Thr Phe Ser Phe Asp Tyr Gln Lys Thr Gly Met Asp Asn
    50                  55                  60

```
Trp Ile Lys Leu Ser Gly Cys Gln Asn Ile Thr Ser Thr Lys Cys Asn
 65                  70                  75                  80

Phe Ser Ser Leu Lys Leu Asn Val Tyr Glu Glu Ile Lys Leu Arg Ile
                 85                  90                  95

Arg Ala Glu Lys Glu Asn Thr Ser Ser Trp Tyr Glu Val Asp Ser Phe
            100                 105                 110

Thr Pro Phe Arg Lys Ala Gln Ile Gly Pro Pro Glu Val His Leu Glu
            115                 120                 125

Ala Glu Asp Lys Ala Ile Val Ile His Ile Ser Pro Gly Thr Lys Asp
            130                 135                 140

Ser Val Met Trp Ala Leu Asp Gly Leu Ser Phe Thr Tyr Ser Leu Val
145                 150                 155                 160

Ile Trp Lys Asn Ser Ser Gly Val Glu Glu Arg Ile Glu Asn Ile Tyr
                165                 170                 175

Ser Arg His Lys Ile Tyr Lys Leu Ser Pro Glu Thr Thr Tyr Cys Leu
            180                 185                 190

Lys Val Lys Ala Ala Leu Leu Thr Ser Trp Lys Ile Gly Val Tyr Ser
            195                 200                 205

Pro Val His Cys Ile Lys Thr Thr Val Glu Asn Glu Leu Pro Pro Pro
210                 215                 220

Glu Asn Ile Glu Val Ser Val Gln Asn Gln Asn Tyr Val Leu Lys Trp
225                 230                 235                 240

Asp Tyr Thr Tyr Ala Asn Met Thr Phe Gln Val Gln Trp Leu His Ala
                245                 250                 255

Phe Leu Lys Arg Asn Pro Gly Asn His Leu Tyr Lys Trp Lys Gln Ile
            260                 265                 270

Pro Asp Cys Glu Asn Val Lys Thr Thr Gln Cys Val Phe Pro Gln Asn
            275                 280                 285

Val Phe Gln Lys Gly Ile Tyr Leu Leu Arg Val Gln Ala Ser Asp Gly
            290                 295                 300

Asn Asn Thr Ser Phe Trp Ser Glu Glu Ile Lys Phe Asp Thr Glu Ile
305                 310                 315                 320

Gln Ala Phe Leu Leu Pro Pro Val Phe Asn Ile Arg Ser Leu Ser Asp
                325                 330                 335

Ser Phe His Ile Tyr Ile Gly Ala Pro Lys Gln Ser Gly Asn Thr Pro
            340                 345                 350

Val Ile Gln Asp Tyr Pro Leu Ile Tyr Glu Ile Ile Phe Trp Glu Asn
            355                 360                 365

Thr Ser Asn Ala Glu Arg Lys Ile Ile Glu Lys Lys Thr Asp Val Thr
            370                 375                 380

Val Pro Asn Leu Lys Pro Leu Thr Val Tyr Cys Val Lys Ala Arg Ala
385                 390                 395                 400

His Thr Met Asp Glu Lys Leu Asn Lys Ser Ser Val Phe Ser Asp Ala
                405                 410                 415

Val Cys Glu Lys Thr Lys Pro Gly Asn Thr Ser Lys Glu Pro Lys Ser
            420                 425                 430

Cys Asp Lys Thr His Thr Cys Pro Pro Cys Pro Ala Pro Glu Leu Leu
            435                 440                 445

Gly Gly Pro Ser Val Phe Leu Phe Pro Pro Lys Pro Lys Asp Thr Leu
            450                 455                 460

Met Ile Ser Arg Thr Pro Glu Val Thr Cys Val Val Val Asp Val Ser
465                 470                 475                 480

His Glu Asp Pro Glu Val Lys Phe Asn Trp Tyr Val Asp Gly Val Glu
```

485                 490                 495
Val His Asn Ala Lys Thr Lys Pro Arg Glu Glu Gln Tyr Asn Ser Thr
                500                 505                 510

Tyr Arg Val Val Ser Val Leu Thr Val Leu His Gln Asp Trp Leu Asn
            515                 520                 525

Gly Lys Glu Tyr Lys Cys Lys Val Ser Asn Lys Ala Leu Pro Ala Pro
        530                 535                 540

Ile Glu Lys Thr Ile Ser Lys Ala Lys Gly Gln Pro Arg Glu Pro Gln
545                 550                 555                 560

Val Tyr Thr Leu Pro Pro Ser Arg Asp Glu Leu Thr Lys Asn Gln Val
                565                 570                 575

Ser Leu Thr Cys Leu Val Lys Gly Phe Tyr Pro Ser Asp Ile Ala Val
            580                 585                 590

Glu Trp Glu Ser Asn Gly Gln Pro Glu Asn Asn Tyr Lys Thr Thr Pro
        595                 600                 605

Pro Val Leu Asp Ser Asp Gly Ser Phe Phe Leu Thr Ser Lys Leu Thr
    610                 615                 620

Val Asp Lys Ser Arg Trp Gln Gln Gly Asn Val Phe Ser Cys Ser Val
625                 630                 635                 640

Met His Glu Ala Leu His Asn His Tyr Thr Gln Lys Ser Leu Ser Leu
                645                 650                 655

Ser Pro Gly Lys
            660

<210> SEQ ID NO 81
<211> LENGTH: 641
<212> TYPE: PRT
<213> ORGANISM: Artificial Sequence
<220> FEATURE:
<223> OTHER INFORMATION: Synthetic: IFNAR1 (aa28-436)- IgG1 Fc domain
      with Y407T mutation without a leader sequence

<400> SEQUENCE: 81

Lys Asn Leu Lys Ser Pro Gln Lys Val Glu Val Asp Ile Ile Asp Asp
1               5                   10                  15

Asn Phe Ile Leu Arg Trp Asn Arg Ser Asp Glu Ser Val Gly Asn Val
            20                  25                  30

Thr Phe Ser Phe Asp Tyr Gln Lys Thr Gly Met Asp Asn Trp Ile Lys
        35                  40                  45

Leu Ser Gly Cys Gln Asn Ile Thr Ser Thr Lys Cys Asn Phe Ser Ser
    50                  55                  60

Leu Lys Leu Asn Val Tyr Glu Glu Ile Lys Leu Arg Ile Arg Ala Glu
65                  70                  75                  80

Lys Glu Asn Thr Ser Ser Trp Tyr Glu Val Asp Ser Phe Thr Pro Phe
                85                  90                  95

Arg Lys Ala Gln Ile Gly Pro Pro Glu Val His Leu Glu Ala Glu Asp
            100                 105                 110

Lys Ala Ile Val Ile His Ile Ser Pro Gly Thr Lys Asp Ser Val Met
        115                 120                 125

Trp Ala Leu Asp Gly Leu Ser Phe Thr Tyr Ser Leu Val Ile Trp Lys
    130                 135                 140

Asn Ser Ser Gly Val Glu Glu Arg Ile Glu Asn Ile Tyr Ser Arg His
145                 150                 155                 160

Lys Ile Tyr Lys Leu Ser Pro Glu Thr Thr Tyr Cys Leu Lys Val Lys
                165                 170                 175

```
Ala Ala Leu Leu Thr Ser Trp Lys Ile Gly Val Tyr Ser Pro Val His
            180                 185                 190

Cys Ile Lys Thr Thr Val Glu Asn Glu Leu Pro Pro Glu Asn Ile
        195                 200                 205

Glu Val Ser Val Gln Asn Gln Asn Tyr Val Leu Lys Trp Asp Tyr Thr
    210                 215                 220

Tyr Ala Asn Met Thr Phe Gln Val Gln Trp Leu His Ala Phe Leu Lys
225                 230                 235                 240

Arg Asn Pro Gly Asn His Leu Tyr Lys Trp Lys Gln Ile Pro Asp Cys
                245                 250                 255

Glu Asn Val Lys Thr Thr Gln Cys Val Phe Pro Gln Asn Val Phe Gln
            260                 265                 270

Lys Gly Ile Tyr Leu Leu Arg Val Gln Ala Ser Asp Gly Asn Asn Thr
        275                 280                 285

Ser Phe Trp Ser Glu Glu Ile Lys Phe Asp Thr Glu Ile Gln Ala Phe
    290                 295                 300

Leu Leu Pro Pro Val Phe Asn Ile Arg Ser Leu Ser Asp Ser Phe His
305                 310                 315                 320

Ile Tyr Ile Gly Ala Pro Lys Gln Ser Gly Asn Thr Pro Val Ile Gln
                325                 330                 335

Asp Tyr Pro Leu Ile Tyr Glu Ile Ile Phe Trp Glu Asn Thr Ser Asn
            340                 345                 350

Ala Glu Arg Lys Ile Ile Glu Lys Lys Thr Asp Val Thr Val Pro Asn
        355                 360                 365

Leu Lys Pro Leu Thr Val Tyr Cys Val Lys Ala Arg Ala His Thr Met
    370                 375                 380

Asp Glu Lys Leu Asn Lys Ser Ser Val Phe Ser Asp Ala Val Cys Glu
385                 390                 395                 400

Lys Thr Lys Pro Gly Asn Thr Ser Lys Glu Pro Lys Ser Cys Asp Lys
                405                 410                 415

Thr His Thr Cys Pro Pro Cys Pro Ala Pro Glu Leu Leu Gly Gly Pro
            420                 425                 430

Ser Val Phe Leu Phe Pro Pro Lys Pro Lys Asp Thr Leu Met Ile Ser
        435                 440                 445

Arg Thr Pro Glu Val Thr Cys Val Val Val Asp Val Ser His Glu Asp
    450                 455                 460

Pro Glu Val Lys Phe Asn Trp Tyr Val Asp Gly Val Glu Val His Asn
465                 470                 475                 480

Ala Lys Thr Lys Pro Arg Glu Glu Gln Tyr Asn Ser Thr Tyr Arg Val
                485                 490                 495

Val Ser Val Leu Thr Val Leu His Gln Asp Trp Leu Asn Gly Lys Glu
            500                 505                 510

Tyr Lys Cys Lys Val Ser Asn Lys Ala Leu Pro Ala Pro Ile Glu Lys
        515                 520                 525

Thr Ile Ser Lys Ala Lys Gly Gln Pro Arg Glu Pro Gln Val Tyr Thr
    530                 535                 540

Leu Pro Pro Ser Arg Asp Glu Leu Thr Lys Asn Gln Val Ser Leu Thr
545                 550                 555                 560

Cys Leu Val Lys Gly Phe Tyr Pro Ser Asp Ile Ala Val Glu Trp Glu
                565                 570                 575

Ser Asn Gly Gln Pro Glu Asn Asn Tyr Lys Thr Thr Pro Pro Val Leu
            580                 585                 590

Asp Ser Asp Gly Ser Phe Phe Leu Thr Ser Lys Leu Thr Val Asp Lys
```

```
            595                 600                 605
Ser Arg Trp Gln Gln Gly Asn Val Phe Ser Cys Ser Val Met His Glu
610                 615                 620

Ala Leu His Asn His Tyr Thr Gln Lys Ser Leu Ser Leu Ser Pro Gly
625                 630                 635                 640

Lys

<210> SEQ ID NO 82
<211> LENGTH: 449
<212> TYPE: PRT
<213> ORGANISM: Artificial Sequence
<220> FEATURE:
<223> OTHER INFORMATION: Synthetic: IFNAR2 (aa27-243)- IgG1 Fc domain
      with Y407T mutation without a leader sequence

<400> SEQUENCE: 82

Ile Ser Tyr Asp Ser Pro Asp Tyr Thr Asp Glu Ser Cys Thr Phe Lys
1               5                   10                  15

Ile Ser Leu Arg Asn Phe Arg Ser Ile Leu Ser Trp Glu Leu Lys Asn
            20                  25                  30

His Ser Ile Val Pro Thr His Tyr Thr Leu Leu Tyr Thr Ile Met Ser
        35                  40                  45

Lys Pro Glu Asp Leu Lys Val Val Lys Asn Cys Ala Asn Thr Thr Arg
50                  55                  60

Ser Phe Cys Asp Leu Thr Asp Glu Trp Arg Ser Thr His Glu Ala Tyr
65                  70                  75                  80

Val Thr Val Leu Glu Gly Phe Ser Gly Asn Thr Thr Leu Phe Ser Cys
                85                  90                  95

Ser His Asn Phe Trp Leu Ala Ile Asp Met Ser Phe Glu Pro Pro Glu
            100                 105                 110

Phe Glu Ile Val Gly Phe Thr Asn His Ile Asn Val Met Val Lys Phe
        115                 120                 125

Pro Ser Ile Val Glu Glu Glu Leu Gln Phe Asp Leu Ser Leu Val Ile
    130                 135                 140

Glu Glu Gln Ser Glu Gly Ile Val Lys Lys His Lys Pro Glu Ile Lys
145                 150                 155                 160

Gly Asn Met Ser Gly Asn Phe Thr Tyr Ile Ile Asp Lys Leu Ile Pro
                165                 170                 175

Asn Thr Asn Tyr Cys Val Ser Val Tyr Leu Glu His Ser Asp Glu Gln
            180                 185                 190

Ala Val Ile Lys Ser Pro Leu Lys Cys Thr Leu Leu Pro Pro Gly Gln
        195                 200                 205

Glu Ser Glu Ser Ala Glu Ser Ala Lys Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
```

```
            305                 310                 315                 320
Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Thr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys

<210> SEQ ID NO 83
<211> LENGTH: 680
<212> TYPE: PRT
<213> ORGANISM: Artificial Sequence
<220> FEATURE:
<223> OTHER INFORMATION: Synthetic: Leader- IFNAR1 (aa28-436)-
      (Gly4Ser)4- IgG1 Fc domain with T366W mutation

<400> SEQUENCE: 83

Met Asp Trp Thr Trp Arg Ile Leu Phe Leu Val Ala Ala Ala Thr Gly
1               5                   10                  15

Thr His Ala Lys Asn Leu Lys Ser Pro Gln Lys Val Glu Val Asp Ile
                20                  25                  30

Ile Asp Asp Asn Phe Ile Leu Arg Trp Asn Arg Ser Asp Glu Ser Val
            35                  40                  45

Gly Asn Val Thr Phe Ser Phe Asp Tyr Gln Lys Thr Gly Met Asp Asn
50                  55                  60

Trp Ile Lys Leu Ser Gly Cys Gln Asn Ile Thr Ser Thr Lys Cys Asn
65                  70                  75                  80

Phe Ser Ser Leu Lys Leu Asn Val Tyr Glu Glu Ile Lys Leu Arg Ile
                85                  90                  95

Arg Ala Glu Lys Glu Asn Thr Ser Ser Trp Tyr Glu Val Asp Ser Phe
                100                 105                 110

Thr Pro Phe Arg Lys Ala Gln Ile Gly Pro Pro Glu Val His Leu Glu
            115                 120                 125

Ala Glu Asp Lys Ala Ile Val Ile His Ile Ser Pro Gly Thr Lys Asp
            130                 135                 140

Ser Val Met Trp Ala Leu Asp Gly Leu Ser Phe Thr Tyr Ser Leu Val
145                 150                 155                 160

Ile Trp Lys Asn Ser Ser Gly Val Glu Glu Arg Ile Glu Asn Ile Tyr
                165                 170                 175

Ser Arg His Lys Ile Tyr Lys Leu Ser Pro Glu Thr Thr Tyr Cys Leu
                180                 185                 190

Lys Val Lys Ala Ala Leu Leu Thr Ser Trp Lys Ile Gly Val Tyr Ser
            195                 200                 205

Pro Val His Cys Ile Lys Thr Thr Val Glu Asn Glu Leu Pro Pro Pro
```

```
            210                 215                 220
Glu Asn Ile Glu Val Ser Val Gln Asn Gln Asn Tyr Val Leu Lys Trp
225                 230                 235                 240

Asp Tyr Thr Tyr Ala Asn Met Thr Phe Gln Val Gln Trp Leu His Ala
                245                 250                 255

Phe Leu Lys Arg Asn Pro Gly Asn His Leu Tyr Lys Trp Lys Gln Ile
                260                 265                 270

Pro Asp Cys Glu Asn Val Lys Thr Thr Gln Cys Val Phe Pro Gln Asn
            275                 280                 285

Val Phe Gln Lys Gly Ile Tyr Leu Leu Arg Val Gln Ala Ser Asp Gly
            290                 295                 300

Asn Asn Thr Ser Phe Trp Ser Glu Glu Ile Lys Phe Asp Thr Glu Ile
305                 310                 315                 320

Gln Ala Phe Leu Leu Pro Pro Val Phe Asn Ile Arg Ser Leu Ser Asp
                325                 330                 335

Ser Phe His Ile Tyr Ile Gly Ala Pro Lys Gln Ser Gly Asn Thr Pro
                340                 345                 350

Val Ile Gln Asp Tyr Pro Leu Ile Tyr Glu Ile Ile Phe Trp Glu Asn
            355                 360                 365

Thr Ser Asn Ala Glu Arg Lys Ile Ile Glu Lys Lys Thr Asp Val Thr
370                 375                 380

Val Pro Asn Leu Lys Pro Leu Thr Val Tyr Cys Val Lys Ala Arg Ala
385                 390                 395                 400

His Thr Met Asp Glu Lys Leu Asn Lys Ser Ser Val Phe Ser Asp Ala
                405                 410                 415

Val Cys Glu Lys Thr Lys Pro Gly Asn Thr Ser Lys Gly Gly Gly Gly
            420                 425                 430

Ser Gly Gly Gly Gly Ser Gly Gly Gly Ser Gly Gly Gly Gly Ser
            435                 440                 445

Glu Pro Lys Ser Cys Asp Lys Thr His Thr Cys Pro Pro Cys Pro Ala
450                 455                 460

Pro Glu Leu Leu Gly Gly Pro Ser Val Phe Leu Phe Pro Pro Lys Pro
465                 470                 475                 480

Lys Asp Thr Leu Met Ile Ser Arg Thr Pro Glu Val Thr Cys Val Val
                485                 490                 495

Val Asp Val Ser His Glu Asp Pro Glu Val Lys Phe Asn Trp Tyr Val
                500                 505                 510

Asp Gly Val Glu Val His Asn Ala Lys Thr Lys Pro Arg Glu Glu Gln
            515                 520                 525

Tyr Asn Ser Thr Tyr Arg Val Val Ser Val Leu Thr Val Leu His Gln
            530                 535                 540

Asp Trp Leu Asn Gly Lys Glu Tyr Lys Cys Lys Val Ser Asn Lys Ala
545                 550                 555                 560

Leu Pro Ala Pro Ile Glu Lys Thr Ile Ser Lys Ala Lys Gly Gln Pro
                565                 570                 575

Arg Glu Pro Gln Val Tyr Thr Leu Pro Pro Ser Arg Asp Glu Leu Thr
                580                 585                 590

Lys Asn Gln Val Ser Leu Trp Cys Leu Val Lys Gly Phe Tyr Pro Ser
            595                 600                 605

Asp Ile Ala Val Glu Trp Glu Ser Asn Gly Gln Pro Glu Asn Asn Tyr
            610                 615                 620

Lys Thr Thr Pro Pro Val Leu Asp Ser Asp Gly Ser Phe Phe Leu Tyr
625                 630                 635                 640
```

```
Ser Lys Leu Thr Val Asp Lys Ser Arg Trp Gln Gln Gly Asn Val Phe
                645                 650                 655

Ser Cys Ser Val Met His Glu Ala Leu His Asn His Tyr Thr Gln Lys
                660                 665                 670

Ser Leu Ser Leu Ser Pro Gly Lys
            675                 680

<210> SEQ ID NO 84
<211> LENGTH: 661
<212> TYPE: PRT
<213> ORGANISM: Artificial Sequence
<220> FEATURE:
<223> OTHER INFORMATION: Synthetic: IFNAR1 (aa28-436)- (Gly4Ser)4- IgG1
      Fc domain with T366W mutation without a leader sequence

<400> SEQUENCE: 84

Lys Asn Leu Lys Ser Pro Gln Lys Val Glu Val Asp Ile Ile Asp Asp
1               5                   10                  15

Asn Phe Ile Leu Arg Trp Asn Arg Ser Asp Glu Ser Val Gly Asn Val
            20                  25                  30

Thr Phe Ser Phe Asp Tyr Gln Lys Thr Gly Met Asp Asn Trp Ile Lys
        35                  40                  45

Leu Ser Gly Cys Gln Asn Ile Thr Ser Thr Lys Cys Asn Phe Ser Ser
50                  55                  60

Leu Lys Leu Asn Val Tyr Glu Glu Ile Lys Leu Arg Ile Arg Ala Glu
65                  70                  75                  80

Lys Glu Asn Thr Ser Ser Trp Tyr Glu Val Asp Ser Phe Thr Pro Phe
                85                  90                  95

Arg Lys Ala Gln Ile Gly Pro Pro Glu Val His Leu Glu Ala Glu Asp
            100                 105                 110

Lys Ala Ile Val Ile His Ile Ser Pro Gly Thr Lys Asp Ser Val Met
        115                 120                 125

Trp Ala Leu Asp Gly Leu Ser Phe Thr Tyr Ser Leu Val Ile Trp Lys
130                 135                 140

Asn Ser Ser Gly Val Glu Glu Arg Ile Glu Asn Ile Tyr Ser Arg His
145                 150                 155                 160

Lys Ile Tyr Lys Leu Ser Pro Glu Thr Thr Tyr Cys Leu Lys Val Lys
                165                 170                 175

Ala Ala Leu Leu Thr Ser Trp Lys Ile Gly Val Tyr Ser Pro Val His
            180                 185                 190

Cys Ile Lys Thr Thr Val Glu Asn Glu Leu Pro Pro Pro Glu Asn Ile
        195                 200                 205

Glu Val Ser Val Gln Asn Gln Asn Tyr Val Leu Lys Trp Asp Tyr Thr
210                 215                 220

Tyr Ala Asn Met Thr Phe Gln Val Gln Trp Leu His Ala Phe Leu Lys
225                 230                 235                 240

Arg Asn Pro Gly Asn His Leu Tyr Lys Trp Lys Gln Ile Pro Asp Cys
                245                 250                 255

Glu Asn Val Lys Thr Thr Gln Cys Val Phe Pro Gln Asn Val Phe Gln
            260                 265                 270

Lys Gly Ile Tyr Leu Leu Arg Val Gln Ala Ser Asp Gly Asn Asn Thr
        275                 280                 285

Ser Phe Trp Ser Glu Glu Ile Lys Phe Asp Thr Glu Ile Gln Ala Phe
290                 295                 300

Leu Leu Pro Pro Val Phe Asn Ile Arg Ser Leu Ser Asp Ser Phe His
```

```
            305                 310                 315                 320
Ile Tyr Ile Gly Ala Pro Lys Gln Ser Gly Asn Thr Pro Val Ile Gln
                325                 330                 335
Asp Tyr Pro Leu Ile Tyr Glu Ile Ile Phe Trp Glu Asn Thr Ser Asn
                340                 345                 350
Ala Glu Arg Lys Ile Ile Glu Lys Thr Asp Val Thr Val Pro Asn
                355                 360                 365
Leu Lys Pro Leu Thr Val Tyr Cys Val Lys Ala Arg Ala His Thr Met
    370                 375                 380
Asp Glu Lys Leu Asn Lys Ser Ser Val Phe Ser Asp Ala Val Cys Glu
385                 390                 395                 400
Lys Thr Lys Pro Gly Asn Thr Ser Lys Gly Gly Gly Gly Ser Gly Gly
                405                 410                 415
Gly Gly Ser Gly Gly Gly Gly Ser Gly Gly Gly Gly Ser Glu Pro Lys
                420                 425                 430
Ser Cys Asp Lys Thr His Thr Cys Pro Pro Cys Pro Ala Pro Glu Leu
                435                 440                 445
Leu Gly Gly Pro Ser Val Phe Leu Phe Pro Pro Lys Pro Lys Asp Thr
    450                 455                 460
Leu Met Ile Ser Arg Thr Pro Glu Val Thr Cys Val Val Val Asp Val
465                 470                 475                 480
Ser His Glu Asp Pro Glu Val Lys Phe Asn Trp Tyr Val Asp Gly Val
                485                 490                 495
Glu Val His Asn Ala Lys Thr Lys Pro Arg Glu Glu Gln Tyr Asn Ser
                500                 505                 510
Thr Tyr Arg Val Val Ser Val Leu Thr Val Leu His Gln Asp Trp Leu
                515                 520                 525
Asn Gly Lys Glu Tyr Lys Cys Lys Val Ser Asn Lys Ala Leu Pro Ala
                530                 535                 540
Pro Ile Glu Lys Thr Ile Ser Lys Ala Lys Gly Gln Pro Arg Glu Pro
545                 550                 555                 560
Gln Val Tyr Thr Leu Pro Pro Ser Arg Asp Glu Leu Thr Lys Asn Gln
                565                 570                 575
Val Ser Leu Trp Cys Leu Val Lys Gly Phe Tyr Pro Ser Asp Ile Ala
                580                 585                 590
Val Glu Trp Glu Ser Asn Gly Gln Pro Glu Asn Asn Tyr Lys Thr Thr
                595                 600                 605
Pro Pro Val Leu Asp Ser Asp Gly Ser Phe Phe Leu Tyr Ser Lys Leu
                610                 615                 620
Thr Val Asp Lys Ser Arg Trp Gln Gln Gly Asn Val Phe Ser Cys Ser
625                 630                 635                 640
Val Met His Glu Ala Leu His Asn His Tyr Thr Gln Lys Ser Leu Ser
                645                 650                 655
Leu Ser Pro Gly Lys
                660

<210> SEQ ID NO 85
<211> LENGTH: 469
<212> TYPE: PRT
<213> ORGANISM: Artificial Sequence
<220> FEATURE:
<223> OTHER INFORMATION: Synthetic: IFNAR2 (aa27-243) (Gly4Ser)4- IgG1
      Fc domain with T366W mutation without a leader sequence

<400> SEQUENCE: 85
```

```
Ile Ser Tyr Asp Ser Pro Asp Tyr Thr Asp Glu Ser Cys Thr Phe Lys
1               5                   10                  15

Ile Ser Leu Arg Asn Phe Arg Ser Ile Leu Ser Trp Glu Leu Lys Asn
            20                  25                  30

His Ser Ile Val Pro Thr His Tyr Thr Leu Leu Tyr Thr Ile Met Ser
                35                  40                  45

Lys Pro Glu Asp Leu Lys Val Val Lys Asn Cys Ala Asn Thr Thr Arg
        50                  55                  60

Ser Phe Cys Asp Leu Thr Asp Glu Trp Arg Ser Thr His Glu Ala Tyr
65                      70                  75                  80

Val Thr Val Leu Glu Gly Phe Ser Gly Asn Thr Thr Leu Phe Ser Cys
                85                  90                  95

Ser His Asn Phe Trp Leu Ala Ile Asp Met Ser Phe Glu Pro Pro Glu
            100                 105                 110

Phe Glu Ile Val Gly Phe Thr Asn His Ile Asn Val Met Val Lys Phe
            115                 120                 125

Pro Ser Ile Val Glu Glu Leu Gln Phe Asp Leu Ser Leu Val Ile
            130                 135                 140

Glu Glu Gln Ser Glu Gly Ile Val Lys Lys His Lys Pro Glu Ile Lys
145                 150                 155                 160

Gly Asn Met Ser Gly Asn Phe Thr Tyr Ile Ile Asp Lys Leu Ile Pro
                165                 170                 175

Asn Thr Asn Tyr Cys Val Ser Val Tyr Leu Glu His Ser Asp Glu Gln
                180                 185                 190

Ala Val Ile Lys Ser Pro Leu Lys Cys Thr Leu Leu Pro Pro Gly Gln
            195                 200                 205

Glu Ser Glu Ser Ala Glu Ser Ala Lys Gly Gly Gly Ser Gly Gly
210                 215                 220

Gly Gly Ser Gly Gly Gly Ser Gly Gly Gly Ser Glu Pro Lys
225                 230                 235                 240

Ser Cys Asp Lys Thr His Thr Cys Pro Pro Cys Pro Ala Pro Glu Leu
            245                 250                 255

Leu Gly Gly Pro Ser Val Phe Leu Phe Pro Pro Lys Pro Lys Asp Thr
                260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
            325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Asp Glu Leu Thr Lys Asn Gln
    370                 375                 380

Val Ser Leu Trp Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
            405                 410                 415

Pro Pro Val Leu Asp Ser Asp Gly Ser Phe Phe Leu Tyr Ser Lys Leu
```

420                 425                 430
Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly Lys
465

<210> SEQ ID NO 86
<211> LENGTH: 680
<212> TYPE: PRT
<213> ORGANISM: Artificial Sequence
<220> FEATURE:
<223> OTHER INFORMATION: Synthetic: Leader- IFNAR1 (aa28-436)-
      (Gly4Ser)4- IgG1 Fc domain with T366S, L368A, and Y407V mutations

<400> SEQUENCE: 86

Met Asp Trp Thr Trp Arg Ile Leu Phe Leu Val Ala Ala Thr Gly
1               5                   10                  15

Thr His Ala Lys Asn Leu Lys Ser Pro Gln Lys Val Glu Val Asp Ile
                20                  25                  30

Ile Asp Asp Asn Phe Ile Leu Arg Trp Asn Arg Ser Asp Glu Ser Val
            35                  40                  45

Gly Asn Val Thr Phe Ser Phe Asp Tyr Gln Lys Thr Gly Met Asp Asn
    50                  55                  60

Trp Ile Lys Leu Ser Gly Cys Gln Asn Ile Thr Ser Thr Lys Cys Asn
65                  70                  75                  80

Phe Ser Ser Leu Lys Leu Asn Val Tyr Glu Glu Ile Lys Leu Arg Ile
                85                  90                  95

Arg Ala Glu Lys Glu Asn Thr Ser Ser Trp Tyr Glu Val Asp Ser Phe
                100                 105                 110

Thr Pro Phe Arg Lys Ala Gln Ile Gly Pro Pro Glu Val His Leu Glu
            115                 120                 125

Ala Glu Asp Lys Ala Ile Val Ile His Ile Ser Pro Gly Thr Lys Asp
    130                 135                 140

Ser Val Met Trp Ala Leu Asp Gly Leu Ser Phe Thr Tyr Ser Leu Val
145                 150                 155                 160

Ile Trp Lys Asn Ser Ser Gly Val Glu Glu Arg Ile Glu Asn Ile Tyr
                165                 170                 175

Ser Arg His Lys Ile Tyr Lys Leu Ser Pro Glu Thr Thr Tyr Cys Leu
                180                 185                 190

Lys Val Lys Ala Ala Leu Leu Thr Ser Trp Lys Ile Gly Val Tyr Ser
            195                 200                 205

Pro Val His Cys Ile Lys Thr Thr Val Glu Asn Glu Leu Pro Pro Pro
    210                 215                 220

Glu Asn Ile Glu Val Ser Val Gln Asn Gln Asn Tyr Val Leu Lys Trp
225                 230                 235                 240

Asp Tyr Thr Tyr Ala Asn Met Thr Phe Gln Val Gln Trp Leu His Ala
                245                 250                 255

Phe Leu Lys Arg Asn Pro Gly Asn His Leu Tyr Lys Trp Lys Gln Ile
                260                 265                 270

Pro Asp Cys Glu Asn Val Lys Thr Thr Gln Cys Val Phe Pro Gln Asn
            275                 280                 285

Val Phe Gln Lys Gly Ile Tyr Leu Leu Arg Val Gln Ala Ser Asp Gly
    290                 295                 300

```
Asn Asn Thr Ser Phe Trp Ser Glu Glu Ile Lys Phe Asp Thr Glu Ile
305                 310                 315                 320

Gln Ala Phe Leu Leu Pro Pro Val Phe Asn Ile Arg Ser Leu Ser Asp
                325                 330                 335

Ser Phe His Ile Tyr Ile Gly Ala Pro Lys Gln Ser Gly Asn Thr Pro
            340                 345                 350

Val Ile Gln Asp Tyr Pro Leu Ile Tyr Glu Ile Phe Trp Glu Asn
        355                 360                 365

Thr Ser Asn Ala Glu Arg Lys Ile Ile Glu Lys Lys Thr Asp Val Thr
    370                 375                 380

Val Pro Asn Leu Lys Pro Leu Thr Val Tyr Cys Val Lys Ala Arg Ala
385                 390                 395                 400

His Thr Met Asp Glu Lys Leu Asn Lys Ser Ser Val Phe Ser Asp Ala
                405                 410                 415

Val Cys Glu Lys Thr Lys Pro Gly Asn Thr Ser Lys Gly Gly Gly Gly
            420                 425                 430

Ser Gly Gly Gly Gly Ser Gly Gly Gly Gly Ser Gly Gly Gly Gly Ser
        435                 440                 445

Glu Pro Lys Ser Cys Asp Lys Thr His Thr Cys Pro Pro Cys Pro Ala
    450                 455                 460

Pro Glu Leu Leu Gly Gly Pro Ser Val Phe Leu Phe Pro Pro Lys Pro
465                 470                 475                 480

Lys Asp Thr Leu Met Ile Ser Arg Thr Pro Glu Val Thr Cys Val Val
                485                 490                 495

Val Asp Val Ser His Glu Asp Pro Glu Val Lys Phe Asn Trp Tyr Val
            500                 505                 510

Asp Gly Val Glu Val His Asn Ala Lys Thr Lys Pro Arg Glu Glu Gln
        515                 520                 525

Tyr Asn Ser Thr Tyr Arg Val Val Ser Val Leu Thr Val Leu His Gln
    530                 535                 540

Asp Trp Leu Asn Gly Lys Glu Tyr Lys Cys Lys Val Ser Asn Lys Ala
545                 550                 555                 560

Leu Pro Ala Pro Ile Glu Lys Thr Ile Ser Lys Ala Lys Gly Gln Pro
                565                 570                 575

Arg Glu Pro Gln Val Tyr Thr Leu Pro Pro Ser Arg Asp Glu Leu Thr
            580                 585                 590

Lys Asn Gln Val Ser Leu Ser Cys Ala Val Lys Gly Phe Tyr Pro Ser
        595                 600                 605

Asp Ile Ala Val Glu Trp Glu Ser Asn Gly Gln Pro Glu Asn Asn Tyr
    610                 615                 620

Lys Thr Thr Pro Pro Val Leu Asp Ser Asp Gly Ser Phe Phe Leu Val
625                 630                 635                 640

Ser Lys Leu Thr Val Asp Lys Ser Arg Trp Gln Gln Gly Asn Val Phe
                645                 650                 655

Ser Cys Ser Val Met His Glu Ala Leu His Asn His Tyr Thr Gln Lys
            660                 665                 670

Ser Leu Ser Leu Ser Pro Gly Lys
        675                 680

<210> SEQ ID NO 87
<211> LENGTH: 661
<212> TYPE: PRT
<213> ORGANISM: Artificial Sequence
<220> FEATURE:
<223> OTHER INFORMATION: Synthetic: IFNAR1 (aa28-436)- (Gly4Ser)4- IgG1
```

Fc domain with T366S, L368A, and Y407V mutations without a leader sequence

<400> SEQUENCE: 87

```
Lys Asn Leu Lys Ser Pro Gln Lys Val Glu Val Asp Ile Ile Asp
1               5                   10                  15

Asn Phe Ile Leu Arg Trp Asn Arg Ser Asp Glu Ser Val Gly Asn Val
            20                  25                  30

Thr Phe Ser Phe Asp Tyr Gln Lys Thr Gly Met Asp Asn Trp Ile Lys
        35                  40                  45

Leu Ser Gly Cys Gln Asn Ile Thr Ser Thr Lys Cys Asn Phe Ser Ser
50                  55                  60

Leu Lys Leu Asn Val Tyr Glu Glu Ile Lys Leu Arg Ile Arg Ala Glu
65                  70                  75                  80

Lys Glu Asn Thr Ser Ser Trp Tyr Glu Val Asp Ser Phe Thr Pro Phe
                85                  90                  95

Arg Lys Ala Gln Ile Gly Pro Pro Glu Val His Leu Glu Ala Glu Asp
            100                 105                 110

Lys Ala Ile Val Ile His Ile Ser Pro Gly Thr Lys Asp Ser Val Met
        115                 120                 125

Trp Ala Leu Asp Gly Leu Ser Phe Thr Tyr Ser Leu Val Ile Trp Lys
130                 135                 140

Asn Ser Ser Gly Val Glu Glu Arg Ile Glu Asn Ile Tyr Ser Arg His
145                 150                 155                 160

Lys Ile Tyr Lys Leu Ser Pro Glu Thr Thr Tyr Cys Leu Lys Val Lys
                165                 170                 175

Ala Ala Leu Leu Thr Ser Trp Lys Ile Gly Val Tyr Ser Pro Val His
            180                 185                 190

Cys Ile Lys Thr Thr Val Glu Asn Glu Leu Pro Pro Pro Glu Asn Ile
        195                 200                 205

Glu Val Ser Val Gln Asn Gln Asn Tyr Val Leu Lys Trp Asp Tyr Thr
210                 215                 220

Tyr Ala Asn Met Thr Phe Gln Val Gln Trp Leu His Ala Phe Leu Lys
225                 230                 235                 240

Arg Asn Pro Gly Asn His Leu Tyr Lys Trp Lys Gln Ile Pro Asp Cys
                245                 250                 255

Glu Asn Val Lys Thr Thr Gln Cys Val Phe Pro Gln Asn Val Phe Gln
            260                 265                 270

Lys Gly Ile Tyr Leu Leu Arg Val Gln Ala Ser Asp Gly Asn Asn Thr
        275                 280                 285

Ser Phe Trp Ser Glu Glu Ile Lys Phe Asp Thr Glu Ile Gln Ala Phe
290                 295                 300

Leu Leu Pro Pro Val Phe Asn Ile Arg Ser Leu Ser Asp Ser Phe His
305                 310                 315                 320

Ile Tyr Ile Gly Ala Pro Lys Gln Ser Gly Asn Thr Pro Val Ile Gln
                325                 330                 335

Asp Tyr Pro Leu Ile Tyr Glu Ile Ile Phe Trp Glu Asn Thr Ser Asn
            340                 345                 350

Ala Glu Arg Lys Ile Ile Glu Lys Lys Thr Asp Val Thr Val Pro Asn
        355                 360                 365

Leu Lys Pro Leu Thr Val Tyr Cys Val Lys Ala Arg Ala His Thr Met
370                 375                 380

Asp Glu Lys Leu Asn Lys Ser Ser Val Phe Ser Asp Ala Val Cys Glu
385                 390                 395                 400
```

Lys Thr Lys Pro Gly Asn Thr Ser Lys Gly Gly Gly Ser Gly Gly
                405                 410                 415

Gly Gly Ser Gly Gly Gly Ser Gly Gly Gly Ser Glu Pro Lys
            420                 425                 430

Ser Cys Asp Lys Thr His Thr Cys Pro Pro Cys Pro Ala Pro Glu Leu
            435                 440                 445

Leu Gly Gly Pro Ser Val Phe Leu Phe Pro Pro Lys Pro Lys Asp Thr
450                 455                 460

Leu Met Ile Ser Arg Thr Pro Glu Val Thr Cys Val Val Val Asp Val
465                 470                 475                 480

Ser His Glu Asp Pro Glu Val Lys Phe Asn Trp Tyr Val Asp Gly Val
                485                 490                 495

Glu Val His Asn Ala Lys Thr Lys Pro Arg Glu Glu Gln Tyr Asn Ser
            500                 505                 510

Thr Tyr Arg Val Val Ser Val Leu Thr Val Leu His Gln Asp Trp Leu
        515                 520                 525

Asn Gly Lys Glu Tyr Lys Cys Lys Val Ser Asn Lys Ala Leu Pro Ala
    530                 535                 540

Pro Ile Glu Lys Thr Ile Ser Lys Ala Lys Gly Gln Pro Arg Glu Pro
545                 550                 555                 560

Gln Val Tyr Thr Leu Pro Pro Ser Arg Asp Glu Leu Thr Lys Asn Gln
                565                 570                 575

Val Ser Leu Ser Cys Ala Val Lys Gly Phe Tyr Pro Ser Asp Ile Ala
            580                 585                 590

Val Glu Trp Glu Ser Asn Gly Gln Pro Glu Asn Tyr Lys Thr Thr
        595                 600                 605

Pro Pro Val Leu Asp Ser Asp Gly Ser Phe Phe Leu Val Ser Lys Leu
    610                 615                 620

Thr Val Asp Lys Ser Arg Trp Gln Gln Gly Asn Val Phe Ser Cys Ser
625                 630                 635                 640

Val Met His Glu Ala Leu His Asn His Tyr Thr Gln Lys Ser Leu Ser
                645                 650                 655

Leu Ser Pro Gly Lys
            660

<210> SEQ ID NO 88
<211> LENGTH: 488
<212> TYPE: PRT
<213> ORGANISM: Artificial Sequence
<220> FEATURE:
<223> OTHER INFORMATION: Synthetic: Leader- IFNAR2 (aa27-243)-
      (Gly4Ser)4- IgG1 Fc domain with T366S, L368A, and Y407V mutations

<400> SEQUENCE: 88

Met Asp Trp Thr Trp Arg Ile Leu Phe Leu Val Ala Ala Ala Thr Gly
1               5                   10                  15

Thr His Ala Ile Ser Tyr Asp Ser Pro Asp Tyr Thr Asp Glu Ser Cys
            20                  25                  30

Thr Phe Lys Ile Ser Leu Arg Asn Phe Arg Ser Ile Leu Ser Trp Glu
        35                  40                  45

Leu Lys Asn His Ser Ile Val Pro Thr His Tyr Thr Leu Leu Tyr Thr
    50                  55                  60

Ile Met Ser Lys Pro Glu Asp Leu Lys Val Val Lys Asn Cys Ala Asn
65                  70                  75                  80

Thr Thr Arg Ser Phe Cys Asp Leu Thr Asp Glu Trp Arg Ser Thr His

```
             85                  90                  95
Glu Ala Tyr Val Thr Val Leu Glu Gly Phe Ser Gly Asn Thr Thr Leu
            100                 105                 110
Phe Ser Cys Ser His Asn Phe Trp Leu Ala Ile Asp Met Ser Phe Glu
            115                 120                 125
Pro Pro Glu Phe Glu Ile Val Gly Phe Thr Asn His Ile Asn Val Met
130                 135                 140
Val Lys Phe Pro Ser Ile Val Glu Glu Leu Gln Phe Asp Leu Ser
145                 150                 155                 160
Leu Val Ile Glu Glu Gln Ser Glu Gly Ile Val Lys Lys His Lys Pro
            165                 170                 175
Glu Ile Lys Gly Asn Met Ser Gly Asn Phe Thr Tyr Ile Ile Asp Lys
            180                 185                 190
Leu Ile Pro Asn Thr Asn Tyr Cys Val Ser Val Tyr Leu Glu His Ser
            195                 200                 205
Asp Glu Gln Ala Val Ile Lys Ser Pro Leu Lys Cys Thr Leu Leu Pro
210                 215                 220
Pro Gly Gln Glu Ser Glu Ser Ala Glu Ser Ala Lys Gly Gly Gly
225                 230                 235                 240
Ser Gly Gly Gly Gly Ser Gly Gly Gly Gly Ser Gly Gly Gly Gly Ser
            245                 250                 255
Glu Pro Lys Ser Cys Asp Lys Thr His Thr Cys Pro Pro Cys Pro Ala
            260                 265                 270
Pro Glu Leu Leu Gly Gly Pro Ser Val Phe Leu Phe Pro Pro Lys Pro
            275                 280                 285
Lys Asp Thr Leu Met Ile Ser Arg Thr Pro Glu Val Thr Cys Val Val
            290                 295                 300
Val Asp Val Ser His Glu Asp Pro Glu Val Lys Phe Asn Trp Tyr Val
305                 310                 315                 320
Asp Gly Val Glu Val His Asn Ala Lys Thr Lys Pro Arg Glu Glu Gln
            325                 330                 335
Tyr Asn Ser Thr Tyr Arg Val Val Ser Val Leu Thr Val Leu His Gln
            340                 345                 350
Asp Trp Leu Asn Gly Lys Glu Tyr Lys Cys Lys Val Ser Asn Lys Ala
            355                 360                 365
Leu Pro Ala Pro Ile Glu Lys Thr Ile Ser Lys Ala Lys Gly Gln Pro
            370                 375                 380
Arg Glu Pro Gln Val Tyr Thr Leu Pro Pro Ser Arg Asp Glu Leu Thr
385                 390                 395                 400
Lys Asn Gln Val Ser Leu Ser Cys Ala Val Lys Gly Phe Tyr Pro Ser
            405                 410                 415
Asp Ile Ala Val Glu Trp Glu Ser Asn Gly Gln Pro Glu Asn Asn Tyr
            420                 425                 430
Lys Thr Thr Pro Pro Val Leu Asp Ser Asp Gly Ser Phe Phe Leu Val
            435                 440                 445
Ser Lys Leu Thr Val Asp Lys Ser Arg Trp Gln Gln Gly Asn Val Phe
            450                 455                 460
Ser Cys Ser Val Met His Glu Ala Leu His Asn His Tyr Thr Gln Lys
465                 470                 475                 480
Ser Leu Ser Leu Ser Pro Gly Lys
            485

<210> SEQ ID NO 89
```

```
<211> LENGTH: 469
<212> TYPE: PRT
<213> ORGANISM: Artificial Sequence
<220> FEATURE:
<223> OTHER INFORMATION: Synthetic: IFNAR2 (aa27-243)- (Gly4Ser)4- IgG1
      Fc domain with T366S, L368A, and Y407V mutations without a leader
      sequence

<400> SEQUENCE: 89
```

| | | | | | | | | | | | | | | | |
|---|---|---|---|---|---|---|---|---|---|---|---|---|---|---|---|
| Ile | Ser | Tyr | Asp | Ser | Pro | Asp | Tyr | Thr | Asp | Glu | Ser | Cys | Thr | Phe | Lys |
| 1 | | | | 5 | | | | | 10 | | | | |

-continued

```
Gln Val Tyr Thr Leu Pro Pro Ser Arg Asp Glu Leu Thr Lys Asn Gln
        370                 375                 380

Val Ser Leu Ser Cys Ala Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Val Ser Lys Leu
                420                 425                 430

Thr Val Asp Lys Ser Arg Trp Gln Gln Gly Asn Val Phe Ser Cys Ser
                435                 440                 445

Val Met His Glu Ala Leu His Asn His Tyr Thr Gln Lys Ser Leu Ser
        450                 455                 460

Leu Ser Pro Gly Lys
465

<210> SEQ ID NO 90
<211> LENGTH: 670
<212> TYPE: PRT
<213> ORGANISM: Artificial Sequence
<220> FEATURE:
<223> OTHER INFORMATION: Synthetic: Leader- IFNAR1 (aa28-436)-
      (Gly4Ser)2- IgG1 Fc domain with T366W mutation

<400> SEQUENCE: 90

Met Asp Trp Thr Trp Arg Ile Leu Phe Leu Val Ala Ala Ala Thr Gly
1               5                   10                  15

Thr His Ala Lys Asn Leu Lys Ser Pro Gln Lys Val Glu Val Asp Ile
                20                  25                  30

Ile Asp Asp Asn Phe Ile Leu Arg Trp Asn Arg Ser Asp Glu Ser Val
            35                  40                  45

Gly Asn Val Thr Phe Ser Phe Asp Tyr Gln Lys Thr Gly Met Asp Asn
    50                  55                  60

Trp Ile Lys Leu Ser Gly Cys Gln Asn Ile Thr Ser Thr Lys Cys Asn
65                  70                  75                  80

Phe Ser Ser Leu Lys Leu Asn Val Tyr Glu Glu Ile Lys Leu Arg Ile
                85                  90                  95

Arg Ala Glu Lys Glu Asn Thr Ser Ser Trp Tyr Glu Val Asp Ser Phe
                100                 105                 110

Thr Pro Phe Arg Lys Ala Gln Ile Gly Pro Pro Glu Val His Leu Glu
            115                 120                 125

Ala Glu Asp Lys Ala Ile Val Ile His Ile Ser Pro Gly Thr Lys Asp
        130                 135                 140

Ser Val Met Trp Ala Leu Asp Gly Leu Ser Phe Thr Tyr Ser Leu Val
145                 150                 155                 160

Ile Trp Lys Asn Ser Ser Gly Val Glu Glu Arg Ile Glu Asn Ile Tyr
                165                 170                 175

Ser Arg His Lys Ile Tyr Lys Leu Ser Pro Glu Thr Thr Tyr Cys Leu
                180                 185                 190

Lys Val Lys Ala Ala Leu Leu Thr Ser Trp Lys Ile Gly Val Tyr Ser
            195                 200                 205

Pro Val His Cys Ile Lys Thr Thr Val Glu Asn Glu Leu Pro Pro Pro
        210                 215                 220

Glu Asn Ile Glu Val Ser Val Gln Asn Gln Asn Tyr Val Leu Lys Trp
225                 230                 235                 240

Asp Tyr Thr Tyr Ala Asn Met Thr Phe Gln Val Gln Trp Leu His Ala
                245                 250                 255
```

```
Phe Leu Lys Arg Asn Pro Gly Asn His Leu Tyr Lys Trp Lys Gln Ile
            260                 265                 270

Pro Asp Cys Glu Asn Val Lys Thr Thr Gln Cys Val Phe Pro Gln Asn
        275                 280                 285

Val Phe Gln Lys Gly Ile Tyr Leu Leu Arg Val Gln Ala Ser Asp Gly
    290                 295                 300

Asn Asn Thr Ser Phe Trp Ser Glu Glu Ile Lys Phe Asp Thr Glu Ile
305                 310                 315                 320

Gln Ala Phe Leu Leu Pro Pro Val Phe Asn Ile Arg Ser Leu Ser Asp
                325                 330                 335

Ser Phe His Ile Tyr Ile Gly Ala Pro Lys Gln Ser Gly Asn Thr Pro
            340                 345                 350

Val Ile Gln Asp Tyr Pro Leu Ile Tyr Glu Ile Phe Trp Glu Asn
        355                 360                 365

Thr Ser Asn Ala Glu Arg Lys Ile Ile Glu Lys Lys Thr Asp Val Thr
    370                 375                 380

Val Pro Asn Leu Lys Pro Leu Thr Val Tyr Cys Val Lys Ala Arg Ala
385                 390                 395                 400

His Thr Met Asp Glu Lys Leu Asn Lys Ser Ser Val Phe Ser Asp Ala
                405                 410                 415

Val Cys Glu Lys Thr Lys Pro Gly Asn Thr Ser Lys Gly Gly Gly Gly
            420                 425                 430

Ser Gly Gly Gly Gly Ser Glu Pro Lys Ser Cys Asp Lys Thr His Thr
                435                 440                 445

Cys Pro Pro Cys Pro Ala Pro Glu Leu Leu Gly Gly Pro Ser Val Phe
    450                 455                 460

Leu Phe Pro Pro Lys Pro Lys Asp Thr Leu Met Ile Ser Arg Thr Pro
465                 470                 475                 480

Glu Val Thr Cys Val Val Val Asp Val Ser His Glu Asp Pro Glu Val
                485                 490                 495

Lys Phe Asn Trp Tyr Val Asp Gly Val Glu Val His Asn Ala Lys Thr
            500                 505                 510

Lys Pro Arg Glu Glu Gln Tyr Asn Ser Thr Tyr Arg Val Val Ser Val
        515                 520                 525

Leu Thr Val Leu His Gln Asp Trp Leu Asn Gly Lys Glu Tyr Lys Cys
    530                 535                 540

Lys Val Ser Asn Lys Ala Leu Pro Ala Pro Ile Glu Lys Thr Ile Ser
545                 550                 555                 560

Lys Ala Lys Gly Gln Pro Arg Glu Pro Gln Val Tyr Thr Leu Pro Pro
                565                 570                 575

Ser Arg Asp Glu Leu Thr Lys Asn Gln Val Ser Leu Trp Cys Leu Val
            580                 585                 590

Lys Gly Phe Tyr Pro Ser Asp Ile Ala Val Glu Trp Glu Ser Asn Gly
        595                 600                 605

Gln Pro Glu Asn Asn Tyr Lys Thr Thr Pro Pro Val Leu Asp Ser Asp
    610                 615                 620

Gly Ser Phe Phe Leu Tyr Ser Lys Leu Thr Val Asp Lys Ser Arg Trp
625                 630                 635                 640

Gln Gln Gly Asn Val Phe Ser Cys Ser Val Met His Glu Ala Leu His
                645                 650                 655

Asn His Tyr Thr Gln Lys Ser Leu Ser Leu Ser Pro Gly Lys
            660                 665                 670
```

-continued

<210> SEQ ID NO 91
<211> LENGTH: 651
<212> TYPE: PRT
<213> ORGANISM: Artificial Sequence
<220> FEATURE:
<223> OTHER INFORMATION: Synthetic: IFNAR1 (aa28-436)- (Gly4Ser)2- IgG1
      Fc domain with T366W mutation without a leader sequence

<400> SEQUENCE: 91

Lys Asn Leu Lys Ser Pro Gln Lys Val Glu Val Asp Ile Ile Asp
1               5                   10                  15

Asn Phe Ile Leu Arg Trp Asn Arg Ser Asp Glu Ser Val Gly Asn Val
            20                  25                  30

Thr Phe Ser Phe Asp Tyr Gln Lys Thr Gly Met Asp Asn Trp Ile Lys
        35                  40                  45

Leu Ser Gly Cys Gln Asn Ile Thr Ser Thr Lys Cys Asn Phe Ser Ser
    50                  55                  60

Leu Lys Leu Asn Val Tyr Glu Glu Ile Lys Leu Arg Ile Arg Ala Glu
65                  70                  75                  80

Lys Glu Asn Thr Ser Ser Trp Tyr Glu Val Asp Ser Phe Thr Pro Phe
                85                  90                  95

Arg Lys Ala Gln Ile Gly Pro Pro Glu Val His Leu Glu Ala Glu Asp
            100                 105                 110

Lys Ala Ile Val Ile His Ile Ser Pro Gly Thr Lys Asp Ser Val Met
        115                 120                 125

Trp Ala Leu Asp Gly Leu Ser Phe Thr Tyr Ser Leu Val Ile Trp Lys
    130                 135                 140

Asn Ser Ser Gly Val Glu Glu Arg Ile Glu Asn Ile Tyr Ser Arg His
145                 150                 155                 160

Lys Ile Tyr Lys Leu Ser Pro Glu Thr Thr Tyr Cys Leu Lys Val Lys
                165                 170                 175

Ala Ala Leu Leu Thr Ser Trp Lys Ile Gly Val Tyr Ser Pro Val His
            180                 185                 190

Cys Ile Lys Thr Thr Val Glu Asn Glu Leu Pro Pro Pro Glu Asn Ile
        195                 200                 205

Glu Val Ser Val Gln Asn Gln Asn Tyr Val Leu Lys Trp Asp Tyr Thr
    210                 215                 220

Tyr Ala Asn Met Thr Phe Gln Val Gln Trp Leu His Ala Phe Leu Lys
225                 230                 235                 240

Arg Asn Pro Gly Asn His Leu Tyr Lys Trp Lys Gln Ile Pro Asp Cys
                245                 250                 255

Glu Asn Val Lys Thr Thr Gln Cys Val Phe Pro Gln Asn Val Phe Gln
            260                 265                 270

Lys Gly Ile Tyr Leu Leu Arg Val Gln Ala Ser Asp Gly Asn Asn Thr
        275                 280                 285

Ser Phe Trp Ser Glu Glu Ile Lys Phe Asp Thr Glu Ile Gln Ala Phe
    290                 295                 300

Leu Leu Pro Pro Val Phe Asn Ile Arg Ser Leu Ser Asp Ser Phe His
305                 310                 315                 320

Ile Tyr Ile Gly Ala Pro Lys Gln Ser Gly Asn Thr Pro Val Ile Gln
                325                 330                 335

Asp Tyr Pro Leu Ile Tyr Glu Ile Ile Phe Trp Glu Asn Thr Ser Asn
            340                 345                 350

Ala Glu Arg Lys Ile Ile Glu Lys Lys Thr Asp Val Thr Val Pro Asn
        355                 360                 365

```
Leu Lys Pro Leu Thr Val Tyr Cys Val Lys Ala Arg Ala His Thr Met
    370                 375                 380

Asp Glu Lys Leu Asn Lys Ser Ser Val Phe Ser Asp Ala Val Cys Glu
385                 390                 395                 400

Lys Thr Lys Pro Gly Asn Thr Ser Lys Gly Gly Gly Gly Ser Gly Gly
                405                 410                 415

Gly Gly Ser Glu Pro Lys Ser Cys Asp Lys Thr His Thr Cys Pro Pro
            420                 425                 430

Cys Pro Ala Pro Glu Leu Leu Gly Gly Pro Ser Val Phe Leu Phe Pro
        435                 440                 445

Pro Lys Pro Lys Asp Thr Leu Met Ile Ser Arg Thr Pro Glu Val Thr
    450                 455                 460

Cys Val Val Val Asp Val Ser His Glu Asp Pro Glu Val Lys Phe Asn
465                 470                 475                 480

Trp Tyr Val Asp Gly Val Glu Val His Asn Ala Lys Thr Lys Pro Arg
                485                 490                 495

Glu Glu Gln Tyr Asn Ser Thr Tyr Arg Val Val Ser Val Leu Thr Val
            500                 505                 510

Leu His Gln Asp Trp Leu Asn Gly Lys Glu Tyr Lys Cys Lys Val Ser
        515                 520                 525

Asn Lys Ala Leu Pro Ala Pro Ile Glu Lys Thr Ile Ser Lys Ala Lys
    530                 535                 540

Gly Gln Pro Arg Glu Pro Gln Val Tyr Thr Leu Pro Pro Ser Arg Asp
545                 550                 555                 560

Glu Leu Thr Lys Asn Gln Val Ser Leu Trp Cys Leu Val Lys Gly Phe
                565                 570                 575

Tyr Pro Ser Asp Ile Ala Val Glu Trp Glu Ser Asn Gly Gln Pro Glu
            580                 585                 590

Asn Asn Tyr Lys Thr Thr Pro Pro Val Leu Asp Ser Asp Gly Ser Phe
        595                 600                 605

Phe Leu Tyr Ser Lys Leu Thr Val Asp Lys Ser Arg Trp Gln Gln Gly
    610                 615                 620

Asn Val Phe Ser Cys Ser Val Met His Glu Ala Leu His Asn His Tyr
625                 630                 635                 640

Thr Gln Lys Ser Leu Ser Leu Ser Pro Gly Lys
                645                 650

<210> SEQ ID NO 92
<211> LENGTH: 478
<212> TYPE: PRT
<213> ORGANISM: Artificial Sequence
<220> FEATURE:
<223> OTHER INFORMATION: Synthetic: Leader- IFNAR2 (aa27-243)-
      (Gly4Ser)2- IgG1 Fc domain with T366W mutation

<400> SEQUENCE: 92

Met Asp Trp Thr Trp Arg Ile Leu Phe Leu Val Ala Ala Ala Thr Gly
1               5                   10                  15

Thr His Ala Ile Ser Tyr Asp Ser Pro Asp Tyr Thr Asp Glu Ser Cys
            20                  25                  30

Thr Phe Lys Ile Ser Leu Arg Asn Phe Arg Ser Ile Leu Ser Trp Glu
        35                  40                  45

Leu Lys Asn His Ser Ile Val Pro Thr His Tyr Thr Leu Leu Tyr Thr
    50                  55                  60

Ile Met Ser Lys Pro Glu Asp Leu Lys Val Val Lys Asn Cys Ala Asn
```

-continued

```
                65                  70                  75                  80
            Thr Thr Arg Ser Phe Cys Asp Leu Thr Asp Glu Trp Arg Ser Thr His
                            85                  90                  95

Glu Ala Tyr Val Thr Val Leu Glu Gly Phe Ser Gly Asn Thr Thr Leu
                            100                 105                 110

Phe Ser Cys Ser His Asn Phe Trp Leu Ala Ile Asp Met Ser Phe Glu
                            115                 120                 125

Pro Pro Glu Phe Glu Ile Val Gly Phe Thr Asn His Ile Asn Val Met
                            130                 135                 140

Val Lys Phe Pro Ser Ile Val Glu Glu Leu Gln Phe Asp Leu Ser
            145                 150                 155                 160

Leu Val Ile Glu Glu Gln Ser Glu Gly Ile Val Lys Lys His Lys Pro
                            165                 170                 175

Glu Ile Lys Gly Asn Met Ser Gly Asn Phe Thr Tyr Ile Ile Asp Lys
                            180                 185                 190

Leu Ile Pro Asn Thr Asn Tyr Cys Val Ser Val Tyr Leu Glu His Ser
                            195                 200                 205

Asp Glu Gln Ala Val Ile Lys Ser Pro Leu Lys Cys Thr Leu Leu Pro
                            210                 215                 220

Pro Gly Gln Glu Ser Glu Ser Ala Glu Ser Ala Lys Gly Gly Gly Gly
            225                 230                 235                 240

Ser Gly Gly Gly Gly Ser Glu Pro Lys Ser Cys Asp Lys Thr His Thr
                            245                 250                 255

Cys Pro Pro Cys Pro Ala Pro Glu Leu Leu Gly Gly Pro Ser Val Phe
                            260                 265                 270

Leu Phe Pro Pro Lys Pro Lys Asp Thr Leu Met Ile Ser Arg Thr Pro
                            275                 280                 285

Glu Val Thr Cys Val Val Val Asp Val Ser His Glu Asp Pro Glu Val
                            290                 295                 300

Lys Phe Asn Trp Tyr Val Asp Gly Val Glu Val His Asn Ala Lys Thr
            305                 310                 315                 320

Lys Pro Arg Glu Glu Gln Tyr Asn Ser Thr Tyr Arg Val Val Ser Val
                            325                 330                 335

Leu Thr Val Leu His Gln Asp Trp Leu Asn Gly Lys Glu Tyr Lys Cys
                            340                 345                 350

Lys Val Ser Asn Lys Ala Leu Pro Ala Pro Ile Glu Lys Thr Ile Ser
                            355                 360                 365

Lys Ala Lys Gly Gln Pro Arg Glu Pro Gln Val Tyr Thr Leu Pro Pro
            370                 375                 380

Ser Arg Asp Glu Leu Thr Lys Asn Gln Val Ser Leu Trp Cys Leu Val
            385                 390                 395                 400

Lys Gly Phe Tyr Pro Ser Asp Ile Ala Val Glu Trp Glu Ser Asn Gly
                            405                 410                 415

Gln Pro Glu Asn Asn Tyr Lys Thr Thr Pro Pro Val Leu Asp Ser Asp
                            420                 425                 430

Gly Ser Phe Phe Leu Tyr Ser Lys Leu Thr Val Asp Lys Ser Arg Trp
                            435                 440                 445

Gln Gln Gly Asn Val Phe Ser Cys Ser Val Met His Glu Ala Leu His
                            450                 455                 460

Asn His Tyr Thr Gln Lys Ser Leu Ser Leu Ser Pro Gly Lys
            465                 470                 475

<210> SEQ ID NO 93
```

```
<211> LENGTH: 459
<212> TYPE: PRT
<213> ORGANISM: Artificial Sequence
<220> FEATURE:
<223> OTHER INFORMATION: Synthetic: IFNAR2 (aa27-243)- (Gly4Ser)2- IgG1
      Fc domain with T366W mutation without a leader sequence

<400> SEQUENCE: 93
```

| | | | | | | | | | | | | | | | |
|---|---|---|---|---|---|---|---|---|---|---|---|---|---|---|---|
|Ile|Ser|Tyr|Asp|Ser|Pro|Asp|Tyr|Thr|Asp|Glu|Ser|Cys|Thr|Phe|Lys|
|1| | | |5| | | | |10| | | | |15| |
|Ile|Ser|Leu|Arg|Asn|Phe|Arg|Ser|Ile|Le 370                 375                 380
Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Tyr Ser Lys Leu Thr Val Asp Lys Ser Arg Trp Gln Gln Gly
                420                 425                 430

Asn Val Phe Ser Cys Ser Val Met His Glu Ala Leu His Asn His Tyr
                435                 440                 445

Thr Gln Lys Ser Leu Ser Leu Ser Pro Gly Lys
        450                 455

<210> SEQ ID NO 94
<211> LENGTH: 670
<212> TYPE: PRT
<213> ORGANISM: Artificial Sequence
<220> FEATURE:
<223> OTHER INFORMATION: Synthetic: Leader- IFNAR1 (aa28-436)-
      (Gly4Ser)2- IgG1 Fc domain with T366S, L368A, and Y407V mutations

<400> SEQUENCE: 94

Met Asp Trp Thr Trp Arg Ile Leu Phe Leu Val Ala Ala Thr Gly
1               5                   10                  15

Thr His Ala Lys Asn Leu Lys Ser Pro Gln Lys Val Glu Val Asp Ile
            20                  25                  30

Ile Asp Asp Asn Phe Ile Leu Arg Trp Asn Arg Ser Asp Glu Ser Val
            35                  40                  45

Gly Asn Val Thr Phe Ser Phe Asp Tyr Gln Lys Thr Gly Met Asp Asn
50                  55                  60

Trp Ile Lys Leu Ser Gly Cys Gln Asn Ile Thr Ser Thr Lys Cys Asn
65                  70                  75                  80

Phe Ser Ser Leu Lys Leu Asn Val Tyr Glu Glu Ile Lys Leu Arg Ile
                85                  90                  95

Arg Ala Glu Lys Glu Asn Thr Ser Ser Trp Tyr Glu Val Asp Ser Phe
                100                 105                 110

Thr Pro Phe Arg Lys Ala Gln Ile Gly Pro Pro Glu Val His Leu Glu
            115                 120                 125

Ala Glu Asp Lys Ala Ile Val Ile His Ile Ser Pro Gly Thr Lys Asp
130                 135                 140

Ser Val Met Trp Ala Leu Asp Gly Leu Ser Phe Thr Tyr Ser Leu Val
145                 150                 155                 160

Ile Trp Lys Asn Ser Ser Gly Val Glu Glu Arg Ile Glu Asn Ile Tyr
                165                 170                 175

Ser Arg His Lys Ile Tyr Lys Leu Ser Pro Glu Thr Thr Tyr Cys Leu
            180                 185                 190

Lys Val Lys Ala Ala Leu Leu Thr Ser Trp Lys Ile Gly Val Tyr Ser
            195                 200                 205

Pro Val His Cys Ile Lys Thr Thr Val Glu Asn Glu Leu Pro Pro Pro
210                 215                 220

Glu Asn Ile Glu Val Ser Val Gln Asn Gln Asn Tyr Val Leu Lys Trp
225                 230                 235                 240

Asp Tyr Thr Tyr Ala Asn Met Thr Phe Gln Val Gln Trp Leu His Ala
                245                 250                 255

Phe Leu Lys Arg Asn Pro Gly Asn His Leu Tyr Lys Trp Lys Gln Ile
            260                 265                 270

Pro Asp Cys Glu Asn Val Lys Thr Gln Cys Val Phe Pro Gln Asn
            275                 280                 285

Val Phe Gln Lys Gly Ile Tyr Leu Leu Arg Val Gln Ala Ser Asp Gly
290                 295                 300

Asn Asn Thr Ser Phe Trp Ser Glu Glu Ile Lys Phe Asp Thr Glu Ile
305                 310                 315                 320

Gln Ala Phe Leu Leu Pro Val Phe Asn Ile Arg Ser Leu Ser Asp
                325                 330                 335

Ser Phe His Ile Tyr Ile Gly Ala Pro Lys Gln Ser Gly Asn Thr Pro
            340                 345                 350

Val Ile Gln Asp Tyr Pro Leu Ile Tyr Glu Ile Phe Trp Glu Asn
            355                 360                 365

Thr Ser Asn Ala Glu Arg Lys Ile Ile Glu Lys Lys Thr Asp Val Thr
370                 375                 380

Val Pro Asn Leu Lys Pro Leu Thr Val Tyr Cys Val Lys Ala Arg Ala
385                 390                 395                 400

His Thr Met Asp Glu Lys Leu Asn Lys Ser Val Phe Ser Asp Ala
            405                 410                 415

Val Cys Glu Lys Thr Lys Pro Gly Asn Thr Ser Lys Gly Gly Gly
            420                 425                 430

Ser Gly Gly Gly Ser Glu Pro Lys Ser Cys Asp Lys Thr His Thr
            435                 440                 445

Cys Pro Pro Cys Pro Ala Pro Glu Leu Leu Gly Gly Pro Ser Val Phe
450                 455                 460

Leu Phe Pro Pro Lys Pro Lys Asp Thr Leu Met Ile Ser Arg Thr Pro
465                 470                 475                 480

Glu Val Thr Cys Val Val Val Asp Val Ser His Glu Asp Pro Glu Val
            485                 490                 495

Lys Phe Asn Trp Tyr Val Asp Gly Val Glu Val His Asn Ala Lys Thr
            500                 505                 510

Lys Pro Arg Glu Glu Gln Tyr Asn Ser Thr Tyr Arg Val Val Ser Val
            515                 520                 525

Leu Thr Val Leu His Gln Asp Trp Leu Asn Gly Lys Glu Tyr Lys Cys
530                 535                 540

Lys Val Ser Asn Lys Ala Leu Pro Ala Pro Ile Glu Lys Thr Ile Ser
545                 550                 555                 560

Lys Ala Lys Gly Gln Pro Arg Glu Pro Gln Val Tyr Thr Leu Pro Pro
            565                 570                 575

Ser Arg Asp Glu Leu Thr Lys Asn Gln Val Ser Leu Ser Cys Ala Val
            580                 585                 590

Lys Gly Phe Tyr Pro Ser Asp Ile Ala Val Glu Trp Glu Ser Asn Gly
            595                 600                 605

Gln Pro Glu Asn Asn Tyr Lys Thr Thr Pro Pro Val Leu Asp Ser Asp
610                 615                 620

Gly Ser Phe Phe Leu Val Ser Lys Leu Thr Val Asp Lys Ser Arg Trp
625                 630                 635                 640

Gln Gln Gly Asn Val Phe Ser Cys Ser Val Met His Glu Ala Leu His
            645                 650                 655

Asn His Tyr Thr Gln Lys Ser Leu Ser Leu Ser Pro Gly Lys
            660                 665                 670

<210> SEQ ID NO 95
<211> LENGTH: 651
<212> TYPE: PRT

<213> ORGANISM: Artificial Sequence
<220> FEATURE:
<223> OTHER INFORMATION: Synthetic: IFNAR1 (aa28-436)- (Gly4Ser)2- IgG1
    Fc domain with T366S, L368A, and Y407V mutations without a leader
    sequence

<400> SEQUENCE: 95

```
Lys Asn Leu Lys Ser Pro Gln Lys Val Glu Val Asp Ile Ile Asp Asp
1               5                   10                  15

Asn Phe Ile Leu Arg Trp Asn Arg Ser Asp Glu Ser Val Gly Asn Val
            20                  25                  30

Thr Phe Ser Phe Asp Tyr Gln Lys Thr Gly Met Asp Asn Trp Ile Lys
        35                  40                  45

Leu Ser Gly Cys Gln Asn Ile Thr Ser Thr Lys Cys Asn Phe Ser Ser
    50                  55                  60

Leu Lys Leu Asn Val Tyr Glu Glu Ile Lys Leu Arg Ile Arg Ala Glu
65                  70                  75                  80

Lys Glu Asn Thr Ser Ser Trp Tyr Glu Val Asp Ser Phe Thr Pro Phe
                85                  90                  95

Arg Lys Ala Gln Ile Gly Pro Pro Glu Val His Leu Glu Ala Glu Asp
            100                 105                 110

Lys Ala Ile Val Ile His Ile Ser Pro Gly Thr Lys Asp Ser Val Met
        115                 120                 125

Trp Ala Leu Asp Gly Leu Ser Phe Thr Tyr Ser Leu Val Ile Trp Lys
    130                 135                 140

Asn Ser Ser Gly Val Glu Glu Arg Ile Glu Asn Ile Tyr Ser Arg His
145                 150                 155                 160

Lys Ile Tyr Lys Leu Ser Pro Glu Thr Thr Tyr Cys Leu Lys Val Lys
                165                 170                 175

Ala Ala Leu Leu Thr Ser Trp Lys Ile Gly Val Tyr Ser Pro Val His
            180                 185                 190

Cys Ile Lys Thr Thr Val Glu Asn Glu Leu Pro Pro Pro Glu Asn Ile
        195                 200                 205

Glu Val Ser Val Gln Asn Gln Asn Tyr Val Leu Lys Trp Asp Tyr Thr
    210                 215                 220

Tyr Ala Asn Met Thr Phe Gln Val Gln Trp Leu His Ala Phe Leu Lys
225                 230                 235                 240

Arg Asn Pro Gly Asn His Leu Tyr Lys Trp Lys Gln Ile Pro Asp Cys
                245                 250                 255

Glu Asn Val Lys Thr Thr Gln Cys Val Phe Pro Gln Asn Val Phe Gln
            260                 265                 270

Lys Gly Ile Tyr Leu Leu Arg Val Gln Ala Ser Asp Gly Asn Asn Thr
        275                 280                 285

Ser Phe Trp Ser Glu Glu Ile Lys Phe Asp Thr Glu Ile Gln Ala Phe
    290                 295                 300

Leu Leu Pro Pro Val Phe Asn Ile Arg Ser Leu Ser Asp Ser Phe His
305                 310                 315                 320

Ile Tyr Ile Gly Ala Pro Lys Gln Ser Gly Asn Thr Pro Val Ile Gln
                325                 330                 335

Asp Tyr Pro Leu Ile Tyr Glu Ile Ile Phe Trp Glu Asn Thr Ser Asn
            340                 345                 350

Ala Glu Arg Lys Ile Ile Glu Lys Lys Thr Asp Val Thr Val Pro Asn
        355                 360                 365

Leu Lys Pro Leu Thr Val Tyr Cys Val Lys Ala Arg Ala His Thr Met
    370                 375                 380
```

```
Asp Glu Lys Leu Asn Lys Ser Ser Val Phe Ser Asp Ala Val Cys Glu
385                 390                 395                 400

Lys Thr Lys Pro Gly Asn Thr Ser Lys Gly Gly Gly Gly Ser Gly Gly
            405                 410                 415

Gly Gly Ser Glu Pro Lys Ser Cys Asp Lys Thr His Thr Cys Pro Pro
        420                 425                 430

Cys Pro Ala Pro Glu Leu Leu Gly Gly Pro Ser Val Phe Leu Phe Pro
    435                 440                 445

Pro Lys Pro Lys Asp Thr Leu Met Ile Ser Arg Thr Pro Glu Val Thr
450                 455                 460

Cys Val Val Val Asp Val Ser His Glu Asp Pro Glu Val Lys Phe Asn
465                 470                 475                 480

Trp Tyr Val Asp Gly Val Glu Val His Asn Ala Lys Thr Lys Pro Arg
                485                 490                 495

Glu Glu Gln Tyr Asn Ser Thr Tyr Arg Val Val Ser Val Leu Thr Val
            500                 505                 510

Leu His Gln Asp Trp Leu Asn Gly Lys Glu Tyr Lys Cys Lys Val Ser
        515                 520                 525

Asn Lys Ala Leu Pro Ala Pro Ile Glu Lys Thr Ile Ser Lys Ala Lys
530                 535                 540

Gly Gln Pro Arg Glu Pro Gln Val Tyr Thr Leu Pro Pro Ser Arg Asp
545                 550                 555                 560

Glu Leu Thr Lys Asn Gln Val Ser Leu Ser Cys Ala Val Lys Gly Phe
                565                 570                 575

Tyr Pro Ser Asp Ile Ala Val Glu Trp Glu Ser Asn Gly Gln Pro Glu
            580                 585                 590

Asn Asn Tyr Lys Thr Thr Pro Pro Val Leu Asp Ser Asp Gly Ser Phe
        595                 600                 605

Phe Leu Val Ser Lys Leu Thr Val Asp Lys Ser Arg Trp Gln Gln Gly
610                 615                 620

Asn Val Phe Ser Cys Ser Val Met His Glu Ala Leu His Asn His Tyr
625                 630                 635                 640

Thr Gln Lys Ser Leu Ser Leu Ser Pro Gly Lys
                645                 650

<210> SEQ ID NO 96
<211> LENGTH: 478
<212> TYPE: PRT
<213> ORGANISM: Artificial Sequence
<220> FEATURE:
<223> OTHER INFORMATION: Synthetic: Leader- IFNAR2 (aa27-243)-
      (Gly4Ser)2- IgG1 Fc domain with T366S, L368A, and Y407V mutations

<400> SEQUENCE: 96

Met Asp Trp Thr Trp Arg Ile Leu Phe Leu Val Ala Ala Ala Thr Gly
1               5                   10                  15

Thr His Ala Ile Ser Tyr Asp Ser Pro Asp Tyr Thr Asp Glu Ser Cys
            20                  25                  30

Thr Phe Lys Ile Ser Leu Arg Asn Phe Arg Ser Ile Leu Ser Trp Glu
        35                  40                  45

Leu Lys Asn His Ser Ile Val Pro Thr His Tyr Thr Leu Leu Tyr Thr
    50                  55                  60

Ile Met Ser Lys Pro Glu Asp Leu Lys Val Val Lys Asn Cys Ala Asn
65                  70                  75                  80

Thr Thr Arg Ser Phe Cys Asp Leu Thr Asp Glu Trp Arg Ser Thr His
```

```
                    85                  90                  95
Glu Ala Tyr Val Thr Val Leu Glu Gly Phe Ser Gly Asn Thr Thr Leu
                100                 105                 110

Phe Ser Cys Ser His Asn Phe Trp Leu Ala Ile Asp Met Ser Phe Glu
            115                 120                 125

Pro Pro Glu Phe Glu Ile Val Gly Phe Thr Asn His Ile Asn Val Met
        130                 135                 140

Val Lys Phe Pro Ser Ile Val Glu Glu Leu Gln Phe Asp Leu Ser
145                 150                 155                 160

Leu Val Ile Glu Glu Gln Ser Glu Gly Ile Val Lys Lys His Lys Pro
                165                 170                 175

Glu Ile Lys Gly Asn Met Ser Gly Asn Phe Thr Tyr Ile Ile Asp Lys
            180                 185                 190

Leu Ile Pro Asn Thr Asn Tyr Cys Val Ser Val Tyr Leu Glu His Ser
        195                 200                 205

Asp Glu Gln Ala Val Ile Lys Ser Pro Leu Lys Cys Thr Leu Leu Pro
    210                 215                 220

Pro Gly Gln Glu Ser Glu Ser Ala Glu Ser Ala Lys Gly Gly Gly Gly
225                 230                 235                 240

Ser Gly Gly Gly Gly Ser Glu Pro Lys Ser Cys Asp Lys Thr His Thr
                245                 250                 255

Cys Pro Pro Cys Pro Ala Pro Glu Leu Leu Gly Gly Pro Ser Val Phe
            260                 265                 270

Leu Phe Pro Pro Lys Pro Lys Asp Thr Leu Met Ile Ser Arg Thr Pro
        275                 280                 285

Glu Val Thr Cys Val Val Val Asp Val Ser His Glu Asp Pro Glu Val
    290                 295                 300

Lys Phe Asn Trp Tyr Val Asp Gly Val Glu Val His Asn Ala Lys Thr
305                 310                 315                 320

Lys Pro Arg Glu Glu Gln Tyr Asn Ser Thr Tyr Arg Val Val Ser Val
                325                 330                 335

Leu Thr Val Leu His Gln Asp Trp Leu Asn Gly Lys Glu Tyr Lys Cys
            340                 345                 350

Lys Val Ser Asn Lys Ala Leu Pro Ala Pro Ile Glu Lys Thr Ile Ser
        355                 360                 365

Lys Ala Lys Gly Gln Pro Arg Glu Pro Gln Val Tyr Thr Leu Pro Pro
    370                 375                 380

Ser Arg Asp Glu Leu Thr Lys Asn Gln Val Ser Leu Ser Cys Ala Val
385                 390                 395                 400

Lys Gly Phe Tyr Pro Ser Asp Ile Ala Val Glu Trp Glu Ser Asn Gly
                405                 410                 415

Gln Pro Glu Asn Asn Tyr Lys Thr Thr Pro Pro Val Leu Asp Ser Asp
            420                 425                 430

Gly Ser Phe Phe Leu Val Ser Lys Leu Thr Val Asp Lys Ser Arg Trp
        435                 440                 445

Gln Gln Gly Asn Val Phe Ser Cys Ser Val Met His Glu Ala Leu His
    450                 455                 460

Asn His Tyr Thr Gln Lys Ser Leu Ser Leu Ser Pro Gly Lys
465                 470                 475

<210> SEQ ID NO 97
<211> LENGTH: 459
<212> TYPE: PRT
<213> ORGANISM: Artificial Sequence
```

<220> FEATURE:
<223> OTHER INFORMATION: Synthetic: IFNAR2 (aa27-243)- (Gly4Ser)2- IgG1 Fc domain with T366S, L368A, and Y407V mutations without a leader sequence

<400> SEQUENCE: 97

```
Ile Ser Tyr Asp Ser Pro Asp Tyr Thr Asp Glu Ser Cys Thr Phe Lys
1               5                   10                  15
Ile Ser Leu Arg Asn Phe Arg Ser Ile Leu Ser Trp Glu Leu Lys Asn
            20                  25                  30
His Ser Ile Val Pro Thr His Tyr Thr Leu Leu Tyr Thr Ile Met Ser
        35                  40                  45
Lys Pro Glu Asp Leu Lys Val Val Lys Asn Cys Ala Asn Thr Thr Arg
50                  55                  60
Ser Phe Cys Asp Leu Thr Asp Glu Trp Arg Ser Thr His Glu Ala Tyr
65                  70                  75                  80
Val Thr Val Leu Glu Gly Phe Ser Gly Asn Thr Thr Leu Phe Ser Cys
                85                  90                  95
Ser His Asn Phe Trp Leu Ala Ile Asp Met Ser Phe Glu Pro Pro Glu
            100                 105                 110
Phe Glu Ile Val Gly Phe Thr Asn His Ile Asn Val Met Val Lys Phe
        115                 120                 125
Pro Ser Ile Val Glu Glu Leu Gln Phe Asp Leu Ser Leu Val Ile
130                 135                 140
Glu Glu Gln Ser Glu Gly Ile Val Lys Lys His Lys Pro Glu Ile Lys
145                 150                 155                 160
Gly Asn Met Ser Gly Asn Phe Thr Tyr Ile Ile Asp Lys Leu Ile Pro
                165                 170                 175
Asn Thr Asn Tyr Cys Val Ser Val Tyr Leu Glu His Ser Asp Glu Gln
            180                 185                 190
Ala Val Ile Lys Ser Pro Leu Lys Cys Thr Leu Leu Pro Pro Gly Gln
        195                 200                 205
Glu Ser Glu Ser Ala Glu Ser Ala Lys Gly Gly Gly Gly Ser Gly Gly
210                 215                 220
Gly Gly Ser Glu Pro Lys Ser Cys Asp Lys Thr His Thr Cys Pro Pro
225                 230                 235                 240
Cys Pro Ala Pro Glu Leu Leu Gly Gly Pro Ser Val Phe Leu Phe Pro
                245                 250                 255
Pro Lys Pro Lys Asp Thr Leu Met Ile Ser Arg Thr Pro Glu Val Thr
            260                 265                 270
Cys Val Val Val Asp Val Ser His Glu Asp Pro Glu Val Lys Phe Asn
        275                 280                 285
Trp Tyr Val Asp Gly Val Glu Val His Asn Ala Lys Thr Lys Pro Arg
290                 295                 300
Glu Glu Gln Tyr Asn Ser Thr Tyr Arg Val Val Ser Val Leu Thr Val
305                 310                 315                 320
Leu His Gln Asp Trp Leu Asn Gly Lys Glu Tyr Lys Cys Lys Val Ser
                325                 330                 335
Asn Lys Ala Leu Pro Ala Pro Ile Glu Lys Thr Ile Ser Lys Ala Lys
            340                 345                 350
Gly Gln Pro Arg Glu Pro Gln Val Tyr Thr Leu Pro Pro Ser Arg Asp
        355                 360                 365
Glu Leu Thr Lys Asn Gln Val Ser Leu Ser Cys Ala Val Lys Gly Phe
370                 375                 380
```

```
Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
            405                 410                 415

Phe Leu Val Ser Lys Leu Thr Val Asp Lys Ser Arg Trp Gln Gln Gly
        420                 425                 430

Asn Val Phe Ser Cys Ser Val Met His Glu Ala Leu His Asn His Tyr
            435                 440                 445

Thr Gln Lys Ser Leu Ser Leu Ser Pro Gly Lys
    450                 455

<210> SEQ ID NO 98
<211> LENGTH: 660
<212> TYPE: PRT
<213> ORGANISM: Artificial Sequence
<220> FEATURE:
<223> OTHER INFORMATION: Synthetic: Leader- IFNAR1 (aa28-436)- IgG1 Fc
      domain with T366W mutation

<400> SEQUENCE: 98

Met Asp Trp Thr Trp Arg Ile Leu Phe Leu Val Ala Ala Thr Gly
1               5                   10                  15

Thr His Ala Lys Asn Leu Lys Ser Pro Gln Lys Val Glu Val Asp Ile
            20                  25                  30

Ile Asp Asp Asn Phe Ile Leu Arg Trp Asn Arg Ser Asp Glu Ser Val
            35                  40                  45

Gly Asn Val Thr Phe Ser Phe Asp Tyr Gln Lys Thr Gly Met Asp Asn
    50                  55                  60

Trp Ile Lys Leu Ser Gly Cys Gln Asn Ile Thr Ser Thr Lys Cys Asn
65                  70                  75                  80

Phe Ser Ser Leu Lys Leu Asn Val Tyr Glu Glu Ile Lys Leu Arg Ile
                85                  90                  95

Arg Ala Glu Lys Glu Asn Thr Ser Ser Trp Tyr Glu Val Asp Ser Phe
            100                 105                 110

Thr Pro Phe Arg Lys Ala Gln Ile Gly Pro Pro Glu Val His Leu Glu
        115                 120                 125

Ala Glu Asp Lys Ala Ile Val Ile His Ile Ser Pro Gly Thr Lys Asp
    130                 135                 140

Ser Val Met Trp Ala Leu Asp Gly Leu Ser Phe Thr Tyr Ser Leu Val
145                 150                 155                 160

Ile Trp Lys Asn Ser Ser Gly Val Glu Glu Arg Ile Glu Asn Ile Tyr
                165                 170                 175

Ser Arg His Lys Ile Tyr Lys Leu Ser Pro Glu Thr Thr Tyr Cys Leu
            180                 185                 190

Lys Val Lys Ala Ala Leu Leu Thr Ser Trp Lys Ile Gly Val Tyr Ser
        195                 200                 205

Pro Val His Cys Ile Lys Thr Thr Val Glu Asn Glu Leu Pro Pro Pro
    210                 215                 220

Glu Asn Ile Glu Val Ser Val Gln Asn Gln Asn Tyr Val Leu Lys Trp
225                 230                 235                 240

Asp Tyr Thr Tyr Ala Asn Met Thr Phe Gln Val Gln Trp Leu His Ala
                245                 250                 255

Phe Leu Lys Arg Asn Pro Gly Asn His Leu Tyr Lys Trp Lys Gln Ile
            260                 265                 270

Pro Asp Cys Glu Asn Val Lys Thr Thr Gln Cys Val Phe Pro Gln Asn
        275                 280                 285
```

Val Phe Gln Lys Gly Ile Tyr Leu Leu Arg Val Gln Ala Ser Asp Gly
    290                 295                 300

Asn Asn Thr Ser Phe Trp Ser Glu Glu Ile Lys Phe Asp Thr Glu Ile
305                 310                 315                 320

Gln Ala Phe Leu Leu Pro Pro Val Phe Asn Ile Arg Ser Leu Ser Asp
                325                 330                 335

Ser Phe His Ile Tyr Ile Gly Ala Pro Lys Gln Ser Gly Asn Thr Pro
            340                 345                 350

Val Ile Gln Asp Tyr Pro Leu Ile Tyr Glu Ile Ile Phe Trp Glu Asn
        355                 360                 365

Thr Ser Asn Ala Glu Arg Lys Ile Ile Glu Lys Lys Thr Asp Val Thr
    370                 375                 380

Val Pro Asn Leu Lys Pro Leu Thr Val Tyr Cys Val Lys Ala Arg Ala
385                 390                 395                 400

His Thr Met Asp Glu Lys Leu Asn Lys Ser Val Phe Ser Asp Ala
                405                 410                 415

Val Cys Glu Lys Thr Lys Pro Gly Asn Thr Ser Lys Glu Pro Lys Ser
            420                 425                 430

Cys Asp Lys Thr His Thr Cys Pro Pro Cys Pro Ala Pro Glu Leu Leu
        435                 440                 445

Gly Gly Pro Ser Val Phe Leu Phe Pro Pro Lys Pro Lys Asp Thr Leu
    450                 455                 460

Met Ile Ser Arg Thr Pro Glu Val Thr Cys Val Val Val Asp Val Ser
465                 470                 475                 480

His Glu Asp Pro Glu Val Lys Phe Asn Trp Tyr Val Asp Gly Val Glu
                485                 490                 495

Val His Asn Ala Lys Thr Lys Pro Arg Glu Glu Gln Tyr Asn Ser Thr
            500                 505                 510

Tyr Arg Val Val Ser Val Leu Thr Val Leu His Gln Asp Trp Leu Asn
        515                 520                 525

Gly Lys Glu Tyr Lys Cys Lys Val Ser Asn Lys Ala Leu Pro Ala Pro
    530                 535                 540

Ile Glu Lys Thr Ile Ser Lys Ala Lys Gly Gln Pro Arg Glu Pro Gln
545                 550                 555                 560

Val Tyr Thr Leu Pro Pro Ser Arg Asp Glu Leu Thr Lys Asn Gln Val
                565                 570                 575

Ser Leu Trp Cys Leu Val Lys Gly Phe Tyr Pro Ser Asp Ile Ala Val
            580                 585                 590

Glu Trp Glu Ser Asn Gly Gln Pro Glu Asn Asn Tyr Lys Thr Thr Pro
        595                 600                 605

Pro Val Leu Asp Ser Asp Gly Ser Phe Phe Leu Tyr Ser Lys Leu Thr
    610                 615                 620

Val Asp Lys Ser Arg Trp Gln Gln Gly Asn Val Phe Ser Cys Ser Val
625                 630                 635                 640

Met His Glu Ala Leu His Asn His Tyr Thr Gln Lys Ser Leu Ser Leu
                645                 650                 655

Ser Pro Gly Lys
            660

<210> SEQ ID NO 99
<211> LENGTH: 641
<212> TYPE: PRT
<213> ORGANISM: Artificial Sequence
<220> FEATURE:

<223> OTHER INFORMATION: Synthetic: IFNAR1 (aa28-436)- IgG1 Fc domain
with T366W mutation without a leader sequence

<400> SEQUENCE: 99

```
Lys Asn Leu Lys Ser Pro Gln Lys Val Glu Val Asp Ile Ile Asp
 1               5                  10                  15

Asn Phe Ile Leu Arg Trp Asn Arg Ser Asp Glu Ser Val Gly Asn Val
             20                  25                  30

Thr Phe Ser Phe Asp Tyr Gln Lys Thr Gly Met Asp Asn Trp Ile Lys
         35                  40                  45

Leu Ser Gly Cys Gln Asn Ile Thr Ser Thr Lys Cys Asn Phe Ser Ser
 50                  55                  60

Leu Lys Leu Asn Val Tyr Glu Glu Ile Lys Leu Arg Ile Arg Ala Glu
65                  70                  75                  80

Lys Glu Asn Thr Ser Ser Trp Tyr Glu Val Asp Ser Phe Thr Pro Phe
                 85                  90                  95

Arg Lys Ala Gln Ile Gly Pro Pro Glu Val His Leu Glu Ala Glu Asp
            100                 105                 110

Lys Ala Ile Val Ile His Ile Ser Pro Gly Thr Lys Asp Ser Val Met
        115                 120                 125

Trp Ala Leu Asp Gly Leu Ser Phe Thr Tyr Ser Leu Val Ile Trp Lys
130                 135                 140

Asn Ser Ser Gly Val Glu Glu Arg Ile Glu Asn Ile Tyr Ser Arg His
145                 150                 155                 160

Lys Ile Tyr Lys Leu Ser Pro Glu Thr Thr Tyr Cys Leu Lys Val Lys
                165                 170                 175

Ala Ala Leu Leu Thr Ser Trp Lys Ile Gly Val Tyr Ser Pro Val His
            180                 185                 190

Cys Ile Lys Thr Thr Val Glu Asn Glu Leu Pro Pro Pro Glu Asn Ile
        195                 200                 205

Glu Val Ser Val Gln Asn Gln Asn Tyr Val Leu Lys Trp Asp Tyr Thr
210                 215                 220

Tyr Ala Asn Met Thr Phe Gln Val Gln Trp Leu His Ala Phe Leu Lys
225                 230                 235                 240

Arg Asn Pro Gly Asn His Leu Tyr Lys Trp Lys Gln Ile Pro Asp Cys
                245                 250                 255

Glu Asn Val Lys Thr Thr Gln Cys Val Phe Pro Gln Asn Val Phe Gln
            260                 265                 270

Lys Gly Ile Tyr Leu Leu Arg Val Gln Ala Ser Asp Gly Asn Asn Thr
        275                 280                 285

Ser Phe Trp Ser Glu Glu Ile Lys Phe Asp Thr Glu Ile Gln Ala Phe
290                 295                 300

Leu Leu Pro Pro Val Phe Asn Ile Arg Ser Leu Ser Asp Ser Phe His
305                 310                 315                 320

Ile Tyr Ile Gly Ala Pro Lys Gln Ser Gly Asn Thr Pro Val Ile Gln
                325                 330                 335

Asp Tyr Pro Leu Ile Tyr Glu Ile Ile Phe Trp Glu Asn Thr Ser Asn
            340                 345                 350

Ala Glu Arg Lys Ile Ile Glu Lys Lys Thr Asp Val Thr Val Pro Asn
        355                 360                 365

Leu Lys Pro Leu Thr Val Tyr Cys Val Lys Ala Arg Ala His Thr Met
370                 375                 380

Asp Glu Lys Leu Asn Lys Ser Ser Val Phe Ser Asp Ala Val Cys Glu
385                 390                 395                 400
```

```
Lys Thr Lys Pro Gly Asn Thr Ser Lys Glu Pro Lys Ser Cys Asp Lys
                405                 410                 415

Thr His Thr Cys Pro Pro Cys Pro Ala Pro Glu Leu Leu Gly Gly Pro
            420                 425                 430

Ser Val Phe Leu Phe Pro Pro Lys Pro Lys Asp Thr Leu Met Ile Ser
        435                 440                 445

Arg Thr Pro Glu Val Thr Cys Val Val Val Asp Val Ser His Glu Asp
    450                 455                 460

Pro Glu Val Lys Phe Asn Trp Tyr Val Asp Gly Val Glu Val His Asn
465                 470                 475                 480

Ala Lys Thr Lys Pro Arg Glu Glu Gln Tyr Asn Ser Thr Tyr Arg Val
                485                 490                 495

Val Ser Val Leu Thr Val Leu His Gln Asp Trp Leu Asn Gly Lys Glu
            500                 505                 510

Tyr Lys Cys Lys Val Ser Asn Lys Ala Leu Pro Ala Pro Ile Glu Lys
        515                 520                 525

Thr Ile Ser Lys Ala Lys Gly Gln Pro Arg Glu Pro Gln Val Tyr Thr
    530                 535                 540

Leu Pro Pro Ser Arg Asp Glu Leu Thr Lys Asn Gln Val Ser Leu Trp
545                 550                 555                 560

Cys Leu Val Lys Gly Phe Tyr Pro Ser Asp Ile Ala Val Glu Trp Glu
                565                 570                 575

Ser Asn Gly Gln Pro Glu Asn Asn Tyr Lys Thr Thr Pro Pro Val Leu
            580                 585                 590

Asp Ser Asp Gly Ser Phe Phe Leu Tyr Ser Lys Leu Thr Val Asp Lys
        595                 600                 605

Ser Arg Trp Gln Gln Gly Asn Val Phe Ser Cys Ser Val Met His Glu
    610                 615                 620

Ala Leu His Asn His Tyr Thr Gln Lys Ser Leu Ser Leu Ser Pro Gly
625                 630                 635                 640

Lys

<210> SEQ ID NO 100
<211> LENGTH: 468
<212> TYPE: PRT
<213> ORGANISM: Artificial Sequence
<220> FEATURE:
<223> OTHER INFORMATION: Synthetic: Leader- IFNAR2 (aa27-243)- IgG1 Fc
      domain with T366W mutation

<400> SEQUENCE: 100

Met Asp Trp Thr Trp Arg Ile Leu Phe Leu Val Ala Ala Ala Thr Gly
1               5                   10                  15

Thr His Ala Ile Ser Tyr Asp Ser Pro Asp Tyr Thr Asp Glu Ser Cys
            20                  25                  30

Thr Phe Lys Ile Ser Leu Arg Asn Phe Arg Ser Ile Leu Ser Trp Glu
        35                  40                  45

Leu Lys Asn His Ser Ile Val Pro Thr His Tyr Thr Leu Leu Tyr Thr
    50                  55                  60

Ile Met Ser Lys Pro Glu Asp Leu Lys Val Val Lys Asn Cys Ala Asn
65                  70                  75                  80

Thr Thr Arg Ser Phe Cys Asp Leu Thr Asp Glu Trp Arg Ser Thr His
                85                  90                  95

Glu Ala Tyr Val Thr Val Leu Glu Gly Phe Ser Gly Asn Thr Thr Leu
            100                 105                 110
```

Phe Ser Cys Ser His Asn Phe Trp Leu Ala Ile Asp Met Ser Phe Glu
            115                 120                 125

Pro Pro Glu Phe Glu Ile Val Gly Phe Thr Asn His Ile Asn Val Met
        130                 135                 140

Val Lys Phe Pro Ser Ile Val Glu Glu Leu Gln Phe Asp Leu Ser
145                 150                 155                 160

Leu Val Ile Glu Glu Ser Glu Gly Ile Val Lys Lys His Lys Pro
                165                 170                 175

Glu Ile Lys Gly Asn Met Ser Gly Asn Phe Thr Tyr Ile Ile Asp Lys
            180                 185                 190

Leu Ile Pro Asn Thr Asn Tyr Cys Val Ser Val Tyr Leu Glu His Ser
            195                 200                 205

Asp Glu Gln Ala Val Ile Lys Ser Pro Leu Lys Cys Thr Leu Leu Pro
        210                 215                 220

Pro Gly Gln Glu Ser Glu Ser Ala Glu Ser Ala Lys Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
            275                 280                 285

His Glu Asp Pro Glu Val Lys Phe Asn Trp Tyr Val Asp Gly Val Glu
        290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
            355                 360                 365

Val Tyr Thr Leu Pro Pro Ser Arg Asp Glu Leu Thr Lys Asn Gln Val
        370                 375                 380

Ser Leu Trp Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
            435                 440                 445

Met His Glu Ala Leu His Asn His Tyr Thr Gln Lys Ser Leu Ser Leu
450                 455                 460

Ser Pro Gly Lys
465

<210> SEQ ID NO 101
<211> LENGTH: 449
<212> TYPE: PRT
<213> ORGANISM: Artificial Sequence
<220> FEATURE:
<223> OTHER INFORMATION: Synthetic: IFNAR2 (aa27-243)- IgG1 Fc domain
      with T366W mutation without a leader sequence

<400> SEQUENCE: 101

```
Ile Ser Tyr Asp Ser Pro Asp Tyr Thr Asp Glu Ser Cys Thr Phe Lys
1               5                   10                  15

Ile Ser Leu Arg Asn Phe Arg Ser Ile Leu Ser Trp Glu Leu Lys Asn
            20                  25                  30

His Ser Ile Val Pro Thr His Tyr Thr Leu Leu Tyr Thr Ile Met Ser
        35                  40                  45

Lys Pro Glu Asp Leu Lys Val Val Lys Asn Cys Ala Asn Thr Thr Arg
    50                  55                  60

Ser Phe Cys Asp Leu Thr Asp Glu Trp Arg Ser Thr His Glu Ala Tyr
65                  70                  75                  80

Val Thr Val Leu Glu Gly Phe Ser Gly Asn Thr Thr Leu Phe Ser Cys
                85                  90                  95

Ser His Asn Phe Trp Leu Ala Ile Asp Met Ser Phe Glu Pro Pro Glu
            100                 105                 110

Phe Glu Ile Val Gly Phe Thr Asn His Ile Asn Val Met Val Lys Phe
        115                 120                 125

Pro Ser Ile Val Glu Glu Glu Leu Gln Phe Asp Leu Ser Leu Val Ile
    130                 135                 140

Glu Glu Gln Ser Glu Gly Ile Val Lys Lys His Lys Pro Glu Ile Lys
145                 150                 155                 160

Gly Asn Met Ser Gly Asn Phe Thr Tyr Ile Ile Asp Lys Leu Ile Pro
                165                 170                 175

Asn Thr Asn Tyr Cys Val Ser Val Tyr Leu Glu His Ser Asp Glu Gln
            180                 185                 190

Ala Val Ile Lys Ser Pro Leu Lys Cys Thr Leu Leu Pro Pro Gly Gln
        195                 200                 205

Glu Ser Glu Ser Ala Glu Ser Ala Lys Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Trp
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415
```

-continued

```
Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 102
<211> LENGTH: 660
<212> TYPE: PRT
<213> ORGANISM: Artificial Sequence
<220> FEATURE:
<223> OTHER INFORMATION: Synthetic: Leader- IFNAR1 (aa28-436)- IgG1 Fc
      domain with T366S, L368A, and Y407V mutations

<400> SEQUENCE: 102

Met Asp Trp Thr Trp Arg Ile Leu Phe Leu Val Ala Ala Thr Gly
1               5                   10                  15

Thr His Ala Lys Asn Leu Lys Ser Pro Gln Lys Val Glu Val Asp Ile
            20                  25                  30

Ile Asp Asp Asn Phe Ile Leu Arg Trp Asn Arg Ser Asp Glu Ser Val
        35                  40                  45

Gly Asn Val Thr Phe Ser Phe Asp Tyr Gln Lys Thr Gly Met Asp Asn
    50                  55                  60

Trp Ile Lys Leu Ser Gly Cys Gln Asn Ile Thr Ser Thr Lys Cys Asn
65                  70                  75                  80

Phe Ser Ser Leu Lys Leu Asn Val Tyr Glu Glu Ile Lys Leu Arg Ile
                85                  90                  95

Arg Ala Glu Lys Glu Asn Thr Ser Ser Trp Tyr Glu Val Asp Ser Phe
            100                 105                 110

Thr Pro Phe Arg Lys Ala Gln Ile Gly Pro Pro Glu Val His Leu Glu
        115                 120                 125

Ala Glu Asp Lys Ala Ile Val Ile His Ile Ser Pro Gly Thr Lys Asp
    130                 135                 140

Ser Val Met Trp Ala Leu Asp Gly Leu Ser Phe Thr Tyr Ser Leu Val
145                 150                 155                 160

Ile Trp Lys Asn Ser Ser Gly Val Glu Glu Arg Ile Glu Asn Ile Tyr
                165                 170                 175

Ser Arg His Lys Ile Tyr Lys Leu Ser Pro Glu Thr Thr Tyr Cys Leu
            180                 185                 190

Lys Val Lys Ala Ala Leu Leu Thr Ser Trp Lys Ile Gly Val Tyr Ser
        195                 200                 205

Pro Val His Cys Ile Lys Thr Thr Val Glu Asn Glu Leu Pro Pro Pro
    210                 215                 220

Glu Asn Ile Glu Val Ser Val Gln Asn Gln Asn Tyr Val Leu Lys Trp
225                 230                 235                 240

Asp Tyr Thr Tyr Ala Asn Met Thr Phe Gln Val Gln Trp Leu His Ala
                245                 250                 255

Phe Leu Lys Arg Asn Pro Gly Asn His Leu Tyr Lys Trp Lys Gln Ile
            260                 265                 270

Pro Asp Cys Glu Asn Val Lys Thr Thr Gln Cys Val Phe Pro Gln Asn
        275                 280                 285

Val Phe Gln Lys Gly Ile Tyr Leu Leu Arg Val Gln Ala Ser Asp Gly
    290                 295                 300

Asn Asn Thr Ser Phe Trp Ser Glu Glu Ile Lys Phe Asp Thr Glu Ile
305                 310                 315                 320
```

```
Gln Ala Phe Leu Leu Pro Pro Val Phe Asn Ile Arg Ser Leu Ser Asp
                325                 330                 335

Ser Phe His Ile Tyr Ile Gly Ala Pro Lys Gln Ser Gly Asn Thr Pro
            340                 345                 350

Val Ile Gln Asp Tyr Pro Leu Ile Tyr Glu Ile Phe Trp Glu Asn
        355                 360                 365

Thr Ser Asn Ala Glu Arg Lys Ile Ile Glu Lys Thr Asp Val Thr
    370                 375                 380

Val Pro Asn Leu Lys Pro Leu Thr Val Tyr Cys Val Lys Ala Arg Ala
385                 390                 395                 400

His Thr Met Asp Glu Lys Leu Asn Lys Ser Val Phe Ser Asp Ala
                405                 410                 415

Val Cys Glu Lys Thr Lys Pro Gly Asn Thr Ser Lys Glu Pro Lys Ser
                420                 425                 430

Cys Asp Lys Thr His Thr Cys Pro Pro Cys Pro Ala Pro Glu Leu Leu
                435                 440                 445

Gly Gly Pro Ser Val Phe Leu Phe Pro Pro Lys Pro Lys Asp Thr Leu
            450                 455                 460

Met Ile Ser Arg Thr Pro Glu Val Thr Cys Val Val Val Asp Val Ser
465                 470                 475                 480

His Glu Asp Pro Glu Val Lys Phe Asn Trp Tyr Val Asp Gly Val Glu
                485                 490                 495

Val His Asn Ala Lys Thr Lys Pro Arg Glu Glu Gln Tyr Asn Ser Thr
            500                 505                 510

Tyr Arg Val Val Ser Val Leu Thr Val Leu His Gln Asp Trp Leu Asn
                515                 520                 525

Gly Lys Glu Tyr Lys Cys Lys Val Ser Asn Lys Ala Leu Pro Ala Pro
            530                 535                 540

Ile Glu Lys Thr Ile Ser Lys Ala Lys Gly Gln Pro Arg Glu Pro Gln
545                 550                 555                 560

Val Tyr Thr Leu Pro Pro Ser Arg Asp Glu Leu Thr Lys Asn Gln Val
                565                 570                 575

Ser Leu Ser Cys Ala Val Lys Gly Phe Tyr Pro Ser Asp Ile Ala Val
            580                 585                 590

Glu Trp Glu Ser Asn Gly Gln Pro Glu Asn Asn Tyr Lys Thr Thr Pro
                595                 600                 605

Pro Val Leu Asp Ser Asp Gly Ser Phe Phe Leu Val Ser Lys Leu Thr
                610                 615                 620

Val Asp Lys Ser Arg Trp Gln Gln Gly Asn Val Phe Ser Cys Ser Val
625                 630                 635                 640

Met His Glu Ala Leu His Asn His Tyr Thr Gln Lys Ser Leu Ser Leu
                645                 650                 655

Ser Pro Gly Lys
            660

<210> SEQ ID NO 103
<211> LENGTH: 641
<212> TYPE: PRT
<213> ORGANISM: Artificial Sequence
<220> FEATURE:
<223> OTHER INFORMATION: Synthetic: IFNAR1 (aa28-436)- IgG1 Fc domain
      with T366S, L368A, and Y407V mutations without a leader sequence

<400> SEQUENCE: 103

Lys Asn Leu Lys Ser Pro Gln Lys Val Glu Val Asp Ile Ile Asp Asp
```

```
1               5                   10                  15
Asn Phe Ile Leu Arg Trp Asn Arg Ser Asp Glu Ser Val Gly Asn Val
                20                  25                  30
Thr Phe Ser Phe Asp Tyr Gln Lys Thr Gly Met Asp Asn Trp Ile Lys
                35                  40                  45
Leu Ser Gly Cys Gln Asn Ile Thr Ser Thr Lys Cys Asn Phe Ser Ser
                50                  55                  60
Leu Lys Leu Asn Val Tyr Glu Glu Ile Lys Leu Arg Ile Arg Ala Glu
65                  70                  75                  80
Lys Glu Asn Thr Ser Ser Trp Tyr Glu Val Asp Ser Phe Thr Pro Phe
                85                  90                  95
Arg Lys Ala Gln Ile Gly Pro Pro Glu Val His Leu Glu Ala Glu Asp
                100                 105                 110
Lys Ala Ile Val Ile His Ile Ser Pro Gly Thr Lys Asp Ser Val Met
                115                 120                 125
Trp Ala Leu Asp Gly Leu Ser Phe Thr Tyr Ser Leu Val Ile Trp Lys
                130                 135                 140
Asn Ser Ser Gly Val Glu Glu Arg Ile Glu Asn Ile Tyr Ser Arg His
145                 150                 155                 160
Lys Ile Tyr Lys Leu Ser Pro Glu Thr Thr Tyr Cys Leu Lys Val Lys
                165                 170                 175
Ala Ala Leu Leu Thr Ser Trp Lys Ile Gly Val Tyr Ser Pro Val His
                180                 185                 190
Cys Ile Lys Thr Thr Val Glu Asn Glu Leu Pro Pro Pro Glu Asn Ile
                195                 200                 205
Glu Val Ser Val Gln Asn Gln Asn Tyr Val Leu Lys Trp Asp Tyr Thr
210                 215                 220
Tyr Ala Asn Met Thr Phe Gln Val Gln Trp Leu His Ala Phe Leu Lys
225                 230                 235                 240
Arg Asn Pro Gly Asn His Leu Tyr Lys Trp Lys Gln Ile Pro Asp Cys
                245                 250                 255
Glu Asn Val Lys Thr Thr Gln Cys Val Phe Pro Gln Asn Val Phe Gln
                260                 265                 270
Lys Gly Ile Tyr Leu Leu Arg Val Gln Ala Ser Asp Gly Asn Asn Thr
                275                 280                 285
Ser Phe Trp Ser Glu Glu Ile Lys Phe Asp Thr Glu Ile Gln Ala Phe
                290                 295                 300
Leu Leu Pro Pro Val Phe Asn Ile Arg Ser Leu Ser Asp Ser Phe His
305                 310                 315                 320
Ile Tyr Ile Gly Ala Pro Lys Gln Ser Gly Asn Thr Pro Val Ile Gln
                325                 330                 335
Asp Tyr Pro Leu Ile Tyr Glu Ile Ile Phe Trp Glu Asn Thr Ser Asn
                340                 345                 350
Ala Glu Arg Lys Ile Ile Glu Lys Lys Thr Asp Val Thr Val Pro Asn
                355                 360                 365
Leu Lys Pro Leu Thr Val Tyr Cys Val Lys Ala Arg Ala His Thr Met
                370                 375                 380
Asp Glu Lys Leu Asn Lys Ser Val Phe Ser Asp Ala Val Cys Glu
385                 390                 395                 400
Lys Thr Lys Pro Gly Asn Thr Ser Lys Glu Pro Lys Ser Cys Asp Lys
                405                 410                 415
Thr His Thr Cys Pro Pro Cys Pro Ala Pro Glu Leu Leu Gly Gly Pro
                420                 425                 430
```

```
Ser Val Phe Leu Phe Pro Pro Lys Pro Lys Asp Thr Leu Met Ile Ser
        435                 440                 445

Arg Thr Pro Glu Val Thr Cys Val Val Val Asp Val Ser His Glu Asp
    450                 455                 460

Pro Glu Val Lys Phe Asn Trp Tyr Val Asp Gly Val Glu Val His Asn
465                 470                 475                 480

Ala Lys Thr Lys Pro Arg Glu Glu Gln Tyr Asn Ser Thr Tyr Arg Val
                485                 490                 495

Val Ser Val Leu Thr Val Leu His Gln Asp Trp Leu Asn Gly Lys Glu
                500                 505                 510

Tyr Lys Cys Lys Val Ser Asn Lys Ala Leu Pro Ala Pro Ile Glu Lys
                515                 520                 525

Thr Ile Ser Lys Ala Lys Gly Gln Pro Arg Glu Pro Gln Val Tyr Thr
        530                 535                 540

Leu Pro Pro Ser Arg Asp Glu Leu Thr Lys Asn Gln Val Ser Leu Ser
545                 550                 555                 560

Cys Ala Val Lys Gly Phe Tyr Pro Ser Asp Ile Ala Val Glu Trp Glu
                565                 570                 575

Ser Asn Gly Gln Pro Glu Asn Asn Tyr Lys Thr Thr Pro Pro Val Leu
                580                 585                 590

Asp Ser Asp Gly Ser Phe Phe Leu Val Ser Lys Leu Thr Val Asp Lys
                595                 600                 605

Ser Arg Trp Gln Gln Gly Asn Val Phe Ser Cys Ser Val Met His Glu
                610                 615                 620

Ala Leu His Asn His Tyr Thr Gln Lys Ser Leu Ser Leu Ser Pro Gly
625                 630                 635                 640

Lys

<210> SEQ ID NO 104
<211> LENGTH: 468
<212> TYPE: PRT
<213> ORGANISM: Artificial Sequence
<220> FEATURE:
<223> OTHER INFORMATION: Synthetic: Leader- IFNAR2 (aa27-243)- IgG1 Fc
      domain with T366S, L368A, and Y407V mutations

<400> SEQUENCE: 104

Met Asp Trp Thr Trp Arg Ile Leu Phe Leu Val Ala Ala Ala Thr Gly
1               5                   10                  15

Thr His Ala Ile Ser Tyr Asp Ser Pro Asp Tyr Thr Asp Glu Ser Cys
                20                  25                  30

Thr Phe Lys Ile Ser Leu Arg Asn Phe Arg Ser Ile Leu Ser Trp Glu
        35                  40                  45

Leu Lys Asn His Ser Ile Val Pro Thr His Tyr Thr Leu Leu Tyr Thr
    50                  55                  60

Ile Met Ser Lys Pro Glu Asp Leu Lys Val Val Lys Asn Cys Ala Asn
65                  70                  75                  80

Thr Thr Arg Ser Phe Cys Asp Leu Thr Asp Glu Trp Arg Ser Thr His
                85                  90                  95

Glu Ala Tyr Val Thr Val Leu Glu Gly Phe Ser Gly Asn Thr Thr Leu
                100                 105                 110

Phe Ser Cys Ser His Asn Phe Trp Leu Ala Ile Asp Met Ser Phe Glu
        115                 120                 125

Pro Pro Glu Phe Glu Ile Val Gly Phe Thr Asn His Ile Asn Val Met
130                 135                 140
```

Val Lys Phe Pro Ser Ile Val Glu Glu Leu Gln Phe Asp Leu Ser
145                 150                 155                 160

Leu Val Ile Glu Glu Gln Ser Glu Gly Ile Val Lys Lys His Lys Pro
            165                 170                 175

Glu Ile Lys Gly Asn Met Ser Gly Asn Phe Thr Tyr Ile Ile Asp Lys
        180                 185                 190

Leu Ile Pro Asn Thr Asn Tyr Cys Val Ser Val Tyr Leu Glu His Ser
            195                 200                 205

Asp Glu Gln Ala Val Ile Lys Ser Pro Leu Lys Cys Thr Leu Leu Pro
210                 215                 220

Pro Gly Gln Glu Ser Glu Ser Ala Glu Ser Ala Lys Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
            290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Asp Glu Leu Thr Lys Asn Gln Val
370                 375                 380

Ser Leu Ser Cys Ala Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Val Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
450                 455                 460

Ser Pro Gly Lys
465

<210> SEQ ID NO 105
<211> LENGTH: 449
<212> TYPE: PRT
<213> ORGANISM: Artificial Sequence
<220> FEATURE:
<223> OTHER INFORMATION: Synthetic: IFNAR2 (aa27-243)- IgG1 Fc domain
      with T366S, L368A, and Y407V mutations without a leader sequence

<400> SEQUENCE: 105

Ile Ser Tyr Asp Ser Pro Asp Tyr Thr Asp Glu Ser Cys Thr Phe Lys
1               5                   10                  15

Ile Ser Leu Arg Asn Phe Arg Ser Ile Leu Ser Trp Glu Leu Lys Asn

-continued

```
                20                  25                  30
His Ser Ile Val Pro Thr His Tyr Thr Leu Leu Tyr Thr Ile Met Ser
            35                  40                  45

Lys Pro Glu Asp Leu Lys Val Val Lys Asn Cys Ala Asn Thr Thr Arg
 50                  55                  60

Ser Phe Cys Asp Leu Thr Asp Glu Trp Arg Ser Thr His Glu Ala Tyr
 65                  70                  75                  80

Val Thr Val Leu Glu Gly Phe Ser Gly Asn Thr Thr Leu Phe Ser Cys
                85                  90                  95

Ser His Asn Phe Trp Leu Ala Ile Asp Met Ser Phe Glu Pro Pro Glu
                    100                 105                 110

Phe Glu Ile Val Gly Phe Thr Asn His Ile Asn Val Met Val Lys Phe
                115                 120                 125

Pro Ser Ile Val Glu Glu Leu Gln Phe Asp Leu Ser Leu Val Ile
            130                 135                 140

Glu Glu Gln Ser Glu Gly Ile Val Lys Lys His Lys Pro Glu Ile Lys
145                 150                 155                 160

Gly Asn Met Ser Gly Asn Phe Thr Tyr Ile Ile Asp Lys Leu Ile Pro
                    165                 170                 175

Asn Thr Asn Tyr Cys Val Ser Val Tyr Leu Glu His Ser Asp Glu Gln
                180                 185                 190

Ala Val Ile Lys Ser Pro Leu Lys Cys Thr Leu Leu Pro Pro Gly Gln
                195                 200                 205

Glu Ser Glu Ser Ala Glu Ser Ala Lys Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                    245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
                290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                    325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Ser
                355                 360                 365

Cys Ala Val Lys Gly Phe Tyr Pro Ser Asp Ile Ala Val Glu Trp Glu
                370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                    405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445
```

Lys

```
<210> SEQ ID NO 106
<211> LENGTH: 232
<212> TYPE: PRT
<213> ORGANISM: Artificial Sequence
<220> FEATURE:
<223> OTHER INFORMATION: Synthetic: IgG1 Fc domain with T366Y mutation
      (knob hole 1)

<400> SEQUENCE: 106
```

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Tyr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

```
<210> SEQ ID NO 107
<211> LENGTH: 232
<212> TYPE: PRT
<213> ORGANISM: Artificial Sequence
<220> FEATURE:
<223> OTHER INFORMATION: Synthetic: IgG1 Fc domain with Y407T mutation
      (knob hole 1)

<400> SEQUENCE: 107
```

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

```
Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                 85                  90                  95

Asp Trp Leu Asn Gly Lys Glu Tyr Lys Cys Lys Val Ser Asn Lys Ala
                100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Thr
            180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
210                 215                 220

Ser Leu Ser Leu Ser Pro Gly Lys
225                 230

<210> SEQ ID NO 108
<211> LENGTH: 232
<212> TYPE: PRT
<213> ORGANISM: Artificial Sequence
<220> FEATURE:
<223> OTHER INFORMATION: Synthetic: IgG1 Fc domain with T366W mutation
      (knob hole 2)

<400> SEQUENCE: 108

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                 85                  90                  95

Asp Trp Leu Asn Gly Lys Glu Tyr Lys Cys Lys Val Ser Asn Lys Ala
                100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
130                 135                 140

Lys Asn Gln Val Ser Leu Trp Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175
```

```
Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 109
<211> LENGTH: 232
<212> TYPE: PRT
<213> ORGANISM: Artificial Sequence
<220> FEATURE:
<223> OTHER INFORMATION: Synthetic: IgG1 Fc domain with T366S, L368A,
      and Y407V mutations (knob hole 2)

<400> SEQUENCE: 109

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Ser Cys Ala Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Val
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 110
<211> LENGTH: 327
<212> TYPE: PRT
<213> ORGANISM: Homo sapiens
<220> FEATURE:
<221> NAME/KEY: misc_feature
<223> OTHER INFORMATION: Human IgG4

<400> SEQUENCE: 110
```

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
        260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 111
<211> LENGTH: 218
<212> TYPE: PRT
<213> ORGANISM: Homo sapiens
<220> FEATURE:
<221> NAME/KEY: misc_feature
<223> OTHER INFORMATION: Human IgG4 Fc domain

<400> SEQUENCE: 111

Pro Ala Pro Glu Phe Leu Gly Gly Pro Ser Val Phe Leu Phe Pro Pro
1               5                   10                  15

Lys Pro Lys Asp Thr Leu Met Ile Ser Arg Thr Pro Glu Val Thr Cys
```

```
            20                  25                  30
Val Val Val Asp Val Ser Gln Glu Asp Pro Glu Val Gln Phe Asn Trp
         35                  40                  45
Tyr Val Asp Gly Val Glu Val His Asn Ala Lys Thr Lys Pro Arg Glu
 50                  55                  60
Glu Gln Phe Asn Ser Thr Tyr Arg Val Val Ser Val Leu Thr Val Leu
65                  70                  75                  80
His Gln Asp Trp Leu Asn Gly Lys Glu Tyr Lys Cys Lys Val Ser Asn
             85                  90                  95
Lys Gly Leu Pro Ser Ser Ile Glu Lys Thr Ile Ser Lys Ala Lys Gly
            100                 105                 110
Gln Pro Arg Glu Pro Gln Val Tyr Thr Leu Pro Pro Ser Gln Glu Glu
            115                 120                 125
Met Thr Lys Asn Gln Val Ser Leu Thr Cys Leu Val Lys Gly Phe Tyr
        130                 135                 140
Pro Ser Asp Ile Ala Val Glu Trp Glu Ser Asn Gly Gln Pro Glu Asn
145                 150                 155                 160
Asn Tyr Lys Thr Thr Pro Pro Val Leu Asp Ser Asp Gly Ser Phe Phe
                165                 170                 175
Leu Tyr Ser Arg Leu Thr Val Asp Lys Ser Arg Trp Gln Glu Gly Asn
            180                 185                 190
Val Phe Ser Cys Ser Val Met His Glu Ala Leu His Asn His Tyr Thr
        195                 200                 205
Gln Lys Ser Leu Ser Leu Ser Leu Gly Lys
    210                 215

<210> SEQ ID NO 112
<211> LENGTH: 229
<212> TYPE: PRT
<213> ORGANISM: Homo sapiens
<220> FEATURE:
<221> NAME/KEY: misc_feature
<223> OTHER INFORMATION: Human IgG4 Hinge + Fc domain

<400> SEQUENCE: 112

Glu Ser Lys Tyr Gly Pro Pro Cys Pro Ser Cys Pro Ala Pro Glu Phe
1               5                  10                  15
Leu Gly Gly Pro Ser Val Phe Leu Phe Pro Pro Lys Pro Lys Asp Thr
            20                  25                  30
Leu Met Ile Ser Arg Thr Pro Glu Val Thr Cys Val Val Val Asp Val
         35                  40                  45
Ser Gln Glu Asp Pro Glu Val Gln Phe Asn Trp Tyr Val Asp Gly Val
 50                  55                  60
Glu Val His Asn Ala Lys Thr Lys Pro Arg Glu Glu Gln Phe Asn Ser
65                  70                  75                  80
Thr Tyr Arg Val Val Ser Val Leu Thr Val Leu His Gln Asp Trp Leu
             85                  90                  95
Asn Gly Lys Glu Tyr Lys Cys Lys Val Ser Asn Lys Gly Leu Pro Ser
            100                 105                 110
Ser Ile Glu Lys Thr Ile Ser Lys Ala Lys Gly Gln Pro Arg Glu Pro
            115                 120                 125
Gln Val Tyr Thr Leu Pro Pro Ser Gln Glu Glu Met Thr Lys Asn Gln
        130                 135                 140
Val Ser Leu Thr Cys Leu Val Lys Gly Phe Tyr Pro Ser Asp Ile Ala
145                 150                 155                 160
```

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 113
<211> LENGTH: 229
<212> TYPE: PRT
<213> ORGANISM: Artificial Sequence
<220> FEATURE:
<223> OTHER INFORMATION: Synthetic: Representative Fc domain sourced
      from Dulaglutide (S228P, F234A, L235A, L445P (EU) and K478del
      (Kabat)

<400> SEQUENCE: 113

Ala Glu Ser Lys Tyr Gly Pro Pro Cys Pro Pro Cys Pro Ala Pro Glu
1               5                   10                  15

Ala Ala Gly Gly Pro Ser Val Phe Leu Phe Pro Pro Lys Pro Lys Asp
            20                  25                  30

Thr Leu Met Ile Ser Arg Thr Pro Glu Val Thr Cys Val Val Val Asp
        35                  40                  45

Val Ser Gln Glu Asp Pro Glu Val Gln Phe Asn Trp Tyr Val Asp Gly
    50                  55                  60

Val Glu Val His Asn Ala Lys Thr Lys Pro Arg Glu Glu Gln Phe Asn
65                  70                  75                  80

Ser Thr Tyr Arg Val Val Ser Val Leu Thr Val Leu His Gln Asp Trp
                85                  90                  95

Leu Asn Gly Lys Glu Tyr Lys Cys Lys Val Ser Asn Lys Gly Leu Pro
            100                 105                 110

Ser Ser Ile Glu Lys Thr Ile Ser Lys Ala Lys Gly Gln Pro Arg Glu
        115                 120                 125

Pro Gln Val Tyr Thr Leu Pro Pro Ser Gln Glu Glu Met Thr Lys Asn
    130                 135                 140

Gln Val Ser Leu Thr Cys Leu Val Lys Gly Phe Tyr Pro Ser Asp Ile
145                 150                 155                 160

Ala Val Glu Trp Glu Ser Asn Gly Gln Pro Glu Asn Asn Tyr Lys Thr
                165                 170                 175

Thr Pro Pro Val Leu Asp Ser Asp Gly Ser Phe Phe Leu Tyr Ser Arg
            180                 185                 190

Leu Thr Val Asp Lys Ser Arg Trp Gln Glu Gly Asn Val Phe Ser Cys
        195                 200                 205

Ser Val Met His Glu Ala Leu His Asn His Tyr Thr Gln Lys Ser Leu
    210                 215                 220

Ser Leu Ser Leu Gly
225

<210> SEQ ID NO 114
<211> LENGTH: 327
<212> TYPE: PRT
<213> ORGANISM: Artificial Sequence
<220> FEATURE:
<223> OTHER INFORMATION: Synthetic: Human IgG4 with mutations K196Q, S228P, F296Y, E356K, R409K, and H435R mutations from emicizumab

<400> SEQUENCE: 114

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Lys Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Glu Gly Asn Val Phe Ser
    290                 295                 300

Cys Ser Val Met His Glu Ala Leu His Asn Arg Tyr Thr Gln Lys Ser
305                 310                 315                 320

Leu Ser Leu Ser Leu Gly Lys
                325
```

<210> SEQ ID NO 115
<211> LENGTH: 327
<212> TYPE: PRT
<213> ORGANISM: Artificial Sequence
<220> FEATURE:
<223> OTHER INFORMATION: Synthetic: Human IgG4 with mutations K196Q, S228P, F296Y, R409K, and K439E mutations from emicizumab

<400> SEQUENCE: 115

Ala Ser Thr Lys Gly Pro Ser Val Phe Pro Leu Ala Pro Cys Ser Arg

```
              1               5                  10                 15
        Ser Thr Ser Glu Ser Thr Ala Ala Leu Gly Cys Leu Val Lys Asp Tyr
                        20                  25                 30
        Phe Pro Glu Pro Val Thr Val Ser Trp Asn Ser Gly Ala Leu Thr Ser
                        35                  40                 45
        Gly Val His Thr Phe Pro Ala Val Leu Gln Ser Ser Gly Leu Tyr Ser
                        50                  55                 60
        Leu Ser Ser Val Val Thr Val Pro Ser Ser Leu Gly Thr Gln Thr
        65                      70                  75                 80
        Tyr Thr Cys Asn Val Asp His Lys Pro Ser Asn Thr Lys Val Asp Lys
                            85                  90                 95
        Arg Val Glu Ser Lys Tyr Gly Pro Pro Cys Pro Pro Cys Pro Ala Pro
                        100                 105                110
        Glu Phe Leu Gly Gly Pro Ser Val Phe Leu Phe Pro Pro Lys Pro Lys
                        115                 120                125
        Asp Thr Leu Met Ile Ser Arg Thr Pro Glu Val Thr Cys Val Val Val
                        130                 135                140
        Asp Val Ser Gln Glu Asp Pro Glu Val Gln Phe Asn Trp Tyr Val Asp
        145                     150                 155                160
        Gly Val Glu Val His Asn Ala Lys Thr Lys Pro Arg Glu Glu Gln Tyr
                            165                 170                175
        Asn Ser Thr Tyr Arg Val Val Ser Val Leu Thr Val Leu His Gln Asp
                        180                 185                190
        Trp Leu Asn Gly Lys Glu Tyr Lys Cys Lys Val Ser Asn Lys Gly Leu
                        195                 200                205
        Pro Ser Ser Ile Glu Lys Thr Ile Ser Lys Ala Lys Gly Gln Pro Arg
                    210                 215                220
        Glu Pro Gln Val Tyr Thr Leu Pro Pro Ser Gln Glu Glu Met Thr Lys
        225                     230                 235                240
        Asn Gln Val Ser Leu Thr Cys Leu Val Lys Gly Phe Tyr Pro Ser Asp
                        245                 250                255
        Ile Ala Val Glu Trp Glu Ser Asn Gly Gln Pro Glu Asn Asn Tyr Lys
                        260                 265                270
        Thr Thr Pro Pro Val Leu Asp Ser Asp Gly Ser Phe Phe Leu Tyr Ser
                        275                 280                285
        Lys Leu Thr Val Asp Lys Ser Arg Trp Gln Glu Gly Asn Val Phe Ser
                        290                 295                300
        Cys Ser Val Met His Glu Ala Leu His Asn His Tyr Thr Gln Glu Ser
        305                     310                 315                320
        Leu Ser Leu Ser Leu Gly Lys
                        325

<210> SEQ ID NO 116
<211> LENGTH: 218
<212> TYPE: PRT
<213> ORGANISM: Artificial Sequence
<220> FEATURE:
<223> OTHER INFORMATION: Synthetic: Human IgG4 Fc domain with mutations
      F296Y, E356K, R409K, and H435R mutations from emicizumab

<400> SEQUENCE: 116

Pro Ala Pro Glu Phe Leu Gly Gly Pro Ser Val Phe Leu Phe Pro Pro
1               5                  10                 15
Lys Pro Lys Asp Thr Leu Met Ile Ser Arg Thr Pro Glu Val Thr Cys
                20                  25                 30
```

Val Val Val Asp Val Ser Gln Glu Asp Pro Glu Val Gln Phe Asn Trp
            35                  40                  45

Tyr Val Asp Gly Val Glu Val His Asn Ala Lys Thr Lys Pro Arg Glu
 50                  55                  60

Glu Gln Tyr Asn Ser Thr Tyr Arg Val Val Ser Val Leu Thr Val Leu
 65                  70                  75                  80

His Gln Asp Trp Leu Asn Gly Lys Glu Tyr Lys Cys Lys Val Ser Asn
            85                  90                  95

Lys Gly Leu Pro Ser Ser Ile Glu Lys Thr Ile Ser Lys Ala Lys Gly
            100                 105                 110

Gln Pro Arg Glu Pro Gln Val Tyr Thr Leu Pro Pro Ser Gln Lys Glu
            115                 120                 125

Met Thr Lys Asn Gln Val Ser Leu Thr Cys Leu Val Lys Gly Phe Tyr
    130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                    165                 170                 175

Leu Tyr Ser Lys Leu Thr Val Asp Lys Ser Arg Trp Gln Glu Gly Asn
            180                 185                 190

Val Phe Ser Cys Ser Val Met His Glu Ala Leu His Asn Arg Tyr Thr
    195                 200                 205

Gln Lys Ser Leu Ser Leu Ser Leu Gly Lys
    210                 215

<210> SEQ ID NO 117
<211> LENGTH: 218
<212> TYPE: PRT
<213> ORGANISM: Artificial Sequence
<220> FEATURE:
<223> OTHER INFORMATION: Synthetic: Human IgG4 Fc domain with mutations
      F296Y, R409K, and K439E mutations from emicizumab

<400> SEQUENCE: 117

Pro Ala Pro Glu Phe Leu Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser Gln Glu Asp Pro Glu Val Gln Phe Asn Trp
            35                  40                  45

Tyr Val Asp Gly Val Glu Val His Asn Ala Lys Thr Lys Pro Arg Glu
 50                  55                  60

Glu Gln Tyr Asn Ser Thr Tyr Arg Val Val Ser Val Leu Thr Val Leu
 65                  70                  75                  80

His Gln Asp Trp Leu Asn Gly Lys Glu Tyr Lys Cys Lys Val Ser Asn
            85                  90                  95

Lys Gly Leu Pro Ser Ser Ile Glu Lys Thr Ile Ser Lys Ala Lys Gly
            100                 105                 110

Gln Pro Arg Glu Pro Gln Val Tyr Thr Leu Pro Pro Ser Gln Glu Glu
            115                 120                 125

Met Thr Lys Asn Gln Val Ser Leu Thr Cys Leu Val Lys Gly Phe Tyr
    130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                    165                 170                 175

```
Leu Tyr Ser Lys Leu Thr Val Asp Lys Ser Arg Trp Gln Glu Gly Asn
            180                 185                 190

Val Phe Ser Cys Ser Val Met His Glu Ala Leu His Asn His Tyr Thr
        195                 200                 205

Gln Glu Ser Leu Ser Leu Ser Leu Gly Lys
    210                 215
```

<210> SEQ ID NO 118
<211> LENGTH: 227
<212> TYPE: PRT
<213> ORGANISM: Artificial Sequence
<220> FEATURE:
<223> OTHER INFORMATION: Synthetic: Human IgG4 Hinge + Fc domain with
      mutations S228P, F296Y, E356K, R409K, H435R, L445P, G446del (EU)
      and K478del(Kabat) mutations from emicizumab

<400> SEQUENCE: 118

```
Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
50                  55                  60

Glu Val His Asn Ala Lys Thr Lys Pro Arg Glu Glu Gln Tyr Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Lys Glu Met Thr Lys Asn Gln
130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Glu Gly Asn Val Phe Ser Cys Ser
        195                 200                 205

Val Met His Glu Ala Leu His Asn Arg Tyr Thr Gln Lys Ser Leu Ser
    210                 215                 220

Leu Ser Pro
225
```

<210> SEQ ID NO 119
<211> LENGTH: 227
<212> TYPE: PRT
<213> ORGANISM: Artificial Sequence
<220> FEATURE:
<223> OTHER INFORMATION: Synthetic: Human IgG4 Hinge + Fc domain with
      mutations S228P, F296Y, R409K, K439E, L445P, G446del (EU)and
      K478del(Kabat) mutations from emicizumab

<400> SEQUENCE: 119

```
Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                      45

Ser Gln Glu Asp Pro Glu Val Gln Phe Asn Trp Tyr Val Asp Gly Val
50                  55                  60

Glu Val His Asn Ala Lys Thr Lys Pro Arg Glu Gln Tyr Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
                100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Gln Gly Asn Val Phe Ser Cys Ser
            195                 200                 205

Val Met His Glu Ala Leu His Asn His Tyr Thr Gln Glu Ser Leu Ser
210                 215                 220

Leu Ser Pro
225

<210> SEQ ID NO 120
<211> LENGTH: 229
<212> TYPE: PRT
<213> ORGANISM: Artificial Sequence
<220> FEATURE:
<223> OTHER INFORMATION: Synthetic: Human IgG4 Hinge + Fc domain with
      mutations T350V, T366L, K392L, T394W (zymeworks)

<400> SEQUENCE: 120

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                      45

Ser Gln Glu Asp Pro Glu Val Gln Phe Asn Trp Tyr Val Asp Gly Val
50                  55                  60

Glu Val His Asn Ala Lys Thr Lys Pro Arg Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
                100                 105                 110

Ser Ile Glu Lys Thr Ile Ser Lys Ala Lys Gly Gln Pro Arg Glu Pro
            115                 120                 125
```

Gln Val Tyr Val Leu Pro Pro Ser Gln Glu Glu Met Thr Lys Asn Gln
        130                 135                 140

Val Ser Leu Leu Cys Leu Val Lys Gly Phe Tyr Pro Ser Asp Ile Ala
145                 150                 155                 160

Val Glu Trp Glu Ser Asn Gly Gln Pro Glu Asn Asn Tyr Leu Thr Trp
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 121
<211> LENGTH: 229
<212> TYPE: PRT
<213> ORGANISM: Artificial Sequence
<220> FEATURE:
<223> OTHER INFORMATION: Synthetic: Human IgG4 Hinge + Fc domain with
      mutations T350V, L351Y, F405A, Y407V (zymeworks)

<400> SEQUENCE: 121

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Val Tyr Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Ala Leu Val Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

```
<210> SEQ ID NO 122
<211> LENGTH: 229
<212> TYPE: PRT
<213> ORGANISM: Artificial Sequence
<220> FEATURE:
<223> OTHER INFORMATION: Synthetic: Human IgG4 Hinge + Fc domain with
      mutation T366Y (knob hole 1)

<400> SEQUENCE: 122

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Tyr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 123
<211> LENGTH: 229
<212> TYPE: PRT
<213> ORGANISM: Artificial Sequence
<220> FEATURE:
<223> OTHER INFORMATION: Synthetic: Human IgG4 Hinge + Fc domain with
      mutation Y407T (knob hole 1)

<400> SEQUENCE: 123

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
```

```
                65                  70                  75                  80
Thr Tyr Arg Val Val Ser Val Leu Thr Val Leu His Gln Asp Trp Leu
                    85                  90                  95
Asn Gly Lys Glu Tyr Lys Cys Lys Val Ser Asn Lys Gly Leu Pro Ser
                100                 105                 110
Ser Ile Glu Lys Thr Ile Ser Lys Ala Lys Gly Gln Pro Arg Glu Pro
            115                 120                 125
Gln Val Tyr Thr Leu Pro Pro Ser Gln Glu Met Thr Lys Asn Gln
        130                 135                 140
Val Ser Leu Thr Cys Leu Val Lys Gly Phe Tyr Pro Ser Asp Ile Ala
145                 150                 155                 160
Val Glu Trp Glu Ser Asn Gly Gln Pro Glu Asn Asn Tyr Lys Thr Thr
                165                 170                 175
Pro Pro Val Leu Asp Ser Asp Gly Ser Phe Phe Leu Tyr Ser Arg Leu
                180                 185                 190
Thr Val Asp Lys Ser Arg Trp Gln Glu Gly Asn Val Phe Ser Cys Ser
            195                 200                 205
Val Met His Glu Ala Leu His Asn His Tyr Thr Gln Lys Ser Leu Ser
        210                 215                 220
Leu Ser Leu Gly Lys
225

<210> SEQ ID NO 124
<211> LENGTH: 229
<212> TYPE: PRT
<213> ORGANISM: Artificial Sequence
<220> FEATURE:
<223> OTHER INFORMATION: Synthetic: Human IgG4 Hinge + Fc domain with
      mutation T336W (knob hole 2)

<400> SEQUENCE: 124

Glu Ser Lys Tyr Gly Pro Pro Cys Pro Ser Cys Pro Ala Pro Glu Phe
1               5                   10                  15
Leu Gly Gly Pro Ser Val Phe Leu Phe Pro Pro Lys Pro Lys Asp Thr
            20                  25                  30
Leu Met Ile Ser Arg Thr Pro Glu Val Thr Cys Val Val Val Asp Val
        35                  40                  45
Ser Gln Glu Asp Pro Glu Val Gln Phe Asn Trp Tyr Val Asp Gly Val
    50                  55                  60
Glu Val His Asn Ala Lys Thr Lys Pro Arg Glu Glu Gln Phe Asn Ser
65                  70                  75                  80
Thr Tyr Arg Val Val Ser Val Leu Thr Val Leu His Gln Asp Trp Leu
                85                  90                  95
Asn Gly Lys Glu Tyr Lys Cys Lys Val Ser Asn Lys Gly Leu Pro Ser
            100                 105                 110
Ser Ile Glu Lys Thr Ile Ser Lys Ala Lys Gly Gln Pro Arg Glu Pro
        115                 120                 125
Gln Val Tyr Thr Leu Pro Pro Ser Gln Glu Glu Met Thr Lys Asn Gln
    130                 135                 140
Val Ser Leu Trp Cys Leu Val Lys Gly Phe Tyr Pro Ser Asp Ile Ala
145                 150                 155                 160
Val Glu Trp Glu Ser Asn Gly Gln Pro Glu Asn Asn Tyr Lys Thr Thr
                165                 170                 175
Pro Pro Val Leu Asp Ser Asp Gly Ser Phe Phe Leu Tyr Ser Arg Leu
            180                 185                 190
```

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 125
<211> LENGTH: 229
<212> TYPE: PRT
<213> ORGANISM: Artificial Sequence
<220> FEATURE:
<223> OTHER INFORMATION: Synthetic: Human IgG4 Hinge + Fc domain with
      mutations T366S, L368A, Y407V (knob hole 2)

<400> SEQUENCE: 125

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Ser Cys Ala Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Val Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 126
<211> LENGTH: 229
<212> TYPE: PRT
<213> ORGANISM: Artificial Sequence
<220> FEATURE:
<223> OTHER INFORMATION: Synthetic: Human IgG4 Hinge + Fc domain with
      mutation S228P (stability: reduced Fab arm exchange)

<400> SEQUENCE: 126

Glu Ser Lys Tyr Gly Pro Pro Cys Pro Pro Cys Pro Ala Pro Glu Phe
1               5                   10                  15

```
Leu Gly Gly Pro Ser Val Phe Leu Phe Pro Pro Lys Pro Lys Asp Thr
             20                  25                  30

Leu Met Ile Ser Arg Thr Pro Glu Val Thr Cys Val Val Val Asp Val
         35                  40                  45

Ser Gln Glu Asp Pro Glu Val Gln Phe Asn Trp Tyr Val Asp Gly Val
 50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                 85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Tyr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 127
<211> LENGTH: 229
<212> TYPE: PRT
<213> ORGANISM: Artificial Sequence
<220> FEATURE:
<223> OTHER INFORMATION: Synthetic: Human IgG4 Hinge + Fc domain with
      mutation L235E (decrease FcR binding) (Alegre et al 1992)

<400> SEQUENCE: 127

Glu Ser Lys Tyr Gly Pro Pro Cys Pro Ser Cys Pro Ala Pro Glu Phe
1                5                  10                  15

Glu Gly Gly Pro Ser Val Phe Leu Phe Pro Pro Lys Pro Lys Asp Thr
             20                  25                  30

Leu Met Ile Ser Arg Thr Pro Glu Val Thr Cys Val Val Val Asp Val
         35                  40                  45

Ser Gln Glu Asp Pro Glu Val Gln Phe Asn Trp Tyr Val Asp Gly Val
 50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                 85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140
```

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
            165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
210                 215                 220

Leu Ser Leu Gly Lys
225

<210> SEQ ID NO 128
<211> LENGTH: 229
<212> TYPE: PRT
<213> ORGANISM: Artificial Sequence
<220> FEATURE:
<223> OTHER INFORMATION: Synthetic: Human IgG4 Hinge + Fc domain with
      mutation F234A, L235A (decrease FcR binding) Xu et al Cell Immunol
      2000 200(1):16-26)

<400> SEQUENCE: 128

Glu Ser Lys Tyr Gly Pro Pro Cys Pro Ser Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
            165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
210                 215                 220

Leu Ser Leu Gly Lys
225

<210> SEQ ID NO 129
<211> LENGTH: 229

```
<212> TYPE: PRT
<213> ORGANISM: Artificial Sequence
<220> FEATURE:
<223> OTHER INFORMATION: Synthetic: Human IgG4 Hinge + Fc domain with
      mutation S228P, L235E (decrease FcR binding)  Reddy et al., J
      Immunol 2000 164(4):1925-33)

<400> SEQUENCE: 129

Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 130
<211> LENGTH: 229
<212> TYPE: PRT
<213> ORGANISM: Artificial Sequence
<220> FEATURE:
<223> OTHER INFORMATION: Synthetic: Human IgG4 Hinge + Fc domain with
      mutation N297A (affects glycosylation, thus FcR binding) Borrok et
      al ACS Chem Biol 2012 7(9):1596-1602

<400> SEQUENCE: 130

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Ala Ser
```

```
                65                  70                  75                  80
        Thr Tyr Arg Val Val Ser Val Leu Thr Val Leu His Gln Asp Trp Leu
                            85                  90                  95

Asn Gly Lys Glu Tyr Lys Cys Lys Val Ser Asn Lys Gly Leu Pro Ser
                    100                 105                 110

Ser Ile Glu Lys Thr Ile Ser Lys Ala Lys Gly Gln Pro Arg Glu Pro
                115                 120                 125

Gln Val Tyr Thr Leu Pro Pro Ser Gln Glu Met Thr Lys Asn Gln
            130                 135                 140

Val Ser Leu Thr Cys Leu Val Lys Gly Phe Tyr Pro Ser Asp Ile Ala
        145                 150                 155                 160

Val Glu Trp Glu Ser Asn Gly Gln Pro Glu Asn Asn Tyr Lys Thr Thr
                        165                 170                 175

Pro Pro Val Leu Asp Ser Asp Gly Ser Phe Phe Leu Tyr Ser Arg Leu
                    180                 185                 190

Thr Val Asp Lys Ser Arg Trp Gln Glu Gly Asn Val Phe Ser Cys Ser
                195                 200                 205

Val Met His Glu Ala Leu His Asn His Tyr Thr Gln Lys Ser Leu Ser
            210                 215                 220

Leu Ser Leu Gly Lys
        225

<210> SEQ ID NO 131
<211> LENGTH: 50
<212> TYPE: PRT
<213> ORGANISM: Artificial Sequence
<220> FEATURE:
<223> OTHER INFORMATION: Synthetic: linker
<220> FEATURE:
<221> NAME/KEY: misc_feature
<222> LOCATION: (1)..(50)
<223> OTHER INFORMATION: "Gly Gly Gly Gly Ser" is present at least once,
      and may repeat up to 10 times

<400> SEQUENCE: 131

Gly Gly Gly Gly Ser Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
                20                  25                  30

Gly Gly Ser Gly Gly Gly Gly Ser Gly Gly Gly Gly Ser Gly Gly Gly
            35                  40                  45

Gly Ser
    50

<210> SEQ ID NO 132
<211> LENGTH: 25
<212> TYPE: PRT
<213> ORGANISM: Artificial Sequence
<220> FEATURE:
<223> OTHER INFORMATION: Synthetic: linker
<220> FEATURE:
<221> NAME/KEY: misc_feature
<223> OTHER INFORMATION: "Gly Gly Gly Gly Ser" is present at least once,
      and may repeat up to 5 times

<400> SEQUENCE: 132

Gly Gly Gly Gly Ser Gly Gly Gly Gly Ser Gly Gly Gly Gly Ser Gly
1               5                   10                  15

Gly Gly Gly Ser Gly Gly Gly Gly Ser
                20                  25
```

```
<210> SEQ ID NO 133
<211> LENGTH: 27
<212> TYPE: PRT
<213> ORGANISM: Artificial Sequence
<220> FEATURE:
<223> OTHER INFORMATION: Synthetic: linker
<220> FEATURE:
<221> NAME/KEY: misc_feature
<222> LOCATION: (2)..(26)
<223> OTHER INFORMATION: "Glu Ala Ala Ala Lys" repeats at least twice
      and up to 5 times

<400> SEQUENCE: 133

Ala Glu Ala Ala Ala Lys Glu Ala Ala Ala Lys Glu Ala Ala Ala Lys
1               5                   10                  15

Glu Ala Ala Ala Lys Glu Ala Ala Ala Lys Ala
            20                  25

<210> SEQ ID NO 134
<211> LENGTH: 20
<212> TYPE: PRT
<213> ORGANISM: Artificial Sequence
<220> FEATURE:
<223> OTHER INFORMATION: Synthetic: linker
<220> FEATURE:
<221> NAME/KEY: misc_feature
<222> LOCATION: (1)..(20)
<223> OTHER INFORMATION: "Gly Gly Ser Gly" is present at least once and
      may repeat up to 5 times

<400> SEQUENCE: 134

Gly Gly Ser Gly Gly Gly Ser Gly Gly Gly Ser Gly Gly Gly Ser Gly
1               5                   10                  15

Gly Gly Ser Gly
            20

<210> SEQ ID NO 135
<211> LENGTH: 30
<212> TYPE: PRT
<213> ORGANISM: Artificial Sequence
<220> FEATURE:
<223> OTHER INFORMATION: Synthetic: linker
<220> FEATURE:
<221> NAME/KEY: misc_feature
<222> LOCATION: (1)..(30)
<223> OTHER INFORMATION: "Gly Gly Ser Gly Gly Ser" is present at least
      once and may repeat up to 5 times

<400> SEQUENCE: 135

Gly Gly Ser Gly Gly Ser Gly Gly Ser Gly Gly Ser Gly Gly Ser Gly
1               5                   10                  15

Gly Ser Gly Gly Ser Gly Gly Ser Gly Gly Ser Gly Gly Ser
            20                  25                  30

<210> SEQ ID NO 136
<211> LENGTH: 26
<212> TYPE: DNA
<213> ORGANISM: Artificial Sequence
<220> FEATURE:
<223> OTHER INFORMATION: Synthetic: TFRC Probe
<220> FEATURE:
<221> NAME/KEY: misc_feature
<223> OTHER INFORMATION: 56-FAM at 5' end, ZEN modification
      mid-sequence, 3IABkFQ at 3' end

<400> SEQUENCE: 136
ccattgtcat atacccggtt cagcct                                    26
```

<210> SEQ ID NO 137
<211> LENGTH: 23
<212> TYPE: DNA
<213> ORGANISM: Artificial Sequence
<220> FEATURE:
<223> OTHER INFORMATION: Synthetic: TFRC Primer 1

<400> SEQUENCE: 137
atctacagca agtttcatct cca                                    23

<210> SEQ ID NO 138
<211> LENGTH: 25
<212> TYPE: DNA
<213> ORGANISM: Artificial Sequence
<220> FEATURE:
<223> OTHER INFORMATION: Synthetic: TFRC Primer 2

<400> SEQUENCE: 138
tcaagctaga tcagcattct ctaac                                  25

<210> SEQ ID NO 139
<211> LENGTH: 37
<212> TYPE: DNA
<213> ORGANISM: Artificial Sequence
<220> FEATURE:
<223> OTHER INFORMATION: Synthetic: HPRT1 Probe
<220> FEATURE:
<221> NAME/KEY: misc_feature
<223> OTHER INFORMATION: 56-FAM at 5' end, ZEN modification
     mid-sequence, 3IABkFQ at 3' end

<400> SEQUENCE: 139
tccattccta tgactgtaga ttttatcaga ctgaaga                     37

<210> SEQ ID NO 140
<211> LENGTH: 24
<212> TYPE: DNA
<213> ORGANISM: Artificial Sequence
<220> FEATURE:
<223> OTHER INFORMATION: Synthetic: HPRT1 Primer 1

<400> SEQUENCE: 140
ccaattactt ttatgtcccc tgtt                                   24

<210> SEQ ID NO 141
<211> LENGTH: 27
<212> TYPE: DNA
<213> ORGANISM: Artificial Sequence
<220> FEATURE:
<223> OTHER INFORMATION: Synthetic: HPRT1 Primer 2

<400> SEQUENCE: 141
catcaaagca ctgaatagaa atagtga                                27

<210> SEQ ID NO 142
<211> LENGTH: 23
<212> TYPE: DNA
<213> ORGANISM: Artificial Sequence
<220> FEATURE:
<223> OTHER INFORMATION: Synthetic: GUSB Probe
<220> FEATURE:
<221> NAME/KEY: misc_feature
<223> OTHER INFORMATION: 56-FAM at 5' end, ZEN modification
     mid-sequence, 3IABkFQ at 3' end

<400> SEQUENCE: 142
tgcagggttt caccaggatc cac                                    23

<210> SEQ ID NO 143
<211> LENGTH: 22
<212> TYPE: DNA
<213> ORGANISM: Artificial Sequence
<220> FEATURE:
<223> OTHER INFORMATION: Synthetic: GUSB Primer 1

<400> SEQUENCE: 143 gttttttgatc cagacccaga tg                                              22

<210> SEQ ID NO 144
<211> LENGTH: 21
<212> TYPE: DNA
<213> ORGANISM: Artificial Sequence
<220> FEATURE:
<223> OTHER INFORMATION: Synthetic: GUSB Primer 2

<400> SEQUENCE: 144
gcccattatt cagagcgagt a                                                21

<210> SEQ ID NO 145
<211> LENGTH: 22
<212> TYPE: DNA
<213> ORGANISM: Artificial Sequence
<220> FEATURE:
<223> OTHER INFORMATION: Synthetic: CMPK2 Probe
<220> FEATURE:
<221> NAME/KEY: misc_feature
<223> OTHER INFORMATION: 56-FAM at 5' end, ZEN modification
      mid-sequence, 3IABkFQ at 3' end

<400> SEQUENCE: 145
atgccacggg taaaaccacg gt                                               22

<210> SEQ ID NO 146
<211> LENGTH: 22
<212> TYPE: DNA
<213> ORGANISM: Artificial Sequence
<220> FEATURE:
<223> OTHER INFORMATION: Synthetic: CMPK2 Primer 1

<400> SEQUENCE: 146
aggacagcct taagtgaatc tg                                               22

<210> SEQ ID NO 147
<211> LENGTH: 21
<212> TYPE: DNA
<213> ORGANISM: Artificial Sequence
<220> FEATURE:
<223> OTHER INFORMATION: Synthetic: CMPK2 Primer 2

<400> SEQUENCE: 147
gcccaaaaca gatccagaaa g                                                21

<210> SEQ ID NO 148
<211> LENGTH: 23
<212> TYPE: DNA
<213> ORGANISM: Artificial Sequence
<220> FEATURE:
<223> OTHER INFORMATION: Synthetic: HERC5 Probe
<220> FEATURE:
<221> NAME/KEY: misc_feature
<223> OTHER INFORMATION: 56-FAM at 5' end, ZEN modification
      mid-sequence, 3IABkFQ at 3' end

<400> SEQUENCE: 148
atacccaaca agctcagcca cca                                        23

<210> SEQ ID NO 149
<211> LENGTH: 23
<212> TYPE: DNA
<213> ORGANISM: Artificial Sequence
<220> FEATURE:
<223> OTHER INFORMATION: Synthetic: HERC5 Primer 1

<400> SEQUENCE: 149
cccaaatcag aaacataggc aag                                        23

<210> SEQ ID NO 150
<211> LENGTH: 23
<212> TYPE: DNA
<213> ORGANISM: Artificial Sequence
<220> FEATURE:
<223> OTHER INFORMATION: Synthetic: HERC5 Primer 2

<400> SEQUENCE: 150
tcaacacaga atgagctaag acc                                        23

<210> SEQ ID NO 151
<211> LENGTH: 26
<212> TYPE: DNA
<213> ORGANISM: Artificial Sequence
<220> FEATURE:
<223> OTHER INFORMATION: Synthetic: EPSTI1 Probe
<220> FEATURE:
<221> NAME/KEY: misc_feature
<223> OTHER INFORMATION: 56-FAM at 5' end, ZEN modification
      mid-sequence, 3IABkFQ at 3' end

<400> SEQUENCE: 151
agagccaaaa tccaccagac tgaaca                                     26

<210> SEQ ID NO 152
<211> LENGTH: 19
<212> TYPE: DNA
<213> ORGANISM: Artificial Sequence
<220> FEATURE:
<223> OTHER INFORMATION: Synthetic: EPSTI1Primer 1

<400> SEQUENCE: 152
tccaacagcc tccagattg                                             19

<210> SEQ ID NO 153
<211> LENGTH: 23
<212> TYPE: DNA
<213> ORGANISM: Artificial Sequence
<220> FEATURE:
<223> OTHER INFORMATION: Synthetic: EPSTI1 Primer 2

<400> SEQUENCE: 153
gtgaattact ggaactgaaa cgg                                        23

<210> SEQ ID NO 154
<211> LENGTH: 468
<212> TYPE: PRT
<213> ORGANISM: Artificial Sequence
<220> FEATURE:
<223> OTHER INFORMATION: Synthetic: Leader- IFNAR2 (aa27-243)- IgG1 Fc
      domain with Y407T mutation

<400> SEQUENCE: 154

Met Asp Trp Thr Trp Arg Ile Leu Phe Leu Val Ala Ala Ala Thr Gly
1               5                   10                  15

-continued

Thr His Ala Ile Ser Tyr Asp Ser Pro Asp Tyr Thr Asp Glu Ser Cys
            20                  25                  30

Thr Phe Lys Ile Ser Leu Arg Asn Phe Arg Ser Ile Leu Ser Trp Glu
            35                  40                  45

Leu Lys Asn His Ser Ile Val Pro Thr His Tyr Thr Leu Leu Tyr Thr
50                  55                  60

Ile Met Ser Lys Pro Glu Asp Leu Lys Val Val Lys Asn Cys Ala Asn
65                  70                  75                  80

Thr Thr Arg Ser Phe Cys Asp Leu Thr Asp Glu Trp Arg Ser Thr His
                85                  90                  95

Glu Ala Tyr Val Thr Val Leu Glu Gly Phe Ser Gly Asn Thr Thr Leu
            100                 105                 110

Phe Ser Cys Ser His Asn Phe Trp Leu Ala Ile Asp Met Ser Phe Glu
            115                 120                 125

Pro Pro Glu Phe Glu Ile Val Gly Phe Thr Asn His Ile Asn Val Met
130                 135                 140

Val Lys Phe Pro Ser Ile Val Glu Glu Glu Leu Gln Phe Asp Leu Ser
145                 150                 155                 160

Leu Val Ile Glu Glu Gln Ser Glu Gly Ile Val Lys Lys His Lys Pro
                165                 170                 175

Glu Ile Lys Gly Asn Met Ser Gly Asn Phe Thr Tyr Ile Ile Asp Lys
            180                 185                 190

Leu Ile Pro Asn Thr Asn Tyr Cys Val Ser Val Tyr Leu Glu His Ser
            195                 200                 205

Asp Glu Gln Ala Val Ile Lys Ser Pro Leu Lys Cys Thr Leu Leu Pro
            210                 215                 220

Pro Gly Gln Glu Ser Glu Ser Ala Glu Ser Ala Lys Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
            275                 280                 285

His Glu Asp Pro Glu Val Lys Phe Asn Trp Tyr Val Asp Gly Val Glu
            290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
            355                 360                 365

Val Tyr Thr Leu Pro Pro Ser Arg Asp Glu Leu Thr Lys Asn Gln Val
            370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Thr Ser Lys Leu Thr
            420                 425                 430

```
Val Asp Lys Ser Arg Trp Gln Gln Gly Asn Val Phe Ser Cys Ser Val
            435                 440                 445

Met His Glu Ala Leu His Asn His Tyr Thr Gln Lys Ser Leu Ser Leu
    450                 455                 460

Ser Pro Gly Lys
465

<210> SEQ ID NO 155
<211> LENGTH: 488
<212> TYPE: PRT
<213> ORGANISM: Artificial Sequence
<220> FEATURE:
<223> OTHER INFORMATION: Synthetic: Leader- IFNAR2 (aa27-243)
      (Gly4Ser)4- IgG1 Fc domain with T366W mutation

<400> SEQUENCE: 155

Met Asp Trp Thr Trp Arg Ile Leu Phe Leu Val Ala Ala Thr Gly
1               5                   10                  15

Thr His Ala Ile Ser Tyr Asp Ser Pro Asp Tyr Thr Asp Glu Ser Cys
            20                  25                  30

Thr Phe Lys Ile Ser Leu Arg Asn Phe Arg Ser Ile Leu Ser Trp Glu
            35                  40                  45

Leu Lys Asn His Ser Ile Val Pro Thr His Tyr Thr Leu Leu Tyr Thr
    50                  55                  60

Ile Met Ser Lys Pro Glu Asp Leu Lys Val Val Lys Asn Cys Ala Asn
65                  70                  75                  80

Thr Thr Arg Ser Phe Cys Asp Leu Thr Asp Glu Trp Arg Ser Thr His
                85                  90                  95

Glu Ala Tyr Val Thr Val Leu Glu Gly Phe Ser Gly Asn Thr Thr Leu
            100                 105                 110

Phe Ser Cys Ser His Asn Phe Trp Leu Ala Ile Asp Met Ser Phe Glu
        115                 120                 125

Pro Pro Glu Phe Glu Ile Val Gly Phe Thr Asn His Ile Asn Val Met
    130                 135                 140

Val Lys Phe Pro Ser Ile Val Glu Glu Glu Leu Gln Phe Asp Leu Ser
145                 150                 155                 160

Leu Val Ile Glu Glu Gln Ser Glu Gly Ile Val Lys Lys His Lys Pro
                165                 170                 175

Glu Ile Lys Gly Asn Met Ser Gly Asn Phe Thr Tyr Ile Ile Asp Lys
            180                 185                 190

Leu Ile Pro Asn Thr Asn Tyr Cys Val Ser Val Tyr Leu Glu His Ser
        195                 200                 205

Asp Glu Gln Ala Val Ile Lys Ser Pro Leu Lys Cys Thr Leu Leu Pro
    210                 215                 220

Pro Gly Gln Glu Ser Glu Ser Ala Glu Ser Ala Lys Gly Gly Gly Gly
225                 230                 235                 240

Ser Gly Gly Gly Gly Ser Gly Gly Gly Gly Ser Gly Gly Gly Gly Ser
                245                 250                 255

Glu Pro Lys Ser Cys Asp Lys Thr His Thr Cys Pro Pro Cys Pro Ala
            260                 265                 270

Pro Glu Leu Leu Gly Gly Pro Ser Val Phe Leu Phe Pro Pro Lys Pro
        275                 280                 285

Lys Asp Thr Leu Met Ile Ser Arg Thr Pro Glu Val Thr Cys Val Val
    290                 295                 300

Val Asp Val Ser His Glu Asp Pro Glu Val Lys Phe Asn Trp Tyr Val
305                 310                 315                 320
```

```
Asp Gly Val Glu Val His Asn Ala Lys Thr Lys Pro Arg Glu Glu Gln
                325                 330                 335

Tyr Asn Ser Thr Tyr Arg Val Val Ser Val Leu Thr Val Leu His Gln
                340                 345                 350

Asp Trp Leu Asn Gly Lys Glu Tyr Lys Cys Lys Val Ser Asn Lys Ala
                355                 360                 365

Leu Pro Ala Pro Ile Glu Lys Thr Ile Ser Lys Ala Lys Gly Gln Pro
                370                 375                 380

Arg Glu Pro Gln Val Tyr Thr Leu Pro Pro Ser Arg Asp Glu Leu Thr
385                 390                 395                 400

Lys Asn Gln Val Ser Leu Trp Cys Leu Val Lys Gly Phe Tyr Pro Ser
                405                 410                 415

Asp Ile Ala Val Glu Trp Glu Ser Asn Gly Gln Pro Glu Asn Asn Tyr
                420                 425                 430

Lys Thr Thr Pro Pro Val Leu Asp Ser Asp Gly Ser Phe Phe Leu Tyr
                435                 440                 445

Ser Lys Leu Thr Val Asp Lys Ser Arg Trp Gln Gln Gly Asn Val Phe
            450                 455                 460

Ser Cys Ser Val Met His Glu Ala Leu His Asn His Tyr Thr Gln Lys
465                 470                 475                 480

Ser Leu Ser Leu Ser Pro Gly Lys
                485
```

US 10,947,295 B2

HETERODIMERS OF SOLUBLE INTERFERON RECEPTORS AND USES THEREOF

CROSS-REFERENCE TO RELATED APPLICATIONS

This application claims the benefit of U.S. Provisional Application Ser. No. 62/548,737 filed on Aug. 22, 2017. The entire contents of the above-referenced provisional patent applications are incorporated herein by reference.

SEQUENCE LISTING

The instant application contains a Sequence Listing which has been submitted electronically in ASCII format via EFS-Web and is hereby incorporated by reference in its entirety. Said ASCII copy, created Feb. 22, 2019, is named "SBN-001_Sequence-Listing.txt" and is 477435 Kilobytes in size.

BACKGROUND

Systemic lupus erythematosus (SLE) is a chronic, multi-system, autoimmune disease that is characterized by diverse disease manifestations impacting multiple organs, including the skin, CNS, joints, vasculature, and kidneys. There is evidence to suggest that interferon (IFN) is overproduced in subjects with SLE and contributes to the systemic inflammation that is characteristic of SLE. In particular, Type I interferons are the prominent cytokines in SLE and are strongly correlated with disease activity and nephritis. Type I interferons are a subgroup of interferon proteins that include IFN-α, IFN-β, IFN-ε, -κ, -τ, -ζ, -IFN-ω, IFN-ν, all of which bind to the IFN-α receptor (IFNAR) which is comprised of two distinct polypeptide chains, IFNAR1 and IFNAR2. Thus, there exists a need for a means to remove the interferon and/or reduce the inflammation in subjects in need thereof.

SUMMARY OF THE INVENTION

The disclosure relates, in part, to soluble interferon receptors which are capable of binding interferon (e.g., IFN-α, IFN-β). Such soluble interferon receptors are useful to inhibit interferon activity. In some aspects, the soluble interferon receptors of the disclosure are heterodimeric constructs. In some aspects, the disclosure relates to soluble interferon receptors that are beneficial in the treatment of diseases characterized by interferon (e.g., SLE, Sjögren's syndrome).

The present disclosure provides heterodimers which binds type I interferons comprising a first polypeptide and a second polypeptide, wherein the first polypeptide comprises an interferon receptor 1 (IFNAR1) domain operatively coupled with or without a linker domain to a mutant Fc domain, and wherein the second polypeptide comprises an interferon receptor 2 (IFNAR2) domain operatively coupled with or without a linker domain to a mutant Fc domain.

In some aspects, the present disclosure provides a heterodimer which binds type I interferons comprising a first polypeptide and a second polypeptide, wherein the first polypeptide comprises an IFNAR1 domain operatively coupled without a linker domain to a mutant Fc domain, and wherein the second polypeptide comprises an IFNAR2 domain operatively coupled without a linker domain to a mutant Fc domain. In some aspects, the heterodimer of the disclosure in which each of the first and second polypeptides is linked directly to a mutant Fc domain (without a linker) has increased binding to type I interferons relative to a heterodimer in which each of the first and second polypeptides comprise a polypeptide linker domain.

In some aspects, the heterodimer of the disclosure comprises a first polypeptide and a second polypeptide, wherein the first polypeptide comprises an IFNAR1 domain operatively coupled with a linker domain (e.g., a polypeptide linker) to a mutant Fc domain, and wherein the second polypeptide comprises an IFNAR2 domain operatively coupled with a linker domain (e.g., a polypeptide linker) to a mutant Fc domain. In some aspects, the heterodimer of the disclosure comprises a first polypeptide, wherein the first polypeptide comprises a polypeptide linker (e.g., a Gly/Ser linker, e.g., $(G_4S)_n$, wherein n is 1-10, 2-5, 1, 2, 3, 4, or 5). In some aspects, the heterodimer of the disclosure comprises a second polypeptide, wherein the second polypeptide comprises a polypeptide linker (e.g., a Gly/Ser linker, e.g., $(G_4S)_n$, wherein n is 1-10, 2-5, 1, 2, 3, 4, or 5). In some aspects, the polypeptide linker is about 1-50, about 5-40, about 10-30, or about 15-20 amino acids in length. In some aspects, the polypeptide linker is about 20 amino acids or less, about 15 amino acids or less, about 10 amino acids or less, or about 5 amino acids or less in length. In some aspects, the polypeptide linker is 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 amino acids in length.

In some aspects, the heterodimer of the disclosure binds type I interferons selected from interferon-α (INFα), interferon-β (INFβ), or both INFα and INFβ. In some aspects, the type I interferon is INFα. In some aspects, the type I interferon is INFβ. In some aspects, the type I interferon is both INFα and INFβ. In other aspects, the heterodimer of the disclosure inhibits an activity of INFα. In some aspects, the heterodimer of the disclosure inhibits an activity of INFβ. In some aspects, the heterodimer of the disclosure inhibits an activity of both INFα and INFβ. In some aspects, the heterodimer of the disclosure inhibits induction of type I interferon (IFN) gene expression.

In some aspects, the heterodimer of the disclosure comprises a first polypeptide and a second polypeptide, wherein the first polypeptide comprises an IFNAR1 domain operatively coupled with or without a linker domain (e.g., a polypeptide linker) to a mutant Fc domain, and wherein the second polypeptide comprises an IFNAR2 domain operatively coupled with or without a linker domain (e.g., a polypeptide linker) to a mutant Fc domain. In some aspects, the mutant Fc domain of each of the first and second polypeptides comprises a mutant human immunoglobulin Fc domain. In some aspects, the mutant Fc domain of each of the first and second polypeptides comprises one or more mutations in a CH2 domain. In some aspects, the mutant Fc domain of each of the first and second polypeptides comprises one or more mutations in a CH3 domain. In some aspects, the mutant Fc domain of each of the first and second polypeptides comprises one or more mutations in a CH2 domain and one or more mutations in a CH3 domain. In some aspects, the mutant Fc domain of each of the first and second polypeptides comprises a mutant human IgG1 Fc domain. In some aspects, the mutant Fc domain of each of the first and second polypeptides comprises a mutant human IgG4 domain.

In some aspects, the disclosure provides heterodimers which bind type 1 interferons comprising a first polypeptide and a second polypeptide, wherein the first polypeptide comprises an IFNAR1 domain operatively coupled with or without a linker domain (e.g., a polypeptide linker, e.g., a Gly/Ser linker, e.g., $(G_4S)_n$, wherein n is 1-10, 2-5, 1, 2, 3, 4, or 5) to a mutant Fc domain comprising a mutation T366Y, and wherein the second polypeptide comprises an IFNAR2 domain operatively coupled with or without a linker domain (e.g., a polypeptide linker, e.g., a Gly/Ser linker, e.g., $(G_4S)_n$, wherein n is 1-10, 2-5, 1, 2, 3, 4, or 5) to a mutant Fc domain comprising mutation Y407T, according to EU numbering. In some aspects, the first and second polypeptide each comprise a mutant human IgG1 Fc domain. In some aspects, the first and second polypeptide each comprise a mutant human IgG4 Fc domain. In some aspects, the first and second polypeptide each comprise a polypeptide linker, wherein the polypeptide linker is a Gly/Ser linker, e.g., $(G_4S)_n$, wherein n is 1-10, 2-5, 1, 2, 3, 4, or 5.

In some aspects, the disclosure provides heterodimers which bind type 1 interferons comprising a first polypeptide and a second polypeptide, wherein the first polypeptide comprises an IFNAR1 domain operatively coupled with or without a linker domain (e.g., a polypeptide linker, e.g., a Gly/Ser linker, e.g., $(G_4S)_n$, wherein n is 1-10, 2-5, 1, 2, 3, 4, or 5) to a mutant Fc domain comprising a mutation Y407T, and wherein the second polypeptide comprises an IFNAR2 domain operatively coupled with or without a linker domain (e.g., a polypeptide linker, e.g., a Gly/Ser linker, e.g., $(G_4S)_n$, wherein n is 1-10, 2-5, 1, 2, 3, 4, or 5) to a mutant Fc domain comprising mutation T366Y, according to EU numbering. In some aspects, the first and second polypeptide each comprise a mutant human IgG1 Fc domain. In some aspects, the first and second polypeptide each comprise a mutant human IgG4 Fc domain. In some aspects, the first and second polypeptide each comprise a polypeptide linker, wherein the polypeptide linker is a Gly/Ser linker, e.g., $(G_4S)_n$, wherein n is 1-10, 2-5, 1, 2, 3, 4, or 5.

In some aspects, the disclosure provides heterodimers which bind type 1 interferons comprising a first polypeptide and a second polypeptide, wherein the first polypeptide comprises an IFNAR1 domain operatively coupled with or without a linker domain (e.g., a polypeptide linker, e.g., a Gly/Ser linker, e.g., $(G_4S)_n$, wherein n is 1-10, 2-5, 1, 2, 3, 4, or 5) to a mutant Fc domain comprising a mutation T366W, and wherein the second polypeptide comprises an IFNAR2 domain operatively coupled with or without a linker domain (e.g., a polypeptide linker, e.g., a Gly/Ser linker, e.g., $(G_4S)_n$, wherein n is 1-10, 2-5, 1, 2, 3, 4, or 5) to a mutant Fc domain comprising mutations T366S, L368A and Y407V, according to EU numbering. In some aspects, the first and second polypeptide each comprise a mutant human IgG1 Fc domain. In some aspects, the first and second polypeptide each comprise a polypeptide linker, wherein the polypeptide linker is a Gly/Ser linker, e.g., $(G_4S)_n$, wherein n is 1-10, 2-5, 1, 2, 3, 4, or 5.

In some aspects, the disclosure provides heterodimers which bind type 1 interferons comprising a first polypeptide and a second polypeptide, wherein the first polypeptide comprises an IFNAR1 domain operatively coupled with or without a linker domain (e.g., a polypeptide linker, e.g., a Gly/Ser linker, e.g., $(G_4S)_n$, wherein n is 1-10, 2-5, 1, 2, 3, 4, or 5) to a mutant Fc domain comprising mutations T366S, L368A and Y407V, and wherein the second polypeptide comprises an IFNAR2 domain operatively coupled with or without a linker domain (e.g., a polypeptide linker, e.g., a Gly/Ser linker, e.g., $(G_4S)_n$, wherein n is 1-10, 2-5, 1, 2, 3, 4, or 5) to a mutant Fc domain comprising a mutation T366W, according to EU numbering. In some aspects, the first and second polypeptide each comprise a mutant human IgG1 Fc domain. In some aspects, the first and second polypeptide each comprise a polypeptide linker, wherein the polypeptide linker is a Gly/Ser linker, e.g., $(G_4S)_n$, wherein n is 1-10, 2-5, 1, 2, 3, 4, or 5.

In some aspects, the disclosure provides heterodimers which bind type 1 interferons comprising a first polypeptide and a second polypeptide, wherein the first polypeptide comprises an IFNAR1 domain operatively coupled with or without a linker domain (e.g., a polypeptide linker, e.g., a Gly/Ser linker, e.g., $(G_4S)_n$, wherein n is 1-10, 2-5, 1, 2, 3, 4, or 5) to a mutant Fc domain comprising mutations T350V, T366L, K392L and T394W, and wherein the second polypeptide comprises an IFNAR2 domain operatively coupled with or without a linker domain (e.g., a polypeptide linker, e.g., a Gly/Ser linker, e.g., $(G_4S)_n$, wherein n is 1-10, 2-5, 1, 2, 3, 4, or 5) to a mutant Fc domain comprising mutations T350V, L351Y, F405A and Y407V, according to EU numbering. In some aspects, the first and second polypeptide each comprise a mutant human IgG1 Fc domain. In some aspects, the first and second polypeptide each comprise a polypeptide linker, wherein the polypeptide linker is a Gly/Ser linker, e.g., $(G_4S)_n$, wherein n is 1-10, 2-5, 1, 2, 3, 4, or 5.

In some aspects, the disclosure provides heterodimers which bind type 1 interferons comprising a first polypeptide and a second polypeptide, wherein the first polypeptide comprises an IFNAR1 domain operatively coupled with or without a linker domain (e.g., a polypeptide linker, e.g., a Gly/Ser linker, e.g., $(G_4S)_n$, wherein n is 1-10, 2-5, 1, 2, 3, 4, or 5) to a mutant Fc domain comprising mutations T350V, L351Y, F405A and Y407V, and wherein the second polypeptide comprises an IFNAR2 domain operatively coupled with or without a linker domain (e.g., a polypeptide linker, e.g., a Gly/Ser linker, e.g., $(G_4S)_n$, wherein n is 1-10, 2-5, 1, 2, 3, 4, or 5) to a mutant Fc domain comprising mutations T350V, T366L, K392L and T394W, according to EU numbering. In some aspects, the first and second polypeptide each comprise a mutant human IgG1 Fc domain. In some aspects, the first and second polypeptide each comprise a polypeptide linker, wherein the polypeptide linker is a Gly/Ser linker, e.g., $(G_4S)_n$, wherein n is 1-10, 2-5, 1, 2, 3, 4, or 5.

In some aspects, the disclosure provides heterodimers which bind type 1 interferons comprising a first polypeptide and a second polypeptide, wherein the first polypeptide comprises an IFNAR1 domain operatively coupled with or without a linker domain (e.g., a polypeptide linker, e.g., a Gly/Ser linker, e.g., $(G_4S)_n$, wherein n is 1-10, 2-5, 1, 2, 3, 4, or 5) to a mutant Fc domain comprising a mutation T366Y, and wherein the second polypeptide comprises an IFNAR2 domain operatively coupled with or without a linker domain (e.g., a polypeptide linker, e.g., a Gly/Ser linker, e.g., $(G_4S)_n$, wherein n is 1-10, 2-5, 1, 2, 3, 4, or 5) to a mutant Fc domain comprising mutations T366S, L368A and Y407V, according to EU numbering. In some aspects, the first and second polypeptide each comprise a mutant human IgG4 Fc domain. In some aspects, the first and second polypeptide each comprise a polypeptide linker, wherein the polypeptide linker is a Gly/Ser linker, e.g., $(G_4S)_n$, wherein n is 1-10, 2-5, 1, 2, 3, 4, or 5.

In some aspects, the disclosure provides heterodimers which bind type 1 interferons comprising a first polypeptide and a second polypeptide, wherein the first polypeptide comprises an IFNAR1 domain operatively coupled with or without a linker domain (e.g., a polypeptide linker, e.g., a Gly/Ser linker, e.g., $(G_4S)_n$, wherein n is 1-10, 2-5, 1, 2, 3, 4, or 5) to a mutant Fc domain comprising mutations T366S, L368A and Y407V, and wherein the second polypeptide comprises an IFNAR2 domain operatively coupled with or without a linker domain (e.g., a polypeptide linker, e.g., a Gly/Ser linker, e.g., $(G_4S)_n$, wherein n is 1-10, 2-5, 1, 2, 3, 4, or 5) to a mutant Fc domain comprising a mutation T366Y, according to EU numbering. In some aspects, the first and second polypeptide each comprise a mutant human IgG4 Fc domain. In some aspects, the first and second polypeptide each comprise a polypeptide linker, wherein the polypeptide linker is a Gly/Ser linker, e.g., $(G_4S)_n$, wherein n is 1-10, 2-5, 1, 2, 3, 4, or 5.

In some aspects, the disclosure provides heterodimers which bind type 1 interferons comprising a first polypeptide and a second polypeptide, wherein the first polypeptide comprises an IFNAR1 domain operatively coupled with or without a linker domain (e.g., a polypeptide linker, e.g., a Gly/Ser linker, e.g., $(G_4S)_n$, wherein n is 1-10, 2-5, 1, 2, 3, 4, or 5) to a mutant Fc domain comprising mutations T350V, T366L, K392L and T394W, and wherein the second polypeptide comprises an IFNAR2 domain operatively coupled with or without a linker domain (e.g., a polypeptide linker, e.g., a Gly/Ser linker, e.g., $(G_4S)_n$, wherein n is 1-10, 2-5, 1, 2, 3, 4, or 5) to a mutant Fc domain comprising mutations T350V, L351Y, F405A and Y407V, according to EU numbering. In some aspects, the first and second polypeptide each comprise a mutant human IgG4 Fc domain. In some aspects, the first and second polypeptide each comprise a polypeptide linker, wherein the polypeptide linker is a Gly/Ser linker, e.g., $(G_4S)_n$, wherein n is 1-10, 2-5, 1, 2, 3, 4, or 5.

In some aspects, the disclosure provides heterodimers which bind type 1 interferons comprising a first polypeptide and a second polypeptide, wherein the first polypeptide comprises an IFNAR1 domain operatively coupled with or without a linker domain (e.g., a polypeptide linker, e.g., a Gly/Ser linker, e.g., $(G_4S)_n$, wherein n is 1-10, 2-5, 1, 2, 3, 4, or 5) to a mutant Fc domain comprising mutations T350V, L351Y, F405A and Y407V, and wherein the second polypeptide comprises an IFNAR2 domain operatively coupled with or without a linker domain (e.g., a polypeptide linker, e.g., a Gly/Ser linker, e.g., $(G_4S)_n$, wherein n is 1-10, 2-5, 1, 2, 3, 4, or 5) to a mutant Fc domain comprising mutations T350V, T366L, K392L and T394W, according to EU numbering. In some aspects, the first and second polypeptide each comprise a mutant human IgG4 Fc domain. In some aspects, the first and second polypeptide each comprise a polypeptide linker, wherein the polypeptide linker is a Gly/Ser linker, e.g., $(G_4S)_n$, wherein n is 1-10, 2-5, 1, 2, 3, 4, or 5.

In any of the foregoing or related aspects, the heterodimer of the disclosure comprises a first polypeptide comprising an IFNAR1 domain and a second polypeptide comprising an IFNAF2 domain, wherein each of the first and second polypeptides is operably coupled with or without a linker to a mutant Fc domain comprising one or more mutations (e.g., one or more CH2 mutations, one or more CH3 mutations, or one or more CH2 and CH3 mutations), wherein the one or more Fc mutations promotes, increases, or enhances the formation of a heterodimer relative to a heterodimer comprising a first polypeptide comprising an IFNAR1 domain and a second polypeptide comprising an IFNAF2 domain, each comprising a wild-type Fc domain (e.g., an Fc domain of the same isotype (e.g., human IgG1 or human IgG4) without the one or more Fc mutations). In some aspects, the mutant Fc domain is a mutant human IgG1 Fc domain. In some aspects, the mutant Fc domain is a mutant human IgG4 domain In any of the foregoing or related aspects, the heterodimer of the disclosure comprises a first polypeptide comprising an IFNAR1 domain and a second polypeptide comprising an IFNAF2 domain, wherein each of the first and second polypeptides is operably coupled with or without a linker to a mutant Fc domain comprising one or more mutations (e.g., one or more CH2 mutations, one or more CH3 mutations, or one or more CH2 and CH3 mutations), wherein the mutant Fc domain of the first polypeptide and/or the mutant Fc domain of the second polypeptide further comprises one or more mutations which promotes, increases, or enhances stability of the Fc domain, and/or reduces binding to Fc receptors. In some aspects, the mutation is selected from the group consisting of: C220S, C226S, C229S, P238S, and P331S, and a combination thereof, according to EU numbering. In some aspects, the mutations comprise C220S, P238S, and P331S. In some aspects, the mutations comprise C220S, C226S, C229S, P238S, and P331S. In some aspects, the first polypeptide and second polypeptide each comprise a mutant Fc domain comprising mutations C220S, P238S, and P331S. In some aspects, the first polypeptide and second polypeptide each comprise a mutant Fc domain comprising mutations C220S, C226S, C229S, P238S, and P331S.

In any of the foregoing or related aspects, the heterodimer of the disclosure comprises a first polypeptide comprising an IFNAR1 domain and a second polypeptide comprising an IFNAF2 domain, wherein each of the first and second polypeptides is operably coupled with or without a linker to a mutant Fc domain, wherein the first polypeptide comprises an IFNAR1 domain comprising the amino acid sequence in SEQ ID NO: 11 and the second polypeptide comprises an IFNAR2 domain comprising the amino acid sequence in SEQ ID NO: 12.

In some aspects, the disclosure provides a heterodimer which binds type I interferons comprising a first polypeptide and a second polypeptide, wherein the first polypeptide comprises an IFNAR1 domain operatively coupled to a mutant IgG1 Fc domain comprising mutation T366Y, and wherein the second polypeptide comprises an IFNAR2 domain operatively coupled to a mutant IgG1 Fc domain comprising mutation Y407T, according to EU numbering. In some aspects, the first polypeptide comprises an IFNAR1 domain comprising the amino acid sequence in SEQ ID NO: 11 and the second polypeptide comprises an IFNAR2 domain comprising the amino acid sequence in SEQ ID NO: 12. In some aspects, the mutant IgG1 Fc domain comprises the amino acid sequence set forth in SEQ ID NO: 106. In some aspects, the mutant IgG1 Fc domain comprises the amino acid sequence set forth in SEQ ID NO: 107.

In some aspects, the disclosure provides a heterodimer which binds type I interferons comprising a first polypeptide and a second polypeptide, wherein the first polypeptide comprises an IFNAR1 domain operatively coupled to a mutant IgG1 Fc domain comprising mutation Y407T, and wherein the second polypeptide comprises an IFNAR2 domain operatively coupled to a mutant IgG1 Fc domain comprising mutation T336Y, according to EU numbering. In some aspects, the first polypeptide comprises an IFNAR1 domain comprising the amino acid sequence in SEQ ID NO: 11 and the second polypeptide comprises an IFNAR2 domain comprising the amino acid sequence in SEQ ID NO: 12. In some aspects, the mutant IgG1 Fc domain comprises the amino acid sequence set forth in SEQ ID NO: 106. In some aspects, the mutant IgG1 Fc domain comprises the amino acid sequence set forth in SEQ ID NO: 107.

In some aspects, the disclosure provides a heterodimer which binds type I interferons comprising a first polypeptide and a second polypeptide, wherein the first polypeptide comprises an IFNAR1 domain operatively coupled to a mutant IgG1 Fc domain comprising mutation T366W, and wherein the second polypeptide comprises an IFNAR2 domain operatively coupled to a mutant IgG1 Fc domain comprising mutations T366S, L368A and Y407V, according to EU numbering. In some aspects, the first polypeptide comprises an IFNAR1 domain comprising the amino acid sequence in SEQ ID NO: 11 and the second polypeptide comprises an IFNAR2 domain comprising the amino acid sequence in SEQ ID NO: 12. In some aspects, the mutant IgG1 Fc domain comprises the amino acid sequence set forth in SEQ ID NO: 108. In some aspects, the mutant IgG1 Fc domain comprises the amino acid sequence set forth in SEQ ID NO: 109.

In some aspects, the disclosure provides a heterodimer which binds type I interferons comprising a first polypeptide and a second polypeptide, wherein the first polypeptide comprises an IFNAR1 domain operatively coupled to a mutant IgG1 Fc domain comprising mutations T366S, L368A and Y407V, and wherein the second polypeptide comprises an IFNAR2 domain operatively coupled to a mutant IgG1 Fc domain comprising mutation T336W, according to EU numbering. In some aspects, the first polypeptide comprises an IFNAR1 domain comprising the amino acid sequence in SEQ ID NO: 11 and the second polypeptide comprises an IFNAR2 domain comprising the amino acid sequence in SEQ ID NO: 12. In some aspects, the mutant IgG1 Fc domain comprises the amino acid sequence set forth in SEQ ID NO: 108. In some aspects, the mutant IgG1 Fc domain comprises the amino acid sequence set forth in SEQ ID NO: 109.

In some aspects, the disclosure provides a heterodimer which binds type I interferons comprising a first polypeptide and a second polypeptide, wherein the first polypeptide comprises an IFNAR1 domain operatively coupled to a mutant IgG1 Fc domain comprising mutations T350V, T366L, K392L and T394W, and wherein the second polypeptide comprises an IFNAR2 domain operatively coupled to a mutant IgG1 Fc domain comprising mutations T350V, L351Y, F405A and Y407V, according to EU numbering. In some aspects, the first polypeptide comprises an IFNAR1 domain comprising the amino acid sequence in SEQ ID NO: 11 and the second polypeptide comprises an IFNAR2 domain comprising the amino acid sequence in SEQ ID NO: 12. In some aspects, the mutant IgG1 Fc domain comprises the amino acid sequence set forth in SEQ ID NO: 9. In some aspects, the mutant IgG1 Fc domain comprises the amino acid sequence set forth in SEQ ID NO: 10.

In some aspects, the disclosure provides a heterodimer which binds type I interferons comprising a first polypeptide and a second polypeptide, wherein the first polypeptide comprises an IFNAR1 domain operatively coupled to a mutant IgG1 Fc domain comprising mutations T350V, L351Y, F405A and Y407V, and wherein the second polypeptide comprises an IFNAR2 domain operatively coupled to a mutant IgG1 Fc domain comprising mutations T350V, T366L, K392L and T394W, according to EU numbering. In some aspects, the first polypeptide comprises an IFNAR1 domain comprising the amino acid sequence in SEQ ID NO: 11 and the second polypeptide comprises an IFNAR2 domain comprising the amino acid sequence in SEQ ID NO: 12. In some aspects, the mutant IgG1 Fc domain comprises the amino acid sequence set forth in SEQ ID NO: 9. In some aspects, the mutant IgG1 Fc domain comprises the amino acid sequence set forth in SEQ ID NO: 10.

In some aspects, the disclosure provides a heterodimer which binds type I interferons comprising a first polypeptide and a second polypeptide, wherein the first polypeptide comprises an IFNAR1 domain operatively coupled to a mutant IgG4 Fc domain comprising mutation T366Y, and wherein the second polypeptide comprises an IFNAR2 domain operatively coupled to a mutant IgG4 Fc domain comprising mutation Y407T, according to EU numbering. In some aspects, the first polypeptide comprises an IFNAR1 domain comprising the amino acid sequence in SEQ ID NO: 11 and the second polypeptide comprises an IFNAR2 domain comprising the amino acid sequence in SEQ ID NO: 12. In some aspects, the mutant IgG4 Fc domain comprises the amino acid sequence set forth in SEQ ID NO: 122. In some aspects, the mutant IgG4 Fc domain comprises the amino acid sequence set forth in SEQ ID NO: 123.

In some aspects, the disclosure provides a heterodimer which binds type I interferons comprising a first polypeptide and a second polypeptide, wherein the first polypeptide comprises an IFNAR1 domain operatively coupled to a mutant IgG4 Fc domain comprising mutation Y407T, and wherein the second polypeptide comprises an IFNAR2 domain operatively coupled to a mutant IgG4 Fc domain comprising mutation T336Y, according to EU numbering. In some aspects, the first polypeptide comprises an IFNAR1 domain comprising the amino acid sequence in SEQ ID NO: 11 and the second polypeptide comprises an IFNAR2 domain comprising the amino acid sequence in SEQ ID NO: 12. In some aspects, the mutant IgG4 Fc domain comprises the amino acid sequence set forth in SEQ ID NO: 122. In some aspects, the mutant IgG4 Fc domain comprises the amino acid sequence set forth in SEQ ID NO: 123.

In some aspects, the disclosure provides a heterodimer which binds type I interferons comprising a first polypeptide and a second polypeptide, wherein the first polypeptide comprises an IFNAR1 domain operatively coupled to a mutant IgG4 Fc domain comprising mutation T366W, and wherein the second polypeptide comprises an IFNAR2 domain operatively coupled to a mutant IgG4 Fc domain comprising mutations T366S, L368A and Y407V, according to EU numbering. In some aspects, the first polypeptide comprises an IFNAR1 domain comprising the amino acid sequence in SEQ ID NO: 11 and the second polypeptide comprises an IFNAR2 domain comprising the amino acid sequence in SEQ ID NO: 12. In some aspects, the mutant IgG4 Fc domain comprises the amino acid sequence set forth in SEQ ID NO: 124. In some aspects, the mutant IgG4 Fc domain comprises the amino acid sequence set forth in SEQ ID NO: 125.

In some aspects, the disclosure provides a heterodimer which binds type I interferons comprising a first polypeptide and a second polypeptide, wherein the first polypeptide comprises an IFNAR1 domain operatively coupled to a mutant IgG4 Fc domain comprising mutations T366S, L368A and Y407V, and wherein the second polypeptide comprises an IFNAR2 domain operatively coupled to a mutant IgG4 Fc domain comprising mutation T336W, according to EU numbering. In some aspects, the first polypeptide comprises an IFNAR1 domain comprising the amino acid sequence in SEQ ID NO: 11 and the second polypeptide comprises an IFNAR2 domain comprising the amino acid sequence in SEQ ID NO: 12. In some aspects, the mutant IgG4 Fc domain comprises the amino acid sequence set forth in SEQ ID NO: 124. In some aspects, the mutant IgG4 Fc domain comprises the amino acid sequence set forth in SEQ ID NO: 125.

In some aspects, the disclosure provides a heterodimer which binds type I interferons comprising a first polypeptide and a second polypeptide, wherein the first polypeptide comprises an IFNAR1 domain operatively coupled to a mutant IgG4 Fc domain comprising mutations T350V, T366L, K392L and T394W, and wherein the second polypeptide comprises an IFNAR2 domain operatively coupled to a mutant IgG4 Fc domain comprising mutations T350V, L351Y, F405A and Y407V, according to EU numbering. In some aspects, the first polypeptide comprises an IFNAR1 domain comprising the amino acid sequence in SEQ ID NO: 11 and the second polypeptide comprises an IFNAR2 domain comprising the amino acid sequence in SEQ ID NO: 12. In some aspects, the mutant IgG4 Fc domain comprises the amino acid sequence set forth in SEQ ID NO: 120. In some aspects, the mutant IgG4 Fc domain comprises the amino acid sequence set forth in SEQ ID NO: 121.

In some aspects, the disclosure provides a heterodimer which binds type I interferons comprising a first polypeptide and a second polypeptide, wherein the first polypeptide comprises an IFNAR1 domain operatively coupled to a mutant IgG4 Fc domain comprising mutations T350V, L351Y, F405A and Y407V, and wherein the second polypeptide comprises an IFNAR2 domain operatively coupled to a mutant IgG4 Fc domain comprising mutations T350V, T366L, K392L and T394W, according to EU numbering. In some aspects, the first polypeptide comprises an IFNAR1 domain comprising the amino acid sequence in SEQ ID NO: 11 and the second polypeptide comprises an IFNAR2 domain comprising the amino acid sequence in SEQ ID NO: 12. In some aspects, the mutant IgG4 Fc domain comprises the amino acid sequence set forth in SEQ ID NO: 120. In some aspects, the mutant IgG4 Fc domain comprises the amino acid sequence set forth in SEQ ID NO: 121.

In some aspects, the disclosure provides a heterodimer which binds type I interferons comprising a first polypeptide and a second polypeptide, wherein the first polypeptide comprises an IFNAR1 domain operatively coupled with a Gly/Ser linker (e.g., a $(G_4S)_n$ linker, wherein n is 1-5, 1, 2, 3, 4 or 5) to a mutant IgG1 Fc domain comprising mutation T366Y, and wherein the second polypeptide comprises an IFNAR2 domain operatively coupled to a mutant IgG1 Fc domain comprising mutation Y407T, according to EU numbering. In some aspects, the first polypeptide comprises an IFNAR1 domain comprising the amino acid sequence in SEQ ID NO: 11 and the second polypeptide comprises an IFNAR2 domain comprising the amino acid sequence in SEQ ID NO: 12. In some aspects, the mutant IgG1 Fc domain comprises the amino acid sequence set forth in SEQ ID NO: 106. In some aspects, the mutant IgG1 Fc domain comprises the amino acid sequence set forth in SEQ ID NO: 107.

In some aspects, the disclosure provides a heterodimer which binds type I interferons comprising a first polypeptide and a second polypeptide, wherein the first polypeptide comprises an IFNAR1 domain operatively coupled with a Gly/Ser linker (e.g., a $(G_4S)_n$ linker, wherein n is 1-5, 1, 2, 3, 4 or 5) to a mutant IgG1 Fc domain comprising mutation Y407T, and wherein the second polypeptide comprises an IFNAR2 domain operatively coupled to a mutant IgG1 Fc domain comprising mutation T336Y, according to EU numbering. In some aspects, the first polypeptide comprises an IFNAR1 domain comprising the amino acid sequence in SEQ ID NO: 11 and the second polypeptide comprises an IFNAR2 domain comprising the amino acid sequence in SEQ ID NO: 12. In some aspects, the mutant IgG1 Fc domain comprises the amino acid sequence set forth in SEQ ID NO: 106. In some aspects, the mutant IgG1 Fc domain comprises the amino acid sequence set forth in SEQ ID NO: 107.

In some aspects, the disclosure provides a heterodimer which binds type I interferons comprising a first polypeptide and a second polypeptide, wherein the first polypeptide comprises an IFNAR1 domain operatively coupled with a Gly/Ser linker (e.g., a $(G_4S)_n$ linker, wherein n is 1-5, 1, 2, 3, 4 or 5) to a mutant IgG1 Fc domain comprising mutation T366W, and wherein the second polypeptide comprises an IFNAR2 domain operatively coupled to a mutant IgG1 Fc domain comprising mutations T366S, L368A and Y407V, according to EU numbering. In some aspects, the first polypeptide comprises an IFNAR1 domain comprising the amino acid sequence in SEQ ID NO: 11 and the second polypeptide comprises an IFNAR2 domain comprising the amino acid sequence in SEQ ID NO: 12. In some aspects, the mutant IgG1 Fc domain comprises the amino acid sequence set forth in SEQ ID NO: 108. In some aspects, the mutant IgG1 Fc domain comprises the amino acid sequence set forth in SEQ ID NO: 109.

In some aspects, the disclosure provides a heterodimer which binds type I interferons comprising a first polypeptide and a second polypeptide, wherein the first polypeptide comprises an IFNAR1 domain operatively coupled with a Gly/Ser linker (e.g., a $(G_4S)_n$ linker, wherein n is 1-5, 1, 2, 3, 4 or 5) to a mutant IgG1 Fc domain comprising mutations T366S, L368A and Y407V, and wherein the second polypeptide comprises an IFNAR2 domain operatively coupled to a mutant IgG1 Fc domain comprising mutation T336W, according to EU numbering. In some aspects, the first polypeptide comprises an IFNAR1 domain comprising the amino acid sequence in SEQ ID NO: 11 and the second polypeptide comprises an IFNAR2 domain comprising the amino acid sequence in SEQ ID NO: 12. In some aspects, the mutant IgG1 Fc domain comprises the amino acid sequence set forth in SEQ ID NO: 108. In some aspects, the mutant IgG1 Fc domain comprises the amino acid sequence set forth in SEQ ID NO: 109.

In some aspects, the disclosure provides a heterodimer which binds type I interferons comprising a first polypeptide and a second polypeptide, wherein the first polypeptide comprises an IFNAR1 domain operatively coupled with a Gly/Ser linker (e.g., a $(G_4S)_n$ linker, wherein n is 1-5, 1, 2, 3, 4 or 5) to a mutant IgG1 Fc domain comprising mutations T350V, T366L, K392L and T394W, and wherein the second polypeptide comprises an IFNAR2 domain operatively coupled to a mutant IgG1 Fc domain comprising mutations T350V, L351Y, F405A and Y407V, according to EU numbering. In some aspects, the first polypeptide comprises an IFNAR1 domain comprising the amino acid sequence in SEQ ID NO: 11 and the second polypeptide comprises an IFNAR2 domain comprising the amino acid sequence in SEQ ID NO: 12. In some aspects, the mutant IgG1 Fc domain comprises the amino acid sequence set forth in SEQ ID NO: 9. In some aspects, the mutant IgG1 Fc domain comprises the amino acid sequence set forth in SEQ ID NO: 10.

In some aspects, the disclosure provides a heterodimer which binds type I interferons comprising a first polypeptide and a second polypeptide, wherein the first polypeptide comprises an IFNAR1 domain operatively coupled with a Gly/Ser linker (e.g., a $(G_4S)_n$ linker, wherein n is 1-5, 1, 2, 3, 4 or 5) to a mutant IgG1 Fc domain comprising mutations T350V, L351Y, F405A and Y407V, and wherein the second polypeptide comprises an IFNAR2 domain operatively coupled to a mutant IgG1 Fc domain comprising mutations T350V, T366L, K392L and T394W, according to EU numbering. In some aspects, the first polypeptide comprises an IFNAR1 domain comprising the amino acid sequence in SEQ ID NO: 11 and the second polypeptide comprises an IFNAR2 domain comprising the amino acid sequence in SEQ ID NO: 12. In some aspects, the mutant IgG1 Fc domain comprises the amino acid sequence set forth in SEQ ID NO: 9. In some aspects, the mutant IgG1 Fc domain comprises the amino acid sequence set forth in SEQ ID NO: 10.

In some aspects, the disclosure provides a heterodimer which binds type I interferons comprising a first polypeptide and a second polypeptide, wherein the first polypeptide comprises an IFNAR1 domain operatively coupled with a Gly/Ser linker (e.g., a $(G_4S)_n$ linker, wherein n is 1-5, 1, 2, 3, 4 or 5) to a mutant IgG4 Fc domain comprising mutation T366Y, and wherein the second polypeptide comprises an IFNAR2 domain operatively coupled to a mutant IgG4 Fc domain comprising mutation Y407T, according to EU numbering. In some aspects, the first polypeptide comprises an IFNAR1 domain comprising the amino acid sequence in SEQ ID NO: 11 and the second polypeptide comprises an IFNAR2 domain comprising the amino acid sequence in SEQ ID NO: 12. In some aspects, the mutant IgG4 Fc domain comprises the amino acid sequence set forth in SEQ ID NO: 122. In some aspects, the mutant IgG4 Fc domain comprises the amino acid sequence set forth in SEQ ID NO: 123.

In some aspects, the disclosure provides a heterodimer which binds type I interferons comprising a first polypeptide and a second polypeptide, wherein the first polypeptide comprises an IFNAR1 domain operatively coupled with a Gly/Ser linker (e.g., a $(G_4S)_n$ linker, wherein n is 1-5, 1, 2, 3, 4 or 5) to a mutant IgG4 Fc domain comprising mutation Y407T, and wherein the second polypeptide comprises an IFNAR2 domain operatively coupled to a mutant IgG4 Fc domain comprising mutation T336Y, according to EU numbering. In some aspects, the first polypeptide comprises an IFNAR1 domain comprising the amino acid sequence in SEQ ID NO: 11 and the second polypeptide comprises an IFNAR2 domain comprising the amino acid sequence in SEQ ID NO: 12. In some aspects, the mutant IgG4 Fc domain comprises the amino acid sequence set forth in SEQ ID NO: 122. In some aspects, the mutant IgG4 Fc domain comprises the amino acid sequence set forth in SEQ ID NO: 123.

In some aspects, the disclosure provides a heterodimer which binds type I interferons comprising a first polypeptide and a second polypeptide, wherein the first polypeptide comprises an IFNAR1 domain operatively coupled with a Gly/Ser linker (e.g., a $(G_4S)_n$ linker, wherein n is 1-5, 1, 2, 3, 4 or 5) to a mutant IgG4 Fc domain comprising mutation T366W, and wherein the second polypeptide comprises an IFNAR2 domain operatively coupled to a mutant IgG4 Fc domain comprising mutations T366S, L368A and Y407V, according to EU numbering. In some aspects, the first polypeptide comprises an IFNAR1 domain comprising the amino acid sequence in SEQ ID NO: 11 and the second polypeptide comprises an IFNAR2 domain comprising the amino acid sequence in SEQ ID NO: 12. In some aspects, the mutant IgG4 Fc domain comprises the amino acid sequence set forth in SEQ ID NO: 124. In some aspects, the mutant IgG4 Fc domain comprises the amino acid sequence set forth in SEQ ID NO: 125.

In some aspects, the disclosure provides a heterodimer which binds type I interferons comprising a first polypeptide and a second polypeptide, wherein the first polypeptide comprises an IFNAR1 domain operatively coupled with a Gly/Ser linker (e.g., a $(G_4S)_n$ linker, wherein n is 1-5, 1, 2, 3, 4 or 5) to a mutant IgG4 Fc domain comprising mutations T366S, L368A and Y407V, and wherein the second polypeptide comprises an IFNAR2 domain operatively coupled to a mutant IgG4 Fc domain comprising mutation T336W, according to EU numbering. In some aspects, the first polypeptide comprises an IFNAR1 domain comprising the amino acid sequence in SEQ ID NO: 11 and the second polypeptide comprises an IFNAR2 domain comprising the amino acid sequence in SEQ ID NO: 12. In some aspects, the mutant IgG4 Fc domain comprises the amino acid sequence set forth in SEQ ID NO: 124. In some aspects, the mutant IgG4 Fc domain comprises the amino acid sequence set forth in SEQ ID NO: 125.

In some aspects, the disclosure provides a heterodimer which binds type I interferons comprising a first polypeptide and a second polypeptide, wherein the first polypeptide comprises an IFNAR1 domain operatively coupled with a Gly/Ser linker (e.g., a $(G_4S)_n$ linker, wherein n is 1-5, 1, 2, 3, 4 or 5) to a mutant IgG4 Fc domain comprising mutations T350V, T366L, K392L and T394W, and wherein the second polypeptide comprises an IFNAR2 domain operatively coupled to a mutant IgG4 Fc domain comprising mutations T350V, L351Y, F405A and Y407V, according to EU numbering. In some aspects, the first polypeptide comprises an IFNAR1 domain comprising the amino acid sequence in SEQ ID NO: 11 and the second polypeptide comprises an IFNAR2 domain comprising the amino acid sequence in SEQ ID NO: 12. In some aspects, the mutant IgG4 Fc domain comprises the amino acid sequence set forth in SEQ ID NO: 120. In some aspects, the mutant IgG4 Fc domain comprises the amino acid sequence set forth in SEQ ID NO: 121.

In some aspects, the disclosure provides a heterodimer which binds type I interferons comprising a first polypeptide and a second polypeptide, wherein the first polypeptide comprises an IFNAR1 domain operatively coupled with a Gly/Ser linker (e.g., a $(G_4S)_n$ linker, wherein n is 1-5, 1, 2, 3, 4 or 5) to a mutant IgG4 Fc domain comprising mutations T350V, L351Y, F405A and Y407V, and wherein the second polypeptide comprises an IFNAR2 domain operatively coupled to a mutant IgG4 Fc domain comprising mutations T350V, T366L, K392L and T394W, according to EU numbering. In some aspects, the first polypeptide comprises an IFNAR1 domain comprising the amino acid sequence in SEQ ID NO: 11 and the second polypeptide comprises an IFNAR2 domain comprising the amino acid sequence in SEQ ID NO: 12. In some aspects, the mutant IgG4 Fc domain comprises the amino acid sequence set forth in SEQ ID NO: 120. In some aspects, the mutant IgG4 Fc domain comprises the amino acid sequence set forth in SEQ ID NO: 121.

In other aspects, the disclosure provides a heterodimer which binds type I interferons comprising a first polypeptide and a second polypeptide selected from:

(i) a first polypeptide comprising the amino acid sequence of SEQ ID NO: 40 and a second polypeptide comprising the amino acid sequence of SEQ ID NO: 43;

(ii) a first polypeptide comprising the amino acid sequence of SEQ ID NO: 41 and a second polypeptide comprising the amino acid sequence of SEQ ID NO: 42;

(iii) a first polypeptide comprising the amino acid sequence of SEQ ID NO: 53 and a second polypeptide comprising the amino acid sequence of SEQ ID NO: 55; and (iv) a first polypeptide comprising the amino acid sequence of SEQ ID NO: 57 and a second polypeptide comprising the amino acid sequence of SEQ ID NO: 59;

(v) a first polypeptide comprising the amino acid sequence of SEQ ID NO: 40, and a second polypeptide comprising the amino acid sequence selected from SEQ ID NO: 43, SEQ ID NO: 55, and SEQ ID NO: 59;

(vi) a first polypeptide comprising the amino acid sequence of SEQ ID NO: 43, and a second polypeptide comprising the amino acid sequence selected from SEQ ID NO: 40, SEQ ID NO: 53, and SEQ ID NO: 57;

(vii) a first polypeptide comprising the amino acid sequence of SEQ ID NO: 42, and a second polypeptide comprising the amino acid sequence selected from SEQ ID NO: 41, SEQ ID NO: 45, and SEQ ID NO: 47;

(viii) a first polypeptide comprising the amino acid sequence of SEQ ID NO: 41, and a second polypeptide comprising the amino acid sequence selected from SEQ ID NO: 42, SEQ ID NO: 49, and SEQ ID NO: 51;

(ix) a first polypeptide comprising the amino acid sequence of SEQ ID NO: 53, and a second polypeptide comprising the amino acid sequence selected from SEQ ID NO: 43, SEQ ID NO: 55, and SEQ ID NO: 59;

(x) a first polypeptide comprising the amino acid sequence of SEQ ID NO: 55, and a second polypeptide comprising the amino acid sequence selected from SEQ ID NO: 40, SEQ ID NO: 53, and SEQ ID NO: 57;

(xi) a first polypeptide comprising the amino acid sequence of SEQ ID NO: 57, and a second polypeptide comprising the amino acid sequence selected from SEQ ID NO: 43, SEQ ID NO: 55, and SEQ ID NO: 59;

(xii) a first polypeptide comprising the amino acid sequence of SEQ ID NO: 59, and a second polypeptide comprising the amino acid sequence selected from SEQ ID NO: 40, SEQ ID NO: 53, and SEQ ID NO: 57;

(xiii) a first polypeptide comprising the amino acid sequence of SEQ ID NO: 45, and a second polypeptide comprising the amino acid sequence selected from SEQ ID NO: 42, SEQ ID NO: 49, and SEQ ID NO: 51;

(xiv) a first polypeptide comprising the amino acid sequence of SEQ ID NO: 47, and a second polypeptide comprising the amino acid sequence selected from SEQ ID NO: 42, SEQ ID NO: 49, and SEQ ID NO: 51;

(xv) a first polypeptide comprising the amino acid sequence of SEQ ID NO: 49, and a second polypeptide comprising the amino acid sequence selected from SEQ ID NO: 41, SEQ ID NO: 45, and SEQ ID NO: 47;

(xvi) a first polypeptide comprising the amino acid sequence of SEQ ID NO: 51, and a second polypeptide comprising the amino acid sequence selected from SEQ ID NO: 41, SEQ ID NO: 45, and SEQ ID NO: 47;

(xvii) a first polypeptide comprising the amino acid sequence of SEQ ID NO: 61, and a second polypeptide comprising the amino acid sequence selected from SEQ ID NO: 67, SEQ ID NO: 75, and SEQ ID NO: 82;

(xviii) a first polypeptide comprising the amino acid sequence of SEQ ID NO: 63, and a second polypeptide comprising the amino acid sequence selected from SEQ ID NO: 65, SEQ ID NO: 73, and SEQ ID NO: 81;

(xix) a first polypeptide comprising the amino acid sequence of SEQ ID NO: 65, and a second polypeptide comprising the amino acid sequence selected from SEQ ID NO: 63, SEQ ID NO: 71, and SEQ ID NO: 79;

(xx) a first polypeptide comprising the amino acid sequence of SEQ ID NO: 67, and a second polypeptide comprising the amino acid sequence selected from SEQ ID NO: 61, SEQ ID NO: 69, and SEQ ID NO: 77;

(xxi) a first polypeptide comprising the amino acid sequence of SEQ ID NO: 69, and a second polypeptide comprising the amino acid sequence selected from SEQ ID NO: 67, SEQ ID NO: 75, and SEQ ID NO: 82;

(xxii) a first polypeptide comprising the amino acid sequence of SEQ ID NO: 71, and a second polypeptide comprising the amino acid sequence selected from SEQ ID NO: 65, SEQ ID NO: 73, and SEQ ID NO: 81;

(xxiii) a first polypeptide comprising the amino acid sequence of SEQ ID NO: 73, and a second polypeptide comprising the amino acid sequence selected from SEQ ID NO: 63, SEQ ID NO: 71, and SEQ ID NO: 79;

(xxiv) a first polypeptide comprising the amino acid sequence of SEQ ID NO: 75, and a second polypeptide comprising the amino acid sequence selected from SEQ ID NO: 61, SEQ ID NO: 69, and SEQ ID NO: 77;

(xxv) a first polypeptide comprising the amino acid sequence of SEQ ID NO: 77, and a second polypeptide comprising the amino acid sequence selected from SEQ ID NO: 67, SEQ ID NO: 75, and SEQ ID NO: 82;

(xxvi) a first polypeptide comprising the amino acid sequence of SEQ ID NO: 79, and a second polypeptide comprising the amino acid sequence selected from SEQ ID NO: 65, SEQ ID NO: 73, and SEQ ID NO: 81;

(xxvii) a first polypeptide comprising the amino acid sequence of SEQ ID NO: 81, and a second polypeptide comprising the amino acid sequence selected from SEQ ID NO: 63, SEQ ID NO: 71, and SEQ ID NO: 79;

(xxviii) a first polypeptide comprising the amino acid sequence of SEQ ID NO: 82, and a second polypeptide comprising the amino acid sequence selected from SEQ ID NO: 61, SEQ ID NO: 69, and SEQ ID NO: 77;

(xxix) a first polypeptide comprising the amino acid sequence of SEQ ID NO: 84, and a second polypeptide comprising the amino acid sequence selected from SEQ ID NO: 89, SEQ ID NO: 97, and SEQ ID NO: 105;

(xxx) a first polypeptide comprising the amino acid sequence of SEQ ID NO: 85, and a second polypeptide comprising the amino acid sequence selected from SEQ ID NO: 87, SEQ ID NO: 95, and SEQ ID NO: 103;

(xxxi) a first polypeptide comprising the amino acid sequence of SEQ ID NO: 87, and a second polypeptide comprising the amino acid sequence selected from SEQ ID NO: 85, SEQ ID NO: 93, and SEQ ID NO: 101;

(xxxii) a first polypeptide comprising the amino acid sequence of SEQ ID NO: 89, and a second polypeptide comprising the amino acid sequence selected from SEQ ID NO: 84, SEQ ID NO: 91, and SEQ ID NO: 99;

(xxxiii) a first polypeptide comprising the amino acid sequence of SEQ ID NO: 91, and a second polypeptide comprising the amino acid sequence selected from SEQ ID NO: 89, SEQ ID NO: 97, and SEQ ID NO: 105;

(xxxiv) a first polypeptide comprising the amino acid sequence of SEQ ID NO: 93, and a second polypeptide comprising the amino acid sequence selected from SEQ ID NO: 87, SEQ ID NO: 95, and SEQ ID NO: 103;

(xxxv) a first polypeptide comprising the amino acid sequence of SEQ ID NO: 95, and a second polypeptide comprising the amino acid sequence selected from SEQ ID NO: 85, SEQ ID NO: 93, and SEQ ID NO: 101;

(xxxvi) a first polypeptide comprising the amino acid sequence of SEQ ID NO: 97, and a second polypeptide comprising the amino acid sequence selected from SEQ ID NO: 84, SEQ ID NO: 91, and SEQ ID NO: 99;

(xxxvii) a first polypeptide comprising the amino acid sequence of SEQ ID NO: 99, and a second polypeptide comprising the amino acid sequence selected from SEQ ID NO: 89, SEQ ID NO: 97, and SEQ ID NO: 105;

(xxxviii) a first polypeptide comprising the amino acid sequence of SEQ ID NO: 101, and a second polypeptide comprising the amino acid sequence selected from SEQ ID NO: 87, SEQ ID NO: 95, and SEQ ID NO: 103;

(xxxix) a first polypeptide comprising the amino acid sequence of SEQ ID NO: 103, and a second polypeptide comprising the amino acid sequence selected from SEQ ID NO: 85, SEQ ID NO: 93, and SEQ ID NO: 101; and (xl) a first polypeptide comprising the amino acid sequence of SEQ ID NO: 105, and a second polypeptide comprising the amino acid sequence selected from SEQ ID NO: 84, SEQ ID NO: 91, and SEQ ID NO: 99.

In some aspects, the disclosure provides a heterodimer which binds type I interferons comprising a first polypeptide comprising the amino acid sequence of SEQ ID NO: 40 and a second polypeptide comprising the amino acid sequence of SEQ ID NO: 43.

In some aspects, the disclosure provides a heterodimer which binds type I interferons comprising a first polypeptide comprising the amino acid sequence of SEQ ID NO: 41 and a second polypeptide comprising the amino acid sequence of SEQ ID NO: 42.

In some aspects, the disclosure provides a heterodimer which binds type I interferons comprising a first polypeptide comprising the amino acid sequence of SEQ ID NO: 53 and a second polypeptide comprising the amino acid sequence of SEQ ID NO: 55.

In some aspects, the disclosure provides a heterodimer which binds type I interferons comprising a first polypeptide comprising the amino acid sequence of SEQ ID NO: 57 and a second polypeptide comprising the amino acid sequence of SEQ ID NO: 59.

In any of the foregoing or related aspects, the disclosure provides a heterodimer which binds type 1 interferons, wherein the type I interferons are selected from interferon-α (INFα), interferon-β (INFβ), or both INFα and INFβ. In some aspects, the type I interferon is INFα. In some aspects, the type I interferon is INFβ. In some aspects, the type I interferon is both INFα and INFβ. In some aspects, the heterodimer inhibits an activity of INFα. In some aspects, the heterodimer inhibits an activity of INFβ. In some aspects, the heterodimer inhibits an activity of both INFα and INFβ. In some aspects, the heterodimer inhibits induction of type I interferon (IFN) gene expression.

In any of the foregoing or related aspects, the disclosure provides a heterodimer which binds type 1 interferons comprising a first and second polypeptide, wherein each of the first and second polypeptides is linked directly to a mutant Fc domain (without a linker), and wherein the heterodimer has increased binding to type I interferons relative to a heterodimer in which each of the first and second polypeptides comprise a polypeptide linker domain.

In any of the foregoing or related aspects, the disclosure provides a heterodimer which binds type 1 interferons comprising a first polypeptide comprising an IFNAR1 domain and a second polypeptide comprising an IFNAF2 domain, wherein each of the first and second polypeptides is operably coupled to a mutant Fc domain comprising one or more mutations (e.g., one or more CH2 mutations, one or more CH3 mutations, or one or more CH2 and CH3 mutations), and wherein the one or more Fc mutations promotes, increases, or enhances the formation of a heterodimer relative to a heterodimer comprising a first polypeptide comprising an IFNAR1 domain and a second polypeptide comprising an IFNAF2 domain, each comprising a wild-type Fc domain.

In any of the foregoing or related aspects, the heterodimer of the disclosure comprises a first polypeptide comprising an IFNAR1 domain and a second polypeptide comprising an IFNAF2 domain, wherein each of the first and second polypeptides is operably coupled with or without a linker to a mutant Fc domain comprising one or more mutations (e.g., one or more CH2 mutations, one or more CH3 mutations, or one or more CH2 and CH3 mutations), wherein the mutant Fc domain of the first polypeptide and/or the mutant Fc domain of the second polypeptide further comprises one or more mutations which promotes, increases, or enhances stability of the Fc domain, and/or reduces binding to Fc receptors. In some aspects, the mutation is selected from the group consisting of: C220S, C226S, C229S, P238S, and P331S, and a combination thereof, according to EU numbering. In some aspects, the mutations comprise C220S, P238S, and P331S. In some aspects, the mutations comprise C220S, C226S, C229S, P238S, and P331S. In some aspects, the first polypeptide and second polypeptide each comprise a mutant Fc domain comprising mutations C220S, P238S, and P331S. In some aspects, the first polypeptide and second polypeptide each comprise a mutant Fc domain comprising mutations C220S, C226S, C229S, P238S, and P331S.

In other aspects, the disclosure provides a composition comprising a heterodimer of the disclosure and a pharmaceutically acceptable carrier.

In other aspects, the disclosure provides a nucleic acid comprising a nucleotide sequence encoding a first polypeptide of the heterodimer, wherein the first polypeptide comprises an IFNAR1 domain operatively coupled with or without a linker (e.g., a Gly/Ser linker (e.g., a $(G_4S)_n$ linker, wherein n is 1-5, 1, 2, 3, 4 or 5) to a mutant Fc domain (e.g., a mutant human IgG1 Fc domain or a mutant human IgG4 Fc domain). In some aspects, the first polypeptide comprising an IFNAR1 domain comprises the amino acid sequence in SEQ ID NO: 11.

In other aspects, the disclosure provides a nucleic acid comprising a nucleotide sequence encoding a second polypeptide of the heterodimer, wherein the second polypeptide comprises an IFNAR2 domain operatively coupled with or without a linker (e.g., a Gly/Ser linker (e.g., a $(G_4S)_n$ linker, wherein n is 1-5, 1, 2, 3, 4 or 5) to a mutant Fc domain (e.g., a mutant human IgG1 Fc domain or a mutant human IgG4 Fc domain). In some aspects, the second polypeptide comprising an IFNAR2 domain comprises the amino acid sequence in SEQ ID NO: 12.

Other aspects of the disclosure provide recombinant expression vectors and host cells comprising the nucleic acids of the disclosure. In some aspects, the recombinant expression vector and host cell comprises a nucleic acid comprising a nucleotide sequence encoding a first polypeptide of the heterodimer, wherein the first polypeptide comprises an IFNAR1 domain operatively coupled with or without a linker (e.g., a Gly/Ser linker (e.g., a $(G_4S)_n$ linker, wherein n is 1-5, 1, 2, 3, 4 or 5) to a mutant Fc domain (e.g., a mutant human IgG1 Fc domain or a mutant human IgG4 Fc domain). In some aspects, the recombinant expression vector and host cell comprises a nucleic acid comprising a nucleotide sequence encoding a second polypeptide of the heterodimer, wherein the second polypeptide comprises an IFNAR2 domain operatively coupled with or without a linker (e.g., a Gly/Ser linker (e.g., a $(G_4S)_n$ linker, wherein n is 1-5, 1, 2, 3, 4 or 5) to a mutant Fc domain (e.g., a mutant human IgG1 Fc domain or a mutant human IgG4 Fc domain). In some aspects, the recombinant expression vector and host cell comprises both a nucleic acid comprising a nucleotide sequence encoding the first polypeptide of the heterodimer and a nucleic acid comprising a nucleotide sequence encoding the a second polypeptide of the heterodimer. In some aspects, the first polypeptide comprising an IFNAR1 domain comprises the amino acid sequence in SEQ ID NO: 11. In some aspects, the second polypeptide comprising an IFNAR2 domain comprises the amino acid sequence in SEQ ID NO: 12.

Other aspects of the disclosure provide methods of reducing, decreasing, or inhibiting interferon (IFN) gene expression in a subject in need thereof, comprising administering to the subject a heterodimer of the disclosure, or a composition of the disclosure comprising a heterodimer and a pharmaceutically acceptable carrier.

Other aspects of the disclosure provide methods of reducing, decreasing, or inhibiting type I interferons in a subject in need thereof, comprising administering to the subject a heterodimer of the disclosure, or a composition of the disclosure comprising a heterodimer and a pharmaceutically acceptable carrier. In some aspects, the type I interferon is INFα. In some aspects, the type I interferon is INFβ. In some aspects, the type I interferon is both INFα and INFβ.

Other aspects of the disclosure provide methods of treating or inhibiting progression of a disease characterized by type I interferons and methods of treating an autoimmune disease in a subject in need thereof, comprising administering to the subject a heterodimer of the disclosure, or a composition of the disclosure comprising a heterodimer and a pharmaceutically acceptable carrier. In some aspects, the type I interferon is INFα. In some aspects, the type I interferon is INFβ. In some aspects, the type I interferon is both INFα and INFβ. In some aspects, the autoimmune disease is SLE. In some aspects, the autoimmune disease is Sjogren's syndrome.

In some aspects, the disclosure provides methods of reducing, decreasing, or inhibiting interferon (IFN) gene expression, methods of reducing, decreasing, or inhibiting type I interferons (e.g., INFα, INFβ, or both INFα and INFβ), and methods of treating an autoimmune disease (e.g., SLE, Sjogren's syndrome) in a subject in need thereof, the method comprising administering to the subject a heterodimer of the disclosure, or a composition of the disclosure comprising a heterodimer and a pharmaceutically acceptable carrier, wherein the heterodimer comprises a first polypeptide and a second polypeptide, wherein the first polypeptide comprises an IFNAR1 domain operatively coupled to a mutant IgG1 Fc domain comprising mutation T366Y, and wherein the second polypeptide comprises an IFNAR2 domain operatively coupled to a mutant IgG1 Fc domain comprising mutation Y407T, according to EU numbering. In some aspects, the first polypeptide comprises an IFNAR1 domain comprising the amino acid sequence in SEQ ID NO: 11 and the second polypeptide comprises an IFNAR2 domain comprising the amino acid sequence in SEQ ID NO: 12. In some aspects, the mutant IgG1 Fc domain comprises the amino acid sequence set forth in SEQ ID NO: 106. In some aspects, the mutant IgG1 Fc domain comprises the amino acid sequence set forth in SEQ ID NO: 107. In some aspects, the autoimmune disease is SLE. In some aspects, the autoimmune disease is Sjogren's syndrome.

In some aspects, the disclosure provides methods of reducing, decreasing, or inhibiting interferon (IFN) gene expression, methods of reducing, decreasing, or inhibiting type I interferons (e.g., INFα, INFβ, or both INFα and INFβ), and methods of treating an autoimmune disease (e.g., SLE, Sjogren's syndrome) in a subject in need thereof, the method comprising administering to the subject a heterodimer of the disclosure, or a composition of the disclosure comprising a heterodimer and a pharmaceutically acceptable carrier, wherein the heterodimer comprises a first polypeptide and a second polypeptide, wherein the first polypeptide comprises an IFNAR1 domain operatively coupled to a mutant IgG1 Fc domain comprising mutation Y407T, and wherein the second polypeptide comprises an IFNAR2 domain operatively coupled to a mutant IgG1 Fc domain comprising mutation T336Y, according to EU numbering. In some aspects, the first polypeptide comprises an IFNAR1 domain comprising the amino acid sequence in SEQ ID NO: 11 and the second polypeptide comprises an IFNAR2 domain comprising the amino acid sequence in SEQ ID NO: 12. In some aspects, the mutant IgG1 Fc domain comprises the amino acid sequence set forth in SEQ ID NO: 106. In some aspects, the mutant IgG1 Fc domain comprises the amino acid sequence set forth in SEQ ID NO: 107. In some aspects, the autoimmune disease is SLE. In some aspects, the autoimmune disease is Sjogren's syndrome.

In some aspects, the disclosure provides methods of reducing, decreasing, or inhibiting interferon (IFN) gene expression, methods of reducing, decreasing, or inhibiting type I interferons (e.g., INFα, INFβ, or both INFα and INFβ), and methods of treating an autoimmune disease (e.g., SLE, Sjogren's syndrome) in a subject in need thereof, the method comprising administering to the subject a heterodimer of the disclosure, or a composition of the disclosure comprising a heterodimer and a pharmaceutically acceptable carrier, wherein the heterodimer comprises a first polypeptide and a second polypeptide, wherein the first polypeptide comprises an IFNAR1 domain operatively coupled to a mutant IgG1 Fc domain comprising mutation T366W, and wherein the second polypeptide comprises an IFNAR2 domain operatively coupled to a mutant IgG1 Fc domain comprising mutations T366S, L368A and Y407V, according to EU numbering. In some aspects, the first polypeptide comprises an IFNAR1 domain comprising the amino acid sequence in SEQ ID NO: 11 and the second polypeptide comprises an IFNAR2 domain comprising the amino acid sequence in SEQ ID NO: 12. In some aspects, the mutant IgG1 Fc domain comprises the amino acid sequence set forth in SEQ ID NO: 108. In some aspects, the mutant IgG1 Fc domain comprises the amino acid sequence set forth in SEQ ID NO: 109. In some aspects, the autoimmune disease is SLE. In some aspects, the autoimmune disease is Sjogren's syndrome.

In some aspects, the disclosure provides methods of reducing, decreasing, or inhibiting interferon (IFN) gene expression, methods of reducing, decreasing, or inhibiting type I interferons (e.g., INFα, INFβ, or both INFα and INFβ), and methods of treating an autoimmune disease (e.g., SLE, Sjogren's syndrome) in a subject in need thereof, the method comprising administering to the subject a heterodimer of the disclosure, or a composition of the disclosure comprising a heterodimer and a pharmaceutically acceptable carrier, wherein the heterodimer comprises a first polypeptide and a second polypeptide, wherein the first polypeptide comprises an IFNAR1 domain operatively coupled to a mutant IgG1 Fc domain comprising mutations T366S, L368A and Y407V, and wherein the second polypeptide comprises an IFNAR2 domain operatively coupled to a mutant IgG1 Fc domain comprising mutation T336W, according to EU numbering. In some aspects, the first polypeptide comprises an IFNAR1 domain comprising the amino acid sequence in SEQ ID NO: 11 and the second polypeptide comprises an IFNAR2 domain comprising the amino acid sequence in SEQ ID NO: 12. In some aspects, the mutant IgG1 Fc domain comprises the amino acid sequence set forth in SEQ ID NO: 108. In some aspects, the mutant IgG1 Fc domain comprises the amino acid sequence set forth in SEQ ID NO: 109. In some aspects, the autoimmune disease is SLE. In some aspects, the autoimmune disease is Sjogren's syndrome.

In some aspects, the disclosure provides methods of reducing, decreasing, or inhibiting interferon (IFN) gene expression, methods of reducing, decreasing, or inhibiting type I interferons (e.g., INFα, INFβ, or both INFα and INFβ), and methods of treating an autoimmune disease (e.g., SLE, Sjogren's syndrome) in a subject in need thereof, the method comprising administering to the subject a heterodimer of the disclosure, or a composition of the disclosure comprising a heterodimer and a pharmaceutically acceptable carrier, wherein the heterodimer comprises a first polypeptide and a second polypeptide, wherein the first polypeptide comprises an IFNAR1 domain operatively coupled to a mutant IgG1 Fc domain comprising mutations T350V, T366L, K392L and T394W, and wherein the second polypeptide comprises an IFNAR2 domain operatively coupled to a mutant IgG1 Fc domain comprising mutations T350V, L351Y, F405A and Y407V, according to EU numbering. In some aspects, the first polypeptide comprises an IFNAR1 domain comprising the amino acid sequence in SEQ ID NO: 11 and the second polypeptide comprises an IFNAR2 domain comprising the amino acid sequence in SEQ ID NO: 12. In some aspects, the mutant IgG1 Fc domain comprises the amino acid sequence set forth in SEQ ID NO: 9. In some aspects, the mutant IgG1 Fc domain comprises the amino acid sequence set forth in SEQ ID NO: 10. In some aspects, the autoimmune disease is SLE. In some aspects, the autoimmune disease is Sjogren's syndrome.

In some aspects, the disclosure provides methods of reducing, decreasing, or inhibiting interferon (IFN) gene expression, methods of reducing, decreasing, or inhibiting type I interferons (e.g., INFα, INFβ, or both INFα and INFβ), and methods of treating an autoimmune disease (e.g., SLE, Sjogren's syndrome) in a subject in need thereof, the method comprising administering to the subject a heterodimer of the disclosure, or a composition of the disclosure comprising a heterodimer and a pharmaceutically acceptable carrier, wherein the heterodimer comprises a first polypeptide and a second polypeptide, wherein the first polypeptide comprises an IFNAR1 domain operatively coupled to a mutant IgG1 Fc domain comprising mutations T350V, L351Y, F405A and Y407V, and wherein the second polypeptide comprises an IFNAR2 domain operatively coupled to a mutant IgG1 Fc domain comprising mutations T350V, T366L, K392L and T394W, according to EU numbering. In some aspects, the first polypeptide comprises an IFNAR1 domain comprising the amino acid sequence in SEQ ID NO: 11 and the second polypeptide comprises an IFNAR2 domain comprising the amino acid sequence in SEQ ID NO: 12. In some aspects, the mutant IgG1 Fc domain comprises the amino acid sequence set forth in SEQ ID NO: 9. In some aspects, the mutant IgG1 Fc domain comprises the amino acid sequence set forth in SEQ ID NO: 10. In some aspects, the autoimmune disease is SLE. In some aspects, the autoimmune disease is Sjogren's syndrome.

In some aspects, the disclosure provides methods of reducing, decreasing, or inhibiting interferon (IFN) gene expression, methods of reducing, decreasing, or inhibiting type I interferons (e.g., INFα, INFβ, or both INFα and INFβ), and methods of treating an autoimmune disease (e.g., SLE, Sjogren's syndrome) in a subject in need thereof, the method comprising administering to the subject a heterodimer of the disclosure, or a composition of the disclosure comprising a heterodimer and a pharmaceutically acceptable carrier, wherein the heterodimer comprises a first polypeptide and a second polypeptide, wherein the first polypeptide comprises an IFNAR1 domain operatively coupled to a mutant IgG4 Fc domain comprising mutation T366Y, and wherein the second polypeptide comprises an IFNAR2 domain operatively coupled to a mutant IgG4 Fc domain comprising mutation Y407T, according to EU numbering. In some aspects, the first polypeptide comprises an IFNAR1 domain comprising the amino acid sequence in SEQ ID NO: 11 and the second polypeptide comprises an IFNAR2 domain comprising the amino acid sequence in SEQ ID NO: 12. In some aspects, the mutant IgG4 Fc domain comprises the amino acid sequence set forth in SEQ ID NO: 122. In some aspects, the mutant IgG4 Fc domain comprises the amino acid sequence set forth in SEQ ID NO: 123. In some aspects, the autoimmune disease is SLE. In some aspects, the autoimmune disease is Sjogren's syndrome.

In some aspects, the disclosure provides methods of reducing, decreasing, or inhibiting interferon (IFN) gene expression, methods of reducing, decreasing, or inhibiting type I interferons (e.g., INFα, INFβ, or both INFα and INFβ), and methods of treating an autoimmune disease (e.g., SLE, Sjogren's syndrome) in a subject in need thereof, the method comprising administering to the subject a heterodimer of the disclosure, or a composition of the disclosure comprising a heterodimer and a pharmaceutically acceptable carrier, wherein the heterodimer comprises a first polypeptide and a second polypeptide, wherein the first polypeptide comprises an IFNAR1 domain operatively coupled to a mutant IgG4 Fc domain comprising mutation Y407T, and wherein the second polypeptide comprises an IFNAR2 domain operatively coupled to a mutant IgG4 Fc domain comprising mutation T336Y, according to EU numbering. In some aspects, the first polypeptide comprises an IFNAR1 domain comprising the amino acid sequence in SEQ ID NO: 11 and the second polypeptide comprises an IFNAR2 domain comprising the amino acid sequence in SEQ ID NO: 12. In some aspects, the mutant IgG4 Fc domain comprises the amino acid sequence set forth in SEQ ID NO: 122. In some aspects, the mutant IgG4 Fc domain comprises the amino acid sequence set forth in SEQ ID NO: 123. In some aspects, the autoimmune disease is SLE. In some aspects, the autoimmune disease is Sjogren's syndrome.

In some aspects, the disclosure provides methods of reducing, decreasing, or inhibiting interferon (IFN) gene expression, methods of reducing, decreasing, or inhibiting type I interferons (e.g., INFα, INFβ, or both INFα and INFβ), and methods of treating an autoimmune disease (e.g., SLE, Sjogren's syndrome) in a subject in need thereof, the method comprising administering to the subject a heterodimer of the disclosure, or a composition of the disclosure comprising a heterodimer and a pharmaceutically acceptable carrier, wherein the heterodimer comprises a first polypeptide and a second polypeptide, wherein the first polypeptide comprises an IFNAR1 domain operatively coupled to a mutant IgG4 Fc domain comprising mutation T366W, and wherein the second polypeptide comprises an IFNAR2 domain operatively coupled to a mutant IgG4 Fc domain comprising mutations T366S, L368A and Y407V, according to EU numbering. In some aspects, the first polypeptide comprises an IFNAR1 domain comprising the amino acid sequence in SEQ ID NO: 11 and the second polypeptide comprises an IFNAR2 domain comprising the amino acid sequence in SEQ ID NO: 12. In some aspects, the mutant IgG4 Fc domain comprises the amino acid sequence set forth in SEQ ID NO: 124. In some aspects, the mutant IgG4 Fc domain comprises the amino acid sequence set forth in SEQ ID NO: 125. In some aspects, the autoimmune disease is SLE. In some aspects, the autoimmune disease is Sjogren's syndrome.

In some aspects, the disclosure provides methods of reducing, decreasing, or inhibiting interferon (IFN) gene expression, methods of reducing, decreasing, or inhibiting type I interferons (e.g., INFα, INFβ, or both INFα and INFβ), and methods of treating an autoimmune disease (e.g., SLE, Sjogren's syndrome) in a subject in need thereof, the method comprising administering to the subject a heterodimer of the disclosure, or a composition of the disclosure comprising a heterodimer and a pharmaceutically acceptable carrier, wherein the heterodimer comprises a first polypeptide and a second polypeptide, wherein the first polypeptide comprises an IFNAR1 domain operatively coupled to a mutant IgG4 Fc domain comprising mutations T366S, L368A and Y407V, and wherein the second polypeptide comprises an IFNAR2 domain operatively coupled to a mutant IgG4 Fc domain comprising mutation T336W, according to EU numbering. In some aspects, the first polypeptide comprises an IFNAR1 domain comprising the amino acid sequence in SEQ ID NO: 11 and the second polypeptide comprises an IFNAR2 domain comprising the amino acid sequence in SEQ ID NO: 12. In some aspects, the mutant IgG4 Fc domain comprises the amino acid sequence set forth in SEQ ID NO: 124. In some aspects, the mutant IgG4 Fc domain comprises the amino acid sequence set forth in SEQ ID NO: 125. In some aspects, the autoimmune disease is SLE. In some aspects, the autoimmune disease is Sjogren's syndrome. In some aspects, the disclosure provides methods of reducing, decreasing, or inhibiting interferon (IFN) gene expression, methods of reducing, decreasing, or inhibiting type I interferons (e.g., INFα, INFβ, or both INFα and INFβ), and methods of treating an autoimmune disease (e.g., SLE, Sjogren's syndrome) in a subject in need thereof, the method comprising administering to the subject a heterodimer of the disclosure, or a composition of the disclosure comprising a heterodimer and a pharmaceutically acceptable carrier, wherein the heterodimer comprises a first polypeptide and a second polypeptide, wherein the first polypeptide comprises an IFNAR1 domain operatively coupled to a mutant IgG4 Fc domain comprising mutations T350V, T366L, K392L and T394W, and wherein the second polypeptide comprises an IFNAR2 domain operatively coupled to a mutant IgG4 Fc domain comprising mutations T350V, L351Y, F405A and Y407V, according to EU numbering. In some aspects, the first polypeptide comprises an IFNAR1 domain comprising the amino acid sequence in SEQ ID NO: 11 and the second polypeptide comprises an IFNAR2 domain comprising the amino acid sequence in SEQ ID NO: 12. In some aspects, the mutant IgG4 Fc domain comprises the amino acid sequence set forth in SEQ ID NO: 120. In some aspects, the mutant IgG4 Fc domain comprises the amino acid sequence set forth in SEQ ID NO: 121. In some aspects, the autoimmune disease is SLE. In some aspects, the autoimmune disease is Sjogren's syndrome.

In some aspects, the disclosure provides methods of reducing, decreasing, or inhibiting interferon (IFN) gene expression, methods of reducing, decreasing, or inhibiting type I interferons (e.g., INFα, INFβ, or both INFα and INFβ), and methods of treating an autoimmune disease (e.g., SLE, Sjogren's syndrome) in a subject in need thereof, the method comprising administering to the subject a heterodimer of the disclosure, or a composition of the disclosure comprising a heterodimer and a pharmaceutically acceptable carrier, wherein the heterodimer comprises a first polypeptide and a second polypeptide, wherein the first polypeptide comprises an IFNAR1 domain operatively coupled to a mutant IgG4 Fc domain comprising mutations T350V, L351Y, F405A and Y407V, and wherein the second polypeptide comprises an IFNAR2 domain operatively coupled to a mutant IgG4 Fc domain comprising mutations T350V, T366L, K392L and T394W, according to EU numbering. In some aspects, the first polypeptide comprises an IFNAR1 domain comprising the amino acid sequence in SEQ ID NO: 11 and the second polypeptide comprises an IFNAR2 domain comprising the amino acid sequence in SEQ ID NO: 12. In some aspects, the mutant IgG4 Fc domain comprises the amino acid sequence set forth in SEQ ID NO: 120. In some aspects, the mutant IgG4 Fc domain comprises the amino acid sequence set forth in SEQ ID NO: 121. In some aspects, the autoimmune disease is SLE. In some aspects, the autoimmune disease is Sjogren's syndrome.

In some aspects, the disclosure provides methods of reducing, decreasing, or inhibiting interferon (IFN) gene expression, methods of reducing, decreasing, or inhibiting type I interferons (e.g., INFα, INFβ, or both INFα and INFβ), and methods of treating an autoimmune disease (e.g., SLE, Sjogren's syndrome) in a subject in need thereof, the method comprising administering to the subject a heterodimer of the disclosure, or a composition of the disclosure comprising a heterodimer and a pharmaceutically acceptable carrier, wherein the heterodimer comprises a first polypeptide and a second polypeptide, wherein the first polypeptide comprises an IFNAR1 domain operatively coupled with a Gly/Ser linker (e.g., a $(G_4S)_n$ linker, wherein n is 1-5, 1, 2, 3, 4 or 5) to a mutant IgG1 Fc domain comprising mutation T366Y, and wherein the second polypeptide comprises an IFNAR2 domain operatively coupled to a mutant IgG1 Fc domain comprising mutation Y407T, according to EU numbering. In some aspects, the first polypeptide comprises an IFNAR1 domain comprising the amino acid sequence in SEQ ID NO: 11 and the second polypeptide comprises an IFNAR2 domain comprising the amino acid sequence in SEQ ID NO: 12. In some aspects, the mutant IgG1 Fc domain comprises the amino acid sequence set forth in SEQ ID NO: 106. In some aspects, the mutant IgG1 Fc domain comprises the amino acid sequence set forth in SEQ ID NO: 107. In some aspects, the autoimmune disease is SLE. In some aspects, the autoimmune disease is Sjogren's syndrome.

In some aspects, the disclosure provides methods of reducing, decreasing, or inhibiting interferon (IFN) gene expression, methods of reducing, decreasing, or inhibiting type I interferons (e.g., INFα, INFβ, or both INFα and INFβ), and methods of treating an autoimmune disease (e.g., SLE, Sjogren's syndrome) in a subject in need thereof, the method comprising administering to the subject a heterodimer of the disclosure, or a composition of the disclosure comprising a heterodimer and a pharmaceutically acceptable carrier, wherein the heterodimer comprises a first polypeptide and a second polypeptide, wherein the first polypeptide comprises an IFNAR1 domain operatively coupled with a Gly/Ser linker (e.g., a $(G_4S)_n$ linker, wherein n is 1-5, 1, 2, 3, 4 or 5) to a mutant IgG1 Fc domain comprising mutation Y407T, and wherein the second polypeptide comprises an IFNAR2 domain operatively coupled to a mutant IgG1 Fc domain comprising mutation T336Y, according to EU numbering. In some aspects, the first polypeptide comprises an IFNAR1 domain comprising the amino acid sequence in SEQ ID NO: 11 and the second polypeptide comprises an IFNAR2 domain comprising the amino acid sequence in SEQ ID NO: 12. In some aspects, the mutant IgG1 Fc domain comprises the amino acid sequence set forth in SEQ ID NO: 106. In some aspects, the mutant IgG1 Fc domain comprises the amino acid sequence set forth in SEQ ID NO: 107. In some aspects, the autoimmune disease is SLE. In some aspects, the autoimmune disease is Sjogren's syndrome.

In some aspects, the disclosure provides methods of reducing, decreasing, or inhibiting interferon (IFN) gene expression, methods of reducing, decreasing, or inhibiting type I interferons (e.g., INFα, INFβ, or both INFα and INFβ), and methods of treating an autoimmune disease (e.g., SLE, Sjogren's syndrome) in a subject in need thereof, the method comprising administering to the subject a heterodimer of the disclosure, or a composition of the disclosure comprising a heterodimer and a pharmaceutically acceptable carrier, wherein the heterodimer comprises a first polypeptide and a second polypeptide, wherein the first polypeptide comprises an IFNAR1 domain operatively coupled with a Gly/Ser linker (e.g., a $(G_4S)_n$ linker, wherein n is 1-5, 1, 2, 3, 4 or 5) to a mutant IgG1 Fc domain comprising mutation T366W, and wherein the second polypeptide comprises an IFNAR2 domain operatively coupled to a mutant IgG1 Fc domain comprising mutations T366S, L368A and Y407V, according to EU numbering. In some aspects, the first polypeptide comprises an IFNAR1 domain comprising the amino acid sequence in SEQ ID NO: 11 and the second polypeptide comprises an IFNAR2 domain comprising the amino acid sequence in SEQ ID NO: 12. In some aspects, the mutant IgG1 Fc domain comprises the amino acid sequence set forth in SEQ ID NO: 108. In some aspects, the mutant IgG1 Fc domain comprises the amino acid sequence set forth in SEQ ID NO: 109. In some aspects, the autoimmune disease is SLE. In some aspects, the autoimmune disease is Sjogren's syndrome.

In some aspects, the disclosure provides methods of reducing, decreasing, or inhibiting interferon (IFN) gene expression, methods of reducing, decreasing, or inhibiting type I interferons (e.g., INFα, INFβ, or both INFα and INFβ), and methods of treating an autoimmune disease (e.g., SLE, Sjogren's syndrome) in a subject in need thereof, the method comprising administering to the subject a heterodimer of the disclosure, or a composition of the disclosure comprising a heterodimer and a pharmaceutically acceptable carrier, wherein the heterodimer comprises a first polypeptide and a second polypeptide, wherein the first polypeptide comprises an IFNAR1 domain operatively coupled with a Gly/Ser linker (e.g., a $(G_4S)_n$ linker, wherein n is 1-5, 1, 2, 3, 4 or 5) to a mutant IgG1 Fc domain comprising mutations T366S, L368A and Y407V, and wherein the second polypeptide comprises an IFNAR2 domain operatively coupled to a mutant IgG1 Fc domain comprising mutation T336W, according to EU numbering. In some aspects, the first polypeptide comprises an IFNAR1 domain comprising the amino acid sequence in SEQ ID NO: 11 and the second polypeptide comprises an IFNAR2 domain comprising the amino acid sequence in SEQ ID NO: 12. In some aspects, the mutant IgG1 Fc domain comprises the amino acid sequence set forth in SEQ ID NO: 108. In some aspects, the mutant IgG1 Fc domain comprises the amino acid sequence set forth in SEQ ID NO: 109. In some aspects, the autoimmune disease is SLE. In some aspects, the autoimmune disease is Sjogren's syndrome.

In some aspects, the disclosure provides methods of reducing, decreasing, or inhibiting interferon (IFN) gene expression, methods of reducing, decreasing, or inhibiting type I interferons (e.g., INFα, INFβ, or both INFα and INFβ), and methods of treating an autoimmune disease (e.g., SLE, Sjogren's syndrome) in a subject in need thereof, the method comprising administering to the subject a heterodimer of the disclosure, or a composition of the disclosure comprising a heterodimer and a pharmaceutically acceptable carrier, wherein the heterodimer comprises a first polypeptide and a second polypeptide, wherein the first polypeptide comprises an IFNAR1 domain operatively coupled with a Gly/Ser linker (e.g., a $(G_4S)_n$ linker, wherein n is 1-5, 1, 2, 3, 4 or 5) to a mutant IgG1 Fc domain comprising mutations T350V, T366L, K392L and T394W, and wherein the second polypeptide comprises an IFNAR2 domain operatively coupled to a mutant IgG1 Fc domain comprising mutations T350V, L351Y, F405A and Y407V, according to EU numbering. In some aspects, the first polypeptide comprises an IFNAR1 domain comprising the amino acid sequence in SEQ ID NO: 11 and the second polypeptide comprises an IFNAR2 domain comprising the amino acid sequence in SEQ ID NO: 12. In some aspects, the mutant IgG1 Fc domain comprises the amino acid sequence set forth in SEQ ID NO: 9. In some aspects, the mutant IgG1 Fc domain comprises the amino acid sequence set forth in SEQ ID NO: 10. In some aspects, the autoimmune disease is SLE. In some aspects, the autoimmune disease is Sjogren's syndrome.

In some aspects, the disclosure provides methods of reducing, decreasing, or inhibiting interferon (IFN) gene expression, methods of reducing, decreasing, or inhibiting type I interferons (e.g., INFα, INFβ, or both INFα and INFβ), and methods of treating an autoimmune disease (e.g., SLE, Sjogren's syndrome) in a subject in need thereof, the method comprising administering to the subject a heterodimer of the disclosure, or a composition of the disclosure comprising a heterodimer and a pharmaceutically acceptable carrier, wherein the heterodimer comprises a first polypeptide and a second polypeptide, wherein the first polypeptide comprises an IFNAR1 domain operatively coupled with a Gly/Ser linker (e.g., a $(G_4S)_n$ linker, wherein n is 1-5, 1, 2, 3, 4 or 5) to a mutant IgG1 Fc domain comprising mutations T350V, L351Y, F405A and Y407V, and wherein the second polypeptide comprises an IFNAR2 domain operatively coupled to a mutant IgG1 Fc domain comprising mutations T350V, T366L, K392L and T394W, according to EU numbering. In some aspects, the first polypeptide comprises an IFNAR1 domain comprising the amino acid sequence in SEQ ID NO: 11 and the second polypeptide comprises an IFNAR2 domain comprising the amino acid sequence in SEQ ID NO: 12. In some aspects, the mutant IgG1 Fc domain comprises the amino acid sequence set forth in SEQ ID NO: 9. In some aspects, the mutant IgG1 Fc domain comprises the amino acid sequence set forth in SEQ ID NO: 10. In some aspects, the autoimmune disease is SLE. In some aspects, the autoimmune disease is Sjogren's syndrome.

In some aspects, the disclosure provides methods of reducing, decreasing, or inhibiting interferon (IFN) gene expression, methods of reducing, decreasing, or inhibiting type I interferons (e.g., INFα, INFβ, or both INFα and INFβ), and methods of treating an autoimmune disease (e.g., SLE, Sjogren's syndrome) in a subject in need thereof, the method comprising administering to the subject a heterodimer of the disclosure, or a composition of the disclosure comprising a heterodimer and a pharmaceutically acceptable carrier, wherein the heterodimer comprises a first polypeptide and a second polypeptide, wherein the first polypeptide comprises an IFNAR1 domain operatively coupled with a Gly/Ser linker (e.g., a $(G_4S)_n$ linker, wherein n is 1-5, 1, 2, 3, 4 or 5) to a mutant IgG4 Fc domain comprising mutation T366Y, and wherein the second polypeptide comprises an IFNAR2 domain operatively coupled to a mutant IgG4 Fc domain comprising mutation Y407T, according to EU numbering. In some aspects, the first polypeptide comprises an IFNAR1 domain comprising the amino acid sequence in SEQ ID NO: 11 and the second polypeptide comprises an IFNAR2 domain comprising the amino acid sequence in SEQ ID NO: 12. In some aspects, the mutant IgG4 Fc domain comprises the amino acid sequence set forth in SEQ ID NO: 122. In some aspects, the mutant IgG4 Fc domain comprises the amino acid sequence set forth in SEQ ID NO: 123. In some aspects, the autoimmune disease is SLE. In some aspects, the autoimmune disease is Sjogren's syndrome.

In some aspects, the disclosure provides methods of reducing, decreasing, or inhibiting interferon (IFN) gene expression, methods of reducing, decreasing, or inhibiting type I interferons (e.g., INFα, INFβ, or both INFα and INFβ), and methods of treating an autoimmune disease (e.g., SLE, Sjogren's syndrome) in a subject in need thereof, the method comprising administering to the subject a heterodimer of the disclosure, or a composition of the disclosure comprising a heterodimer and a pharmaceutically acceptable carrier, wherein the heterodimer comprises a first polypeptide and a second polypeptide, wherein the first polypeptide comprises an IFNAR1 domain operatively coupled with a Gly/Ser linker (e.g., a $(G_4S)_n$ linker, wherein n is 1-5, 1, 2, 3, 4 or 5) to a mutant IgG4 Fc domain comprising mutation Y407T, and wherein the second polypeptide comprises an IFNAR2 domain operatively coupled to a mutant IgG4 Fc domain comprising mutation T336Y, according to EU numbering. In some aspects, the first polypeptide comprises an IFNAR1 domain comprising the amino acid sequence in SEQ ID NO: 11 and the second polypeptide comprises an IFNAR2 domain comprising the amino acid sequence in SEQ ID NO: 12. In some aspects, the mutant IgG4 Fc domain comprises the amino acid sequence set forth in SEQ ID NO: 122. In some aspects, the mutant IgG4 Fc domain comprises the amino acid sequence set forth in SEQ ID NO: 123. In some aspects, the autoimmune disease is SLE. In some aspects, the autoimmune disease is Sjogren's syndrome.

In some aspects, the disclosure provides methods of reducing, decreasing, or inhibiting interferon (IFN) gene expression, methods of reducing, decreasing, or inhibiting type I interferons (e.g., INFα, INFβ, or both INFα and INFβ), and methods of treating an autoimmune disease (e.g., SLE, Sjogren's syndrome) in a subject in need thereof, the method comprising administering to the subject a heterodimer of the disclosure, or a composition of the disclosure comprising a heterodimer and a pharmaceutically acceptable carrier, wherein the heterodimer comprises a first polypeptide and a second polypeptide, wherein the first polypeptide comprises an IFNAR1 domain operatively coupled with a Gly/Ser linker (e.g., a $(G_4S)_n$ linker, wherein n is 1-5, 1, 2, 3, 4 or 5) to a mutant IgG4 Fc domain comprising mutation T366W, and wherein the second polypeptide comprises an IFNAR2 domain operatively coupled to a mutant IgG4 Fc domain comprising mutations T366S, L368A and Y407V, according to EU numbering. In some aspects, the first polypeptide comprises an IFNAR1 domain comprising the amino acid sequence in SEQ ID NO: 11 and the second polypeptide comprises an IFNAR2 domain comprising the amino acid sequence in SEQ ID NO: 12. In some aspects, the mutant IgG4 Fc domain comprises the amino acid sequence set forth in SEQ ID NO: 124. In some aspects, the mutant IgG4 Fc domain comprises the amino acid sequence set forth in SEQ ID NO: 125. In some aspects, the autoimmune disease is SLE. In some aspects, the autoimmune disease is Sjogren's syndrome.

In some aspects, the disclosure provides methods of reducing, decreasing, or inhibiting interferon (IFN) gene expression, methods of reducing, decreasing, or inhibiting type I interferons (e.g., INFα, INFβ, or both INFα and INFβ), and methods of treating an autoimmune disease (e.g., SLE, Sjogren's syndrome) in a subject in need thereof, the method comprising administering to the subject a heterodimer of the disclosure, or a composition of the disclosure comprising a heterodimer and a pharmaceutically acceptable carrier, wherein the heterodimer comprises a first polypeptide and a second polypeptide, wherein the first polypeptide comprises an IFNAR1 domain operatively coupled with a Gly/Ser linker (e.g., a $(G_4S)_n$ linker, wherein n is 1-5, 1, 2, 3, 4 or 5) to a mutant IgG4 Fc domain comprising mutations T366S, L368A and Y407V, and wherein the second polypeptide comprises an IFNAR2 domain operatively coupled to a mutant IgG4 Fc domain comprising mutation T336W, according to EU numbering. In some aspects, the first polypeptide comprises an IFNAR1 domain comprising the amino acid sequence in SEQ ID NO: 11 and the second polypeptide comprises an IFNAR2 domain comprising the amino acid sequence in SEQ ID NO: 12. In some aspects, the mutant IgG4 Fc domain comprises the amino acid sequence set forth in SEQ ID NO: 124. In some aspects, the mutant IgG4 Fc domain comprises the amino acid sequence set forth in SEQ ID NO: 125. In some aspects, the autoimmune disease is SLE. In some aspects, the autoimmune disease is Sjogren's syndrome.

In some aspects, the disclosure provides methods of reducing, decreasing, or inhibiting interferon (IFN) gene expression, methods of reducing, decreasing, or inhibiting type I interferons (e.g., INFα, INFβ, or both INFα and INFβ), and methods of treating an autoimmune disease (e.g., SLE, Sjogren's syndrome) in a subject in need thereof, the method comprising administering to the subject a heterodimer of the disclosure, or a composition of the disclosure comprising a heterodimer and a pharmaceutically acceptable carrier, wherein the heterodimer comprises a first polypeptide and a second polypeptide, wherein the first polypeptide comprises an IFNAR1 domain operatively coupled with a Gly/Ser linker (e.g., a $(G_4S)_n$ linker, wherein n is 1-5, 1, 2, 3, 4 or 5) to a mutant IgG4 Fc domain comprising mutations T350V, T366L, K392L and T394W, and wherein the second polypeptide comprises an IFNAR2 domain operatively coupled to a mutant IgG4 Fc domain comprising mutations T350V, L351Y, F405A and Y407V, according to EU numbering. In some aspects, the first polypeptide comprises an IFNAR1 domain comprising the amino acid sequence in SEQ ID NO: 11 and the second polypeptide comprises an IFNAR2 domain comprising the amino acid sequence in SEQ ID NO: 12. In some aspects, the mutant IgG4 Fc domain comprises the amino acid sequence set forth in SEQ ID NO: 120. In some aspects, the mutant IgG4 Fc domain comprises the amino acid sequence set forth in SEQ ID NO: 121. In some aspects, the autoimmune disease is SLE. In some aspects, the autoimmune disease is Sjogren's syndrome.

In some aspects, the disclosure provides methods of reducing, decreasing, or inhibiting interferon (IFN) gene expression, methods of reducing, decreasing, or inhibiting type I interferons (e.g., INFα, INFβ, or both INFα and INFβ), and methods of treating an autoimmune disease (e.g., SLE, Sjogren's syndrome) in a subject in need thereof, the method comprising administering to the subject a heterodimer of the disclosure, or a composition of the disclosure comprising a heterodimer and a pharmaceutically acceptable carrier, wherein the heterodimer comprises a first polypeptide and a second polypeptide, wherein the first polypeptide comprises an IFNAR1 domain operatively coupled with a Gly/Ser linker (e.g., a $(G_4S)_n$ linker, wherein n is 1-5, 1, 2, 3, 4 or 5) to a mutant IgG4 Fc domain comprising mutations T350V, L351Y, F405A and Y407V, and wherein the second polypeptide comprises an IFNAR2 domain operatively coupled to a mutant IgG4 Fc domain comprising mutations T350V, T366L, K392L and T394W, according to EU numbering. In some aspects, the first polypeptide comprises an IFNAR1 domain comprising the amino acid sequence in SEQ ID NO: 11 and the second polypeptide comprises an IFNAR2 domain comprising the amino acid sequence in SEQ ID NO: 12. In some aspects, the mutant IgG4 Fc domain comprises the amino acid sequence set forth in SEQ ID NO: 120. In some aspects, the mutant IgG4 Fc domain comprises the amino acid sequence set forth in SEQ ID NO: 121. In some aspects, the autoimmune disease is SLE. In some aspects, the autoimmune disease is Sjogren's syndrome.

In some aspects, the disclosure provides methods of reducing, decreasing, or inhibiting interferon (IFN) gene expression, methods of reducing, decreasing, or inhibiting type I interferons (e.g., INFα, INFβ, or both INFα and INFβ), and methods of treating an autoimmune disease (e.g., SLE, Sjogren's syndrome) in a subject in need thereof, the method comprising administering to the subject a heterodimer of the disclosure, or a composition of the disclosure comprising a heterodimer and a pharmaceutically acceptable carrier, wherein the heterodimer comprises a first polypeptide and a second polypeptide selected from:

(i) a first polypeptide comprising the amino acid sequence of SEQ ID NO: 40 and a second polypeptide comprising the amino acid sequence of SEQ ID NO: 43;

(ii) a first polypeptide comprising the amino acid sequence of SEQ ID NO: 41 and a second polypeptide comprising the amino acid sequence of SEQ ID NO: 42;

(iii) a first polypeptide comprising the amino acid sequence of SEQ ID NO: 53 and a second polypeptide comprising the amino acid sequence of SEQ ID NO: 55; and (iv) a first polypeptide comprising the amino acid sequence of SEQ ID NO: 57 and a second polypeptide comprising the amino acid sequence of SEQ ID NO: 59;

(v) a first polypeptide comprising the amino acid sequence of SEQ ID NO: 40, and a second polypeptide comprising the amino acid sequence selected from SEQ ID NO: 43, SEQ ID NO: 55, and SEQ ID NO: 59;

(vi) a first polypeptide comprising the amino acid sequence of SEQ ID NO: 43, and a second polypeptide comprising the amino acid sequence selected from SEQ ID NO: 40, SEQ ID NO: 53, and SEQ ID NO: 57;

(vii) a first polypeptide comprising the amino acid sequence of SEQ ID NO: 42, and a second polypeptide comprising the amino acid sequence selected from SEQ ID NO: 41, SEQ ID NO: 45, and SEQ ID NO: 47;

(viii) a first polypeptide comprising the amino acid sequence of SEQ ID NO: 41, and a second polypeptide comprising the amino acid sequence selected from SEQ ID NO: 42, SEQ ID NO: 49, and SEQ ID NO: 51;

(ix) a first polypeptide comprising the amino acid sequence of SEQ ID NO: 53, and a second polypeptide comprising the amino acid sequence selected from SEQ ID NO: 43, SEQ ID NO: 55, and SEQ ID NO: 59;

(x) a first polypeptide comprising the amino acid sequence of SEQ ID NO: 55, and a second polypeptide comprising the amino acid sequence selected from SEQ ID NO: 40, SEQ ID NO: 53, and SEQ ID NO: 57;

(xi) a first polypeptide comprising the amino acid sequence of SEQ ID NO: 57, and a second polypeptide comprising the amino acid sequence selected from SEQ ID NO: 43, SEQ ID NO: 55, and SEQ ID NO: 59;

(xii) a first polypeptide comprising the amino acid sequence of SEQ ID NO: 59, and a second polypeptide comprising the amino acid sequence selected from SEQ ID NO: 40, SEQ ID NO: 53, and SEQ ID NO: 57;

(xiii) a first polypeptide comprising the amino acid sequence of SEQ ID NO: 45, and a second polypeptide comprising the amino acid sequence selected from SEQ ID NO: 42, SEQ ID NO: 49, and SEQ ID NO: 51;

(xiv) a first polypeptide comprising the amino acid sequence of SEQ ID NO: 47, and a second polypeptide comprising the amino acid sequence selected from SEQ ID NO: 42, SEQ ID NO: 49, and SEQ ID NO: 51;

(xv) a first polypeptide comprising the amino acid sequence of SEQ ID NO: 49, and a second polypeptide comprising the amino acid sequence selected from SEQ ID NO: 41, SEQ ID NO: 45, and SEQ ID NO: 47;

(xvi) a first polypeptide comprising the amino acid sequence of SEQ ID NO: 51, and a second polypeptide comprising the amino acid sequence selected from SEQ ID NO: 41, SEQ ID NO: 45, and SEQ ID NO: 47;

(xvii) a first polypeptide comprising the amino acid sequence of SEQ ID NO: 61, and a second polypeptide comprising the amino acid sequence selected from SEQ ID NO: 67, SEQ ID NO: 75, and SEQ ID NO: 82;

(xviii) a first polypeptide comprising the amino acid sequence of SEQ ID NO: 63, and a second polypeptide comprising the amino acid sequence selected from SEQ ID NO: 65, SEQ ID NO: 73, and SEQ ID NO: 81;

(xix) a first polypeptide comprising the amino acid sequence of SEQ ID NO: 65, and a second polypeptide comprising the amino acid sequence selected from SEQ ID NO: 63, SEQ ID NO: 71, and SEQ ID NO: 79;

(xx) a first polypeptide comprising the amino acid sequence of SEQ ID NO: 67, and a second polypeptide comprising the amino acid sequence selected from SEQ ID NO: 61, SEQ ID NO: 69, and SEQ ID NO: 77;

(xxi) a first polypeptide comprising the amino acid sequence of SEQ ID NO: 69, and a second polypeptide comprising the amino acid sequence selected from SEQ ID NO: 67, SEQ ID NO: 75, and SEQ ID NO: 82;

(xxii) a first polypeptide comprising the amino acid sequence of SEQ ID NO: 71, and a second polypeptide comprising the amino acid sequence selected from SEQ ID NO: 65, SEQ ID NO: 73, and SEQ ID NO: 81;

(xxiii) a first polypeptide comprising the amino acid sequence of SEQ ID NO: 73, and a second polypeptide comprising the amino acid sequence selected from SEQ ID NO: 63, SEQ ID NO: 71, and SEQ ID NO: 79;

(xxiv) a first polypeptide comprising the amino acid sequence of SEQ ID NO: 75, and a second polypeptide comprising the amino acid sequence selected from SEQ ID NO: 61, SEQ ID NO: 69, and SEQ ID NO: 77;

(xxv) a first polypeptide comprising the amino acid sequence of SEQ ID NO: 77, and a second polypeptide comprising the amino acid sequence selected from SEQ ID NO: 67, SEQ ID NO: 75, and SEQ ID NO: 82;

(xxvi) a first polypeptide comprising the amino acid sequence of SEQ ID NO: 79, and a second polypeptide comprising the amino acid sequence selected from SEQ ID NO: 65, SEQ ID NO: 73, and SEQ ID NO: 81;

(xxvii) a first polypeptide comprising the amino acid sequence of SEQ ID NO: 81, and a second polypeptide comprising the amino acid sequence selected from SEQ ID NO: 63, SEQ ID NO: 71, and SEQ ID NO: 79;

(xxviii) a first polypeptide comprising the amino acid sequence of SEQ ID NO: 82, and a second polypeptide comprising the amino acid sequence selected from SEQ ID NO: 61, SEQ ID NO: 69, and SEQ ID NO: 77;

(xxix) a first polypeptide comprising the amino acid sequence of SEQ ID NO: 84, and a second polypeptide comprising the amino acid sequence selected from SEQ ID NO: 89, SEQ ID NO: 97, and SEQ ID NO: 105;

(xxx) a first polypeptide comprising the amino acid sequence of SEQ ID NO: 85, and a second polypeptide comprising the amino acid sequence selected from SEQ ID NO: 87, SEQ ID NO: 95, and SEQ ID NO: 103;

(xxxi) a first polypeptide comprising the amino acid sequence of SEQ ID NO: 87, and a second polypeptide comprising the amino acid sequence selected from SEQ ID NO: 85, SEQ ID NO: 93, and SEQ ID NO: 101;

(xxxii) a first polypeptide comprising the amino acid sequence of SEQ ID NO: 89, and a second polypeptide comprising the amino acid sequence selected from SEQ ID NO: 84, SEQ ID NO: 91, and SEQ ID NO: 99;

(xxxiii) a first polypeptide comprising the amino acid sequence of SEQ ID NO: 91, and a second polypeptide comprising the amino acid sequence selected from SEQ ID NO: 89, SEQ ID NO: 97, and SEQ ID NO: 105;

(xxxiv) a first polypeptide comprising the amino acid sequence of SEQ ID NO: 93, and a second polypeptide comprising the amino acid sequence selected from SEQ ID NO: 87, SEQ ID NO: 95, and SEQ ID NO: 103;

(xxxv) a first polypeptide comprising the amino acid sequence of SEQ ID NO: 95, and a second polypeptide comprising the amino acid sequence selected from SEQ ID NO: 85, SEQ ID NO: 93, and SEQ ID NO: 101;

(xxxvi) a first polypeptide comprising the amino acid sequence of SEQ ID NO: 97, and a second polypeptide comprising the amino acid sequence selected from SEQ ID NO: 84, SEQ ID NO: 91, and SEQ ID NO: 99;

(xxxvii) a first polypeptide comprising the amino acid sequence of SEQ ID NO: 99, and a second polypeptide comprising the amino acid sequence selected from SEQ ID NO: 89, SEQ ID NO: 97, and SEQ ID NO: 105;

(xxxviii) a first polypeptide comprising the amino acid sequence of SEQ ID NO: 101, and a second polypeptide comprising the amino acid sequence selected from SEQ ID NO: 87, SEQ ID NO: 95, and SEQ ID NO: 103;

(xxxix) a first polypeptide comprising the amino acid sequence of SEQ ID NO: 103, and a second polypeptide comprising the amino acid sequence selected from SEQ ID NO: 85, SEQ ID NO: 93, and SEQ ID NO: 101; and (xl) a first polypeptide comprising the amino acid sequence of SEQ ID NO: 105, and a second polypeptide comprising the amino acid sequence selected from SEQ ID NO: 84, SEQ ID NO: 91, and SEQ ID NO: 99. In some aspects, the autoimmune disease is SLE. In some aspects, the autoimmune disease is Sjogren's syndrome.

In some aspects, the disclosure provides methods of reducing, decreasing, or inhibiting interferon (IFN) gene expression, methods of reducing, decreasing, or inhibiting type I interferons (e.g., INFα, INFβ, or both INFα and INFβ), and methods of treating an autoimmune disease (e.g., SLE, Sjogren's syndrome) in a subject in need thereof, the method comprising administering to the subject a heterodimer of the disclosure, or a composition of the disclosure comprising a heterodimer and a pharmaceutically acceptable carrier, wherein the heterodimer comprises a first polypeptide comprising the amino acid sequence of SEQ ID NO: 40 and a second polypeptide comprising the amino acid sequence of SEQ ID NO: 43. In some aspects, the autoimmune disease is SLE. In some aspects, the autoimmune disease is Sjogren's syndrome.

In some aspects, the disclosure provides methods of reducing, decreasing, or inhibiting interferon (IFN) gene expression, methods of reducing, decreasing, or inhibiting type I interferons (e.g., INFα, INFβ, or both INFα and INFβ), and methods of treating an autoimmune disease (e.g., SLE, Sjogren's syndrome) in a subject in need thereof, the method comprising administering to the subject a heterodimer of the disclosure, or a composition of the disclosure comprising a heterodimer and a pharmaceutically acceptable carrier, wherein the heterodimer comprises a first polypeptide comprising the amino acid sequence of SEQ ID NO: 41 and a second polypeptide comprising the amino acid sequence of SEQ ID NO: 42. In some aspects, the autoimmune disease is SLE. In some aspects, the autoimmune disease is Sjogren's syndrome.

In some aspects, the disclosure provides methods of reducing, decreasing, or inhibiting interferon (IFN) gene expression, methods of reducing, decreasing, or inhibiting type I interferons (e.g., INFα, INFβ, or both INFα and INFβ), and methods of treating an autoimmune disease (e.g., SLE, Sjogren's syndrome) in a subject in need thereof, the method comprising administering to the subject a heterodimer of the disclosure, or a composition of the disclosure comprising a heterodimer and a pharmaceutically acceptable carrier, wherein the heterodimer comprises a first polypeptide comprising the amino acid sequence of SEQ ID NO: 53 and a second polypeptide comprising the amino acid sequence of SEQ ID NO: 55. In some aspects, the autoimmune disease is SLE. In some aspects, the autoimmune disease is Sjogren's syndrome.

In some aspects, the disclosure provides methods of reducing, decreasing, or inhibiting interferon (IFN) gene expression, methods of reducing, decreasing, or inhibiting type I interferons (e.g., INFα, INFβ, or both INFα and INFβ), and methods of treating an autoimmune disease (e.g., SLE, Sjogren's syndrome) in a subject in need thereof, the method comprising administering to the subject a heterodimer of the disclosure, or a composition of the disclosure comprising a heterodimer and a pharmaceutically acceptable carrier, wherein the heterodimer comprises a first polypeptide comprising the amino acid sequence of SEQ ID NO: 57 and a second polypeptide comprising the amino acid sequence of SEQ ID NO: 59. In some aspects, the autoimmune disease is SLE. In some aspects, the autoimmune disease is Sjogren's syndrome.

Other aspects of the disclosure provide use of a heterodimer of the disclosure, and an optional pharmaceutically acceptable carrier, in the manufacture of a medicament for treating or delaying progression of an autoimmune disease in a subject in need thereof, wherein the treatment comprises administration of the medicament to a subject in need thereof.

Other aspects of the disclosure provide kits comprising a medicament comprising a heterodimer of the disclosure, and an optional pharmaceutically acceptable carrier, and a package insert comprising instructions for administration of the medicament for treating or delaying progression of an autoimmune disease in a subject in need thereof.

In some aspects, the disclosure provides a kit comprising a container comprising a heterodimer of the disclosure, and an optional pharmaceutically acceptable carrier, and a package insert comprising instructions for administration of the heterodimer for treating or delaying progression of an autoimmune disease in a subject in need thereof.

BRIEF DESCRIPTION OF THE DRAWINGS

These and other features, aspects, and advantages of the present invention will become better understood with regard to the following description, and accompanying drawing, where.

DETAILED DESCRIPTION

Figure 1:
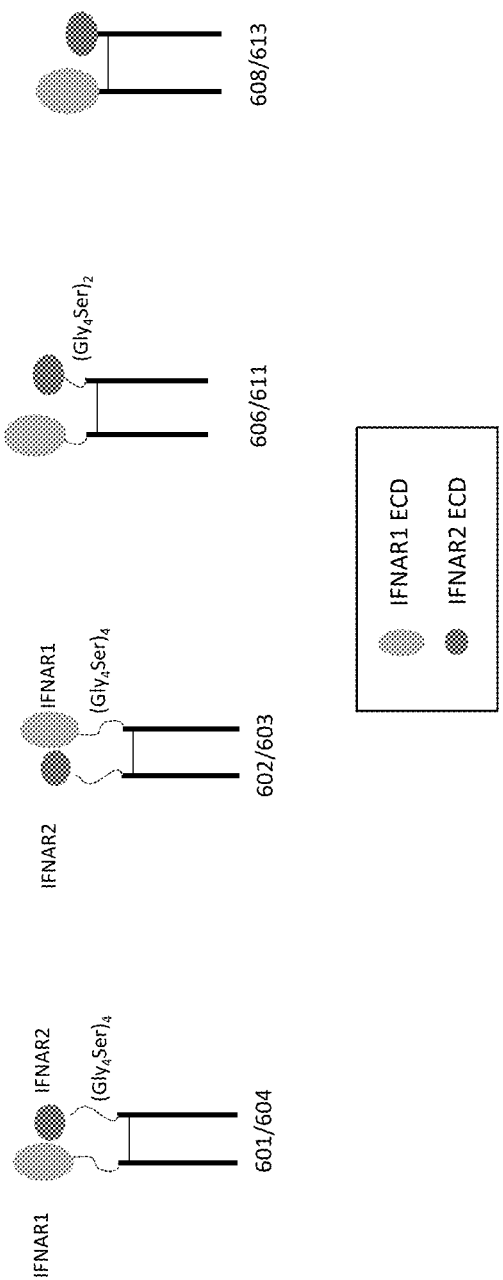
FIG. 1 depicts exemplary soluble interferon receptors RSLV 601-604, RSLV 602-603, RSLV 606-611, and RSLV 608-613.

The present disclosure provides soluble heterodimers which bind type I interferons and methods of reducing, decreasing, or inhibiting interferon (IFN) gene expression, methods of reducing, decreasing, or inhibiting type I interferons and/or type I interferon activity (e.g., INFα, INFβ, or both INFα and INFβ), and methods of treating diseases characterized by type I interferon production in a subject in need thereof.

The disclosure is based, at least in part, on the discovery that heterodimers comprising an IFNAR1 domain and an IFNAR2 domain, each operatively coupled to a mutant Fc domain, potently inhibit IFNα and IFNβ activity and inhibit SLE sera induced interferon gene expression. These results indicate that the heterodimers of the disclosure are capable of binding to and inhibiting the activity of type I interferons in a subject with an autoimmune condition, such as SLE.

It was also discovered that heterodimers comprising an IFNAR1 domain and an IFNAR2 domain, each operatively coupled directly to a mutant Fc domain (i.e., without a polypeptide linker) have increased binding affinity and potency for type I interferons, such as INFα, relative to a heterodimer in which the IFNAR1 domain and IFNAR2 domain are each operatively coupled to a mutant Fc domain with a polypeptide linker. Without being bound by theory, it was believed that IFNAR1 and IRNAR2 required a degree of flexibility to form a pocket for interacting with a type I interferons. It was known that the extracellular domains of IFNAR1 and IFNAR2 bind type I interferons and form a ternary complex, which results in bringing the intracellular domains into close proximity and regulates signaling through the receptor (Li et al., J. Mol. Biol. (2017) 429, 2571-2589). It has also been shown that ligand induced conformation changes to the receptor components are propagated to the membrane-proximal Ig domain of IFNAR1, although this domain does not interact with the ligand. (Id. at 2572). Notably, the crystal structure of a heterotrimeric complex of IFNAR1, IFNAR2, and IFNα2 depicts a linker-like domain between the extracellular domain and the transmembrane domain of both IFNARs. (See Li et al., FIG. 1; also see Piehler et al., Immunological Reviews (2012) 250, 317-334, FIG. 5). Without being bound by theory, it was hypothesized that this linker-like domain may provide a degree of flexibility to facilitate formation of the ternary complex in an appropriate conformation for ligand binding and signaling. Therefore, a study was designed to investigate the effect of various polypeptide linker lengths on IFNAR1 and IFNAR2 ligand binding. Unexpectedly, it was discovered that a heterodimer comprising an IFNAR1 domain and an IFNAR2 domain, each coupled directly to a mutant Fc domain, without a linker, showed increased binding affinity and potency to type I interferon, relative to a heterodimer in which the IFNAR1 domain and IFNAR2 domain are each operatively coupled to a mutant Fc domain with a polypeptide linker (e.g., of 10 or 20 amino acids in length). In particular, when constructs with different polypeptide linker lengths were compared, it was observed that IFN-α binding affinity and potency increased as linker length decreased.

Accordingly, the present disclosure provides heterodimers which binds type I interferons comprising a first polypeptide and a second polypeptide, wherein the first polypeptide comprises an IFNAR1 domain operatively coupled with or without a linker domain to a mutant Fc domain, and wherein the second polypeptide comprises an IFNAR2 domain operatively coupled with or without a linker domain to a mutant Fc domain. The heterodimers of the disclosure are useful in methods of inhibiting type I interferon gene expression, methods of inhibiting type I interferon activity, and methods of treating autoimmune disease, as described herein.

Definitions

Terms used in the claims and specification are defined as set forth below unless otherwise specified.

"Amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refer to chemical compounds that have a structure that is different from the general chemical structure of an amino acid, but that function in a manner similar to a naturally occurring amino acid.

Amino acids can be referred to herein by either their commonly known three letter symbols or by the one-letter symbols recommended by the IUPAC-IUB Biochemical Nomenclature Commission. Nucleotides, likewise, can be referred to by their commonly accepted single-letter codes.

An "amino acid substitution" refers to the replacement of at least one existing amino acid residue in a predetermined amino acid sequence (an amino acid sequence of a starting polypeptide) with a second, different "replacement" amino acid residue. An "amino acid insertion" refers to the incorporation of at least one additional amino acid into a predetermined amino acid sequence. While the insertion will usually consist of the insertion of one or two amino acid residues, larger "peptide insertions" can be made, e.g. insertion of about three to about five or even up to about ten, fifteen, or twenty amino acid residues. The inserted residue(s) may be naturally occurring or non-naturally occurring as disclosed above. An "amino acid deletion" refers to the removal of at least one amino acid residue from a predetermined amino acid sequence.

"Polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

"Nucleic acid" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions can be achieved by generating sequences in which the third position of one or more selected (or all) codons is substituted with mixed-base and/or deoxyinosine residues (Batzer et al., *Nucleic Acid Res* 1991; 19:5081; Ohtsuka et al., JBC 1985; 260: 2605-8); Rossolini et al., *Mol Cell Probes* 1994; 8:91-8). For arginine and leucine, modifications at the second base can also be conservative. The term nucleic acid is used interchangeably with gene, cDNA, and mRNA encoded by a gene.

Polynucleotides of the present invention can be composed of any polyribonucleotide or polydeoxribonucleotide, which can be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, the polynucleotide can be composed of triple-stranded regions comprising RNA or DNA or both RNA and DNA. A polynucleotide can also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

As used herein, the term "operably linked" or "operably coupled" refers to a juxtaposition wherein the components described are in a relationship permitting them to function in their intended manner.

As used herein, the term "glycosylation" or "glycosylated" refers to a process or result of adding sugar moieties to a molecule.

As used herein, the term "altered glycosylation" refers to a molecule that is aglycosylated, deglycosylated, or underglycosylated.

As used herein, "glycosylation site(s)" refers to both sites that potentially could accept a carbohydrate moiety, as well as sites within the protein on which a carbohydrate moiety has actually been attached and includes any amino acid sequence that could act as an acceptor for an oligosaccharide and/or carbohydrate.

As used herein, the term "aglycosylation" or "aglycosylated" refers to the production of a molecule in an unglycosylated form (e.g., by engineering a protein or polypeptide to lack amino acid residues that serve as acceptors of glycosylation). Alternatively, a protein or polypeptide can be expressed in, e.g., *E. coli*, to produce an aglycosylated protein or polypeptide.

As used herein, the term "deglycosylation" or "deglycosylated" refers to the process or result of enzymatic removal of sugar moieties on a molecule.

As used herein, the term "underglycosylation" or "underglycosylated" refers to a molecule in which one or more carbohydrate structures that would normally be present if produced in a mammalian cell has been omitted, removed, modified, or masked.

As used herein, the term "Fc region" and "Fc domain" is the portion of a native immunoglobulin formed by the respective Fc domains (or Fc moieties) of its two heavy chains without the variable regions which bind antigen. In some embodiments, an Fc domain begins in the hinge region just upstream of the papain cleavage site and ending at the C-terminus of the antibody. Accordingly, a complete Fc domain comprises at least a hinge domain, a CH2 domain, and a CH3 domain. In certain embodiments, an Fc domain comprises at least one of: a hinge (e.g., upper, middle, and/or lower hinge region) domain, a CH2 domain, a CH3 domain, a CH4 domain, or a variant, portion, or fragment thereof. In other embodiments, an Fc domain comprises a complete Fc domain (i.e., a hinge domain, a CH2 domain, and a CH3 domain). In one embodiment, an Fc domain comprises a hinge domain (or portion thereof) fused to a CH3 domain (or portion thereof). In another embodiment, an Fc domain comprises a CH2 domain (or portion thereof) fused to a CH3 domain (or portion thereof). In another embodiment, an Fc domain consists of a CH3 domain or portion thereof. In another embodiment, an Fc domain consists of a hinge domain (or portion thereof) and a CH3 domain (or portion thereof). In another embodiment, an Fc domain consists of a CH2 domain (or portion thereof) and a CH3 domain. In another embodiment, an Fc domain consists of a hinge domain (or portion thereof) and a CH2 domain (or portion thereof). In one embodiment, an Fc domain lacks at least a portion of a CH2 domain (e.g., all or part of a CH2 domain). In one embodiment, an Fc domain of the invention comprises at least the portion of an Fc molecule known in the art to be required for FcRn binding. In one embodiment, an Fc domain of the invention comprises at least the portion of an Fc molecule known in the art to be required for Protein A binding. In one embodiment, an Fc domain of the invention comprises at least the portion of an Fc molecule known in the art to be required for protein G binding. An Fc domain herein generally refers to a polypeptide comprising all or part of the Fc domain of an immunoglobulin heavy-chain. This includes, but is not limited to, polypeptides comprising the entire CHI, hinge, CH2, and/or CH3 domains as well as fragments of such peptides comprising only, e.g., the hinge, CH2, and CH3 domain. The Fc domain may be derived from an immunoglobulin of any species and/or any subtype, including, but not limited to, a human IgG1, IgG2, IgG3, IgG4, IgD, IgA, IgE, or IgM antibody. The Fc domain encompasses native Fc and Fc variant molecules. As with Fc variants and native Fc's, the term Fc domain includes molecules in monomeric or multimeric form, whether digested from whole antibody or produced by other means.

As set forth herein, it will be understood by one of ordinary skill in the art that any Fc domain may be modified such that it varies in amino acid sequence from the native Fc domain of a naturally occurring immunoglobulin molecule.

The Fc domains of an interferon receptor Fc construct of the disclosure may be derived from different immunoglobulin molecules. For example, an Fc domain of an interferon receptor Fc construct may comprise a CH2 and/or CH3 domain derived from an IgG1 molecule and a hinge region derived from an IgG3 molecule. In another example, an Fc domain can comprise a chimeric hinge region derived, in part, from an IgG1 molecule and, in part, from an IgG3 molecule. In another example, an Fc domain can comprise a chimeric hinge derived, in part, from an IgG1 molecule and, in part, from an IgG4 molecule. The wild type human IgG1 Fc domain has the amino acid sequence set forth in SEQ ID NO: 26.

As used herein, the term "serum half-life" refers to the time required for the in vivo serum soluble interferon receptor concentration to decline by 50%. The shorter the serum half-life of the soluble interferon receptor, the shorter time it will have to exert a therapeutic effect.

As used herein, the term "soluble interferon receptor" or "heterodimer" refers to a molecule comprising a first IFNAR domain, or variant or fragment thereof, and a second IFNAR domain, or a variant or fragment thereof. In some embodiments, an IFNAR domain is the extracellular domain of an IFNAR. In some embodiments, the soluble interferon receptor comprises a first polypeptide and a second polypeptide, wherein the first polypeptide comprises the extracellular domain of an IFNAR, or a variant or fragment thereof, and the second polypeptide comprises the extracellular domain of an IFNAR, or a variant or fragment thereof. In some embodiments, the first and second polypeptide interact to form a dimer (e.g., a heterodimer). In some embodiments, a soluble interferon receptor comprises a first polypeptide comprising an IFNAR domain, or a variant or fragment thereof operably linked, with or without a linker domain, to an immunoglobulin Fc domain, or a variant or fragment thereof, and wherein the second polypeptide comprises an IFNAR domain, or a variant or fragment thereof operably linked, with or without a linker domain, to an immunoglobulin Fc domain, or a variant or fragment thereof and nucleic acids encoding such polypeptides. In some embodiments, the first polypeptide comprises INFAR1, or a variant or fragment thereof operably linked, with or without a linker domain, to a Fc domain, or variant or fragment thereof. In some embodiments, the second polypeptide comprises INFAR2, or a variant or fragment thereof operably linked, with or without a linker domain, to a variant Fc domain, or variant or fragment thereof. In some embodiments, the first and second polypeptides dimerize to form a heterodimeric construct. In some embodiments, the first and/or second polypeptides may or may not comprise a leader sequence. In some embodiments, the soluble interferon receptor may or may not comprise a leader sequence. In some embodiments, the soluble interferon receptors comprise two or more interferon receptor Fc constructs. In some embodiments, the soluble interferon receptor binds type I interferons, e.g., IFN-α, IFN-β, IFN-ε, -κ, -τ, -ζ, -IFN-ω, IFN-ν.

As used herein, the term "interferon receptor Fc construct" refers to a polypeptide comprising an IFNAR domain (e.g., IFNAR1 or IFNAR2), or a variant or fragment thereof operably linked, with or without a linker domain, to an Fc domain, or a variant or fragment thereof, and nucleic acids encoding such polypeptides. In some embodiments, the IFNAR domain is the extracellular domain of an IFNAR. The interferon receptor Fc construct may or may not comprise a leader sequence. The interferon receptor Fc construct may also be referred to as an "interferon receptor Fc protein".

As used herein, the term "type I interferon" or "type I IFN" refers to a pro-inflammatory cytokine that binds to a heterodimeric cell surface receptor, IFN-α receptor (IFNAR), comprising IFNAR1 and IFNAR2. There are sixteen type I IFNs in humans, including IFN-α, IFN-β, IFN-ε, -κ, -τ, -ζ, -IFN-ω, IFN-ν. Type I IFNs are rapidly produced in multiple different cell types, and known to have a wide variety of effects. Although all type I IFNs bind the same receptor and form structurally very similar ternary complexes, differential IFN activities result from different lifetimes and ligand affinities on each receptor chain, which dictate assembly and dynamics of the signaling complex (Piehler, J. et al. (2012) *Immunological Reviews* 250: 317-334; Li, H. et al. (2017) *J Mo. Biol* 429: 2571-2589).

As used herein, the term "type I IFN activity" refers to a biological activity which results upon interaction of a type I IFN to a receptor (IFNAR), including, but not limited to, those described herein. The canonical consequences of type I IFN production in vivo is the activation of antimicrobial cellular programs and the development of innate and adaptive immune responses. Type I IFN modulates innate immune cell activation (e.g., maturation of dendritic cells) to promote antigen presentation and natural killer cell functions. Type I IFN also promotes the development of high-affinity antigen-specific T and B cell responses and immunological memory (Ivashkiv and Donlin (2014) *Nat Rev Immunol* 14(1):36-49).

Type I IFNs have been shown to activate dendritic cells (DCs) and promote their T cell stimulatory capacity through autocrine signaling (Montoya et al., (2002) *Blood* 99:3263-3271). Type I IFN exposure facilitates maturation of DCs via increasing the expression of chemokine receptors and adhesion molecules (e.g., to promote DC migration into draining lymph nodes), co-stimulatory molecules, and MHC class I and class II antigen presentation. DCs that mature following type I IFN exposure can effectively prime protective T cell responses (Wijesundara et al., (2014) Front Immunol 29(412) and references therein). Accordingly, in some embodiments, type I IFN activity is an increase or induction in DC activation and/or maturation. In some embodiments, type I IFN activity is an increase or induction in DC migration to draining lymph nodes.

Further, type I IFN can either promote T cell activation, proliferation, differentiation and survival (Crouse et al., (2015) *Nat Rev Immunol* 15:231-242). Early studies revealed that MHC-I expression is upregulated in response to type I IFN in multiple cell types (Lindahl et al., (1976), *J Infect Dis* 133(Suppl):A66-A68; Lindahl et al., (1976)

*Proc Natl Acad Sci USA* 17:1284-1287) which is a requirement for optimal T cell stimulation, differentiation, expansion and cytolytic activity. In addition, type I IFNs can exert potent co-stimulatory effects on CD8 T cells, enhancing CD8 T cell proliferation and differentiation (Curtsinger et al., (2005) *J Immunol* 174:4465-4469; Kolumam et al., (2005) *J Exp Med* 202:637-650). Accordingly, in some embodiments, type I IFN activity is an increase or induction in T cell proliferation. In some embodiments, type I IFN activity is an increase or induction in CD8+ T cell proliferation. In some embodiments, type I IFN activity is an increase or induction in T cell differentiation. In some embodiments, type I IFN activity is an increase or induction in CD8+ T cell differentiation.

With regards to B cells, type I IFN exposure has been shown to promote B cell activation, antibody production and isotype switch following viral infection or following experimental immunization (Le Bon et al., (2006) *J Immunol* 176:4:2074-2078; Swanson et al., (2010) J Exp Med 207: 1485-1500). Accordingly, in some embodiments, type I IFN activity is an increase or induction in antibody production.

In some embodiments, a type I IFN activity results upon IFNα binding to IFNAR. In some embodiments, a type I IFN activity results upon IFNβ binding to IFNAR. In some embodiments, a type I IFN activity is selected from the group consisting of: (i) an increase or induction in T cell proliferation (e.g., CD8+ T cell proliferation); (ii) an increase or induction in DC maturation; (iii) an increase or induction in DC migration into draining lymph nodes; (iv) an increase or induction in T cell differentiation (e.g., CD8+ T cell differentiation); (v) an increase or induction in antibody production; and (vi) any combination of (i)-(v). In some embodiments, a type I IFN activity is determined in vitro. In some embodiments, a type I IFN activity is determined in vivo.

In some embodiments, the heterodimers described herein inhibit or reduce a type I IFN activity. For example, in some embodiments, the heterodimers described herein: (i) inhibit or reduce T cell proliferation (e.g., CD8+ T cell proliferation); (ii) inhibitor reduce DC maturation; (iii) inhibit or reduce DC migration into draining lymph nodes; (iv) inhibit or reduce T cell differentiation (e.g., CD8+ T cell differentiation); (v) inhibit or reduce IFN-mediated antibody production; or (vi) any combination of (i)-(v). In some embodiments, inhibition or reduction of type I IFN activity by the heterodimers described herein is relative to the activity in the absence of a heterodimer. Methods for determining inhibition or reduction of T cell proliferation, DC maturation, DC migration, T cell differentiation, and IFN-mediated antibody production are known to those of skill in the art.

As used herein, the term "dimer" refers to a macromolecular complex formed by two macromolecules (e.g., polypeptides). A "homodimer" refers to a dimer that is formed by two identical macromolecules (e.g., polypeptides). A "heterodimer" refers to a dimer that is formed by two different macromolecules (e.g., polypeptides).

As used herein, the term "variant" refers to a polypeptide derived from a wild-type interferon receptor or Fc domain and differs from the wild-type by one or more alteration(s), i.e., a substitution, insertion, and/or deletion, at one or more positions. A substitution means a replacement of an amino acid occupying a position with a different amino acid. A deletion means removal of an amino acid occupying a position. An insertion means adding 1 or more, such as 1-3 amino acids, immediately adjacent to an amino acid occupying a position. Variant polypeptides necessarily have less than 100% sequence identity or similarity with the wild-type polypeptide. In some embodiments, the variant polypeptide will have an amino acid sequence from about 75% to less than 100% amino acid sequence identity or similarity with the amino acid sequence of wild-type polypeptide, or from about 80% to less than 100%, or from about 85% to less than 100%, or from about 90% to less than 100% (e.g., 91%, 92%, 93%, 94%, 95%, 96%, 97%, 98% o, 99%) or from about 95% to less than 100%, e.g., over the length of the variant polypeptide.

In certain aspects, the interferon receptor Fc constructs employ one or more "linker domains," such as polypeptide linkers. As used herein, the term "linker domain" refers to one or more amino acids which connect two or more peptide domains in a linear polypeptide sequence. As used herein, the term "polypeptide linker" refers to a peptide or polypeptide sequence (e.g., a synthetic peptide or polypeptide sequence) which connects two or more polypeptide domains in a linear amino acid sequence of a protein. For example, polypeptide linkers may be used to operably link an interferon receptor to an Fc domain. Such polypeptide linkers in some embodiments provide flexibility to the polypeptide molecule. In some embodiments the polypeptide linker is used to connect (e.g., genetically fuse), for example, an IFNAR1 domain to an Fc domain and/or an IFNAR2 domain to an Fc domain. An interferon receptor Fc construct may include more than one linker domain or peptide linker. Various peptide linkers are known in the art.

As used herein, the term "gly-ser polypeptide linker" refers to a peptide that consists of glycine and serine residues. An exemplary gly/ser polypeptide linker comprises the amino acid sequence $(Gly_4Ser)n$. In some embodiments, n is 1 or more, such as 2 or more, 3 or more, 4 or more, 5 or more, 6 or more, 7 or more, 8 or more, 9 or more, or 10 or more (e.g., $(Gly_4Ser)10$). Another exemplary gly/ser polypeptide linker comprises the amino acid sequence Ser(Gly4Ser)n. In some embodiments, n is 1 or more, such as 2 or more, 3 or more, 4 or more, 5 or more, 6 or more, 7 or more, 8 or more, 9 or more, or 10 or more (e.g., Ser(Gly4Ser)10).

As used herein, the terms "coupled," "conjugated," "linked," "fused," or "fusion," are used interchangeably. These terms refer to the joining together of two more elements or components or domains, by whatever means including chemical conjugation or recombinant means. Methods of chemical conjugation (e.g., using heterobifunctional crosslinking agents) are known in the art.

A polypeptide or amino acid sequence "derived from" a designated polypeptide or protein refers to the origin of the polypeptide. Preferably, the polypeptide or amino acid sequence which is derived from a particular sequence has an amino acid sequence that is essentially identical to that sequence or a portion thereof, wherein the portion consists of at least 10-20 amino acids, preferably at least 20-30 amino acids, more preferably at least 30-50 amino acids, or which is otherwise identifiable to one of ordinary skill in the art as having its origin in the sequence. Polypeptides derived from another polypeptide may have one or more mutations relative to the starting polypeptide, e.g., one or more amino acid residues which have been substituted with another amino acid residue or which has one or more amino acid residue insertions or deletions.

In one embodiment, there is one amino acid difference between a starting polypeptide sequence and the sequence derived therefrom. Identity or similarity with respect to this sequence is defined herein as the percentage of amino acid residues in the candidate sequence that are identical (i.e., same residue) with the starting amino acid residues, after aligning the sequences and introducing gaps, if necessary, to achieve the maximum percent sequence identity.

In one embodiment, a polypeptide of the disclosure consists of, consists essentially of, or comprises an amino acid sequence as set forth in the Sequence Listing or Sequence Table disclosed herein and functionally active variants thereof. In an embodiment, a polypeptide includes an amino acid sequence at least 80%, such as at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to an amino acid sequence set forth in the Sequence Listing or Sequence Table disclosed herein. In some embodiments, a polypeptide includes a contiguous amino acid sequence at least 80%, such as at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to a contiguous amino acid sequence set forth in the Sequence Listing or Sequence Table disclosed herein. In some embodiments, a polypeptide includes an amino acid sequence having at least 10, such as at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 200, at least 300, at least 400, or at least 500 (or any integer within these numbers) contiguous amino acids of an amino acid sequence set forth in Sequence Listing or Sequence Table disclosed herein.

In some embodiments, the interferon receptor Fc constructs of the disclosure are encoded by a nucleotide sequence. Nucleotide sequences of the disclosure can be useful for a number of applications, including: cloning, gene therapy, protein expression and purification, mutation introduction, DNA vaccination of a host in need thereof, antibody generation for, e.g., passive immunization, PCR, primer and probe generation, siRNA design and generation (see, e.g., the Dharmacon siDesign website), and the like. In some embodiments, the nucleotide sequence of the disclosure comprises, consists of, or consists essentially of, a nucleotide sequence that encodes the amino acid sequence of the interferon receptor Fc constructs selected from the Sequence Table or Sequence Listing. In some embodiments, a nucleotide sequence includes a nucleotide sequence at least 80%, such as at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to a nucleotide sequence encoding an amino acid sequence of the Sequence Listing or Sequence Table disclosed herein. In some embodiments, a nucleotide sequence includes a contiguous nucleotide sequence at least 80%, such as at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to a contiguous nucleotide sequence encoding an amino acid sequence set forth in the Sequence Listing or Sequence Table disclosed herein. In some embodiments, a nucleotide sequence includes a nucleotide sequence having at least 10, such as at least 15, such as at least 20, at least 25, at least 30, at least 35, at least 40, at least 45, at least 50, at least 55, at least 60, at least 65, at least 70, at least 75, at least 80, at least 85, at least 90, at least 95, at least 100, at least 200, at least 300, at least 400, or at least 500 (or any integer within these numbers) contiguous nucleotides of a nucleotide sequence encoding an amino acid sequence set forth in the Sequence Listing or Sequence Table disclosed herein.

It will also be understood by one of ordinary skill in the art that the interferon receptor Fc constructs may be altered such that they vary in sequence from the naturally occurring or native sequences from which their components (e.g., interferon receptor domains, linker domains, and Fc domains) are derived, while retaining the desirable activity of the native sequences. For example, nucleotide or amino acid substitutions leading to conservative substitutions or changes at "non-essential" amino acid residues may be made. An isolated nucleic acid molecule encoding a non-natural variant can be created by introducing one or more nucleotide substitutions, additions or deletions into the nucleotide sequence of the interferon receptor Fc constructs such that one or more amino acid substitutions, additions or deletions are introduced into the encoded protein. Mutations may be introduced by standard techniques, such as site-directed mutagenesis and PCR-mediated mutagenesis.

The interferon receptor Fc constructs may comprise conservative amino acid substitutions at one or more amino acid residues, e.g., at essential or non-essential amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine). Thus, a nonessential amino acid residue in an interferon receptor Fc construct is preferably replaced with another amino acid residue from the same side chain family. In another embodiment, a string of amino acids can be replaced with a structurally similar string that differs in order and/or composition of side chain family members. Alternatively, in another embodiment, mutations may be introduced randomly along all or part of a coding sequence, such as by saturation mutagenesis, and the resultant mutants can be incorporated into the interferon receptor Fc constructs and screened for their ability to bind to the desired target.

The term "ameliorating" refers to any therapeutically beneficial result in the treatment of a disease state, e.g., an autoimmune disease state (e.g., SLE, Sjogren's syndrome), including prophylaxis, lessening in the severity or progression, remission, or cure thereof.

The term "in situ" refers to processes that occur in a living cell growing separate from a living organism, e.g., growing in tissue culture.

The term "in vivo" refers to processes that occur in a living organism. The term "mammal" or "subject" or "patient" as used herein includes both humans and non-humans and include but is not limited to humans, non-human primates, canines, felines, murines, bovines, equines, and porcines.

The term percent "identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv Appl Math* 1981; 2:482, by the homology alignment algorithm of Needleman & Wunsch, *J Mol Biol* 1970; 48:443, by the search for similarity method of Pearson & Lipman, *PNAS* 1988; 85:2444, by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al, infra).

One example of an algorithm that is suitable for determining percent sequence identity and sequence similarity is the BLAST algorithm, which is described in Altschul et al., *J Mol Biol* 1990; 215:403-10. Software for performing BLAST analyses is publicly available through the National Center for Biotechnology Information website.

The term "sufficient amount" means an amount sufficient to produce a desired effect.

The term "therapeutically effective amount" is an amount that is effective to ameliorate a symptom of a disease. A therapeutically effective amount can be a "prophylactically effective amount" as prophylaxis can be considered therapy.

The term "about" will be understood by persons of ordinary skill and will vary to some extent depending on the context in which it is used. If there are uses of the term which are not clear to persons of ordinary skill given the context in which it is used, "about" will mean up to plus or minus 10% of the particular value.

It must be noted that, as used in the specification and the appended claims, the singular forms "a," "an" and "the" include plural referents unless the context clearly dictates otherwise.

Soluble Interferon Receptors

In some embodiments, the soluble interferon receptors of the disclosure include a first polypeptide and a second polypeptide, wherein each polypeptide comprises an interferon receptor Fc construct with or without a leader sequence. An interferon receptor Fc construct includes an interferon receptor domain (e.g., IFNAR1 or IFNAR2), with or without a leader sequence, or a variant or fragment thereof, operably coupled with or without a linker domain to a Fc domain, or a variant or fragment thereof. In some embodiments, the first and second polypeptides dimerize to form a dimer; for example, a heterodimer.

In some embodiments, a composition of the disclosure includes a soluble interferon receptor.

In some embodiment, the interferon receptor domain is operably coupled to an Fc domain, or a variant of fragment thereof without a linker domain.

In some embodiments, the interferon receptor domain is operably coupled to an Fc domain, or a variant or fragment thereof, via a linker domain. In some embodiments, the linker domain is a linker peptide. In some embodiments, the linker domain is a linker nucleotide.

In some embodiments, linker domains include (gly4ser) 2, 3, 4 or 5 variants that alter the length of the linker by 5 amino acid progressions. In another embodiment, a linker domain is approximately 18 amino acids in length and includes an N-linked glycosylation site, which can be sensitive to protease cleavage in vivo. In some embodiments, an N-linked glycosylation site can protect the soluble interferon receptor from cleavage in the linker domain. In some embodiments, an N-linked glycosylation site can assist in separating the folding of independent functional domains separated by the linker domain.

In some embodiments, the linker domain is an NLG linker (VDGASSPVNVSSPSVQDI) (SEQ ID NO: 18).

In some embodiments, the interferon receptor Fc construct includes a leader molecule, e.g., a leader peptide. In some embodiments, the leader molecule is a leader peptide positioned at the N-terminus of the interferon receptor domain. In some embodiments, an interferon receptor Fc construct of the invention comprises a leader peptide at the N-terminus of the molecule, wherein the leader peptide is later cleaved from the interferon receptor Fc construct. Methods for generating nucleic acid sequences encoding a leader peptide fused to a recombinant protein are well known in the art. In some embodiments, any of the interferon receptor Fc constructs of the present invention can be expressed or synthesized either with or without a leader fused to their N-terminus. The protein sequence of an interferon receptor Fc construct of the present disclosure following cleavage of a fused leader peptide can be predicted and/or deduced by one of skill in the art.

In some embodiments, the leader peptide comprises the amino acid sequence: MDWTWRILFLVAAATGTHA (SEQ ID NO: 13). In some embodiments the leader is a VK3 leader peptide (VK3LP), which comprises the amino acid sequence: METPAQLLFLLLLWLPDTTG (SEQ ID NO: 14). In some embodiments, the leader peptide is fused to the N-terminus of the interferon receptor Fc construct. Such leader sequences can improve the level of synthesis and secretion of the interferon receptor Fc construct in mammalian cells. In some embodiments, the leader is cleaved, yielding interferon receptor Fc constructs. In some embodiments, an interferon receptor Fc construct of the present invention is expressed without a leader peptide fused to its N-terminus, and the resulting interferon receptor Fc construct has an N-terminal methionine.

In some embodiments, the soluble interferon receptors of the disclosure include a first and a second polypeptide, wherein each of the polypeptides includes an interferon receptor domain (e.g. IFNAR1, IFNAR2), with or without a leader sequence, or variant or fragment thereof operably coupled, with or without a linker domain, to the N- or C-terminus of an immunoglobulin Fc domain, or a variant or fragment thereof. In some embodiments, the interferon receptor domains of each of the two polypeptides are different, e.g., IFNAR1 and IFNAR2. In some embodiments, a soluble interferon receptor is a dimeric molecule. In some embodiments, the first and second polypeptides dimerize to form a heterodimer.

In some embodiments, the interferon receptor Fc construct includes substantially all or at least an active fragment of an interferon receptor. In some embodiments, the interferon receptor is IFNAR1, for example, the extracellular domain of a human IFNAR1 (SEQ ID NO: 11), or a variant or fragment thereof. In some embodiments, the interferon receptor is IFNAR2, for example, a the extracellular domain of human IFNAR2 (SEQ ID NO: 12), or a variant or fragment thereof. In some embodiments, a IFNAR-linker-Fc containing a 20 or 25 aa linker domain is made. In some embodiments, a IFNAR-linker-Fc containing a 10 aa linker domain is made. In some embodiments, a IFNAR-linker-Fc containing a 5 aa linker domain is made. In some embodiments, a IFNAR-Fc without a linker domain is made. In some embodiments, the interferon receptor may or may not include a leader sequence.

In some embodiments, interferon receptor Fc constructs include IFNAR-linker-Fc, wherein the IFNAR domain is located at the COOH side of the Fc. In other embodiments, interferon receptor Fc constructs include IFNAR-linker-Fc, wherein the IFNAR domain is located at the NH2 side of the Fc. In some embodiments, soluble interferon receptors include: IFNAR1-Fc and IFNAR2-Fc; IFNAR1-linker-Fc and IFNAR2-linker-Fc; Fc-IFNAR1 and Fc-IFNAR2; Fc-linker-IFNAR1 and Fc-linker-IFNAR2. The interferon receptor Fc constructs may or may not include a leader sequence.

In some embodiments, fusion junctions between interferon receptor domains and the other domains of the interferon receptor Fc constructs are optimized.

FIG. 1 displays exemplary configurations of the soluble interferon receptors, and the Sequence Table provides the sequences of exemplary interferon receptor Fc constructs of various configurations.

In one embodiment, the interferon receptor domain is operably coupled (e.g., chemically conjugated or genetically fused (e.g., either directly or via a linker, such as a polypeptide linker)) to the N-terminus of a Fc domain, or a variant or fragment thereof. In another embodiment, the interferon receptor domain is operably coupled (e.g., chemically conjugated or genetically fused (e.g., either directly or via a linker, such as a polypeptide linker)) to the C-terminus of a Fc domain, or a variant or fragment thereof. In other embodiments, an interferon receptor domain is operably coupled (e.g., chemically conjugated or genetically fused (e.g., either directly or via a linker, such as a polypeptide linker)) via an amino acid side chain of a Fc domain, or a variant or fragment thereof.

In some embodiments, the soluble interferon receptors comprise at least two of the same or different interferon receptor domains (e.g., IFNAR1 and IFNAR2), or a variant or fragment thereof, and at least two of the same or different Fc domains, or a variant or fragment thereof, with an optional linker domain between the interferon receptor domains and the Fc domains.

In some embodiments, the interferon receptor Fc constructs form a heterodimer.

In some embodiments, the soluble interferon receptor of the disclosure comprise a Fc domain, or a variant or fragment thereof, as described herein, thereby increasing serum half-life and bioavailability of the soluble interferon receptors.

It will be understood by the skilled artisan that other configurations of the interferon receptor domains and Fc domains are possible, with the inclusion of optional linkers between the interferon receptor domain and Fc domain. It will also be understood that domain orientation can be altered, so long as the interferon receptor domains are active in the particular configuration tested.

In certain embodiments, the soluble interferon receptor of the disclosure have at least one interferon receptor domain specific for a target molecule which mediates a biological effect. In another embodiment, binding of the soluble interferon receptor of the disclosure to a target molecule, such as type I interferon (e.g. IFN-α, INF-β, IFN-ε, -κ, -τ, -ζ, -IFN-ω, IFN-ν), results in the reduction or elimination of the target molecule, e.g., from a cell, a tissue, or from circulation.

In other embodiments, the interferon receptor Fc constructs of the disclosure may be assembled together or with other interferon receptor Fc constructs or polypeptides to form binding proteins having two or more polypeptides ("multimers"), wherein at least one polypeptide of the multimer is an interferon receptor Fc construct of the disclosure. Exemplary multimeric forms include dimeric, trimeric, tetrameric, and hexameric altered binding proteins and the like. In one embodiment, the polypeptides of the multimer are the same (i.e., homomeric binding proteins, e.g., homodimers, homotetramers). In another embodiment, the polypeptides of the multimer are different (e.g., heteromeric binding proteins, e.g., heterodimers).

In some embodiments, a soluble interferon receptor has a serum half-life that is increased at least about 1.5-fold, such as at least 3-fold, at least 5-fold, at least 10-fold, at least about 20-fold, at least about 50-fold, at least about 100-fold, at least about 200-fold, at least about 300-fold, at least about 400-fold, at least about 500-fold, at least about 600-fold, at least about 700-fold, at least about 800-fold, at least about 900-fold, at least about 1000-fold, or 1000-fold or greater relative to the corresponding interferon receptor molecules not fused to the Fc domain, or a variant or fragment thereof. In other embodiments, a soluble interferon receptor has a serum half-life that is decreased at least about 1.5-fold, such as at least 3-fold, at least 5-fold, at least 10-fold, at least about 20-fold, at least about 50-fold, at least about 100-fold, at least about 200-fold, at least about 300-fold, at least about 400-fold, at least about 500-fold, or 500-fold or lower relative to the corresponding interferon receptor molecules not fused to the Fc domain, or a variant or fragment thereof. Routine art-recognized methods can be used to determine the serum half-life of the soluble interferon receptors of the disclosure.

In some embodiments, the activity of the interferon receptor (e.g., IFNAR1 or IFNAR2) in the soluble interferon receptor is not less than about 10-fold less, such as 9-fold less, 8-fold less, 7-fold less, 6-fold less, 5-fold less, 4-fold less, 3-fold less, or 2-fold less than the activity of a naturally coccuring, wild type interferon receptor molecule. In some embodiments, the activity of the interferon receptor in the soluble interferon receptor is about equal to the activity of a naturally occuring, wild type interferon receptor molecule.

In some embodiments, the soluble interferon receptor can bind to and decrease the effects of interferon.

In some embodiments, the activity of the soluble interferon receptor is detectable in vitro and/or in vivo. In some embodiments, the soluble interferon receptor construct binds to a cell, a diseased cell, a malignant cell, or a cancer cell and interferes with its biologic activity.

In another aspect, a multifunctional soluble interferon receptor is provided that is attached to an enzyme or antibody having binding specificity, such as an scFv targeted to type I interferons. For example, type I interferons include IFN-α, IFN-β, IFN-ε, -κ, -τ, -ζ, -IFN-ω, IFN-ν.

In some embodiments, the targets of the IFNAR domains of the soluble interferon receptor are primarily extracellular type I interferons. For example, IFN-α, IFN-β, IFN-ε, -κ, -τ, -ζ, -IFN-ω, IFN-ν. In some embodiments, the soluble interferon receptor is active in the acidic environment of the endocytic vesicles. In some embodiments, a soluble interferon receptor, including a Fc domain, or a variant or fragment thereof, is adapted to be active both extracellularly and in the endocytic environment. In some embodiments, the IFNAR domain of a soluble interferon receptor is not active in the cytoplasm of a cell.

In some embodiments, soluble interferon receptors include both IFNAR1 and IFNAR2. In some embodiments, these soluble interferon receptors improve therapy of SLE because they bind interferon (IFN), e.g., IFNα or IFNβ, and negate or reduce the inflammatory effects of the cytokine.

Interferon Receptors Domains

In some embodiments, the interferon receptor Fc constructs of the present disclosure comprise one or more interferon receptor domains (IFNAR), or a variant or fragment thereof operably coupled with or without a linker domain to an immunoglobulin Fc domain, or a variant or fragment thereof. In some embodiments, the interferon receptor domain is a variant or fragment of an interferon receptor domain. In some embodiments, the interferon receptor domain comprises the extracellular domain of the interferon receptor. For example, the extracellular domain of IFNAR1 or the extracellular domain of IFNAR2. In some embodiments, the interferon receptor domain includes a leader sequence. In some embodiments, the interferon receptor domain does not include a leader sequence.

Suitable IFNAR domains are well-known in the art and include, but are not limited to, IFNAR1 and IFNAR2. For example, IFNAR domains are discussed in deWeerd et al., Type I Interferon Receptors: Biochemistry and Biological Functions, J. of Biol. Chem., Vol. 282, No. 28, 20053-20057 (2007), the entire contents of which is hereby incorporated herein by reference.

The type I interferon-α/β receptor (IFNAR) is a heteromeric cell surface receptor comprised of multiple components, designated IFNAR1 and IFNAR2. The INFAR complex is unique among cytokine receptors as it binds to and/or mediates signaling by more than 15 different but related type I interferon (IFN) ligands, including, for example, IFN-α and IFN-β, several IFNα subtypes, IFN-ω, IFN-ε, IFN-κ, and others. Upon binding of type I IFNs, IFNAR activates the JAK-STAT signaling pathway.

In some embodiments, the interferon receptor Fc constructs of the disclosure bind interferon (e.g., IFN-α, INF-β, IFN-ε, -κ, -τ, -ζ, -IFN-ω, IFN-ν) when complexed with another interferon receptor Fc construct in the form of a heterodimer. For example, a heterodimer of the disclosure capable of binding interferon comprises a first interferon receptor Fc construct, wherein the IFNAR is IFNAR1, and a second interferon receptor Fc construct, wherein the IFNAR is IFNAR2.

In some embodiments, the IFNAR domain of an interferon receptor Fc construct is a naturally occurring wild-type IFNAR1 protein having the amino acid sequence set forth as SEQ ID NO:5. In some embodiments, the IFNAR domain is a variant or fragment of the IFNAR1 protein. In some embodiments, the IFNAR domain comprises 50-100, 100-150, 150-200, 200-250, 250-300, 300-350, 350-400, 400-450, 450-500, or 450-557 amino acids of the amino acids sequence set forth as SEQ ID NO: 5. In some embodiments, the IFNAR domain comprises 350-360, 360-370, 370-380, 380-390, 390-400, 400-410, 410-420, 420-430, 430-440, 440-450, 450-470, 460-470, 470-480, 480-490, or 490-500 amino acids of the amino acid sequence set forth as SEQ ID NO: 5. In some embodiments, the IFNAR1 domain comprises amino acids 28-436 of the amino acid sequence set forth as SEQ ID NO: 5.

In some embodiments, the IFNAR domain comprises an amino acid sequence at least 70% identical, such as 70%, 75%, 80%, 85%, 90%, 91%, 92%, 93%, 94%, 95%, 96%, 97%, 98%, 99%, or at least 99.5% identical to the amino acid sequence set forth as SEQ ID NO: 5.

In some embodiments, the IFNAR domain of an interferon receptor Fc construct comprises the amino acid sequence set forth as SEQ ID NO:7. In some embodiments, the IFNAR domain comprises the amino acid sequence set forth as SEQ ID NO:11. In some embodiments, the IFNAR domain comprises an amino acid sequence at least 80% identical, such as 80%, 81%, 82%, 83%, 84%, 85%, 86%, 87%, 88%, 89%, 90%, 91%, 92%, 93%, 94%, 95%, 96%, 97%, 98%, 99%, or at least 99.5% identical to the amino acid sequence set forth as SEQ ID NO: 7 or SEQ ID NO: 11.

In some embodiments, the IFNAR domain is a naturally occurring human wild-type IFNAR2 protein having the amino acid sequence set forth as SEQ ID NO: 6. In some embodiments, the IFNAR domain is a variant or fragment of the IFNAR2 protein. In some embodiments, the IFNAR domain comprises 50-100, 100-150, 150-200, 200-250, 250-300, 300-350, 350-400, 400-450, 450-500, or 450-515 amino acids of the amino acids sequence set forth as SEQ ID NO: 6. In some embodiments, the IFNAR domain comprises 150-160, 160-170, 170-180, 180-190, 190-200, 200-210, 210-220, 220-230, 230-240, 240-250, 250-260, 260-270, 270-280, 280-290, 290-300 amino acids of the amino acids sequence set forth as SEQ ID NO: 6. In some embodiments, the IFNAR2 domain comprises amino acids 27-243 of the amino acid sequence set forth as SEQ ID NO: 6.

In some embodiments, the IFNAR domain comprises an amino acid sequence at least 70% identical, such as 70%, 75%, 80%, 85%, 90%, 91%, 92%, 93%, 94%, 95%, 96%, 97%, 98%, 99%, or at least 99.5% identical to the amino acid sequence set forth as SEQ ID NO: 6.

In some embodiments, the IFNAR domain of an interferon receptor Fc construct comprises the amino acid sequence set forth as SEQ ID NO:8. In some embodiments, the IFNAR domain comprises the amino acid sequence set forth as SEQ ID NO:12. In some embodiments, the IFNAR domain comprises an amino acid sequence at least 80% identical, such as 80%, 81%, 82%, 83%, 84%, 85%, 86%, 87%, 88%, 89%, 90%, 91%, 92%, 93%, 94%, 95%, 96%, 97%, 98%, 99%, or at least 99.5% identical to the amino acid sequence set forth as SEQ ID NO: 8 or SEQ ID NO: 12.

In some embodiments, the interferon receptor domain comprises the extracellular domain of an interferon receptor. In some embodiments, the interferon receptor domain comprises the extracellular domain of IFNAR1. In some embodiments, the interferon receptor domain comprises the extracellular domain of IFNAR2. In some embodiments, the extracellular domain of an interferon receptor (e.g., IFNAR1 or IFNAR2) is essentially free of the transmembrane and cytoplasmic domains. In some embodiments, the extracellular domain of an interferon receptor (e.g., IFNAR1 or IFNAR2) is anything less that the transmembrane and cytoplasmic domains.

In some embodiments, the extracellular domain of IFNAR1 comprises the amino acid sequence set forth as SEQ ID NO: 7 or SEQ ID NO: 11. In some embodiments, the extracellular domains of IFNAR1 comprises amino acids 28-436 of the amino acid sequence set forth as SEQ ID NO: 5. In some embodiments, the extracellular domains of IFNAR1 comprises amino acids 1-436 of the amino acid sequence set forth as SEQ ID NO: 5.

In some embodiments, the extracellular domain of IFNAR2 comprises the amino acid sequence set forth as SEQ ID NO: 8 or SEQ ID NO: 12. In some embodiments, the extracellular domain of IFNAR2 domain comprises amino acids 27-243 of the amino acid sequence set forth as SEQ ID NO: 6. In some embodiments, the extracellular domain of IFNAR2 domain comprises amino acids 1-243 of the amino acid sequence set forth as SEQ ID NO: 6.

In some embodiments, an IFNAR domain is altered or modified, e.g., by mutation which results in an amino acid addition, deletion, or substitution. As used herein, the term "IFNAR domain variant" refers to an IFNAR domain having at least one amino acid modification, such as an amino acid substitution, as compared to the wild-type IFNAR, or fragment thereof, from which the IFNAR domain is derived. For example, wherein the IFNAR domain is derived from a human wild-type IFNAR, a variant comprises at least one amino acid mutation (e.g., substitution) as compared to a wild type amino acid at the corresponding position of the human wild-type IFNAR. For example, wherein the IFNAR domain is derived from the extracellular domain of a human IFNAR, a variant comprises at least one amino acid mutation (e.g., substitution) as compared to an amino acid at the corresponding position of the extracellular IFNAR.

In some embodiments, the IFNAR variant comprises one or more amino acid substitutions at an amino acid position(s) located in the extracellular domain of the IFNAR.

In some embodiments of the disclosure, the soluble interferon receptors include one or more IFNAR domains. In some embodiments, the soluble interferon receptors include two IFNAR domains. In some embodiments, the IFNAR domains of the soluble interferon receptors are different (e.g., IFNAR1 and IFNAR2).

In some embodiments, the soluble interferon receptor includes a first polypeptide and a second polypeptide. In some embodiments, both the first polypeptide and the second polypeptide comprise an interferon receptor Fc construct. In some embodiments, the IFNAR domain of the interferon receptor Fc construct is IFNAR1, or a variant or fragment thereof. In some embodiments, the IFNAR domain of the interferon receptor Fc construct is IFNAR2, or a variant or fragment thereof. In some embodiments, the IFNAR domain of the first polypeptide of the soluble interferon receptor comprises IFNAR1, or a variant or fragment thereof. In some embodiments, the IFNAR domain of the second polypeptide of the soluble interferon receptor comprises IFNAR2, or a variant or fragment thereof. In some embodiments, the IFNAR domain of the interferon receptor Fc construct is human IFNAR1 or human IFNAR2. In some embodiments, the IFNAR domain of the interferon receptor Fc construct is a fragment or variant of IFNAR1 or a fragment or variant of IFNAR2. In some embodiments, the IFNAR domain of the interferon receptor Fc construct is the extracellular domain of human IFNAR1 or the extracellular domain of human IFNAR2.

Linker Domains

In some embodiments, an interferon receptor Fc construct includes a linker domain. In some embodiments, an interferon receptor Fc construct includes a plurality of linker domains. In some embodiments, the linker domain is a polypeptide linker. In certain aspects, it is desirable to employ a polypeptide linker to fuse Fc, or a variant or fragment thereof, with one or more interferon receptor domains to form an interferon receptor Fc construct. In some embodiments, an interferon receptor Fc construct does not include a linker domain.

In one embodiment, the polypeptide linker is synthetic. As used herein, the term "synthetic" with respect to a polypeptide linker includes peptides (or polypeptides) which comprise an amino acid sequence (which may or may not be naturally occurring) that is linked in a linear sequence of amino acids to a sequence (which may or may not be naturally occurring) (e.g., a Fc sequence) to which it is not naturally linked in nature. For example, the polypeptide linker may comprise non-naturally occurring polypeptides which are modified forms of naturally occurring polypeptides (e.g., comprising a mutation such as an addition, substitution or deletion) or which comprise a first amino acid sequence (which may or may not be naturally occurring). The polypeptide linkers of the invention may be employed, for instance, to ensure that Fc, or a variant or fragment thereof, is juxtaposed to ensure proper folding and formation of a functional Fc, or a variant or fragment thereof. Preferably, a polypeptide linker compatible with the instant invention will be relatively non-immunogenic and not inhibit any non-covalent association among monomer subunits of a binding protein.

In certain embodiments, the interferon receptor Fc construct employs an NLG linker as set forth in SEQ ID NO: 18.

In certain embodiments, the interferon receptor Fc constructs of the disclosure employ a polypeptide linker to join any two or more domains in frame in a single polypeptide chain. In one embodiment, the two or more domains may be independently selected from any of the Fc domains, or variants or fragments thereof, or interferon receptor domains discussed herein. For example, in certain embodiments, a polypeptide linker can be used to fuse an Fc domain, or variant or fragment thereof to an IFNAR. In some embodiments, a polypeptide linker of the invention can be used to genetically fuse the C-terminus of an IFNAR to the N-terminus of a Fc domain, or variant or fragment thereof to form an interferon receptor Fc construct. In other embodiments, a polypeptide linker of the invention can be used to genetically fuse the C-terminus of a Fc domain, or variant or fragment thereof to the N-terminus of an IFNAR to form and interferon receptor Fc construct. In other embodiments, a polypeptide linker of the invention can be used to genetically fuse the C-terminus of an IFNAR to the C-terminus of a Fc domain, or variant or fragment thereof to form and interferon receptor Fc construct. In other embodiments, a polypeptide linker of the invention can be used to genetically fuse the N-terminus of an IFNAR to the N-terminus of a Fc domain, or variant or fragment thereof to form and interferon receptor Fc construct.

In one embodiment, a polypeptide linker comprises a portion of a Fc domain, or a variant or fragment thereof. For example, in one embodiment, a polypeptide linker can comprise a Fc fragment (e.g., C or N domain), or a different portion of a Fc domain or variant thereof.

In another embodiment, a polypeptide linker comprises or consists of a gly-ser linker. As used herein, the term "gly-ser linker" refers to a peptide that consists of glycine and serine residues. An exemplary gly/ser linker comprises an amino acid sequence of the formula $(Gly_4Ser)n$, wherein n is a positive integer (e.g., 1-10, 1, 2, 3, 4, or 5). A preferred gly/ser linker is $(Gly_4Ser)_1$. Another preferred gly/ser linker is $(Gly_4Ser)_2$. Another preferred gly/ser linker is $(Gly_4Ser)_3$. Another preferred gly/ser linker is $(Gly_4Ser)_4$. Another preferred gly/ser linker is $(Gly_4Ser)_5$. In certain embodiments, the gly-ser linker may be inserted between two other sequences of the polypeptide linker (e.g., any of the polypeptide linker sequences described herein). In other embodiments, a gly-ser linker is attached at one or both ends of another sequence of the polypeptide linker (e.g., any of the polypeptide linker sequences described herein). In yet other embodiments, two or more gly-ser linker are incorporated in series in a polypeptide linker.

In other embodiments, a polypeptide linker of the invention comprises a biologically relevant peptide sequence or a sequence portion thereof. For example, a biologically relevant peptide sequence may include, but is not limited to, sequences derived from an anti-rejection or anti-inflammatory peptide. Said anti-rejection or anti-inflammatory peptides may be selected from the group consisting of a cytokine inhibitory peptide, a cell adhesion inhibitory peptide, a thrombin inhibitory peptide, and a platelet inhibitory peptide. In a preferred embodiment, a polypeptide linker comprises a peptide sequence selected from the group consisting of an IL-1 inhibitory or antagonist peptide sequence, an erythropoietin (EPO)-mimetic peptide sequence, a thrombopoietin (TPO)-mimetic peptide sequence, G-CSF mimetic peptide sequence, a TNF-antagonist peptide sequence, an integrin-binding peptide sequence, a selectin antagonist peptide sequence, an anti-pathogenic peptide sequence, a vasoactive intestinal peptide (VIP) mimetic peptide sequence, a calmodulin antagonist peptide sequence, a mast cell antagonist, a SH3 antagonist peptide sequence, an urokinase receptor (UKR) antagonist peptide sequence, a somatostatin or cortistatin mimetic peptide sequence, and a macrophage and/or T-cell inhibiting peptide sequence. Exemplary peptide sequences, any one of which may be employed as a polypeptide linker, are disclosed in U.S. Pat. No. 6,660,843, which is incorporated by reference herein.

Other linkers that are suitable for use in interferon receptor Fc constructs are known in the art, for example, the serine-rich linkers disclosed in U.S. Pat. No. 5,525,491, the helix forming peptide linkers (e.g., A(EAAAK)nA (n=2-5)) disclosed in Arai et al., *Protein Eng* 2001; 14:529-32, and the stable linkers disclosed in Chen et al., *Mol Pharm* 2011; 8:457-65, i.e., the dipeptide linker LE, a thrombin-sensitive disulfide cyclopeptide linker, and the alpha-helix forming linker LEA(EAAAK)4ALEA(EAAAK)4ALE (SEQ ID NO: 19).

Other exemplary linkers include GS linkers (i.e., (GS)n), GGSG (SEQ ID NO: 27) linkers (i.e., (GGSG)n), GSAT linkers (SEQ ID NO: 28), SEG linkers, and GGS linkers (i.e., (GGSGGS)n), wherein n is a positive integer (e.g., 1, 2, 3, 4, or 5). Other suitable linkers for use in the interferon receptor Fc constructs can be found using publicly available databases, such as the Linker Database (ibi.vu.nl/programs/linkerdbwww). The Linker Database is a database of inter-domain linkers in multi-functional enzymes which serve as potential linkers in novel fusion proteins (see, e.g., George et al., *Protein Engineering* 2002; 15:871-9).

It will be understood that variant forms of these exemplary polypeptide linkers can be created by introducing one or more nucleotide substitutions, additions or deletions into the nucleotide sequence encoding a polypeptide linker such that one or more amino acid substitutions, additions or deletions are introduced into the polypeptide linker. Mutations may be introduced by standard techniques, such as site-directed mutagenesis and PCR-mediated mutagenesis.

Polypeptide linkers of the disclosure are at least one amino acid in length and can be of varying lengths. In one embodiment, a polypeptide linker of the invention is from about 1 to about 50 amino acids in length. As used in this context, the term "about" indicates+/−two amino acid residues. Since linker length must be a positive integer, the length of from about 1 to about 50 amino acids in length, means a length of from 1 to 48-52 amino acids in length. In another embodiment, a polypeptide linker of the disclosure is from about 5-10 amino acids in length. In another embodiment, a polypeptide linker of the disclosure is from about 10-20 amino acids in length. In another embodiment, a polypeptide linker of the disclosure is from about 15-30 amino acids in length. In another embodiment, a polypeptide linker of the disclosure is from about 15 to about 50 amino acids in length.

In another embodiment, a polypeptide linker of the disclosure is from about 20 to about 45 amino acids in length. In another embodiment, a polypeptide linker of the disclosure is from about 15 to about 25 amino acids in length. In another embodiment, a polypeptide linker of the disclosure is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, or 61 or more amino acids in length.

Polypeptide linkers can be introduced into polypeptide sequences using techniques known in the art. Modifications can be confirmed by DNA sequence analysis. Plasmid DNA can be used to transform host cells for stable production of the polypeptides produced.

Fc Domains

In some embodiments, the polypeptide comprising one or more interferon receptor domains, or a variant or fragment thereof is operably coupled, with or without a linker domain, to a Fc domain, which serves as a scaffold as well as a means to increase the serum half-life of the polypeptide. In some embodiments, the one or more interferon receptor domains and/or the Fc domain is aglycosylated, deglycosylated, or underglycosylated. In some embodiments, the Fc domain is a mutant or variant Fc domain, or a fragment of an Fc domain.

Suitable Fc domains are well-known in the art and include, but are not limited to, Fc and Fc variants, such as those disclosed in WO2011/053982, WO 02/060955, WO 02/096948, WO05/047327, WO05/018572, and US 2007/0111281 (the contents of the foregoing are incorporated herein by reference). It is within the abilities of the skilled artisan to use routine methods to introduce Fc domains (e.g., cloning, conjugation) into the interferon receptor Fc constructs disclosed herein (with or without altered glycosylation).

In some embodiments, the Fc domain is a wild type human IgG1 Fc, such as is shown in SEQ ID NO: 26. In some embodiments, the Fc domain is a wild type human IgG4 Fc, such as is shown in SEQ ID NO: 112.

In some embodiments, an Fc domain is altered or modified, e.g., by mutation which results in an amino acid addition, deletion, or substitution. As used herein, the term "Fc domain variant" refers to an Fc domain having at least one amino acid modification, such as an amino acid substitution, as compared to the wild-type Fc from which the Fc domain is derived. For example, wherein the Fc domain is derived from a human IgG1 antibody, a variant comprises at least one amino acid mutation (e.g., substitution) as compared to a wild type amino acid at the corresponding position of the human IgG1 Fc region. The amino acid substitution(s) of an Fc variant may be located at a position within the Fc domain referred to as corresponding to the position number that that residue would be given in an Fc region in an antibody (numbering according to EU index).

In one embodiment, the Fc variant comprises one or more amino acid substitutions at an amino acid position(s) located in a hinge region or portion thereof. In another embodiment, the Fc variant comprises one or more amino acid substitutions at an amino acid position(s) located in a CH2 domain or portion thereof. In another embodiment, the Fc variant comprises one or more amino acid substitutions at an amino acid position(s) located in a CH3 domain or portion thereof. In another embodiment, the Fc variant comprises one or more amino acid substitutions at an amino acid position(s) located in a CH4 domain or portion thereof.

In some embodiments, the Fc variant comprises one or more of the following amino acid substitutions: T350V, L351Y, F405A, and Y407V. In some embodiments, the Fc variant comprises one or more of the following amino acid substitutions: T350V, T366L, K392L, and T394W. In some embodiments, the Fc region has a mutation at N83 (i.e., N297 by Kabat numbering), yielding an aglycosylated Fc region (e.g., Fc N83S).

In some embodiments, the Fc domain includes mutations in one or more of the three hinge region cysteines (residues 220, 226, and 229, numbering according to the EU index). In some embodiments, one or more of the three hinge cysteines in the Fc domain can be mutated to SCC (SEQ ID NO: 20) or SSS (SEQ ID NO: 21), where in "S" represents an amino acid substitution of cysteine with serine (wherein CCC refers to the three cysteines present in the wild type hinge domain). Accordingly "SCC" indicates an amino acid substitution to serine of only the first cysteine of the three hinge region cysteines (residues 220, 226, and 229, numbering according to the EU index), whereas "SSS" indicates that all three cysteines in the hinge region are substituted with serine (residues 220, 226, and 229, numbering according to the EU index).

In some aspects, the Fc domain is a mutant human IgG1 Fc domain. In some aspects, a mutant Fc domain comprises one or more mutations in the hinge, CH2, and/or CH3 domains.

In some aspects, the Fc domain is a mutant human IgG4 Fc domain. In some embodiments, mutations in the IgG4 Fc domain include one or more mutations selected from the following group of mutations: F296Y, E356K, R409K, and H345R. In some embodiments, mutations in the IgG4 Fc domain includes one or more mutation selected from the following group of mutations: F296Y, R409K, and K439E. In some embodiments, the soluble interferon receptors disclosed herein include a first polypeptide comprising a mutant IgG4 Fc domain, wherein the Fc domain includes mutations F296Y, E356K, R409K, and H345R, and a second polypeptide comprising a mutant IgG4 Fc domain, wherein the CH3 domain includes mutations F296Y, R409K, and K439E. In some embodiments, a mutant IgG4 Fc domain comprises one or more mutations in the hinge, CH2, and/or CH3 domains.

A. CH2 Substitutions

In some aspects, a mutant Fc domain includes a P238S mutation. In some aspects, a mutant Fc domain includes a P331S mutation. In some aspects, a mutant Fc domain includes a P238S mutation and a P331S mutation. In some aspects, a mutant Fc domain comprises P238S and/or P331S, and may include mutations in one or more of the three hinge cysteines (residues 220, 226, and 229), numbering according to the EU index. In some aspects, a mutant Fc domain comprises P238S and/or P331S, and/or one or more mutations in the three hinge cysteines (residues 220, 226, and 229), numbering according to the EU index. In some aspects, a mutant Fc domain comprises P238S and/or P331S, and/or mutations in a hinge cysteine to SCC or in the three hinge cysteines to SSS. In some aspects, a mutant Fc domain comprises P238S and P331S and mutations in at least one of the three hinge cysteines. In some aspects, a mutant Fc domain comprises P238S and P331S and SCC. In some aspects, a mutant Fc domain comprises P238S and P331S and SSS. In some aspects, a mutant Fc domain includes P238S and SCC or SSS. In some aspects, a mutant Fc domain includes P331S and SCC or SSS. (All numbering according to the EU index).

In some aspects, a mutant Fc domain includes a mutation at a site of N-linked glycosylation, such as N297, e.g., a substitution of asparagine for another amino acid such as serine, e.g., N297S. In some aspects, a mutant Fc domain includes a mutation at a site of N-linked glycosylation, such as N297, e.g., a substitution of asparagine for another amino acid such as serine, e.g., N297S and a mutation in one or more of the three hinge cysteines. In some aspects, a mutant Fc domain includes a mutation at a site of N-linked glycosylation, such as N297, e.g., a substitution of asparagine for another amino acid such as serine, e.g., N297S and mutations in one of the three hinge cysteines to SCC or all three cysteines to SSS. In some aspects, a mutant Fc domain includes a mutation at a site of N-linked glycosylation, such as N297, e.g., a substitution of asparagine for another amino acid such as serine, e.g., N297 and one or more mutations in the CH2 domain which decrease FcγR binding and/or complement activation, such as mutations at P238 or P331 or both, e.g., P238S or P331S or both P238S and P331S. In some aspects, such mutant Fc domains can further include a mutation in the hinge region, e.g., SCC or SSS. (All numbering according to the EU index.) In some aspects, the mutant Fc domain is as shown in the Sequence Table or Sequence Listing herein.

B. CH3 Substitutions

In some embodiments, heterodimers are formed by mutations in the CH3 domain of the Fc domain on the interferon receptor Fc constructs disclosed herein. Heavy chains were first engineered for heterodimerization using a "knobs-into-holes" strategy (Rigway B, et al., Protein Eng., 9 (1996) pp. 617-621), incorporated herein by reference. The term "knob-into-hole" refers to the technology directing the pairing of two polypeptides together in vitro or in vivo by introducing a pertuberance (knob) into one polypeptide and a cavity (hole) into the other polypeptide at an interface in which they interact. See e.g., WO 96/027011, WO 98/050431, U.S. Pat. No. 5,731,168, US2007/0178552, WO2009089004, US 20090182127. In particular, a combination of mutations in the CH3 domain can be used to form heterodimers, for example, S354C, T366W in the "knob" heavy chain, and Y349C, T366S, L368A, Y407V in the "hole" heavy chain. In another example, T366Y in the "knob" heavy chain, and Y407T in the "hole" heavy chain. In some embodiments, the soluble interferon receptors disclosed herein includes a first CH3 domain having the knob mutation T366W and a second CH3 domain having the hole mutations T366S, L368A, and Y407V. (Numbering according to the EU index.) In some embodiments, the soluble interferon receptors disclosed herein includes a first CH3 domain having the knob mutation T366Y and a second CH3 domain having the hole mutation Y407T.

In some embodiments, the CH3 mutations are those described in US 2012/0149876 A1, US 2017/0158779, U.S. Pat. Nos. 9,574,010, and 9,562,109, each of which is incorporated herein by reference in its entirety; and Von Kreudenstein, T. S. et al. mABs, 5 (2013), pp. 646-654, incorporated herein by reference, and include the following mutations: T350V, L351Y, F405A, and Y407V (first CH3 domain); and T350V, T366L, K392L, T394W (second CH3 domain). In some embodiments, the soluble interferon receptors disclosed herein include a first CH3 domain having T350V, L351Y, F405A, and Y407V mutations and a second CH3 domain having T350V, T366L, K392L, T394W mutations. (Numbering according to the EU index.)

In some embodiments, heterodimers are formed by mutations in the CH3 domain of the Fc domain on the interferon receptor Fc constructs disclosed herein. In particular, a combination of mutations in the CH3 domain can be used to form heterodimers with high heterodimeric stability and purity; for example, See e.g., Von Kreudenstein et al., mAbs 5:5, 646-654; September-October 2013, and US 2012/0149876 A1, US 2017/0158779, U.S. Pat. Nos. 9,574,010, and 9,562,109, each of which is incorporated herein by reference in its entirety. In some embodiments, mutations in the Fc domain include one or more mutations selected from the following group of mutations: T350V, L351Y, F405A, and Y407V. In some embodiments, mutations in the Fc domain include one or more mutation selected from the following group of mutations: T350V, T366L, K392L, and T394W. In some embodiments, the interferon receptor Fc constructs disclosed herein include a CH3 domain having mutations T350V, L351Y, F405A, and Y407V. In some embodiments, the interferon receptor Fc constructs disclosed herein include a CH3 domain having mutations T350V, T366L, K392L, and T394W. In some embodiments, the soluble interferon receptors disclosed herein include a first polypeptide comprising a mutant Fc domain, wherein the CH3 domain includes mutations T350V, L351Y, F405A, and Y407V, and a second polypeptide comprising a mutant Fc domain, wherein the CH3 domain includes mutations T350V, T366L, K392L, and T394W.

Other mutations in the CH3 domain of the Fc domain are contemplated to preferentially form heterodimers. For example, See e.g., Von Kreudenstein et al., mAbs 5:5, 646-654; September-October 2013, incorporated herein by reference). In some embodiments, mutations in the Fc domain of the first polypeptide include one or more mutations selected from, the following group of mutations: T350V, L351Y, F405A, and Y407V, and mutations in the Fc domain of the second polypeptide include one or more mutations selected from the following group of mutations: T350V, T366L, K392M, and T394W. In some embodiments, mutations in the Fc domain of the first polypeptide include one or more mutations selected from the following group of mutations: L351Y, F405A, and Y407V, mutations in the Fc domain of the second polypeptide include one or more mutations selected from the following group of mutations: T366L, K392M, and T394W.

In some embodiments, the CH3 mutations are those described by Moore, G. L. et al. (mABs, 3 (2011), pp. 546-557) and include the following mutations: S364H and F405A (first CH3 domain); and Y349T and T394F (second CH3 domain). In some embodiments, the interferon receptor Fc constructs disclosed herein include a first CH3 domain having S364H and F405A mutations and a second CH3 domain having Y349T and T394F mutations. (Numbering according to the EU index.)

In some embodiments, the CH3 mutations are those described by Gunasekaran, K. et al. (J. Biol. Chem., 285 (2010), pp. 19637-19646) and include the following mutations: K409D and K392D (first CH3 domain); and D399K and E365K (second CH3 domain). In some embodiments, the interferon receptor Fc constructs disclosed herein includes a first CH3 domain having K409D and K392D mutations and a second CH3 domain having D399K and E365K mutations. (Numbering according to the EU index.)

The interferon receptor Fc constructs of the disclosure may employ art-recognized Fc variants which are known to impart an alteration in effector function and/or FcR binding. For example, a change (e.g., a substitution) at one or more of the amino acid positions disclosed in International PCT Publications WO88/07089A1, WO96/14339A1, WO98/05787A1, WO98/23289A1, WO99/51642A1, WO99/58572A1, WO00/09560A2, WO00/32767A1, WO00/42072A2, WO02/44215A2, WO02/060919A2, WO03/074569A2, WO04/016750A2, WO04/029207A2, WO04/035752A2, WO04/063351 A2, WO04/074455A2, WO04/099249A2, WO05/040217A2, WO04/044859, WO05/070963A1, WO05/077981A2, WO05/092925A2, WO05/123780A2, WO06/019447A1, WO06/047350A2, and WO06/085967A2; US Patent Publication Nos. US2007/0231329, US2007/0231329, US2007/0237765, US2007/0237766, US2007/0237767, US2007/0243188, US20070248603, US20070286859, US20080057056; or U.S. Pat. Nos. 5,648,260; 5,739,277; 5,834,250; 5,869,046; 6,096,871; 6,121,022; 6,194,551; 6,242,195; 6,277,375; 6,528,624; 6,538,124; 6,737,056; 6,821,505; 6,998,253; 7,083,784; and 7,317,091, each of which is incorporated by reference herein. In one embodiment, the specific change (e.g., the specific substitution of one or more amino acids disclosed in the art) may be made at one or more of the disclosed amino acid positions. In another embodiment, a different change at one or more of the disclosed amino acid positions (e.g., the different substitution of one or more amino acid position disclosed in the art) may be made.

Other amino acid mutations in the Fc domain are contemplated to reduce binding to the Fc gamma receptor and Fc gamma receptor subtypes. The assignment of amino acids residue numbers to an Fc domain is in accordance with the definitions of Kabat. See, e.g., Sequences of Proteins of Immunological Interest (Table of Contents, Introduction and Constant Region Sequences sections), 5th edition, Bethesda, Md.:NIH vol. 1:647-723 (1991); Kabat et al., "Introduction" *Sequences of Proteins of Immunological Interest*, US Dept of Health and Human Services, NIH, 5th edition, Bethesda, Md. vol. 1:xiii-xcvi (1991); Chothia & Lesk, *J. Mol. Biol.* 196:901-917 (1987); Chothia et al., *Nature* 342:878-883 (1989), each of which is herein incorporated by reference for all purposes."

For example, mutations at positions 238, 239, 248, 249, 252, 254, 255, 256, 258, 265, 267, 268, 269, 270, 272, 279, 280, 283, 285, 298, 289, 290, 292, 293, 294, 295, 296, 298, 301, 303, 305, 307, 312, 315, 322, 324, 327, 329, 330, 331, 333, 334, 335, 337, 338, 340, 356, 360, 373, 376, 378, 379, 382, 388, 389, 398, 414, 416, 419, 430, 434, 435, 437, 438 or 439 of the Fc region can alter binding as described in U.S. Pat. No. 6,737,056, issued May 18, 2004, incorporated herein by reference in its entirety. This patent reported that changing Pro331 in IgG3 to Ser resulted in six fold lower affinity as compared to unmutated IgG3, indicating the involvement of Pro331 in Fc gamma RI binding. In addition, amino acid modifications at positions 234, 235, 236, and 237, 297, 318, 320 and 322 are disclosed as potentially altering receptor binding affinity in U.S. Pat. No. 5,624,821, issued Apr. 29, 1997 and incorporated herein by reference in its entirety. (Numbering according to the EU index.)

Further mutations contemplated for use include, e.g., those described in U.S. Pat. App. Pub. No. 2006/0235208, published Oct. 19, 2006 and incorporated herein by reference in its entirety. This publications describe Fc variants that exhibit reduced binding to Fc gamma receptors, reduced antibody dependent cell-mediated cytotoxicity, or reduced complement dependent cytotoxicity, that comprise at least one amino acid modification in the Fc region, including 232G, 234G, 234H, 235D, 235G, 235H, 236I, 236N, 236P, 236R, 237K, 237L, 237N, 237P, 238K, 239R, 265G, 267R, 269R, 270H, 297S, 299A, 299I, 299V, 325A, 325L, 327R, 328R, 329K, 330I, 330L, 330N, 330P, 330R, and 331L (numbering is according to the EU index), as well as double mutants 236R/237K, 236R/325L, 236R/328R, 237K/325L, 237K/328R, 325L/328R, 235G/236R, 267R/269R, 234G/235G, 236R/237K/325L, 236R/325L/328R, 235G/236R/237K, and 237K/325L/328R. Other mutations contemplated for use as described in this publication include 227G, 234D, 234E, 234G, 234I, 234Y, 235D, 235I, 235S, 236S, 239D, 246H, 255Y, 258H, 260H, 264I, 267D, 267E, 268D, 268E, 272H, 272I, 272R, 281D, 282G, 283H, 284E, 293R, 295E, 304T, 324G, 324I, 327D, 327A, 328A, 328D, 328E, 328F, 328I, 328M, 328N, 328Q, 328T, 328V, 328Y, 330I, 330L, 330Y, 332D, 332E, 335D, an insertion of G between positions 235 and 236, an insertion of A between positions 235 and 236, an insertion of S between positions 235 and 236, an insertion of T between positions 235 and 236, an insertion of N between positions 235 and 236, an insertion of D between positions 235 and 236, an insertion of V between positions 235 and 236, an insertion of L between positions 235 and 236, an insertion of G between positions 235 and 236, an insertion of A between positions 235 and 236, an insertion of S between positions 235 and 236, an insertion of T between positions 235 and 236, an insertion of N between positions 235 and 236, an insertion of D between positions 235 and 236, an insertion of V between positions 235 and 236, an insertion of L between positions 235 and 236, an insertion of G between positions 297 and 298, an insertion of A between positions 297 and 298, an insertion of S between positions 297 and 298, an insertion of D between positions 297 and 298, an insertion of G between positions 326 and 327, an insertion of A between positions 326 and 327, an insertion of T between positions 326 and 327, an insertion of D between positions 326 and 327, and an insertion of E between positions 326 and 327 (numbering is according to the EU index). Additionally, mutations described in U.S. Pat. App. Pub. No. 2006/0235208 include 227G/332E, 234D/332E, 234E/332E, 234Y/332E, 234I/332E, 234G/332E, 235I/332E, 235S/332E, 235D/332E, 235E/332E, 236S/332E, 236A/332E, 236S/332D, 236A/332D, 239D/268E, 246H/332E, 255Y/332E, 258H/332E, 260H/332E, 264I/332E, 267E/332E, 267D/332E, 268D/332D, 268E/332D, 268E/332E, 268D/332E, 268E/330Y, 268D/330Y, 272R/332E, 272H/332E, 283H/332E, 284E/332E, 293R/332E, 295E/332E, 304T/332E, 324I/332E, 324G/332E, 324I/332D, 324G/332D, 327D/332E, 328A/332E, 328T/332E, 328V/332E, 328I/332E, 328F/332E, 328Y/332E, 328M/332E, 328D/332E, 328E/332E, 328N/332E, 328Q/332E, 328A/332D, 328T/332D, 328V/332D, 328I/332D, 328F/332D, 328Y/332D, 328M/332D, 328D/332D, 328E/332D, 328N/332D, 328Q/332D, 330L/332E, 330Y/332E, 330I/332E, 332D/330Y, 335D/332E, 239D/332E, 239D/332E/330Y, 239D/332E/330L, 239D/332E/330I, 239D/332E/268E, 239D/332E/268D, 239D/332E/327D, 239D/332E/284E, 239D/268E/330Y, 239D/332E/268E/330Y, 239D/332E/327A, 239D/332E/268E/327A, 239D/332E/330Y/327A, 332E/330Y/268E/327A, 239D/332E/268E/330Y/327A, Insert G>297-298/332E, Insert A>297-298/332E, Insert S>297-298/332E, Insert D>297-298/332E, Insert G>326-327/332E, Insert A>326-327/332E, Insert T>326-327/332E, Insert D>326-327/332E, Insert E>326-327/332E, Insert G>235-236/332E, Insert A>235-236/332E, Insert S>235-236/332E, Insert T>235-236/332E, Insert N>235-236/332E, Insert D>235-236/332E, Insert V>235-236/332E, Insert L>235-236/332E, Insert G>235-236/332D, Insert A>235-236/332D, Insert S>235-236/332D, Insert T>235-236/332D, Insert N>235-236/332D, Insert D>235-236/332D, Insert V>235-236/332D, and Insert L>235-236/332D (numbering according to the EU index) are contemplated for use. The mutant L234A/L235A is described, e.g., in U.S. Pat. App. Pub. No. 2003/0108548, published Jun. 12, 2003 and incorporated herein by reference in its entirety. In embodiments, the described modifications are included either individually or in combination. (Numbering according to the EU index.)

C. Alternative Scaffolds

The modular architecture of immunoglobulins can be utilized to create alternative scaffolds. For example, an alternative scaffold may be an alternative Fc format. In some embodiments, an alternative scaffold may be utilized to generate a heterodimeric construct.

In some embodiments of the present disclosure, the soluble interferon receptor includes an alternative Fc domain. In some embodiments, an alternative Fc domain is any of the suitable alternative Fc formats known in the art. For example the Fc domain may comprises any of the alternative Fc formats discussed in Spiess et al. Molecular Immunology, 2015, October; 67 (2 Pt A)95-106, the entire contents of which is incorporated herein by reference. For example the alternative Fc format may be selected from any one of the following formats: (i) bispecific IgG (BsIgG), (ii) appended IgG, (iii) bispecific fragments, (iv) bispecific fusion proteins, (v) bispecific conjugates, (vi) and IgG4 Fab arm exchange, and (vii) alternative scaffolds.

In some embodiments, the heterodimers of the disclosure can be formed by utilizing alternative Fc formats. In some embodiments, the Fc domain can be engineered to facilitate heterodimerization. In some embodiments, heterodimers are formed by mutations in the CH3 domain of the Fc domain of the soluble interferon receptors disclosed herein.

(i) Bispecific IgG (BsIgG)

Bispecific IgG is an alternative Fc format that can be utilized to facilitate heterodimerization of two Fc domains and overcome homodimerization. In some embodiments, the CH3 domain of an Fc can be mutated to facilitate heterodimerization.

In some embodiments, "knobs-into-holes" can be used to facilitate heterodimerization of Fc domains. A combination of mutations in the CH3 domain can be used to form heterodimers. In some embodiments, the "knobs" are created by replacing small amino acid side chains at the interface between CH3 domains with larger amino acid side chains, and "holes" are created by replacing large amino acid side chains at the interface between CH3 domains with small amino acid side chains. In some embodiments, the soluble interferon receptors of the disclosure include a first interferon receptor Fc construct comprising a first CH3 domain having the knob mutation T366W and a second interferon receptor Fc construct comprising a second CH3 domain having the hole mutations T366S, L368A, and Y407V. (Ridgeway et al., (1996) Prot. Eng. 9, 617-621 and Atwell et al., (1997) J. Mol. Biol. 270, 26-35, both of which are incorporated herein by reference). In some embodiments, the soluble interferon receptors of the disclosure include a first interferon receptor Fc construct comprising a first CH3 domain having the knob mutation T366Y and a second interferon receptor Fc construct comprising a second CH3 domain having the hole mutation Y407V (Ridgeway et al., (1996) Prot. Eng. 9, 617-621). The "hole" mutations provide efficient pairing with the "knob" mutation to promote heterodimerization of the Fc domains.

In certain embodiments, a "duobody" can also be used to facilitate heterodimerization of Fc domains (Labrijn et al., (2013) Proc. Natl. Acad. Sci. U.S.A. 110, 5145-5150, the entire contents of which is herein incorporated by reference). For example, the Fc domain of a first interferon receptor Fc construct may include a F405L mutation and the Fc domain of a second interferon receptor Fc construct may include a K409R mutation.

In other embodiments, "azymetric mutations" can be introduced into interferon receptor Fc constructs to promote the formation of heterodimers. (Von Kreudenstein et al., (2013) mAbs 5, 646-654, the entire contents of which is incorporated herein by reference, and US 2012/0149876 A1, US 2017/0158779, U.S. Pat. Nos. 9,574,010, and 9,562,109, each of which is incorporated herein by reference in its entirety). In some embodiments, the azymetric mutations include T350V, L351Y, F405A, and Y407V in the Fc domain of a first interferon receptor Fc construct, and T350V, T366L, K392L, and T394W in the Fc domain of a second interferon receptor Fc construct.

In some embodiments, "charge pair" mutations, which were identified by rational design of electrostatic steering mutations, can also be introduced into interferon receptor Fc constructs to promote heterodimerization (Gunasekaran et al., (2010) J. Biol. Chem. 285, 19637-19646, and Strop et al., (2012) J. Mol. Biol. 420, 204-219, both of which are incorporated herein by reference). The "charge pair" mutations create altered charge polarity across the Fc dimer interface such that co-expression of electrostatically matched Fc chains support favorable attractive interactions thereby promoting Fc heterodimer formation. Unfavorable repulsive charge interactions suppress homodimer formation (Gunasekaran et al., (2010)). For example, in some embodiments, the Fc domain of a first interferon receptor Fc construct may include K409D and K392D, and the Fc domain of a second interferon receptor Fc construct may include D399K and E356K. In other embodiments, the Fc domain of a first interferon receptor Fc construct may include D221E, P228E, L368E, and the Fc domain of a second interferon receptor Fc construct may include D221R, P228R, and K409R.

Heterodimerization of the Fc domains of at least two interferon receptor Fc constructs can also be facilitated by the introduction of "HA-TF" mutations. (Moore et al., (2011) mAbs 3, 546-557, the entire contents of which is incorporated herein by reference). For example, in some embodiments, the Fc domain of a first interferon receptor Fc construct includes S364H and F405A, and the Fc domain of a second interferon receptor Fc construct includes Y349T and T394F.

The formation of heterodimeric soluble interferon receptors can also be promoted by exploiting the structural similarity and sequence divergence between immunoglobulins from different classes. For example, the SEED platform uses the sequence divergence but structural similarity of the CH3 domains of IgG and IgA (Davis et al., (2010) Protein Eng. Des. Sel. 23, 195-202, the entire contents of which is herein incorporated by reference). In some embodiments, the Fc domain of a first interferon receptor Fc construct includes and IgG/A chimera and the Fc domain of a second interferon receptor Fc construct includes and IgA/G chimera.

In other embodiments, the inability of IgG3 to bind protein A can be used for differential tagging of the Fc domain to enable efficient purification of heterodimers (Davis et al., 2013, U.S. Pat. No. 8,586,713, the entire contents of which are herein incorporated by reference). For example, in some embodiments, the Fc domain of a interferon receptor Fc construct includes an H354R mutation.

In some embodiments, CH3 domain mutations can be introduced into IgG1, IgG2, and IgG4 constant regions to promote heterodimerization. In some embodiments, the Fc domain of a first interferon receptor Fc construct may include a 407A substitution, and the Fc domain of a second interferon receptor Fc construct may include a 366V or 366M substitution and a 409V substitution. In some embodiments, the Fc domain of a first interferon receptor Fc construct may include a 407A substitution as well as one or more substitutions selected from the following group of substitutions: 356G, 357D, 360D, 364Q, 364R, and 399M. In some embodiments, the Fc domain of a second interferon receptor Fc construct may include a 366V or 366M substitution and a 409V substitution as well as one or more substitutions selected from the following group of substitutions: 345R, 347R, 349S, 366V, 370Y, and 399M. In some embodiments, the Fc domain of a second interferon receptor Fc construct may include a 366V and a 409V substitution as well as one or more substitutions selected from the following group of substitutions: 345R, 347R, 349S, 366V, 370Y, and 399M. In some embodiments, the Fc domain of a second interferon receptor Fc construct may include a 366M and a 409V substitution as well as one or more substitutions selected from the following group of substitutions: 345R, 347R, 349S, 366V, 370Y, and 399M. (see US2018/0009908 and Lewis et al., nature Biotechnology (2014) 32(2), 191-198, both of which are incorporated by reference in their entirety).

(ii) Appended IgG

In some embodiments, an Fc domain can be engineered to include two different binding domains by appending either the amino and/or carboxyl termini of the Fc domain with one or more binding domains. In some embodiments, the one or more binding domains may be appended to the Fc domain via a peptide linker.

In some embodiments, the binding domain is an IFNAR (e.g., IFNAR1 or IFNAR2), or variant or fragment thereof. In some embodiments, the binding domain is the extracellular domain of IFNAR1 or IFNAR2.

(iii) Bispecific Fragments

In some embodiments, the soluble interferon receptor can lack some or all of the Fc domain. In some embodiments, binding domains and partial Fc domains of a soluble interferon receptor that lacks some or all of the Fc domain may be connected via a peptide linker. In some embodiments, a soluble interferon receptor can be generated using polypeptide linkers to connect each of the domains of the soluble interferon receptor (e.g., binding domains, Fc domains) and thereby generate a single polypeptide chain.

In some embodiments, the binding domain is an IFNAR (e.g., IFNAR1 or IFNAR2), or variant or fragment thereof. In some embodiments, the binding domain is the extracellular domain of IFNAR1 or IFNAR2.

(iv) Bispecific Fusion Proteins

In some embodiments, the binding domains of the soluble interferon receptor are linked to other proteins to add additional functionality of specificity. In some embodiments, the binding domain is an IFNAR (e.g., IFNAR1 or IFNAR2), or variant or fragment thereof. In some embodiments, the binding domain is the extracellular domain of IFNAR1 or IFNAR2.

(v) Bispecific Conjugates

In some embodiments, the binding domains of the soluble interferon receptor are chemically conjugated to each other and/or to an Fc domain. In some embodiments, the binding domain is an IFNAR (e.g., IFNAR1 or IFNAR2), or variant or fragment thereof. In some embodiments, the binding domain is the extracellular domain of IFNAR1 or IFNAR2.

(vi) IgG4 Fab Arm Exchange

In some embodiments, Fab arm exchange can be used to facilitate the heterodimerization of Fc domains. Fab arm exchange is a post translational modification of IgG4 antibodies that involves the third constant domain of IgG4 in addition to the hinge region of IgG4 and requires a reducing environment to be activated. (van der Neut Kolfschoten et al. (2007) Science 317, 1554-1557, the entire contents of which is incorporated herein by reference). IgG4 antibodies exchange Fab arms by swapping a heavy chain and attached light chain with a heavy chain pair from another molecule, which results in bispecific antibodies. (van der Neut Kolfschoten et al. (2007)). In some embodiments, heterodimerization of the soluble interferon receptors of the disclosure can be promoted by replacing the CH3 domain in an IgG1 Fc with the CH3 domain from an IgG4 Fc as well as replacing the IgG1 core hinge sequence with the IgG4 sequence (i.e., by replacing Pro228 with Ser (P228S)).

(vii) Additional Alternative Scaffolds

In some embodiments, engineered proteins scaffolds (e.g., Affibody, DARPin, Adnectins) may be used to generate a molecule with at least two IFNAR binding domains. In some embodiments, the binding domain is the extracellular domain of IFNAR1 or IFNAR2.

PK Moieties

In some embodiments, the soluble interferon receptor is operably coupled to a PK moiety, which serves as a scaffold as well as a means to increase the serum half-life of the soluble interferon receptor.

Suitable PK moieties are well-known in the art and include, but are not limited to, albumin, transferrin, Fc, and their variants, and polyethylene glycol (PEG) and its derivatives. Suitable PK moieties include, but are not limited to, HSA, or variants or fragments thereof, such as those disclosed in U.S. Pat. No. 5,876,969, WO 2011/124718, and WO 2011/0514789; Fc and Fc variants, such as those disclosed in WO2011/053982, WO 02/060955, WO 02/096948, WO05/047327, WO05/018572, and US 2007/0111281; transferrin, or variants or fragments thereof, as disclosed in U.S. Pat. Nos. 7,176,278 and 8,158,579; and PEG or derivatives, such as those disclosed in Zalipsky et al. ("Use of Functionalized Poly(Ethylene Glycols) for Modification of Polypeptides" in Polyethylene Glycol Chemistry: Biotechnical and Biomedical Applications, J. M. Harris, Plenus Press, New York (1992)), and in Zalipsky et al. *Advanced Drug Reviews* 1995:16: 157-182), and U.S. Pat. Nos. 4,640,835, 4,496,689, 4,301,144, 4,670,417, 4,791,192, 4,179,337, and 5,932,462 (the contents of the foregoing are incorporated herein by reference). It is within the abilities of the skilled artisan to use routine methods to introduce PK moieties (e.g., cloning, conjugation) into the soluble interferon receptor of the invention.

In some embodiments, the PK moiety is HSA, which is naturally aglycosylated.

In some embodiments, the PK moiety is a wild type Fc (SEQ ID NO: 26).

In certain embodiments, an Fc domain is altered or modified, e.g., by amino acid mutation (e.g., addition, deletion, or substitution). As used herein, the term "Fc domain variant" refers to an Fc domain having at least one amino acid modification, such as an amino acid substitution, as compared to the wild-type Fc from which the Fc domain is derived. For example, wherein the Fc domain is derived from a human IgG1 antibody, a variant comprises at least one amino acid mutation (e.g., substitution) as compared to a wild type amino acid at the corresponding position of the human IgG1 Fc region.

In some embodiments, the PK moiety is any of the Fc variants described herein.

In some embodiments, the PK moiety is a wild type HST. In other embodiments, the PK moiety is a HST with a mutations at N413 and/or N611 and/or S12 (S12 is a potential O-linked glycosylation site), yielding a HST with altered glycosylation (i.e., HST N413S, HST N611S, HST N413S/N611S and HST S12A/N413S/N611S).

Exemplary Soluble Interferon Receptors

The soluble interferon receptors of the disclosure can be configured to incorporate various interferon receptor Fc constructs. Likewise, the interferon receptor Fc constructs of the invention can be configured to incorporate various domains.

For example, in one embodiment, the interferon receptor Fc construct may include the IFNAR1 domain set forth in (SEQ ID NO: 11). In another embodiment, the interferon receptor Fc construct may include the IFNAR2 domain set forth in (SEQ ID NO: 12). In another embodiment, the interferon receptor Fc construct may include a linker domain. In another embodiment, the IFNAR1 domain is operatively coupled with a linker domain (e.g., a polypeptide linker) to a mutant Fc domain. In some embodiments, the IFNAR2 domain is operatively coupled with a linker domain (e.g., a polypeptide linker) to a mutant Fc domain. In some embodiments, the linker domain is a polypeptide linker (e.g., a Gly/Ser linker, e.g., $(G_4S)_n$, wherein n is 1-10, 2-5, 1, 2, 3, 4, or 5). In some embodiments, the polypeptide linker is about 1-50, about 5-40, about 10-30, or about 15-20 amino acids in length. In some aspects, the polypeptide linker is about 20 amino acids or less, about 15 amino acids or less, about 10 amino acids or less, or about 5 amino acids or less in length. In some aspects, the polypeptide linker is 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 amino acids in length. In another embodiment, the interferon receptor Fc construct may include the $(Gly_4Ser)_4$ linker domain set forth in SEQ ID NO: 15. In another embodiment, the interferon receptor Fc construct may include the $(Gly_4Ser)_2$ linker domain set forth in SEQ ID NO: 38. In another embodiment, the interferon receptor Fc construct does not include a linker domain.

In another embodiment, the interferon receptor Fc construct may include a leader sequence set forth in SEQ ID NO: 13.

In some embodiments, the interferon receptor Fc construct may include an IgG1 Fc domain comprising mutations C220S, P238S, P331S, and T350V, T366L, K392L, and T394W as set forth in (SEQ ID NO: 10). In some embodiments, the interferon receptor Fc construct may include an IgG1 Fc domain comprising mutations C220S, P238S, P331S, and T350V, L351Y, F405A, and Y407V as set forth in (SEQ ID NO: 9). In some embodiments, the interferon Fc receptor construct may include an IgG1 Fc domain comprising the mutation T366Y as set forth in SEQ ID NO: 106, and optionally, one or more mutations selected from C220S, P238S, and P331S. In some embodiments, the interferon Fc receptor construct may include an IgG1 Fc domain comprising the mutation Y407T as set forth in SEQ ID NO: 107, and optionally, one or more mutations selected from C220S, P238S, and P331S. In some embodiments, the interferon Fc receptor construct may include an IgG1 Fc domain comprising the mutation T366W as set forth in SEQ ID NO: 108, and optionally, one or more mutations selected from C220S, P238S, and P331S. In some embodiments, the interferon Fc construct may include an IgG1 Fc domain comprising mutations T366S, L368A, and Y407V as set forth in SEQ ID NO: 109, and optionally, one or more mutations selected from C220S, P238S, and P331S.

In some embodiments, the interferon Fc receptor construct comprises a mutant IgG4 Fc domain comprising mutation S228P, F296Y, E356K, R409K, H435R and L445P according to EU numbering. In some embodiments, the heterodimer comprises a mutant IgG4 Fc domain comprising mutations T366S, L368A and Y407V, according to EU numbering. In some embodiments, the interferon Fc construct comprises the IgG4 Fc domain comprising mutations S228P, F234A, L235A, L445P (EU) and K478del (Kabat) as set forth in SEQ ID NO: 113. In some embodiments, the interferon Fc construct comprises the IgG4 Fc domain with mutations F296Y, E356K, R409K, and H435R (EU) as set forth in SEQ ID NO: 116. In some embodiments, the interferon Fc construct comprises the IgG4 Fc domain with mutations F296Y, R409K, and K439E (EU) as set forth in SEQ ID NO: 117. In some embodiments, the interferon Fc construct comprises the IgG4 Fc domain with mutations S228P, F296Y, E356K, R409K, H435R, L445P, G446del (EU) and K478del(Kabat) as set forth in SEQ ID NO: 118. In some embodiments, the interferon Fc construct comprises the IgG4 Fc domain with mutations S228P, F296Y, R409K, K439E, L445P, G446del (EU) and K478del(Kabat) as set forth in SEQ ID NO: 119.

It will be understood to the skilled artisan that these individual domains can be operably coupled to each other in any order to form an interferon receptor Fc construct that is enzymatically active. For example, as detailed in the specific examples below, an IFNAR1 extracellular domain can be operatively coupled to an Fc domain via a $(Gly_4Ser)_4$ linker domain. In another example, an IFNAR2 extracellular domain can be operatively coupled to an Fc domain via a $(Gly_4Ser)_4$ linker domain. In another example, an IFNAR1 extracellular domain can be operatively coupled to an Fc domain via a $(Gly_4Ser)_2$ linker domain. In another example, an IFNAR2 extracellular domain can be operatively coupled to an Fc domain via a $(Gly_4Ser)_2$ linker domain. In another example, an IFNAR1 extracellular domain can be operably coupled to an Fc domain. In another example, an IFNAR2 extracellular domain can be operably coupled to an Fc domain. Various other configurations are possible, with non-limiting exemplary configurations disclosed herein, in FIG. 1 and in the Sequence Table.

In some embodiments, the interferon receptor Fc construct comprises an IFNAR1 extracellular domain operably coupled to an IgG1 Fc domain comprising mutations C220S, P238S, P331S, and T350V, T366L, K392L, and T394W via a linker domain, such as a $(Gly_4Ser)_4$ linker domain, with or without a leader sequence.

In some embodiments, the interferon receptor Fc construct comprises an IFNAR1 extracellular domain operably coupled to an IgG1 Fc domain comprising mutations C220S, P238S, P331S, and T350V, T366L, K392L, and T394W via a linker domain, such as a $(Gly_4Ser)_2$ linker domain, with or without a leader sequence.

In some embodiments, the interferon receptor Fc construct comprises an IFNAR1 extracellular domain operably coupled to an IgG1 Fc domain comprising mutations C220S, P238S, P331S, and T350V, T366L, K392L, and T394W without a linker domain, with or without a leader sequence.

In some embodiments, the interferon receptor Fc construct comprises an IFNAR2 extracellular domain operably coupled to an IgG1 Fc domain comprising mutations C220S, P238S, P331S, and T350V, T366L, K392L, and T394W via a linker domain, such as a $(Gly_4Ser)_4$ linker domain, with or without a leader sequence.

In some embodiments, the interferon receptor Fc construct comprises an IFNAR2 extracellular domain operably coupled to an IgG1 Fc domain comprising mutations C220S, P238S, P331S, and T350V, T366L, K392L, and T394W via a linker domain, such as a $(Gly_4Ser)_2$ linker domain, with or without a leader sequence.

In some embodiments, the interferon receptor Fc construct comprises an IFNAR2 extracellular domain operably coupled to an IgG1 Fc domain comprising mutations C220S, P238S, P331S, and T350V, T366L, K392L, and T394W without a linker domain, with or without a leader sequence.

In some embodiments, the interferon receptor Fc construct comprises an IFNAR1 extracellular domain operably coupled to an IgG1 Fc domain comprising mutations C220S, P238S, P331S, and T350V, L351Y, F405A, and Y407V via a linker domain, such as a $(Gly_4Ser)_4$ linker domain, with or without a leader sequence.

In some embodiments, the interferon receptor Fc construct comprises an IFNAR1 extracellular domain operably coupled to an IgG1 Fc domain comprising mutations C220S, P238S, P331S, and T350V, L351Y, F405A, and Y407V via a linker domain, such as a $(Gly_4Ser)_2$ linker domain, with or without a leader sequence.

In some embodiments, the interferon receptor Fc construct comprises an IFNAR1 extracellular domain operably coupled to an IgG1 Fc domain comprising mutations C220S, P238S, P331S, and T350V, L351Y, F405A, and Y407V without a linker domain, with or without a leader sequence.

In some embodiments, the interferon receptor Fc construct comprises an IFNAR2 extracellular domain operably coupled to an IgG1 Fc domain comprising mutations C220S, P238S, P331S, and T350V, L351Y, F405A, and Y407V via a linker domain, such as a $(Gly_4Ser)_4$ linker domain, with or without a leader sequence.

In some embodiments, the interferon receptor Fc construct comprises an IFNAR2 extracellular domain operably coupled to an IgG1 Fc domain comprising mutations C220S, P238S, P331S, and T350V, L351Y, F405A, and Y407V via a linker domain, such as a $(Gly_4Ser)_2$ linker domain, with or without a leader sequence.

In some embodiments, the interferon receptor Fc construct comprises an IFNAR2 extracellular domain operably coupled to an IgG1 Fc domain comprising mutations C220S, P238S, P331S, and T350V, L351Y, F405A, and Y407V without a linker domain, with or without a leader sequence.

In some embodiments, the interferon receptor Fc construct comprises an IFNAR1 extracellular domain operably coupled to an IgG1 Fc domain comprising mutation T366Y via a linker domain, such as a $(Gly_4Ser)_4$ linker domain, with or without a leader sequence, and optionally, one or more mutations selected from C220S, P238S, and P331S.

In some embodiments, the interferon receptor Fc construct comprises an IFNAR1 extracellular domain operably coupled to an IgG1 Fc domain comprising mutation T366Y via a linker domain, such as a $(Gly_4Ser)_2$ linker domain, with or without a leader sequence, and optionally, one or more mutations selected from C220S, P238S, and P331S.

In some embodiments, the interferon receptor Fc construct comprises an IFNAR1 extracellular domain operably coupled to an IgG1 Fc domain comprising mutation T366Y without a linker domain, with or without a leader sequence, and optionally, one or more mutations selected from C220S, P238S, and P331S.

In some embodiments, the interferon receptor Fc construct comprises an IFNAR2 extracellular domain operably coupled to an IgG1 Fc domain comprising mutation T366Y via a linker domain, such as a $(Gly_4Ser)_4$ linker domain, with or without a leader sequence, and optionally, one or more mutations selected from C220S, P238S, and P331S.

In some embodiments, the interferon receptor Fc construct comprises an IFNAR2 extracellular domain operably coupled to an IgG1 Fc domain comprising mutation T366Y via a linker domain, such as a (Gly$_4$Ser)$_2$ linker domain, with or without a leader sequence, and optionally, one or more mutations selected from C220S, P238S, and P331S.

In some embodiments, the interferon receptor Fc construct comprises an IFNAR2 extracellular domain operably coupled to an IgG1 Fc domain comprising mutation T366Y without a linker domain, with or without a leader sequence, and optionally, one or more mutations selected from C220S, P238S, and P331S.

In some embodiments, the interferon receptor Fc construct comprises an IFNAR1 extracellular domain operably coupled to an IgG1 Fc domain comprising mutation Y407T via a linker domain, such as a (Gly$_4$Ser)$_4$ linker domain, with or without a leader sequence, and optionally, one or more mutations selected from C220S, P238S, and P331S.

In some embodiments, the interferon receptor Fc construct comprises an IFNAR1 extracellular domain operably coupled to an IgG1 Fc domain comprising mutation Y407T via a linker domain, such as a (Gly$_4$Ser)$_2$ linker domain, with or without a leader sequence, and optionally, one or more mutations selected from C220S, P238S, and P331S.

In some embodiments, the interferon receptor Fc construct comprises an IFNAR1 extracellular domain operably coupled to an IgG1 Fc domain comprising mutation Y407T without a linker domain, with or without a leader sequence, and optionally, one or more mutations selected from C220S, P238S, and P331S.

In some embodiments, the interferon receptor Fc construct comprises an IFNAR2 extracellular domain operably coupled to an IgG1 Fc domain comprising mutation Y407T via a linker domain, such as a (Gly$_4$Ser)$_4$ linker domain, with or without a leader sequence, and optionally, one or more mutations selected from C220S, P238S, and P331S.

In some embodiments, the interferon receptor Fc construct comprises an IFNAR2 extracellular domain operably coupled to an IgG1 Fc domain comprising mutation Y407T via a linker domain, such as a (Gly$_4$Ser)$_2$ linker domain, with or without a leader sequence, and optionally, one or more mutations selected from C220S, P238S, and P331S.

In some embodiments, the interferon receptor Fc construct comprises an IFNAR2 extracellular domain operably coupled to an IgG1 Fc domain comprising mutation Y407T without a linker domain, with or without a leader sequence, and optionally, one or more mutations selected from C220S, P238S, and P331S.

In some embodiments, the interferon receptor Fc construct comprises an IFNAR1 extracellular domain operably coupled to an IgG1 Fc domain comprising mutation T366W via a linker domain, such as a (Gly$_4$Ser)$_4$ linker domain, with or without a leader sequence, and optionally, one or more mutations selected from C220S, P238S, and P331S.

In some embodiments, the interferon receptor Fc construct comprises an IFNAR1 extracellular domain operably coupled to an IgG1 Fc domain comprising mutation T366W via a linker domain, such as a (Gly$_4$Ser)$_2$ linker domain, with or without a leader sequence, and optionally, one or more mutations selected from C220S, P238S, and P331S.

In some embodiments, the interferon receptor Fc construct comprises an IFNAR1 extracellular domain operably coupled to an IgG1 Fc domain comprising mutation T366W without a linker domain, with or without a leader sequence, and optionally, one or more mutations selected from C220S, P238S, and P331S.

In some embodiments, the interferon receptor Fc construct comprises an IFNAR2 extracellular domain operably coupled to an IgG1 Fc domain comprising mutation T366W via a linker domain, such as a (Gly$_4$Ser)$_4$ linker domain, with or without a leader sequence, and optionally, one or more mutations selected from C220S, P238S, and P331S.

In some embodiments, the interferon receptor Fc construct comprises an IFNAR2 extracellular domain operably coupled to an IgG1 Fc domain comprising mutation T366W via a linker domain, such as a (Gly$_4$Ser)$_2$ linker domain, with or without a leader sequence, and optionally, one or more mutations selected from C220S, P238S, and P331S.

In some embodiments, the interferon receptor Fc construct comprises an IFNAR2 extracellular domain operably coupled to an IgG1 Fc domain comprising mutation T366W without a linker domain, with or without a leader sequence, and optionally, one or more mutations selected from C220S, P238S, and P331S.

In some embodiments, the interferon receptor Fc construct comprises an IFNAR1 extracellular domain operably coupled to an IgG1 Fc domain comprising mutations T366S, L368A, and Y407V via a linker domain, such as a (Gly$_4$Ser)$_4$ linker domain, with or without a leader sequence, and optionally, one or more mutations selected from C220S, P238S, and P331S.

In some embodiments, the interferon receptor Fc construct comprises an IFNAR1 extracellular domain operably coupled to an IgG1 Fc domain comprising mutations T366S, L368A, and Y407V via a linker domain, such as a (Gly$_4$Ser)$_2$ linker domain, with or without a leader sequence, and optionally, one or more mutations selected from C220S, P238S, and P331S.

In some embodiments, the interferon receptor Fc construct comprises an IFNAR1 extracellular domain operably coupled to an IgG1 Fc domain comprising mutations T366S, L368A, and Y407V without a linker domain, with or without a leader sequence, and optionally, one or more mutations selected from C220S, P238S, and P331S.

In some embodiments, the interferon receptor Fc construct comprises an IFNAR2 extracellular domain operably coupled to an IgG1 Fc domain comprising mutations T366S, L368A, and Y407V via a linker domain, such as a (Gly$_4$Ser)$_4$ linker domain, with or without a leader sequence, and optionally, one or more mutations selected from C220S, P238S, and P331S.

In some embodiments, the interferon receptor Fc construct comprises an IFNAR2 extracellular domain operably coupled to an IgG1 Fc domain comprising mutations T366S, L368A, and Y407V via a linker domain, such as a (Gly$_4$Ser)$_2$ linker domain, with or without a leader sequence, and optionally, one or more mutations selected from C220S, P238S, and P331S.

In some embodiments, the interferon receptor Fc construct comprises an IFNAR2 extracellular domain operably coupled to an IgG1 Fc domain comprising mutations T366S, L368A, and Y407V without a linker domain, with or without a leader sequence, and optionally, one or more mutations selected from C220S, P238S, and P331S.

In some embodiments, the interferon receptor Fc construct comprises a IFNAR1 operably coupled to an IgG4 Fc domain comprising mutations F296Y, E356K, R409K, and H435R via a linker domain, such as a (Gly$_4$Ser)$_4$ linker domain, with or without a leader sequence.

In some embodiments, the interferon receptor Fc construct comprises a IFNAR1 operably coupled to an IgG4 Fc domain comprising mutations F296Y, E356K, R409K, and H435R via a linker domain, such as a (Gly$_4$Ser)$_2$ linker domain, with or without a leader sequence.

In some embodiments, the interferon receptor Fc construct comprises a IFNAR1 operably coupled to an IgG4 Fc domain comprising mutations F296Y, E356K, R409K, and H435R without a linker domain, with or without a leader sequence.

In some embodiments, the interferon receptor Fc construct comprises a IFNAR2 operably coupled to an IgG4 Fc domain comprising mutations F296Y, E356K, R409K, and H435R via a linker domain, such as a (Gly$_4$Ser)$_4$ linker domain, with or without a leader sequence.

In some embodiments, the interferon receptor Fc construct comprises a IFNAR2 operably coupled to an IgG4 Fc domain comprising mutations F296Y, E356K, R409K, and H435R via a linker domain, such as a (Gly$_4$Ser)$_2$ linker domain, with or without a leader sequence.

In some embodiments, the interferon receptor Fc construct comprises a IFNAR2 operably coupled to an IgG4 Fc domain comprising mutations F296Y, E356K, R409K, and H435R without a linker domain, with or without a leader sequence.

In some embodiments, the interferon receptor Fc construct comprises a IFNAR1 operably coupled to an IgG4 Fc domain comprising mutations F296Y, R409K, and K439E via a linker domain, such as a (Gly$_4$Ser)$_4$ linker domain, with or without a leader sequence.

In some embodiments, the interferon receptor Fc construct comprises a IFNAR1 operably coupled to an IgG4 Fc domain comprising mutations F296Y, R409K, and K439E via a linker domain, such as a (Gly$_4$Ser)$_2$ linker domain, with or without a leader sequence.

In some embodiments, the interferon receptor Fc construct comprises a IFNAR1 operably coupled to an IgG4 Fc domain comprising mutations F296Y, R409K, and K439E without a linker domain, with or without a leader sequence.

In some embodiments, the interferon receptor Fc construct comprises a IFNAR2 operably coupled to an IgG4 Fc domain comprising mutations F296Y, R409K, and K439E via a linker domain, such as a (Gly$_4$Ser)$_4$ linker domain, with or without a leader sequence.

In some embodiments, the interferon receptor Fc construct comprises a IFNAR2 operably coupled to an IgG4 Fc domain comprising mutations F296Y, R409K, and K439E via a linker domain, such as a (Gly$_4$Ser)$_2$ linker domain, with or without a leader sequence.

In some embodiments, the interferon receptor Fc construct comprises a IFNAR2 operably coupled to an IgG4 Fc domain comprising mutations F296Y, R409K, and K439E without a linker domain, with or without a leader sequence.

In some embodiments, the interferon receptor Fc construct comprises the amino acid sequence set forth as SEQ ID NO: 1, with or without a leader sequence, and nucleic acids encoding the amino acid sequence set forth as SEQ ID NO:1.

In some embodiments, the interferon receptor Fc construct comprises the amino acid sequence set forth as SEQ ID NO: 2, with or without a leader sequence, and nucleic acids encoding the amino acid sequence set forth as SEQ ID NO:2.

In some embodiments, the interferon receptor Fc construct comprises the amino acid sequence set forth as SEQ ID NO: 3, with or without a leader sequence, and nucleic acids encoding the amino acid sequence set forth as SEQ ID NO:3.

In some embodiments, the interferon receptor Fc construct comprises the amino acid sequence set forth as SEQ ID NO: 4, with or without a leader sequence, and nucleic acids encoding the amino acid sequence set forth as SEQ ID NO:4.

In some embodiments, the interferon receptor Fc construct comprises the amino acid sequence set forth as SEQ ID NO: 52, with or without a leader sequence, and nucleic acids encoding the amino acid sequence set forth as SEQ ID NO: 52.

In some embodiments, the interferon receptor Fc construct comprises the amino acid sequence set forth as SEQ ID NO: 54, with or without a leader sequence, and nucleic acids encoding the amino acid sequence set forth as SEQ ID NO: 54.

In some embodiments, the interferon receptor Fc construct comprises the amino acid sequence set forth as SEQ ID NO: 56, with or without a leader sequence, and nucleic acids encoding the amino acid sequence set forth as SEQ ID NO: 56.

In some embodiments, the interferon receptor Fc construct comprises the amino acid sequence set forth as SEQ ID NO: 58, with or without a leader sequence, and nucleic acids encoding the amino acid sequence set forth as SEQ ID NO: 58.

In some embodiments, the interferon receptor Fc constructs dimerize to form a soluble interferon receptor, such as a heterodimeric soluble interferon receptor. For example, in some embodiments, the soluble interferon receptor comprises a heterodimer comprising an interferon receptor Fc construct comprising an IFNAR1 extracellular domain operably coupled to an IgG1 Fc domain comprising mutations C220S, P238S, P331S, and T350V, T366L, K392L, and T394W via a linker domain, such as a (Gly$_4$Ser)$_4$ linker domain, with or without a leader sequence, and an interferon receptor Fc construct comprising an IFNAR2 extracellular domain operably coupled to an IgG1 Fc domain comprising mutations C220S, P238S, P331S, and T350V, L351Y, F405A, and Y407V via a linker domain, such as a (Gly$_4$Ser)$_4$ linker domain, with or without a leader sequence. For example, in some embodiments, the soluble interferon receptor comprises a heterodimer comprising an interferon receptor Fc construct comprising an IFNAR2 extracellular domain operably coupled to an IgG1 Fc domain comprising mutations C220S, P238S, P331S, and T350V, T366L, K392L, and T394W via a linker domain, such as a (Gly$_4$Ser)$_4$ linker domain, with or without a leader sequence, and an interferon receptor Fc construct comprising an IFNAR1 extracellular domain operably coupled to an IgG1 Fc domain comprising mutations C220S, P238S, P331S, and T350V, L351Y, F405A, and Y407V via a linker domain, such as a (Gly$_4$Ser)$_4$ linker domain, with or without a leader sequence.

In some embodiments, the soluble interferon receptor comprises a heterodimer comprising an interferon receptor Fc construct comprising an IFNAR1 extracellular domain operably coupled to an IgG1 Fc domain comprising mutations C220S, P238S, P331S, and T350V, T366L, K392L, and T394W via a linker domain, such as a (Gly$_4$Ser)$_2$ linker domain, with or without a leader sequence, and an interferon receptor Fc construct comprising an IFNAR2 extracellular domain operably coupled to an IgG1 Fc domain comprising mutations C220S, P238S, P331S, and T350V, L351Y, F405A, and Y407V via a linker domain, such as a (Gly$_4$Ser)$_2$ linker domain, with or without a leader sequence. For example, in some embodiments, the soluble interferon receptor comprises a heterodimer comprising an interferon receptor Fc construct comprising an IFNAR2 extracellular domain operably coupled to an IgG1 Fc domain comprising mutations C220S, P238S, P331S, and T350V, T366L, K392L, and T394W via a linker domain, such as a (Gly$_4$Ser)$_2$ linker domain, with or without a leader sequence, and an interferon receptor Fc construct comprising an IFNAR1 extracellular domain operably coupled to an IgG1 Fc domain comprising mutations C220S, P238S, P331S, and T350V, L351Y, F405A, and Y407V via a linker domain, such as a (Gly$_4$Ser)$_2$ linker domain, with or without a leader sequence.

In some embodiments, the soluble interferon receptor comprises a heterodimer comprising an interferon receptor Fc construct comprising an IFNAR1 extracellular domain operably coupled to an IgG1 Fc domain comprising mutations C220S, P238S, P331S, and T350V, T366L, K392L, and T394W without a linker domain, with or without a leader sequence, and an interferon receptor Fc construct comprising an IFNAR2 extracellular domain operably coupled to an IgG1 Fc domain comprising mutations C220S, P238S, P331S, and T350V, L351Y, F405A, and Y407V without a linker domain, with or without a leader sequence. For example, in some embodiments, the soluble interferon receptor comprises a heterodimer comprising an interferon receptor Fc construct comprising an IFNAR2 extracellular domain operably coupled to an IgG1 Fc domain comprising mutations C220S, P238S, P331S, and T350V, T366L, K392L, and T394W without a linker domain, with or without a leader sequence, and an interferon receptor Fc construct comprising an IFNAR1 extracellular domain operably coupled to an IgG1 Fc domain comprising mutations C220S, P238S, P331S, and T350V, L351Y, F405A, and Y407V without a linker domain, with or without a leader sequence.

In some embodiments, the soluble interferon receptor comprises a heterodimer comprising an interferon receptor Fc construct comprising an IFNAR1 extracellular domain operably coupled to an IgG1 Fc domain comprising mutation T366Y via a linker domain, such as a (Gly$_4$Ser)$_4$ linker domain, with or without a leader sequence, and an interferon receptor Fc construct comprising an IFNAR2 extracellular domain operably coupled to an IgG1 Fc domain comprising mutation Y407T via a linker domain, such as a (Gly$_4$Ser)$_4$ linker domain, with or without a leader sequence. For example, in some embodiments, the soluble interferon receptor comprises a heterodimer comprising an interferon receptor Fc construct comprising an IFNAR1 extracellular domain operably coupled to an IgG1 Fc domain comprising mutation Y407T via a linker domain, such as a (Gly$_4$Ser)$_4$ linker domain, with or without a leader sequence, and an interferon receptor Fc construct comprising an IFNAR2 extracellular domain operably coupled to an IgG1 Fc domain comprising mutation T366Y via a linker domain, such as a (Gly$_4$Ser)$_4$ linker domain, with or without a leader sequence.

In some embodiments, the soluble interferon receptor comprises a heterodimer comprising an interferon receptor Fc construct comprising an IFNAR1 extracellular domain operably coupled to an IgG1 Fc domain comprising mutation T366Y via a linker domain, such as a (Gly$_4$Ser)$_2$ linker domain, with or without a leader sequence, and an interferon receptor Fc construct comprising an IFNAR2 extracellular domain operably coupled to an IgG1 Fc domain comprising mutation Y407T via a linker domain, such as a (Gly$_4$Ser)$_2$ linker domain, with or without a leader sequence. For example, some embodiments, the soluble interferon receptor Fc construct comprises a heterodimer comprising an interferon receptor Fc construct comprising an IFNAR1 extracellular domain operably coupled to an IgG1 Fc domain comprising mutation Y407T via a linker domain, such as a (Gly$_4$Ser)$_2$ linker domain, with or without a leader sequence, and an interferon receptor Fc construct comprising an IFNAR2 extracellular domain operably coupled to an IgG1 Fc domain comprising mutation T366Y via a linker domain, such as a (Gly$_4$Ser)$_2$ linker domain, with or without a leader sequence.

In some embodiments, the soluble interferon receptor comprises a heterodimer comprising an interferon receptor Fc construct comprising an IFNAR1 extracellular domain operably coupled to an IgG1 Fc domain comprising mutation T366Y without a linker domain, with or without a leader sequence, and an interferon receptor Fc construct comprising an IFNAR2 extracellular domain operably coupled to an IgG1 Fc domain comprising mutation Y407T without a linker domain, with or without a leader sequence. For example, in some embodiments, the soluble interferon receptor comprises a heterodimer comprising an interferon receptor Fc construct comprising an IFNAR1 extracellular domain operably coupled to a Fc domain comprising mutation Y407T without a linker domain, with or without a leader sequence, and an interferon receptor Fc construct comprises an IFNAR2 extracellular domain operably coupled to an IgG1 Fc domain comprising mutation T366Y without a linker domain, with or without a leader sequence.

In some embodiments, the soluble interferon receptor comprises a heterodimer comprising an interferon receptor Fc construct comprising an IFNAR1 extracellular domain operably coupled to an IgG1 Fc domain comprising mutation T366W via a linker domain, such as a (Gly$_4$Ser)$_4$ linker domain, with or without a leader sequence, and an interferon receptor Fc construct comprising an IFNAR2 extracellular domain operably coupled to an IgG1 Fc domain comprising mutations T366S, L368A, and Y407V via a linker domain, such as a (Gly$_4$Ser)$_4$ linker domain, with or without a leader sequence. For example, in some embodiments, the soluble interferon receptor comprises a heterodimer comprising an interferon receptor Fc construct comprising an IFNAR1 extracellular domain operably coupled to an IgG1 Fc domain comprising mutations T366S, L368A, and Y407V via a linker domain, such as a (Gly$_4$Ser)$_4$ linker domain, with or without a leader sequence, and an interferon receptor Fc construct comprising an IFNAR2 extracellular domain operably coupled to an IgG1 Fc domain comprising mutation T366W via a linker domain, such as a (Gly$_4$Ser)$_4$ linker domain, with or without a leader sequence.

In some embodiments, the soluble interferon receptor comprises a heterodimer comprising an interferon receptor Fc construct comprising an IFNAR1 extracellular domain operably coupled to an IgG1 Fc domain comprising mutation T366W via a linker domain, such as a (Gly$_4$Ser)$_2$ linker domain, with or without a leader sequence, and an interferon receptor Fc construct comprising an IFNAR2 extracellular domain operably coupled to an IgG1 Fc domain comprising mutations T366S, L368A, and Y407V via a linker domain, such as a (Gly$_4$Ser)$_2$ linker domain, with or without a leader sequence. For example, in some embodiments, the soluble interferon receptor comprises a heterodimer comprising an interferon receptor Fc construct comprising an IFNAR1 extracellular domain operably coupled to an IgG1 Fc domain comprising mutations T366S, L368A, and Y407V via a linker domain, such as a (Gly$_4$Ser)$_2$ linker domain, with or without a leader sequence, and an interferon receptor Fc construct comprising an IFNAR2 extracellular domain operably coupled to an IgG1 Fc domain comprising mutation T366W via a linker domain, such as a (Gly$_4$Ser)$_2$ linker domain, with or without a leader sequence.

In some embodiments, the soluble interferon receptor comprises a heterodimer comprising an interferon receptor Fc construct comprising an IFNAR1 extracellular domain operably coupled to an IgG1 Fc domain comprising mutation T366W without a linker domain, with or without a leader sequence, and an interferon receptor Fc construct comprising an IFNAR2 extracellular domain operably coupled to an IgG1 Fc domain comprising mutations T366S, L368A, and Y407V without a linker domain, with or without a leader sequence. For example, in some embodiments, the soluble interferon receptor comprises a heterodimer comprising an interferon receptor Fc construct comprising an IFNAR1 extracellular domain operably coupled to an IgG1 Fc domain comprising mutations T366S, L368A, and Y407V without a linker domain, with or without a leader sequence, and an interferon receptor Fc construct comprising an IFNAR2 extracellular domain operably coupled to an IgG1 Fc domain comprising mutation T366W without a linker domain, with or without a leader sequence.

In some embodiments, the soluble interferon receptor comprises a heterodimer comprising an interferon receptor Fc construct comprising a IFNAR1 operably coupled to an IgG4 Fc domain comprising mutations F296Y, E356K, R409K, and H435R via a linker domain, such as a (Gly$_4$Ser)$_4$ linker domain, with or without a leader sequence, and an interferon receptor Fc construct comprising a IFNAR2 operably coupled to an IgG4 Fc domain comprising mutations F296Y, R409K, and K439E via a linker domain, such as a (Gly$_4$Ser)$_4$ linker domain, with or without a leader sequence. For example, in some embodiments, the soluble interferon receptor comprises a heterodimer comprising an interferon receptor Fc construct comprising a IFNAR1 operably coupled to an IgG4 Fc domain comprising mutations F296Y, R409K, and K439E via a linker domain, such as a (Gly$_4$Ser)$_4$ linker domain, with or without a leader sequence, and an interferon receptor Fc construct comprising a IFNAR2 operably coupled to an IgG4 Fc domain comprising mutations F296Y, E356K, R409K, and H435R via a linker domain, such as a (Gly$_4$Ser)$_4$ linker domain, with or without a leader sequence.

In some embodiments, the soluble interferon receptor comprises a heterodimer comprising an interferon receptor Fc construct comprising a IFNAR1 operably coupled to an IgG4 Fc domain comprising mutations F296Y, E356K, R409K, and H435R via a linker domain, such as a (Gly$_4$Ser)$_2$ linker domain, with or without a leader sequence, and an interferon receptor Fc construct comprising a IFNAR2 operably coupled to an IgG4 Fc domain comprising mutations F296Y, R409K, and K439E via a linker domain, such as a (Gly$_4$Ser)$_2$ linker domain, with or without a leader sequence. For example, in some embodiments, the soluble interferon receptor Fc construct comprises a heterodimer comprising an interferon receptor Fc construct comprising a IFNAR1 operably coupled to an IgG4 Fc domain comprising mutations F296Y, R409K, and K439E via a linker domain, such as a (Gly$_4$Ser)$_2$ linker domain, with or without a leader sequence, and an interferon receptor Fc construct comprising a IFNAR2 operably coupled to an IgG4 Fc domain comprising mutations F296Y, E356K, R409K, and H435R via a linker domain, such as a (Gly$_4$Ser)$_2$ linker domain, with or without a leader sequence.

In some embodiments, the soluble interferon receptor comprises a heterodimer comprising an interferon receptor Fc construct comprising a IFNAR1 operably coupled to an IgG4 Fc domain comprising mutations F296Y, E356K, R409K, and H435R without a linker domain, with or without a leader sequence, and an interferon receptor Fc construct comprising a IFNAR2 operably coupled to an IgG4 Fc domain comprising mutations F296Y, R409K, and K439E without a linker domain, with or without a leader sequence. For example, in some embodiments, the soluble interferon receptor Fc construct comprises a heterodimer comprising an interferon receptor Fc construct comprising a IFNAR1 operably coupled to an IgG4 Fc domain comprising mutations F296Y, R409K, and K439E without a linker domain, with or without a leader sequence, and an interferon receptor Fc construct comprising a IFNAR2 operably coupled to an IgG4 Fc domain comprising mutations F296Y, E356K, R409K, and H435R without a linker domain, with or without a leader sequence.

In some embodiments, a soluble interferon receptor is a heterodimer comprising a polypeptide comprising the amino acid sequence set forth in SEQ ID NO: 1 and a polypeptide comprising the amino acid sequence set for in SEQ ID NO: 4.

In some embodiments, a soluble interferon receptor is a heterodimer comprising a polypeptide comprising the amino acid sequence set forth in SEQ ID NO: 2 and a polypeptide comprising the amino acid sequence set for in SEQ ID NO: 3.

In some embodiments, a soluble interferon receptor is a heterodimer comprising a polypeptide comprising the amino acid sequence set forth in SEQ ID NO: 52 and a polypeptide comprising the amino acid sequence set for in SEQ ID NO: 54.

In some embodiments, a soluble interferon receptor is a heterodimer comprising a polypeptide comprising the amino acid sequence set forth in SEQ ID NO: 56 and a polypeptide comprising the amino acid sequence set for in SEQ ID NO: 58.

In some embodiments, a soluble interferon receptor is a heterodimer comprising a polypeptide comprising the amino acid sequence set forth in SEQ ID NO: 40 and a polypeptide comprising the amino acid sequence set for in SEQ ID NO: 43.

In some embodiments, a soluble interferon receptor is a heterodimer comprising a polypeptide comprising the amino acid sequence set forth in SEQ ID NO: 41 and a polypeptide comprising the amino acid sequence set for in SEQ ID NO: 42.

In some embodiments, a soluble interferon receptor is a heterodimer comprising a polypeptide comprising the amino acid sequence set forth in SEQ ID NO: 53 and a polypeptide comprising the amino acid sequence set for in SEQ ID NO: 55.

In some embodiments, a soluble interferon receptor is a heterodimer comprising a polypeptide comprising the amino acid sequence set forth in SEQ ID NO: 57 and a polypeptide comprising the amino acid sequence set for in SEQ ID NO: 59.

In some embodiments, an interferon receptor Fc construct comprises a polypeptide having an amino acid sequence at least 70% identical, such as 70%, 75%, 80%, 85%, 90%, 91%, 92%, 93%, 94%, 95%, 96%, 97%, 98%, 99%, or at least 99.5% identical to the amino acid sequence of SEQ ID NO: 1. In some embodiments, an interferon receptor Fc construct comprises a polypeptide having an amino acid sequence at least 70% identical, such as 70%, 75%, 80%, 85%, 90%, 91%, 92%, 93%, 94%, 95%, 96%, 97%, 98%, 99%, or at least 99.5% identical to the amino acid sequence of SEQ ID NO: 2. In some embodiments, an interferon receptor Fc construct comprises a polypeptide having an amino acid sequence at least 70% identical, such as 70%, 75%, 80%, 85%, 90%, 91%, 92%, 93%, 94%, 95%, 96%, 97%, 98%, 99%, or at least 99.5% identical to the amino acid sequence of SEQ ID NO: 3. In some embodiments, an interferon receptor Fc construct comprises a polypeptide having an amino acid sequence at least 70% identical, such as 70%, 75%, 80%, 85%, 90%, 91%, 92%, 93%, 94%, 95%, 96%, 97%, 98%, 99%, or at least 99.5% identical to the amino acid sequence of SEQ ID NO: 4. In some embodiments, an interferon receptor Fc construct comprises a polypeptide having an amino acid sequence at least 70% identical, such as 70%, 75%, 80%, 85%, 90%, 91%, 92%, 93%, 94%, 95%, 96%, 97%, 98%, 99%, or at least 99.5% identical to the amino acid sequence of SEQ ID NO: 52. In some embodiments, an interferon receptor Fc construct comprises a polypeptide having an amino acid sequence at least 70% identical, such as 70%, 75%, 80%, 85%, 90%, 91%, 92%, 93%, 94%, 95%, 96%, 97%, 98%, 99%, or at least 99.5% identical to the amino acid sequence of SEQ ID NO: 54. In some embodiments, an interferon receptor Fc construct comprises a polypeptide having an amino acid sequence at least 70% identical, such as 70%, 75%, 80%, 85%, 90%, 91%, 92%, 93%, 94%, 95%, 96%, 97%, 98%, 99%, or at least 99.5% identical to the amino acid sequence of SEQ ID NO: 56. In some embodiments, an interferon receptor Fc construct comprises a polypeptide having an amino acid sequence at least 70% identical, such as 70%, 75%, 80%, 85%, 90%, 91%, 92%, 93%, 94%, 95%, 96%, 97%, 98%, 99%, or at least 99.5% identical to the amino acid sequence of SEQ ID NO: 58. In some embodiments, an interferon receptor Fc construct comprises a polypeptide having an amino acid sequence at least 70% identical, such as 70%, 75%, 80%, 85%, 90%, 91%, 92%, 93%, 94%, 95%, 96%, 97%, 98%, 99%, or at least 99.5% identical to the amino acid sequence of SEQ ID NO: 40. In some embodiments, an interferon receptor Fc construct comprises a polypeptide having an amino acid sequence at least 70% identical, such as 70%, 75%, 80%, 85%, 90%, 91%, 92%, 93%, 94%, 95%, 96%, 97%, 98%, 99%, or at least 99.5% identical to the amino acid sequence of SEQ ID NO: 43. In some embodiments, an interferon receptor Fc construct comprises a polypeptide having an amino acid sequence at least 70% identical, such as 70%, 75%, 80%, 85%, 90%, 91%, 92%, 93%, 94%, 95%, 96%, 97%, 98%, 99%, or at least 99.5% identical to the amino acid sequence of SEQ ID NO: 41. In some embodiments, an interferon receptor Fc construct comprises a polypeptide having an amino acid sequence at least 70% identical, such as 70%, 75%, 80%, 85%, 90%, 91%, 92%, 93%, 94%, 95%, 96%, 97%, 98%, 99%, or at least 99.5% identical to the amino acid sequence of SEQ ID NO: 42. In some embodiments, an interferon receptor Fc construct comprises a polypeptide having an amino acid sequence at least 70% identical, such as 70%, 75%, 80%, 85%, 90%, 91%, 92%, 93%, 94%, 95%, 96%, 97%, 98%, 99%, or at least 99.5% identical to the amino acid sequence of SEQ ID NO: 53. In some embodiments, an interferon receptor Fc construct comprises a polypeptide having an amino acid sequence at least 70% identical, such as 70%, 75%, 80%, 85%, 90%, 91%, 92%, 93%, 94%, 95%, 96%, 97%, 98%, 99%, or at least 99.5% identical to the amino acid sequence of SEQ ID NO: 55. In some embodiments, an interferon receptor Fc construct comprises a polypeptide having an amino acid sequence at least 70% identical, such as 70%, 75%, 80%, 85%, 90%, 91%, 92%, 93%, 94%, 95%, 96%, 97%, 98%, 99%, or at least 99.5% identical to the amino acid sequence of SEQ ID NO: 57. In some embodiments, an interferon receptor Fc construct comprises a polypeptide having an amino acid sequence at least 70% identical, such as 70%, 75%, 80%, 85%, 90%, 91%, 92%, 93%, 94%, 95%, 96%, 97%, 98%, 99%, or at least 99.5% identical to the amino acid sequence of SEQ ID NO: 59. In some embodiments, the polypeptide comprises an amino acid sequence selected from any one of SEQ ID NOs: 1-4, 52, 54, 56, 58, 40, 43, 41, 42, 43, 55, 57 or 59.

In some embodiments, the foregoing interferon receptor Fc constructs have a leader sequence. In some embodiments, the foregoing interferon receptor Fc constructs do not have a leader sequence.

It will be understood by one of ordinary skill that the leader and linker sequences are optional and are not limited to those described in the embodiments above. For example, the IFNAR domains (e.g., IFNAR1, IFNAR2) can be directly fused to the N- and/or C-terminus of an Fc domain, or variant or fragment thereof; the leader domain can be any of those known in the art to be useful for its intended purpose, e.g., to increase protein expression and/or secretion (e.g., MDWTWRILFLVAAATGTHA; SEQ ID NO: 13); the linker can be any linker known in the art, e.g., $(Gly_4Ser)_n$, NLG (VDGASSPVNVSSPSVQDI; SEQ ID NO: 18), LE, thrombin-sensitive disulphide cyclopeptide linker, LEA $(EAAAK)_4ALEA(EAAAK)_4$ (SEQ ID NO: 19), or an in vivo cleavable disulphide linker, as described herein. It will also be understood that it is within the abilities of a skilled artisan to make the corresponding changes to the amino acid sequences of the interferon receptor Fc constructs using routine cloning and recombination methods.

Methods of Making Soluble Interferon Receptors

The interferon receptor Fc constructs of this disclosure largely may be made in transformed or transfected host cells using recombinant DNA techniques. To do so, a recombinant DNA molecule coding for the peptide is prepared. Methods of preparing such DNA molecules are well known in the art. For instance, sequences coding for the interferon receptor Fc constructs could be excised from DNA using suitable restriction enzymes. Alternatively, the DNA molecule could be synthesized using chemical synthesis techniques, such as the phosphoramidate method. Also, a combination of these techniques could be used.

The invention also includes a vector capable of expressing the interferon receptor Fc constructs in an appropriate host. The vector comprises the DNA molecule that codes for the interferon receptor Fc construct operably coupled to appropriate expression control sequences. Methods of affecting this operative linking, either before or after the DNA molecule is inserted into the vector, are well known. Expression control sequences include promoters, activators, enhancers, operators, ribosomal nuclease domains, start signals, stop signals, cap signals, polyadenylation signals, and other signals involved with the control of transcription or translation.

The resulting vector having the DNA molecule thereon is used to transform or transfect an appropriate host. In some embodiments, the soluble interferon receptors of the disclosure may be made by co-transfecting or co-transforming two or more expression vectors comprising DNA that codes for an interferon receptor Fc construct into an appropriate host. This transformation or transfection may be performed using methods well known in the art.

Any of a large number of available and well-known host cells may be used in the practice of this invention. The selection of a particular host is dependent upon a number of factors recognized by the art. These include, for example, compatibility with the chosen expression vector, toxicity of the interferon receptor Fc constructs encoded by the DNA molecule, rate of transformation or transfection, ease of recovery of the interferon receptor Fc constructs, expression characteristics, bio-safety and costs. A balance of these factors must be struck with the understanding that not all hosts may be equally effective for the expression of a particular DNA sequence. Within these general guidelines, useful microbial hosts include bacteria (such as *E. coli*), yeast (such as Saccharomyces) and other fungi, insects, plants, mammalian (including human) cells in culture, or other hosts known in the art. In some embodiments, the interferon receptor Fc constructs are produced in CHO cells.

Next, the transformed or transfected host is cultured and purified. Host cells may be cultured under conventional fermentation or culture conditions so that the desired compounds are expressed. Such fermentation and culture conditions are well known in the art. Finally, the interferon receptor Fc constructs are purified from culture by methods well known in the art.

The compounds may also be made by synthetic methods. For example, solid phase synthesis techniques may be used. Suitable techniques are well known in the art, and include those described in Merrifield (1973), Chem. Polypeptides, pp. 335-61 (Katsoyannis and Panayotis eds.); Merrifield (1963), J. Am. Chem. Soc. 85: 2149; Davis et al., *Biochem Intl* 1985; 10: 394-414; Stewart and Young (1969), Solid Phase Peptide Synthesis; U.S. Pat. No. 3,941,763; Finn et al. (1976), The Proteins (3rd ed.) 2: 105-253; and Erickson et al. (1976), The Proteins (3rd ed.) 2: 257-527. In some embodiments, compounds that contain derivatized peptides or which contain non-peptide groups may be synthesized by well-known organic chemistry techniques.

Other methods are of molecule expression/synthesis are generally known in the art to one of ordinary skill.

Soluble Interferon Receptors with Altered Glycosylation

Glycosylation (e.g., O-linked or N-linked glycosylation) can impact the serum half-life of the soluble interferon receptor of the disclosure by, e.g., minimizing their removal from circulation by mannose and asialoglycoprotein receptors and other lectin-like receptors. Accordingly, in some embodiments, the soluble interferon receptors of the disclosure are prepared in aglycosylated, deglycosylated, or under-glycosylated form. Preferably, N-linked glycosylation is altered and the soluble interferon receptor is aglycosyated.

In some embodiments, all asparagine residues in a soluble interferon receptor that conform to the Asn-X-Ser/Thr (X can be any other naturally occurring amino acid except Pro) consensus are mutated to residues that do not serve as acceptors of N-linked glycosylation (e.g., serine, glutamine), thereby eliminating glycosylation of the soluble interferon receptor when synthesized in a cell that glycosylates proteins.

In some embodiments, soluble interferon receptor lacking N-linked glycosylation sites are produced in mammalian cells. In one embodiment, the mammalian cell is a CHO cell. Accordingly, in a specific embodiment, an aglycosylated soluble interferon receptor is produced in a CHO cell.

In other embodiments, a reduction or lack of N-glycosylation is achieved by, e.g., producing soluble interferon receptors in a host (e.g., bacteria such as *E. coli*), mammalian cells engineered to lack one or more enzymes important for glycosylation, or mammalian cells treated with agents that prevent glycosylation, such as tunicamycin (an inhibitor of Dol-PP-GlcNAc formation).

In some embodiments, the soluble interferon receptors are produced in lower eukaryotes engineered to produce glycoproteins with complex N-glycans, rather than high mannose type sugars (see, e.g., US2007/0105127).

In some embodiments, glycosylated soluble interferon receptors (e.g., those produced in mammalian cells such as CHO cells) are treated chemically or enzymatically to remove one or more carbohydrate residues (e.g., one or more mannose, fucose, and/or N-acetylglucosamine residues) or to modify or mask one or more carbohydrate residues. Such modifications or masking may reduce binding of the soluble interferon receptors to mannose receptors, and/or asialoglycoprotein receptors, and/or other lectin-like receptors. Chemical deglycosylation can be achieved by treating a soluble interferon receptor with trifluoromethane sulfonic acid (TFMS), as disclosed in, e.g., Sojar et al., *JBC* 1989; 264:2552-9 and Sojar et al., *Methods Enzymol* 1987; 138: 341-50, or by treating with hydrogen fluoride, as disclosed in Sojar et al. (1987, supra). Enzymatic removal of N-linked carbohydrates from soluble interferon receptor can be achieved by treating a soluble interferon receptor with protein N-glycosidase (PNGase) A or F, as disclosed in Thotakura et al. (*Methods Enzymol* 1987; 138:350-9). Other art-recognized commercially available deglycosylating enzymes that are suitable for use include endo-alpha-N-acetyl-galactosaminidase, endoglycosidase F1, endoglycosidase F2, endoglycosidase F3, and endoglycosidase H. In some embodiments, one or more of these enzymes can be used to deglycosylate the soluble interferon receptors of the disclosure. Alternative methods for deglycosylation are disclosed in, e.g., U.S. Pat. No. 8,198,063.

In some embodiments, the soluble interferon receptor are partially deglycosylated. Partial deglycosylation can be achieved by treating the soluble interferon receptor with an endoglycosidase (e.g., endoglycosidase H), which cleaves N-linked high mannose carbohydrate but not complex type carbohydrates, leaving a single GlcNAc residue linked to the asparagine. Soluble interferon receptor treated with endoglycosidase H will lack high mannose carbohydrates, resulting in a reduced interaction with the hepatic mannose receptor. Although this receptor recognizes terminal GlcNAc, the probability of a productive interaction with the single GlcNAc on the protein surface is not as great as with an intact high mannose structure.

In other embodiments, glycosylation of a soluble interferon receptor is modified, e.g., by oxidation, reduction, dehydration, substitution, esterification, alkylation, sialylation, carbon-carbon bond cleavage, or the like, to reduce clearance of the soluble interferon receptors from blood. In some embodiments, the soluble interferon receptors are treated with periodate and sodium borohydride to modify the carbohydrate structure. Periodate treatment oxidizes vicinal diols, cleaving the carbon-carbon bond and replacing the hydroxyl groups with aldehyde groups; borohydride reduces the aldehydes to hydroxyls. Many sugar residues include vicinal diols and, therefore, are cleaved by this treatment. Prolonged serum half-life with periodate and sodium borohydride is exemplified by the sequential treatment of the lysosomal enzyme β-glucuronidase with these agents (see, e.g., Houba et al. (1996) *Bioconjug Chem* 1996:7:606-11; Stahl et al. *PNAS* 1976; 73:4045-9; Achord et al. *Pediat. Res* 1977; 11:816-22; Achord et al. *Cell* 1978; 15:269-78). A method for treatment with periodate and sodium borohydride is disclosed in Hickman et al., *BBRC* 1974; 57:55-61. A method for treatment with periodate and cyanoborohydride, which increases the serum half-life and tissue distribution of ricin, is disclosed in Thorpe et al. *Eur J Biochem* 1985; 147:197-206.

In one embodiment, the carbohydrate structures of a soluble interferon receptor can be masked by addition of one or more additional moieties (e.g., carbohydrate groups, phosphate groups, alkyl groups, etc.) that interfere with recognition of the structure by a mannose or asialoglycoprotein receptor or other lectin-like receptors.

In some embodiments, one or more potential glycosylation sites are removed by mutation of the nucleic acid encoding the soluble interferon receptor, thereby reducing glycosylation (underglycosylation) of the soluble interferon receptor when synthesized in a cell that glycosylates proteins, e.g., a mammalian cell such as a CHO cell. In some embodiments, it may be desirable to selectively underglycosylate the soluble interferon receptors by mutating the potential N-linked glycosylation sites therein if, e.g., the underglycosylated soluble interferon receptor exhibits increased activity or contributes to increased serum half-life. In other embodiments, it may be desirable to underglycosylate portions of the soluble interferon receptor such that certain domains lack N-glycosylation if, for example, such a modification improves the serum half-life of the soluble interferon receptors. Alternatively, other amino acids in the vicinity of glycosylation acceptors can be modified, disrupting a recognition motif for glycosylation enzymes without necessarily changing the amino acid that would normally be glycosylated.

In some embodiments, glycosylation of a soluble interferon receptor can be altered by introducing glycosylation sites. For example, the amino acid sequence of the soluble interferon receptor can be modified to introduce the consensus sequence for N-linked glycosylation of Asn-X-Ser/Thr (X is any amino acid other than proline). Additional N-linked glycosylation sites can be added anywhere throughout the amino acid sequence of the soluble interferon receptor. Preferably, the glycosylation sites are introduced in position in the amino acid sequence that does not substantially reduce the activity of the soluble interferon receptor.

The addition of O-linked glycosylation sites has been reported to alter serum half-life of proteins, such as growth hormone, follicle-stimulating hormone, IGFBP-6, Factor IX, and many others (e.g., as disclosed in Okada et al., *Endocr Rev* 2011; 32:2-342; Weenen et al., *J Clin Endocrinol Metab* 2004; 89:5204-12; Marinaro et al., *European Journal of Endocrinology* 2000; 142:512-6; US 2011/0154516). Accordingly, in some embodiments, O-linked glycosylation (on serine/threonine residues) of the soluble interferon receptor is altered. Methods for altering O-linked glycosylation are routine in the art and can be achieved, e.g., by beta-elimination (see, e.g., Huang et al., *Rapid Communications in Mass Spectrometry* 2002; 16:1199-204; Conrad, *Curr Protoc Mol Biol* 2001; Chapter 17:Unit17.15A; Fukuda, *Curr Protoc Mol Biol* 2001; Chapter 17; Unit 17.15B; Zachara et al., *Curr Protoc Mol Biol* 2011; Unit 17.6;); by using commercially available kits (e.g., GlycoProfile™ Beta-Elimination Kit, Sigma); or by subjecting soluble interferon receptors to treatment with a series of exoglycosidases such as, but not limited to, β1-4 galactosidase and β-N-acetylglucosaminidase, until only Gal β1-3GalNAc and/or GlcNAc β1-3GalNAc remains, followed by treatment with, e.g., endo-α-N-acetylgalactosaminidase (i.e., O-glycosidase). Such enzymes are commercially available from, e.g., New England Biolabs. In yet other embodiments, the soluble interferon receptors are altered to introduce O-linked glycosylation in the soluble interferon receptor as disclosed in, e.g., Okada et al. (supra), Weenen et al. (supra), US2008/0274958; and US2011/0171218. In some embodiments, one or more O-linked glycosylation consensus sites are introduced into the soluble interferon receptors, such as CXXGGT/S-C (SEQ ID NO: 29) (van den Steen et al., In *Critical Reviews in Biochemistry and Molecular Biology*, Michael Cox, ed., 1998; 33:151-208), NST-E/D-A (SEQ ID NO: 30), NITQS (SEQ ID NO: 31), QSTQS (SEQ ID NO: 32), D/E-FT-R/K-V (SEQ ID NO: 33), C-E/D-SN (SEQ ID NO: 34), and GGSC-K/R (SEQ ID NO: 35). Additional O-linked glycosylation sites can be added anywhere throughout the amino acid sequence of the soluble interferon receptor. Preferably, the glycosylation sites are introduced in position in the amino acid sequence that does not substantially reduce the activity of the soluble interferon receptors. Alternatively, O-linked sugar moieties are introduced by chemically modifying an amino acid in the soluble interferon receptors as described in, e.g., WO 87/05330 and Aplin et al., *CRC Crit Rev Biochem* 1981; 259-306).

In some embodiments, both N-linked and O-linked glycosylation sites are introduced into the soluble interferon receptors, preferably in positions in the amino acid sequence that do not substantially reduce the activity of the soluble interferon receptors.

It is well within the abilities of the skilled artisan to introduce, reduce, or eliminate glycosylation (e.g., N-linked or O-linked glycosylation) in a soluble interferon receptor and determine using routine methods in the art whether such modifications in glycosylation status increases or decreases the activity or serum half-life of the soluble interferon receptor.

In some embodiments, the soluble interferon receptor may comprise an altered glycoform (e.g., an underfucosylated or fucose-free glycan).

In some embodiments, a soluble interferon receptor with altered glycosylation has a serum half-life that is increased at least about 1.5-fold, such as at least 3-fold, at least 5-fold, at least 10-fold, at least about 20-fold, at least about 50-fold, at least about 100-fold, at least about 200-fold, at least about 300-fold, at least about 400-fold, at least about 500-fold, at least about 600-fold, at least about 700-fold, at least about 800-fold, at least about 900-fold, at least about 1000-fold, or 1000-fold or greater relative to the corresponding glycosylated soluble interferon receptors (e.g., a soluble interferon receptor in which potential N-linked glycosylation sites are not mutated). Routine art-recognized methods can be used to determine the serum half-life of soluble interferon receptors with altered glycosylation status.

In some embodiments, a soluble interferon receptor with altered glycosylation (e.g., a aglycosylated, deglycosylated, or underglycosylated soluble interferon receptors) retains at least 50%, such as at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.5%, or 100% of the activity of the corresponding glycosylated soluble interferon receptor (e.g., a soluble interferon receptor in which potential N-linked glycosylation sites are not mutated).

In some embodiments, altering the glycosylation status of the soluble interferon receptors may increase activity, either by directly increasing activity, or by increasing bioavailability (e.g., serum half-life). Accordingly, in some embodiments, the activity of a soluble interferon receptor with altered glycosylation is increased by at least 1.3-fold, such as at least 1.5-fold, at least 2-fold, at least 2.5-fold, at least 3-fold, at least 3.5-fold, at least 4-fold, at least 4.5-fold, at least 5-fold, at least 5.5-fold, at least 6-fold, at least 6.5-fold, at least 7-fold, at least 7.5-fold, at least 8-fold, at least 8.5-fold, at least 9-fold, at least 9.5 fold, or 10-fold or greater, relative to the corresponding glycosylated soluble interferon receptor (e.g., a soluble interferon receptor in which potential N-linked glycosylation sites are not mutated).

The skilled artisan can readily determine the glycosylation status of soluble interferon receptors using art-recognized methods. In a preferred embodiment, the glycosylation status is determined using mass spectrometry. In other embodiments, interactions with Concanavalin A (Con A) can be assessed to determine whether a soluble interferon receptor is underglycosylated. An underglycosylated soluble interferon receptor is expected to exhibit reduced binding to Con A-Sepharose when compared to the corresponding glycosylated soluble interferon receptor. SDS-PAGE analysis can also be used to compare the mobility of an underglycosylated protein and corresponding glycosylated protein. The underglycosylated protein is expected to have a greater mobility in SDS-PAGE compared to the glycosylated protein. Other suitable art-recognized methods for analyzing protein glycosylation status are disclosed in, e.g., Roth et al., *International Journal of Carbohydrate Chemistry* 2012; 1-10.

Pharmacokinetics, such as serum half-life, of soluble interferon receptors with different glycosylation status can be assayed using routine methods, e.g., by introducing the soluble interferon receptors in mice, e.g., intravenously, taking blood samples at pre-determined time points, and assaying and comparing levels and/or activity of the soluble interferon receptors in the samples.

Pharmaceutical Compositions

In certain embodiments, a soluble interferon receptor is administered alone. In certain embodiments, a soluble interferon receptor is administered prior to the administration of at least one other therapeutic agent. In certain embodiments, a soluble interferon receptor is administered concurrent with the administration of at least one other therapeutic agent. In certain embodiments, a soluble interferon receptor is administered subsequent to the administration of at least one other therapeutic agent. In other embodiments, a soluble interferon receptor is administered prior to the administration of at least one other therapeutic agent. As will be appreciated by one of skill in the art, in some embodiments, the soluble interferon receptor is combined with the other agent/compound. In some embodiments, the soluble interferon receptor and other agent are administered concurrently. In some embodiments, the soluble interferon receptor and other agent are not administered simultaneously, with the soluble interferon receptor being administered before or after the agent is administered. In some embodiments, the subject receives both the soluble interferon receptor and the other agent during a same period of prevention, occurrence of a disorder, and/or period of treatment.

Pharmaceutical compositions of the disclosure can be administered in combination therapy, i.e., combined with other agents. In certain embodiments, the combination therapy comprises the soluble interferon receptor, in combination with at least one other agent. Agents include, but are not limited to, in vitro synthetically prepared chemical compositions, antibodies, antigen binding regions, and combinations and conjugates thereof. In certain embodiments, an agent can act as an agonist, antagonist, allosteric modulator, or toxin.

In certain embodiments, the disclosure provides for pharmaceutical compositions comprising a soluble interferon receptor together with a pharmaceutically acceptable diluent, carrier, solubilizer, emulsifier, preservative and/or adjuvant.

In certain embodiments, the invention provides for pharmaceutical compositions comprising a soluble interferon receptor and a therapeutically effective amount of at least one additional therapeutic agent, together with a pharmaceutically acceptable diluent, carrier, solubilizer, emulsifier, preservative and/or adjuvant.

In certain embodiments, acceptable formulation materials preferably are nontoxic to recipients at the dosages and concentrations employed. In some embodiments, the formulation material(s) are for s.c. and/or I.V. administration. In certain embodiments, the pharmaceutical composition can contain formulation materials for modifying, maintaining or preserving, for example, the pH, osmolality, viscosity, clarity, color, isotonicity, odor, sterility, stability, rate of dissolution or release, adsorption or penetration of the composition. In certain embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as gelatin); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (Remington's Pharmaceutical Sciences, 18th Edition, A. R. Gennaro, ed., Mack Publishing Company (1995). In some embodiments, the formulation comprises PBS; 20 mM NaOAC, pH 5.2, 50 mM NaCl; and/or 10 mM NAOAC, pH 5.2, 9% Sucrose.

In certain embodiments, a soluble interferon receptor and/or a therapeutic molecule is linked to a half-life extending vehicle known in the art. Such vehicles include, but are not limited to, polyethylene glycol, glycogen (e.g., glycosylation of the soluble interferon receptor), and dextran. Such vehicles are described, e.g., in U.S. application Ser. No. 09/428,082, now U.S. Pat. No. 6,660,843 and published Application No. WO 99/25044.

In certain embodiments, the optimal pharmaceutical composition will be determined by one skilled in the art depending upon, for example, the intended route of administration, delivery format and desired dosage. See, for example, Remington's Pharmaceutical Sciences, supra. In certain embodiments, such compositions may influence the physical state, stability, rate of in vivo release and rate of in vivo clearance of the antibodies of the invention.

In certain embodiments, the primary vehicle or carrier in a pharmaceutical composition can be either aqueous or non-aqueous in nature. For example, in certain embodiments, a suitable vehicle or carrier can be water for injection, physiological saline solution or artificial cerebrospinal fluid, possibly supplemented with other materials common in compositions for parenteral administration. In some embodiments, the saline comprises isotonic phosphate-buffered saline. In certain embodiments, pharmaceutical compositions comprise Tris buffer of about pH 7.0-8.5, or acetate buffer of about H 4.0-5.5, which can further include sorbitol or a suitable substitute therefore. In certain embodiments, a composition comprising a soluble interferon receptor, with or without at least one additional therapeutic agents, can be prepared for storage by mixing the selected composition having the desired degree of purity with optional formulation agents (Remington's Pharmaceutical Sciences, supra) in the form of a lyophilized cake or an aqueous solution. Further, in certain embodiments, a composition comprising a soluble interferon receptor, with or without at least one additional therapeutic agent, can be formulated as a lyophilizate using appropriate excipients such as sucrose.

In certain embodiments, the pharmaceutical composition can be selected for parenteral delivery. In certain embodiments, the compositions can be selected for inhalation or for delivery through the digestive tract, such as orally. The preparation of such pharmaceutically acceptable compositions is within the ability of one skilled in the art.

In certain embodiments, the formulation components are present in concentrations that are acceptable to the site of administration. In certain embodiments, buffers are used to maintain the composition at physiological pH or at a slightly lower pH, typically within a pH range of from about 5 to about 8.

In certain embodiments, when parenteral administration is contemplated, a therapeutic composition can be in the form of a pyrogen-free, parenterally acceptable aqueous solution comprising a desired a soluble interferon receptor, with or without additional therapeutic agents, in a pharmaceutically acceptable vehicle. In certain embodiments, a vehicle for parenteral injection is sterile distilled water in which soluble interferon receptor, with or without at least one additional therapeutic agent, is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that can provide for the controlled or sustained release of the product which can then be delivered via a depot injection. In certain embodiments, hyaluronic acid can also be used, and can have the effect of promoting sustained duration in the circulation. In certain embodiments, implantable drug delivery devices can be used to introduce the desired molecule.

In certain embodiments, a pharmaceutical composition can be formulated for inhalation. In certain embodiments, a soluble interferon receptor, with or without at least one additional therapeutic agent, can be formulated as a dry powder for inhalation. In certain embodiments, an inhalation solution comprising a soluble interferon receptor, with or without at least one additional therapeutic agent, can be formulated with a propellant for aerosol delivery. In certain embodiments, solutions can be nebulized. Pulmonary administration is further described in PCT application no. PCT/US94/001875, which describes pulmonary delivery of chemically modified proteins.

In certain embodiments, it is contemplated that formulations can be administered orally. In certain embodiments, a soluble interferon receptor, with or without at least one additional therapeutic agents, that is administered in this fashion can be formulated with or without those carriers customarily used in the compounding of solid dosage forms such as tablets and capsules. In certain embodiments, a capsule can be designed to release the active portion of the formulation at the point in the gastrointestinal tract when bioavailability is maximized and pre-systemic degradation is minimized. In certain embodiments, at least one additional agent can be included to facilitate absorption of a soluble interferon receptor and/or any additional therapeutic agents. In certain embodiments, diluents, flavorings, low melting point waxes, vegetable oils, lubricants, suspending agents, tablet disintegrating agents, and binders can also be employed.

In certain embodiments, a pharmaceutical composition can involve an effective quantity of a soluble interferon receptor, with or without at least one additional therapeutic agents, in a mixture with non-toxic excipients which are suitable for the manufacture of tablets. In certain embodiments, by dissolving the tablets in sterile water, or another appropriate vehicle, solutions can be prepared in unit-dose form. In certain embodiments, suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving a soluble interferon receptor, with or without at least one additional therapeutic agent(s), in sustained- or controlled-delivery formulations. In certain embodiments, techniques for formulating a variety of other sustained- or controlled-delivery means, such as liposome carriers, bio-erodible microparticles or porous beads and depot injections, are also known to those skilled in the art. See for example, PCT Application No. PCT/US93/00829 which describes the controlled release of porous polymeric microparticles for the delivery of pharmaceutical compositions. In certain embodiments, sustained-release preparations can include semipermeable polymer matrices in the form of shaped articles, e.g. films, or microcapsules. Sustained release matrices can include polyesters, hydrogels, polylactides (U.S. Pat. No. 3,773,919 and EP 058,481), copolymers of L-glutamic acid and gamma ethyl-L-glutamate (Sidman et al., *Biopolymers,* 22:547-556 (1983)), poly (2-hydroxyethyl-methacrylate) (Langer et al., *J Biomed Mater Res,* 15: 167-277 (1981) and Langer, *Chem Tech,* 12:98-105 (1982)), ethylene vinyl acetate (Langer et al, supra) or poly-D(−)-3-hydroxybutyric acid (EP 133,988). In certain embodiments, sustained release compositions can also include liposomes, which can be prepared by any of several methods known in the art. See, e.g., Eppstein et al, *PNAS,* 82:3688-3692 (1985); EP 036, 676; EP 088,046 and EP 143,949.

The pharmaceutical composition to be used for in vivo administration typically is sterile. In certain embodiments, this can be accomplished by filtration through sterile filtration membranes. In certain embodiments, where the composition is lyophilized, sterilization using this method can be conducted either prior to or following lyophilization and reconstitution. In certain embodiments, the composition for parenteral administration can be stored in lyophilized form or in a solution. In certain embodiments, parenteral compositions generally are placed into a container having a sterile access port, for example, an intravenous solution bag or vial having a stopper pierceable by a hypodermic injection needle.

In certain embodiments, once the pharmaceutical composition has been formulated, it can be stored in sterile vials as a solution, suspension, gel, emulsion, solid, or as a dehydrated or lyophilized powder. In certain embodiments, such formulations can be stored either in a ready-to-use form or in a form (e.g., lyophilized) that is reconstituted prior to administration.

In certain embodiments, kits are provided for producing a single-dose administration unit. In certain embodiments, the kit can contain both a first container having a dried protein and a second container having an aqueous formulation. In certain embodiments, kits containing single and multi-chambered pre-filled syringes (e.g., liquid syringes and lyosyringes) are included.

In certain embodiments, the effective amount of a pharmaceutical composition comprising a soluble interferon receptor, with or without at least one additional therapeutic agent, to be employed therapeutically will depend, for example, upon the therapeutic context and objectives. One skilled in the art will appreciate that the appropriate dosage levels for treatment, according to certain embodiments, will thus vary depending, in part, upon the molecule delivered, the indication for which a soluble interferon receptor, with or without at least one additional therapeutic agent, is being used, the route of administration, and the size (body weight, body surface or organ size) and/or condition (the age and general health) of the patient. In certain embodiments, the clinician can titer the dosage and modify the route of administration to obtain the optimal therapeutic effect. In certain embodiments, a typical dosage can range from about 0.1 µg/kg to up to about 100 mg/kg or more, depending on the factors mentioned above. In certain embodiments, the dosage can range from 0.1 µg/kg up to about 100 mg/kg; or 1 µg/kg up to about 100 mg/kg; or 5 µg/kg up to about 100 mg/kg.

In certain embodiments, the frequency of dosing will take into account the pharmacokinetic parameters of a soluble interferon receptor and/or any additional therapeutic agents in the formulation used. In certain embodiments, a clinician will administer the composition until a dosage is reached that achieves the desired effect. In certain embodiments, the composition can therefore be administered as a single dose, or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. In certain embodiments, appropriate dosages can be ascertained through use of appropriate dose-response data.

In certain embodiments, the route of administration of the pharmaceutical composition is in accord with known methods, e.g. orally, through injection by intravenous, intraperitoneal, intracerebral (intra-parenchymal), intracerebroventricular, intramuscular, subcutaneously, intra-ocular, intraarterial, intraportal, or intralesional routes; by sustained release systems or by implantation devices. In certain embodiments, the compositions can be administered by bolus injection or continuously by infusion, or by implantation device.

In certain embodiments, the composition can be administered locally via implantation of a membrane, sponge or another appropriate material onto which the desired molecule has been absorbed or encapsulated. In certain embodiments, where an implantation device is used, the device can be implanted into any suitable tissue or organ, and delivery of the desired molecule can be via diffusion, timed-release bolus, or continuous administration.

In certain embodiments, it can be desirable to use a pharmaceutical composition comprising a soluble interferon receptor, with or without at least one additional therapeutic agent, in an ex vivo manner. In such instances, cells, tissues and/or organs that have been removed from the patient are exposed to a pharmaceutical composition comprising a soluble interferon receptor, with or without at least one additional therapeutic agent, after which the cells, tissues and/or organs are subsequently implanted back into the patient.

In certain embodiments, a soluble interferon receptor and/or any additional therapeutic agents can be delivered by implanting certain cells that have been genetically engineered, using methods such as those described herein, to express and secrete the polypeptides. In certain embodiments, such cells can be animal or human cells, and can be autologous, heterologous, or xenogeneic. In certain embodiments, the cells can be immortalized. In certain embodiments, in order to decrease the chance of an immunological response, the cells can be encapsulated to avoid infiltration of surrounding tissues. In certain embodiments, the encapsulation materials are typically biocompatible, semi-permeable polymeric enclosures or membranes that allow the release of the protein product(s) but prevent the destruction of the cells by the patient's immune system or by other detrimental factors from the surrounding tissues.

In Vitro Assays

Various in vitro assays known in the art can be used to assess the efficacy of the soluble interferon receptors of the invention.

For example, soluble interferon receptors can be assessed for their ability to inhibit IFN-α and/or IFN-β induced secreted alkaline phosphatase (SEAP) production in HEK-Blue α/β cells. HEK-Blue IFN-α/β cells (Invivogen, Catalog #hkb-ifnab) produce and secrete SEAP in response to stimulation by IFN-α or IFN-β.

To assess the ability of the soluble interferon receptors to inhibit IFN-α and/or IFN-β activity, IFNα and/or IFN-β can be added to inhibitors (e.g., soluble interferon receptors (e.g., RSLV-601-604, RSLV-602-603) as well as control molecules such as anti-IFN-α, anti-IFN-β, and human IgG) in a tissue culture plate. HEK-Blue IFN-α/β cells can then be added to the plate and incubated for a predetermined amount of time at 37° C. To assess SEAP activity, cell supernatant can then be added to QUANTI-Blue reagent and incubated for a predetermined amount of time at 37° C. SEAP activity can be detected by measuring absorbance at 620 nm.

The effectiveness of the soluble interferon receptors is demonstrated by comparing the results of an assay from cells treated with the soluble interferon receptors disclosed herein to the results of the assay from cells treated with a control. After treatment with an effective soluble interferon receptor, the levels of IFN-α and/or IFN-β are generally comparable to the levels measured following treatment with an anti-IFN-α or anti-IFN-β control. After treatment with an effective soluble interferon receptor, the levels of IFN-α and/or IFN-β are generally reduced relative to the levels measured following treatment with a negative control such as human IgG.

Methods of Treatment

The soluble interferon receptors of the disclosure are particularly effective in the treatment of autoimmune disorders or abnormal immune responses. In this regard, it will be appreciated that the soluble interferon receptors of the present disclosure may be used to control, suppress, modulate, treat, or eliminate dysregulated immune responses resulting from excess production of interferon.

In another aspect, a soluble interferon receptors is adapted for preventing (prophylactic) or treating (therapeutic) a disease or disorder, such as an autoimmune disease, in a mammal by administering a soluble interferon receptor in a therapeutically effective amount or a sufficient amount to the mammal in need thereof, wherein the disease is prevented or treated. Any route of administration suitable for achieving the desired effect is contemplated by the invention (e.g., intravenous, intramuscular, subcutaneous). Treatment of the disease condition may result in a decrease in the symptoms associated with the condition, which may be long-term or short-term, or even a transient beneficial effect.

Numerous disease conditions are suitable for treatment with the soluble interferon receptors of the disclosure. For example, in some aspects, the disease or disorder is an autoimmune disease or cancer. In some such aspects, the autoimmune disease is insulin-dependent diabetes mellitus, multiple sclerosis, experimental autoimmune encephalomyelitis, rheumatoid arthritis, experimental autoimmune arthritis, myasthenia gravis, thyroiditis, an experimental form of uveoretinitis, Hashimoto's thyroiditis, primary myxoedema, thyrotoxicosis, pernicious anaemia, autoimmune atrophic gastritis, Addison's disease, premature menopause, male infertility, juvenile diabetes, Goodpasture's syndrome, pemphigus vulgaris, pemphigoid, sympathetic ophthalmia, phacogenic uveitis, autoimmune haemolytic anaemia, idiopathic leucopenia, primary biliary cirrhosis, active chronic hepatitis Hbs-ve, cryptogenic cirrhosis, ulcerative colitis, Sjogren's syndrome, scleroderma, Wegener's granulomatosis, polymyositis, dermatomyositis, discoid LE, SLE, or connective tissue disease.

In a specific embodiment, a soluble interferon receptor is used to prevent or treat SLE or Sjogren's syndrome. The effectiveness of a soluble interferon receptor is demonstrated by comparing the level of expression of certain known IFN regulated genes in mammals treated with a soluble interferon receptor disclosed herein to mammals treated with control formulations. In some embodiments, the expression level of one, two, three, four, five or more IFN regulated genes is measured. For example, in some embodiments, the expression level of three or more IFN regulated genes (e.g., HERC5, EPSTI, CMPK2) is measured. In some embodiments the IFN regulated genes include those described by Bennett et al., J. Exp. Med., Vol. 197, No. 6, 711-723, March 2003. and Kennedy et al. Lupus Science and Medicine, 2015; 2:e00080. Doi:10.1136/lupus-2014-000080., both of which are incorporated herein by reference.

For example, a human subject in need of treatment is selected or identified (e.g., a patient who fulfills the American College of Rheumatology criteria for SLE, or a patient who fulfills the American-European Consensus Sjogren's Classification Criteria). The subject can be in need of, e.g., reducing a cause or symptom of SLE or Sjogren's syndrome. The identification of the subject can occur in a clinical setting, or elsewhere, e.g., in the subject's home through the subject's own use of a self-testing kit.

At time zero, a suitable first dose of a soluble interferon receptor is administered to the subject. The soluble interferon receptor is formulated as described herein. After a period of time following the first dose, e.g., 7 days, 14 days, and 21 days, the subject's condition is evaluated, e.g., by measuring IFN regulated gene expression. For example, the expression of one or more of HERC5, EPSTI, and CMPK2, which are interferon stimulated genes, can be assessed. Other relevant criteria can also be measured. The number and strength of doses are adjusted according to the subject's needs. The progress of treatment may be monitored by assaying for a change in IFN regulated gene expression. After treatment, a decrease and/or improvement can be noted in the expression of the subject's IFN regulated gene expression relative to the IFN regulated gene expression prior to the treatment, or relative to the levels measured in a similarly afflicted but untreated/control subject. For example, the expression of HERC5, EPSTI, and/or CMPK2, which are interferon stimulated genes, would be decreased relative to the expression of these three genes prior to treatment, or relative to the levels of these genes in a similarly afflicted by untreated/control subject.

In some embodiments, the IFN regulated gene expression is measured by drawing whole blood from a subject, extracting the RNA and analyzing the expression of the interferon regulated genes (for example, HERC5, EPSTI, and/or CMPK2) by using techniques well-known in the art, such as PCR. Methods for assaying for IFN regulated gene expression are described in Kennedy et al. Lupus Science and Medicine, 2015; 2:e00080. Doi:10.1136/lupus-2014-000080 and Furie et al., Arthritis & Rheumatology, Vo. 69, No. 2, February 2017, 376-386, both of which are incorporated herein by reference.

In another example, a rodent subject in need of treatment is selected or identified. The identification of the subject can occur in a laboratory setting or elsewhere. At time zero, a suitable first dose of a soluble interferon receptor is administered to the subject. The a soluble interferon receptor is formulated as described herein. After a period of time following the first dose, e.g., 7 days, 14 days, and 21 days, the subject's condition is evaluated, e.g., by measuring IFN regulated gene expression. Other relevant criteria can also be measured. The number and strength of doses are adjusted according to the subject's needs. The progress of treatment may be monitored by assaying for a change in IFN regulated gene expression.

After treatment, the subject's IFN regulated gene expression are lowered and/or improved relative to the IFN regulated gene expression prior to the treatment, or relative to the levels measured in a similarly afflicted but untreated/control subject.

In some embodiments, IFN regulated genes that may be upregulated in an autoimmune disorder (e.g., SLE) include, IFP35 IFN inducible, IRF7B, MX1, MX2, XIAP ass. factor, GS3686, P69 2'5' oligoA synthetase, hep-C ass. microtubular agg. prot., RIGE/TSA1 sim to mouse Ly6, agrin prec, IFI-56 IFN inducible, EST sim. to IFN ind 17 kD protein, cig 5, ISG 15, TRIP 14 2'5' oligoA synthetase-like, cig49, MCP-1 monocyte chemoattractant, Tudor rpt ass with PCTAIRE, MMTRA 1B phospholipid scramblase, FACL 1 fatty acid coenzyme-A ligase, TRAIL, 2'5' oligoA synthetase E18 isoform, GBP-1 guanylate binding protein 1, C1-INH CC1 inhibitor, CD64 rec for Fc fragment of IgG, C2 complement component, hPD-ECGF end. platelet der. GF1, ISGF3, EST hute1, TSC403 DC LAMP, MAC2-BP scavenger receptor, 1-8U, TAP1, IFI 6-16, Novel phorbolin-like gene, G6PD guanosine monoP reductase, HERC5, EPSTI, and CMPK2.

In some embodiments, IFN regulated genes that may be downregulated in an autoimmune disorder (e.g., SLE)

include TCRγ T-cell receptor delta, LEU 1 leukemia ass. genel, COX11P cyt C oxidase ass. prot, JKTBP nuc ribonucleoprotein D-like, TPRD tetra tricopeptide rpt, DAP3 death ass. protein, mRNA U90916, PRIP prion protein, ANT 3 ADP.ATP translocase, E1F-4B transl.initiation fac, PABP4 polyA binding protein, RAB 4A GTP binding protein, and CD3γ.

In some embodiments, the effectiveness of a soluble interferon receptor is demonstrated by assessing the Cutaneous Lupus Erythematosus Disease Area and Severity Index (CLASI), British Isles Lupus Assessment Group (BILAG) index, Systemic Lupus Erythematosus (SLE) Responder Index (SRI-4), and/or the Functional Assessment of Chronic Illness Therapy (FACIT) fatigue scale in mammals treated with a soluble interferon receptor disclosed herein when compared to mammals treated with control formulations. In some embodiments, a mammal treated with a soluble interferon receptor will demonstrate an improvement in the CLASI severity index, BILAG index, SRI-4 index, and/or the FACIT fatigue scale when compared to the mammal's CLASI severity index, BILAG index, SRI-4 index, and/or the FACIT fatigue scale prior to the treatment, or when compared to a mammal treated with a control formulation.

In some embodiments, the effectiveness of a soluble interferon receptor is demonstrated by assessing a reduction in steroid use in mammals treated with a soluble interferon receptor disclosed herein when compared to mammals treated with control formulations. In some embodiments, a mammal treated with a soluble interferon receptor will demonstrate a reduction in steroid use when compared to the mammal's steroid use prior to the treatment, or when compared to a mammal treated with a control formulation.

For example, a human subject in need of treatment is selected or identified (e.g., a patient who fulfills the American College of Rheumatology criteria for SLE, or a patient who fulfills the American-European Consensus Sjogren's Classification Criteria). The subject can be in need of, e.g., reducing a cause or symptom of SLE or Sjogren's syndrome. The identification of the subject can occur in a clinical setting, or elsewhere, e.g., in the subject's home through the subject's own use of a self-testing kit.

At time zero, a suitable first dose of a soluble interferon receptor is administered to the subject. The soluble interferon receptor is formulated as described herein. After a period of time following the first dose, e.g., 7 days, 14 days, and 21 days, the subject's condition is evaluated, e.g., by CLASI severity index, BILAG index, SRI-4 index, the FACIT fatigue scale, and/or a reduction in steroid use. Other relevant criteria can also be measured. The number and strength of doses are adjusted according to the subject's needs. After treatment, an improvement in one or more of the following outcomes can be noted: (1) an improvement in the CLASI severity index relative to the CLASI severity index prior to treatment, or relative to a similarly afflicted but untreated/control subject, (2) an improvement in the BILAG index relative to the BILAG index prior to treatment, or relative to a similarly afflicted but untreated/control subject, (3) an improvement in the SRI-4 index relative to the SRI-4 index prior to treatment, or relative to a similarly afflicted but untreated/control subject, (4) an improvement can be noted in the FACIT fatigue scale relative to the FACIT fatigue scale prior to treatment, or relative to a similarly afflicted but untreated/control subject, (5) a reduction in steroid use relative to steroid use prior to treatment, or relative to a similarly affected but untreated/control subject.

In another example, a rodent subject in need of treatment is selected or identified. The identification of the subject can occur in a laboratory setting or elsewhere. At time zero, a suitable first dose of a soluble interferon receptor is administered to the subject. The soluble interferon receptor is formulated as described herein. After a period of time following the first dose, e.g., 7 days, 14 days, and 21 days, the subject's condition is evaluated, e.g., by CLASI severity index, BILAG index, SRI-4 index, the FACIT fatigue scale, and/or a reduction in steroid use. Other relevant criteria can also be measured. The number and strength of doses are adjusted according to the subject's needs.

After treatment, an improvement in one or more of the following outcomes can be noted: (1) an improvement in the CLASI severity index relative to the CLASI severity index prior to treatment, or relative to a similarly afflicted but untreated/control subject, (2) an improvement in the BILAG index relative to the BILAG index prior to treatment, or relative to a similarly afflicted but untreated/control subject, (3) an improvement in the SRI-4 index relative to the SRI-4 index prior to treatment, or relative to a similarly afflicted but untreated/control subject, (4) an improvement can be noted in the FACIT fatigue scale relative to the FACIT fatigue scale prior to treatment, or relative to a similarly afflicted but untreated/control subject, (5) a reduction in steroid use relative to steroid use prior to treatment, or relative to a similarly affected but untreated/control subject.

Another aspect of the present invention is to use gene therapy methods for treating or preventing disorders, diseases, and conditions with one or more soluble interferon receptors. The gene therapy methods relate to the introduction of interferon receptor Fc construct nucleic acid (DNA, RNA and antisense DNA or RNA) sequences into an animal in need thereof to achieve expression of the polypeptide or polypeptides of the present disclosure. This method can include introduction of one or more polynucleotides encoding a interferon receptor Fc construct of the present disclosure operably coupled to a promoter and any other genetic elements necessary for the expression of the polypeptide by the target tissue.

In gene therapy applications, interferon receptor Fc construct genes are introduced into cells in order to achieve in vivo synthesis of a therapeutically effective genetic product. "Gene therapy" includes both conventional gene therapies where a lasting effect is achieved by a single treatment, and the administration of gene therapeutic agents, which involves the one time or repeated administration of a therapeutically effective DNA or mRNA. The oligonucleotides can be modified to enhance their uptake, e.g., by substituting their negatively charged phosphodiester groups by uncharged groups.

Other Embodiments

The disclosure also relates to the following embodiments which feature heterodimers of the disclosure and use thereof. Throughout this section, the term embodiment is abbreviated as 'E' followed by an ordinal. For example, E1 is equivalent to Embodiment 1.

E1. A heterodimer comprising a first polypeptide and a second polypeptide, wherein the first polypeptide comprises an interferon receptor 1 (IFNAR1) domain operatively coupled with or without a linker domain to a variant Fc domain, and wherein the second polypeptide comprises an interferon receptor 2 (IFNAR2) domain operatively coupled with or without a linker domain to a variant Fc domain.

E2. The heterodimer of claim E1, wherein the variant Fc domain of the first or second polypeptide comprises one or more amino acid substitutions which increase the formation of heterodimers as compared to wild-type.

E3. The heterodimer of claim E2, wherein the variant Fc domain of the first or second polypeptide comprises one or more amino acid substitutions selected from the group consisting of T350V, L351Y, F405A, and Y407V.

E4. The heterodimer of claim E2, wherein the variant Fc domain of the first or second polypeptide comprises one or more amino acid substitutions selected from the group consisting of T350V, T366L, K392L, and T394W.

E5. The heterodimer of claim E1, wherein the Fc domain of the first or second polypeptide comprises a human immunoglobulin Fc domain, such as a human IgG1 Fc domain.

E6. The heterodimer of claim E5, wherein the Fc domain of the first or second polypeptide comprises a hinge domain, a CH2 domain and a CH3 domain.

E7. The heterodimer of claim E5, wherein the Fc domain comprises an amino acid sequence having one or more of the amino acid substitutions P238S, P331S, SCC, SSS (residues 220, 226, and 229), G236R, L328R, L234A, and L235A.

E8. The heterodimer of claim E1, wherein the variant Fc domain of the first or second polypeptide further comprises one or more amino acid substitutions selected from the group consisting of C220S, P238S, and P331S.

E9. The heterodimer of any one of claims E1-E4, wherein the variant Fc domain further comprises one or more amino acid substitutions selected from the group consisting of C220S, P238S, and P331S.

E10. The heterodimer of claim E1, wherein the interferon receptor 1 (IFNAR1) domain of the first polypeptide is operatively coupled to the variant Fc domain via a linker domain.

E11. The heterodimer of claim E1, wherein the interferon receptor 2 (IFNAR2) domain of the second polypeptide is operatively coupled to the variant Fc domain via a linker domain.

E12. The heterodimer of claim E10 or claim E11, wherein the linker domain is a polypeptide linker.

E13. The heterodimer of claim E12, wherein the linker domain is a Gly-Ser linker.

E14. The heterodimer of claim E1, wherein the variant Fc domain of the first polypeptide is different than the variant Fc domain of the second polypeptide.

E15. The heterodimer of claim E14, wherein the variant Fc domain of the first polypeptide comprises one or more amino acid substitutions selected from the group consisting of T350V, L351Y, F405A, and Y407V, and wherein the variant Fc domain of the second polypeptide comprises one or more amino acid substitutions selected from the group consisting of T350V, T366L, K392L, and T394W.

E16. The heterodimer of claim E14, wherein the variant Fc domain of the first polypeptide comprises one or more amino acid substitutions selected from the group consisting of T350V, T366L, K392L, and T394W, and wherein the variant Fc domain of the second polypeptide comprises one or more amino acid substitutions selected from the group consisting of T350V, L351Y, F405A, and Y407V.

E17. The heterodimer of any one claims E15 or E16, wherein the variant Fc domain of the first polypeptide further comprises one or more amino acid substitutions selected from the group consisting of C220S, P238S, and P331S, and wherein the variant Fc domain of the second polypeptide further comprises one or more amino acid substitutions selected from the group consisting of C220S, P238S, and P331S.

E18. A heterodimer comprising a first polypeptide and a second polypeptide,
wherein the first polypeptide comprises an interferon receptor 2 (IFNAR2) domain operatively coupled with or without a linker domain to a variant Fc domain comprising one or more amino acid substitutions selected from the group consisting of T350V, L351Y, F405A, and Y407V, and
wherein the second polypeptide comprises an interferon receptor 1 (IFNAR1) domain operatively coupled with or without a linker domain to a variant Fc domain comprising one or more amino acid substitutions selected from the group consisting of T350V, T366L, K392L, and T394W.

E19. A heterodimer comprising a first polypeptide and a second polypeptide,
wherein the first polypeptide comprises an interferon receptor 1 (IFNAR1) domain operatively coupled with or without a linker domain to a variant Fc domain comprising one or more amino acid substitutions selected from the group consisting of T350V, L351Y, F405A, and Y407V, and
wherein the second polypeptide comprises an interferon receptor 2 (IFNAR2) domain operatively coupled with or without a linker domain to a variant Fc domain comprising one or more amino acid substitutions selected from the group consisting of T350V, T366L, K392L, and T394W.

E20. The heterodimer of any one claims E18-E19, wherein the variant Fc domain of the first polypeptide further comprises one or more mutation selected from the group consisting of C220S, P238S, and P331S, and wherein the variant Fc domain of the second polypeptide further comprises one or more mutation selected from the group consisting of C220S, P238S, and P331S.

E21. A heterodimer comprising
a first polypeptide and a second polypeptide,
wherein the first polypeptide comprises an interferon receptor 2 (IFNAR2) domain operatively coupled via a Gly-Ser linker domain to a variant Fc domain, wherein the variant Fc domain of the first polypeptide comprises one or more amino acid substitutions selected from the group consisting of T350V, L351Y, F405A, and Y407V, and wherein the variant Fc domain of the first polypeptide further comprises one or more mutation selected from the group consisting of C220S, P238S, and P331S; and
wherein the second polypeptide comprises an interferon receptor 1 (IFNAR1) operatively coupled via a Gly-Ser linker domain to a variant Fc domain, wherein the variant Fc domain of the second polypeptide comprises one or more amino acid substitutions selected from the group consisting of T350V, T366L, K392L, and T394W, and wherein the variant Fc domain of the second polypeptide further comprises one or more mutation selected from the group consisting of C220S, P238S, and P331S.

E22. A heterodimer comprising
a first polypeptide and a second polypeptide,
wherein the first polypeptide comprises an interferon receptor 1 (IFNAR1) domain operatively coupled via a Gly-Ser linker domain to a variant Fc domain, wherein the variant Fc domain of the first polypeptide comprises one or more amino acid substitutions selected from the group consisting of T350V, L351Y, F405A, and Y407V, and wherein the variant Fc domain of the first polypeptide further comprises one or more mutation selected from the group consisting of C220S, P238S, and P331S; and
wherein the second polypeptide comprises an interferon receptor 2 (IFNAR2) operatively coupled via a Gly-Ser linker domain to a variant Fc domain, wherein the variant Fc domain of the second polypeptide comprises one or more amino acid substitutions selected from the group consisting of T350V, T366L, K392L, and T394W, and wherein the variant Fc domain of the second polypeptide further comprises one or more mutation selected from the group consisting of C220S, P238S, and P331S.

E23. A composition comprising the heterodimer of any of the preceding claims and a pharmaceutically acceptable carrier.

E24. A nucleic acid encoding the first polypeptide of the heterodimer according to claim E1.

E25. A nucleic acid encoding the second polypeptide of the heterodimer according to claim E1.

E26. A recombinant expression vector comprising a nucleic acid according to claim E24.

E27. A recombinant expression vector comprising a nucleic acid according to claim E25.

E28. A host cell transformed with the recombinant expression vector of claim E26 and the recombinant expression vector of claim E27.

E29. A method of making the heterodimer of claim E1, comprising: providing a host cell comprising a nucleic acid sequence that encodes the first polypeptide and a nucleic acid that encodes the second polypeptide; and maintaining the host cell under conditions in which the first and second polypeptides are expressed.

E30. The heterodimer of claim E1 for use in a method for treating or preventing a condition associated with an abnormal immune response.

E31. The heterodimer of claim E30, wherein the condition is an autoimmune disease.

E32. The heterodimer of claim E31, wherein the autoimmune disease is SLE.

E33. The heterodimer of claim E1 for use in the manufacture of a medicament for treating or preventing a condition associated with an abnormal immune response.

E34. The heterodimer of claim E33, wherein the condition is an autoimmune disease.

E35. The heterodimer of claim E34, wherein the autoimmune disease is SLE.

E36. The heterodimer of claim E1, wherein the heterodimer binds type I interferons.

E37. The heterodimer of claim E36, wherein the type I interferon is interferon α.

E38. The heterodimer of claim E36, wherein the type I interferon is interferon β.

E39. The heterodimer of claim E1, wherein the heterodimer binds interferon α to a similar extent as a control anti-IFNα antibody.

E40. The heterodimer of claim E1, wherein the heterodimer binds interferon β to a similar extent as a control anti-IFNβ antibody.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, Proteins: Structures and Molecular Properties (W.H. Freeman and Company, 1993); A. L. Lehninger, Biochemistry (Worth Publishers, Inc., current addition); Sambrook, et al, Molecular Cloning: A Laboratory Manual (2nd Edition, 1989); Methods In Enzymology (S. Colowick and N. Kaplan eds., Academic Press, Inc.); Remington's Pharmaceutical Sciences, 18th Edition (Easton, Pa.: Mack Publishing Company, 1990); Carey and Sundberg Advanced Organic Chemistry $3^{rd}$ Ed. (Plenum Press) Vols A and B (1992).

Example 1

Generating Soluble Interferon Receptors

Various embodiments of the soluble interferon receptors are shown in FIG. 1 with amino acid sequences of each presented in Table 1. The following interferon receptor extracellular domain (ECD)-immunoglobulin Fc fusion proteins were constructed: RSLV-601, RSLV-602, RSLV-603, RSLV-604, RSLV-606, RSLV-608, RSLV-611, and RSLV-613 (FIG. 1). Constructs were generated through direct synthesis using commercially available services. Amino acid sequences were provided to GeneArt; and codon utilization was optimized for and the genes were synthesized and inserted into the mammalian cell expression vector pcDNA3.1⁻

RSLV-601 (SEQ ID NO:1) has the configuration: Leader Sequence (MDWTWRILFLVAAATGTHA)-IFNAR1 ECD-$(Gly_4Ser)_4$-Fc domain (216-447) with mutations C220S/P238S/P331S/T350V/T366L/K392L/T394W, wherein the IFNAR1 ECD is operably coupled via a $(Gly_4Ser)_4$ sequence to an Fc domain (216-447) with mutations C220S/P238S/P331S/T350V/T366L/K392L/T394W.

RSLV-602 (SEQ ID NO:2) has the configuration: Leader Sequence (MDWTWRILFLVAAATGTHA)-IFNAR2 ECD-$(Gly_4Ser)_4$-Fc domain (216-447) with mutations C220S/P238S/P331S/T350V/T366L/K392L/T394W, wherein IFNAR2 ECD is operably coupled via a $(Gly_4Ser)_4$ sequence to an Fc domain (216-447) with mutations C220S/P238S/P331S/T350V/T366L/K392L/T394W.

RSLV-603 (SEQ ID NO:3) has the configuration: Leader Sequence (MDWTWRILFLVAAATGTHA)-IFNAR1 ECD-$(Gly_4Ser)_4$-Fc domain (216-447) with mutations C220S/P238S/P331S/T350V/L351Y/F405A/Y407V, wherein the IFNAR1 ECD is operably coupled via a $(Gly_4Ser)_4$ sequence to an Fc domain (216-447) with mutations C220S/P238S/P331S/T350V/L351Y/F405A/Y407V.

RSLV-604 (SEQ ID NO:4) has the configuration: Leader Sequence (MDWTWRILFLVAAATGTHA)-IFNAR2 ECD-$(Gly_4Ser)_4$-Fc domain (216-447) with mutations C220S/P238S/P331S/T350V/L351Y/F405A/Y407V, wherein the IFNAR2 ECD is operably coupled via a $(Gly_4Ser)_4$ sequence to an Fc domain (216-447) with mutations C220S/P238S/P331S/T350V/L351Y/F405A/Y407V.

RSLV-606 (SEQ ID NO: 52) has the configuration: Leader Sequence (MDWTWRILFLVAAATGTHA)-IFNAR1 ECD-$(Gly_4Ser)_2$-Fc domain (216-447) with mutations C220S/P238S/P331S/T350V/T366L/K392L/T394W, wherein the IFNAR1 ECD is operably coupled via a $(Gly_4Ser)_2$ sequence to an Fc domain (216-447) with mutations C220S/P238S/P331S/T350V/T366L/K392L/T394W.

RSLV-608 (SEQ ID NO: 56) has the configuration: Leader Sequence (MDWTWRILFLVAAATGTHA)-IFNAR1 ECD-Fc domain (216-447) with mutations C220S/P238S/P331S/T350V/T366L/K392L/T394W, wherein the IFNAR1 ECD is operably coupled to an Fc domain (216-447) with mutations C220S/P238S/P331S/T350V/T366L/K392L/T394W.

RSLV-611 (SEQ ID NO: 54) has the configuration: Leader Sequence (MDWTWRILFLVAAATGTHA)-IFNAR2 ECD-(Gly$_4$Ser)$_2$-Fc domain (216-447) with mutations C220S/P238S/P331S/T350V/L351Y/F405A/Y407V, wherein the IFNAR2 ECD is operably coupled via a (Gly$_4$Ser)$_2$ sequence to an Fc domain (216-447) with mutations C220S/P238S/P331S/T350V/L351Y/F405A/Y407V.

RSLV-613 (SEQ ID NO:58) has the configuration: Leader Sequence (MDWTWRILFLVAAATGTHA)-IFNAR2 ECD-Fc domain (216-447) with mutations C220S/P238S/P331S/T350V/L351Y/F405A/Y407V, wherein the IFNAR2 ECD is operably coupled via a (Gly4Ser) sequence to an Fc domain (216-447) with mutations C220S/P238S/P331S/T350V/L351Y/F405A/Y407V.

The interferon receptor Fc constructs of the invention can also be generated using conventional cloning techniques well-known in the art, for example, by preparing modular cassettes of each component of the interferon receptor Fc constructs (e.g., INFAR ECD, linker domain, Fc) with compatible restriction enzyme sites to allow for shuttling and domain swapping. A polynucleotide encoding each component of the interferon receptor Fc constructs (e.g., INFAR ECD, linker domain, immunoglobulin Fc) can be readily obtained by amplifying the component of interest using polymerase chain reaction (PCR) from an appropriate cDNA library. For example, the full length nucleotide sequences of human INFAR ECD, linker domain, and immunoglobulin Fc can be amplified from random primed and oligo dT primed cDNA derived from commercially available human pancreatic total RNA using sequence specific 5' and 3' primers based on published sequences of the component being amplified.

Linkers (e.g., (Gly4Ser)4) linkers can be generated by overlap PCR using routine methods, or through direct synthesis using commercially available services, and designed to have overhangs or be blunt to facilitate subsequent cloning to allow for fusion with other domains of interest.

Example 2

Transient Expression Of Soluble Interferon Receptors

For transient expression, pairs of expression vectors containing the interferon receptor ECD-Fc constructs from Example 1 were co-transfected into CHO-S cells. For example, RSLV-601 and RSLV-604; RSLV-602 and RSLV-603; RSLV-606 and RSLV-611; and RSLV-608 and RSLV-613 were co-transfected into CHO-S cells.

Plasmids obtained from GeneArt were transformed into DH10B competent *E. coli* and the cultures expanded under ampicillin selection. Plasmid DNA subsequently was isolated from the cultures using QIAGEN plasmid plus maxi kits.

Transfections were performed using the FreeStyle MAX CHO Expression System obtained from Life Technologies. One day prior to transfection, CHO-S cells were seeded at a density of 5×10$^5$ cells/ml in 100 ml of FreeStyle CHO expression medium supplemented with 8 mM L-glutamine; the flasks subsequently were placed on an orbital shaker rotating at 120-135 rpm and incubated overnight in an 8% CO$_2$ incubator at 37° C. On the day of transfection, the CHO-S cells were harvested then re-seeded at a density of 1×10$^6$ cells/ml in 100 ml of FreeStyle CHO Expression Medium supplemented with 8 mM L-glutamine. 1:1 co-transfections were performed. 62.5 μg of RSLV-601 and 62.5 μg of RSLV-604; and 62.5 μg of RSLV-602 and 62.5 μg or RSLV-603 were added into OptiPRO SFM with a final volume of 2 ml, and mixed by repeated inversion. In a separate tube, 125 μl of FreeStyle MAX transfection reagent was mixed with 1875 μl of OptiPRO SFM and mixed by repeated inversion. The diluted FreeStyle MAX transfection reagent then was immediately added to the diluted plasmid DNA solution (total volume=4 ml); the resulting solution was mixed gently by inversion and complexes were allowed to form for 10 min at room temperature. The transfection mixture then was slowly added to the 100 ml culture of CHO-S cells while gently swirling the flask. Similarly, 37.5 RSLV-606 and 37.5 μg RSLV-611; and 37.5 μg RSLV-608 and 37.5 μg RSLV-613, were co-transfected into 60 ml of CHO-S cultures.

The cultures were incubated on an orbital shaker platform (120-135 rpm) at 37° C. in an 8% CO2 incubator. After 7 days of growth, cells were harvested by centrifugation (1000 rpm for 10 min) and the conditioned medium was recovered and filtered by passage through a 0.22 um membrane.

Each clarified culture medium (co-transfected RSLV-601/604, RSLV-602/603, RSLV-606/611, and RSLV-608/613) was purified by passing over a protein-A column (Bio-Rad BioScale Mini Protein A, Catalog #7324600) and washed with 10 column volumes of PBS buffer at pH 7.2. The bound material was eluted with 5 column volumes of citrate buffer at pH 3.6 with each fraction neutralized with TRIS at pH 11. The fractions containing protein were pooled and equilibrated into PBS by dialysis using a 10 k MWCO dialysis unit.

Western Blot Analysis: Expression of the soluble interferon receptors was assayed by standard Western Blot analysis. Based on estimated protein concentration, 4 μg of protein were loaded into each lane and the samples electrophoresed on Novex 4-20% Tris Glycine gradient gel under denaturing conditions+/−reducing agent (R, NR). Purified rhu IFNAR1 and rhu IFNAR2 samples (Sino Biological, Catalog #13222-H08H and #10359-H08H) were run as controls. Duplicate gels were prepared and each gel contained a single lane of molecular weight standards. Following electrophoresis, proteins were blotted onto nitrocellulose and the blots subsequently blocked by incubation in Odyssey Blocking Buffer for 1 hr. Blot 1 was then exposed sequentially to: 0.1 μg/ml of polyclonal goat anti human IFNAR1 antibody (R&D Systems, Catalog #AF245), and a 1:10,000 dilution of Dylight 800 conjugated donkey anti goat IgG (Rockland, Catalog #605-745-002). Blot 2 was exposed sequentially to 1 μg/ml of polyclonal sheep anti human IFNAR2 (R&D Systems, Catalog #AF4015), and a 1:50,000 dilution of Alexa Fluor 680-conjugated AffiniPure Donkey Anti-Sheep IgG (Jackson, Catalog #713-625-147). The blots were imaged using a Licor Odyssey.

Expression of the RSLV 601-604 and RSLV 602-603 soluble interferon receptors was observed to run slightly higher than the predicted molecular weight, possibly due to glycosylation of the proteins (data not shown).

SDS-PAGE, Coomassie Blue: The soluble interferon receptors were purified, electrophoresed, and visualized using Coomassie blue. Fractions generated during Protein A purifications of conditioned medium harvested from RSLV 601-604, RSLV 602-603, and RSLV 608-613 co-transfections in CHO-S cells were visualized by SDS-PAGE with Coomassie Blue staining. 15 ul of each sample was diluted with 5 l of 4× Protein Loading Buffer and heat denatured. Samples were applied to Novex 4-20% Tris Glycine gradient gels and stained with Simply Blue Safe stain following electrophoresis, and imaged using a Licor Odyssey. Each gel had a single lane of MW standards for reference.

Positive fractions identified were pooled and equilibrated into PBS by dialysis using a 10 k MWCO dialysis cassette. Protein concentration estimates were determined by OD280 values. 500 ng of each soluble interferon receptor (RSLV 601-604, RSLV 602-603, and RSLV 608-613)+/−reducing agent were applied to a Novex 4-20% Tris Glycine gradient gel and stained with Simply Blue Safe stain following electrophoresis, and imaged using Licor Odyssey.

A major band was detected in the starting material and in fractions 2-5 of the purified RSLV 602-603 soluble interferon receptor (data not shown). The theoretical mass of the RSLV-602-603 soluble interferon receptor is 130,754 Daltons and ran higher than predicted on SDS-PAGE possibly due to glycosylation. Likewise, a major band was detected in the starting material and in fractions 2-4 of the purified RSLV 601-604 soluble interferon receptor (data not shown). The theoretical mass of the RSLV-601-604 soluble interferon receptor is 130,754 Daltons and ran higher than predicted on SDS-PAGE possibly due to glycosylation. Similar results were obtained for RSLV-608-613 as well as RSLV-606 and RSLV-611 (data not shown). Reduced and non-reduced fractions of Protein A purified RSLV 608-613 were subjected to SDS-PAGE analysis and the identity and molecular weight of RSLV 608-613 expressed in CHO supernatants was verified by western blot using anti-IFNAR antibodies (data not shown).

Example 3

Inhibition of IFNα Activity

The soluble interferon receptors were assessed for their ability to inhibit IFNα induced secreted alkaline phosphatase (SEAP) production in HEK-Blue α/β cells.

HEK-Blue IFN-α/β cells (Invivogen, Catalog #hkb-ifnab) produce and secrete SEAP in response to stimulation by IFN-α or IFN-β. To assess inhibition of IFN-α activity, replicate titrations of inhibitors (RSLV 601-604, RSLV 602-603, and anti-human IFNα control) were prepared in a 96 well plate. A fixed concentration of IFNα (0.2 ng/ml final concentration) was added to the wells. HEK-Blue IFN-α/β cells were then added to the plate at 50,000 cells/well and plates were incubated 20-24 hours at 37° C. in 5% $CO_2$. 20 µl of cell supernatant was then added to 180 µl of QUANTI-Blue reagent in a 96 well tissue culture plate, and incubated for 1-3 hr at 37° C. SEAP activity was then detected by measuring absorbance at 620 nm.

Figure 2:
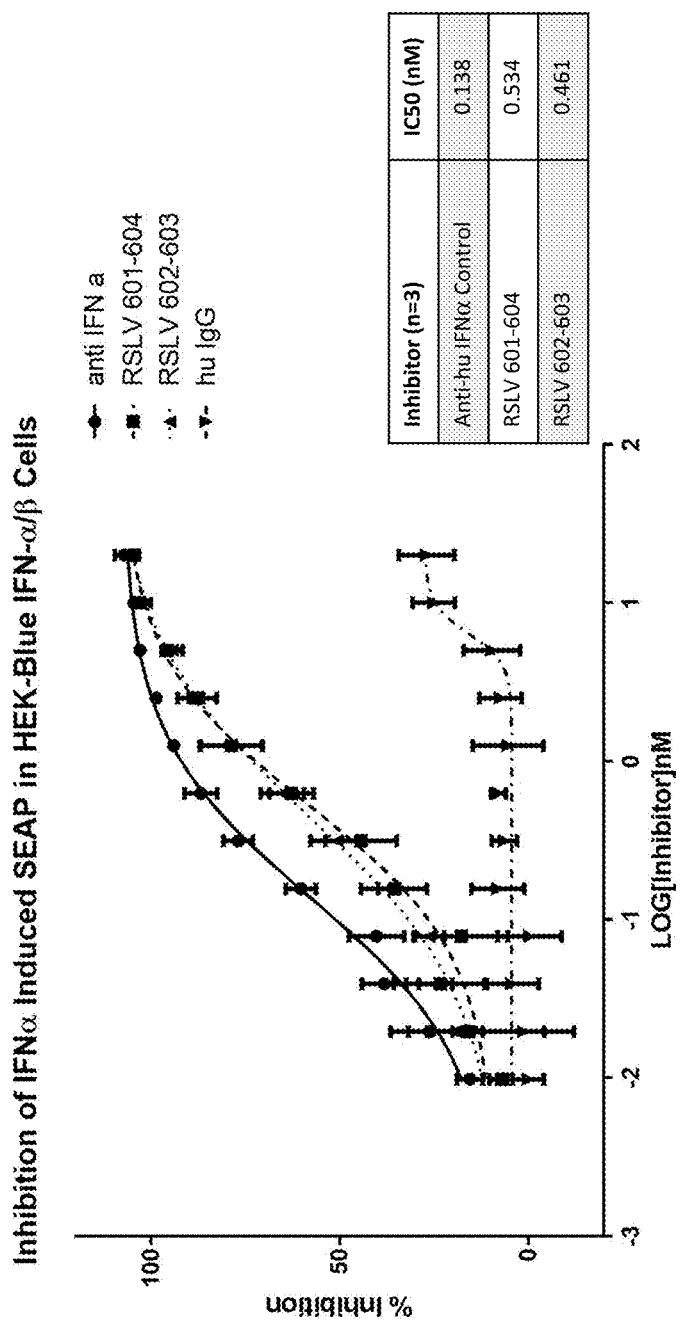
FIG. 2 graphically depicts the inhibition of IFNα induced SEAP production in HEK-Blue α/β cells by the inhibitors RSLV 601-604, RSLV 602-603, and anti-human IFNα positive control. Human IgG was used as a negative control.

The inhibition assays of IFNα activity were performed in triplicate. As shown in FIG. 2, both RSLV 601-604 and RSLV 602-603 were able to inhibit IFNα induced SEAP production to a similar extent as the anti-IFNα control molecule. RSLV 601-604 had an $IC_{50}$ value of 0.534 nM, RSLV 602-603 had an $IC_{50}$ value of 0.461 nM, and the anti-IFNα control had an $IC_{50}$ value of 0.138 nM.

Example 4

Inhibition of IFNβ Activity

The soluble interferon receptors were assessed for their ability to inhibit IFNβ induced secreted alkaline phosphatase (SEAP) production in HEK-Blue α/β cells.

HEK-Blue IFN-α/β cells (Invivogen, Catalog #hkb-ifnab) produce and secrete SEAP in response to stimulation by IFN-α or IFN-β. To assess inhibition of IFN-β activity, replicate titrations of inhibitors (RSLV 601-604, RSLV 602-603, and anti-human IFNβ control) were prepared in a 96 well plate. A fixed concentration of IFNβ (5 pg/ml final concentration) was added to the wells. HEK-Blue IFN-α/β cells were then added to the plate at 50,000 cells/well and plates were incubated 20-24 hours at 37° C. in 5% $CO_2$. 20 µl of cell supernatant was then added to 180 µl of QUANTI-Blue reagent in a 96 well tissue culture plate, and incubated for 1-3 hours at 37° C. SEAP activity was then detected by measuring absorbance at 620 nm.

Figure 3:
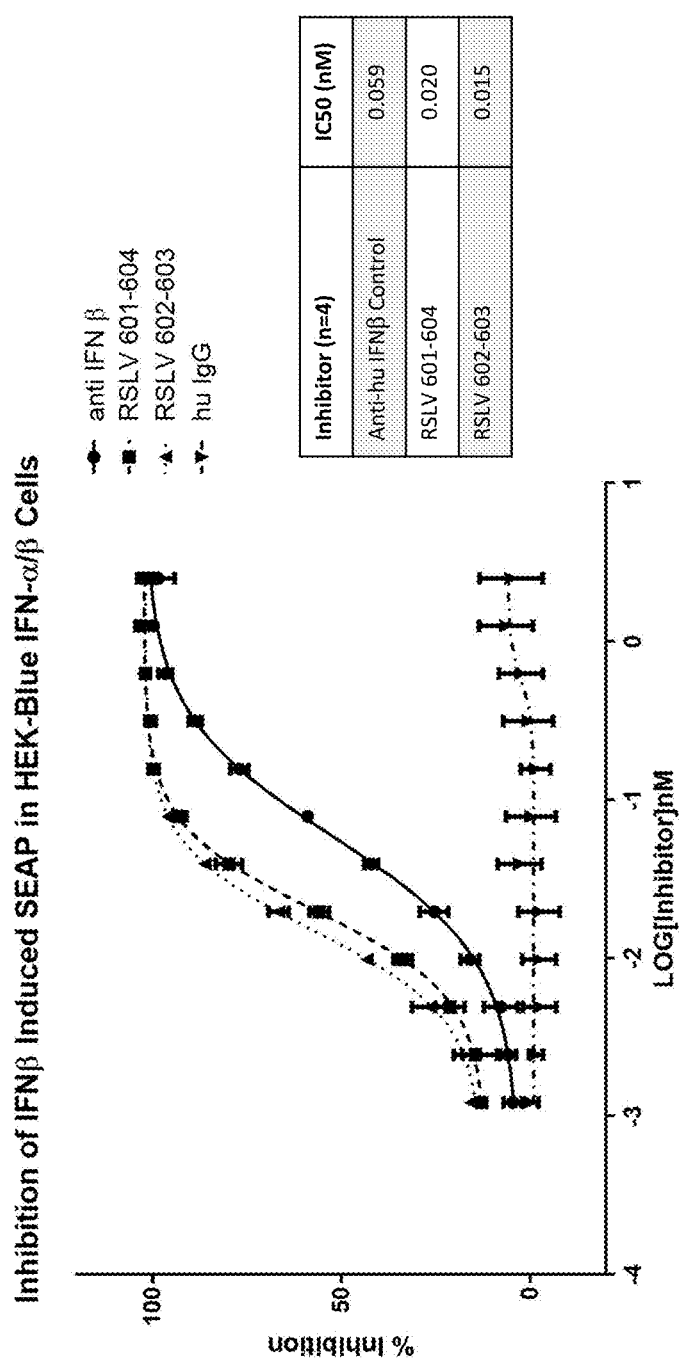
FIG. 3 graphically depicts the inhibition of IFNβ induced SEAP production in HEK-Blue α/β cells by the inhibitors RSLV 601-604, RSLV 602-603, and anti-human IFNβ positive control. Human IgG was used as a negative control.

Four replicates of the inhibition assays of IFNβ activity were performed. As shown in FIG. 3, both RSLV 601-604 and RSLV 602-603 were able to inhibit IFNβ induced SEAP production to a greater extent than the anti-IFNβ control molecule. RSLV 601-604 had an $IC_{50}$ value of 0.020 nM, RSLV 602-603 had an $IC_{50}$ value of 0.015 nM, and the anti-IFNβ control had an $IC_{50}$ value of 0.059 nM.

Example 5

Impact of Linker Length on the Inhibition of IFN-α Activity

The impact of linker length on the ability of the soluble interferon receptors to inhibit IFN-α was assayed according to the methods described in Example 3. The inhibitors used in the assay were RSLV 601-604, RSLV 606-611, RSLV 608-613, and anti-human IFNα control. RSLV 601-604 has a $(Gly_4Ser)_4$ linker; RSLV 606-611 has a $(Gly_4Ser)_2$ linker, and RSLV 608-613 does not include a linker domain.

Figure 4:
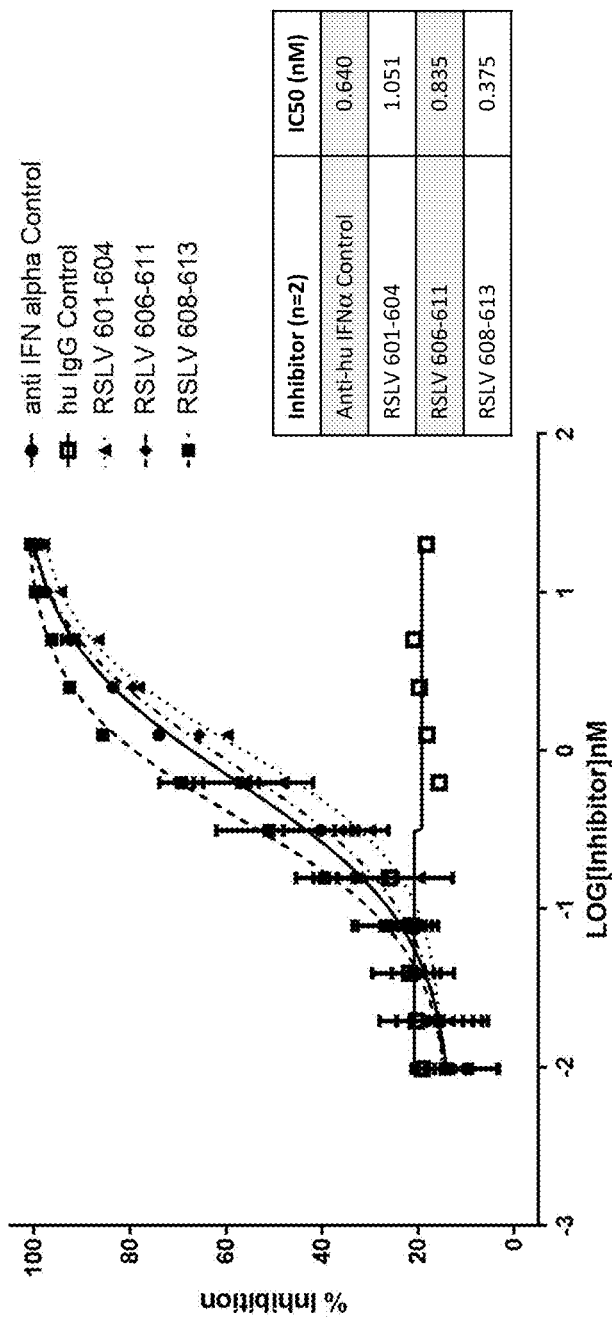
FIG. 4 graphically depicts the impact of linker length on the inhibition of IFNα induced SEAP production in HEK-Blue α/β cells.

The inhibition assays of IFNα activity were performed twice. As shown in FIG. 4, all constructs were able to inhibit IFNα induced SEAP production, although the constructs without linkers or shortened linkers appear to be more potent. For example, RSLV 601-604 had an $IC_{50}$ value of 1.051 nM, RSLV 606-611 had an $IC_{50}$ value of 0.835 nM, and RSLV 608-613 had an $IC_{50}$ value of 0.375. Anti-human IFNα control had an $IC_{50}$ value of 0.640 nM. When the constructs with different linkers were compared to each other, it was observed that IFN-α binding affinity and potency increased as linker length decreased.

Example 6

Impact of Linker Length on the Inhibition of IFN-β Activity

The impact of linker length on the ability of the soluble interferon receptors to inhibit IFN-β was assayed according to the methods described in Example 4. The inhibitors used in the assay were RSLV 601-604, RSLV 606-611, RSLV 608-613, and anti-human IFNα control. RSLV 601-604 has a $(Gly_4Ser)_4$ linker; RSLV 606-611 has a $(Gly_4Ser)_2$ linker, and RSLV 608-613 does not include a linker domain.

Figure 5:
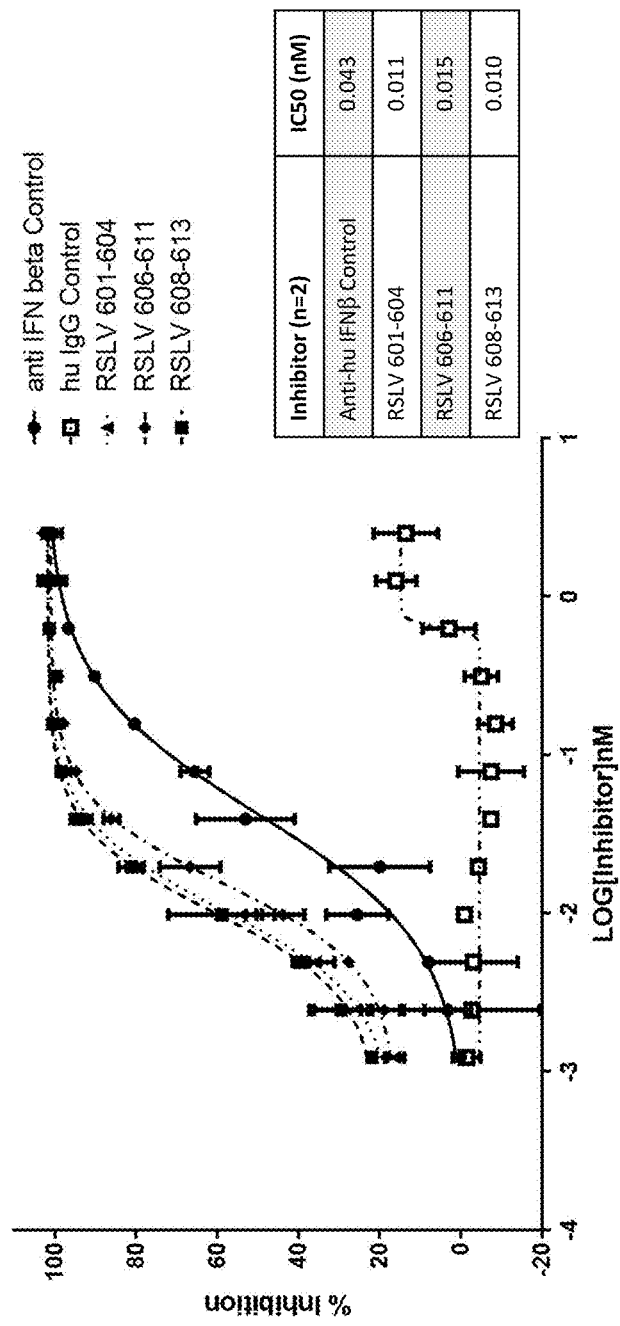
FIG. 5 graphically depicts the impact of linker length on the inhibition of IFNβ induced SEAP production in HEK-Blue α/β cells.

The inhibition assays of IFNβ activity were performed twice. As shown in FIG. 5, all constructs were able to inhibit IFNβ induced SEAP production to a greater extent than the anti-IFNβ control molecule. RSLV 601-604 had an $IC_{50}$ value of 0.011 nM, RSLV 606-611 had an $IC_{50}$ value of 0.015 nM, and RSLV 608-613 had an $IC_{50}$ value of 0.010. Anti-human IFNβ control had an $IC_{50}$ value of 0.043 nM. When the constructs with different linkers were compared to each other, it was observed that linker length did not have an impact on IFN-β binding affinity and potency.

Example 7

Impact of Soluble Interferon Receptor Constructs on the Inhibition of SLE Sera Induced Interferon Gene Expression in PBMC To assess whether interferon (IFN) gene expression could be inhibited by the soluble interferon receptor constructs, interferon regulated genes were induced in peripheral blood mononuclear cells (PBMC) obtained from a health volunteer using systemic lupus erythematosus (SLE) serum from patients that were previously identified as IFN gene signature positive. For example, a three gene (HERC5, EPSTI, and CMPK2) surrogate (interferon signature metric (ISM)) for the interferon signature (IS) can be used as a biomarker to distinguish patients with SLE on serological characteristics (Kennedy et al., Lupus Science and Medicine, 2015; 2:e000080. Doi10.1136/lupus-2014-000080, the entire contents of which is incorporated herein by reference).

Thawing of PBMC

PBMC from a single healthy volunteer were thawed according to the following protocol: RPMI complete media was made by adding 10% heat-inactivated FBS and 1% pen/strep. Nine ml of RPMI complete was aliquoted into a 15-ml conical for each cryovial to be thawed. Each cyrovial was partially submerged in a 37° C. water bath and moved back and forth to partially thaw the vial. The vial was then removed from the water bath and the exterior was sprayed with 70% ethanol. The cryovial was then uncapped and 1 ml of RPMI complete was added to the vial dropwise. The thawed PMBC were then transferred to the 9 ml aliquot of RPMI complete. The PBMC cells in RPMI complete were then centrifuged at 300×g for 7-10 minutes at room temperature. The supernatant was removed from the cells and the cells were suspended in RPMI complete to $2\times10^6$ cells/ml. the cells were then transferred to a 25 ml tissue culture flask and allowed to rest overnight in 5% $CO_2$ at 37° C.

Stimulation of PBMC with SLE Patient Sera+/−RSLV Inhibitors

PBMC were stimulated with SLE patient sera from six patients (with or without the RSLV 608-613 inhibitor or with or without the RSLV601-604 inhibitor) according to the following protocol: SLE patient sera was pre-incubated with the RSLV inhibitor by adding 15 µg RSLV 608-613 (27 µl of RSLV-608-613 at 555 µg/ml) or 15 µg RSLV 601-604 (50 µl of RSLV 601-604 at 306 µg/ml) to 200 µl SLE patient sera in duplicate wells of a 24-well plate. For SLE patient sera without inhibitors, 27 µl of RPMI complete was added to 200 µl of SLE patient sera to duplicate wells of a 24-well plate. The samples were mixed gently and incubated for 30 minutes at 37° C. During the 30 minute incubation, PBMC were harvested from the 25 ml tissue culture flasks an centrifuged to pellet. The PBMC were counted and resuspended to $2\times10^7$ cells/ml in RPMI complete. The resuspended PBMC were added to wells containing the SLE serum and incubated for six hours in 5% $CO_2$ at 37° C.

Preparation of RNA from Stimulated PBMC Using RNeasy Plus Mini Kit

Following incubation of the PBMCs with or without the RSLV constructs, RNA from the stimulated PBMC was prepared using the RNeasy® Plus Mini Kit from Qiagen® according to the manufacturer's protocol. PBMC were harvested from each well of the 24-well plate into 1.5 ml Eppendorf tubes and centrifuged for 2 minutes at 1000×g to pellet the cells. The supernatant was aspirated from the tubes and the pelleted cells were retained. Any remaining PBMC in the wells of the 24-well plate were lysed with 350 ml buffer RLT plus. The cell lysates were then added to the appropriate cell pellet and vortexed for 30 seconds. The homogenized lysate was transferred to a gDNA Eliminator spin column and placed in a 2 ml collection tube. The tubes were centrifuges for 30 seconds at ≥8000×g (≥10,000 rpm). The flow-though was saved and the column was discarded. 350 µl of 70% ethanol was added to the flow-through and mixed well by pipetting. 700 µl of the sample, including any precipitate was immediately transferred to a RNeasy spin column and placed in a 2 ml collection tube. The tubes were centrifuged for 15 seconds at ≥8,000×g and the flow-though was discarded. 700 µl of buffer RW1 was added to the RNeasy Mini spin column (in a 2 ml collection tube), the lids were closed, and the tubes were centrifuged for 15 seconds at ≥8,000×g. The flow-through was discarded. 500 µl of buffer RPE was added to the RNeasy Mini spin column (in a 2 ml collection tube), the lids were closed, and the tubes were centrifuged for 15 seconds at ≥8,000×g. The flow-through was discarded. 500 µl of buffer RPE was added to the RNeasy Mini spin column (in a 2 ml collection tube), the lids were closed, and the tubes were centrifuged for 2 minutes at ≥8,000×g. The flow-through was discarded. The RNeasy spin column was then placed in a new 2 ml collection tube and centrifuged at full speed for 1 minute to further dry the membrane. The RNeasy spin column was then placed in a new 1.5 ml collection tube and 30 µl of RNase-free water was added directly to the spin column membrane. The lids were closed and the tubes were then centrifuged for 1 minute at ≥8,000×g to elute the RNA.

cDNA Synthesis

The RNA derived from the PBMCs treated with or without the RSLV constructs was converted into cDNA as follows: First-strand cDNA was generated from the isolated RNA (as described above) using the SuperScript VILO cDNA synthesis kit (Life Technologies). cDNA was synthesized from 10 ng of RNA in a 20 µl reaction. A control without reverse transcriptase was also performed for each sample. RNA was quantitated based on absorbance at 260 nm on a Nanodrop 2000 spectrophotometer (ThermoFisher) using a conversion factor of $1_{A260}$=40 µg/ml. 10 ng RNA was used as input for cDNA synthesis.

The cDNA reaction mixture was prepare for all reactions to be run. The mix for a single reaction consists of: 4 µl 5× VILO Reaction Mix, 2 µl 10× SuperScript Enzyme Mix, and 10 µl molecular grade water. Enough Reaction mix lacking the 10× Enzyme mix was prepared for use with one RNA sample from each sample (patient sample with or without the RSLV inhibitor, IFN positive RNA control, and IFN negative RNA control). The cDNA reaction plate was placed on ice, and for each reaction 16 µl of the appropriate reaction mix was added to the desired well of a 96 well QPCR plate. 4 µl of RNA was added to each reaction well and mixed by pipetting up and down several times. The wells were capped and the plate was transferred to a thermal cycler and incubated at 25° C. for 10 minutes, followed by 42° C. for 1 hour, followed by 80° C. for five minutes. 80 µl of RNase free water was added to each cDNA reaction and mixed by pipetting up and down several times.

QPCR Measurement of Interferon Signature

QPCR (Taqman) was used to measure the levels of three interferon-inducible genes (HERC5, EPSTI1, and CMPK2) and three reference genes (HPRT1, GUSB, and TFRC) present in the cDNAs prepared above. 1 µl of 1 mM ROX reference dye (provided with Brilliant Multiplex Masters Mix) was added to to 500 µl water to produce a 2 µM stock solution. QPCR reaction mix was prepared for all reactions.

The QPCR reaction mix was divided into seven aliquots with enough reaction mix for each of the six primer/probe sets (sequences shown below) plus an additional aliquot of mix for a set of no RT controls. A single primer/probe set was added to each aliquot. The stock concentration of the primer probe sets was 40×. Therefore, 0.625 μl of primer/probe was used for each 25 μl reaction. A primer and probe set was prepared for each of the six genes, and a single primer/probe set was prepared for the no RT control wells. 20 μl of each reaction mixture was transferred to the wells of a QPCR 96 well plate. 5 μl of each cDNA sample was loaded into the QPCR wells containing each primer/probe mix, and mixed thoroughly by pipetting up and down. All wells were capped with QPCR strip caps, and the plate was spun briefly at 1000 rpm. The plate was loaded into an Mx3005p QPCR instrument and run according to the following cycling conditions: 95° C. for 10 minutes, followed by 40 cycles of: 95° C. for 15 seconds and 60° C. for 1 minute. The following detection settings were used: data was collected using FAM, and ROX filter sets at the end of each 60° C. step (filter gain settings: ROX x 1, FAM x 8).

```
TFRC Probe
/56-FAM/CCA TTG TCA/ZEN/TAT ACC CGG TTC AGC CT/
3IABkFQ/

TFRC Primer 1
ATC TAC AGC AAG TTT CAT CTC CA

TFRC Primer 2
TCA AGC TAG ATC AGC ATT CTC TAA C

HPRT1 Probe
/56-FAM/TCC ATT CCT /ZEN/ATG ACT GTA GAT TTT ATC
AGA CTG AAG A/3IABkFQ/

HPRT1 Primer 1
CCA ATT ACT TTT ATG TCC CCT GTT

HPRT1 Primer 2
CAT CAA AGC ACT GAA TAG AAA TAG TGA

GUSB Probe
/56-FAM/TGC AGG GTT/ZEN/TCA CCA GGA TCC AC/
3IABkFQ/

GUSB Primer 1
GTT TTT GAT CCA GAC CCA GAT G

GUSB Primer 2
GCC CAT TAT TCA GAG CGA GTA

CMPK2 Probe
/56-FAM/ATG CCA CGG/ZEN/GTA AAA CCA CGG T/3IABkFQ/

CMPK2 Primer 1
AGG ACA GCC TTA AGT GAA TCT G

CMPK2 Primer 2
GCC CAA AAC AGA TCC AGA AAG

HERC5 Probe
/56-FAM/ATA CCC AAC/ZEN/AAG CTC AGC CAC CA/
3IABkFQ/

HERC5 Primer 1
CCC AAA TCA GAA ACA TAG GCA AG

HERC5 Primer 2
TCA ACA CAG AAT GAG CTA AGA CC

EPSTI1 Probe
/56-FAM/AGA GCC AAA/ZEN/ATC CAC CAG ACT GAA CA/
3IABkFQ/

EPSTI1 Primer 1
TCC AAC AGC CTC CAG ATT G

EPSTI1 Primer 2
GTG AAT TAC TGG AAC TGA AAC GG
```

Data Analysis

The QPCR data was then analyzed. Cycle threshold (Ct) values for each QPCR reaction were obtained using MxPro version 4.10 software. Threshold fluorescence values were set automatically by the software with amplification-based threshold, adaptive baseline, and moving average options checked. For each sample the loge scaled relative expression of IFN-regulated genes was calculated as the mean Ct of the 3 IFN-regulated genes (CMPK2, HERC5, and EPSTI1) minus the mean Ct of the 3 reference genes (GUSB, HPRT1, and TFRC). This quantity was multiplied by −1 to give the correct directionality to the value.

Summary

Figure 6:
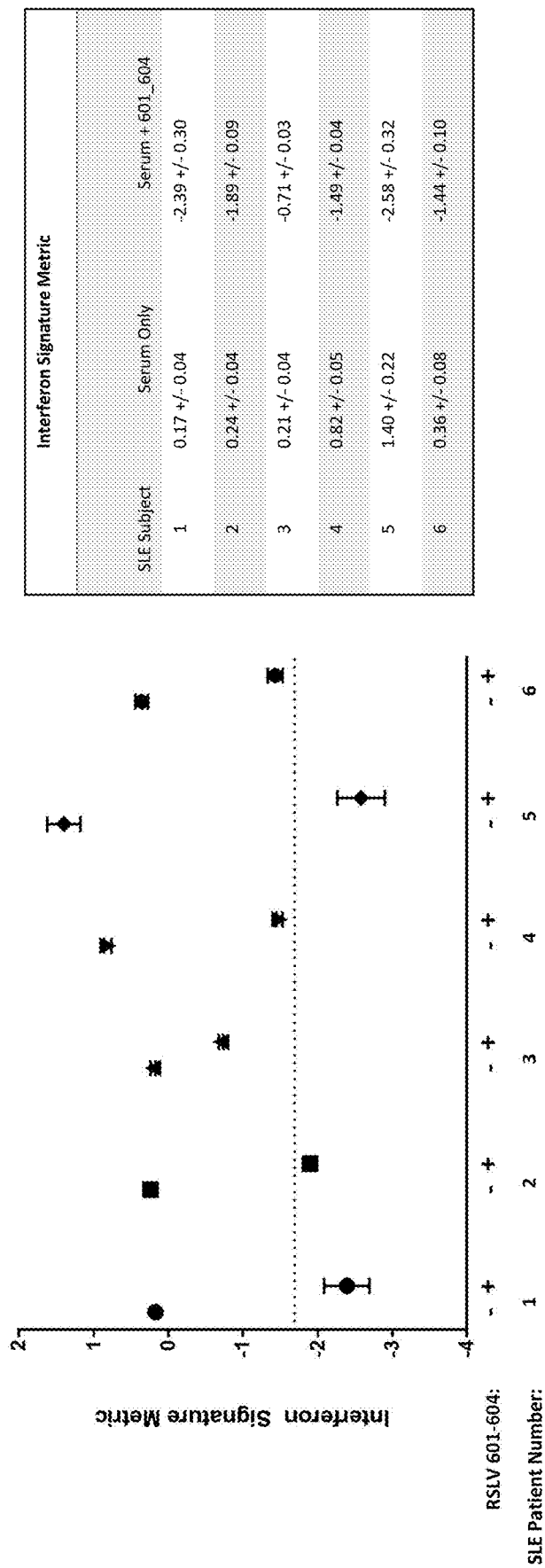
FIG. 6 depicts the inhibition of SLE sera induced interferon gene expression in PBMC with soluble interferon receptor RSLV 601-604.
Figure 7:
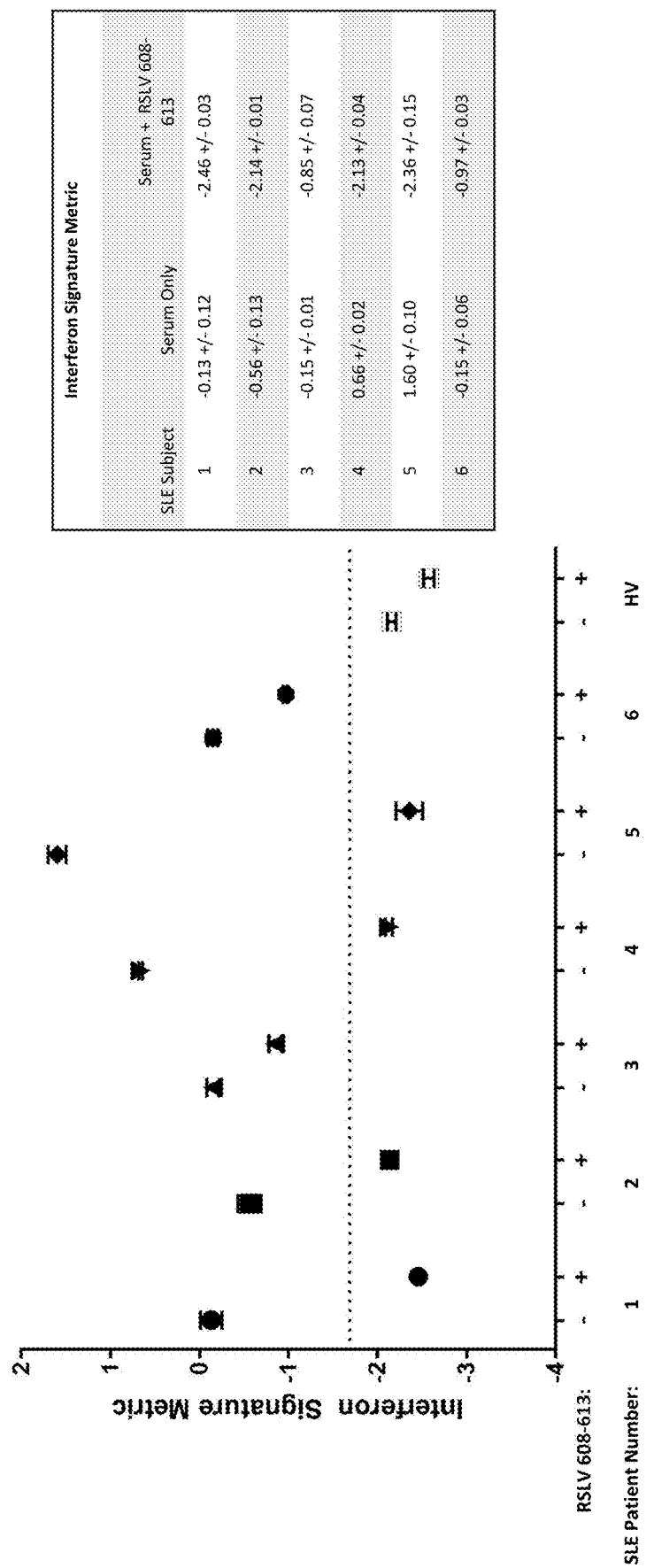
FIG. 7 depicts the inhibition of SLE sera induced interferon gene expression in PBMC with soluble interferon receptor RSLV 608-613.

As shown in FIG. 6, RSLV-601-604 inhibited SLE sera induced interferon gene expression in PBMC from each of the six SLE patients. Similarly, RSLV 608-613 also inhibited SLE patient sera induced interferon gene stimulation (FIG. 7) These data demonstrate that the soluble interferon receptor constructs are effective at inhibiting the cytokines in SLE serum which are responsible for inducing interferon gene expression.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

TABLE 1

| SEQUENCE LISTING | | |
|---|---|---|
| SEQ ID NO: | DESCRIPTION | SEQUENCE |
| 1 | RSLV-601 Leader-IFNAR1 (aa28-436)-(Gly4Ser)4-IgG1 Fc (aa216-447) with mutations C220S, P238S, | MDWTWRILFLVAAATGTHAKNLKSPQKVEVDIIDDNFILRWNRSD ESVGNVTFSFDYQKTGMDNWIKLSGCQNITSTKCNFSSLKLNVYE EIKLRIRAEKENTSSWYEVDSFTPFRKAQIGPPEVHLEAEDKAIV IHISPGTKDSVMWALDGLSFTYSLVIWKNSSGVEERIENIYSRHK IYKLSPETTYCLKVKAALLTSWKIGVYSPVHCIKTTVENELPPPE NIEVSVQNQNYVLKWDYTYANMTFQVQWLHAFLKRNPGNHLYKWK QIPDCENVKTTQCVFPQNVFQKGIYLLRVQASDGNNTSFWSEEIK FDTEIQAFLLPPVFNIRSLSDSFHIYIGAPKQSGNTPVIQDYPLI YEIIFWENTSNAERKIIEKKTDVTVPNLKPLTVYCVKARAHTMDE |

TABLE 1-continued

SEQUENCE LISTING

| SEQ ID NO: | DESCRIPTION | SEQUENCE |
|---|---|---|
| | P331S, T350V, T366L, K392L, T394W | KLNKSSVFSDAVCEKTKPGNTSKGGGGSGGGGSGGGGSGGGGSEP KSSDKTHTCPPCPAPELLGGSSVFLFPPKPKDTLMISRTPEVTCV VVDVSHEDPEVKFNWYVDGVEVHNAKTKPREEQYNSTYRVVSVLT VLHQDWLNGKEYKCKVSNKALPASIEKTISKAKGQPREPQVYVLP PSRDELTKNQVSLLCLVKGFYPSDIAVEWESNGQPENNYLTWPPV LDSDGSFFLYSKLTVDKSRWQQGNVFSCSVMHEALHNHYTQKSLS LSPGK |
| 2 | RSLV-602 Leader-IFNAR2 (aa27-243)- (Gly4Ser)4- IgG1 Fc (aa 216-447) with mutations C220S, P238S, P331S, T350V, T366L, K392L, T394W | MDWTWRILFLVAAATGTHAISYDSPDYTDESCTFKISLRNFRSIL SWELKNHSIVPTHYTLLYTIMSKPEDLKVVKNCANTTRSFCDLTD EWRSTHEAYVTVLEGFSGNTTLFSCSHNFWLAIDMSFEPPEFEIV GFTNHINVMVKFPSIVEEELQFDLSLVIEEQSEGIVKKHKPEIKG NMSGNFTYIIDKLIPNTNYCVSVYLEHSDEQAVIKSPLKCTLLPP GQESESAESAKGGGGSGGGGSGGGGSGGGGSEPKSSDKTHTCPPC RAPELLGGSSVFLEPPKPKDTLMISRTPEVTCVVVDVSHEDPEVK FNWYVDGVEVHNAKTKPREEQYNSTYRVVSVLTVLHQDWLNGKEY KCKVSNKALPASIEKTISKAKGQPREPQVYVLPPSRDELTKNQVS LLCLVKGFYPSDIAVEWESNGQPENNYLTWPPVLDSDGSFFLYSK LTVDKSRWQQGNVFSCSVMHEALHNHYTQKSLSLSPGK |
| 3 | RSLV-603 Leader-IFNAR1 (aa28-436)- (Gly4Ser)4- IgG1 Fc (aa 216-447) with mutations C220S, P238S, P331S, T350V, L351Y, F405A, Y407V | MDWTWRILFLVAAATGTHAKNLKSPQKVEVDIIDDNFILRWNRSD ESVGNVTFSFDYQKTGMDNWIKLSGCQNITSTKCNFSSLKLNVYE EIKLRIRAEKENTSSWYEVDSFTPFRKAQIGPPEVHLEAEDKAIV IHISPGTKDSVMWALDGLSFTYSLVIWKNSSGVEERIENIYSRHK IYKLSPETTYCLKVKAALLTSWKIGVYSPVHCIKTTVENELPPPE NIEVSVQNQNYVLKWDYTYANMTFQVQWLHAFLKRNPGNHLYKWK QIPDCENVKTTQCVFPQNVFQKGIYLLRVQASDGNNTSFWSEEIK FDTEIQAFLLPPVFNIRSLSDSFHIYIGAPKQSGNTPVIQDYPLI YEIIFWENTSNAERKIIEKKTDVTVPNLKPLTVYCVKARAHTMDE KLNKSSVFSDAVCEKTKPGNTSKGGGGSGGGGSGGGGSGGGGSEP KSSDKTHTCPPCPAPELLGGSSVFLFPPKPKDTLMISRTPEVTCV VVDVSHEDPEVKFNWYVDGVEVHNAKTKPREEQYNSTYRVVSVLT VLHQDWLNGKEYKCKVSNKALPASIEKTISKAKGQPREPQVYVYP PSRDELTKNQVSLTCLVKGFYPSDIAVEWESNGQPENNYKTTPPV LDSDGSFALVSKLTVDKSRWQQGNVFSCSVMHEALHNHYTQKSLS LSPGK |
| 4 | RSLV-604 Leader-IFNAR2 (aa27-243)- (Gly4Ser)4- IgG1 Fc (aa 216-447) with mutations C220S, P238S, P331S, and ZW1 Chain A mutations T350V, L351Y, F405A, Y407V | MDWTWRILFLVAAATGTHAISYDSPDYTDESCTFKISLRNFRSIL SWELKNHSIVPTHYTLLYTIMSKPEDLKVVKNCANTTRSFCDLTD EWRSTHEAYVTVLEGFSGNTTLFSCSHNFWLAIDMSFEPPEFEIV GFTNHINVMVKFPSIVEEELQFDLSLVIEEQSEGIVKKHKPEIKG NMSGNFTYIIDKLIPNTNYCVSVYLEHSDEQAVIKSPLKCTLLPP GQESESAESAKGGGGSGGGGSGGGGSGGGGSEPKSSDKTHTCPPC PAPELLGGSSVFLEPPKPKDILMISRIPEVICVVVDVSHEDPEVK FNWYVDGVEVHNAKTKPREEQYNSTYRVVSVLTVLHQDWLNGKEY KCKVSNKALPASIEKTISKAKGQPREPQVYVYPPSRDELTKNQVS LICLVKGFYPSDIAVEWESNGQPENNYKTIPPVLDSDGSFALVSK LTVDKSRWQQGNVESCSVMHEALHNHYTQKSLSLSPGK |
| 5 | IFNAR1 ACCESSION NP_000620 | MMVVLLGATTLVLVAVAPWVLSAAAGGKNLKSPQKVEVDIIDDNF ILRWNRSDESVGNVIFSFDYQKTGMDNWIKLSGCQNITSTKCNFS SLKLNVYEEIKLRIRAEKENTSSWYEVDSFTPFRKAQIGPPEVHL EAEDKAIVIHISPGIKDSVMWALDGLSETYSLVIWKNSSGVEERI ENIYSRHKIYKLSPETTYCLKVKAALLTSWKIGVYSPVHCIKTTV ENELPPPENIEVSVQNQNYVLKWDYTYANMTFQVQWLHAFLKRNP GNHLYKWKQIPDCENVKTTQCVFPQNVFQKGIYLLRVQASDGNNT SFWSEEIKFDTEIQAFLLPPVFNIRSLSDSFHIYIGAPKQSGNIP VIQDYPLIYEIIFWENTSNAERKIIEKKTDVIVPNLKPLIVYCVK ARAHTMDEKLNKSSVESDAVCEKTKPGNISKIWLIVGICIALFAL PFVIYAAKVFLRCINYVFFPSLKPSSSIDEYFSEQPLKNLLLSTS EEQIEKCFIIENISTIATVEETNQTDEDHKKYSSQTSQDSGNYSN EDESESKTSEELQQDFV |
| 6 | IFNAR2 ACCESSION NP_997468 | MLLSQNAFIFRSLNLVLMVYISLVEGISYDSPDYTDESCIFKISL RNFRSILSWELKNHSIVPTHYILLYTIMSKPEDLKVVKNCANTIR SFCDLTDEWRSTHEAYVTVLEGFSGNITLFSCSHNFWLAIDMSFE PPEFEIVGFTNHINVMVKFPSIVEEELQFDLSLVIEEQSEGIVKK HKPEIKGNMSGNFTYIIDKLIPNTNYCVSVYLEHSDEQAVIKSPL KCILLPPGQESESAESAKIGGIITVFLIALVLISTIVILKWIGYI CLRNSLPKVLNFHNFLAWPFPNLPPLEAMDMVEVIYINRKKKVWD YNYDDESDSDTEAAPRTSGGGYTMHGLIVRPLGQASATSTESQLI |

TABLE 1-continued

SEQUENCE LISTING

| SEQ ID NO: | DESCRIPTION | SEQUENCE |
|---|---|---|
| | | DPESEEEPDLPEVDVELPTMPKDSPQQLELLSGPCERRKSPLQDP<br>FPEEDYSSTEGSGGRITFNVDLNSVFLRVLDDEDSDDLEAPLMLS<br>SHLEEMVDPEDPDNVQSNHLLASGEGTQPIFPSPSSEGLWSEDAP<br>SDQSDTSESDVDLGDGYIMR |
| 7 | IFNAR1 Extracellular domain (with signal sequence) | MMVVLLGATTLVLVAVAPWVLSAAAGGKNLKSPQKVEVDIIDDNF<br>ILRWNRSDESVGNVIFSFDYQKTGMDNWIKLSGCQNITSTKCNFS<br>SLKLNVYEEIKLRIRAEKENTSSWYEVDSFTPFRKAQIGPPEVHL<br>EAEDKAIVIHISPGIKDSVMWALDGLSETYSLLIWKNSSGVEERI<br>ENIYSRHKIYKLSPETTYCLKVKAALLTSWKIGVYSPVHCIKTTV<br>ENELPPPENIEVSVQNQNYVLKWDYTYANMTFQVQWLHAFLKRNP<br>GNHLYKWKQIPDCENVKTTQCVFPQNVFQKGIYLLRVQASDGNNT<br>SFWSEEIKFDTEIQAFLLPPVFNIRSLSDSFHIYIGAPKQSGNIP<br>VIQDYPLIYEIIFWENTSNAERKIIEKKTDVIVPNLKPLIVYCVK<br>ARAHTMDEKLNKSSVESDAVCEKTKPGNISK |
| 8 | IFNAR2 Extracellular domain (with signal sequence) | MLLSQNAFIFRSLNLVLMVYISLVEGISYDSPDYTDESCIFKISL<br>RNFRSILSWELKNHSIVPTHYILLYTIMSKPEDLKVVKNCANTIR<br>SFCDLTDEWRSTHEAYVTVLEGFSGNITLFSCSHNFWLAIDMSFE<br>PPEFEIVGFTNHINVMVKFPSIVEEELQFDLSLVIEEQSEGIVKK<br>HKPEIKGNMSGNFTYIIDKLIPNTNYCVSVYLEHSDEQAVIKSPL<br>KCTLLPPGQESESAESAK |
| 9 | IgG1 Fc (aa 216-447) with mutations C220S, P238S, P331S, T350V, L351Y, F405A, Y407V | EPKSSDKTHTCPPCPAPELLGGSSVFLFPPKPKDTLMISRTPEVT<br>CVVVDVSHEDPEVKFNWYVDGVEVHNAKTKPREEQYNSTYRVVSV<br>LTVLHQDWLNGKEYKCKVSNKALPASIEKTISKAKGQPREPQVYV<br>YPPSRDELTKNQVSLTCLVKGFYPSDIAVEWESNGQPENNYKTTP<br>PVLDSDGSFALVSKLTVDKSRWQQGNVFSCSVMHEALHNHYTQKS<br>LSLSPGK |
| 10 | IgG1 Fc (aa216-447) with mutations C220S, P238S, P331S, T350V, T366L, K392L, T394W | EPKSSDKTHTCPPCPAPELLGGSSVFLFPPKPKDTLMISRTPEVT<br>CVVVDVSHEDPEVKFNWYVDGVEVHNAKTKPREEQYNSTYRVVSV<br>LTVLHQDWLNGKEYKCKVSNKALPASIEKTISKAKGQPREPQVYV<br>LPPSRDELTKNQVSLLCLVKGFYPSDIAVEWESNGQPENNYLTWP<br>PVLDSDGSFFLYSKLTVDKSRWQQGNVESCSVMHEALHNHYTQKS<br>LSLSPGK |
| 11 | IFNAR1 (aa28-436) | KNLKSPQKVEVDIIDDNFILRWNRSDESVGNVTFSFDYQKTGMDN<br>WIKLSGCQNITSTKCNFSSLKLNVYEEIKLRIRAEKENTSSWYEV<br>DSFTPFRKAQIGPPEVHLEAEDKAIVIHISPGTKDSVMWALDGLS<br>FTYSLVIWKNSSGVEERIENIYSRHKIYKLSPETTYCLKVKAALL<br>TSWKIGVYSPVHCIKTTVENELPPPENIEVSVQNQNYVLKWDYTY<br>ANMTFQVQWLHAFLKRNPGNHLYKWKQIPDCENVKTTQCVFPQNV<br>FQKGIYLLRVQASDGNNTSFWSEEIKFDTEIQAFLLPPVFNIRSL<br>SDSFHIYIGAPKQSGNTPVIQDYPLIYEIIFWENTSNAERKIIEK<br>KTDVTVPNLKPLTVYCVKARAHTMDEKLNKSSVFSDAVCEKTKPG<br>NTSK |
| 12 | IFNAR2 (aa27-243) | ISYDSPDYTDESCTFKISLRNFRSILSWELKNHSIVPTHYTLLYT<br>IMSKPEDLKVVKNCANTTRSFCDLTDEWRSTHEAYVTVLEGFSGN<br>TTLFSCSHNFWLAIDMSFEPPEFEIVGFTNHINVMVKFPSIVEEE<br>LQFDLSLVIEEQSEGIVKKHKPEIKGNMSGNFTYIIDKLIPNTNY<br>CVSVYLEHSDEQAVIKSPLKCTLLPPGQESESAESAK |
| 13 | Leader Sequence | MDWTWRILFLVAAATGTHA |
| 14 | VK3LP leader sequence | METPAQLLFLLLLWLPDTTG |
| 15 | (Gly4Ser)4 | GGGGSGGGGSGGGGSGGGGS |
| 16 | (Gly4Ser)3 | GGGGSGGGGSGGGGS |
| 17 | (Gly4Ser)5 | GGGGSGGGGSGGGGSGGGGSGGGGS |
| 18 | NLG linker | VDGASSPVNVSSPSVQDI |
| 19 | linker | LEA(EAAAK)$_4$ALEA(EAAAK)$_4$ALE |
| 20 | IgG1 Fc (SCC hinge) | EPKSSDKTHTCPPCPAPELLGGPSVFLFPPKPKDTLMISRTPEVT<br>CVVVDVSHEDPEVKFNWYVDGVEVHNAKTKPREEQYNSTYRVVSV<br>LTVLHQDWLNGKEYKCKVSNKALPAPIEKTISKAKGQPREPQVYT |

TABLE 1-continued

SEQUENCE LISTING

| SEQ ID NO: | DESCRIPTION | SEQUENCE |
|---|---|---|
| | | LPPSRDELTKNQVSLTCLVKGFYPSDIAVEWESNGQPENNYKTTP<br>PVLDSDGSFFLYSKLTVDKSRWQQGNVESCSVMHEALHNHYTQKS<br>LSLSPGK |
| 21 | IgG1 Fc domain (SSS hinge) | EPKSSDKTHTSPPSPAPELLGGPSVFLFPPKPKDTLMISRTPEVT<br>CVVVDVSHEDPEVKFNWYVDGVEVHNAKTKPREEQYNSTYRVVSV<br>LTVLHQDWLNGKEYKCKVSNKALPAPIEKTISKAKGQPREPQVYT<br>LPPSRDELTKNQVSLTCLVKGFYPSDIAVEWESNGQPENNYKTTP<br>PVLDSDGSFFLYSKLTVDKSRWQQGNVESCSVMHEALHNHYTQKS<br>LSLSPGK |
| 22 | IgG1 Fc domain with P238S (SCC hinge) | EPKSSDKTHTCPPCPAPELLGGSSVFLFPPKPKDTLMISRTPEVT<br>CVVVDVSHEDPEVKFNWYVDGVEVHNAKTKPREEQYNSTYRVVSV<br>LTVLHQDWLNGKEYKCKVSNKALPAPIEKTISKAKGQPREPQVYT<br>LPPSRDELTKNQVSLTCLVKGFYPSDIAVEWESNGQPENNYKTTP<br>PVLDSDGSFFLYSKLTVDKSRWQQGNVESCSVMHEALHNHYTQKS<br>LSLSPGK |
| 23 | IgG1 Fc domain with P331S | EPKSSDKTHTCPPCPAPELLGGPSVFLFPPKPKDTLMISRTPEVT<br>CVVVDVSHEDPEVKFNWYVDGVEVHNAKTKPREEQYNSTYRVVSV<br>LTVLHQDWLNGKEYKCKVSNKALPASIEKTISKAKGQPREPQVYT<br>LPPSRDELTKNQVSLTCLVKGFYPSDIAVEWESNGQPENNYKTTP<br>PVLDSDGSFFLYSKLTVDKSRWQQGNVESCSVMHEALHNHYTQKS<br>LSLSPGK |
| 24 | IgG1 Fc domain with SSS, P238S, and P331S | EPKSSDKTHTSPPSPAPELLGGSSVFLFPPKPKDTLMISRTPEVT<br>CVVVDVSHEDPEVKFNWYVDGVEVHNAKTKPREEQYNSTYRVVSV<br>LTVLHQDWLNGKEYKCKVSNKALPASIEKTISKAKGQPREPQVYT<br>LPPSRDELTKNQVSLTCLVKGFYPSDIAVEWESNGQPENNYKTTP<br>PVLDSDGSFFLYSKLTVDKSRWQQGNVESCSVMHEALHNHYTQKS<br>LSLSPGK |
| 25 | IgG1 Fc domain with SCC, P238S, and P331S | EPKSSDKTHTCPPCPAPELLGGSSVFLFPPKPKDTLMISRTPEVT<br>CVVVDVSHEDPEVKFNWYVDGVEVHNAKTKPREEQYNSTYRVVSV<br>LTVLHQDWLNGKEYKCKVSNKALPASIEKTISKAKGQPREPQVYT<br>LPPSRDELTKNQVSLTCLVKGFYPSDIAVEWESNGQPENNYKTTP<br>PVLDSDGSFFLYSKLTVDKSRWQQGNVESCSVMHEALHNHYTQKS<br>LSLSPGK |
| 26 | Human IgG1 Fc domain (wild-type) | EPKSCDKTHTCPPCPAPELLGGPSVFLFPPKPKDTLMISRTPEVT<br>CVVVDVSHEDPEVKFNWYVDGVEVHNAKTKPREEQYNSTYRVVSV<br>LTVLHQDWLNGKEYKCKVSNKALPAPIEKTISKAKGQPREPQVYT<br>LPPSRDELTKNQVSLTCLVKGFYPSDIAVEWESNGQPENNYKTTP<br>PVLDSDGSFFLYSKLTVDKSRWQQGNVESCSVMHEALHNHYTQKS<br>LSLSPGK |
| 27 | linker | GGSG |
| 28 | linker | GSAT |
| 29 | O-linked glycosylation consensus site | CXXGGT/S-C |
| 30 | O-linked glycosylation consensus site | NST-E/D-A |
| 31 | O-linked glycosylation consensus site | NITQS |
| 32 | O-linked glycosylation consensus site | QSTQS |
| 33 | O-linked glycosylation consensus site | D/E-FT-R/K-V |
| 34 | O-linked glycosylation consensus site | C-E/D-SN |

TABLE 1-continued

SEQUENCE LISTING

| SEQ ID NO: | DESCRIPTION | SEQUENCE |
|---|---|---|
| 35 | O-linked glycosylation consensus site | GGSC-K/R |
| 36 | IFNAR1 (without signal sequence) | KNLKSPQKVEVDIIDDNFILRWNRSDESVGNVTFSFDYQKTGMDN WIKLSGCQNITSTKCNFSSLKLNVYEEIKLRIRAEKENTSSWYEV DSFTPFRKAQIGPPEVHLEAEDKAIVIHISPGTKDSVMWALDGLS FTYSLVIWKNSSGVEERIENIYSRHKIYKLSPETTYCLKVKAALL TSWKIGVYSPVHCIKTTVENELPPPENIEVSVQNQNYVLKWDYTY ANMTFQVQWLHAFLKRNPGNHLYKWKQIPDCENVKTTQCVFPQNV FQKGIYLLRVQASDGNNTSFWSEEIKFDTEIQAFLLPPVFNIRSL SDSFHIYIGAPKQSGNTPVIQDYPLIYEIIFWENTSNAERKIIEK KTDVIVPNLKPLIVYCVKARAHTMDEKLNKSSVESDAVCEKTKPG NTSKIWLIVGICIALFALPFVIYAAKVFLRCINYVFFPSLKPSSS IDEYFSEQPLKNLLLSTSEEQIEKCFIIENISTIATVEETNQTDE DHKKYSSQTSQDSGNYSNEDESESKTSEELQQDFV |
| 37 | IFNAR2 (without signal sequence) | ISYDSPDYTDESCIFKISLRNFRSILSWELKNHSIVPTHYTLLYT IMSKPEDLKVVKNCANTIRSFCDLTDEWRSTHEAYVTVLEGFSGN TTLFSCSHNFWLAIDMSFEPPEFEIVGFINHINVMVKFPSIVEEE LQFDLSLVIEEQSEGIVKKHKPEIKGNMSGNFTYIIDKLIPNTNY CVSVYLEHSDEQAVIKSPLKCILLPPGQESESAESAKIGGIITVF LIALVLISTIVILKWIGYICLRNSLPKVLNFHNFLAWPFPNLPPL EAMDMVEVIYINRKKKVWDYNYDDESDSDTEAAPRTSGGGYTMHG LIVRPLGQASATSTESQLIDPESEEEPDLPEVDVELPIMPKDSPQ QLELLSGPCERRKSPLQDPFPEEDYSSTEGSGGRITFNVDLNSVF LRVLDDEDSDDLEAPLMLSSHLEEMVDPEDPDNVQSNHLLASGEG TQPIFPSPSSEGLWSEDAPSDQSDISESDVDLGDGYIMR |
| 38 | (Gly4Ser)2 | GGGGSGGGGS |
| 39 | (Gly4Ser)1 | GGGGS |
| 40 | RSLV-601 Without a leader sequence | KNLKSPQKVEVDIIDDNFILRWNRSDESVGNVIFSFDYQKTGMDN WIKLSGCQNITSTKCNFSSLKLNVYEEIKLRIRAEKENTSSWYEV DSFTPERKAQIGPPEVHLEAEDKAIVIHISPGIKDSVMWALDGLS FTYSLVIWKNSSGVEERIENIYSRHKIYKLSPETTYCLKVKAALL TSWKIGVYSPVHCIKTIVENELPPPENIEVSVQNQNYVLKWDYTY ANMTFQVQWLHAFLKRNPGNHLYKWKQIPDCENVKITQCVFPQNV FQKGIYLLRVQASDGNNTSFWSEEIKFDTEIQAFLLPPVFNIRSL SDSFHIYIGAPKQSGNTPVIQDYPLIYEIIFWENTSNAERKIIEK KTDVIVPNLKPLIVYCVKARAHTMDEKLNKSSVESDAVCEKTKPG NTSKGGGGSGGGGSGGGGSGGGGSEPKSSDKTHTCPPCPAPELLG GSSVFLFPPKPKDILMISRIPEVICVVVDVSHEDPEVKFNWYVDG VEVHNAKTKPREEQYNSTYRVVSVLTVLHQDWLNGKEYKCKVSNK ALPASIEKTISKAKGQPREPQVYVLPPSRDELTKNQVSLLCLVKG FYPSDIAVEWESNGQPENNYLIWPPVLDSDGSFFLYSKLIVDKSR WQQGNVFSCSVMHEALHNHYTQKSLSLSPGK |
| 41 | RSLV-602 Without a leader sequence | ISYDSPDYTDESCIFKISLRNFRSILSWELKNHSIVPTHYTLLYT IMSKPEDLKVVKNCANTIRSFCDLTDEWRSTHEAYVTVLEGFSGN TTLFSCSHNFWLAIDMSFEPPEFEIVGFINHINVMVKFPSIVEEE LQFDLSLVIEEQSEGIVKKHKPEIKGNMSGNFTYIIDKLIPNTNY CVSVYLEHSDEQAVIKSPLKCTLLPPGQESESAESAKGGGGSGGG GSGGGGSGGGGSEPKSSDKTHTCPPCPAPELLGGSSVFLFPPKPK DILMISRIPEVICVVVDVSHEDPEVKFNWYVDGVEVHNAKTKPRE EQYNSTYRVVSVLTVLHQDWLNGKEYKCKVSNKALPASIEKTISK AKGQPREPQVYVLPPSRDELTKNQVSLLCLVKGFYPSDIAVEWES NGQPENNYLIWPPVLDSDGSFFLYSKLIVDKSRWQQGNVESCSVM HEALHNHYTQKSLSLSPGK |
| 42 | RSLV-603 Without a leader sequence | KNLKSPQKVEVDIIDDNFILRWNRSDESVGNVIFSFDYQKTGMDN WIKLSGCQNITSTKCNFSSLKLNVYEEIKLRIRAEKENTSSWYEV DSFTPERKAQIGPPEVHLEAEDKAIVIHISPGIKDSVMWALDGLS FTYSLVIWKNSSGVEERIENIYSRHKIYKLSPETTYCLKVKAALL TSWKIGVYSPVHCIKTIVENELPPPENIEVSVQNQNYVLKWDYTY ANMTFQVQWLHAFLKRNPGNHLYKWKQIPDCENVKITQCVFPQNV FQKGIYLLRVQASDGNNTSFWSEEIKFDTEIQAFLLPPVFNIRSL SDSFHIYIGAPKQSGNTPVIQDYPLIYEIIFWENTSNAERKIIEK KTDVTVPNLKPLTVYCVKARAHTMDEKLNKSSVFSDAVCEKTKPG NTSKGGGGSGGGGSGGGGSGGGGSEPKSSDKTHTCPPCPAPELLG GSSVFLFPPKPKDTLMISRTPEVTCVVVDVSHEDPEVKFNWYVDG VEVHNAKTKPREEQYNSTYRVVSVLTVLHQDWLNGKEYKCKVSNK |

US 10,947,295 B2

107                                                                    108

TABLE 1-continued

| SEQ ID NO: | DESCRIPTION | SEQUENCE |
|---|---|---|
| | | ALPASIEKTISKAKGQPREPQVYVYPPSRDELTKNQVSLTCLVKG<br>FYPSDIAVEWESNGQPENNYKTTPPVLDSDGSFALVSKLTVDKSR<br>WQQGNVFSCSVMHEALHNHYTQKSLSLSPGK |
| 43 | RSLV-604 without a leader sequence | ISYDSPDYTDESCTFKISLRNFRSILSWELKNHSIVPTHYTLLYT<br>IMSKPEDLKVVKNCANTTRSFCDLTDEWRSTHEAYVTVLEGFSGN<br>TTLFSCSHNFWLAIDMSFEPPEFEIVGFTNHINVMVKFPSIVEEE<br>LQFDLSLVIEEQSEGIVKKHKPEIKGNMSGNFTYIIDKLIPNTNY<br>CVSVYLEHSDEQAVIKSPLKCTLLPPGQESESAESAKGGGGSGGG<br>GSGGGGSGGGGSEPKSSDKTHTCPPCPAPELLGGSSVFLFPPKPK<br>DTLMISRTPEVTCVVVDVSHEDPEVKFNWYVDGVEVHNAKTKPRE<br>EQYNSTYRVVSVLTVLHQDWLNGKEYKCKVSNKALPASIEKTISK<br>AKGQPREPQVYVYPPSRDELTKNQVSLTCLVKGFYPSDIAVEWES<br>NGQPENNYKTTPPVLDSDGSFALVSKLTVDKSRWQQGNVFSCSVM<br>HEALHNHYTQKSLSLSPGK |
| 44 | Leader-IFNAR2 (aa27-243)-(Gly4Ser)2-IgG1 Fc (aa 216-447) with mutations C220S, P238S, P331S, T350V, T366L, K392L, T394W | MDWTWRILFLVAAATGTHAISYDSPDYTDESCTFKISLRNFRSIL<br>SWELKNHSIVPTHYTLLYTIMSKPEDLKVVKNCANTTRSFCDLTD<br>EWRSTHEAYVTVLEGFSGNTTLFSCSHNFWLAIDMSFEPPEFEIV<br>GFTNHINVMVKFPSIVEEELQFDLSLVIEEQSEGIVKKHKPEIKG<br>NMSGNFTYIIDKLIPNTNYCVSVYLEHSDEQAVIKSPLKCTLLPP<br>GQESESAESAKGGGGSGGGGSEPKSSDKTHTCPPCPAPELLGGSS<br>VFLFPPKPKDTLMISRTPEVTCVVVDVSHEDPEVKFNWYVDGVEV<br>HNAKTKPREEQYNSTYRVVSVLTVLHQDWLNGKEYKCKVSNKALP<br>ASIEKTISKAKGQPREPQVYVLPPSRDELTKNQVSLLCLVKGFYP<br>SDIAVEWESNGQPENNYLTWPPVLDSDGSFFLYSKLTVDKSRWQQ<br>GNVFSCSVMHEALHNHYTQKSLSLSPGK |
| 45 | IFNAR2 (aa27-243)-(Gly4Ser)2-IgG1 Fc (aa 216-447) with mutations C220S, P238S, P331S, T350V, T366L, K392L, T394W, without a leader sequence | ISYDSPDYTDESCTFKISLRNFRSILSWELKNHSIVPTHYTLLYT<br>IMSKPEDLKVVKNCANTTRSFCDLTDEWRSTHEAYVTVLEGFSGN<br>TTLFSCSHNFWLAIDMSFEPPEFEIVGFTNHINVMVKFPSIVEEE<br>LQFDLSLVIEEQSEGIVKKHKPEIKGNMSGNFTYIIDKLIPNTNY<br>CVSVYLEHSDEQAVIKSPLKCTLLPPGQESESAESAKGGGGSGGG<br>GSEPKSSDKTHTCPPCPAPELLGGSSVFLFPPKPKDTLMISRTPE<br>VTCVVVDVSHEDPEVKFNWYVDGVEVHNAKTKPREEQYNSTYRVV<br>SVLTVLHQDWLNGKEYKCKVSNKALPASIEKTISKAKGQPREPQV<br>YVLPPSRDELTKNQVSLLCLVKGFYPSDIAVEWESNGQPENNYLT<br>WPPVLDSDGSFFLYSKLTVDKSRWQQGNVFSCSVMHEALHNHYTQ<br>KSLSLSPGK |
| 46 | Leader-IFNAR2 (aa27-243)-IgG1 Fc (aa 216-447) with mutations C220S, P238S, P331S, T350V, T366L, K392L, T394W | MDWTWRILFLVAAATGTHAISYDSPDYTDESCTFKISLRNFRSIL<br>SWELKNHSIVPTHYTLLYTIMSKPEDLKVVKNCANTTRSFCDLTD<br>EWRSTHEAYVTVLEGFSGNTTLFSCSHNFWLAIDMSFEPPEFEIV<br>GFTNHINVMVKFPSIVEEELQFDLSLVIEEQSEGIVKKHKPEIKG<br>NMSGNFTYIIDKLIPNTNYCVSVYLEHSDEQAVIKSPLKCTLLPP<br>GQESESAESAKEPKSSDKTHTCPPCPAPELLGGSSVFLFPPKPKD<br>TLMISRTPEVTCVVVDVSHEDPEVKFNWYVDGVEVHNAKTKPREE<br>QYNSTYRVVSVLTVLHQDWLNGKEYKCKVSNKALPASIEKTISKA<br>KGQPREPQVYVLPPSRDELTKNQVSLLCLVKGFYPSDIAVEWESN<br>GQPENNYLTWPPVLDSDGSFFLYSKLTVDKSRWQQGNVESCSVMH<br>EALHNHYTQKSLSLSPGK |
| 47 | IFNAR2 (aa27-243)-IgG1 Fc (aa 216-447) with mutations C220S, P238S, P331S, T350V, T366L, K392L, T394W, without a leader sequence | ISYDSPDYTDESCTFKISLRNFRSILSWELKNHSIVPTHYTLLYT<br>IMSKPEDLKVVKNCANTTRSFCDLTDEWRSTHEAYVTVLEGFSGN<br>TTLFSCSHNFWLAIDMSFEPPEFEIVGFTNHINVMVKFPSIVEEE<br>LQFDLSLVIEEQSEGIVKKHKPEIKGNMSGNFTYIIDKLIPNTNY<br>CVSVYLEHSDEQAVIKSPLKCTLLPPGQESESAESAKEPKSSDKT<br>HTCPPCPAPELLGGSSVFLFPPKPKDTLMISRTPEVTCVVVDVSH<br>EDPEVKFNWYVDGVEVHNAKTKPREEQYNSTYRVVSVLTVLHQDW<br>LNGKEYKCKVSNKALPASIEKTISKAKGQPREPQVYVLPPSRDEL<br>TKNQVSLLCLVKGFYPSDIAVEWESNGQPENNYLTWPPVLDSDGS<br>FFLYSKLTVDKSRWQQGNVESCSVMHEALHNHYTQKSLSLSPGK |
| 48 | Leader-IFNAR1 (aa28-436)-(Gly4Ser)2-IgG1 Fc (aa 216-447) with mutations C220S, P238S, P331S, T350V, L351Y, F405A, Y407V | MDWTWRILFLVAAATGTHAKNLKSPQKVEVDIIDDNFILRWNRSD<br>ESVGNVTFSFDYQKTGMDNWIKLSGCQNITSTKCNFSSLKLNVYE<br>EIKLRIRAEKENTSSWYEVDSFTPFRKAQIGPPEVHLEAEDKAIV<br>IHISPGTKDSVMWALDGLSETYSLVIWKNSSGVEERIENTYSRHK<br>IYKLSPETTYCLKVKAALLTSWKIGVYSPVHCIKTTVENELPPPE<br>NIEVSVQNQNYVLKWDYTYANMTFQVQWLHAFLKRNPGNHLYKWK<br>QIPDCENVKTTQCVFPQNVFQKGIYLLRVQASDGNNTSFWSEEIK<br>FDTEIQAFLLPPVFNIRSLSDSFHIYIGAPKQSGNTPVIQDYPLI<br>YEIIFWENTSNAERKIIEKKTDVTVPNLKPLTVYCVKARAHTMDE<br>KLNKSSVFSDAVCEKTKPGNTSKGGGGSGGGGSEPKSSDKTHTCP<br>PCPAPELLGGSSVFLFPPKPKDTLMISRTPEVTCVVVDVSHEDPE |

TABLE 1-continued

SEQUENCE LISTING

| SEQ ID NO: | DESCRIPTION | SEQUENCE |
| --- | --- | --- |
| | | VKFNWYVDGVEVHNAKTKPREEQYNSTYRVVSVLTVLHQDWLNGK
EYKCKVSNKALPASIEKTISKAKGQPREPQVYVYPPSRDELTKNQ
VSLTCLVKGFYPSDIAVEWESNGQPENNYKTTPPVLDSDGSFALV
SKLTVDKSRWQQGNVFSCSVMHEALHNHYTQKSLSLSPGK |
| 49 | IFNAR1 (aa28-436)-(Gly4Ser)2-IgG1 Fc (aa 216-447) with mutations C220S, P238S, P331S, T350V, L351Y, F405A, Y407V, without a leader sequence | KNLKSPQKVEVDIIDDNFILRWNRSDESVGNVTFSFDYQKTGMDN
WIKLSGCQNITSTKCNFSSLKLNVYEEIKLRIRAEKENTSSWYEV
DSFTPFRKAQIGPPEVHLEAEDKAIVIHISPGTKDSVMWALDGLS
FTYSLVIWKNSSGVEERIENIYSRHKIYKLSPETTYCLKVKAALL
TSWKIGVYSPVHCIKTTVENELPPPENIEVSVQNQNYVLKWDYTY
ANMTFQVQWLHAFLKRNPGNHLYKWKQIPDCENVKTTQCVFPQNV
FQKGIYLLRVQASDGNNTSFWSEEIKFDTEIQAFLLPPVFNIRSL
SDSFHIYIGAPKQSGNTPVIQDYPLIYEIIFWENTSNAERKIIEK
KTDVTVPNLKPLTVYCVKARAHTMDEKLNKSSVFSDAVCEKTKPG
NTSKGGGGSGGGGSEPKSSDKTHTCPPCPAPELLGGSSVFLFPPK
PKDTLMISRTPEVTCVVVDVSHEDPEVKFNWYVDGVEVHNAKTKP
REEQYNSTYRVVSVLTVLHQDWLNGKEYKCKVSNKALPASIEKTI
SKAKGQPREPQVYVYPPSRDELTKNQVSLTCLVKGFYPSDIAVEW
ESNGQPENNYKTTPPVLDSDGSFALVSKLTVDKSRWQQGNVFSCS
VMHEALHNHYTQKSLSLSPGK |
| 50 | Leader-IFNAR1 (aa28-436)-IgG1 Fc (aa 216-447) with mutations C220S, P238S, P331S, T350V, L351Y, F405A, Y407V | MDWTWRILFLVAAATGTHAKNLKSPQKVEVDIIDDNFILRWNRSD
ESVGNVTFSFDYQKTGMDNWIKLSGCQNITSTKCNFSSLKLNVYE
EIKLRIRAEKENTSSWYEVDSFTPFRKAQIGPPEVHLEAEDKAIV
IHISPGTKDSVMWALDGLSETYSLVIWKNSSGVEERIENITYSRHK
IYKLSPETTYCLKVKAALLTSWKIGVYSPVHCIKTTVENELPPPE
NIEVSVQNQNYVLKWDYTYANMTFQVQWLHAFLKRNPGNHLYKWK
QIPDCENVKTTQCVFPQNVFQKGIYLLRVQASDGNNTSFWSEEIK
FDTEIQAFLLPPVFNIRSLSDSFHIYIGAPKQSGNTPVIQDYPLI
YEIIFWENTSNAERKIIEKKTDVTVPNLKPLTVYCVKARAHTMDE
KLNKSSVFSDAVCEKTKPGNTSKEPKSSDKTHTCPPCPAPELLGG
SSVFLFPPKPKDTLMISRTPEVTCVVVDVSHEDPEVKFNWYVDGV
EVHNAKTKPREEQYNSTYRVVSVLTVLHQDWLNGKEYKCKVSNKA
LPASIEKTISKAKGQPREPQVYVYPPSRDELTKNQVSLTCLVKGF
YPSDIAVEWESNGQPENNYKTTPPVLDSDGSFALVSKLTVDKSRW
QQGNVFSCSVMHEALHNHYTQKSLSLSPGK |
| 51 | IFNAR1 (aa28-436)-IgG1 Fc (aa 216-447) with mutations C220S, P238S, P331S, T350V, L351Y, F405A, Y407V, without a leader sequence | KNLKSPQKVEVDIIDDNFILRWNRSDESVGNVTFSFDYQKTGMDN
WIKLSGCQNITSTKCNFSSLKLNVYEEIKLRIRAEKENTSSWYEV
DSFTPFRKAQIGPPEVHLEAEDKAIVIHISPGTKDSVMWALDGLS
FTYSLVIWKNSSGVEERIENIYSRHKIYKLSPETTYCLKVKAALL
TSWKIGVYSPVHCIKTTVENELPPPENIEVSVQNQNYVLKWDYTY
ANMTFQVQWLHAFLKRNPGNHLYKWKQIPDCENVKTTQCVFPQNV
FQKGIYLLRVQASDGNNTSFWSEEIKFDTEIQAFLLPPVFNIRSL
SDSFHIYIGAPKQSGNTPVIQDYPLIYEIIFWENTSNAERKIIEK
KTDVTVPNLKPLTVYCVKARAHTMDEKLNKSSVFSDAVCEKTKPG
NTSKEPKSSDKTHTCPPCPAPELLGGSSVFLFPPKPKDTLMISRT
PEVTCVVVDVSHEDPEVKFNWYVDGVEVHNAKTKPREEQYNSTYR
VVSVLTVLHQDWLNGKEYKCKVSNKALPASIEKTISKAKGQPREP
QVYVYPPSRDELTKNQVSLTCLVKGFYPSDIAVEWESNGQPENNY
KTTPPVLDSDGSFALVSKLTVDKSRWQQGNVFSCSVMHEALHNHY
TQKSLSLSPGK |
| 52 | RSLV-606 Leader-IFNAR1 (aa28-436)-(Gly4Ser)2-Fc (aa216-447) with mutations C220S, P238S, P331S, T350V, T366L, K392L, T394W | MDWTWRILFLVAAATGTHAKNLKSPQKVEVDIIDDNFILRWNRSD
ESVGNVTFSFDYQKTGMDNWIKLSGCQNITSTKCNFSSLKLNVYE
EIKLRIRAEKENTSSWYEVDSFTPFRKAQIGPPEVHLEAEDKAIV
IHISPGTKDSVMWALDGLSETYSLVIWKNSSGVEERIENTYSRHK
IYKLSPETTYCLKVKAALLTSWKIGVYSPVHCIKTTVENELPPPE
NIEVSVQNQNYVLKWDYTYANMTFQVQWLHAFLKRNPGNHLYKWK
QIPDCENVKTTQCVFPQNVFQKGIYLLRVQASDGNNTSFWSEEIK
FDTEIQAFLLPPVFNIRSLSDSFHIYIGAPKQSGNTPVIQDYPLI
YEIIFWENTSNAERKIIEKKTDVTVPNLKPLTVYCVKARAHTMDE
KLNKSSVFSDAVCEKTKPGNTSKGGGGSGGGGSEPKSSDKTHTCP
PCPAPELLGGSSVFLFPPKPKDTLMISRTPEVTCVVVDVSHEDPE
VKFNWYVDGVEVHNAKTKPREEQYNSTYRVVSVLTVLHQDWLNGK
EYKCKVSNKALPASIEKTISKAKGQPREPQVYVLPPSRDELTKNQ
VSLLCLVKGFYPSDIAVEWESNGQPENNYLTWPPVLDSDGSFFLY
SKLTVDKSRWQQGNVFSCSVMHEALHNHYTQKSLSLSPGK |
| 53 | RSLV-606 Without a leader sequence | KNLKSPQKVEVDIIDDNFILRWNRSDESVGNVTFSFDYQKTGMDN
WIKLSGCQNITSTKCNFSSLKLNVYEEIKLRIRAEKENTSSWYEV
DSFTPFRKAQIGPPEVHLEAEDKAIVIHISPGTKDSVMWALDGLS
FTYSLVIWKNSSGVEERIENIYSRHKIYKLSPETTYCLKVKAALL
TSWKIGVYSPVHCIKTTVENELPPPENIEVSVQNQNYVLKWDYTY
ANMTFQVQWLHAFLKRNPGNHLYKWKQIPDCENVKTTQCVFPQNV
FQKGIYLLRVQASDGNNTSFWSEEIKFDTEIQAFLLPPVFNIRSL |

TABLE 1-continued

SEQUENCE LISTING

| SEQ ID NO: | DESCRIPTION | SEQUENCE |
|---|---|---|
| | | SDSFHIYIGAPKQSGNTPVIQDYPLIYEIIFWENTSNAERKIIEK KTDVTVPNLKPLTVYCVKARAHTMDEKLNKSSVFSDAVCEKTKPG NTSKGGGGSGGGGSEPKSSDKTHTCPPCPAPELLGGSSVFLFPPK PKDTLMISRTPEVTCVVVDVSHEDPEVKFNWYVDGVEVHNAKTKP REEQYNSTYRVVSVLTVLHQDWLNGKEYKCKVSNKALPASIEKTI SKAKGQPREPQVYVLPPSRDELTKNQVSLLCLVKGFYPSDIAVEW ESNGQPENNYLTWPPVLDSDGSFFLYSKLTVDKSRWQQGNVFSCS VMHEALHNHYTQKSLSLSPGK |
| 54 | RSLV-611 Leader-IFNAR2 (aa27-243)- (Gly4Ser)2-Fc (aa 216-447) with mutations C220S, P238S, P331S, T350V, L351Y, F405A, Y407V | MDWTWRILFLVAAATGTHAISYDSPDYTDESCTFKIS TABLE 1-continued

SEQUENCE LISTING

| SEQ ID NO: | DESCRIPTION | SEQUENCE |
|---|---|---|
| 59 | RSLV-613 Without a leader sequence | ISYDSPDYTDESCTFKISLRNFRSILSWELKNHSIVPTHYTLLYT IMSKPEDLKVVKNCANTTRSFCDLTDEWRSTHEAYVTVLEGFSGN TTLFSCSHNFWLAIDMSFEPPEFEIVGFTNHINVMVKFPSIVEEE LQFDLSLVIEEQSEGIVKKHKPEIKGNMSGNFTYIIDKLIPNTNY CVSVYLEHSDEQAVIKSPLKCTLLPPGQESESAESAKEPKSSDKT HTCPPCPAPELLGGSSVFLFPPKPKDTLMISRTPEVTCVVVDVSH EDPEVKFNWYVDGVEVHNAKTKPREEQYNSTYRVVSVLTVLHQDW LNGKEYKCKVSNKALPASIEKTISKAKGQPREPQVYVPPSRDEL TKNQVSLTCLVKGFYPSDIAVEWESNGQPENNYKTTPPVLDSDGS FALVSKLTVDKSRWQQGNVFSCSVMHEALHNHYTQKSLSLSPGK |
| 60 | Leader-IFNAR1 (aa28-436)-(Gly4Ser)4-IgG1 Fc domain with T366Y mutation | MDWTWRILFLVAAATGTHAKNLKSPQKVEVDIIDDNFILRWNRSD ESVGNVTFSFDYQKTGMDNWIKLSGCQNITSTKCNFSSLKLNVYE EIKLRIRAEKENTSSWYEVDSFTPFRKAQIGPPEVHLEAEDKAIV IHISPGTKDSVMWALDGLSETYSLVIWKNSSGVEERIENTYSRHK IYKLSPETTYCLKVKAALLTSWKIGVYSPVHCIKTTVENELPPPE NIEVSVQNQNYVLKWDYTYANMTFQVQWLHAFLKRNPGNHLYKWK QIPDCENVKTTQCVFPQNVFQKGIYLLRVQASDGNNTSFWSEEIK FDTEIQAFLLPPVFNIRSLSDSFHIYIGAPKQSGNTPVIQDYPLI YEIIFWENTSNAERKIIEKKTDVTVPNLKPLTVYCVKARAHTMDE KLNKSSVFSDAVCEKTKPGNTSKGGGGSGGGGSGGGGSGGGGSEP KSCDKTHTCPPCPAPELLGGPSVFLFPPKPKDTLMISRTPEVTCV VVDVSHEDPEVKFNWYVDGVEVHNAKTKPREEQYNSTYRVVSVLT VLHQDWLNGKEYKCKVSNKALPAPIEKTISKAKGQPREPQVYTLP PSRDELTKNQVSLYCLVKGFYPSDIAVEWESNGQPENNYKTTPPV LDSDGSFFLYSKLTVDKSRWQQGNVESCSVMHEALHNHYTQKSLS LSPGK |
| 61 | IFNAR1 (aa28-436)-(Gly4Ser)4-IgG1 Fc domain with T366Y mutation without a leader sequence | KNLKSPQKVEVDIIDDNFILRWNRSDESVGNVTFSFDYQKTGMDN WIKLSGCQNITSTKCNFSSLKLNVYEEIKLRIRAEKENTSSWYEV DSFTPFRKAQIGPPEVHLEAEDKAIVIHISPGTKDSVMWALDGLS FTYSLVIWKNSSGVEERIENIYSRHKIYKLSPETTYCLKVKAALL TSWKIGVYSPVHCIKTTVENELPPPENIEVSVQNQNYVLKWDYTY ANMTFQVQWLHAFLKRNPGNHLYKWKQIPDCENVKTTQCVFPQNV FQKGIYLLRVQASDGNNTSFWSEEIKFDTEIQAFLLPPVFNIRSL SDSFHIYIGAPKQSGNTPVIQDYPLIYEIIFWENTSNAERKIIEK KTDVTVPNLKPLTVYCVKARAHTMDEKLNKSSVFSDAVCEKTKPG NTSKGGGGSGGGGSGGGGSGGGGSEPKSCDKTHTCPPCPAPELLG GPSVFLFPPKPKDTLMISRTPEVTCVVVDVSHEDPEVKFNWYVDG VEVHNAKTKPREEQYNSTYRVVSVLTVLHQDWLNGKEYKCKVSNK ALPAPIEKTISKAKGQPREPQVYTLPPSRDELTKNQVSLYCLVKG FYPSDIAVEWESNGQPENNYKTTPPVLDSDGSFFLYSKLTVDKSR WQQGNVFSCSVMHEALHNHYTQKSLSLSPGK |
| 62 | Leader-IFNAR2 (aa27-243)-(Gly4Ser)4-IgG1 Fc domain with T366Y mutation | MDWTWRILFLVAAATGTHAISYDSPDYTDESCTFKISLRNFRSIL SWELKNHSIVPTHYTLLYTIMSKPEDLKVVKNCANTTRSFCDLTD EWRSTHEAYVTVLEGFSGNTTLFSCSHNFWLAIDMSFEPPEFEIV GFTNHINVMVKFPSIVEEELQFDLSLVIEEQSEGIVKKHKPEIKG NMSGNFTYIIDKLIPNTNYCVSVYLEHSDEQAVIKSPLKCTLLPP GQESESAESAKGGGGSGGGGSGGGGSGGGGSEPKSCDKTHTCPPC RAPELLGGPSVFLEPPKPKDTLMISRTPEVTCVVVDVSHEDPEVK FNWYVDGVEVHNAKTKPREEQYNSTYRVVSVLTVLHQDWLNGKEY KCKVSNKALPAPIEKTISKAKGQPREPQVYTLPPSRDELTKNQVS LYCLVKGFYPSDIAVEWESNGQPENNYKTTPPVLDSDGSFFLYSK LTVDKSRWQQGNVFSCSVMHEALHNHYTQKSLSLSPGK |
| 63 | IFNAR2 (aa27-243)-(Gly4Ser)4-IgG1 Fc domain with T366Y mutation without a leader sequence | ISYDSPDYTDESCTFKISLRNFRSILSWELKNHSIVPTHYTLLYT IMSKPEDLKVVKNCANTTRSFCDLTDEWRSTHEAYVTVLEGFSGN TTLFSCSHNFWLAIDMSFEPPEFEIVGFTNHINVMVKFPSIVEEE LQFDLSLVIEEQSEGIVKKHKPEIKGNMSGNFTYIIDKLIPNTNY CVSVYLEHSDEQAVIKSPLKCTLLPPGQESESAESAKGGGGSGGG GSGGGGSGGGGSEPKSCDKTHTCPPCPAPELLGGPSVFLFPPKPK DTLMISRTPEVTCVVVDVSHEDPEVKFNWYVDGVEVHNAKTKPRE EQYNSTYRVVSVLTVLHQDWLNGKEYKCKVSNKALPAPIEKTISK AKGQPREPQVYTLPPSRDELTKNQVSLYCLVKGFYPSDIAVEWES NGQPENNYKTTPPVLDSDGSFFLYSKLTVDKSRWQQGNVESCSVM HEALHNHYTQKSLSLSPGK |
| 64 | Leader-IFNAR1 (aa28-436)-(Gly4Ser)4-IgG1 Fc domain with Y407T mutation | MDWTWRILFLVAAATGTHAKNLKSPQKVEVDIIDDNFILRWNRSD ESVGNVTFSFDYQKTGMDNWIKLSGCQNITSTKCNFSSLKLNVYE EIKLRIRAEKENTSSWYEVDSFTPFRKAQIGPPEVHLEAEDKAIV IHISPGTKDSVMWALDGLSETYSLVIWKNSSGVEERIENTYSRHK IYKLSPETTYCLKVKAALLTSWKIGVYSPVHCIKTTVENELPPPE NIEVSVQNQNYVLKWDYTYANMTFQVQWLHAFLKRNPGNHLYKWK QIPDCENVKTTQCVFPQNVFQKGIYLLRVQASDGNNTSFWSEEIK |

TABLE 1-continued

SEQUENCE LISTING

| SEQ ID NO: | DESCRIPTION | SEQUENCE |
|---|---|---|
| | | FDTEIQAFLLPPVFNIRSLSDSFHIYIGAPKQSGNTPVIQDYPLI
YEIIFWENTSNAERKIIEKKTDVTVPNLKPLTVYCVKARAHTMDE
KLNKSSVFSDAVCEKTKPGNTSKGGGGSGGGGSGGGGSGGGGSEP
KSCDKTHTCPPCPAPELLGGPSVFLFPPKPKDTLMISRTPEVTCV
VVDVSHEDPEVKFNWYVDGVEVHNAKTKPREEQYNSTYRVVSVLT
VLHQDWLNGKEYKCKVSNKALPAPIEKTISKAKGQPREPQVYTLP
PSRDELTKNQVSLTCLVKGFYPSDIAVEWESNGQPENNYKTTPPV
LDSDGSFEL<u>T</u>SKLTVDKSRWQQGNVESCSVMHEALHNHYTQKSLS
LSPGK |
| 65 | IFNAR1 (aa28-436)-(Gly4Ser)4-IgG1 Fc domain with Y407T mutation without a leader sequence | KNLKSPQKVEVDIIDDNFILRWNRSDESVGNVTFSFDYQKTGMDN
WIKLSGCQNITSTKCNFSSLKLNVYEEIKLRIRAEKENTSSWYEV
DSFTPFRKAQIGPPEVHLEAEDKAIVIHISPGTKDSVMWALDGLS
FTYSLVIWKNSSGVEERIENIYSRHKIYKLSPETTYCLKVKAALL
TSWKIGVYSPVHCIKTTVENELPPPENIEVSVQNQNYVLKWDYTY
ANMTFQVQWLHAFLKRNPGNHLYKWKQIPDCENVKTTQCVFPQNV
FQKGIYLLRVQASDGNNTSFWSEEIKFDTEIQAFLLPPVFNIRSL
SDSFHIYIGAPKQSGNTPVIQDYPLIYEIIFWENTSNAERKIIEK
KTDVTVPNLKPLTVYCVKARAHTMDEKLNKSSVFSDAVCEKTKPG
NTSKGGGGSGGGGSGGGGSGGGGSEPKSCDKTHTCPPCPAPELLG
GPSVFLFPPKPKDTLMISRTPEVTCVVVDVSHEDPEVKFNWYVDG
VEVHNAKTKPREEQYNSTYRVVSVLTVLHQDWLNGKEYKCKVSNK
ALPAPIEKTISKAKGQPREPQVYTLPPSRDELTKNQVSLTCLVKG
FYPSDIAVEWESNGQPENNYKTTPPVLDSDGSFFL<u>T</u>SKLTVDKSR
WQQGNVFSCSVMHEALHNHYTQKSLSLSPGK |
| 66 | Leader-IFNAR2 (aa27-243)-(Gly4Ser)4-IgG1 Fc domain with Y407T mutation | MDWTWRILFLVAAATGTHAISYDSPDYTDESCTFKISLRNFRSIL
SWELKNHSIVPTHYTLLYTIMSKPEDLKVVKNCANTTRSFCDLTD
EWRSTHEAYVTVLEGFSGNTTLFSCSHNFWLAIDMSFEPPEFEIV
GFTNHINVMVKFPSIVEEELQFDLSLVIEEQSEGIVKKHKPEIKG
NMSGNFTYIIDKLIPNTNYCVSVYLEHSDEQAVIKSPLKCTLLPP
GQESESAESAKGGGGSGGGGSGGGGSGGGGSEPKSCDKTHTCPPC
PAPELLGGPSVFLEPPKPKDTLMISRTPEVTCVVVDVSHEDPEVK
FNWYVDGVEVHNAKTKPREEQYNSTYRVVSVLTVLHQDWLNGKEY
KCKVSNKALPAPIEKTISKAKGQPREPQVYTLPPSRDELTKNQVS
LTCLVKGFYPSDIAVEWESNGQPENNYKTTPPVLDSDGSFFL<u>T</u>SK
LTVDKSRWQQGNVFSCSVMHEALHNHYTQKSLSLSPGK |
| 67 | IFNAR2 (aa27-243)-(Gly4Ser)4-IgG1 Fc domain with Y407T mutation without a leader sequence | ISYDSPDYTDESCTFKISLRNFRSILSWELKNHSIVPTHYTLLYT
IMSKPEDLKVVKNCANTTRSFCDLTDEWRSTHEAYVTVLEGFSGN
TTLFSCSHNFWLAIDMSFEPPEFEIVGFTNHINVMVKFPSIVEEE
LQFDLSLVIEEQSEGIVKKHKPEIKGNMSGNFTYIIDKLIPNTNY
CVSVYLEHSDEQAVIKSPLKCTLLPPGQESESAESAKGGGGSGGG
GSGGGGSGGGGSEPKSCDKTHTCPPCPAPELLGGPSVFLFPPKPK
DTLMISRTPEVTCVVVDVSHEDPEVKFNWYVDGVEVHNAKTKPRE
EQYNSTYRVVSVLTVLHQDWLNGKEYKCKVSNKALPAPIEKTISK
AKGQPREPQVYTLPPSRDELTKNQVSLTCLVKGFYPSDIAVEWES
NGQPENNYKTTPPVLDSDGSFEL<u>T</u>SKLTVDKSRWQQGNVESCSVM
HEALHNHYTQKSLSLSPGK |
| 68 | Leader-IFNAR1 (aa28-436)-(Gly4Ser)2-IgG1 Fc domain with T366Y mutation | MDWTWRILFLVAAATGTHAKNLKSPQKVEVDIIDDNFILRWNRSD
ESVGNVTFSFDYQKTGMDNWIKLSGCQNITSTKCNFSSLKLNVYE
EIKLRIRAEKENTSSWYEVDSFTPFRKAQIGPPEVHLEAEDKAIV
IHISPGTKDSVMWALDGLSETYSLVIWKNSSGVEERIENTYSRH
IYKLSPETTYCLKVKAALLTSWKIGVYSPVHCIKTTVENELPPPE
NIEVSVQNQNYVLKWDYTYANMTFQVQWLHAFLKRNPGNHLYKWK
QIPDCENVKTTQCVFPQNVFQKGIYLLRVQASDGNNTSFWSEEIK
FDTEIQAFLLPPVFNIRSLSDSFHIYIGAPKQSGNTPVIQDYPLI
YEIIFWENTSNAERKIIEKKTDVTVPNLKPLTVYCVKARAHTMDE
KLNKSSVFSDAVCEKTKPGNTSKGGGGSGGGGSEPKSCDKTHTCP
PCPAPELLGGPSVFLFPPKPKDTLMISRTPEVTCVVVDVSHEDPE
VKFNWYVDGVEVHNAKTKPREEQYNSTYRVVSVLTVLHQDWLNGK
EYKCKVSNKALPAPIEKTISKAKGQPREPQVYTLPPSRDELTKNQ
VSL<u>Y</u>CLVKGFYPSDIAVEWESNGQPENNYKTTPPVLDSDGSFFLY
SKLTVDKSRWQQGNVFSCSVMHEALHNHYTQKSLSLSPGK |
| 69 | IFNAR1 (aa28-436)-(Gly4Ser)2-IgG1 Fc domain with T366Y mutation without a leader sequence | KNLKSPQKVEVDIIDDNFILRWNRSDESVGNVTFSFDYQKTGMDN
WIKLSGCQNITSTKCNFSSLKLNVYEEIKLRIRAEKENTSSWYEV
DSFTPFRKAQIGPPEVHLEAEDKAIVIHISPGTKDSVMWALDGLS
FTYSLVIWKNSSGVEERIENIYSRHKIYKLSPETTYCLKVKAALL
TSWKIGVYSPVHCIKTTVENELPPPENIEVSVQNQNYVLKWDYTY
ANMTFQVQWLHAFLKRNPGNHLYKWKQIPDCENVKTTQCVFPQNV
FQKGIYLLRVQASDGNNTSFWSEEIKFDTEIQAFLLPPVFNIRSL
SDSFHIYIGAPKQSGNTPVIQDYPLIYEIIFWENTSNAERKIIEK
KTDVTVPNLKPLTVYCVKARAHTMDEKLNKSSVFSDAVCEKTKPG
NTSKGGGGSGGGGSEPKSCDKTHTCPPCPAPELLGGPSVFLFPPK |

TABLE 1-continued

SEQUENCE LISTING

| SEQ ID NO: | DESCRIPTION | SEQUENCE |
|---|---|---|
|  |  | PKDTLMISRTPEVTCVVVDVSHEDPEVKFNWYVDGVEVHNAKTKP REEQYNSTYRVVSVLTVLHQDWLNGKEYKCKVSNKALPAPIEKTI SKAKGQPREPQVYTLPPSRDELTKNQVSL<u>Y</u>CLVKGFYPSDIAVEW ESNGQPENNYKTTPPVLDSDGSFFLYSKLTVDKSRWQQGNVFSCS VMHEALHNHYTQKSLSLSPGK |
| 70 | Leader-IFNAR2 (aa27-243)-(Gly4Ser)2-IgG1 Fc domain with T366Y mutation | MDWTWRILFLVAAATGTHAISYDSPDYTDESCTFKISLRNFRSIL SWELKNHSIVPTHYTLLYTIMSKPEDLKVVKNCANTTRSFCDLTD EWRSTHEAYVTVLEGFSGNTTLFSCSHNFWLAIDMSFEPPEFEIV GFTNHINVMVKFPSIVEEELQFDLSLVIEEQSEGIVKKHKPEIKG NMSGNFTYIIDKLIPNTNYCVSVYLEHSDEQAVIKSPLKCTLLPP GQESESAESAKGGGGSGGGGSEPKSCDKTHTCPPCPAPELLGGPS VFLFPPKPKDTLMISRTPEVTCVVVDVSHEDPEVKFNWYVDGVEV HNAKTKPREEQYNSTYRVVSVLTVLHQDWLNGKEYKCKVSNKALP APIEKTISKAKGQPREPQVYTLPPSRDELTKNQVSL<u>Y</u>CLVKGFYP SDIAVEWESNGQPENNYKTTPPVLDSDGSFFLYSKLTVDKSRWQQ GNVFSCSVMHEALHNHYTQKSLSLSPGK |
| 71 | IFNAR2 (aa27-243)-(Gly4Ser)2-IgG1 Fc domain with T366Y mutation without a leader sequence | ISYDSPDYTDESCTFKISLRNFRSILSWELKNHSIVPTHYTLLYT IMSKPEDLKVVKNCANTTRSFCDLTDEWRSTHEAYVTVLEGFSGN TTLFSCSHNFWLAIDMSFEPPEFEIVGFTNHINVMVKFPSIVEEE LQFDLSLVIEEQSEGIVKKHKPEIKGNMSGNFTYIIDKLIPNTNY CVSVYLEHSDEQAVIKSPLKCTLLPPGQESESAESAKGGGGSGGG GSEPKSCDKTHTCPPCPAPELLGGPSVFLFPPKPKDTLMISRTPE VTCVVVDVSHEDPEVKFNWYVDGVEVHNAKTKPREEQYNSTYRVV SVLTVLHQDWLNGKEYKCKVSNKALPAPIEKTISKAKGQPREPQV YTLPPSRDELTKNQVSL<u>Y</u>CLVKGFYPSDIAVEWESNGQPENNYKT TPPVLDSDGSFFLYSKLTVDKSRWQQGNVFSCSVMHEALHNHYTQ KSLSLSPGK |
| 72 | Leader-IFNAR1 (aa28-436)-(Gly4Ser)2-IgG1 Fc domain with Y407T mutation | MDWTWRILFLVAAATGTHAKNLKSPQKVEVDIIDDNFILRWNRSD ESVGNVTFSFDYQKTGMDNWIKLSGCQNITSTKCNFSSLKLNVYE EIKLRIRAEKENTSSWYEVDSFTPFRKAQIGPPEVHLEAEDKAIV IHISPGTKDSVMWALDGLSETYSLVIWKNSSGVEERIENTYSRHK IYKLSPETTYCLKVKAALLTSWKIGVYSPVHCIKTTVENELPPPE NIEVSVQNQNYVLKWDYTYANMTFQVQWLHAFLKRNPGNHLYKWK QIPDCENVKTTQCVFPQNVFQKGIYLLRVQASDGNNTSFWSEEIK FDTEIQAFLLPPVFNIRSLSDSFHIYIGAPKQSGNTPVIQDYPLI YEIIFWENTSNAERKIIEKKTDVTVPNLKPLTVYCVKARAHTMDE KLNKSSVFSDAVCEKTKPGNTSKGGGGSGGGGSEPKSCDKTHTCP PCPAPELLGGPSVFLFPPKPKDTLMISRTPEVTCVVVDVSHEDPE VKFNWYVDGVEVHNAKTKPREEQYNSTYRVVSVLTVLHQDWLNGK EYKCKVSNKALPAPIEKTISKAKGQPREPQVYTLPPSRDELTKNQ VSLTCLVKGFYPSDIAVEWESNGQPENNYKTTPPVLDSDGSFFL<u>T</u> SKLTVDKSRWQQGNVFSCSVMHEALHNHYTQKSLSLSPGK |
| 73 | IFNAR1 (aa28-436)-(Gly4Ser)2-IgG1 Fc domain with Y407T mutation without a leader sequence | KNLKSPQKVEVDIIDDNFILRWNRSDESVGNVTFSFDYQKTGMDN WIKLSGCQNITSTKCNFSSLKLNVYEEIKLRIRAEKENTSSWYEV DSFTPFRKAQIGPPEVHLEAEDKAIVIHISPGTKDSVMWALDGLS ETYSLVIWKNSSGVEERIENIYSRHKIYKLSPETTYCLKVKAALL TSWKIGVYSPVHCIKTTVENELPPPENIEVSVQNQNYVLKWDYTY ANMTFQVQWLHAFLKRNPGNHLYKWKQIPDCENVKTTQCVFPQNV FQKGIYLLRVQASDGNNTSFWSEEIKFDTEIQAFLLPPVFNIRSL SDSFHIYIGAPKQSGNTPVIQDYPLIYEIIFWENTSNAERKIIEK KTDVTVPNLKPLTVYCVKARAHTMDEKLNKSSVFSDAVCEKTKPG NTSKGGGGSGGGGSEPKSCDKTHTCPPCPAPELLGGPSVFLFPPK PKDTLMISRTPEVTCVVVDVSHEDPEVKFNWYVDGVEVHNAKTKP REEQYNSTYRVVSVLTVLHQDWLNGKEYKCKVSNKALPAPIEKTI SKAKGQPREPQVYTLPPSRDELTKNQVSLTCLVKGFYPSDIAVEW ESNGQPENNYKTTPPVLDSDGSFFL<u>T</u>SKLTVDKSRWQQGNVFSCS VMHEALHNHYTQKSLSLSPGK |
| 74 | Leader-IFNAR2 (aa27-243)-(Gly4Ser)2-IgG1 Fc domain with Y407T mutation | MDWTWRILFLVAAATGTHAISYDSPDYTDESCTFKISLRNFRSIL SWELKNHSIVPTHYTLLYTIMSKPEDLKVVKNCANTTRSFCDLTD EWRSTHEAYVTVLEGFSGNTTLFSCSHNFWLAIDMSFEPPEFEIV GFTNHINVMVKFPSIVEEELQFDLSLVIEEQSEGIVKKHKPEIKG NMSGNFTYIIDKLIPNTNYCVSVYLEHSDEQAVIKSPLKCTLLPP GQESESAESAKGGGGSGGGGSEPKSCDKTHTCPPCPAPELLGGPS VFLFPPKPKDTLMISRTPEVTCVVVDVSHEDPEVKFNWYVDGVEV HNAKTKPREEQYNSTYRVVSVLTVLHQDWLNGKEYKCKVSNKALP APIEKTISKAKGQPREPQVYTLPPSRDELTKNQVSLTCLVKGFYP SDIAVEWESNGQPENNYKTTPPVLDSDGSFFL<u>T</u>SKLTVDKSRWQQ GNVFSCSVMHEALHNHYTQKSLSLSPGK |

TABLE 1-continued

SEQUENCE LISTING

| SEQ ID NO: | DESCRIPTION | SEQUENCE |
|---|---|---|
| 75 | IFNAR2 (aa27-243)-(Gly4Ser)2-IgG1 Fc domain with Y407T mutation without a leader sequence | ISYDSPDYTDESCTFKISLRNFRSILSWELKNHSIVPTHYTLLYT IMSKPEDLKVVKNCANTTRSFCDLTDEWRSTHEAYVTVLEGFSGN TTLFSCSHNFWLAIDMSFEPPEFEIVGFTNHINVMVKFPSIVEEE LQFDLSLVIEEQSEGIVKKHKPEIKGNMSGNFTYIIDKLIPNTNY CVSVYLEHSDEQAVIKSPLKCTLLPPGQESESAESAKGGGGSGGG GSEPKSCDKTHTCPPCPAPELLGGPSVFLFPPKPKDTLMISRTPE VTCVVVDVSHEDPEVKFNWYVDGVEVHNAKTKPREEQYNSTYRVV SVLTVLHQDWLNGKEYKCKVSNKALPAPIEKTISKAKGQPREPQV YTLPPSRDELTKNQVSLTCLVKGFYPSDIAVEWESNGQPENNYKT TPPVLDSDGSFFLTSKLTVDKSRWQQGNVFSCSVMHEALHNHYTQ KSLSLSPGK |
| 76 | Leader-IFNAR1 (aa28-436)-IgG1 Fc domain with T366Y mutation | MDWTWRILFLVAAATGTHAKNLKSPQKVEVDIIDDNFILRWNRSD ESVGNVTFSFDYQKTGMDNWIKLSGCQNITSTKCNFSSLKLNVYE EIKLRIRAEKENTSSWYEVDSFTPFRKAQIGPPEVHLEAEDKAIV IHISPGTKDSVMWALDGLSETYSLVIWKNSSGVEERIENTYSRHK IYKLSPETTYCLKVKAALLTSWKIGVYSPVHCIKTTVENELPPPE NIEVSVQNQNYVLKWDYTYANMTFQVQWLHAFLKRNPGNHLYKWK QIPDCENVKTTQCVFPQNVFQKGIYLLRVQASDGNNTSFWSEEIK FDTEIQAFLLPPVFNIRSLSDSFHIYIGAPKQSGNTPVIQDYPLI YEIIFWENTSNAERKIIEKKTDVTVPNLKPLTVYCVKARAHTMDE KLNKSSVFSDAVCEKTKPGNTSKEPKSCDKTHTCPPCPAPELLGG PSVFLFPPKPKDTLMISRTPEVTCVVVDVSHEDPEVKFNWYVDGV EVHNAKTKPREEQYNSTYRVVSVLTVLHQDWLNGKEYKCKVSNKA LPAPIEKTISKAKGQPREPQVYTLPPSRDELTKNQVSLYCLVKGF YPSDIAVEWESNGQPENNYKTTPPVLDSDGSFFLYSKLTVDKSRW QQGNVFSCSVMHEALHNHYTQKSLSLSPGK |
| 77 | IFNAR1 (aa28-436)-IgG1 Fc domain with T366Y mutation without a leader sequence | KNLKSPQKVEVDIIDDNFILRWNRSDESVGNVTFSFDYQKTGMDN WIKLSGCQNITSTKCNFSSLKLNVYEEIKLRIRAEKENTSSWYEV DSFTPFRKAQIGPPEVHLEAEDKAIVIHISPGTKDSVMWALDGLS FTYSLVIWKNSSGVEERIENIYSRHKIYKLSPETTYCLKVKAALL TSWKIGVYSPVHCIKTTVENELPPPENIEVSVQNQNYVLKWDYTY ANMTFQVQWLHAFLKRNPGNHLYKWKQIPDCENVKTTQCVFPQNV FQKGIYLLRVQASDGNNTSFWSEEIKFDTEIQAFLLPPVFNIRSL SDSFHIYIGAPKQSGNTPVIQDYPLIYEIIFWENTSNAERKIIEK KTDVTVPNLKPLTVYCVKARAHTMDEKLNKSSVFSDAVCEKTKPG NTSKEPKSCDKTHTCPPCPAPELLGGPSVFLFPPKPKDTLMISRT PEVTCVVVDVSHEDPEVKFNWYVDGVEVHNAKTKPREEQYNSTYR VVSVLTVLHQDWLNGKEYKCKVSNKALPAPIEKTISKAKGQPREP QVYTLPPSRDELTKNQVSLYCLVKGFYPSDIAVEWESNGQPENNY KTTPPVLDSDGSFFLYSKLTVDKSRWQQGNVESCSVMHEALHNHY TQKSLSLSPGK |
| 78 | Leader-IFNAR2 (aa27-243)-IgG1 Fc domain with T366Y mutation | MDWTWRILFLVAAATGTHAISYDSPDYTDESCTFKISLRNFRSIL SWELKNHSIVPTHYTLLYTIMSKPEDLKVVKNCANTTRSFCDLTD EWRSTHEAYVTVLEGFSGNTTLFSCSHNFWLAIDMSFEPPEFEIV GFTNHINVMVKFPSIVEEELQFDLSLVIEEQSEGIVKKHKPEIKG NMSGNFTYIIDKLIPNTNYCVSVYLEHSDEQAVIKSPLKCTLLPP GQESESAESAKEPKSCDKTHTCPPCPAPELLGGPSVFLFPPKPKD TLMISRTPEVTCVVVDVSHEDPEVKFNWYVDGVEVHNAKTKPREE QYNSTYRVVSVLTVLHQDWLNGKEYKCKVSNKALPAPIEKTISKA KGQPREPQVYTLPPSRDELTKNQVSLYCLVKGFYPSDIAVEWESN GQPENNYKTTPPVLDSDGSFFLYSKLTVDKSRWQQGNVFSCSVMH EALHNHYTQKSLSLSPGK |
| 79 | IFNAR2 (aa27-243)-IgG1 Fc domain with T366Y mutation without a leader sequence | ISYDSPDYTDESCTFKISLRNFRSILSWELKNHSIVPTHYTLLYT IMSKPEDLKVVKNCANTTRSFCDLTDEWRSTHEAYVTVLEGFSGN TTLFSCSHNFWLAIDMSFEPPEFEIVGFTNHINVMVKFPSIVEEE LQFDLSLVIEEQSEGIVKKHKPEIKGNMSGNFTYIIDKLIPNTNY CVSVYLEHSDEQAVIKSPLKCTLLPPGQESESAESAKEPKSCDKT HTCPPCPAPELLGGPSVFLFPPKPKDTLMISRTPEVTCVVVDVSH EDPEVKFNWYVDGVEVHNAKTKPREEQYNSTYRVVSVLTVLHQDW LNGKEYKCKVSNKALPAPIEKTISKAKGQPREPQVYTLPPSRDEL TKNQVSLYCLVKGFYPSDIAVEWESNGQPENNYKTTPPVLDSDGS FFLYSKLTVDKSRWQQGNVFSCSVMHEALHNHYTQKSLSLSPGK |
| 80 | Leader-IFNAR1 (aa28-436)-IgG1 Fc domain with Y407T mutation | MDWTWRILFLVAAATGTHAKNLKSPQKVEVDIIDDNFILRWNRSD ESVGNVTFSFDYQKTGMDNWIKLSGCQNITSTKCNFSSLKLNVYE EIKLRIRAEKENTSSWYEVDSFTPFRKAQIGPPEVHLEAEDKAIV IHISPGTKDSVMWALDGLSETYSLVIWKNSSGVEERIENTYSRHK IYKLSPETTYCLKVKAALLTSWKIGVYSPVHCIKTTVENELPPPE NIEVSVQNQNYVLKWDYTYANMTFQVQWLHAFLKRNPGNHLYKWK QIPDCENVKTTQCVFPQNVFQKGIYLLRVQASDGNNTSFWSEEIK FDTEIQAFLLPPVFNIRSLSDSFHIYIGAPKQSGNTPVIQDYPLI |

TABLE 1-continued

SEQUENCE LISTING

| SEQ ID NO: | DESCRIPTION | SEQUENCE |
|---|---|---|
| | | YEIIFWENTSNAERKIIEKKTDVTVPNLKPLTVYCVKARAHTMDE<br>KLNKSSVFSDAVCEKTKPGNTSKEPKSCDKTHTCPPCPAPELLGG<br>PSVFLFPPKPKDTLMISRTPEVTCVVVDVSHEDPEVKFNWYVDGV<br>EVHNAKTKPREEQYNSTYRVVSVLTVLHQDWLNGKEYKCKVSNKA<br>LPAPIEKTISKAKGQPREPQVYTLPPSRDELTKNQVSLTCLVKGF<br>YPSDIAVEWESNGQPENNYKTTPPVLDSDGSFFLTSKLTVDKSRW<br>QQGNVFSCSVMHEALHNHYTQKSLSLSPGK |
| 81 | IFNAR1 (aa28-436)-IgG1 Fc domain with Y407T mutation without a leader sequence | KNLKSPQKVEVDIIDDNFILRWNRSDESVGNVTFSFDYQKTGMDN<br>WIKLSGCQNITSTKCNFSSLKLNVYEEIKLRIRAEKENTSSWYEV<br>DSFTPFRKAQIGPPEVHLEAEDKAIVIHISPGTKDSVMWALDGLS<br>FTYSLVIWKNSSGVEERIENIYSRHKIYKLSPETTYCLKVKAALL<br>TSWKIGVYSPVHCIKTTVENELPPPENIEVSVQNQNYVLKWDYTY<br>ANMTFQVQWLHAFLKRNPGNHLYKWKQIPDCENVKTTQCVFPQNV<br>FQKGIYLLRVQASDGNNTSFWSEEIKFDTEIQAFLLPPVFNIRSL<br>SDSFHIYIGAPKQSGNTPVIQDYPLIYEIIFWENTSNAERKIIEK<br>KTDVTVPNLKPLTVYCVKARAHTMDEKLNKSSVFSDAVCEKTKPG<br>NTSKEPKSCDKTHTCPPCPAPELLGGPSVFLFPPKPKDTLMISRT<br>PEVTCVVVDVSHEDPEVKFNWYVDGVEVHNAKTKPREEQYNSTYR<br>VVSVLTVLHQDWLNGKEYKCKVSNKALPAPIEKTISKAKGQPREP<br>QVYTLPPSRDELTKNQVSLTCLVKGFYPSDIAVEWESNGQPENNY<br>KTTPPVLDSDGSFELTSKLTVDKSRWQQGNVESCSVMHEALHNHY<br>TQKSLSLSPGK |
| | Leader-IFNAR2 (aa27-243)-IgG1 Fc domain with Y407T mutation | MDWTWRILFLVAAATGTHAISYDSPDYTDESCTFKISLRNFRSIL<br>SWELKNHSIVPTHYTLLYTIMSKPEDLKVVKNCANTTRSFCDLTD<br>EWRSTHEAYVTVLEGFSGNTTLFSCSHNFWLAIDMSFEPPEFEIV<br>GFTNHINVMVKFPSIVEEELQFDLSLVIEEQSEGIVKKHKPEIKG<br>NMSGNFTYIIDKLIPNTNYCVSVYLEHSDEQAVIKSPLKCTLLPP<br>GQESESAESAKEPKSCDKTHTCPPCPAPELLGGPSVFLFPPKPKD<br>TLMISRTPEVTCVVVDVSHEDPEVKFNWYVDGVEVHNAKTKPREE<br>QYNSTYRVVSVLTVLHQDWLNGKEYKCKVSNKALPAPIEKTISKA<br>KGQPREPQVYTLPPSRDELTKNQVSLTCLVKGFYPSDIAVEWESN<br>GQPENNYKTTPPVLDSDGSFELTSKLTVDKSRWQQGNVESCSVMH<br>EALHNHYTQKSLSLSPGK |
| 82 | IFNAR2 (aa27-243)-IgG1 Fc domain with Y407T mutation without a leader sequence | ISYDSPDYTDESCTFKISLRNFRSILSWELKNHSIVPTHYTLLYT<br>IMSKPEDLKVVKNCANTTRSFCDLTDEWRSTHEAYVTVLEGFSGN<br>TTLFSCSHNFWLAIDMSFEPPEFEIVGFTNHINVMVKFPSIVEEE<br>LQFDLSLVIEEQSEGIVKKHKPEIKGNMSGNFTYIIDKLIPNTNY<br>CVSVYLEHSDEQAVIKSPLKCTLLPPGQESESAESAKEPKSCDKT<br>HTCPPCPAPELLGGPSVFLFPPKPKDTLMISRTPEVTCVVVDVSH<br>EDPEVKFNWYVDGVEVHNAKTKPREEQYNSTYRVVSVLTVLHQDW<br>LNGKEYKCKVSNKALPAPIEKTISKAKGQPREPQVYTLPPSRDEL<br>TKNQVSLTCLVKGFYPSDIAVEWESNGQPENNYKTTPPVLDSDGS<br>FFLTSKLTVDKSRWQQGNVESCSVMHEALHNHYTQKSLSLSPGK |
| 83 | Leader-IFNAR1 (aa28-436)-(Gly4Ser)4-IgG1 Fc domain with T366W mutation | MDWTWRILFLVAAATGTHAKNLKSPQKVEVDIIDDNFILRWNRSD<br>ESVGNVTFSFDYQKTGMDNWIKLSGCQNITSTKCNFSSLKLNVYE<br>EIKLRIRAEKENTSSWYEVDSFTPFRKAQIGPPEVHLEAEDKAIV<br>IHISPGTKDSVMWALDGLSETYSLVIWKNSSGVEERIENTYSRHK<br>IYKLSPETTYCLKVKAALLTSWKIGVYSPVHCIKTTVENELPPPE<br>NIEVSVQNQNYVLKWDYTYANMTFQVQWLHAFLKRNPGNHLYKWK<br>QIPDCENVKTTQCVFPQNVFQKGIYLLRVQASDGNNTSFWSEEIK<br>FDTEIQAFLLPPVFNIRSLSDSFHIYIGAPKQSGNTPVIQDYPLI<br>YEIIFWENTSNAERKIIEKKTDVTVPNLKPLTVYCVKARAHTMDE<br>KLNKSSVFSDAVCEKTKPGNTSKGGGGSGGGGSGGGGSGGGGSEP<br>KSCDKTHTCPPCPAPELLGGPSVFLFPPKPKDTLMISRTPEVTCV<br>VVDVSHEDPEVKFNWYVDGVEVHNAKTKPREEQYNSTYRVVSVLT<br>VLHQDWLNGKEYKCKVSNKALPAPIEKTISKAKGQPREPQVYTLP<br>PSRDELTKNQVSLWCLVKGFYPSDIAVEWESNGQPENNYKTTPPV<br>LDSDGSFFLYSKLTVDKSRWQQGNVFSCSVMHEALHNHYTQKSLS<br>LSPGK |
| 84 | IFNAR1 (aa28-436)-(Gly4Ser)4-IgG1 Fc domain with T366W mutation without a leader sequence | KNLKSPQKVEVDIIDDNFILRWNRSDESVGNVTFSFDYQKTGMDN<br>WIKLSGCQNITSTKCNFSSLKLNVYEEIKLRIRAEKENTSSWYEV<br>DSFTPFRKAQIGPPEVHLEAEDKAIVIHISPGTKDSVMWALDGLS<br>FTYSLVIWKNSSGVEERIENIYSRHKIYKLSPETTYCLKVKAALL<br>TSWKIGVYSPVHCIKTTVENELPPPENIEVSVQNQNYVLKWDYTY<br>ANMTFQVQWLHAFLKRNPGNHLYKWKQIPDCENVKTTQCVFPQNV<br>FQKGIYLLRVQASDGNNTSFWSEEIKFDTEIQAFLLPPVFNIRSL<br>SDSFHIYIGAPKQSGNTPVIQDYPLIYEIIFWENTSNAERKIIEK<br>KTDVTVPNLKPLTVYCVKARAHTMDEKLNKSSVFSDAVCEKTKPG<br>NTSKGGGGSGGGGSGGGGSGGGGSEPKSCDKTHTCPPCPAPELLG<br>GPSVFLFPPKPKDTLMISRTPEVTCVVVDVSHEDPEVKFNWYVDG<br>VEVHNAKTKPREEQYNSTYRVVSVLTVLHQDWLNGKEYKCKVSNK |

| SEQ ID NO: | DESCRIPTION | SEQUENCE |
|---|---|---|
| | | ALPAPIEKTISKAKGQPREPQVYTLPPSRDELTKNQVSLWCLVKG<br>FYPSDIAVEWESNGQPENNYKTTPPVLDSDGSFFLYSKLTVDKSR<br>WQQGNVFSCSVMHEALHNHYTQKSLSLSPGK |
| | Leader-IFNAR2<br>(aa27-243)-<br>(Gly4Ser)4-<br>IgG1 Fc domain<br>with T366W<br>mutation | MDWTWRILFLVAAATGTHAISYDSPDYTDESCTFKISLRNFRSIL<br>SWELKNHSIVPTHYTLLYTIMSKPEDLKVVKNCANTTRSFCDLTD<br>EWRSTHEAYVTVLEGFSGNTTLFSCSHNFWLAIDMSFEPPEFEIV<br>GFTNHINVMVKFPSIVEEELQFDLSLVIEEQSEGIVKKHKPEIKG<br>NMSGNFTYIIDKLIPNTNYCVSVYLEHSDEQAVIKSPLKCTLLPP<br>GQESESAESAKGGGGSGGGGSGGGGSGGGGSEPKSCDKTHTCPPC<br>PAPELLGGPSVFLFPPKPKDTLMISRTPEVTCVVVDVSHEDPEVK<br>FNWYVDGVEVHNAKTKPREEQYNSTYRVVSVLTVLHQDWLNGKEY<br>KCKVSNKALPAPIEKTISKAKGQPREPQVYTLPPSRDELTKNQVS<br>LWCLVKGFYPSDIAVEWESNGQPENNYKTTPPVLDSDGSFFLYSK<br>LTVDKSRWQQGNVFSCSVMHEALHNHYTQKSLSLSPGK |
| 85 | IFNAR2 (aa27-<br>243)-<br>(Gly4Ser)4-<br>IgG1 Fc domain<br>with T366W<br>mutation<br>without a<br>leader<br>sequence | ISYDSPDYTDESCTFKISLRNFRSILSWELKNHSIVPTHYTLLYT<br>IMSKPEDLKVVKNCANTTRSFCDLTDEWRSTHEAYVTVLEGFSGN<br>TTLFSCSHNFWLAIDMSFEPPEFEIVGFTNHINVMVKFPSIVEEE<br>LQFDLSLVIEEQSEGIVKKHKPEIKGNMSGNFTYIIDKLIPNTNY<br>CVSVYLEHSDEQAVIKSPLKCTLLPPGQESESAESAKGGGGSGGG<br>GSGGGGSGGGGSEPKSCDKTHTCPPCPAPELLGGPSVFLFPPKPK<br>DTLMISRTPEVTCVVVDVSHEDPEVKFNWYVDGVEVHNAKTKPRE<br>EQYNSTYRVVSVLTVLHQDWLNGKEYKCKVSNKALPAPIEKTISK<br>AKGQPREPQVYTLPPSRDELTKNQVSLWCLVKGFYPSDIAVEWES<br>NGQPENNYKTTPPVLDSDGSFFLYSKLTVDKSRWQQGNVFSCSVM<br>HEALHNHYTQKSLSLSPGK |
| 86 | Leader-IFNAR1<br>(aa28-436)-<br>(Gly4Ser)4-<br>IgG1 Fc domain<br>with T366S,<br>L368A, and<br>Y407V<br>mutations | MDWTWRILFLVAAATGTHAKNLKSPQKVEVDIIDDNFILRWNRSD<br>ESVGNVTFSFDYQKTGMDNWIKLSGCQNITSTKCNFSSLKLNVYE<br>EIKLRIRAEKENTSSWYEVDSFTPFRKAQIGPPEVHLEAEDKAIV<br>IHISPGTKDSVMWALDGLSETYSLVIWKNSSGVEERIENTYSRHK<br>IYKLSPETTYCLKVKAALLTSWKIGVYSPVHCIKTTVENELPPPE<br>NIEVSVQNQNYVLKWDYTYANMTFQVQWLHAFLKRNPGNHLYKWK<br>QIPDCENVKTTQCVFPQNVFQKGIYLLRVQASDGNNTSFWSEEIK<br>FDTEIQAFLLPPVFNIRSLSDSFHIYIGAPKQSGNTPVIQDYPLI<br>YEIIFWENTSNAERKIIEKKTDVTVPNLKPLTVYCVKARAHTMDE<br>KLNKSSVFSDAVCEKTKPGNTSKGGGGSGGGGSGGGGSGGGGSEP<br>KSCDKTHTCPPCPAPELLGGPSVFLFPPKPKDTLMISRTPEVTCV<br>VVDVSHEDPEVKFNWYVDGVEVHNAKTKPREEQYNSTYRVVSVLT<br>VLHQDWLNGKEYKCKVSNKALPAPIEKTISKAKGQPREPQVYTLP<br>PSRDELTKNQVSLSCAVKGFYPSDIAVEWESNGQPENNYKTTPPV<br>LDSDGSFELVSKLTVDKSRWQQGNVESCSVMHEALHNHYTQKSLS<br>LSPGK |
| 87 | IFNAR1 (aa28-<br>436)-<br>(Gly4Ser)4-<br>IgG1 Fc domain<br>with T366S,<br>L368A, and<br>Y407V<br>mutations<br>without a<br>leader<br>sequence | KNLKSPQKVEVDIIDDNFILRWNRSDESVGNVTFSFDYQKTGMDN<br>WIKLSGCQNITSTKCNFSSLKLNVYEEIKLRIRAEKENTSSWYEV<br>DSFTPFRKAQIGPPEVHLEAEDKAIVIHISPGTKDSVMWALDGLS<br>FTYSLVIWKNSSGVEERIENIYSRHKIYKLSPETTYCLKVKAALL<br>TSWKIGVYSPVHCIKTTVENELPPPENIEVSVQNQNYVLKWDYTY<br>ANMTFQVQWLHAFLKRNPGNHLYKWKQIPDCENVKTTQCVFPQNV<br>FQKGIYLLRVQASDGNNTSFWSEEIKFDTEIQAFLLPPVFNIRSL<br>SDSFHIYIGAPKQSGNTPVIQDYPLIYEIIFWENTSNAERKIIEK<br>KTDVTVPNLKPLTVYCVKARAHTMDEKLNKSSVFSDAVCEKTKPG<br>NTSKGGGGSGGGGSGGGGSGGGGSEPKSCDKTHTCPPCPAPELLG<br>GPSVFLFPPKPKDTLMISRTPEVTCVVVDVSHEDPEVKFNWYVDG<br>VEVHNAKTKPREEQYNSTYRVVSVLTVLHQDWLNGKEYKCKVSNK<br>ALPAPIEKTISKAKGQPREPQVYTLPPSRDELTKNQVSLSCAVKG<br>FYPSDIAVEWESNGQPENNYKTTPPVLDSDGSFFLVSKLTVDKSR<br>WQQGNVFSCSVMHEALHNHYTQKSLSLSPGK |
| 88 | Leader-IFNAR2<br>(aa27-243)-<br>(Gly4Ser)4-<br>IgG1 Fc domain<br>with T366S,<br>L368A, and<br>Y407V<br>mutations | MDWTWRILFLVAAATGTHAISYDSPDYTDESCTFKISLRNFRSIL<br>SWELKNHSIVPTHYTLLYTIMSKPEDLKVVKNCANTTRSFCDLTD<br>EWRSTHEAYVTVLEGFSGNTTLFSCSHNFWLAIDMSFEPPEFEIV<br>GFTNHINVMVKFPSIVEEELQFDLSLVIEEQSEGIVKKHKPEIKG<br>NMSGNFTYIIDKLIPNTNYCVSVYLEHSDEQAVIKSPLKCTLLPP<br>GQESESAESAKGGGGSGGGGSGGGGSGGGGSEPKSCDKTHTCPPC<br>PAPELLGGPSVFLEPPKPKDTLMISRTPEVTCVVVDVSHEDPEVK<br>FNWYVDGVEVHNAKTKPREEQYNSTYRVVSVLTVLHQDWLNGKEY<br>KCKVSNKALPAPIEKTISKAKGQPREPQVYTLPPSRDELTKNQVS<br>LSCAVKGFYPSDIAVEWESNGQPENNYKTTPPVLDSDGSFFLVSK<br>LTVDKSRWQQGNVFSCSVMHEALHNHYTQKSLSLSPGK |
| 89 | IFNAR2 (aa27-<br>243)-<br>(Gly4Ser)4- | ISYDSPDYTDESCTFKISLRNFRSILSWELKNHSIVPTHYTLLYT<br>IMSKPEDLKVVKNCANTTRSFCDLTDEWRSTHEAYVTVLEGFSGN<br>TTLFSCSHNFWLAIDMSFEPPEFEIVGFTNHINVMVKFPSIVEEE |

TABLE 1-continued

SEQUENCE LISTING

| SEQ ID NO: | DESCRIPTION | SEQUENCE |
|---|---|---|
|  | IgG1 Fc domain with T366S, L368A, and Y407V mutations without a leader sequence | LQFDLSLVIEEQSEGIVKKHKPEIKGNMSGNFTYIIDKLIPNTNY CVSVYLEHSDEQAVIKSPLKCTLLPPGQESESAESAKGGGGSGGG GSGGGGSGGGGSEPKSCDKTHTCPPCPAPELLGGPSVFLFPPKPK DTLMISRTPEVTCVVVDVSHEDPEVKFNWYVDGVEVHNAKTKPRE EQYNSTYRVVSVLTVLHQDWLNGKEYKCKVSNKALPAPIEKTISK AKGQPREPQVYTLPPSRDELTKNQVSLSCAVKGFYPSDIAVEWES NGQPENNYKTTPPVLDSDGSFELVSKLTVDKSRWQQGNVESCSVM HEALHNHYTQKSLSLSPGK |
| 90 | Leader-IFNAR1 (aa28-436)-(Gly4Ser)2-IgG1 Fc domain with T366W mutation | MDWTWRILFLVAAATGTHAKNLKSPQKVEVDIIDDNFILRWNRSD ESVGNVTFSFDYQKTGMDNWIKLSGCQNITSTKCNFSSLKLNVYE EIKLRIRAEKENTSSWYEVDSFTPFRKAQIGPPEVHLEAEDKAIV IHISPGTKDSVMWALDGLSETYSLVIWKNSSGVEERIENTYSRHK IYKLSPETTYCLKVKAALLTSWKIGVYSPVHCIKTTVENELPPPE NIEVSVQNQNYVLKWDYTYANMTFQVQWLHAFLKRNPGNHLYKWK QIPDCENVKTTQCVFPQNVFQKGIYLLRVQASDGNNTSFWSEEIK FDTEIQAFLLPPVFNIRSLSDSFHIYIGAPKQSGNTPVIQDYPLI YEIIFWENTSNAERKIIEKKTDVTVPNLKPLTVYCVKARAHTMDE KLNKSSVFSDAVCEKTKPGNTSKGGGGSGGGGSEPKSCDKTHTCP PCPAPELLGGPSVFLFPPKPKDTLMISRTPEVTCVVVDVSHEDPE VKFNWYVDGVEVHNAKTKPREEQYNSTYRVVSVLTVLHQDWLNGK EYKCKVSNKALPAPIEKTISKAKGQPREPQVYTLPPSRDELTKNQ VSLWCLVKGFYPSDIAVEWESNGQPENNYKTTPPVLDSDGSFFLY SKLTVDKSRWQQGNVFSCSVMHEALHNHYTQKSLSLSPGK |
| 91 | IFNAR1 (aa28-436)-(Gly4Ser)2-IgG1 Fc domain with T366W mutation without a leader sequence | KNLKSPQKVEVDIIDDNFILRWNRSDESVGNVTFSFDYQKTGMDN WIKLSGCQNITSTKCNFSSLKLNVYEEIKLRIRAEKENTSSWYEV DSFTPFRKAQIGPPEVHLEAEDKAIVIHISPGTKDSVMWALDGLS FTYSLVIWKNSSGVEERIENIYSRHKIYKLSPETTYCLKVKAALL TSWKIGVYSPVHCIKTTVENELPPPENIEVSVQNQNYVLKWDYTY ANMTFQVQWLHAFLKRNPGNHLYKWKQIPDCENVKTTQCVFPQNV FQKGIYLLRVQASDGNNTSFWSEEIKFDTEIQAFLLPPVFNIRSL SDSFHIYIGAPKQSGNTPVIQDYPLIYEIIFWENTSNAERKIIEK KTDVTVPNLKPLTVYCVKARAHTMDEKLNKSSVFSDAVCEKTKPG NTSKGGGGSGGGGSEPKSCDKTHTCPPCPAPELLGGPSVFLFPPK PKDTLMISRTPEVTCVVVDVSHEDPEVKFNWYVDGVEVHNAKTKP REEQYNSTYRVVSVLTVLHQDWLNGKEYKCKVSNKALPAPIEKTI SKAKGQPREPQVYTLPPSRDELTKNQVSLWCLVKGFYPSDIAVEW ESNGQPENNYKTTPPVLDSDGSFFLYSKLTVDKSRWQQGNVFSCS VMHEALHNHYTQKSLSLSPGK |
| 92 | Leader-IFNAR2 (aa27-243)-(Gly4Ser)2-IgG1 Fc domain with T366W mutation | MDWTWRILFLVAAATGTHAISYDSPDYTDESCTFKISLRNFRSIL SWELKNHSIVPTHYTLLYTIMSKPEDLKVVKNCANTTRSFCDLTD EWRSTHEAYVTVLEGFSGNTTLFSCSHNFWLAIDMSFEPPEFEIV GFTNHINVMVKFPSIVEEELQFDLSLVIEEQSEGIVKKHKPEIKG NMSGNFTYIIDKLIPNTNYCVSVYLEHSDEQAVIKSPLKCTLLPP GQESESAESAKGGGGSGGGGSEPKSCDKTHTCPPCPAPELLGGPS VFLFPPKPKDTLMISRTPEVTCVVVDVSHEDPEVKFNWYVDGVEV HNAKTKPREEQYNSTYRVVSVLTVLHQDWLNGKEYKCKVSNKALP APIEKTISKAKGQPREPQVYTLPPSRDELTKNQVSLWCLVKGFYP SDIAVEWESNGQPENNYKTTPPVLDSDGSFFLYSKLTVDKSRWQQ GNVFSCSVMHEALHNHYTQKSLSLSPGK |
| 93 | IFNAR2 (aa27-243)-(Gly4Ser)2-IgG1 Fc domain with T366W mutation without a leader sequence | ISYDSPDYTDESCTFKISLRNFRSILSWELKNHSIVPTHYTLLYT IMSKPEDLKVVKNCANTTRSFCDLTDEWRSTHEAYVTVLEGFSGN TTLFSCSHNFWLAIDMSFEPPEFEIVGFTNHINVMVKFPSIVEEE LQFDLSLVIEEQSEGIVKKHKPEIKGNMSGNFTYIIDKLIPNTNY CVSVYLEHSDEQAVIKSPLKCTLLPPGQESESAESAKGGGGSGGG GSEPKSCDKTHTCPPCPAPELLGGPSVFLFPPKPKDTLMISRTPE VTCVVVDVSHEDPEVKFNWYVDGVEVHNAKTKPREEQYNSTYRVV SVLTVLHQDWLNGKEYKCKVSNKALPAPIEKTISKAKGQPREPQV YTLPPSRDELTKNQVSLWCLVKGFYPSDIAVEWESNGQPENNYKT TPPVLDSDGSFFLYSKLTVDKSRWQQGNVESCSVMHEALHNHYTQ KSLSLSPGK |
| 94 | Leader-IFNAR1 (aa28-436)-(Gly4Ser)2-IgG1 Fc domain with T366S, L368A, and Y407V mutations | MDWTWRILFLVAAATGTHAKNLKSPQKVEVDIIDDNFILRWNRSD ESVGNVTFSFDYQKTGMDNWIKLSGCQNITSTKCNFSSLKLNVYE EIKLRIRAEKENTSSWYEVDSFTPFRKAQIGPPEVHLEAEDKAIV IHISPGTKDSVMWALDGLSETYSLVIWKNSSGVEERIENTYSRHK IYKLSPETTYCLKVKAALLTSWKIGVYSPVHCIKTTVENELPPPE NIEVSVQNQNYVLKWDYTYANMTFQVQWLHAFLKRNPGNHLYKWK QIPDCENVKTTQCVFPQNVFQKGIYLLRVQASDGNNTSFWSEEIK FDTEIQAFLLPPVFNIRSLSDSFHIYIGAPKQSGNTPVIQDYPLI YEIIFWENTSNAERKIIEKKTDVTVPNLKPLTVYCVKARAHTMDE KLNKSSVFSDAVCEKTKPGNTSKGGGGSGGGGSEPKSCDKTHTCP PCPAPELLGGPSVFLFPPKPKDTLMISRTPEVTCVVVDVSHEDPE |

TABLE 1-continued

SEQUENCE LISTING

| SEQ ID NO: | DESCRIPTION | SEQUENCE |
|---|---|---|
|  |  | VKFNWYVDGVEVHNAKTKPREEQYNSTYRVVSVLTVLHQDWLNGK EYKCKVSNKALPAPIEKTISKAKGQPREPQVYTLPPSRDELTKNQ VSLSCAVKGFYPSDIAVEWESNGQPENNYKTTPPVLDSDGSFFLV SKLTVDKSRWQQGNVFSCSVMHEALHNHYTQKSLSLSPGK |
| 95 | IFNAR1 (aa28-436)-(Gly4Ser)2-IgG1 Fc domain with T366S, L368A, and Y407V mutations without a leader sequence | KNLKSPQKVEVDIIDDNFILRWNRSDESVGNVTFSFDYQKTGMDN WIKLSGCQNITSTKCNFSSLKLNVYEEIKLRIRAEKENTSSWYEV DSFTPFRKAQIGPPEVHLEAEDKAIVIHISPGTKDSVMWALDGLS FTYSLVIWKNSSGVEERIENIYSRHKIYKLSPETTYCLKVKAALL TSWKIGVYSPVHCIKTTVENELPPPENIEVSVQNQNYVLKWDYTY ANMTFQVQWLHAFLKRNPGNHLYKWKQIPDCENVKTTQCVFPQNV FQKGIYLLRVQASDGNNTSFWSEEIKFDTEIQAFLLPPVFNIRSL SDSFHIYIGAPKQSGNTPVIQDYPLIYEIIFWENTSNAERKIIEK KTDVTVPNLKPLTVYCVKARAHTMDEKLNKSSVFSDAVCEKTKPG NTSKGGGGSGGGGSEPKSCDKTHTCPPCPAPELLGGPSVFLFPPK PKDTLMISRTPEVTCVVVDVSHEDPEVKFNWYVDGVEVHNAKTKP REEQYNSTYRVVSVLTVLHQDWLNGKEYKCKVSNKALPAPIEKTI SKAKGQPREPQVYTLPPSRDELTKNQVSLSCAVKGFYPSDIAVEW ESNGQPENNYKTTPPVLDSDGSFFLVSKLTVDKSRWQQGNVFSCS VMHEALHNHYTQKSLSLSPGK |
| 96 | Leader-IFNAR2 (aa27-243)-(Gly4Ser)2-IgG1 Fc domain with T366S, L368A, and Y407V mutations | MDWTWRILFLVAAATGTHAISYDSPDYTDESCTFKISLRNFRSIL SWELKNHSIVPTHYTLLYTIMSKPEDLKVVKNCANTTRSFCDLTD EWRSTHEAYVTVLEGFSGNTTLFSCSHNFWLAIDMSFEPPEFEIV GFTNHINVMVKFPSIVEEELQFDLSLVIEEQSEGIVKKHKPEIKG NMSGNFTYIIDKLIPNTNYCVSVYLEHSDEQAVIKSPLKCTLLPP GQESESAESAKGGGGSGGGGSEPKSCDKTHTCPPCPAPELLGGPS VFLFPPKPKDTLMISRTPEVTCVVVDVSHEDPEVKFNWYVDGVEV HNAKTKPREEQYNSTYRVVSVLTVLHQDWLNGKEYKCKVSNKALP APIEKTISKAKGQPREPQVYTLPPSRDELTKNQVSLSCAVKGFYP SDIAVEWESNGQPENNYKTTPPVLDSDGSFFLVSKLTVDKSRWQQ GNVFSCSVMHEALHNHYTQKSLSLSPGK |
| 97 | IFNAR2 (aa27-243)-(Gly4Ser)2-IgG1 Fc domain with T366S, L368A, and Y407V mutations without a leader sequence | ISYDSPDYTDESCTFKISLRNFRSILSWELKNHSIVPTHYTLLYT IMSKPEDLKVVKNCANTTRSFCDLTDEWRSTHEAYVTVLEGFSGN TTLFSCSHNFWLAIDMSFEPPEFEIVGFTNHINVMVKFPSIVEEE LQFDLSLVIEEQSEGIVKKHKPEIKGNMSGNFTYIIDKLIPNTNY CVSVYLEHSDEQAVIKSPLKCTLLPPGQESESAESAKGGGGSGGG GSEPKSCDKTHTCPPCPAPELLGGPSVFLFPPKPKDTLMISRTPE VTCVVVDVSHEDPEVKFNWYVDGVEVHNAKTKPREEQYNSTYRVV SVLTVLHQDWLNGKEYKCKVSNKALPAPIEKTISKAKGQPREPQV YTLPPSRDELTKNQVSLSCAVKGFYPSDIAVEWESNGQPENNYKT TPPVLDSDGSFELVSKLTVDKSRWQQGNVESCSVMHEALHNHYTQ KSLSLSPGK |
| 98 | Leader-IFNAR1 (aa28-436)-IgG1 Fc domain with T366W mutation | MDWTWRILFLVAAATGTHAKNLKSPQKVEVDIIDDNFILRWNRSD ESVGNVTFSFDYQKTGMDNWIKLSGCQNITSTKCNFSSLKLNVYE EIKLRIRAEKENTSSWYEVDSFTPFRKAQIGPPEVHLEAEDKAIV IHISPGTKDSVMWALDGLSETYSLVIWKNSSGVEERIENTYSRHK IYKLSPETTYCLKVKAALLTSWKIGVYSPVHCIKTTVENELPPPE NIEVSVQNQNYVLKWDYTYANMTFQVQWLHAFLKRNPGNHLYKWK QIPDCENVKTTQCVFPQNVFQKGIYLLRVQASDGNNTSFWSEEIK FDTEIQAFLLPPVFNIRSLSDSFHIYIGAPKQSGNTPVIQDYPLI YEIIFWENTSNAERKIIEKKTDVTVPNLKPLTVYCVKARAHTMDE KLNKSSVFSDAVCEKTKPGNTSKEPKSCDKTHTCPPCPAPELLGG PSVFLFPPKPKDTLMISRTPEVTCVVVDVSHEDPEVKFNWYVDGV EVHNAKTKPREEQYNSTYRVVSVLTVLHQDWLNGKEYKCKVSNKA LPAPIEKTISKAKGQPREPQVYTLPPSRDELTKNQVSLWCLVKGF YPSDIAVEWESNGQPENNYKTTPPVLDSDGSFFLYSKLTVDKSRW QQGNVFSCSVMHEALHNHYTQKSLSLSPGK |
| 99 | IFNAR1 (aa28-436)-IgG1 Fc domain with T366W mutation without a leader sequence | KNLKSPQKVEVDIIDDNFILRWNRSDESVGNVTFSFDYQKTGMDN WIKLSGCQNITSTKCNFSSLKLNVYEEIKLRIRAEKENTSSWYEV DSFTPFRKAQIGPPEVHLEAEDKAIVIHISPGTKDSVMWALDGLS FTYSLVIWKNSSGVEERIENIYSRHKIYKLSPETTYCLKVKAALL TSWKIGVYSPVHCIKTTVENELPPPENIEVSVQNQNYVLKWDYTY ANMTFQVQWLHAFLKRNPGNHLYKWKQIPDCENVKTTQCVFPQNV FQKGIYLLRVQASDGNNTSFWSEEIKFDTEIQAFLLPPVFNIRSL SDSFHIYIGAPKQSGNTPVIQDYPLIYEIIFWENTSNAERKIIEK KTDVTVPNLKPLTVYCVKARAHTMDEKLNKSSVFSDAVCEKTKPG NTSKEPKSCDKTHTCPPCPAPELLGGPSVFLFPPKPKDTLMISRT PEVTCVVVDVSHEDPEVKFNWYVDGVEVHNAKTKPREEQYNSTYR VVSVLTVLHQDWLNGKEYKCKVSNKALPAPIEKTISKAKGQPREP QVYTLPPSRDELTKNQVSLWCLVKGFYPSDIAVEWESNGQPENNY KTTPPVLDSDGSFFLYSKLTVDKSRWQQGNVESCSVMHEALHNHY TQKSLSLSPGK |

TABLE 1-continued

SEQUENCE LISTING

| SEQ ID NO: | DESCRIPTION | SEQUENCE |
|---|---|---|
| 100 | Leader-IFNAR2 (aa27-243)-IgG1 Fc domain with T366W mutation | MDWTWRILFLVAAATGTHAISYDSPDYTDESCTFKISLRNFRSIL SWELKNHSIVPTHYTLLYTIMSKPEDLKVVKNCANTTRSFCDLTD EWRSTHEAYVTVLEGFSGNTTLFSCSHNFWLAIDMSFEPPEFEIV GFTNHINVMVKFPSIVEEELQFDLSLVIEEQSEGIVKKHKPEIKG NMSGNFTYIIDKLIPNTNYCVSVYLEHSDEQAVIKSPLKCTLLPP GQESESAESAKEPKSCDKTHTCPPCPAPELLGGPSVFLFPPKPKD TLMISRTPEVTCVVVDVSHEDPEVKFNWYVDGVEVHNAKTKPREE QYNSTYRVVSVLTVLHQDWLNGKEYKCKVSNKALPAPIEKTISKA KGQPREPQVYTLPPSRDELTKNQVSL<u>W</u>CLVKGFYPSDIAVEWESN GQPENNYKTTPPVLDSDGSFFLYSKLTVDKSRWQQGNVFSCSVMH EALHNHYTQKSLSLSPGK |
| 101 | IFNAR2 (aa27-243)-IgG1 Fc domain with T366W mutation without a leader sequence | ISYDSPDYTDESCTFKISLRNFRSILSWELKNHSIVPTHYTLLYT IMSKPEDLKVVKNCANTTRSFCDLTDEWRSTHEAYVTVLEGFSGN TTLFSCSHNFWLAIDMSFEPPEFEIVGFTNHINVMVKFPSIVEEE LQFDLSLVIEEQSEGIVKKHKPEIKGNMSGNFTYIIDKLIPNTNY CVSVYLEHSDEQAVIKSPLKCTLLPPGQESESAESAKEPKSCDKT HTCPPCPAPELLGGPSVFLFPPKPKDTLMISRTPEVTCVVVDVSH EDPEVKFNWYVDGVEVHNAKTKPREEQYNSTYRVVSVLTVLHQDW LNGKEYKCKVSNKALPAPIEKTISKAKGQPREPQVYTLPPSRDEL TKNQVSL<u>W</u>CLVKGFYPSDIAVEWESNGQPENNYKTTPPVLDSDGS FFLYSKLTVDKSRWQQGNVFSCSVMHEALHNHYTQKSLSLSPGK |
| 102 | Leader-IFNAR1 (aa28-436)-IgG1 Fc domain with T366S, L368A, and Y407V mutations | MDWTWRILFLVAAATGTHAKNLKSPQKVEVDIIDDNFILRWNRSD ESVGNVTFSFDYQKTGMDNWIKLSGCQNITSTKCNFSSLKLNVYE EIKLRIRAEKENTSSWYEVDSFTPFRKAQIGPPEVHLEAEDKAIV IHISPGTKDSVMWALDGLSETYSLVIWKNSSGVEERIENTYSRHK IYKLSPETTYCLKVKAALLTSWKIGVYSPVHCIKTTVENELPPPE NIEVSVQNQNYVLKWDYTYANMTFQVQWLHAFLKRNPGNHLYKWK QIPDCENVKTTQCVFPQNVFQKGIYLLRVQASDGNNTSFWSEEIK FDTEIQAFLLPPVFNIRSLSDSFHIYIGAPKQSGNTPVIQDYPLI YEIIFWENTSNAERKIIEKKTDVTVPNLKPLTVYCVKARAHTMDE KLNKSSVFSDAVCEKTKPGNTSKEPKSCDKTHTCPPCPAPELLGG PSVFLFPPKPKDTLMISRTPEVTCVVVDVSHEDPEVKFNWYVDGV EVHNAKTKPREEQYNSTYRVVSVLTVLHQDWLNGKEYKCKVSNKA LPAPIEKTISKAKGQPREPQVYTLPPSRDELTKNQVSL<u>S</u>C<u>A</u>VKGF YPSDIAVEWESNGQPENNYKTTPPVLDSDGSFFL<u>V</u>SKLTVDKSRW QQGNVFSCSVMHEALHNHYTQKSLSLSPGK |
| 103 | IFNAR1 (aa28-436)-IgG1 Fc domain with T366S, L368A, and Y407V mutations without a leader sequence | KNLKSPQKVEVDIIDDNFILRWNRSDESVGNVTFSFDYQKTGMDN WIKLSGCQNITSTKCNFSSLKLNVYEEIKLRIRAEKENTSSWYEV DSFTPFRKAQIGPPEVHLEAEDKAIVIHISPGTKDSVMWALDGLS FTYSLVIWKNSSGVEERIENIYSRHKIYKLSPETTYCLKVKAALL TSWKIGVYSPVHCIKTTVENELPPPENIEVSVQNQNYVLKWDYTY ANMTFQVQWLHAFLKRNPGNHLYKWKQIPDCENVKTTQCVFPQNV FQKGIYLLRVQASDGNNTSFWSEEIKFDTEIQAFLLPPVFNIRSL SDSFHIYIGAPKQSGNTPVIQDYPLIYEIIFWENTSNAERKIIEK KTDVTVPNLKPLTVYCVKARAHTMDEKLNKSSVFSDAVCEKTKPG NTSKEPKSCDKTHTCPPCPAPELLGGPSVFLFPPKPKDTLMISRT PEVTCVVVDVSHEDPEVKFNWYVDGVEVHNAKTKPREEQYNSTYR VVSVLTVLHQDWLNGKEYKCKVSNKALPAPIEKTISKAKGQPREP QVYTLPPSRDELTKNQVSL<u>S</u>C<u>A</u>VKGFYPSDIAVEWESNGQPENNY KTTPPVLDSDGSFEL<u>V</u>SKLTVDKSRWQQGNVFSCSVMHEALHNHY TQKSLSLSPGK |
| 104 | Leader-IFNAR2 (aa27-243)-IgG1 Fc domain with T366S, L368A, and Y407V mutations | MDWTWRILFLVAAATGTHAISYDSPDYTDESCTFKISLRNFRSIL SWELKNHSIVPTHYTLLYTIMSKPEDLKVVKNCANTTRSFCDLTD EWRSTHEAYVTVLEGFSGNTTLFSCSHNFWLAIDMSFEPPEFEIV GFTNHINVMVKFPSIVEEELQFDLSLVIEEQSEGIVKKHKPEIKG NMSGNFTYIIDKLIPNTNYCVSVYLEHSDEQAVIKSPLKCTLLPP GQESESAESAKEPKSCDKTHTCPPCPAPELLGGPSVFLFPPKPKD TLMISRTPEVTCVVVDVSHEDPEVKFNWYVDGVEVHNAKTKPREE QYNSTYRVVSVLTVLHQDWLNGKEYKCKVSNKALPAPIEKTISKA KGQPREPQVYTLPPSRDELTKNQVSL<u>S</u>C<u>A</u>VKGFYPSDIAVEWESN GQPENNYKTTPPVLDSDGSFEL<u>V</u>SKLTVDKSRWQQGNVFSCSVMH EALHNHYTQKSLSLSPGK |
| 105 | IFNAR2 (aa27-243)-IgG1 Fc domain with T366S, L368A, and Y407V | ISYDSPDYTDESCTFKISLRNFRSILSWELKNHSIVPTHYTLLYT IMSKPEDLKVVKNCANTTRSFCDLTDEWRSTHEAYVTVLEGFSGN TTLFSCSHNFWLAIDMSFEPPEFEIVGFTNHINVMVKFPSIVEEE LQFDLSLVIEEQSEGIVKKHKPEIKGNMSGNFTYIIDKLIPNTNY CVSVYLEHSDEQAVIKSPLKCTLLPPGQESESAESAKEPKSCDKT |

TABLE 1-continued

SEQUENCE LISTING

| SEQ ID NO: | DESCRIPTION | SEQUENCE |
|---|---|---|
| | mutations without a leader sequence | HTCPPCPAPELLGGPSVFLFPPKPKDTLMISRTPEVTCVVVDVSH EDPEVKFNWYVDGVEVHNAKTKPREEQYNSTYRVVSVLTVLHQDW LNGKEYKCKVSNKALPAPIEKTISKAKGQPREPQVYTLPPSRDEL TKNQVSLSCAVKGFYPSDIAVEWESNGQPENNYKTTPPVLDSDGS FELVSKLTVDKSRWQQGNVESCSVMHEALHNHYTQKSLSLSPGK |
| 106 | IgG1 Fc domain with T366Y mutation (knob hole 1) | EPKSCDKTHTCPPCPAPELLGGPSVFLFPPKPKDTLMISRTPEVT CVVVDVSHEDPEVKFNWYVDGVEVHNAKTKPREEQYNSTYRVVSV LTVLHQDWLNGKEYKCKVSNKALPAPIEKTISKAKGQPREPQVYT LPPSRDELTKNQVSLYCLVKGFYPSDIAVEWESNGQPENNYKTTP PVLDSDGSFFLYSKLTVDKSRWQQGNVESCSVMHEALHNHYTQKS LSLSPGK |
| 107 | IgG1 Fc domain with Y407T mutation (knob hole 1) | EPKSCDKTHTCPPCPAPELLGGPSVFLFPPKPKDTLMISRTPEVT CVVVDVSHEDPEVKFNWYVDGVEVHNAKTKPREEQYNSTYRVVSV LTVLHQDWLNGKEYKCKVSNKALPAPIEKTISKAKGQPREPQVYT LPPSRDELTKNQVSLTCLVKGFYPSDIAVEWESNGQPENNYKTTP PVLDSDGSFELTSKLTVDKSRWQQGNVESCSVMHEALHNHYTQKS LSLSPGK |
| 108 | IgG1 Fc domain with T366W mutation (knob hole 2) | EPKSCDKTHTCPPCPAPELLGGPSVFLFPPKPKDTLMISRTPEVT CVVVDVSHEDPEVKFNWYVDGVEVHNAKTKPREEQYNSTYRVVSV LTVLHQDWLNGKEYKCKVSNKALPAPIEKTISKAKGQPREPQVYT LPPSRDELTKNQVSLWCLVKGFYPSDIAVEWESNGQPENNYKTTP PVLDSDGSFFLYSKLTVDKSRWQQGNVESCSVMHEALHNHYTQKS LSLSPGK |
| 109 | IgG1 Fc domain with T366S, L368A, and Y407V mutations (knob hole 2) | EPKSCDKTHTCPPCPAPELLGGPSVFLFPPKPKDTLMISRTPEVT CVVVDVSHEDPEVKFNWYVDGVEVHNAKTKPREEQYNSTYRVVSV LTVLHQDWLNGKEYKCKVSNKALPAPIEKTISKAKGQPREPQVYT LPPSRDELTKNQVSLSCAVKGFYPSDIAVEWESNGQPENNYKTTP PVLDSDGSFELVSKLTVDKSRWQQGNVESCSVMHEALHNHYTQKS LSLSPGK |
| 110 | Human IgG4 | ASTKGPSVFPLAPCSRSTSESTAALGCLVKDYFPEPVTVSWNSGA LTSGVHTFPAVLQSSGLYSLSSVVTVPSSSLGTKTYTCNVDHKPS NTKVDKRVESKYGPPCPSCPAPEFLGGPSVFLFPPKPKDTLMISR TPEVTCVVVDVSQEDPEVQFNWYVDGVEVHNAKTKPREEQFNSTY RVVSVLTVLHQDWLNGKEYKCKVSNKGLPSSIEKTISKAKGQPRE PQVYTLPPSQEEMTKNQVSLTCLVKGFYPSDIAVEWESNGQPENN YKTTPPVLDSDGSFFLYSRLTVDKSRWQEGNVFSCSVMHEALHNH YTQKSLSLSLGK |
| 111 | Human IgG4 Fc domain | PAPEFLGGPSVFLFPPKPKDTLMISRTPEVTCVVVDVSQEDPEVQ FNWYVDGVEVHNAKTKPREEQFNSTYRVVSVLTVLHQDWLNGKEY KCKVSNKGLPSSIEKTISKAKGQPREPQVYTLPPSQEEMTKNQVS LTCLVKGFYPSDIAVEWESNGQPENNYKTTPPVLDSDGSFFLYSR LTVDKSRWQEGNVFSCSVMHEALHNHYTQKSLSLSLGK |
| 112 | Human IgG4 Hinge + Fc domain | ESKYGPPCPSCPAPEFLGGPSVFLFPPKPKDTLMISRTPEVTCVV VDVSQEDPEVQFNWYVDGVEVHNAKTKPREEQFNSTYRVVSVLTV LHQDWLNGKEYKCKVSNKGLPSSIEKTISKAKGQPREPQVYTLPP SQEEMTKNQVSLTCLVKGFYPSDIAVEWESNGQPENNYKTTPPVL DSDGSFFLYSRLTVDKSRWQEGNVESCSVMHEALHNHYTQKSLSL SLGK |
| 113 | Representative Fc domain sourced from Dulaglutide (S228P, F234A, L235A, L445P (EU) and K478del (Kabat) | AESKYGPPCPPCPAPEAAGGPSVFLFPPKPKDTLMISRTPEVTCV VVDVSQEDPEVQFNWYVDGVEVHNAKTKPREEQFNSTYRVVSVLT VLHQDWLNGKEYKCKVSNKGLPSSIEKTISKAKGQPREPQVYTL PPSQEEMTKNQVSLTCLVKGFYPSDIAVEWESNGQPENNYKTTPP VLDSDGSFFLYSRLTVDKSRWQEGNVESCSVMHEALHNHYTQKSL SLSLG- |
| 114 | Human IgG4 with mutations K196Q, S228P, F296Y, E356K, R409K, and H435R mutations from emicizumab | ASTKGPSVFPLAPCSRSTSESTAALGCLVKDYFPEPVTVSWNSGA LTSGVHTFPAVLQSSGLYSLSSVVTVPSSSLGTQTYTCNVDHKPS NTKVDKRVESKYGPPCPPCPAPEFLGGPSVFLFPPKPKDTLMISR TPEVTCVVVDVSQEDPEVQFNWYVDGVEVHNAKTKPREEQYNSTY RVVSVLTVLHQDWLNGKEYKCKVSNKGLPSSIEKTISKAKGQPRE PQVYTLPPSQKEMTKNQVSLTCLVKGFYPSDIAVEWESNGQPENN YKTTPPVLDSDGSFFLYSKLTVDKSRWQEGNVESCSVMHEALHNR YTQKSLSLSLGK |

TABLE 1-continued

SEQUENCE LISTING

| SEQ ID NO: | DESCRIPTION | SEQUENCE |
|---|---|---|
| 115 | Human IgG4 with mutations K196Q, S228P, F296Y, R409K, and K439E mutations from emicizumab | ASTKGPSVFPLAPCSRSTSESTAALGCLVKDYFPEPVTVSWNSGA LTSGVHTFPAVLQSSGLYSLSSVVTVPSSSLGTQTYTCNVDHKPS NTKVDKRVESKYGPPCPPCPAPEFLGGPSVFLFPPKPKDTLMISR TPEVTCVVVDVSQEDPEVQFNWYVDGVEVHNAKTKPREEQYNSTY RVVSVLTVLHQDWLNGKEYKCKVSNKGLPSSIEKTISKAKGQPRE PQVYTLPPSQEEMTKNQVSLTCLVKGFYPSDIAVEWESNGQPENN YKTTPPVLDSDGSFFLYSKLTVDKSRWQEGNVESCSVMHEALHNH YTQESLSLSLGK |
| 116 | Human IgG4 Fc domain with mutations F296Y, E356K, R409K, and H435R mutations from emicizumab | PAPEFLGGPSVFLFPPKPKDTLMISRTPEVTCVVVDVSQEDPEVQ FNWYVDGVEVHNAKTKPREEQYNSTYRVVSVLTVLHQDWLNGKEY KCKVSNKGLPSSIEKTISKAKGQPREPQVYTLPPSQKEMTKNQVS LTCLVKGFYPSDIAVEWESNGQPENNYKTTPPVLDSDGSFFLYSK LTVDKSRWQEGNVFSCSVMHEALHNRYTQKSLSLSLGK |
| 117 | Human IgG4 Fc domain with mutations F296Y, R409K, and K439E mutations from emicizumab | PAPEFLGGPSVFLFPPKPKDTLMISRTPEVTCVVVDVSQEDPEVQ FNWYVDGVEVHNAKTKPREEQYNSTYRVVSVLTVLHQDWLNGKEY KCKVSNKGLPSSIEKTISKAKGQPREPQVYTLPPSQEEMTKNQVS LTCLVKGFYPSDIAVEWESNGQPENNYKTTPPVLDSDGSFFLYSK LTVDKSRWQEGNVFSCSVMHEALHNHYTQESLSLSLGK |
| 118 | Human IgG4 Hinge + Fc domain with mutations S228P, F296Y, E356K, R409K, H435R, L445P, G446del (EU) and K478del(Kabat) mutations from emicizumab | ESKYGPPCPPCPAPEFLGGPSVFLFPPKPKDTLMISRTPEVTC VVVDVSQEDPEVQFNWYVDGVEVHNAKTKPREEQYNSTYRVVS VLTVLHQDWLNGKEYKCKVSNKGLPSSIEKTISKAKGQPREPQ VYTLPPSQKEMTKNQVSLTCLVKGFYPSDIAVEWESNGQPENN YKTTPPVLDSDGSFFLYSKLTVDKSRWQEGNVESCSVMHEALH NRYTQKSLSLSP-- |
| 119 | Human IgG4 Hinge + Fc domain with mutations S228P, F296Y, R409K, K439E, L445P, G446del (EU) and K478del(Kabat) mutations from emicizumab | ESKYGPPCPPCPAPEFLGGPSVFLFPPKPKDTLMISRTPEVTC VVVDVSQEDPEVQFNWYVDGVEVHNAKTKPREEQYNSTYRVVS VLTVLHQDWLNGKEYKCKVSNKGLPSSIEKTISKAKGQPREPQ VYTLPPSQEEMTKNQVSLTCLVKGFYPSDIAVEWESNGQPENN YKTTPPVLDSDGSFFLYSKLTVDKSRWQEGNVESCSVMHEAL HNHYTQESLSLSP-- |
| 120 | Human IgG4 Hinge + Fc domain with mutations T350V, T366L, K392L, T394W (zymeworks) | ESKYGPPCPSCPAPEFLGGPSVFLFPPKPKDTLMISRTPEVTC VVVDVSQEDPEVQFNWYVDGVEVHNAKTKPREEQFNSTYRVVS VLTVLHQDWLNGKEYKCKVSNKGLPSSIEKTISKAKGQPREPQ VYVLPPSQEEMTKNQVSLLCLVKGFYPSDIAVEWESNGQPENN YLTWPPVLDSDGSFFLYSRLTVDKSRWQEGNVFSCSVMHEALH NHYTQKSLSLSLGK |
| 121 | Human IgG4 Hinge + Fc domain with mutations T350V, L351Y, F405A, Y407V (zymeworks) | ESKYGPPCPSCPAPEFLGGPSVFLFPPKPKDTLMISRTPEVTC VVVDVSQEDPEVQFNWYVDGVEVHNAKTKPREEQFNSTYRVVS VLTVLHQDWLNGKEYKCKVSNKGLPSSIEKTISKAKGQPREPQ VYVYPPSQEEMTKNQVSLTCLVKGFYPSDIAVEWESNGQPENN YKTTPPVLDSDGSFALVSRLTVDKSRWQEGNVFSCSVMHEALH NHYTQKSLSLSLGK |
| 122 | Human IgG4 Hinge + Fc domain with mutation T366Y (knob hole 1) | ESKYGPPCPSCPAPEFLGGPSVFLFPPKPKDTLMISRTPEVTC VVVDVSQEDPEVQFNWYVDGVEVHNAKTKPREEQFNSTYRVVS VLTVLHQDWLNGKEYKCKVSNKGLPSSIEKTISKAKGQPREPQ VYTLPPSQEEMTKNQVSLYCLVKGFYPSDIAVEWESNGQPENN YKTTPPVLDSDGSFFLYSRLTVDKSRWQEGNVESCSVMHEALH NHYTQKSLSLSLGK |

TABLE 1-continued

SEQUENCE LISTING

| SEQ ID NO: | DESCRIPTION | SEQUENCE |
| --- | --- | --- |
| 123 | Human IgG4 Hinge + Fc domain with mutation Y407T (knob hole 1) | ESKYGPPCPSCPAPEFLGGPSVFLFPPKPKDTLMISRTPEVTC VVVDVSQEDPEVQFNWYVDGVEVHNAKTKPREEQFNSTYRVVS VLTVLHQDWLNGKEYKCKVSNKGLPSSIEKTISKAKGQPREPQ VYTLPPSQEEMTKNQVSLTCLVKGFYPSDIAVEWESNGQPENN YKTTPPVLDSDGSFFL<u>Y</u>SRLTVDKSRWQEGNVESCSVMHEALH NHYTQKSLSLSLGK |
| 124 | Human IgG4 Hinge + Fc domain with mutation T336W (knob hole 2) | ESKYGPPCPSCPAPEFLGGPSVFLFPPKPKDTLMISRTPEVTC VVVDVSQEDPEVQFNWYVDGVEVHNAKTKPREEQFNSTYRVVS VLTVLHQDWLNGKEYKCKVSNKGLPSSIEKTISKAKGQPREPQ VYTLPPSQEEMTKNQVSL<u>W</u>CLVKGFYPSDIAVEWESNGQPENN YKTTPPVLDSDGSFFLYSRLTVDKSRWQEGNVESCSVMHEALH NHYTQKSLSLSLGK |
| 125 | Human IgG4 Hinge + Fc domain with mutations T366S, L368A, Y407V (knob hole 2) | ESKYGPPCPSCPAPEFLGGPSVFLFPPKPKDTLMISRTPEVTC VVVDVSQEDPEVQFNWYVDGVEVHNAKTKPREEQFNSTYRVVS VLTVLHQDWLNGKEYKCKVSNKGLPSSIEKTISKAKGQPREPQ VYTLPPSQEEMTKNQVSLSCAVKGFYPSDIAVEWESNGQPENN YKTTPPVLDSDGSFEL<u>V</u>SRLTVDKSRWQEGNVESCSVMHEALH NHYTQKSLSLSLGK |
| 126 | Human IgG4 Hinge + Fc domain with mutation S228P (stability: reduced Fab arm exchange) | ESKYGPPCP<u>P</u>CPAPEFLGGPSVFLFPPKPKDTLMISRTPEVTC VVVDVSQEDPEVQFNWYVDGVEVHNAKTKPREEQFNSTYRVVS VLTVLHQDWLNGKEYKCKVSNKGLPSSIEKTISKAKGQPREPQ VYTLPPSQEEMTKNQVSL<u>Y</u>CLVKGFYPSDIAVEWESNGQPENN YKTTPPVLDSDGSFFLYSRLTVDKSRWQEGNVESCSVMHEALH NHYTQKSLSLSLGK |
| 127 | Human IgG4 Hinge + Fc domain with mutation L235E (decrease FcR binding) (Alegre et al 1992) | ESKYGPPCPSCPAPEF<u>E</u>GGPSVFLFPPKPKDTLMISRTPEVTC VVVDVSQEDPEVQFNWYVDGVEVHNAKTKPREEQFNSTYRVVS VLTVLHQDWLNGKEYKCKVSNKGLPSSIEKTISKAKGQPREPQ VYTLPPSQEEMTKNQVSLTCLVKGFYPSDIAVEWESNGQPENN YKTTPPVLDSDGSFFLYSRLTVDKSRWQEGNVESCSVMHEALH NHYTQKSLSLSLGK |
| 128 | Human IgG4 Hinge + Fc domain with mutation F234A, L235A (decrease FcR binding) Xu et al Cell Immunol 2000 200(1):16-26) | ESKYGPPCPSCPAPE<u>AA</u>GGPSVFLFPPKPKDTLMISRTPEVTC VVVDVSQEDPEVQFNWYVDGVEVHNAKTKPREEQFNSTYRVVS VLTVLHQDWLNGKEYKCKVSNKGLPSSIEKTISKAKGQPREPQ VYTLPPSQEEMTKNQVSLTCLVKGFYPSDIAVEWESNGQPENN YKTTPPVLDSDGSFFLYSRLTVDKSRWQEGNVESCSVMHEALH NHYTQKSLSLSLGK |
| 129 | Human IgG4 Hinge + Fc domain with mutation S228P, L235E (decrease FcR binding) Reddy et al., J Immunol 2000 164(4):1925-33) | ESKYGPPCP<u>P</u>CPAPEF<u>E</u>GGPSVFLFPPKPKDTLMISRTPEVTC VVVDVSQEDPEVQFNWYVDGVEVHNAKTKPREEQFNSTYRVVS VLTVLHQDWLNGKEYKCKVSNKGLPSSIEKTISKAKGQPREPQ VYTLPPSQEEMTKNQVSLTCLVKGFYPSDIAVEWESNGQPENN YKTTPPVLDSDGSFFLYSRLTVDKSRWQEGNVESCSVMHEALH NHYTQKSLSLSLGK |
| 130 | Human IgG4 Hinge + Fc domain with mutation N297A (affects glycosylation, thus FcR binding) Borrok et al ACS Chem Biol 2012 7(9):1596-1602 | ESKYGPPCPSCPAPEFLGGPSVFLFPPKPKDTLMISRTPEVTC VVVDVSQEDPEVQFNWYVDGVEVHNAKTKPREEQF<u>A</u>STYRVVS VLTVLHQDWLNGKEYKCKVSNKGLPSSIEKTISKAKGQPREPQ VYTLPPSQEEMTKNQVSLTCLVKGFYPSDIAVEWESNGQPENN YKTTPPVLDSDGSFFLYSRLTVDKSRWQEGNVESCSVMHEALH NHYTQKSLSLSLGK |

REFERENCES

Von Kreudenstein et al., mAbs 5:5, 646-654; September-October 2013.
Bennett et al., J. Exp. Med., Vol. 197, No. 6, 711-723, March 2003.
Kennedy et al. Lupus Science and Medicine, 2015; 2:e00080. Doi:10.1136/lupus-2014-000080.
Spiess et al. Molecular Immunology, 2015, October; 67 (2 Pt A)95-106.
Ridgeway et al., (1996) Prot. Eng. 9, 617-621.
Atwell et al., (1997) J. Mol. Biol. 270, 26-35.
Labrijn et al., (2013) Proc. Natl. Acad. Sci. U.S.A. 110, 5145-5150.
Gunasekaran et al, (2010) J. Biol. Chem. 285, 19637-19646.
Strop et al., (2012) J. Mol. Biol. 420, 204-219.
Moore et al., (2011) mAbs 3, 546-557.
Davis et al., (2010) Protein Eng. Des. Sel. 23, 195-202
Davis et al., (2013), U.S. Pat. No. 8,586,713
Doedens et al., J. immunol., Aug. 17, 2016, doi:10.4049/jimmunol.1601142.
Khamashta et al., Ann Rheum Dis 2016; 0:1-8. Doi:10.1136/annrheumdis-2015-208562.
deWeerd et al., J. Biol. Chem., (2007) Vol. 282, No. 28, 20053-20057.
Furie et al., Arthritis & Rheumatology, Vo. 69, No. 2, February 2017, 376-386.

EQUIVALENTS

Those skilled in the art will recognize or be able to ascertain, using no more than routine experimentation, many equivalents of the specific embodiments described herein. Such equivalents are intended to be encompassed by the following claims.

---

We claim:

1. A heterodimer which binds type I interferons comprising a first polypeptide and a second polypeptide selected from:
   (i) a first polypeptide comprising the amino acid sequence of SEQ ID NO: 40 and a second polypeptide comprising the amino acid sequence of SEQ ID NO: 43;
   (ii) a first polypeptide comprising the amino acid sequence of SEQ ID NO: 41 and a second polypeptide comprising the amino acid sequence of SEQ ID NO: 42;
   (iii) a first polypeptide comprising the amino acid sequence of SEQ ID NO: 53 and a second polypeptide comprising the amino acid sequence of SEQ ID NO: 55; and
   (iv) a first polypeptide comprising the amino acid sequence of SEQ ID NO: 57 and a second polypeptide comprising the amino acid sequence of SEQ ID NO: 59;
   (v) a first polypeptide comprising the amino acid sequence of SEQ ID NO: 40, and a second polypeptide comprising the amino acid sequence selected from SEQ ID NO: 43, SEQ ID NO: 55, and SEQ ID NO: 59;
   (vi) a first polypeptide comprising the amino acid sequence of SEQ ID NO: 43, and a second polypeptide comprising the amino acid sequence selected from SEQ ID NO: 40, SEQ ID NO: 53, and SEQ ID NO: 57;
   (vii) a first polypeptide comprising the amino acid sequence of SEQ ID NO: 42, and a second polypeptide comprising the amino acid sequence selected from SEQ ID NO: 41, SEQ ID NO: 45, and SEQ ID NO: 47;
   (viii) a first polypeptide comprising the amino acid sequence of SEQ ID NO: 41 and a second polypeptide comprising the amino acid sequence selected from SEQ ID NO: 42, SEQ ID NO: 49, and SEQ ID NO: 51;
   (ix) a first polypeptide comprising the amino acid sequence of SEQ ID NO: 53, and a second polypeptide comprising the amino acid sequence selected from SEQ ID NO: 43, SEQ ID NO: 55, and SEQ ID NO: 59;
   (x) a first polypeptide comprising the amino acid sequence of SEQ ID NO: 55, and a second polypeptide comprising the amino acid sequence selected from SEQ ID NO: 40, SEQ ID NO: 53, and SEQ ID NO: 57;
   (xi) a first polypeptide comprising the amino acid sequence of SEQ ID NO: 57, and a second polypeptide comprising the amino acid sequence selected from SEQ ID NO: 43, SEQ ID NO: 55, and SEQ ID NO: 59;
   (xii) a first polypeptide comprising the amino acid sequence of SEQ ID NO: 59, and a second polypeptide comprising the amino acid sequence selected from SEQ ID NO: 40, SEQ ID NO: 53, and SEQ ID NO: 57;
   (xiii) a first polypeptide comprising the amino acid sequence of SEQ ID NO: 45, and a second polypeptide comprising the amino acid sequence selected from SEQ ID NO: 42, SEQ ID NO: 49, and SEQ ID NO: 51;
   (xiv) a first polypeptide comprising the amino acid sequence of SEQ ID NO: 47, and a second polypeptide comprising the amino acid sequence selected from SEQ ID NO: 42, SEQ ID NO: 49, and SEQ ID NO: 51;
   (xv) a first polypeptide comprising the amino acid sequence of SEQ ID NO: 49, and a second polypeptide comprising the amino acid sequence selected from SEQ ID NO: 41, SEQ ID NO: 45, and SEQ ID NO: 47;
   (xvi) a first polypeptide comprising the amino acid sequence of SEQ ID NO: 51, and a second polypeptide comprising the amino acid sequence selected from SEQ ID NO: 41, SEQ ID NO: 45, and SEQ ID NO: 47;
   (xvii) a first polypeptide comprising the amino acid sequence of SEQ ID NO: 61, and a second polypeptide comprising the amino acid sequence selected from SEQ ID NO: 67, SEQ ID NO: 75, and SEQ ID NO: 82;

(xviii) a first polypeptide comprising the amino acid sequence of SEQ ID NO: 63, and a second polypeptide comprising the amino acid sequence selected from SEQ ID NO: 65, SEQ ID NO: 73, and SEQ ID NO: 81;

(xix) a first polypeptide comprising the amino acid sequence of SEQ ID NO: 65, and a second polypeptide comprising the amino acid sequence selected from SEQ ID NO: 63, SEQ ID NO: 71, and SEQ ID NO: 79;

(xx) a first polypeptide comprising the amino acid sequence of SEQ ID NO: 67, and a second polypeptide comprising the amino acid sequence selected from SEQ ID NO: 61, SEQ ID NO: 69, and SEQ ID NO: 77;

(xxi) a first polypeptide comprising the amino acid sequence of SEQ ID NO: 69, and a second polypeptide comprising the amino acid sequence selected from SEQ ID NO: 67, SEQ ID NO: 75, and SEQ ID NO: 82;

(xxii) a first polypeptide comprising the amino acid sequence of SEQ ID NO: 71, and a second polypeptide comprising the amino acid sequence selected from SEQ ID NO: 65, SEQ ID NO: 73, and SEQ ID NO: 81;

(xxiii) a first polypeptide comprising the amino acid sequence of SEQ ID NO: 73, and a second polypeptide comprising the amino acid sequence selected from SEQ ID NO: 63, SEQ ID NO: 71, and SEQ ID NO: 79;

(xxiv) a first polypeptide comprising the amino acid sequence of SEQ ID NO: 75, and a second polypeptide comprising the amino acid sequence selected from SEQ ID NO: 61, SEQ ID NO: 69, and SEQ ID NO: 77;

(xxv) a first polypeptide comprising the amino acid sequence of SEQ ID NO: 77, and a second polypeptide comprising the amino acid sequence selected from SEQ ID NO: 67, SEQ ID NO: 75, and SEQ ID NO: 82;

(xxvi) a first polypeptide comprising the amino acid sequence of SEQ ID NO: 79, and a second polypeptide comprising the amino acid sequence selected from SEQ ID NO: 65, SEQ ID NO: 73, and SEQ ID NO: 81;

(xxvii) a first polypeptide comprising the amino acid sequence of SEQ ID NO: 81, and a second polypeptide comprising the amino acid sequence selected from SEQ ID NO: 63, SEQ ID NO: 71, and SEQ ID NO: 79;

(xxviii) a first polypeptide comprising the amino acid sequence of SEQ ID NO: 82, and a second polypeptide comprising the amino acid sequence selected from SEQ ID NO: 61, SEQ ID NO: 69, and SEQ ID NO: 77;

(xxix) a first polypeptide comprising the amino acid sequence of SEQ ID NO: 84, and a second polypeptide comprising the amino acid sequence selected from SEQ ID NO: 89, SEQ ID NO: 97, and SEQ ID NO: 105;

(xxx) a first polypeptide comprising the amino acid sequence of SEQ ID NO: 85, and a second polypeptide comprising the amino acid sequence selected from SEQ ID NO: 87, SEQ ID NO: 95, and SEQ ID NO: 103;

(xxxi) a first polypeptide comprising the amino acid sequence of SEQ ID NO: 87, and a second polypeptide comprising the amino acid sequence selected from SEQ ID NO: 85, SEQ ID NO: 93, and SEQ ID NO: 101;

(xxxii) a first polypeptide comprising the amino acid sequence of SEQ ID NO: 89, and a second polypeptide comprising the amino acid sequence selected from SEQ ID NO: 84, SEQ ID NO: 91, and SEQ ID NO: 99;

(xxxiii) a first polypeptide comprising the amino acid sequence of SEQ ID NO: 91, and a second polypeptide comprising the amino acid sequence selected from SEQ ID NO: 89, SEQ ID NO: 97, and SEQ ID NO: 105;

(xxxiv) a first polypeptide comprising the amino acid sequence of SEQ ID NO: 93, and a second polypeptide comprising the amino acid sequence selected from SEQ ID NO: 87, SEQ ID NO: 95, and SEQ ID NO: 103;

(xxxv) a first polypeptide comprising the amino acid sequence of SEQ ID NO: 95, and a second polypeptide comprising the amino acid sequence selected from SEQ ID NO: 85, SEQ ID NO: 93, and SEQ ID NO: 101;

(xxxvi) a first polypeptide comprising the amino acid sequence of SEQ ID NO: 97, and a second polypeptide comprising the amino acid sequence selected from SEQ ID NO: 84, SEQ ID NO: 91, and SEQ ID NO: 99;

(xxxvii) a first polypeptide comprising the amino acid sequence of SEQ ID NO: 99, and a second polypeptide comprising the amino acid sequence selected from SEQ ID NO: 89, SEQ ID NO: 97, and SEQ ID NO: 105;

(xxxviii) a first polypeptide comprising the amino acid sequence of SEQ ID NO: 101, and a second polypeptide comprising the amino acid sequence selected from SEQ ID NO: 87, SEQ ID NO: 95, and SEQ ID NO: 103;

(xxxix) a first polypeptide comprising the amino acid sequence of SEQ ID NO: 103, and a second polypeptide comprising the amino acid sequence selected from SEQ ID NO: 85, SEQ ID NO: 93, and SEQ ID NO: 101; and (xl) a first polypeptide comprising the amino acid sequence of SEQ ID NO: 105, and a second polypeptide comprising the amino acid sequence selected from SEQ ID NO: 84, SEQ ID NO: 91, and SEQ ID NO: 99.

2. A composition comprising the heterodimer of claim 1 and a pharmaceutically acceptable carrier.

3. A kit comprising a container comprising a heterodimer of claim 1, and an optional pharmaceutically acceptable carrier, and a package insert comprising instructions for administration of the heterodimer for treating or delaying progression of an autoimmune disease in a subject in need thereof.

4. The heterodimer of claim 1, wherein the heterodimer binds type I interferons selected from interferon-α (INFα), interferon-β (INFβ), or both INFα and INFβ.

5. The heterodimer of claim 1, wherein the heterodimer binds INF-α.

6. The heterodimer of claim 1, wherein the heterodimer binds INF-β.

7. The heterodimer of claim 1, wherein the heterodimer inhibits an activity of INFα, INFβ, or both INFα and INFβ.

8. The heterodimer of claim 1, wherein the heterodimer inhibits an activity of INFα.

9. The heterodimer of claim 1, wherein the heterodimer inhibits an activity of INFβ.

10. The heterodimer of claim 1, wherein the heterodimer inhibits induction of type I interferon (IFN) gene expression.

11. A heterodimer which binds type I interferons comprising a first polypeptide comprising the amino acid sequence of SEQ ID NO: 40 and a second polypeptide comprising the amino acid sequence of SEQ ID NO: 43.

12. A composition comprising the heterodimer of claim 11 and a pharmaceutically acceptable carrier.

13. The heterodimer of claim 11, wherein the heterodimer binds type I interferons selected from interferon-α (INFα), interferon-β (INFβ), or both INFα and INFβ.

14. The heterodimer of claim 11, wherein the heterodimer binds INF-α.

15. The heterodimer of claim 11, wherein the heterodimer binds INF-β.

16. The heterodimer of claim 11, wherein the heterodimer inhibits an activity of INFα, INFβ, or both INFα and INFβ.

17. The heterodimer of claim 11, wherein the heterodimer inhibits an activity of INFα.

18. The heterodimer of claim 11, wherein the heterodimer inhibits an activity of INFβ.

19. The heterodimer of claim 11, wherein the heterodimer inhibits induction of type I interferon (IFN) gene expression.

20. A heterodimer which binds type I interferons comprising a first polypeptide comprising the amino acid sequence of SEQ ID NO: 41 and a second polypeptide comprising the amino acid sequence of SEQ ID NO: 42.

21. A composition comprising the heterodimer of claim 20 and a pharmaceutically acceptable carrier.

22. The heterodimer of claim 20, wherein the heterodimer binds type I interferons selected from interferon-α (INFα), interferon-β (INFβ), or both INFα and INFβ.

23. The heterodimer of claim 20, wherein the heterodimer binds INF-α.

24. The heterodimer of claim 20, wherein the heterodimer binds INF-β.

25. The heterodimer of claim 20, wherein the heterodimer inhibits an activity of INFα, INFβ, or both INFα and INFβ.

26. The heterodimer of claim 20, wherein the heterodimer inhibits an activity of INFα.

27. The heterodimer of claim 20, wherein the heterodimer inhibits an activity of INFβ.

28. The heterodimer of claim 20, wherein the heterodimer inhibits induction of type I interferon (IFN) gene expression.

29. A heterodimer which binds type I interferons comprising a first polypeptide comprising the amino acid sequence of SEQ ID NO: 53 and a second polypeptide comprising the amino acid sequence of SEQ ID NO: 55.

30. A composition comprising the heterodimer of claim 29 and a pharmaceutically acceptable carrier.

31. The heterodimer of claim 29, wherein the heterodimer binds type I interferons selected from interferon-α (INFα), interferon-β (INFβ), or both INFα and INFβ.

32. The heterodimer of claim 29, wherein the heterodimer binds INF-α.

33. The heterodimer of claim 29, wherein the heterodimer binds INF-β.

34. The heterodimer of claim 29, wherein the heterodimer inhibits an activity of INFα, INFβ, or both INFα and INFβ.

35. The heterodimer of claim 29, wherein the heterodimer inhibits an activity of INFα.

36. The heterodimer of claim 29, wherein the heterodimer inhibits an activity of INFβ.

37. The heterodimer of claim 29, wherein the heterodimer inhibits induction of type I interferon (IFN) gene expression.

38. A heterodimer which binds type I interferons comprising a first polypeptide comprising the amino acid sequence of SEQ ID NO: 57 and a second polypeptide comprising the amino acid sequence of SEQ ID NO: 59.

39. A composition comprising the heterodimer of claim 38 and a pharmaceutically acceptable carrier.

40. The heterodimer of claim 38, wherein the heterodimer binds type I interferons selected from interferon-α (INFα), interferon-β (INFβ), or both INFα and INFβ.

41. The heterodimer of claim 38, wherein the heterodimer binds INF-α.

42. The heterodimer of claim 38, wherein the heterodimer binds INF-β.

43. The heterodimer of claim 38, wherein the heterodimer inhibits an activity of INFα, INFβ, or both INFα and INFβ.

44. The heterodimer of claim 38, wherein the heterodimer inhibits an activity of INFα.

45. The heterodimer of claim 38, wherein the heterodimer inhibits an activity of INFβ.

46. The heterodimer of claim 38, wherein the heterodimer inhibits induction of type I interferon (IFN) gene expression.

* * * * *